United States Patent
Boriack-Sjodin et al.

[11] Patent Number: 6,156,526
[45] Date of Patent: Dec. 5, 2000

[54] CRYSTAL OF A RAS-SOS COMPLEX AND METHODS OF USE THEREOF

[75] Inventors: Ann Boriack-Sjodin, Watertown, Mass.; S. Mariana Margarit, Setauket, N.Y.; Dafna Bar-Sagi, Stony Brook, N.Y.; Philip Cole, New York, N.Y.; John Kuriyan, Riverdale, N.Y.

[73] Assignees: The Rockerfeller University, New York; The Research Foundation of State University of New York, Albany, both of N.Y.

[21] Appl. No.: 09/119,794

[22] Filed: Jul. 21, 1998

[51] Int. Cl.[7] ................................................ C12Q 1/34
[52] U.S. Cl. ....................... 435/18; 435/195; 530/350; 702/19; 702/22
[58] Field of Search ................ 435/18, 195; 530/350; 702/19, 22

[56] References Cited

FOREIGN PATENT DOCUMENTS

WO 94/29727  12/1994  WIPO .

OTHER PUBLICATIONS

Corbalan–Garcia et al., 1998, Mol Cell Biol, 18:880–6.
Dunbrack et al., 1997, 2:R27–R42.
Wittinghofer, 1998, Nature, 394:317–20.
Jurnak, *Science*, 230:32–36 (1985).
Kawashima et al., *Nature*, 379:511–518 (1996).
Kemp, and Stites, *Tetrahedron Lett.* 29:5057 (1988).
Lai et al., *Mol. Cell. Biol.*, 13:1345–1352 (1993).
Lenzen et al., *Biochemistry* 37:7420–7430 (1998).
Medema et al., *Molec. Cell. Biol.*, 13:155–162 (1993).
Milburn et al., *Science*, 247:939–945 (1990).
Mitsou et al., *EMBO J.*, 11:2391–2397 (1992).
Mosteller et al., *Molec. Cell. Biol.*, 14:1104–1112 (1994).
Mossessova et al., *Cell*, 92:415–423 (1998).

Nagai et al., *Tetrahedron* 49:3577 (1993).
Nicholls et al., *Proteins: Struct. Funct. and Genetics*, 11:281–296 (1991).
Nicholson et al. *Nature* 376:37 (1995).
Otwinowski and Minor, *Meth. Enzymol.*, 276:307–326 (1997).
Pai et al., *EMBO J.*, 9:2351–2359 (1990).
Poullet et al., *Eur. J. Biochem.*, 227:537–544 (1995).
Powers et al., *Molec. and Cell. Biol.*, 9:390–395 (1989.
Renault et al., *Nature*, 392:97–101 (1998).
Ripka et al., *Tetrahedron* 49:3593 (1993).
Rotunda et al. *Nature Structural Biology* 3:619–625 (1996).
Sato,and Nagai *J. Chem. Soc. Perkin Trans.* 1:1231 (1986).
Scheffzek et al., *Nature*, 384:591–596 (1996).
Schlessinger, *Trends Biochem. Sci.*, 18:273–275 (1994).
Segal et al., *Proc. Natl. Acad. Sci.* 90:5564–5568 (1993).
Yu and Schreiber, *Nature*, 376:788–791 (1995).
Wagner, and Feigel, *Tetrahedron* 49:10831 (1993).
Wang et al., *Nat. Struct. Biol.*, 4:650–656 (1997.
Westbrook and Naday, *Meth. Enzymol.*, 276:244–268 (1997).
Bar–Sagi, *Trends Endocrin. Metab.*, 5:165–169 (1994).
Bernstein et al., *Archives of Biochemistry & Biophysics*, 185:584–591 (1978(.
Bourne et al., *Nature*, 349:117–127 (1991).

(List continued on next page.)

*Primary Examiner*—Nashaat Nashed
*Attorney, Agent, or Firm*—Klauber & Jackson

[57] ABSTRACT

A detailed three-dimensional structure for the complex formed between Ras and the Son of sevenless (Sos) protein is provided. Crystals of this complex are also included in the invention. The present invention farther provides procedures for identifying agents that can inhibit tumor proliferation through the use of rational drug design predicated on the crystals and crystallographic data disclosed.

32 Claims, 97 Drawing Sheets

(7 of 97 Drawing Sheet(s) Filed in Color)

OTHER PUBLICATIONS

Boguski and McCormick, *Nature*, 366:643–654 (1993).
Brandmeier et al. *Helv. Chim. Acta*. 77:70 (1994).
Brünger et al., *Structure*, 5:325–336 (1997).
Buday and Downward, *Cell*, 73:611–620 (1993).
Bugg et al., *Scientific American*, Dec.:92–98 (1993).
Carson, *J. Appl. Cryst.*, 24:958–961 (1991).
Chardin et al., *Science*, 260:1338–1343 (1993).
Chen et al., *Oncogene* 9:2691–2698 (1994).
Cherfils et al., *Nature*, 392:101–105 (1998).
Collaborative Computing Project, N. The CCP4 Suite: Programs for protein cyrstallagraphy*Acta Cryst.*, D50:760–763 (1994).
Cowtan, *Joint CCP4 and ESF–EACBM Newsletter on Protein Crystallography*, 31:34–38 (1994).
Crechet et al., *J. Biol. Chem.*, 271:17234–17240 (1996).
Dunbrack et al., *Folding & Design*, 2:27–42 (1997).
Feigel, *J. Am. Chem. Soc.* 108:181 (1986).
Gale et al., *Nature*, 363:88–92 (1993).
Gante, *Angew. Chem. Int. Ed. Engl.* 33–1699–1720 (1994).
Genin, and Johnson, *J. Am. Chem. Soc.* 114:8778 (1992).
Haney and Broach, *J. Biol. Chem.*, 269:16541–16548 (1994).

Harrison et al., *Science*, 276:431–435 (1997).
Holm and Sander, *J. Mol. Biol.* 233:123–138 (1993).
Jones et al., *Acta Crystallogr.*, A47:110–119 (1991).
Boriack–Sjoidin et al. "The structure basis of the activation of Ras by Sos" Nature, 394, 337–343, Jul. 1998.
Zheng et al. "The solution structure of the Pleckstrin homology domain of human SOS1" J. Biol. Chem. 272, 30340–30344, Nov. 1997.
Tong et al. "Crystal structure at 2.2 A resolution of the catalytic domains of normal ras protein and oncogenic mutant complex with GDP" J. Mol. Biol. 217, 503–516, 1991.
Kraulis et al. "Solution structure and dynamics of Ras p21.GDP determined by heternuclear . . . " Biochemistry 33, 3515–3531, 1994.
Soisson et al. "Crystal structure of the Dbl and Pleckstrin homology domains from the human son of sevenless protein" Cell 95, 259–268, Oct. 1998.
de Vos et al. "Three–dimentional structure of oncogenic protein : Catalytic . . . " Science 239, 888–893, Feb. 1988.
Pai et al., "Structure of the guanine–nucleotide–binding domain of the Ha–ras . . . " Nature 341, 209–214, Sep. 1989.

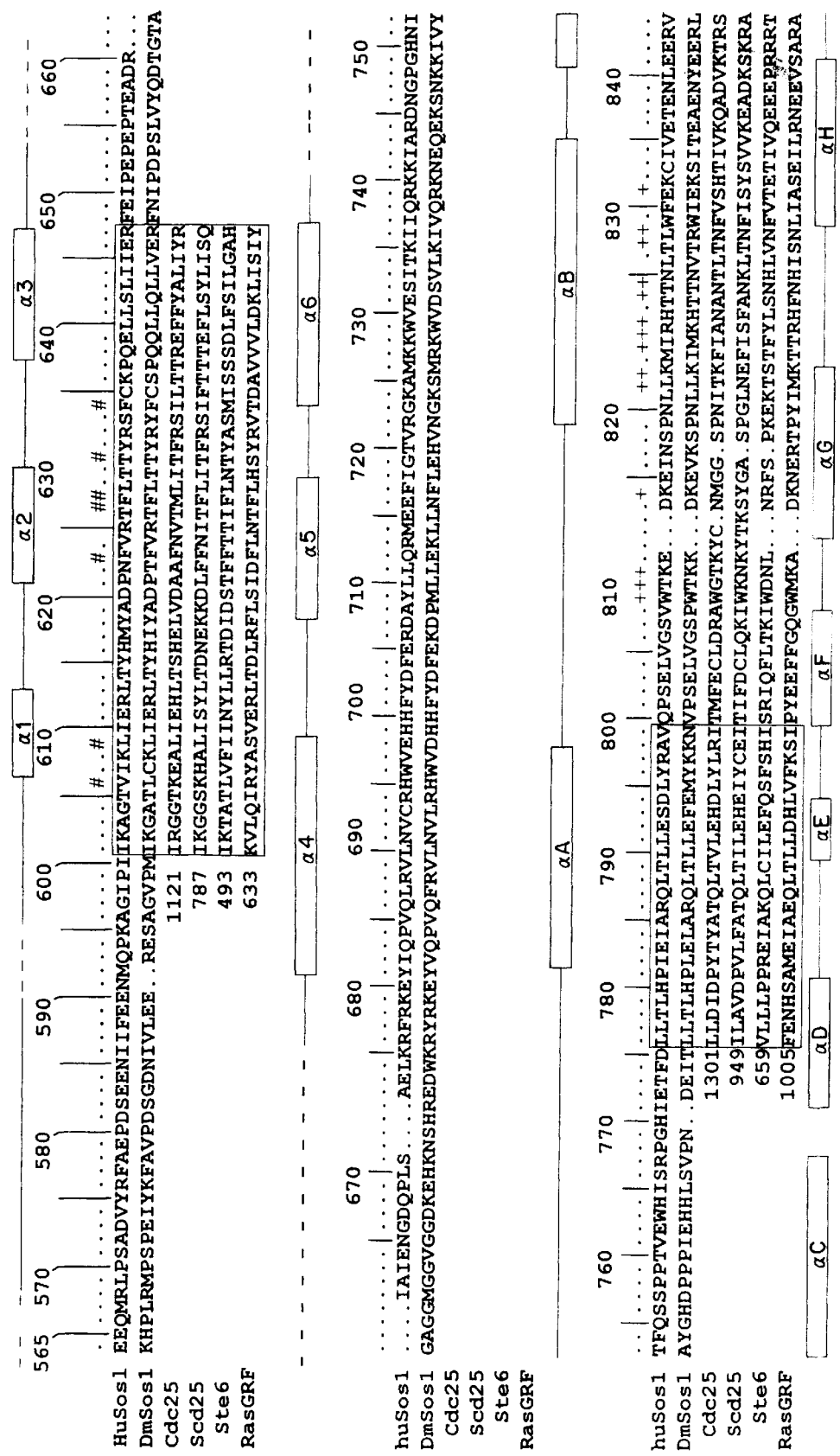

Ras-Sos

Ras-GTP

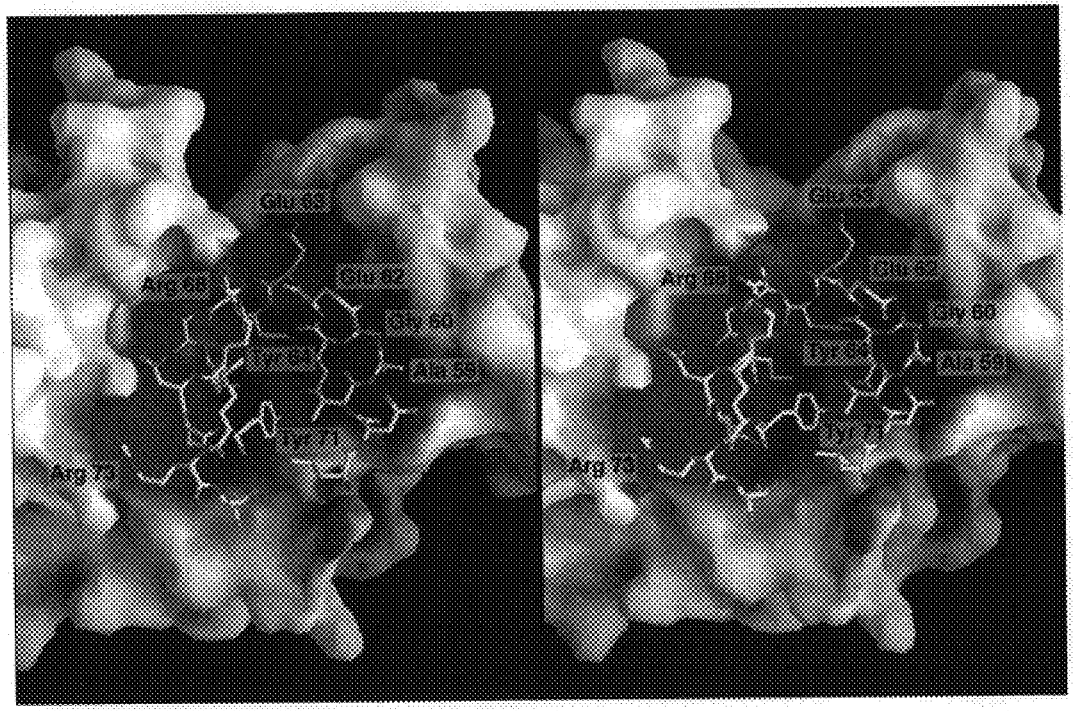

Schematic of GTP in Sos-Ras complex

R=analogs of the ribose triphosphate moiety

Further Analogs and Proposed Mechanisms of inhibition

Modifications of ribose-phosphate moiety

X= guanine or derivatives discussed above

18

19

20

21

Y=hydrogen bonding group such as $CO_2^-$, OH

22

23

Y=hydrogen bonding group such as $CO_2^-$, OH

Z=hydrophobic group such as alkyl or aryl

24  Ras β-turn

25

26

27

28

29

Z = alkyl or aryl group

Figure 8-1

PDB Coordinates for the Ras-Sos Structure:

DATA SET FOR REFINED COORDINATES

```
REMARK coordinates from minimization refinement
REMARK refinement resolution: 30.0 - 2.8 A
REMARK starting r= 0.2223 free_r= 0.2807
REMARK final     r= 0.2220 free_r= 0.2811
REMARK rmsd bonds= 0.006712  rmsd angles=  1.25899
REMARK wa= 2.83987
REMARK target= mlf cycles= 1 steps= 300
REMARK sg= I422 a= 142.73 b= 142.73 c= 207.89 alpha= 90 beta= 90 gamma= 90
REMARK parameter file 1  : CNS_TOPPAR:protein.param
REMARK parameter file 2  : CNS_TOPPAR:water.param
REMARK molecular structure file: rsa4_gen.psf
REMARK input coordinates: rsa4_gen.pdb
REMARK reflection file= nat3_Rfree.hkl_xplor
REMARK ncs= none
REMARK B-correction resolution: 6.0 - 2.8
REMARK initial B-factor correction applied to fobs :
REMARK    B11=  -6.191 B22=  -6.191 B33=  12.382
REMARK    B12=   0.000 B13=   0.000 B23=   0.000
REMARK B-factor correction applied to coordinate array B:    1.267
REMARK bulk solvent: density level= 0.272909 e/A^3, B-factor= 10.7814 A^2
REMARK reflections with |Fobs|/sigma_F < 0.0 rejected
REMARK reflections with |Fobs| > 10000 * rms(Fobs) rejected
REMARK theoretical total number of refl. in resol. range:    26748 (100.0 % )
REMARK number of unobserved reflections (no entry or |F|=0):   246 (  0.9 % )
REMARK number of reflections rejected:                           0 (  0.0 % )
REMARK total number of reflections used:                     26502 ( 99.1 % )
REMARK number of reflections in working set:                 25175 ( 94.1 % )
REMARK number of reflections in test set:                     1327 (  5.0 % )
REMARK FILENAME="rsa4_min.pdb"
REMARK DATE:03-Apr-98   15:43:51         created by user: boriacp
ATOM      1  CB  ARG   568      65.030  36.388  12.267  1.00 86.85      sos
ATOM      2  CG  ARG   568      64.365  35.070  12.634  1.00 85.46      sos
ATOM      3  CD  ARG   568      63.268  35.255  13.671  1.00 81.64      sos
ATOM      4  NE  ARG   568      62.720  33.976  14.118  0.00 83.05      sos
ATOM      5  CZ  ARG   568      63.295  33.188  15.022  0.00 82.83      sos
ATOM      6  NH1 ARG   568      64.442  33.540  15.587  0.00 83.01      sos
ATOM      7  NH2 ARG   568      62.724  32.039  15.359  0.00 83.01      sos
ATOM      8  C   ARG   568      66.656  37.661  10.841  1.00 92.14      sos
ATOM      9  O   ARG   568      67.860  37.822  10.643  1.00 91.54      sos
ATOM     10  N   ARG   568      67.174  35.327  11.569  1.00 88.89      sos
ATOM     11  CA  ARG   568      66.093  36.276  11.164  1.00 90.80      sos
ATOM     12  N   LEU   569      65.773  38.655  10.781  1.00 94.54      sos
ATOM     13  CA  LEU   569      66.162  40.032  10.484  1.00 96.99      sos
ATOM     14  CB  LEU   569      66.058  40.306   8.973  1.00 96.57      sos
ATOM     15  CG  LEU   569      65.071  39.506   8.106  0.00 96.72      sos
ATOM     16  CD1 LEU   569      63.639  39.621   8.612  0.00 96.66      sos
ATOM     17  CD2 LEU   569      65.162  39.988   6.668  0.00 96.66      sos
ATOM     18  C   LEU   569      65.318  41.034  11.278  1.00 98.72      sos
ATOM     19  O   LEU   569      64.288  41.509  10.798  1.00 99.61      sos
ATOM     20  N   PRO   570      65.742  41.360  12.517  1.00100.00      sos
ATOM     21  CD  PRO   570      66.924  40.814  13.210  1.00101.82      sos
ATOM     22  CA  PRO   570      65.026  42.306  13.383  1.00 98.66      sos
ATOM     23  CB  PRO   570      65.670  42.066  14.747  1.00 99.43      sos
ATOM     24  CG  PRO   570      67.082  41.759  14.387  1.00101.26      sos
ATOM     25  C   PRO   570      65.172  43.756  12.932  1.00 96.84      sos
ATOM     26  O   PRO   570      65.841  44.041  11.939  1.00 94.96      sos
ATOM     27  N   SER   571      64.556  44.667  13.677  1.00 96.14      sos
```

Figure 8-2

| ATOM | 28 | CA | SER | 571 | 64.596 | 46.087 | 13.349 | 1.00 | 96.60 | sos |
|---|---|---|---|---|---|---|---|---|---|---|
| ATOM | 29 | CB | SER | 571 | 63.583 | 46.853 | 14.195 | 1.00 | 98.88 | sos |
| ATOM | 30 | OG | SER | 571 | 62.264 | 46.422 | 13.900 | 1.00 | 101.55 | sos |
| ATOM | 31 | C | SER | 571 | 65.975 | 46.748 | 13.414 | 1.00 | 96.15 | sos |
| ATOM | 32 | O | SER | 571 | 66.964 | 46.121 | 13.804 | 1.00 | 94.52 | sos |
| ATOM | 33 | N | ALA | 572 | 66.011 | 48.031 | 13.053 | 1.00 | 96.56 | sos |
| ATOM | 34 | CA | ALA | 572 | 67.241 | 48.825 | 12.992 | 1.00 | 97.38 | sos |
| ATOM | 35 | CB | ALA | 572 | 66.997 | 50.088 | 12.162 | 1.00 | 95.98 | sos |
| ATOM | 36 | C | ALA | 572 | 67.978 | 49.193 | 14.286 | 1.00 | 97.38 | sos |
| ATOM | 37 | O | ALA | 572 | 68.924 | 49.987 | 14.232 | 1.00 | 98.97 | sos |
| ATOM | 38 | N | ASP | 573 | 67.577 | 48.630 | 15.428 | 1.00 | 94.68 | sos |
| ATOM | 39 | CA | ASP | 573 | 68.233 | 48.927 | 16.708 | 1.00 | 92.01 | sos |
| ATOM | 40 | CB | ASP | 573 | 69.754 | 48.656 | 16.596 | 1.00 | 91.55 | sos |
| ATOM | 41 | CG | ASP | 573 | 70.607 | 49.655 | 17.361 | 0.00 | 91.98 | sos |
| ATOM | 42 | OD1 | ASP | 573 | 71.130 | 50.591 | 16.727 | 0.00 | 92.02 | sos |
| ATOM | 43 | OD2 | ASP | 573 | 70.776 | 49.498 | 18.586 | 0.00 | 92.02 | sos |
| ATOM | 44 | C | ASP | 573 | 67.907 | 50.334 | 17.231 | 1.00 | 91.71 | sos |
| ATOM | 45 | O | ASP | 573 | 67.975 | 50.584 | 18.431 | 1.00 | 90.14 | sos |
| ATOM | 46 | N | VAL | 574 | 67.570 | 51.241 | 16.314 | 1.00 | 93.56 | sos |
| ATOM | 47 | CA | VAL | 574 | 67.189 | 52.618 | 16.638 | 1.00 | 93.77 | sos |
| ATOM | 48 | CB | VAL | 574 | 67.535 | 53.589 | 15.470 | 1.00 | 96.52 | sos |
| ATOM | 49 | CG1 | VAL | 574 | 67.317 | 55.045 | 15.889 | 1.00 | 97.68 | sos |
| ATOM | 50 | CG2 | VAL | 574 | 68.980 | 53.370 | 15.013 | 1.00 | 96.04 | sos |
| ATOM | 51 | C | VAL | 574 | 65.671 | 52.628 | 16.899 | 1.00 | 92.97 | sos |
| ATOM | 52 | O | VAL | 574 | 65.047 | 53.687 | 16.978 | 1.00 | 94.05 | sos |
| ATOM | 53 | N | TYR | 575 | 65.095 | 51.429 | 17.026 | 1.00 | 91.05 | sos |
| ATOM | 54 | CA | TYR | 575 | 63.668 | 51.233 | 17.297 | 1.00 | 86.99 | sos |
| ATOM | 55 | CB | TYR | 575 | 62.864 | 51.093 | 15.989 | 1.00 | 88.09 | sos |
| ATOM | 56 | CG | TYR | 575 | 62.862 | 52.290 | 15.063 | 0.00 | 88.43 | sos |
| ATOM | 57 | CD1 | TYR | 575 | 63.770 | 52.375 | 14.008 | 0.00 | 88.72 | sos |
| ATOM | 58 | CE1 | TYR | 575 | 63.755 | 53.453 | 13.127 | 0.00 | 88.91 | sos |
| ATOM | 59 | CD2 | TYR | 575 | 61.933 | 53.319 | 15.217 | 0.00 | 88.72 | sos |
| ATOM | 60 | CE2 | TYR | 575 | 61.908 | 54.404 | 14.340 | 0.00 | 88.91 | sos |
| ATOM | 61 | CZ | TYR | 575 | 62.823 | 54.463 | 13.298 | 0.00 | 88.97 | sos |
| ATOM | 62 | OH | TYR | 575 | 62.812 | 55.528 | 12.428 | 0.00 | 89.07 | sos |
| ATOM | 63 | C | TYR | 575 | 63.486 | 49.929 | 18.088 | 1.00 | 84.03 | sos |
| ATOM | 64 | O | TYR | 575 | 62.369 | 49.406 | 18.159 | 1.00 | 83.83 | sos |
| ATOM | 65 | N | ARG | 576 | 64.548 | 49.432 | 18.729 | 1.00 | 79.53 | sos |
| ATOM | 66 | CA | ARG | 576 | 64.444 | 48.154 | 19.432 | 1.00 | 76.12 | sos |
| ATOM | 67 | CB | ARG | 576 | 64.435 | 47.058 | 18.366 | 1.00 | 71.29 | sos |
| ATOM | 68 | CG | ARG | 576 | 63.082 | 46.552 | 17.964 | 1.00 | 62.74 | sos |
| ATOM | 69 | CD | ARG | 576 | 62.651 | 45.477 | 18.898 | 1.00 | 57.01 | sos |
| ATOM | 70 | NE | ARG | 576 | 61.576 | 45.928 | 19.762 | 1.00 | 54.20 | sos |
| ATOM | 71 | CZ | ARG | 576 | 60.933 | 45.135 | 20.611 | 1.00 | 57.03 | sos |
| ATOM | 72 | NH1 | ARG | 576 | 61.263 | 43.851 | 20.724 | 1.00 | 52.90 | sos |
| ATOM | 73 | NH2 | ARG | 576 | 59.911 | 45.613 | 21.302 | 1.00 | 59.79 | sos |
| ATOM | 74 | C | ARG | 576 | 65.458 | 47.731 | 20.517 | 1.00 | 77.98 | sos |
| ATOM | 75 | O | ARG | 576 | 66.225 | 48.530 | 21.063 | 1.00 | 75.52 | sos |
| ATOM | 76 | N | PHE | 577 | 65.342 | 46.443 | 20.860 | 1.00 | 79.44 | sos |
| ATOM | 77 | CA | PHE | 577 | 66.186 | 45.702 | 21.804 | 1.00 | 76.34 | sos |
| ATOM | 78 | CB | PHE | 577 | 65.344 | 44.685 | 22.600 | 1.00 | 74.10 | sos |
| ATOM | 79 | CG | PHE | 577 | 64.490 | 45.287 | 23.683 | 1.00 | 70.97 | sos |
| ATOM | 80 | CD1 | PHE | 577 | 63.486 | 46.199 | 23.382 | 1.00 | 68.95 | sos |
| ATOM | 81 | CD2 | PHE | 577 | 64.690 | 44.929 | 25.013 | 1.00 | 67.32 | sos |
| ATOM | 82 | CE1 | PHE | 577 | 62.696 | 46.747 | 24.390 | 1.00 | 67.33 | sos |
| ATOM | 83 | CE2 | PHE | 577 | 63.906 | 45.471 | 26.021 | 1.00 | 65.54 | sos |
| ATOM | 84 | CZ | PHE | 577 | 62.908 | 46.381 | 25.710 | 1.00 | 65.61 | sos |
| ATOM | 85 | C | PHE | 577 | 67.085 | 44.886 | 20.868 | 1.00 | 77.81 | sos |
| ATOM | 86 | O | PHE | 577 | 67.724 | 43.911 | 21.277 | 1.00 | 79.06 | sos |
| ATOM | 87 | N | ALA | 578 | 67.057 | 45.265 | 19.592 | 1.00 | 77.34 | sos |
| ATOM | 88 | CA | ALA | 578 | 67.801 | 44.615 | 18.525 | 1.00 | 76.91 | sos |

Figure 8-3

| | | | | | | | | | | |
|---|---|---|---|---|---|---|---|---|---|---|
| ATOM | 89 | CB | ALA | 578 | 67.456 | 45.261 | 17.193 | 1.00 | 78.12 | SOS |
| ATOM | 90 | C | ALA | 578 | 69.312 | 44.543 | 18.694 | 1.00 | 76.18 | SOS |
| ATOM | 91 | O | ALA | 578 | 69.966 | 43.792 | 17.970 | 1.00 | 78.31 | SOS |
| ATOM | 92 | N | GLU | 579 | 69.871 | 45.323 | 19.620 | 1.00 | 72.57 | SOS |
| ATOM | 93 | CA | GLU | 579 | 71.315 | 45.300 | 19.852 | 1.00 | 71.66 | SOS |
| ATOM | 94 | CB | GLU | 579 | 71.690 | 46.160 | 21.061 | 1.00 | 73.46 | SOS |
| ATOM | 95 | CG | GLU | 579 | 71.215 | 47.598 | 20.977 | 0.00 | 73.77 | SOS |
| ATOM | 96 | CD | GLU | 579 | 71.592 | 48.412 | 22.198 | 0.00 | 74.29 | SOS |
| ATOM | 97 | OE1 | GLU | 579 | 72.686 | 49.015 | 22.198 | 0.00 | 74.50 | SOS |
| ATOM | 98 | OE2 | GLU | 579 | 70.792 | 48.454 | 23.156 | 0.00 | 74.50 | SOS |
| ATOM | 99 | C | GLU | 579 | 71.728 | 43.853 | 20.097 | 1.00 | 70.05 | SOS |
| ATOM | 100 | O | GLU | 579 | 71.145 | 43.168 | 20.932 | 1.00 | 69.21 | SOS |
| ATOM | 101 | N | PRO | 580 | 72.674 | 43.342 | 19.300 | 1.00 | 70.16 | SOS |
| ATOM | 102 | CD | PRO | 580 | 73.300 | 43.983 | 18.129 | 1.00 | 71.48 | SOS |
| ATOM | 103 | CA | PRO | 580 | 73.136 | 41.960 | 19.453 | 1.00 | 71.03 | SOS |
| ATOM | 104 | CB | PRO | 580 | 73.894 | 41.714 | 18.148 | 1.00 | 72.63 | SOS |
| ATOM | 105 | CG | PRO | 580 | 74.468 | 43.067 | 17.842 | 1.00 | 72.32 | SOS |
| ATOM | 106 | C | PRO | 580 | 74.022 | 41.736 | 20.675 | 1.00 | 69.79 | SOS |
| ATOM | 107 | O | PRO | 580 | 74.730 | 42.638 | 21.120 | 1.00 | 69.35 | SOS |
| ATOM | 108 | N | ASP | 581 | 73.967 | 40.520 | 21.208 | 1.00 | 68.02 | SOS |
| ATOM | 109 | CA | ASP | 581 | 74.755 | 40.137 | 22.368 | 1.00 | 68.10 | SOS |
| ATOM | 110 | CB | ASP | 581 | 74.579 | 38.643 | 22.665 | 1.00 | 66.00 | SOS |
| ATOM | 111 | CG | ASP | 581 | 73.167 | 38.281 | 23.095 | 1.00 | 67.92 | SOS |
| ATOM | 112 | OD1 | ASP | 581 | 72.350 | 39.188 | 23.368 | 1.00 | 64.83 | SOS |
| ATOM | 113 | OD2 | ASP | 581 | 72.882 | 37.067 | 23.171 | 1.00 | 67.36 | SOS |
| ATOM | 114 | C | ASP | 581 | 76.232 | 40.400 | 22.130 | 1.00 | 70.54 | SOS |
| ATOM | 115 | O | ASP | 581 | 76.747 | 40.131 | 21.046 | 1.00 | 73.64 | SOS |
| ATOM | 116 | N | SER | 582 | 76.902 | 40.928 | 23.151 | 1.00 | 72.53 | SOS |
| ATOM | 117 | CA | SER | 582 | 78.337 | 41.211 | 23.097 | 1.00 | 72.27 | SOS |
| ATOM | 118 | CB | SER | 582 | 78.613 | 42.607 | 22.517 | 1.00 | 70.00 | SOS |
| ATOM | 119 | OG | SER | 582 | 78.193 | 43.638 | 23.391 | 1.00 | 64.24 | SOS |
| ATOM | 120 | C | SER | 582 | 78.866 | 41.126 | 24.517 | 1.00 | 73.94 | SOS |
| ATOM | 121 | O | SER | 582 | 78.137 | 40.746 | 25.432 | 1.00 | 75.37 | SOS |
| ATOM | 122 | N | GLU | 583 | 80.137 | 41.458 | 24.706 | 1.00 | 77.16 | SOS |
| ATOM | 123 | CA | GLU | 583 | 80.717 | 41.422 | 26.040 | 1.00 | 77.96 | SOS |
| ATOM | 124 | CB | GLU | 583 | 82.232 | 41.221 | 25.971 | 1.00 | 82.27 | SOS |
| ATOM | 125 | CG | GLU | 583 | 82.615 | 39.865 | 25.379 | 1.00 | 86.85 | SOS |
| ATOM | 126 | CD | GLU | 583 | 84.111 | 39.613 | 25.371 | 1.00 | 91.33 | SOS |
| ATOM | 127 | OE1 | GLU | 583 | 84.664 | 39.284 | 26.443 | 1.00 | 90.57 | SOS |
| ATOM | 128 | OE2 | GLU | 583 | 84.728 | 39.728 | 24.289 | 1.00 | 93.09 | SOS |
| ATOM | 129 | C | GLU | 583 | 80.336 | 42.686 | 26.801 | 1.00 | 76.39 | SOS |
| ATOM | 130 | O | GLU | 583 | 80.553 | 42.784 | 28.002 | 1.00 | 77.91 | SOS |
| ATOM | 131 | N | GLU | 584 | 79.729 | 43.633 | 26.089 | 1.00 | 75.31 | SOS |
| ATOM | 132 | CA | GLU | 584 | 79.265 | 44.889 | 26.672 | 1.00 | 74.47 | SOS |
| ATOM | 133 | CB | GLU | 584 | 79.508 | 46.049 | 25.710 | 1.00 | 75.89 | SOS |
| ATOM | 134 | CG | GLU | 584 | 80.940 | 46.255 | 25.258 | 1.00 | 80.37 | SOS |
| ATOM | 135 | CD | GLU | 584 | 81.109 | 47.532 | 24.439 | 1.00 | 82.28 | SOS |
| ATOM | 136 | OE1 | GLU | 584 | 80.086 | 48.153 | 24.067 | 1.00 | 79.89 | SOS |
| ATOM | 137 | OE2 | GLU | 584 | 82.269 | 47.920 | 24.176 | 1.00 | 84.81 | SOS |
| ATOM | 138 | C | GLU | 584 | 77.756 | 44.817 | 26.930 | 1.00 | 74.13 | SOS |
| ATOM | 139 | O | GLU | 584 | 77.140 | 45.822 | 27.289 | 1.00 | 74.42 | SOS |
| ATOM | 140 | N | ASN | 585 | 77.166 | 43.640 | 26.710 | 1.00 | 73.41 | SOS |
| ATOM | 141 | CA | ASN | 585 | 75.725 | 43.419 | 26.880 | 1.00 | 68.85 | SOS |
| ATOM | 142 | CB | ASN | 585 | 75.108 | 42.913 | 25.575 | 1.00 | 70.58 | SOS |
| ATOM | 143 | CG | ASN | 585 | 74.971 | 43.986 | 24.549 | 1.00 | 75.07 | SOS |
| ATOM | 144 | OD1 | ASN | 585 | 74.410 | 45.050 | 24.819 | 1.00 | 81.03 | SOS |
| ATOM | 145 | ND2 | ASN | 585 | 75.473 | 43.722 | 23.351 | 1.00 | 77.96 | SOS |
| ATOM | 146 | C | ASN | 585 | 75.354 | 42.420 | 27.955 | 1.00 | 63.87 | SOS |
| ATOM | 147 | O | ASN | 585 | 74.586 | 42.728 | 28.857 | 1.00 | 61.19 | SOS |
| ATOM | 148 | N | ILE | 586 | 75.817 | 41.189 | 27.773 | 1.00 | 59.95 | SOS |
| ATOM | 149 | CA | ILE | 586 | 75.529 | 40.101 | 28.689 | 1.00 | 58.70 | SOS |

Figure 8-4

```
ATOM    150  CB   ILE   586      74.411  39.162  28.127  1.00  58.57      SOS
ATOM    151  CG2  ILE   586      74.187  37.971  29.042  1.00  59.34      SOS
ATOM    152  CG1  ILE   586      73.086  39.901  28.003  1.00  57.61      SOS
ATOM    153  CD1  ILE   586      71.901  38.983  27.761  1.00  59.39      SOS
ATOM    154  C    ILE   586      76.768  39.251  28.900  1.00  58.71      SOS
ATOM    155  O    ILE   586      77.625  39.149  28.024  1.00  58.57      SOS
ATOM    156  N    ILE   587      76.855  38.661  30.084  1.00  58.34      SOS
ATOM    157  CA   ILE   587      77.940  37.767  30.451  1.00  59.71      SOS
ATOM    158  CB   ILE   587      78.862  38.387  31.513  1.00  61.79      SOS
ATOM    159  CG2  ILE   587      80.029  37.452  31.811  1.00  63.62      SOS
ATOM    160  CG1  ILE   587      79.398  39.728  31.032  1.00  60.78      SOS
ATOM    161  CD1  ILE   587      80.229  40.415  32.071  1.00  67.41      SOS
ATOM    162  C    ILE   587      77.219  36.581  31.073  1.00  59.71      SOS
ATOM    163  O    ILE   587      76.279  36.762  31.847  1.00  60.53      SOS
ATOM    164  N    PHE   588      77.625  35.372  30.716  1.00  60.66      SOS
ATOM    165  CA   PHE   588      76.975  34.192  31.264  1.00  62.04      SOS
ATOM    166  CB   PHE   588      76.554  33.234  30.143  1.00  61.74      SOS
ATOM    167  CG   PHE   588      75.557  33.826  29.184  1.00  62.23      SOS
ATOM    168  CD1  PHE   588      75.981  34.452  28.019  1.00  61.10      SOS
ATOM    169  CD2  PHE   588      74.198  33.794  29.466  1.00  65.02      SOS
ATOM    170  CE1  PHE   588      75.065  35.042  27.151  1.00  62.45      SOS
ATOM    171  CE2  PHE   588      73.272  34.383  28.600  1.00  64.84      SOS
ATOM    172  CZ   PHE   588      73.708  35.007  27.443  1.00  62.30      SOS
ATOM    173  C    PHE   588      77.857  33.483  32.271  1.00  64.51      SOS
ATOM    174  O    PHE   588      79.071  33.685  32.310  1.00  62.57      SOS
ATOM    175  N    GLU   589      77.226  32.675  33.110  1.00  68.76      SOS
ATOM    176  CA   GLU   589      77.935  31.925  34.124  1.00  73.95      SOS
ATOM    177  CB   GLU   589      76.946  31.399  35.164  1.00  75.56      SOS
ATOM    178  CG   GLU   589      77.507  31.326  36.572  1.00  80.54      SOS
ATOM    179  CD   GLU   589      77.942  32.685  37.096  1.00  83.75      SOS
ATOM    180  OE1  GLU   589      77.066  33.548  37.336  1.00  84.48      SOS
ATOM    181  OE2  GLU   589      79.162  32.888  37.269  1.00  86.36      SOS
ATOM    182  C    GLU   589      78.667  30.772  33.443  1.00  77.05      SOS
ATOM    183  O    GLU   589      78.106  30.097  32.578  1.00  76.63      SOS
ATOM    184  N    GLU   590      79.933  30.583  33.811  1.00  82.51      SOS
ATOM    185  CA   GLU   590      80.769  29.519  33.250  1.00  85.84      SOS
ATOM    186  CB   GLU   590      82.249  29.937  33.273  1.00  89.26      SOS
ATOM    187  CG   GLU   590      82.551  31.333  32.695  1.00  93.22      SOS
ATOM    188  CD   GLU   590      82.360  31.440  31.183  1.00  95.89      SOS
ATOM    189  OE1  GLU   590      82.034  30.423  30.529  1.00  98.74      SOS
ATOM    190  OE2  GLU   590      82.549  32.555  30.645  1.00  94.69      SOS
ATOM    191  C    GLU   590      80.597  28.206  34.021  1.00  83.56      SOS
ATOM    192  O    GLU   590      79.973  27.279  33.461  1.00  80.20      SOS
ATOM    193  OT   GLU   590   9999.0009999.0009999.000  1.00   0.00      SOS
ATOM    194  C    GLY   597      70.237  25.098  28.552  1.00  77.87      SOS
ATOM    195  O    GLY   597      71.012  25.599  27.734  1.00  77.86      SOS
ATOM    196  N    GLY   597      69.745  23.230  30.134  1.00  77.12      SOS
ATOM    197  CA   GLY   597      70.199  23.597  28.760  1.00  77.61      SOS
ATOM    198  N    ILE   598      69.396  25.810  29.302  1.00  77.50      SOS
ATOM    199  CA   ILE   598      69.295  27.270  29.237  1.00  75.71      SOS
ATOM    200  CB   ILE   598      68.060  27.772  30.029  1.00  74.77      SOS
ATOM    201  CG2  ILE   598      67.792  29.234  29.721  1.00  70.59      SOS
ATOM    202  CG1  ILE   598      66.825  26.935  29.684  1.00  74.32      SOS
ATOM    203  CD1  ILE   598      65.671  27.122  30.654  1.00  70.94      SOS
ATOM    204  C    ILE   598      70.539  27.928  29.845  1.00  75.15      SOS
ATOM    205  O    ILE   598      71.023  27.500  30.895  1.00  74.88      SOS
ATOM    206  N    PRO   599      71.085  28.963  29.176  1.00  74.88      SOS
ATOM    207  CD   PRO   599      70.711  29.418  27.828  1.00  75.59      SOS
ATOM    208  CA   PRO   599      72.272  29.688  29.646  1.00  74.39      SOS
ATOM    209  CB   PRO   599      72.595  30.618  28.470  1.00  74.55      SOS
ATOM    210  CG   PRO   599      72.027  29.916  27.294  1.00  76.23      SOS
```

Figure 8-5

| ATOM | 211 | C | PRO | 599 | 71.955 | 30.517 | 30.889 | 1.00 | 73.52 | SOS |
|---|---|---|---|---|---|---|---|---|---|---|
| ATOM | 212 | O | PRO | 599 | 70.953 | 31.241 | 30.918 | 1.00 | 74.59 | SOS |
| ATOM | 213 | N | ILE | 600 | 72.796 | 30.407 | 31.914 | 1.00 | 70.47 | SOS |
| ATOM | 214 | CA | ILE | 600 | 72.594 | 31.180 | 33.135 | 1.00 | 68.92 | SOS |
| ATOM | 215 | CB | ILE | 600 | 73.123 | 30.441 | 34.377 | 1.00 | 69.43 | SOS |
| ATOM | 216 | CG2 | ILE | 600 | 72.898 | 31.288 | 35.622 | 1.00 | 70.41 | SOS |
| ATOM | 217 | CG1 | ILE | 600 | 72.403 | 29.100 | 34.544 | 1.00 | 70.54 | SOS |
| ATOM | 218 | CD1 | ILE | 600 | 72.942 | 28.253 | 35.696 | 1.00 | 71.17 | SOS |
| ATOM | 219 | C | ILE | 600 | 73.292 | 32.539 | 33.012 | 1.00 | 66.64 | SOS |
| ATOM | 220 | O | ILE | 600 | 74.493 | 32.607 | 32.749 | 1.00 | 66.39 | SOS |
| ATOM | 221 | N | ILE | 601 | 72.523 | 33.613 | 33.178 | 1.00 | 62.89 | SOS |
| ATOM | 222 | CA | ILE | 601 | 73.051 | 34.974 | 33.086 | 1.00 | 59.56 | SOS |
| ATOM | 223 | CB | ILE | 601 | 71.910 | 35.988 | 32.850 | 1.00 | 58.42 | SOS |
| ATOM | 224 | CG2 | ILE | 601 | 72.459 | 37.401 | 32.700 | 1.00 | 57.84 | SOS |
| ATOM | 225 | CG1 | ILE | 601 | 71.136 | 35.601 | 31.597 | 1.00 | 57.80 | SOS |
| ATOM | 226 | CD1 | ILE | 601 | 70.002 | 36.521 | 31.291 | 1.00 | 60.74 | SOS |
| ATOM | 227 | C | ILE | 601 | 73.829 | 35.379 | 34.341 | 1.00 | 57.16 | SOS |
| ATOM | 228 | O | ILE | 601 | 73.446 | 35.037 | 35.457 | 1.00 | 57.38 | SOS |
| ATOM | 229 | N | LYS | 602 | 74.940 | 36.081 | 34.142 | 1.00 | 55.79 | SOS |
| ATOM | 230 | CA | LYS | 602 | 75.771 | 36.550 | 35.247 | 1.00 | 54.82 | SOS |
| ATOM | 231 | CB | LYS | 602 | 77.251 | 36.336 | 34.927 | 1.00 | 54.39 | SOS |
| ATOM | 232 | CG | LYS | 602 | 78.208 | 36.662 | 36.058 | 1.00 | 56.18 | SOS |
| ATOM | 233 | CD | LYS | 602 | 79.620 | 36.162 | 35.735 | 1.00 | 59.09 | SOS |
| ATOM | 234 | CE | LYS | 602 | 80.577 | 36.319 | 36.916 | 1.00 | 60.43 | SOS |
| ATOM | 235 | NZ | LYS | 602 | 81.786 | 35.452 | 36.774 | 1.00 | 60.26 | SOS |
| ATOM | 236 | C | LYS | 602 | 75.492 | 38.030 | 35.432 | 1.00 | 55.34 | SOS |
| ATOM | 237 | O | LYS | 602 | 75.254 | 38.495 | 36.548 | 1.00 | 57.62 | SOS |
| ATOM | 238 | N | ALA | 603 | 75.479 | 38.757 | 34.320 | 1.00 | 52.61 | SOS |
| ATOM | 239 | CA | ALA | 603 | 75.227 | 40.185 | 34.346 | 1.00 | 51.90 | SOS |
| ATOM | 240 | CB | ALA | 603 | 76.482 | 40.920 | 34.753 | 1.00 | 54.87 | SOS |
| ATOM | 241 | C | ALA | 603 | 74.757 | 40.681 | 32.991 | 1.00 | 53.33 | SOS |
| ATOM | 242 | O | ALA | 603 | 74.864 | 39.969 | 31.992 | 1.00 | 53.54 | SOS |
| ATOM | 243 | N | GLY | 604 | 74.248 | 41.912 | 32.968 | 1.00 | 52.47 | SOS |
| ATOM | 244 | CA | GLY | 604 | 73.774 | 42.508 | 31.734 | 1.00 | 50.13 | SOS |
| ATOM | 245 | C | GLY | 604 | 72.957 | 43.774 | 31.911 | 1.00 | 51.08 | SOS |
| ATOM | 246 | O | GLY | 604 | 72.476 | 44.075 | 33.001 | 1.00 | 50.96 | SOS |
| ATOM | 247 | N | THR | 605 | 72.813 | 44.525 | 30.826 | 1.00 | 52.63 | SOS |
| ATOM | 248 | CA | THR | 605 | 72.033 | 45.759 | 30.814 | 1.00 | 56.20 | SOS |
| ATOM | 249 | CB | THR | 605 | 72.111 | 46.428 | 29.419 | 1.00 | 58.46 | SOS |
| ATOM | 250 | OG1 | THR | 605 | 73.484 | 46.637 | 29.071 | 1.00 | 57.02 | SOS |
| ATOM | 251 | CG2 | THR | 605 | 71.383 | 47.774 | 29.418 | 1.00 | 62.73 | SOS |
| ATOM | 252 | C | THR | 605 | 70.568 | 45.420 | 31.115 | 1.00 | 55.60 | SOS |
| ATOM | 253 | O | THR | 605 | 70.119 | 44.313 | 30.828 | 1.00 | 57.20 | SOS |
| ATOM | 254 | N | VAL | 606 | 69.828 | 46.362 | 31.694 | 1.00 | 54.05 | SOS |
| ATOM | 255 | CA | VAL | 606 | 68.420 | 46.128 | 32.004 | 1.00 | 53.82 | SOS |
| ATOM | 256 | CB | VAL | 606 | 67.764 | 47.386 | 32.650 | 1.00 | 53.58 | SOS |
| ATOM | 257 | CG1 | VAL | 606 | 67.586 | 48.497 | 31.631 | 1.00 | 52.86 | SOS |
| ATOM | 258 | CG2 | VAL | 606 | 66.440 | 47.029 | 33.284 | 1.00 | 56.97 | SOS |
| ATOM | 259 | C | VAL | 606 | 67.688 | 45.742 | 30.715 | 1.00 | 56.74 | SOS |
| ATOM | 260 | O | VAL | 606 | 66.750 | 44.944 | 30.736 | 1.00 | 58.68 | SOS |
| ATOM | 261 | N | ILE | 607 | 68.174 | 46.279 | 29.594 | 1.00 | 59.73 | SOS |
| ATOM | 262 | CA | ILE | 607 | 67.628 | 46.029 | 28.259 | 1.00 | 59.05 | SOS |
| ATOM | 263 | CB | ILE | 607 | 68.363 | 46.893 | 27.197 | 1.00 | 59.32 | SOS |
| ATOM | 264 | CG2 | ILE | 607 | 68.048 | 46.408 | 25.801 | 1.00 | 64.10 | SOS |
| ATOM | 265 | CG1 | ILE | 607 | 67.977 | 48.366 | 27.337 | 1.00 | 60.20 | SOS |
| ATOM | 266 | CD1 | ILE | 607 | 66.511 | 48.643 | 27.094 | 1.00 | 58.35 | SOS |
| ATOM | 267 | C | ILE | 607 | 67.797 | 44.557 | 27.890 | 1.00 | 58.65 | SOS |
| ATOM | 268 | O | ILE | 607 | 66.827 | 43.858 | 27.603 | 1.00 | 58.45 | SOS |
| ATOM | 269 | N | LYS | 608 | 69.044 | 44.103 | 27.904 | 1.00 | 58.82 | SOS |
| ATOM | 270 | CA | LYS | 608 | 69.378 | 42.727 | 27.573 | 1.00 | 59.95 | SOS |
| ATOM | 271 | CB | LYS | 608 | 70.896 | 42.577 | 27.491 | 1.00 | 63.61 | SOS |

Figure 8-6

| ATOM | 272 | CG | LYS | 608 | 71.394 | 42.080 | 26.152 | 1.00 | 66.70 | SOS |
| ATOM | 273 | CD | LYS | 608 | 71.068 | 43.057 | 25.045 | 1.00 | 72.38 | SOS |
| ATOM | 274 | CE | LYS | 608 | 71.564 | 42.528 | 23.716 | 1.00 | 75.93 | SOS |
| ATOM | 275 | NZ | LYS | 608 | 70.881 | 41.270 | 23.316 | 1.00 | 73.78 | SOS |
| ATOM | 276 | C | LYS | 608 | 68.815 | 41.732 | 28.585 | 1.00 | 57.95 | SOS |
| ATOM | 277 | O | LYS | 608 | 68.530 | 40.582 | 28.252 | 1.00 | 58.82 | SOS |
| ATOM | 278 | N | LEU | 609 | 68.666 | 42.185 | 29.823 | 1.00 | 54.88 | SOS |
| ATOM | 279 | CA | LEU | 609 | 68.148 | 41.355 | 30.899 | 1.00 | 51.61 | SOS |
| ATOM | 280 | CB | LEU | 609 | 68.306 | 42.100 | 32.220 | 1.00 | 48.45 | SOS |
| ATOM | 281 | CG | LEU | 609 | 68.975 | 41.392 | 33.389 | 1.00 | 47.60 | SOS |
| ATOM | 282 | CD1 | LEU | 609 | 70.239 | 40.683 | 32.954 | 1.00 | 50.17 | SOS |
| ATOM | 283 | CD2 | LEU | 609 | 69.280 | 42.431 | 34.449 | 1.00 | 50.18 | SOS |
| ATOM | 284 | C | LEU | 609 | 66.681 | 41.049 | 30.627 | 1.00 | 51.87 | SOS |
| ATOM | 285 | O | LEU | 609 | 66.249 | 39.895 | 30.692 | 1.00 | 50.36 | SOS |
| ATOM | 286 | N | ILE | 610 | 65.932 | 42.097 | 30.297 | 1.00 | 52.38 | SOS |
| ATOM | 287 | CA | ILE | 610 | 64.510 | 41.993 | 29.985 | 1.00 | 53.73 | SOS |
| ATOM | 288 | CB | ILE | 610 | 63.866 | 43.394 | 30.002 | 1.00 | 49.31 | SOS |
| ATOM | 289 | CG2 | ILE | 610 | 62.609 | 43.443 | 29.152 | 1.00 | 45.64 | SOS |
| ATOM | 290 | CG1 | ILE | 610 | 63.571 | 43.770 | 31.451 | 1.00 | 47.66 | SOS |
| ATOM | 291 | CD1 | ILE | 610 | 63.205 | 45.206 | 31.650 | 1.00 | 54.78 | SOS |
| ATOM | 292 | C | ILE | 610 | 64.272 | 41.256 | 28.657 | 1.00 | 56.00 | SOS |
| ATOM | 293 | O | ILE | 610 | 63.215 | 40.645 | 28.440 | 1.00 | 54.57 | SOS |
| ATOM | 294 | N | GLU | 611 | 65.272 | 41.300 | 27.783 | 1.00 | 56.27 | SOS |
| ATOM | 295 | CA | GLU | 611 | 65.191 | 40.610 | 26.511 | 1.00 | 56.64 | SOS |
| ATOM | 296 | CB | GLU | 611 | 66.384 | 40.964 | 25.634 | 1.00 | 60.47 | SOS |
| ATOM | 297 | CG | GLU | 611 | 66.454 | 40.193 | 24.331 | 1.00 | 62.70 | SOS |
| ATOM | 298 | CD | GLU | 611 | 67.766 | 40.415 | 23.614 | 1.00 | 68.23 | SOS |
| ATOM | 299 | OE1 | GLU | 611 | 68.154 | 41.594 | 23.452 | 1.00 | 74.10 | SOS |
| ATOM | 300 | OE2 | GLU | 611 | 68.413 | 39.416 | 23.224 | 1.00 | 66.84 | SOS |
| ATOM | 301 | C | GLU | 611 | 65.191 | 39.119 | 26.811 | 1.00 | 56.37 | SOS |
| ATOM | 302 | O | GLU | 611 | 64.317 | 38.402 | 26.340 | 1.00 | 60.82 | SOS |
| ATOM | 303 | N | ARG | 612 | 66.150 | 38.668 | 27.621 | 1.00 | 53.78 | SOS |
| ATOM | 304 | CA | ARG | 612 | 66.262 | 37.253 | 28.000 | 1.00 | 53.05 | SOS |
| ATOM | 305 | CB | ARG | 612 | 67.596 | 36.985 | 28.697 | 1.00 | 52.36 | SOS |
| ATOM | 306 | CG | ARG | 612 | 68.791 | 36.994 | 27.774 | 1.00 | 56.53 | SOS |
| ATOM | 307 | CD | ARG | 612 | 68.726 | 35.850 | 26.780 | 1.00 | 58.02 | SOS |
| ATOM | 308 | NE | ARG | 612 | 69.817 | 35.917 | 25.812 | 1.00 | 64.18 | SOS |
| ATOM | 309 | CZ | ARG | 612 | 70.646 | 34.912 | 25.537 | 1.00 | 64.70 | SOS |
| ATOM | 310 | NH1 | ARG | 612 | 70.514 | 33.745 | 26.154 | 1.00 | 64.70 | SOS |
| ATOM | 311 | NH2 | ARG | 612 | 71.616 | 35.076 | 24.649 | 1.00 | 63.45 | SOS |
| ATOM | 312 | C | ARG | 612 | 65.123 | 36.779 | 28.901 | 1.00 | 52.66 | SOS |
| ATOM | 313 | O | ARG | 612 | 64.907 | 35.578 | 29.068 | 1.00 | 52.34 | SOS |
| ATOM | 314 | N | LEU | 613 | 64.422 | 37.733 | 29.505 | 1.00 | 52.72 | SOS |
| ATOM | 315 | CA | LEU | 613 | 63.302 | 37.445 | 30.387 | 1.00 | 50.31 | SOS |
| ATOM | 316 | CB | LEU | 613 | 63.030 | 38.653 | 31.285 | 1.00 | 51.42 | SOS |
| ATOM | 317 | CG | LEU | 613 | 62.017 | 38.399 | 32.399 | 1.00 | 56.01 | SOS |
| ATOM | 318 | CD1 | LEU | 613 | 62.733 | 37.628 | 33.488 | 1.00 | 58.64 | SOS |
| ATOM | 319 | CD2 | LEU | 613 | 61.418 | 39.692 | 32.948 | 1.00 | 50.95 | SOS |
| ATOM | 320 | C | LEU | 613 | 62.081 | 37.176 | 29.526 | 1.00 | 51.22 | SOS |
| ATOM | 321 | O | LEU | 613 | 61.086 | 36.621 | 29.990 | 1.00 | 53.46 | SOS |
| ATOM | 322 | N | THR | 614 | 62.176 | 37.599 | 28.269 | 1.00 | 54.70 | SOS |
| ATOM | 323 | CA | THR | 614 | 61.120 | 37.466 | 27.268 | 1.00 | 55.39 | SOS |
| ATOM | 324 | CB | THR | 614 | 60.425 | 38.848 | 27.062 | 1.00 | 55.34 | SOS |
| ATOM | 325 | OG1 | THR | 614 | 59.732 | 39.222 | 28.258 | 1.00 | 54.40 | SOS |
| ATOM | 326 | CG2 | THR | 614 | 59.423 | 38.805 | 25.945 | 1.00 | 62.65 | SOS |
| ATOM | 327 | C | THR | 614 | 61.796 | 36.994 | 25.969 | 1.00 | 56.62 | SOS |
| ATOM | 328 | O | THR | 614 | 61.515 | 37.490 | 24.876 | 1.00 | 56.20 | SOS |
| ATOM | 329 | N | TYR | 615 | 62.701 | 36.029 | 26.100 | 1.00 | 56.59 | SOS |
| ATOM | 330 | CA | TYR | 615 | 63.446 | 35.518 | 24.951 | 1.00 | 58.48 | SOS |
| ATOM | 331 | CB | TYR | 615 | 64.594 | 34.634 | 25.431 | 1.00 | 54.44 | SOS |
| ATOM | 332 | CG | TYR | 615 | 65.784 | 34.623 | 24.506 | 1.00 | 47.69 | SOS |

Figure 8-7

| ATOM | 333 | CD1 | TYR | 615 | 66.125 | 35.755 | 23.779 | 1.00 | 48.76 | SOS |
| ATOM | 334 | CE1 | TYR | 615 | 67.230 | 35.767 | 22.942 | 1.00 | 48.97 | SOS |
| ATOM | 335 | CD2 | TYR | 615 | 66.581 | 33.491 | 24.376 | 1.00 | 44.10 | SOS |
| ATOM | 336 | CE2 | TYR | 615 | 67.692 | 33.491 | 23.545 | 1.00 | 46.56 | SOS |
| ATOM | 337 | CZ | TYR | 615 | 68.013 | 34.637 | 22.826 | 1.00 | 48.62 | SOS |
| ATOM | 338 | OH | TYR | 615 | 69.118 | 34.668 | 21.996 | 1.00 | 49.37 | SOS |
| ATOM | 339 | C | TYR | 615 | 62.580 | 34.759 | 23.941 | 1.00 | 63.01 | SOS |
| ATOM | 340 | O | TYR | 615 | 61.722 | 33.954 | 24.319 | 1.00 | 65.13 | SOS |
| ATOM | 341 | N | HIS | 616 | 62.819 | 35.015 | 22.656 | 1.00 | 65.90 | SOS |
| ATOM | 342 | CA | HIS | 616 | 62.060 | 34.364 | 21.588 | 1.00 | 67.88 | SOS |
| ATOM | 343 | CB | HIS | 616 | 62.201 | 35.139 | 20.271 | 1.00 | 67.74 | SOS |
| ATOM | 344 | CG | HIS | 616 | 63.558 | 35.040 | 19.646 | 1.00 | 70.92 | SOS |
| ATOM | 345 | CD2 | HIS | 616 | 64.064 | 34.159 | 18.749 | 1.00 | 72.98 | SOS |
| ATOM | 346 | ND1 | HIS | 616 | 64.574 | 35.928 | 19.924 | 1.00 | 73.67 | SOS |
| ATOM | 347 | CE1 | HIS | 616 | 65.647 | 35.599 | 19.227 | 1.00 | 74.17 | SOS |
| ATOM | 348 | NE2 | HIS | 616 | 65.365 | 34.529 | 18.506 | 1.00 | 72.98 | SOS |
| ATOM | 349 | C | HIS | 616 | 62.454 | 32.899 | 21.388 | 1.00 | 68.65 | SOS |
| ATOM | 350 | O | HIS | 616 | 61.613 | 32.065 | 21.050 | 1.00 | 67.98 | SOS |
| ATOM | 351 | N | MET | 617 | 63.726 | 32.589 | 21.618 | 1.00 | 69.57 | SOS |
| ATOM | 352 | CA | MET | 617 | 64.225 | 31.230 | 21.458 | 1.00 | 72.45 | SOS |
| ATOM | 353 | CB | MET | 617 | 65.737 | 31.187 | 21.676 | 1.00 | 78.56 | SOS |
| ATOM | 354 | CG | MET | 617 | 66.561 | 31.929 | 20.631 | 1.00 | 84.49 | SOS |
| ATOM | 355 | SD | MET | 617 | 66.502 | 31.143 | 19.019 | 1.00 | 91.82 | SOS |
| ATOM | 356 | CE | MET | 617 | 67.449 | 29.636 | 19.356 | 1.00 | 90.00 | SOS |
| ATOM | 357 | C | MET | 617 | 63.548 | 30.243 | 22.403 | 1.00 | 72.82 | SOS |
| ATOM | 358 | O | MET | 617 | 63.036 | 29.213 | 21.964 | 1.00 | 73.55 | SOS |
| ATOM | 359 | N | TYR | 618 | 63.521 | 30.575 | 23.693 | 1.00 | 72.73 | SOS |
| ATOM | 360 | CA | TYR | 618 | 62.920 | 29.706 | 24.710 | 1.00 | 70.75 | SOS |
| ATOM | 361 | CB | TYR | 618 | 63.984 | 28.747 | 25.257 | 1.00 | 71.76 | SOS |
| ATOM | 362 | CG | TYR | 618 | 65.296 | 29.428 | 25.590 | 1.00 | 74.47 | SOS |
| ATOM | 363 | CD1 | TYR | 618 | 65.398 | 30.300 | 26.673 | 1.00 | 75.66 | SOS |
| ATOM | 364 | CE1 | TYR | 618 | 66.588 | 30.970 | 26.950 | 1.00 | 77.18 | SOS |
| ATOM | 365 | CD2 | TYR | 618 | 66.424 | 29.238 | 24.793 | 1.00 | 75.73 | SOS |
| ATOM | 366 | CE2 | TYR | 618 | 67.621 | 29.903 | 25.064 | 1.00 | 75.98 | SOS |
| ATOM | 367 | CZ | TYR | 618 | 67.693 | 30.768 | 26.141 | 1.00 | 76.38 | SOS |
| ATOM | 368 | OH | TYR | 618 | 68.858 | 31.447 | 26.405 | 1.00 | 76.62 | SOS |
| ATOM | 369 | C | TYR | 618 | 62.290 | 30.477 | 25.872 | 1.00 | 68.07 | SOS |
| ATOM | 370 | O | TYR | 618 | 62.465 | 31.690 | 25.997 | 1.00 | 69.55 | SOS |
| ATOM | 371 | N | ALA | 619 | 61.541 | 29.764 | 26.706 | 1.00 | 63.43 | SOS |
| ATOM | 372 | CA | ALA | 619 | 60.907 | 30.359 | 27.879 | 1.00 | 59.10 | SOS |
| ATOM | 373 | CB | ALA | 619 | 59.509 | 29.795 | 28.076 | 1.00 | 57.60 | SOS |
| ATOM | 374 | C | ALA | 619 | 61.788 | 30.028 | 29.078 | 1.00 | 57.74 | SOS |
| ATOM | 375 | O | ALA | 619 | 62.330 | 28.928 | 29.170 | 1.00 | 56.99 | SOS |
| ATOM | 376 | N | ASP | 620 | 61.915 | 30.974 | 30.001 | 1.00 | 56.80 | SOS |
| ATOM | 377 | CA | ASP | 620 | 62.756 | 30.788 | 31.178 | 1.00 | 53.95 | SOS |
| ATOM | 378 | CB | ASP | 620 | 63.952 | 31.742 | 31.081 | 1.00 | 52.93 | SOS |
| ATOM | 379 | CG | ASP | 620 | 65.210 | 31.190 | 31.725 | 1.00 | 54.68 | SOS |
| ATOM | 380 | OD1 | ASP | 620 | 65.121 | 30.330 | 32.637 | 1.00 | 54.91 | SOS |
| ATOM | 381 | OD2 | ASP | 620 | 66.302 | 31.636 | 31.309 | 1.00 | 52.57 | SOS |
| ATOM | 382 | C | ASP | 620 | 61.966 | 31.075 | 32.455 | 1.00 | 53.26 | SOS |
| ATOM | 383 | O | ASP | 620 | 62.189 | 32.097 | 33.106 | 1.00 | 50.46 | SOS |
| ATOM | 384 | N | PRO | 621 | 61.051 | 30.163 | 32.844 | 1.00 | 52.73 | SOS |
| ATOM | 385 | CD | PRO | 621 | 60.755 | 28.871 | 32.203 | 1.00 | 52.92 | SOS |
| ATOM | 386 | CA | PRO | 621 | 60.229 | 30.331 | 34.049 | 1.00 | 53.44 | SOS |
| ATOM | 387 | CB | PRO | 621 | 59.383 | 29.049 | 34.080 | 1.00 | 50.66 | SOS |
| ATOM | 388 | CG | PRO | 621 | 60.221 | 28.062 | 33.360 | 1.00 | 51.48 | SOS |
| ATOM | 389 | C | PRO | 621 | 61.004 | 30.547 | 35.346 | 1.00 | 53.02 | SOS |
| ATOM | 390 | O | PRO | 621 | 60.503 | 31.212 | 36.249 | 1.00 | 54.53 | SOS |
| ATOM | 391 | N | ASN | 622 | 62.212 | 29.989 | 35.438 | 1.00 | 54.69 | SOS |
| ATOM | 392 | CA | ASN | 622 | 63.046 | 30.153 | 36.634 | 1.00 | 56.97 | SOS |
| ATOM | 393 | CB | ASN | 622 | 64.146 | 29.085 | 36.707 | 1.00 | 61.77 | SOS |

Figure 8-8

| | | | | | | | | | |
|---|---|---|---|---|---|---|---|---|---|
| ATOM | 394 | CG | ASN | 622 | 63.622 | 27.730 | 37.169 | 1.00 65.08 | SOS |
| ATOM | 395 | OD1 | ASN | 622 | 62.787 | 27.643 | 38.076 | 1.00 67.33 | SOS |
| ATOM | 396 | ND2 | ASN | 622 | 64.119 | 26.666 | 36.551 | 1.00 65.16 | SOS |
| ATOM | 397 | C | ASN | 622 | 63.668 | 31.543 | 36.690 | 1.00 54.75 | SOS |
| ATOM | 398 | O | ASN | 622 | 63.757 | 32.145 | 37.758 | 1.00 56.52 | SOS |
| ATOM | 399 | N | PHE | 623 | 64.103 | 32.042 | 35.538 | 1.00 51.80 | SOS |
| ATOM | 400 | CA | PHE | 623 | 64.691 | 33.373 | 35.450 | 1.00 52.20 | SOS |
| ATOM | 401 | CB | PHE | 623 | 65.337 | 33.577 | 34.076 | 1.00 51.65 | SOS |
| ATOM | 402 | CG | PHE | 623 | 65.909 | 34.949 | 33.862 | 1.00 51.14 | SOS |
| ATOM | 403 | CD1 | PHE | 623 | 66.804 | 35.500 | 34.771 | 1.00 53.96 | SOS |
| ATOM | 404 | CD2 | PHE | 623 | 65.562 | 35.685 | 32.740 | 1.00 51.74 | SOS |
| ATOM | 405 | CE1 | PHE | 623 | 67.345 | 36.767 | 34.565 | 1.00 54.74 | SOS |
| ATOM | 406 | CE2 | PHE | 623 | 66.097 | 36.952 | 32.526 | 1.00 57.11 | SOS |
| ATOM | 407 | CZ | PHE | 623 | 66.992 | 37.494 | 33.442 | 1.00 57.00 | SOS |
| ATOM | 408 | C | PHE | 623 | 63.617 | 34.434 | 35.694 | 1.00 51.45 | SOS |
| ATOM | 409 | O | PHE | 623 | 63.916 | 35.519 | 36.179 | 1.00 53.28 | SOS |
| ATOM | 410 | N | VAL | 624 | 62.373 | 34.114 | 35.345 | 1.00 49.90 | SOS |
| ATOM | 411 | CA | VAL | 624 | 61.249 | 35.026 | 35.539 | 1.00 49.19 | SOS |
| ATOM | 412 | CB | VAL | 624 | 60.022 | 34.600 | 34.695 | 1.00 46.07 | SOS |
| ATOM | 413 | CG1 | VAL | 624 | 58.781 | 35.375 | 35.121 | 1.00 41.56 | SOS |
| ATOM | 414 | CG2 | VAL | 624 | 60.300 | 34.845 | 33.226 | 1.00 44.77 | SOS |
| ATOM | 415 | C | VAL | 624 | 60.857 | 35.088 | 37.012 | 1.00 51.47 | SOS |
| ATOM | 416 | O | VAL | 624 | 60.441 | 36.138 | 37.503 | 1.00 52.12 | SOS |
| ATOM | 417 | N | ARG | 625 | 60.993 | 33.959 | 37.704 | 1.00 52.41 | SOS |
| ATOM | 418 | CA | ARG | 625 | 60.669 | 33.864 | 39.124 | 1.00 53.68 | SOS |
| ATOM | 419 | CB | ARG | 625 | 60.598 | 32.390 | 39.557 | 1.00 58.06 | SOS |
| ATOM | 420 | CG | ARG | 625 | 60.669 | 32.166 | 41.071 | 1.00 66.44 | SOS |
| ATOM | 421 | CD | ARG | 625 | 60.760 | 30.690 | 41.443 | 1.00 70.49 | SOS |
| ATOM | 422 | NE | ARG | 625 | 59.444 | 30.052 | 41.470 | 1.00 78.23 | SOS |
| ATOM | 423 | CZ | ARG | 625 | 59.140 | 28.979 | 42.198 | 1.00 78.52 | SOS |
| ATOM | 424 | NH1 | ARG | 625 | 60.059 | 28.408 | 42.968 | 1.00 75.68 | SOS |
| ATOM | 425 | NH2 | ARG | 625 | 57.909 | 28.483 | 42.169 | 1.00 79.21 | SOS |
| ATOM | 426 | C | ARG | 625 | 61.705 | 34.612 | 39.960 | 1.00 51.61 | SOS |
| ATOM | 427 | O | ARG | 625 | 61.367 | 35.258 | 40.950 | 1.00 56.36 | SOS |
| ATOM | 428 | N | THR | 626 | 62.961 | 34.526 | 39.543 | 1.00 47.43 | SOS |
| ATOM | 429 | CA | THR | 626 | 64.065 | 35.171 | 40.238 | 1.00 45.43 | SOS |
| ATOM | 430 | CB | THR | 626 | 65.408 | 34.528 | 39.824 | 1.00 46.74 | SOS |
| ATOM | 431 | OG1 | THR | 626 | 65.436 | 33.161 | 40.258 | 1.00 47.56 | SOS |
| ATOM | 432 | CG2 | THR | 626 | 66.579 | 35.267 | 40.432 | 1.00 45.03 | SOS |
| ATOM | 433 | C | THR | 626 | 64.099 | 36.678 | 39.991 | 1.00 44.73 | SOS |
| ATOM | 434 | O | THR | 626 | 64.309 | 37.460 | 40.919 | 1.00 49.40 | SOS |
| ATOM | 435 | N | PHE | 627 | 63.871 | 37.080 | 38.746 | 1.00 41.86 | SOS |
| ATOM | 436 | CA | PHE | 627 | 63.867 | 38.490 | 38.361 | 1.00 39.24 | SOS |
| ATOM | 437 | CB | PHE | 627 | 63.716 | 38.608 | 36.843 | 1.00 36.03 | SOS |
| ATOM | 438 | CG | PHE | 627 | 63.779 | 40.017 | 36.316 | 1.00 34.05 | SOS |
| ATOM | 439 | CD1 | PHE | 627 | 64.971 | 40.530 | 35.808 | 1.00 34.02 | SOS |
| ATOM | 440 | CD2 | PHE | 627 | 62.640 | 40.819 | 36.284 | 1.00 29.53 | SOS |
| ATOM | 441 | CE1 | PHE | 627 | 65.024 | 41.816 | 35.278 | 1.00 31.53 | SOS |
| ATOM | 442 | CE2 | PHE | 627 | 62.684 | 42.107 | 35.754 | 1.00 30.19 | SOS |
| ATOM | 443 | CZ | PHE | 627 | 63.876 | 42.605 | 35.252 | 1.00 31.38 | SOS |
| ATOM | 444 | C | PHE | 627 | 62.746 | 39.262 | 39.051 | 1.00 40.68 | SOS |
| ATOM | 445 | O | PHE | 627 | 62.967 | 40.357 | 39.550 | 1.00 43.71 | SOS |
| ATOM | 446 | N | LEU | 628 | 61.544 | 38.700 | 39.089 | 1.00 39.71 | SOS |
| ATOM | 447 | CA | LEU | 628 | 60.437 | 39.403 | 39.718 | 1.00 41.19 | SOS |
| ATOM | 448 | CB | LEU | 628 | 59.089 | 38.839 | 39.261 | 1.00 38.77 | SOS |
| ATOM | 449 | CG | LEU | 628 | 58.684 | 39.181 | 37.819 | 1.00 35.69 | SOS |
| ATOM | 450 | CD1 | LEU | 628 | 57.415 | 38.447 | 37.450 | 1.00 39.36 | SOS |
| ATOM | 451 | CD2 | LEU | 628 | 58.482 | 40.668 | 37.655 | 1.00 31.48 | SOS |
| ATOM | 452 | C | LEU | 628 | 60.534 | 39.436 | 41.233 | 1.00 43.83 | SOS |
| ATOM | 453 | O | LEU | 628 | 59.767 | 40.134 | 41.897 | 1.00 47.08 | SOS |
| ATOM | 454 | N | THR | 629 | 61.494 | 38.701 | 41.779 | 1.00 42.92 | SOS |

Figure 8-9

```
ATOM    455  CA   THR   629      61.691  38.669  43.221  1.00  43.73      SOS
ATOM    456  CB   THR   629      62.046  37.237  43.711  1.00  44.20      SOS
ATOM    457  OG1  THR   629      60.879  36.413  43.680  1.00  46.48      SOS
ATOM    458  CG2  THR   629      62.584  37.252  45.132  1.00  45.85      SOS
ATOM    459  C    THR   629      62.801  39.625  43.649  1.00  44.11      SOS
ATOM    460  O    THR   629      62.761  40.168  44.752  1.00  45.21      SOS
ATOM    461  N    THR   630      63.738  39.900  42.747  1.00  40.08      SOS
ATOM    462  CA   THR   630      64.872  40.740  43.095  1.00  40.13      SOS
ATOM    463  CB   THR   630      66.140  39.880  43.111  1.00  39.82      SOS
ATOM    464  OG1  THR   630      66.402  39.429  41.780  1.00  39.36      SOS
ATOM    465  CG2  THR   630      65.968  38.659  44.008  1.00  37.31      SOS
ATOM    466  C    THR   630      65.193  41.962  42.233  1.00  41.28      SOS
ATOM    467  O    THR   630      66.227  42.587  42.435  1.00  47.95      SOS
ATOM    468  N    TYR   631      64.320  42.329  41.304  1.00  43.44      SOS
ATOM    469  CA   TYR   631      64.581  43.457  40.400  1.00  42.86      SOS
ATOM    470  CB   TYR   631      63.635  43.387  39.201  1.00  40.59      SOS
ATOM    471  CG   TYR   631      62.279  44.006  39.464  1.00  40.71      SOS
ATOM    472  CD1  TYR   631      62.025  45.335  39.113  1.00  40.09      SOS
ATOM    473  CE1  TYR   631      60.804  45.926  39.374  1.00  37.78      SOS
ATOM    474  CD2  TYR   631      61.261  43.279  40.084  1.00  37.57      SOS
ATOM    475  CE2  TYR   631      60.029  43.866  40.344  1.00  37.78      SOS
ATOM    476  CZ   TYR   631      59.812  45.189  39.987  1.00  37.58      SOS
ATOM    477  OH   TYR   631      58.606  45.788  40.238  1.00  40.33      SOS
ATOM    478  C    TYR   631      64.541  44.883  40.964  1.00  44.96      SOS
ATOM    479  O    TYR   631      65.202  45.786  40.436  1.00  45.58      SOS
ATOM    480  N    ARG   632      63.735  45.092  41.998  1.00  43.98      SOS
ATOM    481  CA   ARG   632      63.564  46.410  42.597  1.00  43.53      SOS
ATOM    482  CB   ARG   632      62.519  46.330  43.706  1.00  39.29      SOS
ATOM    483  CG   ARG   632      61.202  45.755  43.224  1.00  39.34      SOS
ATOM    484  CD   ARG   632      60.322  45.296  44.364  1.00  38.22      SOS
ATOM    485  NE   ARG   632      59.163  44.541  43.896  1.00  33.46      SOS
ATOM    486  CZ   ARG   632      59.207  43.271  43.492  1.00  32.49      SOS
ATOM    487  NH1  ARG   632      60.353  42.603  43.490  1.00  26.44      SOS
ATOM    488  NH2  ARG   632      58.095  42.655  43.117  1.00  27.38      SOS
ATOM    489  C    ARG   632      64.846  47.076  43.092  1.00  45.88      SOS
ATOM    490  O    ARG   632      64.842  48.262  43.421  1.00  47.71      SOS
ATOM    491  N    SER   633      65.943  46.324  43.111  1.00  47.84      SOS
ATOM    492  CA   SER   633      67.233  46.853  43.554  1.00  50.15      SOS
ATOM    493  CB   SER   633      68.050  45.780  44.296  1.00  50.62      SOS
ATOM    494  OG   SER   633      68.441  44.713  43.449  1.00  51.12      SOS
ATOM    495  C    SER   633      68.058  47.446  42.412  1.00  50.55      SOS
ATOM    496  O    SER   633      69.088  48.070  42.652  1.00  52.49      SOS
ATOM    497  N    PHE   634      67.619  47.235  41.172  1.00  48.98      SOS
ATOM    498  CA   PHE   634      68.329  47.769  40.016  1.00  46.61      SOS
ATOM    499  CB   PHE   634      69.235  46.700  39.385  1.00  46.79      SOS
ATOM    500  CG   PHE   634      68.501  45.496  38.854  1.00  46.33      SOS
ATOM    501  CD1  PHE   634      67.780  45.564  37.664  1.00  45.17      SOS
ATOM    502  CD2  PHE   634      68.545  44.289  39.536  1.00  42.62      SOS
ATOM    503  CE1  PHE   634      67.118  44.451  37.169  1.00  43.98      SOS
ATOM    504  CE2  PHE   634      67.885  43.170  39.045  1.00  41.64      SOS
ATOM    505  CZ   PHE   634      67.170  43.252  37.859  1.00  42.71      SOS
ATOM    506  C    PHE   634      67.378  48.369  38.980  1.00  46.82      SOS
ATOM    507  O    PHE   634      67.807  48.887  37.947  1.00  45.98      SOS
ATOM    508  N    CYS   635      66.085  48.315  39.282  1.00  46.36      SOS
ATOM    509  CA   CYS   635      65.052  48.844  38.400  1.00  44.82      SOS
ATOM    510  CB   CYS   635      64.725  47.821  37.302  1.00  48.67      SOS
ATOM    511  SG   CYS   635      63.444  48.312  36.122  1.00  51.68      SOS
ATOM    512  C    CYS   635      63.816  49.122  39.239  1.00  41.98      SOS
ATOM    513  O    CYS   635      63.499  48.358  40.153  1.00  42.11      SOS
ATOM    514  N    LYS   636      63.142  50.232  38.952  1.00  41.36      SOS
ATOM    515  CA   LYS   636      61.931  50.608  39.682  1.00  44.77      SOS
```

Figure 8-10

| ATOM | 516 | CB | LYS | 636 | 61.806 | 52.135 | 39.743 | 1.00 | 43.56 | SOS |
| ATOM | 517 | CG | LYS | 636 | 62.954 | 52.824 | 40.464 | 0.00 | 44.19 | SOS |
| ATOM | 518 | CD | LYS | 636 | 62.774 | 54.331 | 40.474 | 0.00 | 44.08 | SOS |
| ATOM | 519 | CE | LYS | 636 | 63.930 | 55.019 | 41.181 | 0.00 | 44.09 | SOS |
| ATOM | 520 | NZ | LYS | 636 | 63.769 | 56.498 | 41.197 | 0.00 | 44.13 | SOS |
| ATOM | 521 | C | LYS | 636 | 60.712 | 49.989 | 38.991 | 1.00 | 46.44 | SOS |
| ATOM | 522 | O | LYS | 636 | 60.692 | 49.869 | 37.767 | 1.00 | 48.88 | SOS |
| ATOM | 523 | N | PRO | 637 | 59.693 | 49.565 | 39.766 | 1.00 | 48.32 | SOS |
| ATOM | 524 | CD | PRO | 637 | 59.595 | 49.623 | 41.237 | 1.00 | 48.62 | SOS |
| ATOM | 525 | CA | PRO | 637 | 58.484 | 48.955 | 39.191 | 1.00 | 46.75 | SOS |
| ATOM | 526 | CB | PRO | 637 | 57.504 | 48.966 | 40.367 | 1.00 | 45.79 | SOS |
| ATOM | 527 | CG | PRO | 637 | 58.399 | 48.714 | 41.529 | 1.00 | 46.54 | SOS |
| ATOM | 528 | C | PRO | 637 | 57.934 | 49.704 | 37.980 | 1.00 | 44.93 | SOS |
| ATOM | 529 | O | PRO | 637 | 57.622 | 49.090 | 36.962 | 1.00 | 46.38 | SOS |
| ATOM | 530 | N | GLN | 638 | 57.861 | 51.029 | 38.075 | 1.00 | 43.64 | SOS |
| ATOM | 531 | CA | GLN | 638 | 57.360 | 51.848 | 36.974 | 1.00 | 45.35 | SOS |
| ATOM | 532 | CB | GLN | 638 | 57.272 | 53.310 | 37.394 | 1.00 | 41.07 | SOS |
| ATOM | 533 | CG | GLN | 638 | 56.103 | 53.612 | 38.296 | 1.00 | 41.15 | SOS |
| ATOM | 534 | CD | GLN | 638 | 54.792 | 53.607 | 37.555 | 1.00 | 42.11 | SOS |
| ATOM | 535 | OE1 | GLN | 638 | 54.761 | 53.669 | 36.326 | 1.00 | 44.62 | SOS |
| ATOM | 536 | NE2 | GLN | 638 | 53.694 | 53.554 | 38.297 | 1.00 | 42.46 | SOS |
| ATOM | 537 | C | GLN | 638 | 58.218 | 51.732 | 35.716 | 1.00 | 49.14 | SOS |
| ATOM | 538 | O | GLN | 638 | 57.691 | 51.710 | 34.601 | 1.00 | 49.56 | SOS |
| ATOM | 539 | N | GLU | 639 | 59.535 | 51.670 | 35.900 | 1.00 | 49.51 | SOS |
| ATOM | 540 | CA | GLU | 639 | 60.471 | 51.554 | 34.786 | 1.00 | 52.59 | SOS |
| ATOM | 541 | CB | GLU | 639 | 61.901 | 51.781 | 35.277 | 1.00 | 57.12 | SOS |
| ATOM | 542 | CG | GLU | 639 | 62.092 | 53.094 | 36.033 | 1.00 | 63.21 | SOS |
| ATOM | 543 | CD | GLU | 639 | 63.496 | 53.257 | 36.615 | 1.00 | 67.11 | SOS |
| ATOM | 544 | OE1 | GLU | 639 | 64.204 | 52.237 | 36.807 | 1.00 | 65.53 | SOS |
| ATOM | 545 | OE2 | GLU | 639 | 63.884 | 54.416 | 36.888 | 1.00 | 64.00 | SOS |
| ATOM | 546 | C | GLU | 639 | 60.370 | 50.181 | 34.127 | 1.00 | 52.40 | SOS |
| ATOM | 547 | O | GLU | 639 | 60.561 | 50.049 | 32.914 | 1.00 | 49.09 | SOS |
| ATOM | 548 | N | LEU | 640 | 60.072 | 49.169 | 34.944 | 1.00 | 52.64 | SOS |
| ATOM | 549 | CA | LEU | 640 | 59.938 | 47.788 | 34.485 | 1.00 | 49.13 | SOS |
| ATOM | 550 | CB | LEU | 640 | 59.733 | 46.844 | 35.671 | 1.00 | 42.05 | SOS |
| ATOM | 551 | CG | LEU | 640 | 60.098 | 45.358 | 35.551 | 1.00 | 38.52 | SOS |
| ATOM | 552 | CD1 | LEU | 640 | 59.033 | 44.534 | 36.219 | 1.00 | 31.35 | SOS |
| ATOM | 553 | CD2 | LEU | 640 | 60.274 | 44.915 | 34.123 | 1.00 | 38.01 | SOS |
| ATOM | 554 | C | LEU | 640 | 58.744 | 47.669 | 33.558 | 1.00 | 51.47 | SOS |
| ATOM | 555 | O | LEU | 640 | 58.842 | 47.056 | 32.501 | 1.00 | 54.80 | SOS |
| ATOM | 556 | N | LEU | 641 | 57.611 | 48.232 | 33.969 | 1.00 | 51.66 | SOS |
| ATOM | 557 | CA | LEU | 641 | 56.406 | 48.172 | 33.157 | 1.00 | 52.31 | SOS |
| ATOM | 558 | CB | LEU | 641 | 55.224 | 48.803 | 33.893 | 1.00 | 51.03 | SOS |
| ATOM | 559 | CG | LEU | 641 | 53.860 | 48.693 | 33.205 | 1.00 | 49.43 | SOS |
| ATOM | 560 | CD1 | LEU | 641 | 53.619 | 47.268 | 32.730 | 1.00 | 48.19 | SOS |
| ATOM | 561 | CD2 | LEU | 641 | 52.763 | 49.125 | 34.159 | 1.00 | 48.61 | SOS |
| ATOM | 562 | C | LEU | 641 | 56.639 | 48.864 | 31.824 | 1.00 | 54.50 | SOS |
| ATOM | 563 | O | LEU | 641 | 56.204 | 48.371 | 30.785 | 1.00 | 58.19 | SOS |
| ATOM | 564 | N | SER | 642 | 57.362 | 49.982 | 31.858 | 1.00 | 55.38 | SOS |
| ATOM | 565 | CA | SER | 642 | 57.676 | 50.742 | 30.651 | 1.00 | 55.92 | SOS |
| ATOM | 566 | CB | SER | 642 | 58.341 | 52.079 | 31.002 | 1.00 | 52.50 | SOS |
| ATOM | 567 | OG | SER | 642 | 57.407 | 52.993 | 31.560 | 1.00 | 48.33 | SOS |
| ATOM | 568 | C | SER | 642 | 58.570 | 49.937 | 29.708 | 1.00 | 57.93 | SOS |
| ATOM | 569 | O | SER | 642 | 58.352 | 49.927 | 28.495 | 1.00 | 63.27 | SOS |
| ATOM | 570 | N | LEU | 643 | 59.565 | 49.255 | 30.270 | 1.00 | 55.90 | SOS |
| ATOM | 571 | CA | LEU | 643 | 60.476 | 48.435 | 29.477 | 1.00 | 55.05 | SOS |
| ATOM | 572 | CB | LEU | 643 | 61.648 | 47.966 | 30.339 | 1.00 | 50.64 | SOS |
| ATOM | 573 | CG | LEU | 643 | 62.634 | 49.080 | 30.683 | 1.00 | 53.66 | SOS |
| ATOM | 574 | CD1 | LEU | 643 | 63.521 | 48.676 | 31.843 | 1.00 | 55.32 | SOS |
| ATOM | 575 | CD2 | LEU | 643 | 63.460 | 49.424 | 29.459 | 1.00 | 51.36 | SOS |
| ATOM | 576 | C | LEU | 643 | 59.744 | 47.239 | 28.868 | 1.00 | 55.37 | SOS |

Figure 8-11

```
ATOM    577  O    LEU  643      60.020  46.846  27.730  1.00  55.39       SOS
ATOM    578  N    ILE  644      58.808  46.678  29.633  1.00  54.04       SOS
ATOM    579  CA   ILE  644      58.008  45.536  29.201  1.00  53.16       SOS
ATOM    580  CB   ILE  644      57.150  44.990  30.366  1.00  53.75       SOS
ATOM    581  CG2  ILE  644      55.808  44.490  29.890  1.00  51.47       SOS
ATOM    582  CG1  ILE  644      57.896  43.870  31.075  1.00  56.44       SOS
ATOM    583  CD1  ILE  644      57.082  43.239  32.169  1.00  61.06       SOS
ATOM    584  C    ILE  644      57.119  45.952  28.041  1.00  53.99       SOS
ATOM    585  O    ILE  644      56.979  45.211  27.069  1.00  54.20       SOS
ATOM    586  N    ILE  645      56.523  47.138  28.155  1.00  51.93       SOS
ATOM    587  CA   ILE  645      55.662  47.671  27.108  1.00  50.99       SOS
ATOM    588  CB   ILE  645      54.909  48.931  27.582  1.00  49.18       SOS
ATOM    589  CG2  ILE  645      54.193  49.601  26.409  1.00  44.13       SOS
ATOM    590  CG1  ILE  645      53.928  48.549  28.696  1.00  42.90       SOS
ATOM    591  CD1  ILE  645      53.021  49.660  29.140  1.00  38.51       SOS
ATOM    592  C    ILE  645      56.500  47.974  25.867  1.00  53.50       SOS
ATOM    593  O    ILE  645      56.079  47.684  24.746  1.00  53.68       SOS
ATOM    594  N    GLU  646      57.701  48.517  26.073  1.00  55.37       SOS
ATOM    595  CA   GLU  646      58.603  48.816  24.962  1.00  58.37       SOS
ATOM    596  CB   GLU  646      59.831  49.607  25.430  1.00  61.55       SOS
ATOM    597  CG   GLU  646      60.742  50.075  24.282  1.00  64.68       SOS
ATOM    598  CD   GLU  646      62.073  50.678  24.743  1.00  69.95       SOS
ATOM    599  OE1  GLU  646      63.029  50.672  23.934  1.00  70.54       SOS
ATOM    600  OE2  GLU  646      62.169  51.161  25.897  1.00  68.67       SOS
ATOM    601  C    GLU  646      59.054  47.516  24.293  1.00  58.61       SOS
ATOM    602  O    GLU  646      59.388  47.522  23.114  1.00  60.61       SOS
ATOM    603  N    ARG  647      59.065  46.413  25.046  1.00  58.85       SOS
ATOM    604  CA   ARG  647      59.457  45.104  24.511  1.00  59.23       SOS
ATOM    605  CB   ARG  647      59.861  44.136  25.632  1.00  56.11       SOS
ATOM    606  CG   ARG  647      60.350  42.780  25.114  1.00  55.13       SOS
ATOM    607  CD   ARG  647      61.560  42.991  24.212  1.00  58.92       SOS
ATOM    608  NE   ARG  647      61.916  41.875  23.331  1.00  55.07       SOS
ATOM    609  CZ   ARG  647      62.348  40.688  23.740  1.00  56.18       SOS
ATOM    610  NH1  ARG  647      62.459  40.422  25.036  1.00  60.08       SOS
ATOM    611  NH2  ARG  647      62.777  39.804  22.849  1.00  52.88       SOS
ATOM    612  C    ARG  647      58.332  44.463  23.697  1.00  60.88       SOS
ATOM    613  O    ARG  647      58.587  43.727  22.741  1.00  59.41       SOS
ATOM    614  N    PHE  648      57.094  44.749  24.089  1.00  61.79       SOS
ATOM    615  CA   PHE  648      55.909  44.203  23.435  1.00  63.84       SOS
ATOM    616  CB   PHE  648      54.689  44.427  24.329  1.00  61.12       SOS
ATOM    617  CG   PHE  648      53.449  43.729  23.857  1.00  61.25       SOS
ATOM    618  CD1  PHE  648      53.228  42.392  24.169  1.00  60.29       SOS
ATOM    619  CD2  PHE  648      52.476  44.418  23.139  1.00  63.20       SOS
ATOM    620  CE1  PHE  648      52.056  41.749  23.777  1.00  58.75       SOS
ATOM    621  CE2  PHE  648      51.297  43.782  22.741  1.00  61.54       SOS
ATOM    622  CZ   PHE  648      51.088  42.445  23.063  1.00  61.11       SOS
ATOM    623  C    PHE  648      55.661  44.823  22.065  1.00  66.88       SOS
ATOM    624  O    PHE  648      55.420  44.110  21.083  1.00  66.03       SOS
ATOM    625  N    GLU  649      55.712  46.153  22.017  1.00  68.68       SOS
ATOM    626  CA   GLU  649      55.479  46.917  20.794  1.00  67.82       SOS
ATOM    627  CB   GLU  649      55.180  48.370  21.151  1.00  66.02       SOS
ATOM    628  CG   GLU  649      53.966  48.500  22.060  1.00  69.00       SOS
ATOM    629  CD   GLU  649      53.696  49.920  22.516  1.00  69.98       SOS
ATOM    630  OE1  GLU  649      54.589  50.787  22.371  1.00  68.73       SOS
ATOM    631  OE2  GLU  649      52.583  50.163  23.033  1.00  70.74       SOS
ATOM    632  C    GLU  649      56.634  46.819  19.803  1.00  68.63       SOS
ATOM    633  O    GLU  649      57.412  47.760  19.624  1.00  67.46       SOS
ATOM    634  N    ILE  650      56.695  45.670  19.136  1.00  70.26       SOS
ATOM    635  CA   ILE  650      57.729  45.362  18.158  1.00  71.86       SOS
ATOM    636  CB   ILE  650      57.962  43.836  18.072  1.00  68.39       SOS
ATOM    637  CG2  ILE  650      59.217  43.545  17.289  1.00  65.63       SOS
```

Figure 8-12

| | | | | | | | | | |
|---|---|---|---|---|---|---|---|---|---|
| ATOM | 638 | CG1 | ILE | 650 | 58.087 | 43.241 | 19.472 | 1.00 68.75 | SOS |
| ATOM | 639 | CD1 | ILE | 650 | 58.156 | 41.737 | 19.495 | 1.00 70.35 | SOS |
| ATOM | 640 | C | ILE | 650 | 57.377 | 45.861 | 16.759 | 1.00 75.52 | SOS |
| ATOM | 641 | O | ILE | 650 | 56.288 | 45.593 | 16.249 | 1.00 74.42 | SOS |
| ATOM | 642 | N | PRO | 651 | 58.280 | 46.640 | 16.143 | 1.00 79.66 | SOS |
| ATOM | 643 | CD | PRO | 651 | 59.389 | 47.339 | 16.808 | 1.00 81.47 | SOS |
| ATOM | 644 | CA | PRO | 651 | 58.078 | 47.181 | 14.796 | 1.00 82.25 | SOS |
| ATOM | 645 | CB | PRO | 651 | 58.938 | 48.453 | 14.800 | 1.00 81.29 | SOS |
| ATOM | 646 | CG | PRO | 651 | 59.220 | 48.721 | 16.264 | 1.00 84.16 | SOS |
| ATOM | 647 | C | PRO | 651 | 58.611 | 46.187 | 13.759 | 1.00 85.37 | SOS |
| ATOM | 648 | O | PRO | 651 | 59.611 | 45.505 | 14.006 | 1.00 85.34 | SOS |
| ATOM | 649 | N | GLU | 652 | 57.938 | 46.100 | 12.611 | 1.00 87.40 | SOS |
| ATOM | 650 | CA | GLU | 652 | 58.354 | 45.202 | 11.530 | 1.00 88.17 | SOS |
| ATOM | 651 | CB | GLU | 652 | 57.156 | 44.857 | 10.639 | 1.00 89.30 | SOS |
| ATOM | 652 | CG | GLU | 652 | 55.981 | 44.252 | 11.400 | 1.00 92.43 | SOS |
| ATOM | 653 | CD | GLU | 652 | 54.732 | 44.088 | 10.545 | 1.00 94.97 | SOS |
| ATOM | 654 | OE1 | GLU | 652 | 54.367 | 45.039 | 9.817 | 1.00 95.56 | SOS |
| ATOM | 655 | OE2 | GLU | 652 | 54.105 | 43.008 | 10.613 | 1.00 93.73 | SOS |
| ATOM | 656 | C | GLU | 652 | 59.459 | 45.878 | 10.707 | 1.00 86.89 | SOS |
| ATOM | 657 | O | GLU | 652 | 59.498 | 47.105 | 10.601 | 1.00 85.50 | SOS |
| ATOM | 658 | N | PRO | 653 | 60.386 | 45.086 | 10.138 | 1.00 86.96 | SOS |
| ATOM | 659 | CD | PRO | 653 | 60.507 | 43.629 | 10.306 | 1.00 86.11 | SOS |
| ATOM | 660 | CA | PRO | 653 | 61.499 | 45.601 | 9.327 | 1.00 87.88 | SOS |
| ATOM | 661 | CB | PRO | 653 | 62.327 | 44.341 | 9.044 | 1.00 87.11 | SOS |
| ATOM | 662 | CG | PRO | 653 | 61.989 | 43.435 | 10.187 | 1.00 85.53 | SOS |
| ATOM | 663 | C | PRO | 653 | 61.044 | 46.270 | 8.025 | 1.00 88.52 | SOS |
| ATOM | 664 | O | PRO | 653 | 61.835 | 47.069 | 7.475 | 1.00 87.36 | SOS |
| ATOM | 665 | OT | PRO | 653 | 9999.000 | 9999.000 | 9999.000 | 1.00 0.00 | SOS |
| ATOM | 666 | CB | ARG | 676 | 58.381 | 38.321 | 6.648 | 1.00 93.22 | SOS |
| ATOM | 667 | CG | ARG | 676 | 59.077 | 39.268 | 7.619 | 0.00 93.71 | SOS |
| ATOM | 668 | CD | ARG | 676 | 60.333 | 39.866 | 7.004 | 0.00 93.59 | SOS |
| ATOM | 669 | NE | ARG | 676 | 60.048 | 40.625 | 5.787 | 0.00 93.64 | SOS |
| ATOM | 670 | CZ | ARG | 676 | 60.612 | 40.392 | 4.606 | 0.00 93.63 | SOS |
| ATOM | 671 | NH1 | ARG | 676 | 61.501 | 39.416 | 4.468 | 0.00 93.63 | SOS |
| ATOM | 672 | NH2 | ARG | 676 | 60.284 | 41.133 | 3.557 | 0.00 93.63 | SOS |
| ATOM | 673 | C | ARG | 676 | 57.423 | 36.520 | 8.142 | 1.00 95.86 | SOS |
| ATOM | 674 | O | ARG | 676 | 56.518 | 35.842 | 8.637 | 1.00 96.59 | SOS |
| ATOM | 675 | N | ARG | 676 | 56.230 | 38.689 | 7.839 | 1.00 92.19 | SOS |
| ATOM | 676 | CA | ARG | 676 | 57.097 | 37.667 | 7.185 | 1.00 94.55 | SOS |
| ATOM | 677 | N | PHE | 677 | 58.714 | 36.305 | 8.390 | 1.00 97.03 | SOS |
| ATOM | 678 | CA | PHE | 677 | 59.190 | 35.255 | 9.290 | 1.00 97.70 | SOS |
| ATOM | 679 | CB | PHE | 677 | 60.695 | 35.043 | 9.058 | 1.00 100.65 | SOS |
| ATOM | 680 | CG | PHE | 677 | 61.238 | 33.737 | 9.597 | 1.00 102.75 | SOS |
| ATOM | 681 | CD1 | PHE | 677 | 60.388 | 32.694 | 9.960 | 1.00 104.17 | SOS |
| ATOM | 682 | CD2 | PHE | 677 | 62.615 | 33.554 | 9.730 | 1.00 103.01 | SOS |
| ATOM | 683 | CE1 | PHE | 677 | 60.902 | 31.491 | 10.450 | 1.00 105.09 | SOS |
| ATOM | 684 | CE2 | PHE | 677 | 63.138 | 32.356 | 10.218 | 1.00 103.49 | SOS |
| ATOM | 685 | CZ | PHE | 677 | 62.280 | 31.323 | 10.579 | 1.00 105.45 | SOS |
| ATOM | 686 | C | PHE | 677 | 58.922 | 35.665 | 10.748 | 1.00 97.70 | SOS |
| ATOM | 687 | O | PHE | 677 | 59.220 | 34.916 | 11.682 | 1.00 97.24 | SOS |
| ATOM | 688 | N | ARG | 678 | 58.346 | 36.855 | 10.926 | 1.00 96.95 | SOS |
| ATOM | 689 | CA | ARG | 678 | 58.020 | 37.394 | 12.246 | 1.00 94.54 | SOS |
| ATOM | 690 | CB | ARG | 678 | 57.927 | 38.916 | 12.184 | 1.00 95.28 | SOS |
| ATOM | 691 | CG | ARG | 678 | 59.120 | 39.566 | 11.498 | 1.00 98.88 | SOS |
| ATOM | 692 | CD | ARG | 678 | 60.433 | 39.231 | 12.191 | 1.00 99.01 | SOS |
| ATOM | 693 | NE | ARG | 678 | 60.486 | 39.775 | 13.546 | 1.00 103.15 | SOS |
| ATOM | 694 | CZ | ARG | 678 | 60.590 | 41.068 | 13.840 | 1.00 103.50 | SOS |
| ATOM | 695 | NH1 | ARG | 678 | 60.656 | 41.977 | 12.878 | 1.00 105.48 | SOS |
| ATOM | 696 | NH2 | ARG | 678 | 60.620 | 41.456 | 15.105 | 1.00 106.10 | SOS |
| ATOM | 697 | C | ARG | 678 | 56.731 | 36.793 | 12.811 | 1.00 93.37 | SOS |
| ATOM | 698 | O | ARG | 678 | 55.705 | 37.466 | 12.967 | 1.00 90.34 | SOS |

Figure 8-13

```
ATOM    699  N    LYS   679      56.807  35.489  13.048  1.00 92.67      sos
ATOM    700  CA   LYS   679      55.743  34.667  13.613  1.00 90.06      sos
ATOM    701  CB   LYS   679      55.075  33.826  12.524  1.00 91.87      sos
ATOM    702  CG   LYS   679      54.395  34.654  11.442  0.00 91.21      sos
ATOM    703  CD   LYS   679      53.771  33.784  10.367  0.00 91.41      sos
ATOM    704  CE   LYS   679      53.111  34.637   9.295  0.00 91.36      sos
ATOM    705  NZ   LYS   679      52.486  33.812   8.226  0.00 91.44      sos
ATOM    706  C    LYS   679      56.486  33.768  14.602  1.00 88.90      sos
ATOM    707  O    LYS   679      55.892  33.151  15.486  1.00 88.37      sos
ATOM    708  N    GLU   680      57.800  33.686  14.403  1.00 86.31      sos
ATOM    709  CA   GLU   680      58.694  32.931  15.265  1.00 83.50      sos
ATOM    710  CB   GLU   680      59.602  32.015  14.439  1.00 82.46      sos
ATOM    711  CG   GLU   680      58.875  30.818  13.837  0.00 82.91      sos
ATOM    712  CD   GLU   680      59.813  29.811  13.195  0.00 82.88      sos
ATOM    713  OE1  GLU   680      60.942  29.627  13.699  0.00 82.95      sos
ATOM    714  OE2  GLU   680      59.415  29.194  12.185  0.00 82.95      sos
ATOM    715  C    GLU   680      59.515  33.936  16.098  1.00 81.22      sos
ATOM    716  O    GLU   680      60.522  33.583  16.720  1.00 78.99      sos
ATOM    717  N    TYR   681      59.067  35.194  16.091  1.00 77.80      sos
ATOM    718  CA   TYR   681      59.702  36.265  16.855  1.00 73.84      sos
ATOM    719  CB   TYR   681      60.643  37.112  15.995  1.00 68.85      sos
ATOM    720  CG   TYR   681      61.480  38.058  16.833  1.00 65.12      sos
ATOM    721  CD1  TYR   681      62.711  37.652  17.348  1.00 62.90      sos
ATOM    722  CE1  TYR   681      63.463  38.489  18.162  1.00 59.90      sos
ATOM    723  CD2  TYR   681      61.023  39.340  17.156  1.00 63.21      sos
ATOM    724  CE2  TYR   681      61.773  40.189  17.974  1.00 58.57      sos
ATOM    725  CZ   TYR   681      62.990  39.753  18.471  1.00 59.86      sos
ATOM    726  OH   TYR   681      63.743  40.567  19.281  1.00 61.11      sos
ATOM    727  C    TYR   681      58.668  37.177  17.519  1.00 72.32      sos
ATOM    728  O    TYR   681      58.703  37.376  18.727  1.00 73.16      sos
ATOM    729  N    ILE   682      57.758  37.740  16.735  1.00 70.57      sos
ATOM    730  CA   ILE   682      56.741  38.624  17.290  1.00 68.56      sos
ATOM    731  CB   ILE   682      56.053  39.459  16.187  1.00 66.12      sos
ATOM    732  CG2  ILE   682      54.848  40.196  16.746  1.00 64.84      sos
ATOM    733  CG1  ILE   682      57.053  40.451  15.586  1.00 63.60      sos
ATOM    734  CD1  ILE   682      56.444  41.411  14.591  1.00 63.42      sos
ATOM    735  C    ILE   682      55.694  37.880  18.119  1.00 69.59      sos
ATOM    736  O    ILE   682      55.278  38.356  19.173  1.00 70.79      sos
ATOM    737  N    GLN   683      55.275  36.709  17.651  1.00 71.87      sos
ATOM    738  CA   GLN   683      54.272  35.927  18.372  1.00 71.88      sos
ATOM    739  CB   GLN   683      53.724  34.778  17.500  1.00 75.52      sos
ATOM    740  CG   GLN   683      52.681  35.193  16.444  1.00 80.29      sos
ATOM    741  CD   GLN   683      51.296  35.457  17.037  1.00 84.71      sos
ATOM    742  OE1  GLN   683      50.379  34.639  16.899  1.00 86.08      sos
ATOM    743  NE2  GLN   683      51.141  36.602  17.695  1.00 83.82      sos
ATOM    744  C    GLN   683      54.785  35.412  19.719  1.00 67.10      sos
ATOM    745  O    GLN   683      54.093  35.536  20.731  1.00 68.22      sos
ATOM    746  N    PRO   684      55.995  34.822  19.752  1.00 62.55      sos
ATOM    747  CD   PRO   684      56.822  34.347  18.630  1.00 61.86      sos
ATOM    748  CA   PRO   684      56.523  34.319  21.025  1.00 62.04      sos
ATOM    749  CB   PRO   684      57.651  33.380  20.587  1.00 60.29      sos
ATOM    750  CG   PRO   684      58.106  33.961  19.316  1.00 60.42      sos
ATOM    751  C    PRO   684      57.005  35.392  22.007  1.00 60.47      sos
ATOM    752  O    PRO   684      56.863  35.218  23.213  1.00 61.56      sos
ATOM    753  N    VAL   685      57.568  36.490  21.504  1.00 57.77      sos
ATOM    754  CA   VAL   685      58.040  37.558  22.381  1.00 56.29      sos
ATOM    755  CB   VAL   685      58.846  38.636  21.619  1.00 54.97      sos
ATOM    756  CG1  VAL   685      59.052  39.869  22.489  1.00 50.52      sos
ATOM    757  CG2  VAL   685      60.200  38.077  21.222  1.00 54.54      sos
ATOM    758  C    VAL   685      56.869  38.199  23.109  1.00 57.74      sos
ATOM    759  O    VAL   685      56.925  38.408  24.320  1.00 59.80      sos
```

Figure 8-14

```
ATOM    760  N    GLN  686     55.803  38.497  22.374  1.00  58.30      SOS
ATOM    761  CA   GLN  686     54.615  39.090  22.973  1.00  59.82      SOS
ATOM    762  CB   GLN  686     53.570  39.393  21.900  1.00  64.80      SOS
ATOM    763  CG   GLN  686     53.950  40.506  20.932  1.00  68.63      SOS
ATOM    764  CD   GLN  686     52.805  40.877  20.001  1.00  72.17      SOS
ATOM    765  OE1  GLN  686     51.631  40.686  20.330  1.00  74.46      SOS
ATOM    766  NE2  GLN  686     53.142  41.418  18.837  1.00  71.83      SOS
ATOM    767  C    GLN  686     54.024  38.133  24.011  1.00  59.90      SOS
ATOM    768  O    GLN  686     53.440  38.562  25.006  1.00  61.22      SOS
ATOM    769  N    LEU  687     54.202  36.836  23.776  1.00  59.03      SOS
ATOM    770  CA   LEU  687     53.702  35.804  24.671  1.00  60.70      SOS
ATOM    771  CB   LEU  687     53.884  34.421  24.042  1.00  68.03      SOS
ATOM    772  CG   LEU  687     53.274  33.244  24.811  1.00  73.44      SOS
ATOM    773  CD1  LEU  687     51.768  33.226  24.571  1.00  74.75      SOS
ATOM    774  CD2  LEU  687     53.903  31.925  24.361  1.00  75.66      SOS
ATOM    775  C    LEU  687     54.435  35.843  26.004  1.00  58.91      SOS
ATOM    776  O    LEU  687     53.810  35.866  27.061  1.00  59.54      SOS
ATOM    777  N    ARG  688     55.763  35.831  25.942  1.00  57.08      SOS
ATOM    778  CA   ARG  688     56.596  35.863  27.139  1.00  56.04      SOS
ATOM    779  CB   ARG  688     58.080  35.795  26.767  1.00  59.69      SOS
ATOM    780  CG   ARG  688     58.468  34.745  25.739  1.00  61.07      SOS
ATOM    781  CD   ARG  688     58.569  33.352  26.317  1.00  64.17      SOS
ATOM    782  NE   ARG  688     59.243  32.466  25.371  1.00  69.25      SOS
ATOM    783  CZ   ARG  688     58.677  31.418  24.774  1.00  73.71      SOS
ATOM    784  NH1  ARG  688     57.408  31.099  25.025  1.00  71.90      SOS
ATOM    785  NH2  ARG  688     59.378  30.702  23.902  1.00  71.93      SOS
ATOM    786  C    ARG  688     56.334  37.142  27.944  1.00  53.20      SOS
ATOM    787  O    ARG  688     56.300  37.109  29.171  1.00  53.12      SOS
ATOM    788  N    VAL  689     56.160  38.266  27.251  1.00  48.26      SOS
ATOM    789  CA   VAL  689     55.889  39.537  27.916  1.00  46.29      SOS
ATOM    790  CB   VAL  689     55.672  40.690  26.897  1.00  44.08      SOS
ATOM    791  CG1  VAL  689     55.065  41.911  27.581  1.00  31.99      SOS
ATOM    792  CG2  VAL  689     56.986  41.069  26.243  1.00  43.08      SOS
ATOM    793  C    VAL  689     54.637  39.411  28.774  1.00  46.39      SOS
ATOM    794  O    VAL  689     54.618  39.835  29.926  1.00  48.84      SOS
ATOM    795  N    LEU  690     53.598  38.817  28.206  1.00  45.19      SOS
ATOM    796  CA   LEU  690     52.341  38.648  28.915  1.00  45.65      SOS
ATOM    797  CB   LEU  690     51.226  38.361  27.910  1.00  45.57      SOS
ATOM    798  CG   LEU  690     50.939  39.600  27.050  1.00  47.07      SOS
ATOM    799  CD1  LEU  690     50.273  39.235  25.743  1.00  45.45      SOS
ATOM    800  CD2  LEU  690     50.084  40.587  27.843  1.00  47.89      SOS
ATOM    801  C    LEU  690     52.395  37.616  30.050  1.00  46.47      SOS
ATOM    802  O    LEU  690     51.652  37.732  31.029  1.00  44.77      SOS
ATOM    803  N    ASN  691     53.284  36.627  29.933  1.00  45.71      SOS
ATOM    804  CA   ASN  691     53.444  35.619  30.983  1.00  49.13      SOS
ATOM    805  CB   ASN  691     54.195  34.386  30.479  1.00  52.53      SOS
ATOM    806  CG   ASN  691     53.259  33.340  29.891  1.00  59.93      SOS
ATOM    807  OD1  ASN  691     52.092  33.236  30.292  1.00  58.21      SOS
ATOM    808  ND2  ASN  691     53.763  32.562  28.928  1.00  59.64      SOS
ATOM    809  C    ASN  691     54.175  36.221  32.175  1.00  48.89      SOS
ATOM    810  O    ASN  691     54.036  35.751  33.303  1.00  50.51      SOS
ATOM    811  N    VAL  692     54.964  37.258  31.903  1.00  46.73      SOS
ATOM    812  CA   VAL  692     55.705  37.983  32.928  1.00  41.82      SOS
ATOM    813  CB   VAL  692     56.821  38.868  32.298  1.00  35.77      SOS
ATOM    814  CG1  VAL  692     57.197  39.988  33.228  1.00  33.35      SOS
ATOM    815  CG2  VAL  692     58.052  38.020  31.992  1.00  30.24      SOS
ATOM    816  C    VAL  692     54.696  38.850  33.681  1.00  43.49      SOS
ATOM    817  O    VAL  692     54.693  38.886  34.911  1.00  47.09      SOS
ATOM    818  N    CYS  693     53.822  39.520  32.933  1.00  41.83      SOS
ATOM    819  CA   CYS  693     52.796  40.367  33.522  1.00  40.66      SOS
ATOM    820  CB   CYS  693     51.916  41.005  32.432  1.00  41.17      SOS
```

Figure 8-15

```
ATOM    821  SG   CYS   693      52.735  42.151  31.247  1.00  44.94           SOS
ATOM    822  C    CYS   693      51.937  39.515  34.456  1.00  43.49           SOS
ATOM    823  O    CYS   693      51.617  39.937  35.563  1.00  43.89           SOS
ATOM    824  N    ARG   694      51.590  38.305  34.018  1.00  47.17           SOS
ATOM    825  CA   ARG   694      50.766  37.394  34.820  1.00  48.90           SOS
ATOM    826  CB   ARG   694      50.453  36.116  34.033  1.00  50.18           SOS
ATOM    827  CG   ARG   694      49.702  35.058  34.844  1.00  52.82           SOS
ATOM    828  CD   ARG   694      49.649  33.715  34.124  1.00  59.50           SOS
ATOM    829  NE   ARG   694      48.873  33.786  32.886  1.00  65.07           SOS
ATOM    830  CZ   ARG   694      49.115  33.059  31.799  1.00  67.24           SOS
ATOM    831  NH1  ARG   694      50.116  32.186  31.786  1.00  72.05           SOS
ATOM    832  NH2  ARG   694      48.373  33.229  30.712  1.00  68.20           SOS
ATOM    833  C    ARG   694      51.452  37.019  36.135  1.00  47.46           SOS
ATOM    834  O    ARG   694      50.841  37.066  37.204  1.00  44.74           SOS
ATOM    835  N    HIS   695      52.723  36.639  36.031  1.00  46.55           SOS
ATOM    836  CA   HIS   695      53.544  36.240  37.173  1.00  45.44           SOS
ATOM    837  CB   HIS   695      54.918  35.803  36.654  1.00  45.78           SOS
ATOM    838  CG   HIS   695      55.705  34.966  37.612  1.00  49.77           SOS
ATOM    839  CD2  HIS   695      56.366  33.799  37.434  1.00  51.55           SOS
ATOM    840  ND1  HIS   695      55.912  35.324  38.927  1.00  53.47           SOS
ATOM    841  CE1  HIS   695      56.669  34.416  39.516  1.00  50.51           SOS
ATOM    842  NE2  HIS   695      56.957  33.480  38.632  1.00  52.27           SOS
ATOM    843  C    HIS   695      53.689  37.417  38.148  1.00  44.09           SOS
ATOM    844  O    HIS   695      53.648  37.243  39.363  1.00  45.13           SOS
ATOM    845  N    TRP   696      53.844  38.613  37.594  1.00  40.28           SOS
ATOM    846  CA   TRP   696      53.994  39.830  38.370  1.00  39.12           SOS
ATOM    847  CB   TRP   696      54.240  40.997  37.412  1.00  42.76           SOS
ATOM    848  CG   TRP   696      54.702  42.288  38.037  1.00  46.66           SOS
ATOM    849  CD2  TRP   696      55.109  43.471  37.339  1.00  44.88           SOS
ATOM    850  CE2  TRP   696      55.469  44.429  38.312  1.00  45.81           SOS
ATOM    851  CE3  TRP   696      55.205  43.815  35.984  1.00  44.24           SOS
ATOM    852  CD1  TRP   696      54.827  42.569  39.371  1.00  47.84           SOS
ATOM    853  NE1  TRP   696      55.287  43.852  39.542  1.00  49.26           SOS
ATOM    854  CZ2  TRP   696      55.919  45.709  37.974  1.00  45.03           SOS
ATOM    855  CZ3  TRP   696      55.653  45.092  35.646  1.00  45.61           SOS
ATOM    856  CH2  TRP   696      56.005  46.022  36.639  1.00  47.75           SOS
ATOM    857  C    TRP   696      52.739  40.079  39.198  1.00  37.78           SOS
ATOM    858  O    TRP   696      52.798  40.207  40.415  1.00  41.13           SOS
ATOM    859  N    VAL   697      51.597  40.108  38.532  1.00  37.38           SOS
ATOM    860  CA   VAL   697      50.323  40.355  39.191  1.00  39.69           SOS
ATOM    861  CB   VAL   697      49.223  40.568  38.143  1.00  40.31           SOS
ATOM    862  CG1  VAL   697      47.918  40.884  38.814  1.00  42.37           SOS
ATOM    863  CG2  VAL   697      49.615  41.701  37.211  1.00  41.66           SOS
ATOM    864  C    VAL   697      49.902  39.244  40.153  1.00  39.53           SOS
ATOM    865  O    VAL   697      49.224  39.494  41.150  1.00  34.79           SOS
ATOM    866  N    GLU   698      50.333  38.024  39.859  1.00  41.97           SOS
ATOM    867  CA   GLU   698      49.993  36.862  40.670  1.00  46.79           SOS
ATOM    868  CB   GLU   698      50.133  35.587  39.818  1.00  51.41           SOS
ATOM    869  CG   GLU   698      49.754  34.282  40.512  1.00  55.99           SOS
ATOM    870  CD   GLU   698      48.261  34.151  40.766  1.00  60.96           SOS
ATOM    871  OE1  GLU   698      47.822  34.445  41.897  1.00  62.22           SOS
ATOM    872  OE2  GLU   698      47.525  33.736  39.843  1.00  65.34           SOS
ATOM    873  C    GLU   698      50.818  36.729  41.954  1.00  47.14           SOS
ATOM    874  O    GLU   698      50.262  36.666  43.048  1.00  48.55           SOS
ATOM    875  N    HIS   699      52.140  36.713  41.814  1.00  47.82           SOS
ATOM    876  CA   HIS   699      53.046  36.547  42.949  1.00  46.95           SOS
ATOM    877  CB   HIS   699      54.187  35.608  42.557  1.00  47.42           SOS
ATOM    878  CG   HIS   699      53.721  34.286  42.042  1.00  47.76           SOS
ATOM    879  CD2  HIS   699      53.895  33.684  40.842  1.00  45.49           SOS
ATOM    880  ND1  HIS   699      52.944  33.430  42.791  1.00  49.64           SOS
ATOM    881  CE1  HIS   699      52.658  32.358  42.074  1.00  46.66           SOS
```

Figure 8-16

| | | | | | | | | | | |
|---|---|---|---|---|---|---|---|---|---|---|
| ATOM | 882 | NE2 | HIS | 699 | 53.224 | 32.487 | 40.888 | 1.00 | 44.42 | SOS |
| ATOM | 883 | C | HIS | 699 | 53.627 | 37.809 | 43.585 | 1.00 | 45.43 | SOS |
| ATOM | 884 | O | HIS | 699 | 54.258 | 37.729 | 44.645 | 1.00 | 45.22 | SOS |
| ATOM | 885 | N | HIS | 700 | 53.434 | 38.964 | 42.957 | 1.00 | 39.42 | SOS |
| ATOM | 886 | CA | HIS | 700 | 53.978 | 40.198 | 43.512 | 1.00 | 35.64 | SOS |
| ATOM | 887 | CB | HIS | 700 | 55.272 | 40.564 | 42.783 | 1.00 | 31.36 | SOS |
| ATOM | 888 | CG | HIS | 700 | 56.323 | 39.505 | 42.872 | 1.00 | 35.18 | SOS |
| ATOM | 889 | CD2 | HIS | 700 | 56.690 | 38.539 | 41.999 | 1.00 | 36.14 | SOS |
| ATOM | 890 | ND1 | HIS | 700 | 57.083 | 39.307 | 44.005 | 1.00 | 38.78 | SOS |
| ATOM | 891 | CE1 | HIS | 700 | 57.868 | 38.260 | 43.828 | 1.00 | 37.18 | SOS |
| ATOM | 892 | NE2 | HIS | 700 | 57.649 | 37.776 | 42.619 | 1.00 | 35.62 | SOS |
| ATOM | 893 | C | HIS | 700 | 52.990 | 41.348 | 43.459 | 1.00 | 33.92 | SOS |
| ATOM | 894 | O | HIS | 700 | 53.359 | 42.479 | 43.180 | 1.00 | 39.51 | SOS |
| ATOM | 895 | N | PHE | 701 | 51.746 | 41.079 | 43.823 | 1.00 | 34.30 | SOS |
| ATOM | 896 | CA | PHE | 701 | 50.730 | 42.115 | 43.769 | 1.00 | 36.50 | SOS |
| ATOM | 897 | CB | PHE | 701 | 49.327 | 41.554 | 44.030 | 1.00 | 33.99 | SOS |
| ATOM | 898 | CG | PHE | 701 | 48.228 | 42.427 | 43.488 | 1.00 | 37.18 | SOS |
| ATOM | 899 | CD1 | PHE | 701 | 48.064 | 42.584 | 42.113 | 1.00 | 39.62 | SOS |
| ATOM | 900 | CD2 | PHE | 701 | 47.380 | 43.122 | 44.343 | 1.00 | 36.70 | SOS |
| ATOM | 901 | CE1 | PHE | 701 | 47.068 | 43.425 | 41.598 | 1.00 | 39.69 | SOS |
| ATOM | 902 | CE2 | PHE | 701 | 46.386 | 43.963 | 43.839 | 1.00 | 37.32 | SOS |
| ATOM | 903 | CZ | PHE | 701 | 46.230 | 44.115 | 42.464 | 1.00 | 35.48 | SOS |
| ATOM | 904 | C | PHE | 701 | 50.990 | 43.310 | 44.667 | 1.00 | 37.12 | SOS |
| ATOM | 905 | O | PHE | 701 | 50.419 | 44.376 | 44.442 | 1.00 | 38.71 | SOS |
| ATOM | 906 | N | TYR | 702 | 51.860 | 43.148 | 45.664 | 1.00 | 39.49 | SOS |
| ATOM | 907 | CA | TYR | 702 | 52.174 | 44.249 | 46.581 | 1.00 | 37.66 | SOS |
| ATOM | 908 | CB | TYR | 702 | 53.163 | 43.820 | 47.678 | 1.00 | 33.03 | SOS |
| ATOM | 909 | CG | TYR | 702 | 54.454 | 43.206 | 47.180 | 1.00 | 32.53 | SOS |
| ATOM | 910 | CD1 | TYR | 702 | 55.537 | 44.001 | 46.807 | 1.00 | 34.09 | SOS |
| ATOM | 911 | CE1 | TYR | 702 | 56.723 | 43.432 | 46.346 | 1.00 | 33.30 | SOS |
| ATOM | 912 | CD2 | TYR | 702 | 54.590 | 41.827 | 47.082 | 1.00 | 30.53 | SOS |
| ATOM | 913 | CE2 | TYR | 702 | 55.764 | 41.251 | 46.625 | 1.00 | 30.66 | SOS |
| ATOM | 914 | CZ | TYR | 702 | 56.826 | 42.054 | 46.257 | 1.00 | 32.87 | SOS |
| ATOM | 915 | OH | TYR | 702 | 57.984 | 41.464 | 45.796 | 1.00 | 36.91 | SOS |
| ATOM | 916 | C | TYR | 702 | 52.684 | 45.478 | 45.824 | 1.00 | 37.46 | SOS |
| ATOM | 917 | O | TYR | 702 | 52.456 | 46.610 | 46.253 | 1.00 | 37.07 | SOS |
| ATOM | 918 | N | ASP | 703 | 53.321 | 45.250 | 44.676 | 1.00 | 34.07 | SOS |
| ATOM | 919 | CA | ASP | 703 | 53.819 | 46.344 | 43.852 | 1.00 | 35.59 | SOS |
| ATOM | 920 | CB | ASP | 703 | 54.550 | 45.811 | 42.625 | 1.00 | 32.96 | SOS |
| ATOM | 921 | CG | ASP | 703 | 56.018 | 45.555 | 42.870 | 1.00 | 33.99 | SOS |
| ATOM | 922 | OD1 | ASP | 703 | 56.523 | 45.740 | 44.002 | 1.00 | 35.44 | SOS |
| ATOM | 923 | OD2 | ASP | 703 | 56.679 | 45.162 | 41.897 | 1.00 | 32.69 | SOS |
| ATOM | 924 | C | ASP | 703 | 52.667 | 47.218 | 43.379 | 1.00 | 38.33 | SOS |
| ATOM | 925 | O | ASP | 703 | 52.817 | 48.434 | 43.266 | 1.00 | 40.68 | SOS |
| ATOM | 926 | N | PHE | 704 | 51.521 | 46.591 | 43.110 | 1.00 | 37.68 | SOS |
| ATOM | 927 | CA | PHE | 704 | 50.333 | 47.299 | 42.629 | 1.00 | 38.03 | SOS |
| ATOM | 928 | CB | PHE | 704 | 49.510 | 46.397 | 41.696 | 1.00 | 34.72 | SOS |
| ATOM | 929 | CG | PHE | 704 | 50.283 | 45.902 | 40.509 | 1.00 | 32.27 | SOS |
| ATOM | 930 | CD1 | PHE | 704 | 50.928 | 44.674 | 40.548 | 1.00 | 33.00 | SOS |
| ATOM | 931 | CD2 | PHE | 704 | 50.430 | 46.694 | 39.385 | 1.00 | 30.60 | SOS |
| ATOM | 932 | CE1 | PHE | 704 | 51.717 | 44.245 | 39.486 | 1.00 | 33.28 | SOS |
| ATOM | 933 | CE2 | PHE | 704 | 51.211 | 46.277 | 38.322 | 1.00 | 33.01 | SOS |
| ATOM | 934 | CZ | PHE | 704 | 51.862 | 45.046 | 38.371 | 1.00 | 34.67 | SOS |
| ATOM | 935 | C | PHE | 704 | 49.454 | 47.861 | 43.741 | 1.00 | 40.94 | SOS |
| ATOM | 936 | O | PHE | 704 | 48.684 | 48.796 | 43.510 | 1.00 | 45.42 | SOS |
| ATOM | 937 | N | GLU | 705 | 49.543 | 47.282 | 44.937 | 1.00 | 42.08 | SOS |
| ATOM | 938 | CA | GLU | 705 | 48.754 | 47.759 | 46.070 | 1.00 | 42.65 | SOS |
| ATOM | 939 | CB | GLU | 705 | 48.749 | 46.731 | 47.201 | 1.00 | 44.94 | SOS |
| ATOM | 940 | CG | GLU | 705 | 48.308 | 45.337 | 46.790 | 1.00 | 54.57 | SOS |
| ATOM | 941 | CD | GLU | 705 | 48.372 | 44.322 | 47.935 | 1.00 | 60.40 | SOS |
| ATOM | 942 | OE1 | GLU | 705 | 49.436 | 44.217 | 48.592 | 1.00 | 59.20 | SOS |

Figure 8-17

| | | | | | | | | | |
|---|---|---|---|---|---|---|---|---|---|
| ATOM | 943 | OE2 | GLU | 705 | 47.357 | 43.624 | 48.168 | 1.00 57.35 | SOS |
| ATOM | 944 | C | GLU | 705 | 49.392 | 49.045 | 46.572 | 1.00 41.53 | SOS |
| ATOM | 945 | O | GLU | 705 | 48.715 | 49.925 | 47.112 | 1.00 38.46 | SOS |
| ATOM | 946 | N | ARG | 706 | 50.697 | 49.153 | 46.337 | 1.00 40.41 | SOS |
| ATOM | 947 | CA | ARG | 706 | 51.488 | 50.297 | 46.769 | 1.00 42.57 | SOS |
| ATOM | 948 | CB | ARG | 706 | 52.899 | 49.827 | 47.139 | 1.00 39.45 | SOS |
| ATOM | 949 | CG | ARG | 706 | 52.895 | 48.790 | 48.261 | 1.00 38.88 | SOS |
| ATOM | 950 | CD | ARG | 706 | 54.275 | 48.268 | 48.610 | 1.00 35.98 | SOS |
| ATOM | 951 | NE | ARG | 706 | 54.179 | 47.139 | 49.536 | 1.00 38.10 | SOS |
| ATOM | 952 | CZ | ARG | 706 | 55.222 | 46.541 | 50.105 | 1.00 34.18 | SOS |
| ATOM | 953 | NH1 | ARG | 706 | 56.450 | 46.973 | 49.855 | 1.00 31.53 | SOS |
| ATOM | 954 | NH2 | ARG | 706 | 55.038 | 45.474 | 50.877 | 1.00 24.47 | SOS |
| ATOM | 955 | C | ARG | 706 | 51.548 | 51.463 | 45.787 | 1.00 43.28 | SOS |
| ATOM | 956 | O | ARG | 706 | 51.980 | 52.553 | 46.150 | 1.00 47.69 | SOS |
| ATOM | 957 | N | ASP | 707 | 51.117 | 51.240 | 44.551 | 1.00 41.42 | SOS |
| ATOM | 958 | CA | ASP | 707 | 51.132 | 52.291 | 43.541 | 1.00 42.49 | SOS |
| ATOM | 959 | CB | ASP | 707 | 52.447 | 52.249 | 42.749 | 1.00 42.39 | SOS |
| ATOM | 960 | CG | ASP | 707 | 52.600 | 53.421 | 41.778 | 1.00 43.12 | SOS |
| ATOM | 961 | OD1 | ASP | 707 | 51.662 | 54.238 | 41.631 | 1.00 46.34 | SOS |
| ATOM | 962 | OD2 | ASP | 707 | 53.678 | 53.525 | 41.158 | 1.00 40.90 | SOS |
| ATOM | 963 | C | ASP | 707 | 49.942 | 52.141 | 42.605 | 1.00 45.28 | SOS |
| ATOM | 964 | O | ASP | 707 | 50.014 | 51.432 | 41.602 | 1.00 45.83 | SOS |
| ATOM | 965 | N | ALA | 708 | 48.865 | 52.854 | 42.921 | 1.00 48.09 | SOS |
| ATOM | 966 | CA | ALA | 708 | 47.637 | 52.817 | 42.134 | 1.00 50.52 | SOS |
| ATOM | 967 | CB | ALA | 708 | 46.633 | 53.821 | 42.678 | 1.00 50.89 | SOS |
| ATOM | 968 | C | ALA | 708 | 47.872 | 53.067 | 40.651 | 1.00 51.13 | SOS |
| ATOM | 969 | O | ALA | 708 | 47.281 | 52.399 | 39.802 | 1.00 54.41 | SOS |
| ATOM | 970 | N | TYR | 709 | 48.746 | 54.017 | 40.339 | 1.00 51.70 | SOS |
| ATOM | 971 | CA | TYR | 709 | 49.036 | 54.332 | 38.945 | 1.00 53.36 | SOS |
| ATOM | 972 | CB | TYR | 709 | 49.859 | 55.623 | 38.833 | 1.00 51.81 | SOS |
| ATOM | 973 | CG | TYR | 709 | 50.159 | 56.060 | 37.413 | 1.00 51.56 | SOS |
| ATOM | 974 | CD1 | TYR | 709 | 49.137 | 56.222 | 36.469 | 1.00 53.37 | SOS |
| ATOM | 975 | CE1 | TYR | 709 | 49.425 | 56.631 | 35.155 | 1.00 50.88 | SOS |
| ATOM | 976 | CD2 | TYR | 709 | 51.468 | 56.320 | 37.013 | 1.00 50.88 | SOS |
| ATOM | 977 | CE2 | TYR | 709 | 51.761 | 56.732 | 35.714 | 1.00 50.20 | SOS |
| ATOM | 978 | CZ | TYR | 709 | 50.742 | 56.883 | 34.795 | 1.00 50.03 | SOS |
| ATOM | 979 | OH | TYR | 709 | 51.062 | 57.281 | 33.525 | 1.00 48.29 | SOS |
| ATOM | 980 | C | TYR | 709 | 49.732 | 53.168 | 38.238 | 1.00 52.53 | SOS |
| ATOM | 981 | O | TYR | 709 | 49.524 | 52.953 | 37.045 | 1.00 56.26 | SOS |
| ATOM | 982 | N | LEU | 710 | 50.538 | 52.403 | 38.970 | 1.00 48.67 | SOS |
| ATOM | 983 | CA | LEU | 710 | 51.217 | 51.265 | 38.366 | 1.00 44.49 | SOS |
| ATOM | 984 | CB | LEU | 710 | 52.143 | 50.583 | 39.369 | 1.00 42.56 | SOS |
| ATOM | 985 | CG | LEU | 710 | 52.897 | 49.373 | 38.812 | 1.00 42.33 | SOS |
| ATOM | 986 | CD1 | LEU | 710 | 54.102 | 49.844 | 38.014 | 1.00 43.81 | SOS |
| ATOM | 987 | CD2 | LEU | 710 | 53.331 | 48.457 | 39.934 | 1.00 40.14 | SOS |
| ATOM | 988 | C | LEU | 710 | 50.168 | 50.269 | 37.879 | 1.00 42.06 | SOS |
| ATOM | 989 | O | LEU | 710 | 50.290 | 49.716 | 36.795 | 1.00 40.61 | SOS |
| ATOM | 990 | N | LEU | 711 | 49.128 | 50.062 | 38.683 | 1.00 41.56 | SOS |
| ATOM | 991 | CA | LEU | 711 | 48.065 | 49.136 | 38.324 | 1.00 42.83 | SOS |
| ATOM | 992 | CB | LEU | 711 | 47.096 | 48.937 | 39.493 | 1.00 36.17 | SOS |
| ATOM | 993 | CG | LEU | 711 | 45.982 | 47.903 | 39.257 | 1.00 33.63 | SOS |
| ATOM | 994 | CD1 | LEU | 711 | 46.592 | 46.551 | 38.955 | 1.00 26.89 | SOS |
| ATOM | 995 | CD2 | LEU | 711 | 45.059 | 47.815 | 40.472 | 1.00 29.00 | SOS |
| ATOM | 996 | C | LEU | 711 | 47.318 | 49.668 | 37.106 | 1.00 48.70 | SOS |
| ATOM | 997 | O | LEU | 711 | 47.044 | 48.919 | 36.159 | 1.00 49.01 | SOS |
| ATOM | 998 | N | GLN | 712 | 47.019 | 50.969 | 37.126 | 1.00 48.39 | SOS |
| ATOM | 999 | CA | GLN | 712 | 46.323 | 51.622 | 36.023 | 1.00 48.33 | SOS |
| ATOM | 1000 | CB | GLN | 712 | 46.207 | 53.119 | 36.288 | 1.00 49.16 | SOS |
| ATOM | 1001 | CG | GLN | 712 | 45.391 | 53.869 | 35.254 | 1.00 56.87 | SOS |
| ATOM | 1002 | CD | GLN | 712 | 45.306 | 55.355 | 35.546 | 1.00 62.93 | SOS |
| ATOM | 1003 | OE1 | GLN | 712 | 45.066 | 55.767 | 36.687 | 1.00 65.50 | SOS |

Figure 8-18

```
ATOM   1004  NE2  GLN  712    45.503  56.172  34.514  1.00  64.89      SOS
ATOM   1005  C    GLN  712    47.056  51.375  34.699  1.00  47.63      SOS
ATOM   1006  O    GLN  712    46.471  50.864  33.753  1.00  48.27      SOS
ATOM   1007  N    ARG  713    48.344  51.700  34.654  1.00  46.21      SOS
ATOM   1008  CA   ARG  713    49.147  51.500  33.452  1.00  46.35      SOS
ATOM   1009  CB   ARG  713    50.608  51.883  33.697  1.00  43.47      SOS
ATOM   1010  CG   ARG  713    50.876  53.348  33.957  1.00  35.81      SOS
ATOM   1011  CD   ARG  713    52.367  53.587  33.962  1.00  35.68      SOS
ATOM   1012  NE   ARG  713    52.949  53.135  32.704  1.00  40.74      SOS
ATOM   1013  CZ   ARG  713    54.212  52.753  32.536  1.00  44.52      SOS
ATOM   1014  NH1  ARG  713    55.069  52.759  33.550  1.00  44.85      SOS
ATOM   1015  NH2  ARG  713    54.619  52.364  31.338  1.00  47.71      SOS
ATOM   1016  C    ARG  713    49.092  50.045  32.994  1.00  50.79      SOS
ATOM   1017  O    ARG  713    49.167  49.766  31.795  1.00  53.73      SOS
ATOM   1018  N    MET  714    48.999  49.124  33.955  1.00  51.70      SOS
ATOM   1019  CA   MET  714    48.924  47.696  33.658  1.00  53.37      SOS
ATOM   1020  CB   MET  714    49.147  46.870  34.917  1.00  52.18      SOS
ATOM   1021  CG   MET  714    50.419  46.055  34.891  1.00  55.86      SOS
ATOM   1022  SD   MET  714    50.334  44.698  33.742  1.00  51.90      SOS
ATOM   1023  CE   MET  714    48.874  43.928  34.369  1.00  52.55      SOS
ATOM   1024  C    MET  714    47.577  47.340  33.054  1.00  55.72      SOS
ATOM   1025  O    MET  714    47.509  46.552  32.114  1.00  55.68      SOS
ATOM   1026  N    GLU  715    46.507  47.916  33.602  1.00  57.20      SOS
ATOM   1027  CA   GLU  715    45.161  47.664  33.097  1.00  60.51      SOS
ATOM   1028  CB   GLU  715    44.107  48.133  34.108  1.00  58.42      SOS
ATOM   1029  CG   GLU  715    44.194  47.353  35.419  1.00  63.35      SOS
ATOM   1030  CD   GLU  715    42.966  47.483  36.304  1.00  63.90      SOS
ATOM   1031  OE1  GLU  715    42.110  46.576  36.270  1.00  63.21      SOS
ATOM   1032  OE2  GLU  715    42.868  48.470  37.060  1.00  67.20      SOS
ATOM   1033  C    GLU  715    44.958  48.296  31.710  1.00  62.15      SOS
ATOM   1034  O    GLU  715    44.268  47.727  30.854  1.00  60.89      SOS
ATOM   1035  N    GLU  716    45.604  49.440  31.480  1.00  63.15      SOS
ATOM   1036  CA   GLU  716    45.529  50.127  30.195  1.00  65.01      SOS
ATOM   1037  CB   GLU  716    46.118  51.542  30.279  1.00  67.96      SOS
ATOM   1038  CG   GLU  716    45.298  52.538  31.114  1.00  76.79      SOS
ATOM   1039  CD   GLU  716    45.879  53.961  31.110  1.00  82.50      SOS
ATOM   1040  OE1  GLU  716    47.122  54.113  31.115  1.00  84.75      SOS
ATOM   1041  OE2  GLU  716    45.089  54.933  31.109  1.00  84.28      SOS
ATOM   1042  C    GLU  716    46.305  49.304  29.172  1.00  64.83      SOS
ATOM   1043  O    GLU  716    45.849  49.128  28.047  1.00  68.50      SOS
ATOM   1044  N    PHE  717    47.463  48.786  29.579  1.00  62.42      SOS
ATOM   1045  CA   PHE  717    48.300  47.969  28.706  1.00  59.61      SOS
ATOM   1046  CB   PHE  717    49.641  47.677  29.362  1.00  56.95      SOS
ATOM   1047  CG   PHE  717    50.461  46.664  28.620  1.00  56.51      SOS
ATOM   1048  CD1  PHE  717    50.939  46.937  27.340  1.00  54.86      SOS
ATOM   1049  CD2  PHE  717    50.745  45.429  29.192  1.00  56.64      SOS
ATOM   1050  CE1  PHE  717    51.688  45.993  26.640  1.00  56.61      SOS
ATOM   1051  CE2  PHE  717    51.494  44.476  28.499  1.00  58.56      SOS
ATOM   1052  CZ   PHE  717    51.967  44.759  27.219  1.00  56.81      SOS
ATOM   1053  C    PHE  717    47.638  46.646  28.339  1.00  63.89      SOS
ATOM   1054  O    PHE  717    47.737  46.199  27.195  1.00  63.15      SOS
ATOM   1055  N    ILE  718    47.040  45.986  29.331  1.00  66.60      SOS
ATOM   1056  CA   ILE  718    46.347  44.718  29.111  1.00  67.17      SOS
ATOM   1057  CB   ILE  718    45.750  44.153  30.437  1.00  66.94      SOS
ATOM   1058  CG2  ILE  718    44.725  43.059  30.154  1.00  66.53      SOS
ATOM   1059  CG1  ILE  718    46.859  43.588  31.327  1.00  62.82      SOS
ATOM   1060  CD1  ILE  718    47.549  42.376  30.757  1.00  61.97      SOS
ATOM   1061  C    ILE  718    45.232  44.961  28.093  1.00  69.02      SOS
ATOM   1062  O    ILE  718    45.061  44.178  27.157  1.00  68.81      SOS
ATOM   1063  N    GLY  719    44.520  46.078  28.253  1.00  69.67      SOS
ATOM   1064  CA   GLY  719    43.442  46.431  27.340  1.00  71.55      SOS
```

Figure 8-19

| ATOM | 1065 | C   | GLY | 719 | 43.898 | 46.906 | 25.965 | 1.00 | 72.80 | sos |
|------|------|-----|-----|-----|--------|--------|--------|------|-------|-----|
| ATOM | 1066 | O   | GLY | 719 | 43.076 | 47.243 | 25.118 | 1.00 | 73.22 | sos |
| ATOM | 1067 | N   | THR | 720 | 45.210 | 46.939 | 25.748 | 1.00 | 74.43 | sos |
| ATOM | 1068 | CA  | THR | 720 | 45.803 | 47.362 | 24.480 | 1.00 | 75.60 | sos |
| ATOM | 1069 | CB  | THR | 720 | 47.072 | 48.247 | 24.748 | 1.00 | 76.04 | sos |
| ATOM | 1070 | OG1 | THR | 720 | 46.669 | 49.610 | 24.939 | 1.00 | 74.75 | sos |
| ATOM | 1071 | CG2 | THR | 720 | 48.106 | 48.172 | 23.618 | 1.00 | 75.11 | sos |
| ATOM | 1072 | C   | THR | 720 | 46.122 | 46.152 | 23.583 | 1.00 | 78.01 | sos |
| ATOM | 1073 | O   | THR | 720 | 46.484 | 46.308 | 22.413 | 1.00 | 78.76 | sos |
| ATOM | 1074 | N   | VAL | 721 | 45.946 | 44.946 | 24.118 | 1.00 | 78.71 | sos |
| ATOM | 1075 | CA  | VAL | 721 | 46.215 | 43.730 | 23.357 | 1.00 | 80.46 | sos |
| ATOM | 1076 | CB  | VAL | 721 | 46.054 | 42.472 | 24.233 | 1.00 | 80.43 | sos |
| ATOM | 1077 | CG1 | VAL | 721 | 46.234 | 41.210 | 23.397 | 1.00 | 81.36 | sos |
| ATOM | 1078 | CG2 | VAL | 721 | 47.077 | 42.497 | 25.349 | 1.00 | 80.51 | sos |
| ATOM | 1079 | C   | VAL | 721 | 45.293 | 43.655 | 22.144 | 1.00 | 81.83 | sos |
| ATOM | 1080 | O   | VAL | 721 | 44.074 | 43.785 | 22.269 | 1.00 | 80.46 | sos |
| ATOM | 1081 | N   | ARG | 722 | 45.895 | 43.453 | 20.973 | 1.00 | 84.66 | sos |
| ATOM | 1082 | CA  | ARG | 722 | 45.160 | 43.393 | 19.711 | 1.00 | 88.60 | sos |
| ATOM | 1083 | CB  | ARG | 722 | 46.015 | 43.969 | 18.575 | 1.00 | 89.89 | sos |
| ATOM | 1084 | CG  | ARG | 722 | 46.496 | 45.391 | 18.809 | 0.00 | 90.39 | sos |
| ATOM | 1085 | CD  | ARG | 722 | 47.384 | 45.863 | 17.668 | 0.00 | 91.12 | sos |
| ATOM | 1086 | NE  | ARG | 722 | 47.913 | 47.205 | 17.897 | 0.00 | 91.66 | sos |
| ATOM | 1087 | CZ  | ARG | 722 | 48.957 | 47.482 | 18.674 | 0.00 | 91.94 | sos |
| ATOM | 1088 | NH1 | ARG | 722 | 49.600 | 46.510 | 19.308 | 0.00 | 92.12 | sos |
| ATOM | 1089 | NH2 | ARG | 722 | 49.361 | 48.737 | 18.817 | 0.00 | 92.12 | sos |
| ATOM | 1090 | C   | ARG | 722 | 44.637 | 42.017 | 19.303 | 1.00 | 89.53 | sos |
| ATOM | 1091 | O   | ARG | 722 | 43.441 | 41.862 | 19.054 | 1.00 | 91.26 | sos |
| ATOM | 1092 | N   | GLY | 723 | 45.536 | 41.037 | 19.206 | 1.00 | 89.38 | sos |
| ATOM | 1093 | CA  | GLY | 723 | 45.161 | 39.687 | 18.802 | 1.00 | 91.07 | sos |
| ATOM | 1094 | C   | GLY | 723 | 43.798 | 39.175 | 19.246 | 1.00 | 91.71 | sos |
| ATOM | 1095 | O   | GLY | 723 | 43.537 | 39.048 | 20.445 | 1.00 | 91.80 | sos |
| ATOM | 1096 | N   | LYS | 724 | 42.928 | 38.888 | 18.276 | 1.00 | 92.09 | sos |
| ATOM | 1097 | CA  | LYS | 724 | 41.576 | 38.379 | 18.544 | 1.00 | 92.24 | sos |
| ATOM | 1098 | CB  | LYS | 724 | 40.838 | 38.102 | 17.231 | 1.00 | 92.49 | sos |
| ATOM | 1099 | CG  | LYS | 724 | 40.618 | 39.335 | 16.367 | 0.00 | 93.20 | sos |
| ATOM | 1100 | CD  | LYS | 724 | 39.910 | 38.988 | 15.065 | 0.00 | 93.68 | sos |
| ATOM | 1101 | CE  | LYS | 724 | 38.518 | 38.424 | 15.316 | 0.00 | 94.01 | sos |
| ATOM | 1102 | NZ  | LYS | 724 | 37.827 | 38.071 | 14.045 | 0.00 | 94.27 | sos |
| ATOM | 1103 | C   | LYS | 724 | 41.620 | 37.107 | 19.392 | 1.00 | 91.16 | sos |
| ATOM | 1104 | O   | LYS | 724 | 40.727 | 36.851 | 20.204 | 1.00 | 90.41 | sos |
| ATOM | 1105 | N   | ALA | 725 | 42.666 | 36.313 | 19.184 | 1.00 | 89.30 | sos |
| ATOM | 1106 | CA  | ALA | 725 | 42.867 | 35.083 | 19.931 | 1.00 | 86.44 | sos |
| ATOM | 1107 | CB  | ALA | 725 | 43.709 | 34.110 | 19.123 | 1.00 | 88.36 | sos |
| ATOM | 1108 | C   | ALA | 725 | 43.557 | 35.414 | 21.249 | 1.00 | 84.63 | sos |
| ATOM | 1109 | O   | ALA | 725 | 43.234 | 34.835 | 22.280 | 1.00 | 84.48 | sos |
| ATOM | 1110 | N   | MET | 726 | 44.494 | 36.361 | 21.212 | 1.00 | 83.16 | sos |
| ATOM | 1111 | CA  | MET | 726 | 45.219 | 36.766 | 22.413 | 1.00 | 83.95 | sos |
| ATOM | 1112 | CB  | MET | 726 | 46.336 | 37.755 | 22.088 | 1.00 | 87.18 | sos |
| ATOM | 1113 | CG  | MET | 726 | 47.613 | 37.122 | 21.592 | 1.00 | 91.73 | sos |
| ATOM | 1114 | SD  | MET | 726 | 49.015 | 38.215 | 21.876 | 1.00 | 97.34 | sos |
| ATOM | 1115 | CE  | MET | 726 | 48.756 | 39.472 | 20.605 | 1.00 | 96.71 | sos |
| ATOM | 1116 | C   | MET | 726 | 44.333 | 37.363 | 23.497 | 1.00 | 82.55 | sos |
| ATOM | 1117 | O   | MET | 726 | 44.609 | 37.187 | 24.682 | 1.00 | 82.24 | sos |
| ATOM | 1118 | N   | LYS | 727 | 43.292 | 38.091 | 23.099 | 1.00 | 80.36 | sos |
| ATOM | 1119 | CA  | LYS | 727 | 42.380 | 38.697 | 24.066 | 1.00 | 80.95 | sos |
| ATOM | 1120 | CB  | LYS | 727 | 41.258 | 39.461 | 23.366 | 1.00 | 82.96 | sos |
| ATOM | 1121 | CG  | LYS | 727 | 41.669 | 40.705 | 22.612 | 1.00 | 84.74 | sos |
| ATOM | 1122 | CD  | LYS | 727 | 40.432 | 41.339 | 22.001 | 1.00 | 87.13 | sos |
| ATOM | 1123 | CE  | LYS | 727 | 40.779 | 42.476 | 21.070 | 1.00 | 89.55 | sos |
| ATOM | 1124 | NZ  | LYS | 727 | 39.567 | 42.952 | 20.348 | 1.00 | 93.43 | sos |
| ATOM | 1125 | C   | LYS | 727 | 41.752 | 37.636 | 24.964 | 1.00 | 80.60 | sos |

Figure 8-20

```
ATOM   1126  O    LYS  727     41.663  37.818  26.176  1.00 80.84      sos
ATOM   1127  N    LYS  728     41.315  36.534  24.359  1.00 80.37      sos
ATOM   1128  CA   LYS  728     40.684  35.438  25.095  1.00 79.77      sos
ATOM   1129  CB   LYS  728     40.125  34.392  24.113  1.00 79.46      sos
ATOM   1130  CG   LYS  728     39.343  33.249  24.761  1.00 76.63      sos
ATOM   1131  CD   LYS  728     38.103  33.748  25.486  1.00 76.50      sos
ATOM   1132  CE   LYS  728     37.435  32.623  26.264  1.00 81.32      sos
ATOM   1133  NZ   LYS  728     36.263  33.086  27.066  1.00 82.40      sos
ATOM   1134  C    LYS  728     41.659  34.790  26.080  1.00 77.73      sos
ATOM   1135  O    LYS  728     41.256  34.299  27.137  1.00 79.45      sos
ATOM   1136  N    TRP  729     42.940  34.805  25.730  1.00 74.08      sos
ATOM   1137  CA   TRP  729     43.983  34.231  26.571  1.00 72.50      sos
ATOM   1138  CB   TRP  729     45.212  33.919  25.705  1.00 71.91      sos
ATOM   1139  CG   TRP  729     46.367  33.303  26.437  1.00 72.24      sos
ATOM   1140  CD2  TRP  729     47.664  33.883  26.629  1.00 74.22      sos
ATOM   1141  CE2  TRP  729     48.434  32.954  27.364  1.00 74.73      sos
ATOM   1142  CE3  TRP  729     48.251  35.101  26.253  1.00 72.05      sos
ATOM   1143  CD1  TRP  729     46.401  32.080  27.044  1.00 72.76      sos
ATOM   1144  NE1  TRP  729     47.640  31.861  27.604  1.00 73.69      sos
ATOM   1145  CZ2  TRP  729     49.760  33.205  27.732  1.00 73.90      sos
ATOM   1146  CZ3  TRP  729     49.568  35.348  26.617  1.00 70.88      sos
ATOM   1147  CH2  TRP  729     50.307  34.404  27.350  1.00 73.01      sos
ATOM   1148  C    TRP  729     44.339  35.211  27.694  1.00 71.13      sos
ATOM   1149  O    TRP  729     44.555  34.812  28.842  1.00 72.64      sos
ATOM   1150  N    VAL  730     44.356  36.497  27.347  1.00 68.50      sos
ATOM   1151  CA   VAL  730     44.676  37.590  28.267  1.00 64.02      sos
ATOM   1152  CB   VAL  730     45.012  38.880  27.453  1.00 61.57      sos
ATOM   1153  CG1  VAL  730     44.657  40.145  28.211  1.00 59.12      sos
ATOM   1154  CG2  VAL  730     46.491  38.879  27.095  1.00 57.17      sos
ATOM   1155  C    VAL  730     43.591  37.836  29.323  1.00 62.13      sos
ATOM   1156  O    VAL  730     43.816  38.530  30.313  1.00 61.69      sos
ATOM   1157  N    GLU  731     42.425  37.231  29.124  1.00 61.36      sos
ATOM   1158  CA   GLU  731     41.322  37.364  30.066  1.00 61.49      sos
ATOM   1159  CB   GLU  731     40.044  36.753  29.491  1.00 61.73      sos
ATOM   1160  CG   GLU  731     39.466  37.531  28.317  1.00 62.97      sos
ATOM   1161  CD   GLU  731     38.180  36.936  27.767  1.00 64.83      sos
ATOM   1162  OE1  GLU  731     37.575  36.065  28.439  1.00 60.42      sos
ATOM   1163  OE2  GLU  731     37.778  37.352  26.654  1.00 63.04      sos
ATOM   1164  C    GLU  731     41.685  36.672  31.370  1.00 62.16      sos
ATOM   1165  O    GLU  731     41.172  37.020  32.433  1.00 59.79      sos
ATOM   1166  N    SER  732     42.577  35.688  31.275  1.00 64.99      sos
ATOM   1167  CA   SER  732     43.033  34.946  32.445  1.00 68.71      sos
ATOM   1168  CB   SER  732     43.860  33.730  32.023  1.00 71.02      sos
ATOM   1169  OG   SER  732     43.076  32.822  31.262  1.00 75.70      sos
ATOM   1170  C    SER  732     43.850  35.861  33.355  1.00 68.64      sos
ATOM   1171  O    SER  732     43.802  35.722  34.577  1.00 70.37      sos
ATOM   1172  N    ILE  733     44.578  36.804  32.749  1.00 65.31      sos
ATOM   1173  CA   ILE  733     45.396  37.769  33.490  1.00 61.66      sos
ATOM   1174  CB   ILE  733     46.348  38.551  32.547  1.00 62.26      sos
ATOM   1175  CG2  ILE  733     47.090  39.638  33.309  1.00 58.02      sos
ATOM   1176  CG1  ILE  733     47.348  37.591  31.897  1.00 64.07      sos
ATOM   1177  CD1  ILE  733     48.420  38.283  31.089  1.00 65.07      sos
ATOM   1178  C    ILE  733     44.494  38.759  34.212  1.00 58.17      sos
ATOM   1179  O    ILE  733     44.720  39.093  35.374  1.00 58.75      sos
ATOM   1180  N    THR  734     43.466  39.216  33.506  1.00 58.09      sos
ATOM   1181  CA   THR  734     42.489  40.163  34.041  1.00 56.56      sos
ATOM   1182  CB   THR  734     41.445  40.550  32.952  1.00 56.88      sos
ATOM   1183  OG1  THR  734     42.109  41.179  31.846  1.00 56.11      sos
ATOM   1184  CG2  THR  734     40.384  41.485  33.514  1.00 49.36      sos
ATOM   1185  C    THR  734     41.766  39.561  35.251  1.00 54.23      sos
ATOM   1186  O    THR  734     41.508  40.254  36.232  1.00 52.16      sos
```

Figure 8-21

```
ATOM   1187  N    LYS  735     41.466  38.265  35.179  1.00  54.07      SOS
ATOM   1188  CA   LYS  735     40.778  37.561  36.259  1.00  54.15      SOS
ATOM   1189  CB   LYS  735     40.444  36.122  35.846  1.00  55.25      SOS
ATOM   1190  CG   LYS  735     39.701  35.316  36.906  0.00  55.31      SOS
ATOM   1191  CD   LYS  735     38.351  35.936  37.241  0.00  55.67      SOS
ATOM   1192  CE   LYS  735     37.654  35.179  38.362  0.00  55.80      SOS
ATOM   1193  NZ   LYS  735     38.434  35.211  39.632  0.00  56.00      SOS
ATOM   1194  C    LYS  735     41.612  37.564  37.532  1.00  52.61      SOS
ATOM   1195  O    LYS  735     41.074  37.754  38.621  1.00  53.85      SOS
ATOM   1196  N    ILE  736     42.924  37.372  37.385  1.00  50.79      SOS
ATOM   1197  CA   ILE  736     43.841  37.374  38.525  1.00  46.96      SOS
ATOM   1198  CB   ILE  736     45.282  37.043  38.100  1.00  45.10      SOS
ATOM   1199  CG2  ILE  736     46.214  37.130  39.297  1.00  46.50      SOS
ATOM   1200  CG1  ILE  736     45.345  35.642  37.497  1.00  44.88      SOS
ATOM   1201  CD1  ILE  736     46.696  35.286  36.894  1.00  44.72      SOS
ATOM   1202  C    ILE  736     43.828  38.746  39.193  1.00  47.19      SOS
ATOM   1203  O    ILE  736     43.761  38.837  40.416  1.00  46.57      SOS
ATOM   1204  N    ILE  737     43.872  39.808  38.389  1.00  46.27      SOS
ATOM   1205  CA   ILE  737     43.847  41.168  38.924  1.00  47.84      SOS
ATOM   1206  CB   ILE  737     43.942  42.234  37.810  1.00  45.05      SOS
ATOM   1207  CG2  ILE  737     43.766  43.624  38.388  1.00  38.43      SOS
ATOM   1208  CG1  ILE  737     45.284  42.128  37.091  1.00  44.64      SOS
ATOM   1209  CD1  ILE  737     45.575  43.285  36.180  1.00  45.58      SOS
ATOM   1210  C    ILE  737     42.584  41.413  39.748  1.00  51.60      SOS
ATOM   1211  O    ILE  737     42.668  41.834  40.898  1.00  54.86      SOS
ATOM   1212  N    GLN  738     41.422  41.110  39.175  1.00  56.90      SOS
ATOM   1213  CA   GLN  738     40.149  41.302  39.870  1.00  60.42      SOS
ATOM   1214  CB   GLN  738     38.980  40.925  38.960  1.00  61.43      SOS
ATOM   1215  CG   GLN  738     38.876  41.768  37.700  0.00  61.69      SOS
ATOM   1216  CD   GLN  738     37.731  41.338  36.806  0.00  62.01      SOS
ATOM   1217  OE1  GLN  738     37.840  40.363  36.062  0.00  62.13      SOS
ATOM   1218  NE2  GLN  738     36.622  42.066  36.873  0.00  62.13      SOS
ATOM   1219  C    GLN  738     40.079  40.500  41.170  1.00  62.11      SOS
ATOM   1220  O    GLN  738     39.466  40.937  42.144  1.00  61.69      SOS
ATOM   1221  N    ARG  739     40.740  39.345  41.185  1.00  64.06      SOS
ATOM   1222  CA   ARG  739     40.769  38.471  42.356  1.00  67.21      SOS
ATOM   1223  CB   ARG  739     41.410  37.131  41.986  1.00  71.05      SOS
ATOM   1224  CG   ARG  739     41.534  36.117  43.120  1.00  73.84      SOS
ATOM   1225  CD   ARG  739     42.331  34.893  42.666  1.00  79.39      SOS
ATOM   1226  NE   ARG  739     41.766  34.287  41.458  1.00  86.04      SOS
ATOM   1227  CZ   ARG  739     42.485  33.843  40.429  1.00  88.92      SOS
ATOM   1228  NH1  ARG  739     43.813  33.932  40.459  1.00  90.12      SOS
ATOM   1229  NH2  ARG  739     41.877  33.325  39.362  1.00  85.58      SOS
ATOM   1230  C    ARG  739     41.536  39.106  43.516  1.00  67.79      SOS
ATOM   1231  O    ARG  739     41.093  39.039  44.667  1.00  69.45      SOS
ATOM   1232  N    LYS  740     42.669  39.735  43.199  1.00  64.96      SOS
ATOM   1233  CA   LYS  740     43.532  40.387  44.189  1.00  63.69      SOS
ATOM   1234  CB   LYS  740     44.883  40.722  43.561  1.00  59.37      SOS
ATOM   1235  CG   LYS  740     45.653  39.535  43.020  1.00  57.16      SOS
ATOM   1236  CD   LYS  740     46.112  38.616  44.131  1.00  53.16      SOS
ATOM   1237  CE   LYS  740     47.139  37.636  43.613  1.00  50.16      SOS
ATOM   1238  NZ   LYS  740     47.875  37.003  44.734  1.00  51.16      SOS
ATOM   1239  C    LYS  740     42.955  41.665  44.796  1.00  66.36      SOS
ATOM   1240  O    LYS  740     43.651  42.377  45.521  1.00  66.35      SOS
ATOM   1241  N    LYS  741     41.685  41.948  44.512  1.00  70.30      SOS
ATOM   1242  CA   LYS  741     41.018  43.151  45.020  1.00  71.17      SOS
ATOM   1243  CB   LYS  741     40.865  44.162  43.873  1.00  71.10      SOS
ATOM   1244  CG   LYS  741     42.187  44.479  43.159  1.00  68.75      SOS
ATOM   1245  CD   LYS  741     42.008  44.834  41.684  1.00  67.10      SOS
ATOM   1246  CE   LYS  741     41.373  46.201  41.478  1.00  65.78      SOS
ATOM   1247  NZ   LYS  741     41.350  46.600  40.033  1.00  64.32      SOS
```

Figure 8-22

```
ATOM   1248  C    LYS  741    39.646  42.835  45.640  1.00  71.08      sos
ATOM   1249  O    LYS  741    39.598  42.075  46.639  1.00  67.97      sos
ATOM   1250  OT   LYS  741  9999.0009999.0009999.000  1.00   0.00      sos
ATOM   1251  CB   ILE  752    46.737  19.718  55.540  1.00  83.59      sos
ATOM   1252  CG2  ILE  752    47.927  18.797  55.260  1.00  79.74      sos
ATOM   1253  CG1  ILE  752    46.949  21.082  54.871  1.00  85.23      sos
ATOM   1254  CD1  ILE  752    47.082  21.036  53.356  1.00  86.58      sos
ATOM   1255  C    ILE  752    44.953  18.059  56.094  1.00  82.97      sos
ATOM   1256  O    ILE  752    44.854  18.393  57.276  1.00  83.53      sos
ATOM   1257  N    ILE  752    44.347  20.076  54.818  1.00  83.95      sos
ATOM   1258  CA   ILE  752    45.420  19.061  55.040  1.00  83.18      sos
ATOM   1259  N    THR  753    44.650  16.840  55.653  1.00  82.13      sos
ATOM   1260  CA   THR  753    44.195  15.777  56.549  1.00  81.07      sos
ATOM   1261  CB   THR  753    43.154  14.861  55.848  1.00  80.20      sos
ATOM   1262  OG1  THR  753    42.067  15.661  55.369  1.00  81.37      sos
ATOM   1263  CG2  THR  753    42.603  13.810  56.813  1.00  76.74      sos
ATOM   1264  C    THR  753    45.382  14.938  57.019  1.00  80.17      sos
ATOM   1265  O    THR  753    46.034  14.264  56.221  1.00  81.94      sos
ATOM   1266  N    PHE  754    45.669  14.999  58.315  1.00  78.70      sos
ATOM   1267  CA   PHE  754    46.776  14.243  58.893  1.00  79.92      sos
ATOM   1268  CB   PHE  754    47.146  14.796  60.279  1.00  79.28      sos
ATOM   1269  CG   PHE  754    47.642  16.215  60.257  1.00  75.33      sos
ATOM   1270  CD1  PHE  754    46.828  17.255  60.697  1.00  75.05      sos
ATOM   1271  CD2  PHE  754    48.911  16.514  59.776  1.00  74.87      sos
ATOM   1272  CE1  PHE  754    47.269  18.578  60.655  1.00  76.53      sos
ATOM   1273  CE2  PHE  754    49.363  17.832  59.731  1.00  76.50      sos
ATOM   1274  CZ   PHE  754    48.538  18.866  60.170  1.00  76.15      sos
ATOM   1275  C    PHE  754    46.407  12.769  59.016  1.00  80.05      sos
ATOM   1276  O    PHE  754    45.225  12.423  59.035  1.00  78.77      sos
ATOM   1277  N    GLN  755    47.422  11.908  59.095  1.00  81.51      sos
ATOM   1278  CA   GLN  755    47.203  10.471  59.237  1.00  83.40      sos
ATOM   1279  CB   GLN  755    48.533   9.720  59.325  1.00  87.54      sos
ATOM   1280  CG   GLN  755    49.396   9.812  58.080  1.00  92.89      sos
ATOM   1281  CD   GLN  755    50.482   8.751  58.056  1.00  95.15      sos
ATOM   1282  OE1  GLN  755    51.616   8.991  58.480  1.00  95.37      sos
ATOM   1283  NE2  GLN  755    50.135   7.564  57.566  1.00  94.53      sos
ATOM   1284  C    GLN  755    46.390  10.214  60.499  1.00  82.60      sos
ATOM   1285  O    GLN  755    45.207   9.884  60.428  1.00  82.52      sos
ATOM   1286  N    SER  756    47.033  10.374  61.653  1.00  82.24      sos
ATOM   1287  CA   SER  756    46.369  10.186  62.939  1.00  80.01      sos
ATOM   1288  CB   SER  756    47.336   9.613  63.982  1.00  80.76      sos
ATOM   1289  OG   SER  756    47.651   8.255  63.712  1.00  86.46      sos
ATOM   1290  C    SER  756    45.832  11.520  63.432  1.00  76.59      sos
ATOM   1291  O    SER  756    46.233  12.582  62.948  1.00  76.46      sos
ATOM   1292  N    SER  757    44.895  11.453  64.369  1.00  74.10      sos
ATOM   1293  CA   SER  757    44.308  12.646  64.963  1.00  71.43      sos
ATOM   1294  CB   SER  757    43.070  12.252  65.782  1.00  71.12      sos
ATOM   1295  OG   SER  757    42.288  13.378  66.144  1.00  74.69      sos
ATOM   1296  C    SER  757    45.393  13.252  65.872  1.00  68.88      sos
ATOM   1297  O    SER  757    46.055  12.524  66.622  1.00  70.62      sos
ATOM   1298  N    PRO  758    45.605  14.582  65.799  1.00  64.07      sos
ATOM   1299  CD   PRO  758    44.779  15.571  65.089  1.00  62.90      sos
ATOM   1300  CA   PRO  758    46.616  15.261  66.619  1.00  60.42      sos
ATOM   1301  CB   PRO  758    46.338  16.741  66.344  1.00  60.37      sos
ATOM   1302  CG   PRO  758    44.881  16.761  66.002  1.00  59.34      sos
ATOM   1303  C    PRO  758    46.474  14.929  68.105  1.00  55.94      sos
ATOM   1304  O    PRO  758    45.364  14.864  68.628  1.00  54.97      sos
ATOM   1305  N    PRO  759    47.604  14.744  68.806  1.00  51.21      sos
ATOM   1306  CD   PRO  759    48.969  14.983  68.307  1.00  49.38      sos
ATOM   1307  CA   PRO  759    47.628  14.414  70.236  1.00  46.82      sos
ATOM   1308  CB   PRO  759    49.122  14.472  70.576  1.00  46.73      sos
```

Figure 8-23

| ATOM | 1309 | CG  | PRO | 759 | 49.678 | 15.410 | 69.554 | 1.00 | 48.35 | sos |
|------|------|-----|-----|-----|--------|--------|--------|------|-------|-----|
| ATOM | 1310 | C   | PRO | 759 | 46.795 | 15.327 | 71.130 | 1.00 | 43.52 | sos |
| ATOM | 1311 | O   | PRO | 759 | 46.596 | 16.499 | 70.827 | 1.00 | 44.26 | sos |
| ATOM | 1312 | N   | THR | 760 | 46.299 | 14.762 | 72.226 | 1.00 | 41.80 | sos |
| ATOM | 1313 | CA  | THR | 760 | 45.479 | 15.483 | 73.198 | 1.00 | 43.64 | sos |
| ATOM | 1314 | CB  | THR | 760 | 45.001 | 14.537 | 74.306 | 1.00 | 44.16 | sos |
| ATOM | 1315 | OG1 | THR | 760 | 44.534 | 13.321 | 73.717 | 1.00 | 49.26 | sos |
| ATOM | 1316 | CG2 | THR | 760 | 43.885 | 15.185 | 75.133 | 1.00 | 41.92 | sos |
| ATOM | 1317 | C   | THR | 760 | 46.216 | 16.617 | 73.903 | 1.00 | 43.09 | sos |
| ATOM | 1318 | O   | THR | 760 | 47.379 | 16.470 | 74.281 | 1.00 | 43.99 | sos |
| ATOM | 1319 | N   | VAL | 761 | 45.511 | 17.728 | 74.109 | 1.00 | 43.41 | sos |
| ATOM | 1320 | CA  | VAL | 761 | 46.055 | 18.889 | 74.807 | 1.00 | 43.37 | sos |
| ATOM | 1321 | CB  | VAL | 761 | 45.024 | 20.039 | 74.889 | 1.00 | 45.13 | sos |
| ATOM | 1322 | CG1 | VAL | 761 | 45.534 | 21.154 | 75.801 | 1.00 | 47.53 | sos |
| ATOM | 1323 | CG2 | VAL | 761 | 44.717 | 20.583 | 73.490 | 1.00 | 46.41 | sos |
| ATOM | 1324 | C   | VAL | 761 | 46.391 | 18.445 | 76.220 | 1.00 | 45.23 | sos |
| ATOM | 1325 | O   | VAL | 761 | 45.523 | 17.985 | 76.957 | 1.00 | 46.18 | sos |
| ATOM | 1326 | N   | GLU | 762 | 47.662 | 18.560 | 76.580 | 1.00 | 47.28 | sos |
| ATOM | 1327 | CA  | GLU | 762 | 48.131 | 18.159 | 77.898 | 1.00 | 49.55 | sos |
| ATOM | 1328 | CB  | GLU | 762 | 49.619 | 17.823 | 77.808 | 1.00 | 48.70 | sos |
| ATOM | 1329 | CG  | GLU | 762 | 50.047 | 16.606 | 78.611 | 1.00 | 56.63 | sos |
| ATOM | 1330 | CD  | GLU | 762 | 49.597 | 15.276 | 78.020 | 1.00 | 59.08 | sos |
| ATOM | 1331 | OE1 | GLU | 762 | 48.889 | 14.530 | 78.729 | 1.00 | 61.99 | sos |
| ATOM | 1332 | OE2 | GLU | 762 | 49.976 | 14.957 | 76.868 | 1.00 | 60.65 | sos |
| ATOM | 1333 | C   | GLU | 762 | 47.872 | 19.265 | 78.937 | 1.00 | 49.25 | sos |
| ATOM | 1334 | O   | GLU | 762 | 47.970 | 20.450 | 78.623 | 1.00 | 50.91 | sos |
| ATOM | 1335 | N   | TRP | 763 | 47.483 | 18.873 | 80.150 | 1.00 | 48.34 | sos |
| ATOM | 1336 | CA  | TRP | 763 | 47.213 | 19.822 | 81.235 | 1.00 | 48.11 | sos |
| ATOM | 1337 | CB  | TRP | 763 | 45.715 | 19.940 | 81.511 | 1.00 | 48.34 | sos |
| ATOM | 1338 | CG  | TRP | 763 | 44.949 | 20.637 | 80.435 | 1.00 | 52.14 | sos |
| ATOM | 1339 | CD2 | TRP | 763 | 44.849 | 22.053 | 80.226 | 1.00 | 53.95 | sos |
| ATOM | 1340 | CE2 | TRP | 763 | 44.052 | 22.250 | 79.077 | 1.00 | 52.89 | sos |
| ATOM | 1341 | CE3 | TRP | 763 | 45.359 | 23.176 | 80.896 | 1.00 | 53.73 | sos |
| ATOM | 1342 | CD1 | TRP | 763 | 44.225 | 20.053 | 79.441 | 1.00 | 50.57 | sos |
| ATOM | 1343 | NE1 | TRP | 763 | 43.685 | 21.011 | 78.621 | 1.00 | 52.45 | sos |
| ATOM | 1344 | CZ2 | TRP | 763 | 43.750 | 23.526 | 78.576 | 1.00 | 53.01 | sos |
| ATOM | 1345 | CZ3 | TRP | 763 | 45.056 | 24.451 | 80.396 | 1.00 | 54.01 | sos |
| ATOM | 1346 | CH2 | TRP | 763 | 44.259 | 24.610 | 79.247 | 1.00 | 53.15 | sos |
| ATOM | 1347 | C   | TRP | 763 | 47.913 | 19.392 | 82.515 | 1.00 | 49.46 | sos |
| ATOM | 1348 | O   | TRP | 763 | 48.130 | 18.199 | 82.734 | 1.00 | 48.08 | sos |
| ATOM | 1349 | N   | HIS | 764 | 48.247 | 20.368 | 83.363 | 1.00 | 52.66 | sos |
| ATOM | 1350 | CA  | HIS | 764 | 48.924 | 20.105 | 84.638 | 1.00 | 52.31 | sos |
| ATOM | 1351 | CB  | HIS | 764 | 50.351 | 20.668 | 84.608 | 1.00 | 51.70 | sos |
| ATOM | 1352 | CG  | HIS | 764 | 51.184 | 20.292 | 85.795 | 1.00 | 54.79 | sos |
| ATOM | 1353 | CD2 | HIS | 764 | 51.269 | 19.139 | 86.499 | 1.00 | 55.61 | sos |
| ATOM | 1354 | ND1 | HIS | 764 | 52.099 | 21.154 | 86.363 | 1.00 | 54.63 | sos |
| ATOM | 1355 | CE1 | HIS | 764 | 52.716 | 20.546 | 87.360 | 1.00 | 51.31 | sos |
| ATOM | 1356 | NE2 | HIS | 764 | 52.230 | 19.323 | 87.463 | 1.00 | 52.00 | sos |
| ATOM | 1357 | C   | HIS | 764 | 48.134 | 20.674 | 85.824 | 1.00 | 52.28 | sos |
| ATOM | 1358 | O   | HIS | 764 | 46.987 | 20.288 | 86.044 | 1.00 | 54.90 | sos |
| ATOM | 1359 | N   | ILE | 765 | 48.737 | 21.597 | 86.570 | 1.00 | 51.58 | sos |
| ATOM | 1360 | CA  | ILE | 765 | 48.097 | 22.195 | 87.736 | 1.00 | 50.96 | sos |
| ATOM | 1361 | CB  | ILE | 765 | 49.117 | 22.940 | 88.596 | 1.00 | 50.44 | sos |
| ATOM | 1362 | CG2 | ILE | 765 | 48.427 | 23.614 | 89.780 | 1.00 | 46.91 | sos |
| ATOM | 1363 | CG1 | ILE | 765 | 50.187 | 21.960 | 89.079 | 1.00 | 45.51 | sos |
| ATOM | 1364 | CD1 | ILE | 765 | 51.372 | 22.629 | 89.732 | 1.00 | 49.05 | sos |
| ATOM | 1365 | C   | ILE | 765 | 46.947 | 23.123 | 87.372 | 1.00 | 54.45 | sos |
| ATOM | 1366 | O   | ILE | 765 | 45.941 | 23.181 | 88.079 | 1.00 | 56.61 | sos |
| ATOM | 1367 | N   | SER | 766 | 47.099 | 23.858 | 86.279 | 1.00 | 55.94 | sos |
| ATOM | 1368 | CA  | SER | 766 | 46.041 | 24.752 | 85.836 | 1.00 | 56.95 | sos |
| ATOM | 1369 | CB  | SER | 766 | 46.616 | 25.892 | 84.997 | 1.00 | 58.10 | sos |

Figure 8-24

| | | | | | | | | | |
|---|---|---|---|---|---|---|---|---|---|
| ATOM | 1370 | OG | SER | 766 | 47.435 | 26.735 | 85.783 | 1.00 58.21 | SOS |
| ATOM | 1371 | C | SER | 766 | 45.009 | 23.980 | 85.021 | 1.00 57.24 | SOS |
| ATOM | 1372 | O | SER | 766 | 45.354 | 23.135 | 84.193 | 1.00 57.67 | SOS |
| ATOM | 1373 | N | ARG | 767 | 43.739 | 24.246 | 85.296 | 1.00 58.66 | SOS |
| ATOM | 1374 | CA | ARG | 767 | 42.642 | 23.598 | 84.587 | 1.00 58.46 | SOS |
| ATOM | 1375 | CB | ARG | 767 | 41.452 | 23.386 | 85.533 | 1.00 57.14 | SOS |
| ATOM | 1376 | CG | ARG | 767 | 41.743 | 22.473 | 86.714 | 0.00 58.41 | SOS |
| ATOM | 1377 | CD | ARG | 767 | 40.512 | 22.292 | 87.588 | 0.00 58.76 | SOS |
| ATOM | 1378 | NE | ARG | 767 | 40.765 | 21.391 | 88.710 | 0.00 59.34 | SOS |
| ATOM | 1379 | CZ | ARG | 767 | 39.840 | 20.994 | 89.580 | 0.00 59.59 | SOS |
| ATOM | 1380 | NH1 | ARG | 767 | 38.587 | 21.417 | 89.467 | 0.00 59.80 | SOS |
| ATOM | 1381 | NH2 | ARG | 767 | 40.168 | 20.170 | 90.565 | 0.00 59.80 | SOS |
| ATOM | 1382 | C | ARG | 767 | 42.231 | 24.481 | 83.407 | 1.00 57.53 | SOS |
| ATOM | 1383 | O | ARG | 767 | 42.373 | 25.707 | 83.457 | 1.00 57.49 | SOS |
| ATOM | 1384 | N | PRO | 768 | 41.747 | 23.870 | 82.316 | 1.00 56.37 | SOS |
| ATOM | 1385 | CD | PRO | 768 | 41.533 | 22.431 | 82.096 | 1.00 55.30 | SOS |
| ATOM | 1386 | CA | PRO | 768 | 41.328 | 24.646 | 81.144 | 1.00 55.88 | SOS |
| ATOM | 1387 | CB | PRO | 768 | 40.724 | 23.582 | 80.221 | 1.00 55.56 | SOS |
| ATOM | 1388 | CG | PRO | 768 | 40.380 | 22.444 | 81.148 | 1.00 57.40 | SOS |
| ATOM | 1389 | C | PRO | 768 | 40.325 | 25.739 | 81.500 | 1.00 57.05 | SOS |
| ATOM | 1390 | O | PRO | 768 | 39.312 | 25.484 | 82.157 | 1.00 57.12 | SOS |
| ATOM | 1391 | N | GLY | 769 | 40.645 | 26.966 | 81.102 | 1.00 58.13 | SOS |
| ATOM | 1392 | CA | GLY | 769 | 39.779 | 28.093 | 81.392 | 1.00 59.78 | SOS |
| ATOM | 1393 | C | GLY | 769 | 40.282 | 28.995 | 82.508 | 1.00 62.31 | SOS |
| ATOM | 1394 | O | GLY | 769 | 39.911 | 30.169 | 82.570 | 1.00 62.32 | SOS |
| ATOM | 1395 | N | HIS | 770 | 41.119 | 28.456 | 83.392 | 1.00 65.22 | SOS |
| ATOM | 1396 | CA | HIS | 770 | 41.662 | 29.228 | 84.509 | 1.00 70.02 | SOS |
| ATOM | 1397 | CB | HIS | 770 | 42.010 | 28.298 | 85.673 | 1.00 73.45 | SOS |
| ATOM | 1398 | CG | HIS | 770 | 41.030 | 28.349 | 86.803 | 1.00 80.04 | SOS |
| ATOM | 1399 | CD2 | HIS | 770 | 40.217 | 27.398 | 87.323 | 1.00 82.67 | SOS |
| ATOM | 1400 | ND1 | HIS | 770 | 40.814 | 29.488 | 87.550 | 1.00 82.69 | SOS |
| ATOM | 1401 | CE1 | HIS | 770 | 39.913 | 29.237 | 88.482 | 1.00 84.61 | SOS |
| ATOM | 1402 | NE2 | HIS | 770 | 39.533 | 27.976 | 88.367 | 1.00 85.45 | SOS |
| ATOM | 1403 | C | HIS | 770 | 42.882 | 30.058 | 84.102 | 1.00 71.74 | SOS |
| ATOM | 1404 | O | HIS | 770 | 44.007 | 29.792 | 84.536 | 1.00 71.69 | SOS |
| ATOM | 1405 | N | ILE | 771 | 42.637 | 31.084 | 83.289 | 1.00 73.43 | SOS |
| ATOM | 1406 | CA | ILE | 771 | 43.680 | 31.977 | 82.781 | 1.00 73.04 | SOS |
| ATOM | 1407 | CB | ILE | 771 | 43.072 | 33.137 | 81.948 | 1.00 74.71 | SOS |
| ATOM | 1408 | CG2 | ILE | 771 | 44.179 | 34.032 | 81.376 | 1.00 76.47 | SOS |
| ATOM | 1409 | CG1 | ILE | 771 | 42.225 | 32.578 | 80.806 | 1.00 75.59 | SOS |
| ATOM | 1410 | CD1 | ILE | 771 | 41.559 | 33.652 | 79.974 | 1.00 80.17 | SOS |
| ATOM | 1411 | C | ILE | 771 | 44.543 | 32.583 | 83.883 | 1.00 71.68 | SOS |
| ATOM | 1412 | O | ILE | 771 | 45.770 | 32.578 | 83.785 | 1.00 72.30 | SOS |
| ATOM | 1413 | N | GLU | 772 | 43.893 | 33.095 | 84.924 | 1.00 69.35 | SOS |
| ATOM | 1414 | CA | GLU | 772 | 44.568 | 33.726 | 86.056 | 1.00 68.16 | SOS |
| ATOM | 1415 | CB | GLU | 772 | 43.576 | 33.941 | 87.191 | 1.00 74.89 | SOS |
| ATOM | 1416 | CG | GLU | 772 | 42.158 | 34.216 | 86.750 | 1.00 85.41 | SOS |
| ATOM | 1417 | CD | GLU | 772 | 41.157 | 33.834 | 87.821 | 1.00 92.40 | SOS |
| ATOM | 1418 | OE1 | GLU | 772 | 40.700 | 32.666 | 87.820 | 1.00 94.82 | SOS |
| ATOM | 1419 | OE2 | GLU | 772 | 40.844 | 34.693 | 88.674 | 1.00 97.12 | SOS |
| ATOM | 1420 | C | GLU | 772 | 45.723 | 32.888 | 86.597 | 1.00 64.87 | SOS |
| ATOM | 1421 | O | GLU | 772 | 46.767 | 33.422 | 86.967 | 1.00 66.64 | SOS |
| ATOM | 1422 | N | THR | 773 | 45.521 | 31.576 | 86.634 | 1.00 59.53 | SOS |
| ATOM | 1423 | CA | THR | 773 | 46.505 | 30.631 | 87.147 | 1.00 55.41 | SOS |
| ATOM | 1424 | CB | THR | 773 | 45.826 | 29.305 | 87.515 | 1.00 56.06 | SOS |
| ATOM | 1425 | OG1 | THR | 773 | 44.634 | 29.580 | 88.251 | 1.00 59.73 | SOS |
| ATOM | 1426 | CG2 | THR | 773 | 46.735 | 28.456 | 88.385 | 1.00 60.66 | SOS |
| ATOM | 1427 | C | THR | 773 | 47.666 | 30.313 | 86.210 | 1.00 52.77 | SOS |
| ATOM | 1428 | O | THR | 773 | 48.707 | 29.842 | 86.661 | 1.00 54.52 | SOS |
| ATOM | 1429 | N | PHE | 774 | 47.488 | 30.544 | 84.913 | 1.00 49.38 | SOS |
| ATOM | 1430 | CA | PHE | 774 | 48.532 | 30.247 | 83.932 | 1.00 46.93 | SOS |

Figure 8-25

| ATOM | 1431 | CB  | PHE | 774 | 48.110 | 30.706 | 82.531 | 1.00 | 48.91 | SOS |
|------|------|-----|-----|-----|--------|--------|--------|------|-------|-----|
| ATOM | 1432 | CG  | PHE | 774 | 47.009 | 29.882 | 81.911 | 1.00 | 49.79 | SOS |
| ATOM | 1433 | CD1 | PHE | 774 | 46.388 | 28.862 | 82.617 | 1.00 | 48.24 | SOS |
| ATOM | 1434 | CD2 | PHE | 774 | 46.607 | 30.125 | 80.595 | 1.00 | 53.24 | SOS |
| ATOM | 1435 | CE1 | PHE | 774 | 45.384 | 28.094 | 82.023 | 1.00 | 51.49 | SOS |
| ATOM | 1436 | CE2 | PHE | 774 | 45.605 | 29.362 | 79.993 | 1.00 | 51.85 | SOS |
| ATOM | 1437 | CZ  | PHE | 774 | 44.993 | 28.344 | 80.709 | 1.00 | 50.82 | SOS |
| ATOM | 1438 | C   | PHE | 774 | 49.888 | 30.859 | 84.291 | 1.00 | 43.65 | SOS |
| ATOM | 1439 | O   | PHE | 774 | 49.971 | 32.029 | 84.660 | 1.00 | 43.32 | SOS |
| ATOM | 1440 | N   | ASP | 775 | 50.936 | 30.044 | 84.188 | 1.00 | 39.66 | SOS |
| ATOM | 1441 | CA  | ASP | 775 | 52.303 | 30.448 | 84.492 | 1.00 | 40.20 | SOS |
| ATOM | 1442 | CB  | ASP | 775 | 52.445 | 30.738 | 85.989 | 1.00 | 42.75 | SOS |
| ATOM | 1443 | CG  | ASP | 775 | 53.493 | 31.802 | 86.286 | 1.00 | 45.57 | SOS |
| ATOM | 1444 | OD1 | ASP | 775 | 54.321 | 32.104 | 85.396 | 1.00 | 43.58 | SOS |
| ATOM | 1445 | OD2 | ASP | 775 | 53.482 | 32.342 | 87.416 | 1.00 | 47.46 | SOS |
| ATOM | 1446 | C   | ASP | 775 | 53.245 | 29.314 | 84.069 | 1.00 | 42.02 | SOS |
| ATOM | 1447 | O   | ASP | 775 | 52.782 | 28.221 | 83.743 | 1.00 | 44.67 | SOS |
| ATOM | 1448 | N   | LEU | 776 | 54.556 | 29.554 | 84.127 | 1.00 | 40.58 | SOS |
| ATOM | 1449 | CA  | LEU | 776 | 55.559 | 28.567 | 83.707 | 1.00 | 39.59 | SOS |
| ATOM | 1450 | CB  | LEU | 776 | 56.975 | 29.141 | 83.854 | 1.00 | 37.05 | SOS |
| ATOM | 1451 | CG  | LEU | 776 | 58.111 | 28.179 | 83.481 | 1.00 | 34.22 | SOS |
| ATOM | 1452 | CD1 | LEU | 776 | 58.062 | 27.869 | 82.008 | 1.00 | 38.01 | SOS |
| ATOM | 1453 | CD2 | LEU | 776 | 59.445 | 28.766 | 83.827 | 1.00 | 41.88 | SOS |
| ATOM | 1454 | C   | LEU | 776 | 55.520 | 27.173 | 84.339 | 1.00 | 40.72 | SOS |
| ATOM | 1455 | O   | LEU | 776 | 55.928 | 26.200 | 83.704 | 1.00 | 42.54 | SOS |
| ATOM | 1456 | N   | LEU | 777 | 55.074 | 27.077 | 85.587 | 1.00 | 41.11 | SOS |
| ATOM | 1457 | CA  | LEU | 777 | 55.023 | 25.788 | 86.280 | 1.00 | 42.11 | SOS |
| ATOM | 1458 | CB  | LEU | 777 | 55.644 | 25.901 | 87.674 | 1.00 | 40.60 | SOS |
| ATOM | 1459 | CG  | LEU | 777 | 57.074 | 26.407 | 87.854 | 1.00 | 38.83 | SOS |
| ATOM | 1460 | CD1 | LEU | 777 | 57.258 | 26.785 | 89.307 | 1.00 | 37.73 | SOS |
| ATOM | 1461 | CD2 | LEU | 777 | 58.082 | 25.360 | 87.435 | 1.00 | 31.91 | SOS |
| ATOM | 1462 | C   | LEU | 777 | 53.608 | 25.257 | 86.432 | 1.00 | 44.45 | SOS |
| ATOM | 1463 | O   | LEU | 777 | 53.414 | 24.113 | 86.838 | 1.00 | 47.16 | SOS |
| ATOM | 1464 | N   | THR | 778 | 52.622 | 26.105 | 86.160 | 1.00 | 45.03 | SOS |
| ATOM | 1465 | CA  | THR | 778 | 51.229 | 25.707 | 86.280 | 1.00 | 45.02 | SOS |
| ATOM | 1466 | CB  | THR | 778 | 50.339 | 26.899 | 86.572 | 1.00 | 45.44 | SOS |
| ATOM | 1467 | OG1 | THR | 778 | 50.727 | 27.984 | 85.729 | 1.00 | 51.28 | SOS |
| ATOM | 1468 | CG2 | THR | 778 | 50.456 | 27.306 | 88.020 | 1.00 | 42.08 | SOS |
| ATOM | 1469 | C   | THR | 778 | 50.740 | 25.004 | 85.031 | 1.00 | 43.78 | SOS |
| ATOM | 1470 | O   | THR | 778 | 49.919 | 24.093 | 85.114 | 1.00 | 48.27 | SOS |
| ATOM | 1471 | N   | LEU | 779 | 51.203 | 25.458 | 83.870 | 1.00 | 39.00 | SOS |
| ATOM | 1472 | CA  | LEU | 779 | 50.821 | 24.817 | 82.620 | 1.00 | 36.61 | SOS |
| ATOM | 1473 | CB  | LEU | 779 | 51.074 | 25.725 | 81.416 | 1.00 | 36.26 | SOS |
| ATOM | 1474 | CG  | LEU | 779 | 50.232 | 26.987 | 81.240 | 1.00 | 36.83 | SOS |
| ATOM | 1475 | CD1 | LEU | 779 | 50.645 | 27.661 | 79.961 | 1.00 | 37.53 | SOS |
| ATOM | 1476 | CD2 | LEU | 779 | 48.763 | 26.650 | 81.188 | 1.00 | 39.39 | SOS |
| ATOM | 1477 | C   | LEU | 779 | 51.671 | 23.572 | 82.479 | 1.00 | 36.14 | SOS |
| ATOM | 1478 | O   | LEU | 779 | 52.679 | 23.419 | 83.163 | 1.00 | 35.62 | SOS |
| ATOM | 1479 | N   | HIS | 780 | 51.255 | 22.674 | 81.596 | 1.00 | 36.34 | SOS |
| ATOM | 1480 | CA  | HIS | 780 | 52.003 | 21.454 | 81.370 | 1.00 | 30.69 | SOS |
| ATOM | 1481 | CB  | HIS | 780 | 51.122 | 20.410 | 80.683 | 1.00 | 32.54 | SOS |
| ATOM | 1482 | CG  | HIS | 780 | 51.741 | 19.050 | 80.635 | 1.00 | 38.22 | SOS |
| ATOM | 1483 | CD2 | HIS | 780 | 52.841 | 18.595 | 79.988 | 1.00 | 35.48 | SOS |
| ATOM | 1484 | ND1 | HIS | 780 | 51.269 | 17.991 | 81.381 | 1.00 | 37.64 | SOS |
| ATOM | 1485 | CE1 | HIS | 780 | 52.057 | 16.945 | 81.203 | 1.00 | 41.62 | SOS |
| ATOM | 1486 | NE2 | HIS | 780 | 53.018 | 17.285 | 80.362 | 1.00 | 41.96 | SOS |
| ATOM | 1487 | C   | HIS | 780 | 53.178 | 21.812 | 80.480 | 1.00 | 30.93 | SOS |
| ATOM | 1488 | O   | HIS | 780 | 53.017 | 22.523 | 79.483 | 1.00 | 31.19 | SOS |
| ATOM | 1489 | N   | PRO | 781 | 54.387 | 21.360 | 80.842 | 1.00 | 32.45 | SOS |
| ATOM | 1490 | CD  | PRO | 781 | 54.769 | 20.578 | 82.026 | 1.00 | 27.87 | SOS |
| ATOM | 1491 | CA  | PRO | 781 | 55.563 | 21.672 | 80.020 | 1.00 | 32.26 | SOS |

Figure 8-26

```
ATOM   1492  CB   PRO  781     56.693  20.901  80.712  1.00  28.92           SOS
ATOM   1493  CG   PRO  781     55.986  19.860  81.526  1.00  28.73           SOS
ATOM   1494  C    PRO  781     55.418  21.285  78.552  1.00  34.19           SOS
ATOM   1495  O    PRO  781     55.864  22.021  77.682  1.00  40.11           SOS
ATOM   1496  N    ILE  782     54.769  20.158  78.268  1.00  37.40           SOS
ATOM   1497  CA   ILE  782     54.591  19.724  76.879  1.00  38.73           SOS
ATOM   1498  CB   ILE  782     53.949  18.329  76.769  1.00  39.19           SOS
ATOM   1499  CG2  ILE  782     53.732  17.973  75.311  1.00  38.14           SOS
ATOM   1500  CG1  ILE  782     54.838  17.269  77.418  1.00  41.00           SOS
ATOM   1501  CD1  ILE  782     54.154  15.933  77.553  1.00  34.99           SOS
ATOM   1502  C    ILE  782     53.703  20.692  76.116  1.00  38.45           SOS
ATOM   1503  O    ILE  782     53.984  21.023  74.961  1.00  41.60           SOS
ATOM   1504  N    GLU  783     52.631  21.144  76.756  1.00  34.85           SOS
ATOM   1505  CA   GLU  783     51.726  22.071  76.097  1.00  38.32           SOS
ATOM   1506  CB   GLU  783     50.417  22.208  76.872  1.00  37.38           SOS
ATOM   1507  CG   GLU  783     49.239  22.571  75.983  1.00  42.65           SOS
ATOM   1508  CD   GLU  783     49.069  21.603  74.820  1.00  46.46           SOS
ATOM   1509  OE1  GLU  783     48.908  20.391  75.062  1.00  47.85           SOS
ATOM   1510  OE2  GLU  783     49.110  22.051  73.658  1.00  52.76           SOS
ATOM   1511  C    GLU  783     52.358  23.442  75.863  1.00  39.89           SOS
ATOM   1512  O    GLU  783     52.054  24.103  74.869  1.00  42.05           SOS
ATOM   1513  N    ILE  784     53.238  23.867  76.772  1.00  38.82           SOS
ATOM   1514  CA   ILE  784     53.906  25.157  76.627  1.00  35.25           SOS
ATOM   1515  CB   ILE  784     54.821  25.475  77.834  1.00  35.64           SOS
ATOM   1516  CG2  ILE  784     55.759  26.630  77.512  1.00  37.16           SOS
ATOM   1517  CG1  ILE  784     53.964  25.836  79.050  1.00  35.48           SOS
ATOM   1518  CD1  ILE  784     54.749  26.033  80.327  1.00  36.97           SOS
ATOM   1519  C    ILE  784     54.710  25.131  75.336  1.00  34.11           SOS
ATOM   1520  O    ILE  784     54.530  25.989  74.468  1.00  32.57           SOS
ATOM   1521  N    ALA  785     55.541  24.106  75.186  1.00  28.59           SOS
ATOM   1522  CA   ALA  785     56.351  23.958  73.984  1.00  31.82           SOS
ATOM   1523  CB   ALA  785     57.285  22.769  74.128  1.00  29.35           SOS
ATOM   1524  C    ALA  785     55.473  23.807  72.732  1.00  34.33           SOS
ATOM   1525  O    ALA  785     55.796  24.330  71.663  1.00  30.46           SOS
ATOM   1526  N    ARG  786     54.353  23.106  72.870  1.00  36.83           SOS
ATOM   1527  CA   ARG  786     53.445  22.918  71.744  1.00  40.76           SOS
ATOM   1528  CB   ARG  786     52.320  21.950  72.104  1.00  42.79           SOS
ATOM   1529  CG   ARG  786     52.656  20.492  71.935  1.00  37.73           SOS
ATOM   1530  CD   ARG  786     51.562  19.673  72.557  1.00  38.47           SOS
ATOM   1531  NE   ARG  786     51.806  18.245  72.408  1.00  37.64           SOS
ATOM   1532  CZ   ARG  786     51.012  17.299  72.896  1.00  34.53           SOS
ATOM   1533  NH1  ARG  786     49.914  17.624  73.574  1.00  25.27           SOS
ATOM   1534  NH2  ARG  786     51.317  16.027  72.694  1.00  35.31           SOS
ATOM   1535  C    ARG  786     52.839  24.233  71.266  1.00  41.15           SOS
ATOM   1536  O    ARG  786     52.874  24.542  70.074  1.00  45.26           SOS
ATOM   1537  N    GLN  787     52.278  25.003  72.191  1.00  40.14           SOS
ATOM   1538  CA   GLN  787     51.664  26.273  71.831  1.00  40.79           SOS
ATOM   1539  CB   GLN  787     50.812  26.806  72.978  1.00  40.49           SOS
ATOM   1540  CG   GLN  787     49.679  25.869  73.368  1.00  46.29           SOS
ATOM   1541  CD   GLN  787     48.723  25.561  72.218  1.00  49.08           SOS
ATOM   1542  OE1  GLN  787     48.464  26.407  71.358  1.00  50.00           SOS
ATOM   1543  NE2  GLN  787     48.174  24.349  72.217  1.00  45.42           SOS
ATOM   1544  C    GLN  787     52.674  27.315  71.362  1.00  39.31           SOS
ATOM   1545  O    GLN  787     52.368  28.127  70.495  1.00  43.08           SOS
ATOM   1546  N    LEU  788     53.877  27.292  71.920  1.00  34.89           SOS
ATOM   1547  CA   LEU  788     54.897  28.235  71.498  1.00  33.64           SOS
ATOM   1548  CB   LEU  788     56.082  28.222  72.455  1.00  36.57           SOS
ATOM   1549  CG   LEU  788     55.901  29.080  73.704  1.00  35.94           SOS
ATOM   1550  CD1  LEU  788     57.033  28.827  74.681  1.00  30.14           SOS
ATOM   1551  CD2  LEU  788     55.838  30.526  73.279  1.00  34.86           SOS
ATOM   1552  C    LEU  788     55.358  27.869  70.101  1.00  35.31           SOS
```

Figure 8-27

| ATOM | 1553 | O | LEU | 788 | 55.767 | 28.738 | 69.324 | 1.00 | 35.36 | SOS |
| ATOM | 1554 | N | THR | 789 | 55.283 | 26.580 | 69.778 | 1.00 | 32.91 | SOS |
| ATOM | 1555 | CA | THR | 789 | 55.679 | 26.112 | 68.456 | 1.00 | 29.66 | SOS |
| ATOM | 1556 | CB | THR | 789 | 55.889 | 24.606 | 68.457 | 1.00 | 24.38 | SOS |
| ATOM | 1557 | OG1 | THR | 789 | 56.876 | 24.291 | 69.441 | 1.00 | 28.48 | SOS |
| ATOM | 1558 | CG2 | THR | 789 | 56.386 | 24.131 | 67.115 | 1.00 | 19.79 | SOS |
| ATOM | 1559 | C | THR | 789 | 54.645 | 26.554 | 67.414 | 1.00 | 31.44 | SOS |
| ATOM | 1560 | O | THR | 789 | 55.006 | 27.030 | 66.340 | 1.00 | 33.08 | SOS |
| ATOM | 1561 | N | LEU | 790 | 53.363 | 26.441 | 67.749 | 1.00 | 31.84 | SOS |
| ATOM | 1562 | CA | LEU | 790 | 52.309 | 26.888 | 66.846 | 1.00 | 34.52 | SOS |
| ATOM | 1563 | CB | LEU | 790 | 50.936 | 26.555 | 67.426 | 1.00 | 33.15 | SOS |
| ATOM | 1564 | CG | LEU | 790 | 50.623 | 25.060 | 67.397 | 1.00 | 37.80 | SOS |
| ATOM | 1565 | CD1 | LEU | 790 | 49.348 | 24.767 | 68.177 | 1.00 | 38.42 | SOS |
| ATOM | 1566 | CD2 | LEU | 790 | 50.510 | 24.583 | 65.952 | 1.00 | 30.50 | SOS |
| ATOM | 1567 | C | LEU | 790 | 52.444 | 28.403 | 66.615 | 1.00 | 36.45 | SOS |
| ATOM | 1568 | O | LEU | 790 | 52.439 | 28.868 | 65.472 | 1.00 | 35.83 | SOS |
| ATOM | 1569 | N | LEU | 791 | 52.601 | 29.156 | 67.704 | 1.00 | 36.76 | SOS |
| ATOM | 1570 | CA | LEU | 791 | 52.765 | 30.608 | 67.641 | 1.00 | 37.82 | SOS |
| ATOM | 1571 | CB | LEU | 791 | 53.008 | 31.185 | 69.036 | 1.00 | 36.78 | SOS |
| ATOM | 1572 | CG | LEU | 791 | 51.829 | 31.805 | 69.778 | 1.00 | 38.93 | SOS |
| ATOM | 1573 | CD1 | LEU | 791 | 52.218 | 32.098 | 71.216 | 1.00 | 38.56 | SOS |
| ATOM | 1574 | CD2 | LEU | 791 | 51.395 | 33.069 | 69.060 | 1.00 | 39.46 | SOS |
| ATOM | 1575 | C | LEU | 791 | 53.957 | 30.950 | 66.784 | 1.00 | 39.70 | SOS |
| ATOM | 1576 | O | LEU | 791 | 53.861 | 31.754 | 65.863 | 1.00 | 42.62 | SOS |
| ATOM | 1577 | N | GLU | 792 | 55.080 | 30.310 | 67.091 | 1.00 | 40.44 | SOS |
| ATOM | 1578 | CA | GLU | 792 | 56.323 | 30.546 | 66.378 | 1.00 | 39.38 | SOS |
| ATOM | 1579 | CB | GLU | 792 | 57.505 | 29.989 | 67.182 | 1.00 | 39.95 | SOS |
| ATOM | 1580 | CG | GLU | 792 | 57.846 | 30.892 | 68.379 | 1.00 | 37.88 | SOS |
| ATOM | 1581 | CD | GLU | 792 | 58.683 | 30.234 | 69.461 | 1.00 | 35.30 | SOS |
| ATOM | 1582 | OE1 | GLU | 792 | 59.593 | 29.436 | 69.152 | 1.00 | 36.26 | SOS |
| ATOM | 1583 | OE2 | GLU | 792 | 58.433 | 30.545 | 70.639 | 1.00 | 34.44 | SOS |
| ATOM | 1584 | C | GLU | 792 | 56.319 | 30.062 | 64.943 | 1.00 | 37.97 | SOS |
| ATOM | 1585 | O | GLU | 792 | 57.042 | 30.607 | 64.112 | 1.00 | 41.98 | SOS |
| ATOM | 1586 | N | SER | 793 | 55.497 | 29.056 | 64.645 | 1.00 | 36.85 | SOS |
| ATOM | 1587 | CA | SER | 793 | 55.398 | 28.541 | 63.278 | 1.00 | 36.16 | SOS |
| ATOM | 1588 | CB | SER | 793 | 54.730 | 27.170 | 63.234 | 1.00 | 35.06 | SOS |
| ATOM | 1589 | OG | SER | 793 | 54.742 | 26.682 | 61.899 | 1.00 | 38.63 | SOS |
| ATOM | 1590 | C | SER | 793 | 54.600 | 29.528 | 62.426 | 1.00 | 33.67 | SOS |
| ATOM | 1591 | O | SER | 793 | 54.997 | 29.860 | 61.315 | 1.00 | 31.85 | SOS |
| ATOM | 1592 | N | ASP | 794 | 53.482 | 30.006 | 62.961 | 1.00 | 30.94 | SOS |
| ATOM | 1593 | CA | ASP | 794 | 52.666 | 30.976 | 62.258 | 1.00 | 32.73 | SOS |
| ATOM | 1594 | CB | ASP | 794 | 51.449 | 31.362 | 63.098 | 1.00 | 33.18 | SOS |
| ATOM | 1595 | CG | ASP | 794 | 50.408 | 30.247 | 63.185 | 1.00 | 36.93 | SOS |
| ATOM | 1596 | OD1 | ASP | 794 | 50.446 | 29.300 | 62.357 | 1.00 | 34.96 | SOS |
| ATOM | 1597 | OD2 | ASP | 794 | 49.536 | 30.336 | 64.080 | 1.00 | 33.25 | SOS |
| ATOM | 1598 | C | ASP | 794 | 53.509 | 32.211 | 61.961 | 1.00 | 37.94 | SOS |
| ATOM | 1599 | O | ASP | 794 | 53.586 | 32.652 | 60.808 | 1.00 | 41.20 | SOS |
| ATOM | 1600 | N | LEU | 795 | 54.186 | 32.726 | 62.992 | 1.00 | 39.32 | SOS |
| ATOM | 1601 | CA | LEU | 795 | 55.041 | 33.904 | 62.862 | 1.00 | 36.31 | SOS |
| ATOM | 1602 | CB | LEU | 795 | 55.728 | 34.225 | 64.191 | 1.00 | 35.57 | SOS |
| ATOM | 1603 | CG | LEU | 795 | 54.843 | 34.697 | 65.351 | 1.00 | 39.55 | SOS |
| ATOM | 1604 | CD1 | LEU | 795 | 55.698 | 34.920 | 66.585 | 1.00 | 32.77 | SOS |
| ATOM | 1605 | CD2 | LEU | 795 | 54.083 | 35.967 | 64.985 | 1.00 | 33.97 | SOS |
| ATOM | 1606 | C | LEU | 795 | 56.082 | 33.714 | 61.767 | 1.00 | 36.51 | SOS |
| ATOM | 1607 | O | LEU | 795 | 56.326 | 34.620 | 60.961 | 1.00 | 34.84 | SOS |
| ATOM | 1608 | N | TYR | 796 | 56.671 | 32.522 | 61.726 | 1.00 | 35.48 | SOS |
| ATOM | 1609 | CA | TYR | 796 | 57.670 | 32.202 | 60.718 | 1.00 | 38.57 | SOS |
| ATOM | 1610 | CB | TYR | 796 | 58.353 | 30.877 | 61.035 | 1.00 | 33.30 | SOS |
| ATOM | 1611 | CG | TYR | 796 | 59.306 | 30.429 | 59.953 | 1.00 | 32.20 | SOS |
| ATOM | 1612 | CD1 | TYR | 796 | 60.484 | 31.125 | 59.706 | 1.00 | 30.99 | SOS |
| ATOM | 1613 | CE1 | TYR | 796 | 61.344 | 30.742 | 58.675 | 1.00 | 33.71 | SOS |

Figure 8-28

```
ATOM   1614  CD2 TYR   796      59.009  29.330  59.147  1.00  33.62       SOS
ATOM   1615  CE2 TYR   796      59.860  28.939  58.118  1.00  32.54       SOS
ATOM   1616  CZ  TYR   796      61.021  29.650  57.885  1.00  34.17       SOS
ATOM   1617  OH  TYR   796      61.852  29.281  56.852  1.00  34.94       SOS
ATOM   1618  C   TYR   796      57.074  32.126  59.319  1.00  41.30       SOS
ATOM   1619  O   TYR   796      57.649  32.651  58.369  1.00  46.55       SOS
ATOM   1620  N   ARG   797      55.924  31.469  59.198  1.00  43.54       SOS
ATOM   1621  CA  ARG   797      55.255  31.297  57.903  1.00  44.26       SOS
ATOM   1622  CB  ARG   797      54.120  30.262  58.016  1.00  43.25       SOS
ATOM   1623  CG  ARG   797      54.519  28.945  58.657  1.00  48.61       SOS
ATOM   1624  CD  ARG   797      53.315  28.052  58.943  1.00  50.33       SOS
ATOM   1625  NE  ARG   797      52.966  27.228  57.790  1.00  53.06       SOS
ATOM   1626  CZ  ARG   797      51.729  27.024  57.357  1.00  49.86       SOS
ATOM   1627  NH1 ARG   797      50.700  27.583  57.978  1.00  50.65       SOS
ATOM   1628  NH2 ARG   797      51.525  26.262  56.295  1.00  52.23       SOS
ATOM   1629  C   ARG   797      54.683  32.592  57.321  1.00  41.37       SOS
ATOM   1630  O   ARG   797      54.302  32.628  56.154  1.00  39.16       SOS
ATOM   1631  N   ALA   798      54.624  33.651  58.123  1.00  37.11       SOS
ATOM   1632  CA  ALA   798      54.056  34.907  57.653  1.00  33.68       SOS
ATOM   1633  CB  ALA   798      53.304  35.591  58.786  1.00  27.85       SOS
ATOM   1634  C   ALA   798      55.028  35.879  56.985  1.00  33.50       SOS
ATOM   1635  O   ALA   798      54.610  36.862  56.368  1.00  37.79       SOS
ATOM   1636  N   VAL   799      56.319  35.595  57.069  1.00  31.91       SOS
ATOM   1637  CA  VAL   799      57.308  36.487  56.479  1.00  32.31       SOS
ATOM   1638  CB  VAL   799      58.707  36.273  57.098  1.00  29.54       SOS
ATOM   1639  CG1 VAL   799      59.666  37.326  56.588  1.00  27.87       SOS
ATOM   1640  CG2 VAL   799      58.625  36.314  58.611  1.00  20.72       SOS
ATOM   1641  C   VAL   799      57.392  36.359  54.964  1.00  34.13       SOS
ATOM   1642  O   VAL   799      57.570  35.269  54.424  1.00  38.42       SOS
ATOM   1643  N   GLN   800      57.253  37.485  54.282  1.00  35.08       SOS
ATOM   1644  CA  GLN   800      57.318  37.503  52.833  1.00  38.04       SOS
ATOM   1645  CB  GLN   800      56.312  38.505  52.269  1.00  40.22       SOS
ATOM   1646  CG  GLN   800      54.864  38.212  52.626  1.00  44.07       SOS
ATOM   1647  CD  GLN   800      54.478  36.762  52.386  1.00  50.52       SOS
ATOM   1648  OE1 GLN   800      54.826  36.162  51.361  1.00  52.62       SOS
ATOM   1649  NE2 GLN   800      53.763  36.185  53.343  1.00  56.05       SOS
ATOM   1650  C   GLN   800      58.714  37.856  52.355  1.00  39.57       SOS
ATOM   1651  O   GLN   800      59.458  38.558  53.037  1.00  45.69       SOS
ATOM   1652  N   PRO   801      59.101  37.360  51.174  1.00  38.94       SOS
ATOM   1653  CD  PRO   801      58.469  36.315  50.349  1.00  36.96       SOS
ATOM   1654  CA  PRO   801      60.437  37.675  50.669  1.00  35.55       SOS
ATOM   1655  CB  PRO   801      60.493  36.890  49.366  1.00  31.15       SOS
ATOM   1656  CG  PRO   801      59.671  35.678  49.694  1.00  31.47       SOS
ATOM   1657  C   PRO   801      60.652  39.167  50.447  1.00  34.71       SOS
ATOM   1658  O   PRO   801      61.789  39.630  50.422  1.00  37.18       SOS
ATOM   1659  N   SER   802      59.560  39.918  50.307  1.00  36.14       SOS
ATOM   1660  CA  SER   802      59.636  41.366  50.093  1.00  35.51       SOS
ATOM   1661  CB  SER   802      58.301  41.905  49.575  1.00  35.48       SOS
ATOM   1662  OG  SER   802      57.287  41.808  50.559  1.00  42.48       SOS
ATOM   1663  C   SER   802      60.043  42.106  51.371  1.00  34.52       SOS
ATOM   1664  O   SER   802      60.193  43.328  51.381  1.00  31.19       SOS
ATOM   1665  N   GLU   803      60.192  41.351  52.453  1.00  35.86       SOS
ATOM   1666  CA  GLU   803      60.603  41.906  53.732  1.00  38.50       SOS
ATOM   1667  CB  GLU   803      59.823  41.246  54.870  1.00  36.50       SOS
ATOM   1668  CG  GLU   803      58.340  41.514  54.823  1.00  43.32       SOS
ATOM   1669  CD  GLU   803      57.604  40.925  56.002  1.00  48.30       SOS
ATOM   1670  OE1 GLU   803      56.822  39.968  55.797  1.00  53.33       SOS
ATOM   1671  OE2 GLU   803      57.798  41.420  57.131  1.00  48.70       SOS
ATOM   1672  C   GLU   803      62.093  41.651  53.923  1.00  38.90       SOS
ATOM   1673  O   GLU   803      62.737  42.267  54.770  1.00  41.02       SOS
ATOM   1674  N   LEU   804      62.638  40.761  53.104  1.00  34.89       SOS
```

Figure 8-29

| | | | | | | | | | |
|---|---|---|---|---|---|---|---|---|---|
| ATOM | 1675 | CA | LEU | 804 | 64.034 | 40.399 | 53.202 | 1.00 32.81 | sos |
| ATOM | 1676 | CB | LEU | 804 | 64.164 | 38.876 | 53.242 | 1.00 30.32 | sos |
| ATOM | 1677 | CG | LEU | 804 | 63.196 | 38.180 | 54.200 | 1.00 29.48 | sos |
| ATOM | 1678 | CD1 | LEU | 804 | 63.322 | 36.694 | 54.060 | 1.00 25.98 | sos |
| ATOM | 1679 | CD2 | LEU | 804 | 63.452 | 38.601 | 55.628 | 1.00 27.46 | sos |
| ATOM | 1680 | C | LEU | 804 | 64.879 | 40.963 | 52.076 | 1.00 32.25 | sos |
| ATOM | 1681 | O | LEU | 804 | 65.965 | 41.473 | 52.309 | 1.00 35.65 | sos |
| ATOM | 1682 | N | VAL | 805 | 64.374 | 40.884 | 50.856 | 1.00 34.37 | sos |
| ATOM | 1683 | CA | VAL | 805 | 65.113 | 41.362 | 49.689 | 1.00 34.40 | sos |
| ATOM | 1684 | CB | VAL | 805 | 64.310 | 41.099 | 48.388 | 1.00 29.10 | sos |
| ATOM | 1685 | CG1 | VAL | 805 | 65.081 | 41.597 | 47.184 | 1.00 31.84 | sos |
| ATOM | 1686 | CG2 | VAL | 805 | 64.054 | 39.610 | 48.248 | 1.00 24.43 | sos |
| ATOM | 1687 | C | VAL | 805 | 65.538 | 42.832 | 49.792 | 1.00 33.89 | sos |
| ATOM | 1688 | O | VAL | 805 | 64.743 | 43.705 | 50.133 | 1.00 31.64 | sos |
| ATOM | 1689 | N | GLY | 806 | 66.808 | 43.093 | 49.510 | 1.00 33.96 | sos |
| ATOM | 1690 | CA | GLY | 806 | 67.302 | 44.453 | 49.595 | 1.00 37.85 | sos |
| ATOM | 1691 | C | GLY | 806 | 67.674 | 44.857 | 51.014 | 1.00 39.98 | sos |
| ATOM | 1692 | O | GLY | 806 | 67.760 | 46.051 | 51.310 | 1.00 42.46 | sos |
| ATOM | 1693 | N | SER | 807 | 67.871 | 43.866 | 51.888 | 1.00 37.67 | sos |
| ATOM | 1694 | CA | SER | 807 | 68.240 | 44.081 | 53.290 | 1.00 35.94 | sos |
| ATOM | 1695 | CB | SER | 807 | 69.694 | 44.530 | 53.383 | 1.00 35.71 | sos |
| ATOM | 1696 | OG | SER | 807 | 70.559 | 43.526 | 52.888 | 1.00 41.01 | sos |
| ATOM | 1697 | C | SER | 807 | 67.339 | 45.112 | 53.945 | 1.00 36.28 | sos |
| ATOM | 1698 | O | SER | 807 | 67.722 | 45.798 | 54.894 | 1.00 36.36 | sos |
| ATOM | 1699 | N | VAL | 808 | 66.118 | 45.173 | 53.437 | 1.00 34.29 | sos |
| ATOM | 1700 | CA | VAL | 808 | 65.105 | 46.113 | 53.868 | 1.00 31.50 | sos |
| ATOM | 1701 | CB | VAL | 808 | 63.851 | 45.909 | 52.990 | 1.00 31.10 | sos |
| ATOM | 1702 | CG1 | VAL | 808 | 62.592 | 45.959 | 53.791 | 1.00 34.35 | sos |
| ATOM | 1703 | CG2 | VAL | 808 | 63.832 | 46.938 | 51.885 | 1.00 28.74 | sos |
| ATOM | 1704 | C | VAL | 808 | 64.797 | 46.204 | 55.373 | 1.00 32.62 | sos |
| ATOM | 1705 | O | VAL | 808 | 64.427 | 47.278 | 55.859 | 1.00 28.91 | sos |
| ATOM | 1706 | N | TRP | 809 | 64.990 | 45.112 | 56.117 | 1.00 33.43 | sos |
| ATOM | 1707 | CA | TRP | 809 | 64.728 | 45.124 | 57.565 | 1.00 30.82 | sos |
| ATOM | 1708 | CB | TRP | 809 | 64.513 | 43.704 | 58.109 | 1.00 24.16 | sos |
| ATOM | 1709 | CG | TRP | 809 | 65.776 | 42.929 | 58.317 | 1.00 27.11 | sos |
| ATOM | 1710 | CD2 | TRP | 809 | 66.550 | 42.269 | 57.313 | 1.00 27.81 | sos |
| ATOM | 1711 | CE2 | TRP | 809 | 67.695 | 41.742 | 57.948 | 1.00 28.87 | sos |
| ATOM | 1712 | CE3 | TRP | 809 | 66.393 | 42.076 | 55.936 | 1.00 26.50 | sos |
| ATOM | 1713 | CD1 | TRP | 809 | 66.456 | 42.765 | 59.492 | 1.00 26.39 | sos |
| ATOM | 1714 | NE1 | TRP | 809 | 67.613 | 42.061 | 59.278 | 1.00 21.95 | sos |
| ATOM | 1715 | CZ2 | TRP | 809 | 68.678 | 41.036 | 57.250 | 1.00 27.71 | sos |
| ATOM | 1716 | CZ3 | TRP | 809 | 67.370 | 41.377 | 55.246 | 1.00 28.78 | sos |
| ATOM | 1717 | CH2 | TRP | 809 | 68.497 | 40.866 | 55.904 | 1.00 27.52 | sos |
| ATOM | 1718 | C | TRP | 809 | 65.827 | 45.829 | 58.375 | 1.00 32.30 | sos |
| ATOM | 1719 | O | TRP | 809 | 65.731 | 45.930 | 59.599 | 1.00 32.47 | sos |
| ATOM | 1720 | N | THR | 810 | 66.877 | 46.295 | 57.704 | 1.00 32.72 | sos |
| ATOM | 1721 | CA | THR | 810 | 67.957 | 46.985 | 58.400 | 1.00 34.60 | sos |
| ATOM | 1722 | CB | THR | 810 | 69.352 | 46.448 | 58.015 | 1.00 34.41 | sos |
| ATOM | 1723 | OG1 | THR | 810 | 69.672 | 46.844 | 56.677 | 1.00 38.94 | sos |
| ATOM | 1724 | CG2 | THR | 810 | 69.390 | 44.931 | 58.120 | 1.00 37.53 | sos |
| ATOM | 1725 | C | THR | 810 | 67.948 | 48.494 | 58.195 | 1.00 35.55 | sos |
| ATOM | 1726 | O | THR | 810 | 68.559 | 49.226 | 58.980 | 1.00 41.48 | sos |
| ATOM | 1727 | N | LYS | 811 | 67.262 | 48.957 | 57.147 | 1.00 34.35 | sos |
| ATOM | 1728 | CA | LYS | 811 | 67.174 | 50.389 | 56.832 | 1.00 31.36 | sos |
| ATOM | 1729 | CB | LYS | 811 | 66.734 | 50.586 | 55.380 | 1.00 33.00 | sos |
| ATOM | 1730 | CG | LYS | 811 | 67.352 | 49.628 | 54.380 | 1.00 30.80 | sos |
| ATOM | 1731 | CD | LYS | 811 | 68.681 | 50.111 | 53.860 | 1.00 37.17 | sos |
| ATOM | 1732 | CE | LYS | 811 | 69.174 | 49.209 | 52.748 | 1.00 43.43 | sos |
| ATOM | 1733 | NZ | LYS | 811 | 68.164 | 49.113 | 51.639 | 1.00 52.12 | sos |
| ATOM | 1734 | C | LYS | 811 | 66.208 | 51.147 | 57.760 | 1.00 33.21 | sos |
| ATOM | 1735 | O | LYS | 811 | 65.470 | 50.542 | 58.544 | 1.00 31.41 | sos |

Figure 8-30

```
ATOM   1736  N    GLU  812     66.181  52.472  57.630  1.00  36.64      SOS
ATOM   1737  CA   GLU  812     65.318  53.311  58.464  1.00  37.16      SOS
ATOM   1738  CB   GLU  812     65.599  54.798  58.218  1.00  35.79      SOS
ATOM   1739  CG   GLU  812     65.255  55.303  56.829  1.00  43.94      SOS
ATOM   1740  CD   GLU  812     65.452  56.812  56.678  1.00  49.71      SOS
ATOM   1741  OE1  GLU  812     64.468  57.511  56.331  1.00  56.35      SOS
ATOM   1742  OE2  GLU  812     66.586  57.297  56.896  1.00  48.88      SOS
ATOM   1743  C    GLU  812     63.818  53.027  58.363  1.00  37.58      SOS
ATOM   1744  O    GLU  812     63.075  53.302  59.305  1.00  39.37      SOS
ATOM   1745  N    ASP  813     63.370  52.483  57.234  1.00  39.99      SOS
ATOM   1746  CA   ASP  813     61.948  52.174  57.057  1.00  41.54      SOS
ATOM   1747  CB   ASP  813     61.467  52.559  55.652  1.00  41.03      SOS
ATOM   1748  CG   ASP  813     61.378  54.064  55.436  1.00  45.66      SOS
ATOM   1749  OD1  ASP  813     61.317  54.854  56.414  1.00  44.80      SOS
ATOM   1750  OD2  ASP  813     61.352  54.453  54.251  1.00  46.93      SOS
ATOM   1751  C    ASP  813     61.631  50.700  57.319  1.00  41.00      SOS
ATOM   1752  O    ASP  813     60.724  50.132  56.713  1.00  40.32      SOS
ATOM   1753  N    LYS  814     62.358  50.091  58.250  1.00  42.35      SOS
ATOM   1754  CA   LYS  814     62.146  48.689  58.578  1.00  38.25      SOS
ATOM   1755  CB   LYS  814     63.261  48.165  59.489  1.00  40.08      SOS
ATOM   1756  CG   LYS  814     63.461  48.912  60.798  1.00  43.89      SOS
ATOM   1757  CD   LYS  814     64.532  48.211  61.631  1.00  52.47      SOS
ATOM   1758  CE   LYS  814     65.033  49.064  62.783  1.00  54.54      SOS
ATOM   1759  NZ   LYS  814     65.708  50.298  62.283  1.00  60.98      SOS
ATOM   1760  C    LYS  814     60.774  48.380  59.173  1.00  36.03      SOS
ATOM   1761  O    LYS  814     60.175  47.364  58.832  1.00  31.79      SOS
ATOM   1762  N    GLU  815     60.270  49.252  60.048  1.00  36.71      SOS
ATOM   1763  CA   GLU  815     58.961  49.030  60.670  1.00  36.45      SOS
ATOM   1764  CB   GLU  815     58.609  50.151  61.656  1.00  34.50      SOS
ATOM   1765  CG   GLU  815     59.606  50.395  62.780  1.00  36.88      SOS
ATOM   1766  CD   GLU  815     59.728  49.256  63.790  1.00  38.07      SOS
ATOM   1767  OE1  GLU  815     60.710  49.272  64.560  1.00  44.19      SOS
ATOM   1768  OE2  GLU  815     58.861  48.363  63.840  1.00  38.38      SOS
ATOM   1769  C    GLU  815     57.868  48.945  59.610  1.00  36.31      SOS
ATOM   1770  O    GLU  815     56.887  48.221  59.774  1.00  39.13      SOS
ATOM   1771  N    ILE  816     58.061  49.692  58.526  1.00  32.49      SOS
ATOM   1772  CA   ILE  816     57.128  49.753  57.410  1.00  30.08      SOS
ATOM   1773  CB   ILE  816     57.331  51.061  56.626  1.00  30.31      SOS
ATOM   1774  CG2  ILE  816     56.581  51.035  55.314  1.00  29.68      SOS
ATOM   1775  CG1  ILE  816     56.893  52.252  57.473  1.00  25.25      SOS
ATOM   1776  CD1  ILE  816     57.327  53.585  56.891  1.00  26.51      SOS
ATOM   1777  C    ILE  816     57.246  48.574  56.446  1.00  31.70      SOS
ATOM   1778  O    ILE  816     56.250  47.925  56.145  1.00  35.11      SOS
ATOM   1779  N    ASN  817     58.465  48.291  55.991  1.00  29.29      SOS
ATOM   1780  CA   ASN  817     58.726  47.219  55.036  1.00  29.09      SOS
ATOM   1781  CB   ASN  817     59.971  47.552  54.221  1.00  33.05      SOS
ATOM   1782  CG   ASN  817     59.799  48.779  53.342  1.00  38.44      SOS
ATOM   1783  OD1  ASN  817     58.790  48.933  52.642  1.00  42.97      SOS
ATOM   1784  ND2  ASN  817     60.798  49.650  53.356  1.00  30.19      SOS
ATOM   1785  C    ASN  817     58.852  45.773  55.526  1.00  33.20      SOS
ATOM   1786  O    ASN  817     58.654  44.844  54.739  1.00  36.73      SOS
ATOM   1787  N    SER  818     59.202  45.560  56.794  1.00  34.38      SOS
ATOM   1788  CA   SER  818     59.363  44.193  57.322  1.00  30.04      SOS
ATOM   1789  CB   SER  818     60.833  43.896  57.606  1.00  22.90      SOS
ATOM   1790  OG   SER  818     61.678  44.341  56.566  1.00  22.85      SOS
ATOM   1791  C    SER  818     58.603  43.998  58.619  1.00  30.52      SOS
ATOM   1792  O    SER  818     59.140  43.447  59.571  1.00  30.86      SOS
ATOM   1793  N    PRO  819     57.319  44.379  58.652  1.00  33.07      SOS
ATOM   1794  CD   PRO  819     56.475  44.859  57.545  1.00  31.35      SOS
ATOM   1795  CA   PRO  819     56.525  44.236  59.875  1.00  31.94      SOS
ATOM   1796  CB   PRO  819     55.189  44.883  59.492  1.00  26.86      SOS
```

Figure 8-31

| | | | | | | | | | |
|---|---|---|---|---|---|---|---|---|---|
| ATOM | 1797 | CG | PRO | 819 | 55.082 | 44.566 | 58.060 | 1.00 31.08 | SOS |
| ATOM | 1798 | C | PRO | 819 | 56.342 | 42.831 | 60.419 | 1.00 31.70 | SOS |
| ATOM | 1799 | O | PRO | 819 | 56.172 | 42.667 | 61.622 | 1.00 39.13 | SOS |
| ATOM | 1800 | N | ASN | 820 | 56.349 | 41.824 | 59.553 | 1.00 30.62 | SOS |
| ATOM | 1801 | CA | ASN | 820 | 56.165 | 40.445 | 60.014 | 1.00 31.72 | SOS |
| ATOM | 1802 | CB | ASN | 820 | 55.672 | 39.545 | 58.878 | 1.00 32.23 | SOS |
| ATOM | 1803 | CG | ASN | 820 | 54.338 | 39.980 | 58.332 | 1.00 30.27 | SOS |
| ATOM | 1804 | OD1 | ASN | 820 | 53.345 | 40.036 | 59.057 | 1.00 27.88 | SOS |
| ATOM | 1805 | ND2 | ASN | 820 | 54.304 | 40.291 | 57.045 | 1.00 29.05 | SOS |
| ATOM | 1806 | C | ASN | 820 | 57.439 | 39.862 | 60.605 | 1.00 31.97 | SOS |
| ATOM | 1807 | O | ASN | 820 | 57.390 | 39.126 | 61.590 | 1.00 34.79 | SOS |
| ATOM | 1808 | N | LEU | 821 | 58.567 | 40.173 | 59.972 | 1.00 28.78 | SOS |
| ATOM | 1809 | CA | LEU | 821 | 59.878 | 39.714 | 60.406 | 1.00 28.17 | SOS |
| ATOM | 1810 | CB | LEU | 821 | 60.947 | 40.268 | 59.469 | 1.00 25.69 | SOS |
| ATOM | 1811 | CG | LEU | 821 | 62.231 | 39.483 | 59.225 | 1.00 26.93 | SOS |
| ATOM | 1812 | CD1 | LEU | 821 | 63.398 | 40.447 | 59.234 | 1.00 23.48 | SOS |
| ATOM | 1813 | CD2 | LEU | 821 | 62.420 | 38.387 | 60.257 | 1.00 27.27 | SOS |
| ATOM | 1814 | C | LEU | 821 | 60.156 | 40.219 | 61.818 | 1.00 32.63 | SOS |
| ATOM | 1815 | O | LEU | 821 | 60.492 | 39.440 | 62.718 | 1.00 35.85 | SOS |
| ATOM | 1816 | N | LEU | 822 | 59.990 | 41.525 | 62.006 | 1.00 31.78 | SOS |
| ATOM | 1817 | CA | LEU | 822 | 60.230 | 42.159 | 63.298 | 1.00 32.96 | SOS |
| ATOM | 1818 | CB | LEU | 822 | 60.155 | 43.682 | 63.147 | 1.00 26.37 | SOS |
| ATOM | 1819 | CG | LEU | 822 | 61.188 | 44.237 | 62.151 | 1.00 27.51 | SOS |
| ATOM | 1820 | CD1 | LEU | 822 | 60.863 | 45.662 | 61.751 | 1.00 24.75 | SOS |
| ATOM | 1821 | CD2 | LEU | 822 | 62.571 | 44.157 | 62.748 | 1.00 20.00 | SOS |
| ATOM | 1822 | C | LEU | 822 | 59.278 | 41.647 | 64.384 | 1.00 33.18 | SOS |
| ATOM | 1823 | O | LEU | 822 | 59.655 | 41.498 | 65.547 | 1.00 31.42 | SOS |
| ATOM | 1824 | N | LYS | 823 | 58.062 | 41.316 | 63.982 | 1.00 33.83 | SOS |
| ATOM | 1825 | CA | LYS | 823 | 57.061 | 40.816 | 64.910 | 1.00 36.85 | SOS |
| ATOM | 1826 | CB | LYS | 823 | 55.708 | 40.740 | 64.194 | 1.00 40.57 | SOS |
| ATOM | 1827 | CG | LYS | 823 | 54.485 | 40.700 | 65.089 | 1.00 47.70 | SOS |
| ATOM | 1828 | CD | LYS | 823 | 53.248 | 41.222 | 64.334 | 1.00 55.15 | SOS |
| ATOM | 1829 | CE | LYS | 823 | 53.451 | 42.678 | 63.854 | 1.00 59.01 | SOS |
| ATOM | 1830 | NZ | LYS | 823 | 52.225 | 43.354 | 63.323 | 1.00 54.77 | SOS |
| ATOM | 1831 | C | LYS | 823 | 57.497 | 39.438 | 65.399 | 1.00 35.91 | SOS |
| ATOM | 1832 | O | LYS | 823 | 57.255 | 39.069 | 66.547 | 1.00 35.24 | SOS |
| ATOM | 1833 | N | MET | 824 | 58.179 | 38.703 | 64.524 | 1.00 36.31 | SOS |
| ATOM | 1834 | CA | MET | 824 | 58.654 | 37.360 | 64.839 | 1.00 35.97 | SOS |
| ATOM | 1835 | CB | MET | 824 | 58.956 | 36.597 | 63.548 | 1.00 36.40 | SOS |
| ATOM | 1836 | CG | MET | 824 | 59.380 | 35.151 | 63.733 | 1.00 35.54 | SOS |
| ATOM | 1837 | SD | MET | 824 | 61.144 | 35.067 | 63.983 | 1.00 50.50 | SOS |
| ATOM | 1838 | CE | MET | 824 | 61.739 | 35.718 | 62.410 | 1.00 36.08 | SOS |
| ATOM | 1839 | C | MET | 824 | 59.871 | 37.421 | 65.751 | 1.00 33.11 | SOS |
| ATOM | 1840 | O | MET | 824 | 59.914 | 36.757 | 66.785 | 1.00 32.16 | SOS |
| ATOM | 1841 | N | ILE | 825 | 60.829 | 38.270 | 65.390 | 1.00 33.02 | SOS |
| ATOM | 1842 | CA | ILE | 825 | 62.032 | 38.439 | 66.188 | 1.00 29.23 | SOS |
| ATOM | 1843 | CB | ILE | 825 | 63.060 | 39.324 | 65.487 | 1.00 27.67 | SOS |
| ATOM | 1844 | CG2 | ILE | 825 | 64.363 | 39.289 | 66.262 | 1.00 24.70 | SOS |
| ATOM | 1845 | CG1 | ILE | 825 | 63.312 | 38.800 | 64.068 | 1.00 25.91 | SOS |
| ATOM | 1846 | CD1 | ILE | 825 | 64.310 | 39.608 | 63.264 | 1.00 20.47 | SOS |
| ATOM | 1847 | C | ILE | 825 | 61.698 | 39.000 | 67.568 | 1.00 28.60 | SOS |
| ATOM | 1848 | O | ILE | 825 | 62.249 | 38.547 | 68.573 | 1.00 32.93 | SOS |
| ATOM | 1849 | N | ARG | 826 | 60.763 | 39.944 | 67.631 | 1.00 26.29 | SOS |
| ATOM | 1850 | CA | ARG | 826 | 60.359 | 40.510 | 68.915 | 1.00 24.09 | SOS |
| ATOM | 1851 | CB | ARG | 826 | 59.478 | 41.739 | 68.728 | 1.00 15.92 | SOS |
| ATOM | 1852 | CG | ARG | 826 | 60.314 | 42.939 | 68.361 | 1.00 26.19 | SOS |
| ATOM | 1853 | CD | ARG | 826 | 59.600 | 43.924 | 67.494 | 1.00 25.33 | SOS |
| ATOM | 1854 | NE | ARG | 826 | 60.530 | 44.949 | 67.043 | 1.00 28.97 | SOS |
| ATOM | 1855 | CZ | ARG | 826 | 60.208 | 45.932 | 66.207 | 1.00 33.48 | SOS |
| ATOM | 1856 | NH1 | ARG | 826 | 58.971 | 46.011 | 65.727 | 1.00 26.29 | SOS |
| ATOM | 1857 | NH2 | ARG | 826 | 61.119 | 46.846 | 65.872 | 1.00 25.52 | SOS |

Figure 8-32

| | | | | | | | | | | |
|---|---|---|---|---|---|---|---|---|---|---|
| ATOM | 1858 | C | ARG | 826 | 59.725 | 39.497 | 69.858 | 1.00 | 25.27 | sos |
| ATOM | 1859 | O | ARG | 826 | 59.831 | 39.651 | 71.071 | 1.00 | 28.85 | sos |
| ATOM | 1860 | N | HIS | 827 | 59.098 | 38.456 | 69.303 | 1.00 | 28.80 | sos |
| ATOM | 1861 | CA | HIS | 827 | 58.488 | 37.383 | 70.100 | 1.00 | 28.18 | sos |
| ATOM | 1862 | CB | HIS | 827 | 57.611 | 36.475 | 69.228 | 1.00 | 26.35 | sos |
| ATOM | 1863 | CG | HIS | 827 | 57.200 | 35.191 | 69.895 | 1.00 | 25.10 | sos |
| ATOM | 1864 | CD2 | HIS | 827 | 57.776 | 33.965 | 69.899 | 1.00 | 19.17 | sos |
| ATOM | 1865 | ND1 | HIS | 827 | 56.038 | 35.068 | 70.633 | 1.00 | 26.75 | sos |
| ATOM | 1866 | CE1 | HIS | 827 | 55.914 | 33.822 | 71.054 | 1.00 | 19.14 | sos |
| ATOM | 1867 | NE2 | HIS | 827 | 56.957 | 33.132 | 70.623 | 1.00 | 22.09 | sos |
| ATOM | 1868 | C | HIS | 827 | 59.618 | 36.547 | 70.682 | 1.00 | 28.25 | sos |
| ATOM | 1869 | O | HIS | 827 | 59.594 | 36.199 | 71.861 | 1.00 | 28.05 | sos |
| ATOM | 1870 | N | THR | 828 | 60.588 | 36.205 | 69.837 | 1.00 | 24.01 | sos |
| ATOM | 1871 | CA | THR | 828 | 61.724 | 35.408 | 70.269 | 1.00 | 27.74 | sos |
| ATOM | 1872 | CB | THR | 828 | 62.716 | 35.179 | 69.107 | 1.00 | 25.58 | sos |
| ATOM | 1873 | OG1 | THR | 828 | 62.088 | 34.387 | 68.098 | 1.00 | 30.68 | sos |
| ATOM | 1874 | CG2 | THR | 828 | 63.947 | 34.456 | 69.580 | 1.00 | 25.91 | sos |
| ATOM | 1875 | C | THR | 828 | 62.419 | 36.115 | 71.432 | 1.00 | 31.88 | sos |
| ATOM | 1876 | O | THR | 828 | 62.643 | 35.519 | 72.492 | 1.00 | 32.90 | sos |
| ATOM | 1877 | N | THR | 829 | 62.688 | 37.406 | 71.246 | 1.00 | 32.17 | sos |
| ATOM | 1878 | CA | THR | 829 | 63.342 | 38.219 | 72.261 | 1.00 | 29.05 | sos |
| ATOM | 1879 | CB | THR | 829 | 63.540 | 39.661 | 71.762 | 1.00 | 23.49 | sos |
| ATOM | 1880 | OG1 | THR | 829 | 64.457 | 39.657 | 70.665 | 1.00 | 33.39 | sos |
| ATOM | 1881 | CG2 | THR | 829 | 64.099 | 40.543 | 72.858 | 1.00 | 12.28 | sos |
| ATOM | 1882 | C | THR | 829 | 62.510 | 38.241 | 73.534 | 1.00 | 31.45 | sos |
| ATOM | 1883 | O | THR | 829 | 63.028 | 38.083 | 74.641 | 1.00 | 34.90 | sos |
| ATOM | 1884 | N | ASN | 830 | 61.206 | 38.386 | 73.362 | 1.00 | 28.56 | sos |
| ATOM | 1885 | CA | ASN | 830 | 60.292 | 38.448 | 74.482 | 1.00 | 29.34 | sos |
| ATOM | 1886 | CB | ASN | 830 | 58.875 | 38.666 | 73.974 | 1.00 | 32.67 | sos |
| ATOM | 1887 | CG | ASN | 830 | 58.178 | 39.783 | 74.681 | 1.00 | 37.22 | sos |
| ATOM | 1888 | OD1 | ASN | 830 | 57.084 | 39.600 | 75.210 | 1.00 | 46.40 | sos |
| ATOM | 1889 | ND2 | ASN | 830 | 58.798 | 40.960 | 74.690 | 1.00 | 37.01 | sos |
| ATOM | 1890 | C | ASN | 830 | 60.337 | 37.190 | 75.310 | 1.00 | 30.76 | sos |
| ATOM | 1891 | O | ASN | 830 | 60.269 | 37.248 | 76.537 | 1.00 | 32.53 | sos |
| ATOM | 1892 | N | LEU | 831 | 60.445 | 36.045 | 74.646 | 1.00 | 32.45 | sos |
| ATOM | 1893 | CA | LEU | 831 | 60.473 | 34.799 | 75.379 | 1.00 | 34.32 | sos |
| ATOM | 1894 | CB | LEU | 831 | 59.978 | 33.627 | 74.545 | 1.00 | 36.69 | sos |
| ATOM | 1895 | CG | LEU | 831 | 58.562 | 33.379 | 75.060 | 1.00 | 38.32 | sos |
| ATOM | 1896 | CD1 | LEU | 831 | 57.540 | 34.044 | 74.156 | 1.00 | 34.85 | sos |
| ATOM | 1897 | CD2 | LEU | 831 | 58.319 | 31.911 | 75.195 | 1.00 | 38.04 | sos |
| ATOM | 1898 | C | LEU | 831 | 61.790 | 34.512 | 76.039 | 1.00 | 35.08 | sos |
| ATOM | 1899 | O | LEU | 831 | 61.813 | 34.036 | 77.175 | 1.00 | 39.64 | sos |
| ATOM | 1900 | N | THR | 832 | 62.885 | 34.825 | 75.354 | 1.00 | 30.32 | sos |
| ATOM | 1901 | CA | THR | 832 | 64.196 | 34.628 | 75.941 | 1.00 | 27.71 | sos |
| ATOM | 1902 | CB | THR | 832 | 65.284 | 35.170 | 75.042 | 1.00 | 26.29 | sos |
| ATOM | 1903 | OG1 | THR | 832 | 65.359 | 34.379 | 73.853 | 1.00 | 33.60 | sos |
| ATOM | 1904 | CG2 | THR | 832 | 66.615 | 35.129 | 75.749 | 1.00 | 32.62 | sos |
| ATOM | 1905 | C | THR | 832 | 64.210 | 35.406 | 77.261 | 1.00 | 32.07 | sos |
| ATOM | 1906 | O | THR | 832 | 64.570 | 34.862 | 78.306 | 1.00 | 36.74 | sos |
| ATOM | 1907 | N | LEU | 833 | 63.715 | 36.643 | 77.221 | 1.00 | 30.92 | sos |
| ATOM | 1908 | CA | LEU | 833 | 63.666 | 37.495 | 78.401 | 1.00 | 27.97 | sos |
| ATOM | 1909 | CB | LEU | 833 | 63.318 | 38.938 | 78.023 | 1.00 | 26.95 | sos |
| ATOM | 1910 | CG | LEU | 833 | 64.355 | 39.680 | 77.157 | 1.00 | 31.77 | sos |
| ATOM | 1911 | CD1 | LEU | 833 | 63.895 | 41.095 | 76.871 | 1.00 | 22.17 | sos |
| ATOM | 1912 | CD2 | LEU | 833 | 65.718 | 39.699 | 77.836 | 1.00 | 25.40 | sos |
| ATOM | 1913 | C | LEU | 833 | 62.723 | 36.997 | 79.488 | 1.00 | 30.66 | sos |
| ATOM | 1914 | O | LEU | 833 | 63.033 | 37.126 | 80.675 | 1.00 | 31.68 | sos |
| ATOM | 1915 | N | TRP | 834 | 61.583 | 36.425 | 79.102 | 1.00 | 30.81 | sos |
| ATOM | 1916 | CA | TRP | 834 | 60.624 | 35.932 | 80.093 | 1.00 | 30.70 | sos |
| ATOM | 1917 | CB | TRP | 834 | 59.306 | 35.560 | 79.419 | 1.00 | 25.41 | sos |
| ATOM | 1918 | CG | TRP | 834 | 58.271 | 34.924 | 80.315 | 1.00 | 23.44 | sos |

Figure 8-33

| | | | | | | | | | |
|---|---|---|---|---|---|---|---|---|---|
| ATOM | 1919 | CD2 | TRP | 834 | 57.846 | 33.555 | 80.289 | 1.00 22.03 | SOS |
| ATOM | 1920 | CE2 | TRP | 834 | 56.776 | 33.428 | 81.205 | 1.00 24.35 | SOS |
| ATOM | 1921 | CE3 | TRP | 834 | 58.260 | 32.423 | 79.573 | 1.00 22.65 | SOS |
| ATOM | 1922 | CD1 | TRP | 834 | 57.477 | 35.550 | 81.234 | 1.00 26.60 | SOS |
| ATOM | 1923 | NE1 | TRP | 834 | 56.568 | 34.659 | 81.772 | 1.00 24.40 | SOS |
| ATOM | 1924 | CZ2 | TRP | 834 | 56.114 | 32.214 | 81.420 | 1.00 21.70 | SOS |
| ATOM | 1925 | CZ3 | TRP | 834 | 57.601 | 31.214 | 79.789 | 1.00 19.58 | SOS |
| ATOM | 1926 | CH2 | TRP | 834 | 56.540 | 31.123 | 80.705 | 1.00 21.38 | SOS |
| ATOM | 1927 | C | TRP | 834 | 61.211 | 34.748 | 80.869 | 1.00 35.00 | SOS |
| ATOM | 1928 | O | TRP | 834 | 60.957 | 34.590 | 82.067 | 1.00 32.32 | SOS |
| ATOM | 1929 | N | PHE | 835 | 62.018 | 33.938 | 80.183 | 1.00 35.45 | SOS |
| ATOM | 1930 | CA | PHE | 835 | 62.664 | 32.791 | 80.806 | 1.00 31.64 | SOS |
| ATOM | 1931 | CB | PHE | 835 | 63.365 | 31.929 | 79.753 | 1.00 31.85 | SOS |
| ATOM | 1932 | CG | PHE | 835 | 62.427 | 31.052 | 78.957 | 1.00 31.11 | SOS |
| ATOM | 1933 | CD1 | PHE | 835 | 62.640 | 30.831 | 77.602 | 1.00 31.59 | SOS |
| ATOM | 1934 | CD2 | PHE | 835 | 61.331 | 30.447 | 79.564 | 1.00 28.75 | SOS |
| ATOM | 1935 | CE1 | PHE | 835 | 61.770 | 30.018 | 76.860 | 1.00 31.83 | SOS |
| ATOM | 1936 | CE2 | PHE | 835 | 60.460 | 29.633 | 78.830 | 1.00 31.83 | SOS |
| ATOM | 1937 | CZ | PHE | 835 | 60.681 | 29.421 | 77.477 | 1.00 26.83 | SOS |
| ATOM | 1938 | C | PHE | 835 | 63.662 | 33.302 | 81.843 | 1.00 32.86 | SOS |
| ATOM | 1939 | O | PHE | 835 | 63.677 | 32.837 | 82.986 | 1.00 34.48 | SOS |
| ATOM | 1940 | N | GLU | 836 | 64.456 | 34.299 | 81.458 | 1.00 28.18 | SOS |
| ATOM | 1941 | CA | GLU | 836 | 65.433 | 34.889 | 82.365 | 1.00 23.70 | SOS |
| ATOM | 1942 | CB | GLU | 836 | 66.206 | 36.004 | 81.668 | 1.00 20.91 | SOS |
| ATOM | 1943 | CG | GLU | 836 | 67.080 | 35.530 | 80.526 | 1.00 20.46 | SOS |
| ATOM | 1944 | CD | GLU | 836 | 67.789 | 36.662 | 79.825 | 1.00 21.62 | SOS |
| ATOM | 1945 | OE1 | GLU | 836 | 67.921 | 37.755 | 80.419 | 1.00 26.46 | SOS |
| ATOM | 1946 | OE2 | GLU | 836 | 68.229 | 36.461 | 78.673 | 1.00 28.51 | SOS |
| ATOM | 1947 | C | GLU | 836 | 64.738 | 35.456 | 83.592 | 1.00 25.88 | SOS |
| ATOM | 1948 | O | GLU | 836 | 65.141 | 35.183 | 84.719 | 1.00 26.09 | SOS |
| ATOM | 1949 | N | LYS | 837 | 63.675 | 36.224 | 83.362 | 1.00 27.21 | SOS |
| ATOM | 1950 | CA | LYS | 837 | 62.906 | 36.848 | 84.435 | 1.00 29.26 | SOS |
| ATOM | 1951 | CB | LYS | 837 | 61.820 | 37.739 | 83.828 | 1.00 33.52 | SOS |
| ATOM | 1952 | CG | LYS | 837 | 60.833 | 38.395 | 84.790 | 1.00 29.02 | SOS |
| ATOM | 1953 | CD | LYS | 837 | 60.058 | 39.464 | 84.019 | 1.00 31.57 | SOS |
| ATOM | 1954 | CE | LYS | 837 | 58.772 | 39.895 | 84.705 | 1.00 32.59 | SOS |
| ATOM | 1955 | NZ | LYS | 837 | 59.014 | 40.772 | 85.863 | 1.00 38.47 | SOS |
| ATOM | 1956 | C | LYS | 837 | 62.303 | 35.813 | 85.375 | 1.00 33.96 | SOS |
| ATOM | 1957 | O | LYS | 837 | 62.309 | 36.003 | 86.589 | 1.00 33.19 | SOS |
| ATOM | 1958 | N | CYS | 838 | 61.810 | 34.707 | 84.815 | 1.00 36.32 | SOS |
| ATOM | 1959 | CA | CYS | 838 | 61.224 | 33.635 | 85.623 | 1.00 35.53 | SOS |
| ATOM | 1960 | CB | CYS | 838 | 60.603 | 32.542 | 84.743 | 1.00 35.79 | SOS |
| ATOM | 1961 | SG | CYS | 838 | 59.084 | 33.032 | 83.882 | 1.00 40.27 | SOS |
| ATOM | 1962 | C | CYS | 838 | 62.291 | 33.022 | 86.516 | 1.00 35.04 | SOS |
| ATOM | 1963 | O | CYS | 838 | 62.066 | 32.816 | 87.706 | 1.00 37.06 | SOS |
| ATOM | 1964 | N | ILE | 839 | 63.459 | 32.757 | 85.940 | 1.00 29.20 | SOS |
| ATOM | 1965 | CA | ILE | 839 | 64.566 | 32.171 | 86.685 | 1.00 29.27 | SOS |
| ATOM | 1966 | CB | ILE | 839 | 65.758 | 31.856 | 85.744 | 1.00 23.78 | SOS |
| ATOM | 1967 | CG2 | ILE | 839 | 66.995 | 31.500 | 86.545 | 1.00 17.80 | SOS |
| ATOM | 1968 | CG1 | ILE | 839 | 65.391 | 30.736 | 84.781 | 1.00 20.67 | SOS |
| ATOM | 1969 | CD1 | ILE | 839 | 66.457 | 30.465 | 83.739 | 1.00 29.40 | SOS |
| ATOM | 1970 | C | ILE | 839 | 65.057 | 33.120 | 87.774 | 1.00 31.40 | SOS |
| ATOM | 1971 | O | ILE | 839 | 64.945 | 32.852 | 88.969 | 1.00 32.73 | SOS |
| ATOM | 1972 | N | VAL | 840 | 65.590 | 34.245 | 87.326 | 1.00 33.52 | SOS |
| ATOM | 1973 | CA | VAL | 840 | 66.154 | 35.262 | 88.190 | 1.00 30.76 | SOS |
| ATOM | 1974 | CB | VAL | 840 | 66.816 | 36.345 | 87.317 | 1.00 27.16 | SOS |
| ATOM | 1975 | CG1 | VAL | 840 | 66.844 | 37.661 | 88.001 | 1.00 28.37 | SOS |
| ATOM | 1976 | CG2 | VAL | 840 | 68.210 | 35.904 | 86.942 | 1.00 16.52 | SOS |
| ATOM | 1977 | C | VAL | 840 | 65.216 | 35.832 | 89.255 | 1.00 31.26 | SOS |
| ATOM | 1978 | O | VAL | 840 | 65.680 | 36.225 | 90.318 | 1.00 35.24 | SOS |
| ATOM | 1979 | N | GLU | 841 | 63.912 | 35.885 | 88.990 | 1.00 30.34 | SOS |

Figure 8-34

| | | | | | | | | | |
|---|---|---|---|---|---|---|---|---|---|
| ATOM | 1980 | CA | GLU | 841 | 62.980 | 36.388 | 90.005 | 1.00 29.58 | SOS |
| ATOM | 1981 | CB | GLU | 841 | 61.784 | 37.122 | 89.396 | 1.00 25.11 | SOS |
| ATOM | 1982 | CG | GLU | 841 | 62.115 | 38.446 | 88.714 | 1.00 28.61 | SOS |
| ATOM | 1983 | CD | GLU | 841 | 60.870 | 39.229 | 88.310 | 1.00 30.25 | SOS |
| ATOM | 1984 | OE1 | GLU | 841 | 59.769 | 38.640 | 88.237 | 1.00 28.99 | SOS |
| ATOM | 1985 | OE2 | GLU | 841 | 60.994 | 40.444 | 88.065 | 1.00 31.14 | SOS |
| ATOM | 1986 | C | GLU | 841 | 62.485 | 35.276 | 90.924 | 1.00 30.21 | SOS |
| ATOM | 1987 | O | GLU | 841 | 61.559 | 35.485 | 91.704 | 1.00 35.34 | SOS |
| ATOM | 1988 | N | THR | 842 | 63.029 | 34.072 | 90.760 | 1.00 32.01 | SOS |
| ATOM | 1989 | CA | THR | 842 | 62.672 | 32.951 | 91.626 | 1.00 36.71 | SOS |
| ATOM | 1990 | CB | THR | 842 | 62.516 | 31.612 | 90.867 | 1.00 37.24 | SOS |
| ATOM | 1991 | OG1 | THR | 842 | 61.476 | 31.731 | 89.889 | 1.00 42.01 | SOS |
| ATOM | 1992 | CG2 | THR | 842 | 62.127 | 30.513 | 91.831 | 1.00 34.88 | SOS |
| ATOM | 1993 | C | THR | 842 | 63.846 | 32.899 | 92.598 | 1.00 39.17 | SOS |
| ATOM | 1994 | O | THR | 842 | 64.874 | 32.237 | 92.359 | 1.00 33.40 | SOS |
| ATOM | 1995 | N | GLU | 843 | 63.691 | 33.687 | 93.658 | 1.00 40.56 | SOS |
| ATOM | 1996 | CA | GLU | 843 | 64.699 | 33.855 | 94.686 | 1.00 42.29 | SOS |
| ATOM | 1997 | CB | GLU | 843 | 64.331 | 35.066 | 95.534 | 1.00 45.77 | SOS |
| ATOM | 1998 | CG | GLU | 843 | 64.451 | 36.350 | 94.720 | 1.00 53.23 | SOS |
| ATOM | 1999 | CD | GLU | 843 | 63.598 | 37.497 | 95.229 | 1.00 58.13 | SOS |
| ATOM | 2000 | OE1 | GLU | 843 | 63.747 | 37.885 | 96.410 | 1.00 62.75 | SOS |
| ATOM | 2001 | OE2 | GLU | 843 | 62.799 | 38.033 | 94.425 | 1.00 54.53 | SOS |
| ATOM | 2002 | C | GLU | 843 | 65.079 | 32.636 | 95.517 | 1.00 40.90 | SOS |
| ATOM | 2003 | O | GLU | 843 | 66.241 | 32.477 | 95.876 | 1.00 40.87 | SOS |
| ATOM | 2004 | N | ASN | 844 | 64.122 | 31.754 | 95.778 | 1.00 39.33 | SOS |
| ATOM | 2005 | CA | ASN | 844 | 64.402 | 30.546 | 96.542 | 1.00 38.63 | SOS |
| ATOM | 2006 | CB | ASN | 844 | 63.094 | 29.939 | 97.051 | 1.00 39.14 | SOS |
| ATOM | 2007 | CG | ASN | 844 | 63.312 | 28.702 | 97.909 | 1.00 43.31 | SOS |
| ATOM | 2008 | OD1 | ASN | 844 | 63.437 | 27.590 | 97.393 | 1.00 42.23 | SOS |
| ATOM | 2009 | ND2 | ASN | 844 | 63.352 | 28.892 | 99.225 | 1.00 38.54 | SOS |
| ATOM | 2010 | C | ASN | 844 | 65.142 | 29.547 | 95.643 | 1.00 39.94 | SOS |
| ATOM | 2011 | O | ASN | 844 | 64.644 | 29.177 | 94.582 | 1.00 47.06 | SOS |
| ATOM | 2012 | N | LEU | 845 | 66.313 | 29.094 | 96.081 | 1.00 38.22 | SOS |
| ATOM | 2013 | CA | LEU | 845 | 67.126 | 28.151 | 95.314 | 1.00 36.15 | SOS |
| ATOM | 2014 | CB | LEU | 845 | 68.375 | 27.764 | 96.097 | 1.00 29.74 | SOS |
| ATOM | 2015 | CG | LEU | 845 | 69.338 | 26.855 | 95.340 | 1.00 28.22 | SOS |
| ATOM | 2016 | CD1 | LEU | 845 | 69.798 | 27.555 | 94.089 | 1.00 34.44 | SOS |
| ATOM | 2017 | CD2 | LEU | 845 | 70.523 | 26.502 | 96.193 | 1.00 30.09 | SOS |
| ATOM | 2018 | C | LEU | 845 | 66.400 | 26.882 | 94.875 | 1.00 39.08 | SOS |
| ATOM | 2019 | O | LEU | 845 | 66.579 | 26.425 | 93.749 | 1.00 39.10 | SOS |
| ATOM | 2020 | N | GLU | 846 | 65.609 | 26.295 | 95.767 | 1.00 42.21 | SOS |
| ATOM | 2021 | CA | GLU | 846 | 64.880 | 25.076 | 95.429 | 1.00 47.26 | SOS |
| ATOM | 2022 | CB | GLU | 846 | 64.123 | 24.539 | 96.648 | 1.00 51.32 | SOS |
| ATOM | 2023 | CG | GLU | 846 | 63.369 | 23.248 | 96.375 | 1.00 60.88 | SOS |
| ATOM | 2024 | CD | GLU | 846 | 62.396 | 22.873 | 97.479 | 1.00 68.19 | SOS |
| ATOM | 2025 | OE1 | GLU | 846 | 61.668 | 23.764 | 97.980 | 1.00 72.90 | SOS |
| ATOM | 2026 | OE2 | GLU | 846 | 62.349 | 21.676 | 97.832 | 1.00 70.29 | SOS |
| ATOM | 2027 | C | GLU | 846 | 63.910 | 25.348 | 94.275 | 1.00 46.86 | SOS |
| ATOM | 2028 | O | GLU | 846 | 63.937 | 24.664 | 93.243 | 1.00 48.77 | SOS |
| ATOM | 2029 | N | GLU | 847 | 63.088 | 26.377 | 94.435 | 1.00 42.40 | SOS |
| ATOM | 2030 | CA | GLU | 847 | 62.130 | 26.741 | 93.409 | 1.00 41.25 | SOS |
| ATOM | 2031 | CB | GLU | 847 | 61.232 | 27.885 | 93.893 | 1.00 40.22 | SOS |
| ATOM | 2032 | CG | GLU | 847 | 60.477 | 27.600 | 95.194 | 1.00 38.69 | SOS |
| ATOM | 2033 | CD | GLU | 847 | 59.528 | 28.723 | 95.598 | 1.00 44.00 | SOS |
| ATOM | 2034 | OE1 | GLU | 847 | 59.879 | 29.917 | 95.431 | 1.00 43.40 | SOS |
| ATOM | 2035 | OE2 | GLU | 847 | 58.423 | 28.407 | 96.093 | 1.00 46.97 | SOS |
| ATOM | 2036 | C | GLU | 847 | 62.834 | 27.130 | 92.105 | 1.00 42.35 | SOS |
| ATOM | 2037 | O | GLU | 847 | 62.375 | 26.761 | 91.016 | 1.00 40.50 | SOS |
| ATOM | 2038 | N | ARG | 848 | 63.960 | 27.841 | 92.210 | 1.00 38.50 | SOS |
| ATOM | 2039 | CA | ARG | 848 | 64.694 | 28.261 | 91.015 | 1.00 36.05 | SOS |
| ATOM | 2040 | CB | ARG | 848 | 65.856 | 29.189 | 91.367 | 1.00 35.14 | SOS |

Figure 8-35

```
ATOM   2041  CG   ARG  848   66.517  29.876  90.154  1.00  34.45   SOS
ATOM   2042  CD   ARG  848   67.784  30.610  90.569  1.00  31.04   SOS
ATOM   2043  NE   ARG  848   67.549  31.275  91.840  1.00  37.94   SOS
ATOM   2044  CZ   ARG  848   68.424  31.339  92.834  1.00  41.45   SOS
ATOM   2045  NH1  ARG  848   69.631  30.794  92.712  1.00  35.83   SOS
ATOM   2046  NH2  ARG  848   68.047  31.875  93.985  1.00  42.13   SOS
ATOM   2047  C    ARG  848   65.207  27.058  90.232  1.00  35.50   SOS
ATOM   2048  O    ARG  848   65.208  27.071  89.001  1.00  36.01   SOS
ATOM   2049  N    VAL  849   65.651  26.027  90.945  1.00  34.15   SOS
ATOM   2050  CA   VAL  849   66.140  24.815  90.297  1.00  34.10   SOS
ATOM   2051  CB   VAL  849   66.777  23.840  91.324  1.00  33.20   SOS
ATOM   2052  CG1  VAL  849   67.034  22.486  90.692  1.00  29.35   SOS
ATOM   2053  CG2  VAL  849   68.089  24.414  91.824  1.00  30.55   SOS
ATOM   2054  C    VAL  849   64.966  24.165  89.559  1.00  32.68   SOS
ATOM   2055  O    VAL  849   65.121  23.683  88.439  1.00  30.36   SOS
ATOM   2056  N    ALA  850   63.781  24.233  90.164  1.00  31.24   SOS
ATOM   2057  CA   ALA  850   62.567  23.687  89.563  1.00  33.61   SOS
ATOM   2058  CB   ALA  850   61.411  23.774  90.548  1.00  29.99   SOS
ATOM   2059  C    ALA  850   62.222  24.455  88.285  1.00  36.10   SOS
ATOM   2060  O    ALA  850   61.820  23.866  87.278  1.00  40.05   SOS
ATOM   2061  N    VAL  851   62.385  25.775  88.340  1.00  37.33   SOS
ATOM   2062  CA   VAL  851   62.108  26.647  87.206  1.00  32.56   SOS
ATOM   2063  CB   VAL  851   62.163  28.149  87.621  1.00  31.27   SOS
ATOM   2064  CG1  VAL  851   62.147  29.052  86.399  1.00  28.67   SOS
ATOM   2065  CG2  VAL  851   60.995  28.488  88.529  1.00  22.62   SOS
ATOM   2066  C    VAL  851   63.087  26.374  86.072  1.00  32.50   SOS
ATOM   2067  O    VAL  851   62.678  26.236  84.919  1.00  37.99   SOS
ATOM   2068  N    VAL  852   64.371  26.266  86.392  1.00  30.98   SOS
ATOM   2069  CA   VAL  852   65.371  26.010  85.353  1.00  33.50   SOS
ATOM   2070  CB   VAL  852   66.826  26.111  85.883  1.00  30.46   SOS
ATOM   2071  CG1  VAL  852   67.826  25.747  84.790  1.00  20.81   SOS
ATOM   2072  CG2  VAL  852   67.098  27.526  86.357  1.00  33.84   SOS
ATOM   2073  C    VAL  852   65.157  24.646  84.740  1.00  34.08   SOS
ATOM   2074  O    VAL  852   65.465  24.430  83.571  1.00  33.03   SOS
ATOM   2075  N    SER  853   64.573  23.745  85.522  1.00  38.05   SOS
ATOM   2076  CA   SER  853   64.319  22.394  85.052  1.00  38.86   SOS
ATOM   2077  CB   SER  853   64.051  21.464  86.224  1.00  41.62   SOS
ATOM   2078  OG   SER  853   64.460  20.152  85.903  1.00  50.46   SOS
ATOM   2079  C    SER  853   63.196  22.307  84.012  1.00  39.97   SOS
ATOM   2080  O    SER  853   63.382  21.638  82.995  1.00  38.79   SOS
ATOM   2081  N    ARG  854   62.060  22.985  84.236  1.00  37.55   SOS
ATOM   2082  CA   ARG  854   60.955  22.950  83.258  1.00  39.20   SOS
ATOM   2083  CB   ARG  854   59.752  23.801  83.666  1.00  39.15   SOS
ATOM   2084  CG   ARG  854   58.982  23.342  84.846  1.00  41.78   SOS
ATOM   2085  CD   ARG  854   58.219  22.045  84.653  1.00  32.23   SOS
ATOM   2086  NE   ARG  854   57.719  21.678  85.975  1.00  29.72   SOS
ATOM   2087  CZ   ARG  854   56.557  22.084  86.471  1.00  32.83   SOS
ATOM   2088  NH1  ARG  854   55.746  22.832  85.735  1.00  31.78   SOS
ATOM   2089  NH2  ARG  854   56.280  21.890  87.755  1.00  37.02   SOS
ATOM   2090  C    ARG  854   61.434  23.529  81.953  1.00  39.16   SOS
ATOM   2091  O    ARG  854   61.097  23.027  80.883  1.00  42.76   SOS
ATOM   2092  N    ILE  855   62.175  24.628  82.047  1.00  35.91   SOS
ATOM   2093  CA   ILE  855   62.683  25.281  80.858  1.00  32.95   SOS
ATOM   2094  CB   ILE  855   63.430  26.584  81.203  1.00  28.30   SOS
ATOM   2095  CG2  ILE  855   63.930  27.267  79.945  1.00  21.69   SOS
ATOM   2096  CG1  ILE  855   62.474  27.535  81.924  1.00  28.28   SOS
ATOM   2097  CD1  ILE  855   63.109  28.846  82.326  1.00  30.15   SOS
ATOM   2098  C    ILE  855   63.530  24.306  80.041  1.00  33.53   SOS
ATOM   2099  O    ILE  855   63.375  24.237  78.825  1.00  37.56   SOS
ATOM   2100  N    ILE  856   64.360  23.501  80.702  1.00  30.79   SOS
ATOM   2101  CA   ILE  856   65.167  22.526  79.972  1.00  33.67   SOS
```

Figure 8-36

```
ATOM   2102  CB   ILE  856    66.246  21.878  80.869  1.00  33.05      SOS
ATOM   2103  CG2  ILE  856    67.030  20.847  80.084  1.00  29.67      SOS
ATOM   2104  CG1  ILE  856    67.222  22.955  81.357  1.00  38.46      SOS
ATOM   2105  CD1  ILE  856    68.337  22.454  82.262  1.00  36.90      SOS
ATOM   2106  C    ILE  856    64.228  21.466  79.368  1.00  35.14      SOS
ATOM   2107  O    ILE  856    64.429  20.999  78.250  1.00  30.98      SOS
ATOM   2108  N    GLU  857    63.158  21.148  80.087  1.00  36.98      SOS
ATOM   2109  CA   GLU  857    62.187  20.184  79.601  1.00  35.90      SOS
ATOM   2110  CB   GLU  857    61.172  19.843  80.690  1.00  33.56      SOS
ATOM   2111  CG   GLU  857    61.730  18.859  81.713  1.00  39.35      SOS
ATOM   2112  CD   GLU  857    60.712  18.413  82.744  1.00  47.07      SOS
ATOM   2113  OE1  GLU  857    59.619  19.018  82.809  1.00  47.78      SOS
ATOM   2114  OE2  GLU  857    61.006  17.452  83.491  1.00  50.82      SOS
ATOM   2115  C    GLU  857    61.508  20.738  78.353  1.00  36.05      SOS
ATOM   2116  O    GLU  857    61.404  20.046  77.332  1.00  33.37      SOS
ATOM   2117  N    ILE  858    61.103  22.006  78.425  1.00  34.08      SOS
ATOM   2118  CA   ILE  858    60.470  22.680  77.298  1.00  30.12      SOS
ATOM   2119  CB   ILE  858    60.076  24.121  77.656  1.00  26.79      SOS
ATOM   2120  CG2  ILE  858    59.671  24.897  76.413  1.00  24.06      SOS
ATOM   2121  CG1  ILE  858    58.935  24.100  78.672  1.00  26.97      SOS
ATOM   2122  CD1  ILE  858    58.569  25.462  79.233  1.00  26.52      SOS
ATOM   2123  C    ILE  858    61.432  22.670  76.109  1.00  30.98      SOS
ATOM   2124  O    ILE  858    61.003  22.545  74.965  1.00  30.92      SOS
ATOM   2125  N    LEU  859    62.732  22.760  76.386  1.00  31.53      SOS
ATOM   2126  CA   LEU  859    63.733  22.734  75.321  1.00  33.51      SOS
ATOM   2127  CB   LEU  859    65.133  22.988  75.867  1.00  31.26      SOS
ATOM   2128  CG   LEU  859    66.249  22.645  74.879  1.00  32.09      SOS
ATOM   2129  CD1  LEU  859    66.329  23.716  73.826  1.00  38.72      SOS
ATOM   2130  CD2  LEU  859    67.574  22.532  75.592  1.00  40.48      SOS
ATOM   2131  C    LEU  859    63.712  21.366  74.661  1.00  37.65      SOS
ATOM   2132  O    LEU  859    63.826  21.253  73.442  1.00  39.05      SOS
ATOM   2133  N    GLN  860    63.559  20.326  75.473  1.00  40.83      SOS
ATOM   2134  CA   GLN  860    63.531  18.976  74.948  1.00  42.80      SOS
ATOM   2135  CB   GLN  860    63.466  17.954  76.076  1.00  45.25      SOS
ATOM   2136  CG   GLN  860    64.350  16.750  75.810  1.00  57.32      SOS
ATOM   2137  CD   GLN  860    63.578  15.453  75.725  1.00  63.55      SOS
ATOM   2138  OE1  GLN  860    63.044  14.965  76.732  1.00  64.50      SOS
ATOM   2139  NE2  GLN  860    63.524  14.874  74.523  1.00  61.86      SOS
ATOM   2140  C    GLN  860    62.371  18.784  73.973  1.00  42.50      SOS
ATOM   2141  O    GLN  860    62.565  18.249  72.883  1.00  41.40      SOS
ATOM   2142  N    VAL  861    61.180  19.260  74.335  1.00  39.28      SOS
ATOM   2143  CA   VAL  861    60.044  19.109  73.444  1.00  38.11      SOS
ATOM   2144  CB   VAL  861    58.713  19.435  74.120  1.00  36.20      SOS
ATOM   2145  CG1  VAL  861    57.569  19.210  73.151  1.00  27.98      SOS
ATOM   2146  CG2  VAL  861    58.523  18.554  75.318  1.00  35.63      SOS
ATOM   2147  C    VAL  861    60.230  19.960  72.197  1.00  40.53      SOS
ATOM   2148  O    VAL  861    59.779  19.579  71.117  1.00  45.33      SOS
ATOM   2149  N    PHE  862    60.913  21.094  72.335  1.00  39.26      SOS
ATOM   2150  CA   PHE  862    61.171  21.952  71.182  1.00  37.48      SOS
ATOM   2151  CB   PHE  862    61.945  23.221  71.574  1.00  37.88      SOS
ATOM   2152  CG   PHE  862    61.077  24.345  72.085  1.00  38.94      SOS
ATOM   2153  CD1  PHE  862    61.596  25.293  72.960  1.00  39.13      SOS
ATOM   2154  CD2  PHE  862    59.742  24.457  71.698  1.00  40.25      SOS
ATOM   2155  CE1  PHE  862    60.806  26.333  73.447  1.00  36.80      SOS
ATOM   2156  CE2  PHE  862    58.944  25.495  72.181  1.00  37.55      SOS
ATOM   2157  CZ   PHE  862    59.479  26.432  73.057  1.00  39.18      SOS
ATOM   2158  C    PHE  862    61.988  21.136  70.194  1.00  36.16      SOS
ATOM   2159  O    PHE  862    61.679  21.097  69.012  1.00  37.67      SOS
ATOM   2160  N    GLN  863    63.004  20.448  70.702  1.00  36.86      SOS
ATOM   2161  CA   GLN  863    63.866  19.615  69.874  1.00  39.30      SOS
ATOM   2162  CB   GLN  863    64.985  19.003  70.721  1.00  39.00      SOS
```

Figure 8-37

| | | | | | | | | | | |
|---|---|---|---|---|---|---|---|---|---|---|
| ATOM | 2163 | CG | GLN | 863 | 66.048 | 19.999 | 71.180 | 1.00 | 44.20 | SOS |
| ATOM | 2164 | CD | GLN | 863 | 67.267 | 20.031 | 70.273 | 1.00 | 42.54 | SOS |
| ATOM | 2165 | OE1 | GLN | 863 | 68.396 | 19.850 | 70.730 | 1.00 | 46.36 | SOS |
| ATOM | 2166 | NE2 | GLN | 863 | 67.043 | 20.243 | 68.982 | 1.00 | 44.21 | SOS |
| ATOM | 2167 | C | GLN | 863 | 63.067 | 18.509 | 69.185 | 1.00 | 40.12 | SOS |
| ATOM | 2168 | O | GLN | 863 | 63.319 | 18.193 | 68.016 | 1.00 | 40.63 | SOS |
| ATOM | 2169 | N | GLU | 864 | 62.110 | 17.928 | 69.911 | 1.00 | 38.70 | SOS |
| ATOM | 2170 | CA | GLU | 864 | 61.266 | 16.859 | 69.371 | 1.00 | 38.97 | SOS |
| ATOM | 2171 | CB | GLU | 864 | 60.356 | 16.255 | 70.456 | 1.00 | 42.58 | SOS |
| ATOM | 2172 | CG | GLU | 864 | 61.080 | 15.441 | 71.538 | 1.00 | 49.66 | SOS |
| ATOM | 2173 | CD | GLU | 864 | 60.163 | 14.953 | 72.669 | 1.00 | 54.52 | SOS |
| ATOM | 2174 | OE1 | GLU | 864 | 58.924 | 15.106 | 72.584 | 1.00 | 52.79 | SOS |
| ATOM | 2175 | OE2 | GLU | 864 | 60.696 | 14.401 | 73.656 | 1.00 | 59.42 | SOS |
| ATOM | 2176 | C | GLU | 864 | 60.409 | 17.424 | 68.251 | 1.00 | 38.08 | SOS |
| ATOM | 2177 | O | GLU | 864 | 60.333 | 16.843 | 67.173 | 1.00 | 41.68 | SOS |
| ATOM | 2178 | N | LEU | 865 | 59.800 | 18.579 | 68.506 | 1.00 | 32.07 | SOS |
| ATOM | 2179 | CA | LEU | 865 | 58.946 | 19.243 | 67.543 | 1.00 | 25.81 | SOS |
| ATOM | 2180 | CB | LEU | 865 | 58.074 | 20.265 | 68.258 | 1.00 | 27.68 | SOS |
| ATOM | 2181 | CG | LEU | 865 | 57.028 | 19.709 | 69.223 | 1.00 | 34.29 | SOS |
| ATOM | 2182 | CD1 | LEU | 865 | 56.338 | 20.843 | 69.971 | 1.00 | 34.50 | SOS |
| ATOM | 2183 | CD2 | LEU | 865 | 56.010 | 18.894 | 68.444 | 1.00 | 38.30 | SOS |
| ATOM | 2184 | C | LEU | 865 | 59.726 | 19.938 | 66.433 | 1.00 | 29.39 | SOS |
| ATOM | 2185 | O | LEU | 865 | 59.126 | 20.549 | 65.535 | 1.00 | 26.35 | SOS |
| ATOM | 2186 | N | ASN | 866 | 61.053 | 19.831 | 66.473 | 1.00 | 28.43 | SOS |
| ATOM | 2187 | CA | ASN | 866 | 61.910 | 20.483 | 65.481 | 1.00 | 34.37 | SOS |
| ATOM | 2188 | CB | ASN | 866 | 61.690 | 19.891 | 64.088 | 1.00 | 40.28 | SOS |
| ATOM | 2189 | CG | ASN | 866 | 62.489 | 18.624 | 63.860 | 1.00 | 48.22 | SOS |
| ATOM | 2190 | OD1 | ASN | 866 | 63.248 | 18.184 | 64.727 | 1.00 | 57.41 | SOS |
| ATOM | 2191 | ND2 | ASN | 866 | 62.340 | 18.039 | 62.680 | 1.00 | 51.12 | SOS |
| ATOM | 2192 | C | ASN | 866 | 61.732 | 22.003 | 65.434 | 1.00 | 35.02 | SOS |
| ATOM | 2193 | O | ASN | 866 | 61.761 | 22.604 | 64.357 | 1.00 | 36.63 | SOS |
| ATOM | 2194 | N | ASN | 867 | 61.468 | 22.608 | 66.593 | 1.00 | 32.87 | SOS |
| ATOM | 2195 | CA | ASN | 867 | 61.312 | 24.056 | 66.684 | 1.00 | 32.02 | SOS |
| ATOM | 2196 | CB | ASN | 867 | 60.235 | 24.445 | 67.688 | 1.00 | 29.34 | SOS |
| ATOM | 2197 | CG | ASN | 867 | 60.066 | 25.951 | 67.783 | 1.00 | 29.91 | SOS |
| ATOM | 2198 | OD1 | ASN | 867 | 60.777 | 26.702 | 67.106 | 1.00 | 23.50 | SOS |
| ATOM | 2199 | ND2 | ASN | 867 | 59.128 | 26.401 | 68.613 | 1.00 | 27.52 | SOS |
| ATOM | 2200 | C | ASN | 867 | 62.648 | 24.682 | 67.093 | 1.00 | 32.97 | SOS |
| ATOM | 2201 | O | ASN | 867 | 62.921 | 24.911 | 68.281 | 1.00 | 27.37 | SOS |
| ATOM | 2202 | N | PHE | 868 | 63.463 | 24.974 | 66.088 | 1.00 | 31.22 | SOS |
| ATOM | 2203 | CA | PHE | 868 | 64.775 | 25.537 | 66.312 | 1.00 | 35.60 | SOS |
| ATOM | 2204 | CB | PHE | 868 | 65.613 | 25.420 | 65.041 | 1.00 | 36.92 | SOS |
| ATOM | 2205 | CG | PHE | 868 | 65.803 | 24.003 | 64.596 | 1.00 | 36.49 | SOS |
| ATOM | 2206 | CD1 | PHE | 868 | 64.989 | 23.454 | 63.614 | 1.00 | 39.78 | SOS |
| ATOM | 2207 | CD2 | PHE | 868 | 66.730 | 23.187 | 65.224 | 1.00 | 38.22 | SOS |
| ATOM | 2208 | CE1 | PHE | 868 | 65.092 | 22.110 | 63.270 | 1.00 | 39.95 | SOS |
| ATOM | 2209 | CE2 | PHE | 868 | 66.840 | 21.842 | 64.889 | 1.00 | 39.84 | SOS |
| ATOM | 2210 | CZ | PHE | 868 | 66.015 | 21.304 | 63.909 | 1.00 | 38.73 | SOS |
| ATOM | 2211 | C | PHE | 868 | 64.746 | 26.951 | 66.862 | 1.00 | 37.45 | SOS |
| ATOM | 2212 | O | PHE | 868 | 65.624 | 27.324 | 67.643 | 1.00 | 38.77 | SOS |
| ATOM | 2213 | N | ASN | 869 | 63.723 | 27.722 | 66.494 | 1.00 | 36.31 | SOS |
| ATOM | 2214 | CA | ASN | 869 | 63.597 | 29.084 | 66.996 | 1.00 | 32.74 | SOS |
| ATOM | 2215 | CB | ASN | 869 | 62.380 | 29.789 | 66.417 | 1.00 | 28.86 | SOS |
| ATOM | 2216 | CG | ASN | 869 | 62.206 | 31.186 | 66.974 | 1.00 | 27.76 | SOS |
| ATOM | 2217 | OD1 | ASN | 869 | 62.893 | 32.127 | 66.561 | 1.00 | 29.16 | SOS |
| ATOM | 2218 | ND2 | ASN | 869 | 61.308 | 31.325 | 67.938 | 1.00 | 20.45 | SOS |
| ATOM | 2219 | C | ASN | 869 | 63.446 | 28.979 | 68.496 | 1.00 | 33.00 | SOS |
| ATOM | 2220 | O | ASN | 869 | 64.120 | 29.685 | 69.243 | 1.00 | 37.32 | SOS |
| ATOM | 2221 | N | GLY | 870 | 62.581 | 28.064 | 68.920 | 1.00 | 34.36 | SOS |
| ATOM | 2222 | CA | GLY | 870 | 62.352 | 27.833 | 70.336 | 1.00 | 36.19 | SOS |
| ATOM | 2223 | C | GLY | 870 | 63.559 | 27.233 | 71.047 | 1.00 | 35.68 | SOS |

Figure 8-38

| | | | | | | | | | | |
|---|---|---|---|---|---|---|---|---|---|---|
| ATOM | 2224 | O | GLY | 870 | 63.693 | 27.377 | 72.254 | 1.00 | 34.88 | sos |
| ATOM | 2225 | N | VAL | 871 | 64.426 | 26.534 | 70.321 | 1.00 | 34.75 | sos |
| ATOM | 2226 | CA | VAL | 871 | 65.605 | 25.950 | 70.946 | 1.00 | 35.94 | sos |
| ATOM | 2227 | CB | VAL | 871 | 66.267 | 24.874 | 70.042 | 1.00 | 34.30 | sos |
| ATOM | 2228 | CG1 | VAL | 871 | 67.700 | 24.600 | 70.479 | 1.00 | 30.94 | sos |
| ATOM | 2229 | CG2 | VAL | 871 | 65.472 | 23.593 | 70.122 | 1.00 | 34.73 | sos |
| ATOM | 2230 | C | VAL | 871 | 66.590 | 27.062 | 71.292 | 1.00 | 36.24 | sos |
| ATOM | 2231 | O | VAL | 871 | 66.966 | 27.233 | 72.458 | 1.00 | 34.39 | sos |
| ATOM | 2232 | N | LEU | 872 | 66.955 | 27.848 | 70.285 | 1.00 | 33.53 | sos |
| ATOM | 2233 | CA | LEU | 872 | 67.876 | 28.953 | 70.474 | 1.00 | 36.66 | sos |
| ATOM | 2234 | CB | LEU | 872 | 68.249 | 29.544 | 69.129 | 1.00 | 34.00 | sos |
| ATOM | 2235 | CG | LEU | 872 | 68.914 | 28.547 | 68.186 | 1.00 | 42.31 | sos |
| ATOM | 2236 | CD1 | LEU | 872 | 69.446 | 29.277 | 66.967 | 1.00 | 45.63 | sos |
| ATOM | 2237 | CD2 | LEU | 872 | 70.046 | 27.830 | 68.893 | 1.00 | 41.62 | sos |
| ATOM | 2238 | C | LEU | 872 | 67.303 | 30.033 | 71.407 | 1.00 | 40.06 | sos |
| ATOM | 2239 | O | LEU | 872 | 68.038 | 30.855 | 71.950 | 1.00 | 42.24 | sos |
| ATOM | 2240 | N | GLU | 873 | 65.990 | 29.993 | 71.606 | 1.00 | 38.54 | sos |
| ATOM | 2241 | CA | GLU | 873 | 65.270 | 30.919 | 72.475 | 1.00 | 36.06 | sos |
| ATOM | 2242 | CB | GLU | 873 | 63.780 | 30.627 | 72.335 | 1.00 | 35.86 | sos |
| ATOM | 2243 | CG | GLU | 873 | 62.873 | 31.810 | 72.266 | 1.00 | 36.06 | sos |
| ATOM | 2244 | CD | GLU | 873 | 61.522 | 31.440 | 71.694 | 1.00 | 37.01 | sos |
| ATOM | 2245 | OE1 | GLU | 873 | 60.899 | 30.486 | 72.200 | 1.00 | 36.50 | sos |
| ATOM | 2246 | OE2 | GLU | 873 | 61.089 | 32.094 | 70.721 | 1.00 | 39.69 | sos |
| ATOM | 2247 | C | GLU | 873 | 65.697 | 30.634 | 73.916 | 1.00 | 38.39 | sos |
| ATOM | 2248 | O | GLU | 873 | 66.005 | 31.547 | 74.683 | 1.00 | 37.30 | sos |
| ATOM | 2249 | N | VAL | 874 | 65.674 | 29.349 | 74.271 | 1.00 | 37.32 | sos |
| ATOM | 2250 | CA | VAL | 874 | 66.053 | 28.870 | 75.593 | 1.00 | 32.44 | sos |
| ATOM | 2251 | CB | VAL | 874 | 65.544 | 27.430 | 75.810 | 1.00 | 28.56 | sos |
| ATOM | 2252 | CG1 | VAL | 874 | 65.967 | 26.899 | 77.179 | 1.00 | 24.50 | sos |
| ATOM | 2253 | CG2 | VAL | 874 | 64.035 | 27.397 | 75.672 | 1.00 | 24.19 | sos |
| ATOM | 2254 | C | VAL | 874 | 67.576 | 28.918 | 75.756 | 1.00 | 35.18 | sos |
| ATOM | 2255 | O | VAL | 874 | 68.082 | 29.421 | 76.762 | 1.00 | 34.54 | sos |
| ATOM | 2256 | N | VAL | 875 | 68.302 | 28.424 | 74.755 | 1.00 | 34.79 | sos |
| ATOM | 2257 | CA | VAL | 875 | 69.762 | 28.431 | 74.801 | 1.00 | 35.22 | sos |
| ATOM | 2258 | CB | VAL | 875 | 70.392 | 27.951 | 73.460 | 1.00 | 31.64 | sos |
| ATOM | 2259 | CG1 | VAL | 875 | 71.887 | 28.118 | 73.500 | 1.00 | 33.87 | sos |
| ATOM | 2260 | CG2 | VAL | 875 | 70.078 | 26.498 | 73.209 | 1.00 | 28.70 | sos |
| ATOM | 2261 | C | VAL | 875 | 70.251 | 29.846 | 75.102 | 1.00 | 37.38 | sos |
| ATOM | 2262 | O | VAL | 875 | 71.122 | 30.046 | 75.948 | 1.00 | 42.10 | sos |
| ATOM | 2263 | N | SER | 876 | 69.641 | 30.828 | 74.447 | 1.00 | 36.74 | sos |
| ATOM | 2264 | CA | SER | 876 | 70.024 | 32.216 | 74.642 | 1.00 | 33.39 | sos |
| ATOM | 2265 | CB | SER | 876 | 69.321 | 33.112 | 73.630 | 1.00 | 28.63 | sos |
| ATOM | 2266 | OG | SER | 876 | 69.932 | 32.961 | 72.359 | 1.00 | 28.80 | sos |
| ATOM | 2267 | C | SER | 876 | 69.781 | 32.695 | 76.061 | 1.00 | 33.94 | sos |
| ATOM | 2268 | O | SER | 876 | 70.615 | 33.392 | 76.633 | 1.00 | 34.57 | sos |
| ATOM | 2269 | N | ALA | 877 | 68.645 | 32.312 | 76.631 | 1.00 | 33.52 | sos |
| ATOM | 2270 | CA | ALA | 877 | 68.325 | 32.692 | 77.995 | 1.00 | 32.84 | sos |
| ATOM | 2271 | CB | ALA | 877 | 66.931 | 32.242 | 78.352 | 1.00 | 29.08 | sos |
| ATOM | 2272 | C | ALA | 877 | 69.347 | 32.034 | 78.918 | 1.00 | 35.34 | sos |
| ATOM | 2273 | O | ALA | 877 | 69.870 | 32.673 | 79.831 | 1.00 | 35.43 | sos |
| ATOM | 2274 | N | MET | 878 | 69.662 | 30.769 | 78.650 | 1.00 | 34.41 | sos |
| ATOM | 2275 | CA | MET | 878 | 70.622 | 30.047 | 79.473 | 1.00 | 33.97 | sos |
| ATOM | 2276 | CB | MET | 878 | 70.711 | 28.574 | 79.070 | 1.00 | 28.45 | sos |
| ATOM | 2277 | CG | MET | 878 | 69.471 | 27.750 | 79.421 | 1.00 | 27.29 | sos |
| ATOM | 2278 | SD | MET | 878 | 69.026 | 27.925 | 81.147 | 1.00 | 34.03 | sos |
| ATOM | 2279 | CE | MET | 878 | 67.293 | 27.448 | 81.197 | 1.00 | 22.57 | sos |
| ATOM | 2280 | C | MET | 878 | 71.998 | 30.697 | 79.438 | 1.00 | 37.59 | sos |
| ATOM | 2281 | O | MET | 878 | 72.659 | 30.804 | 80.472 | 1.00 | 40.08 | sos |
| ATOM | 2282 | N | ASN | 879 | 72.409 | 31.179 | 78.269 | 1.00 | 34.80 | sos |
| ATOM | 2283 | CA | ASN | 879 | 73.715 | 31.816 | 78.151 | 1.00 | 31.61 | sos |
| ATOM | 2284 | CB | ASN | 879 | 74.335 | 31.534 | 76.785 | 1.00 | 31.29 | sos |

Figure 8-39

```
ATOM   2285  CG   ASN  879    74.888  30.129  76.683  1.00  34.71    SOS
ATOM   2286  OD1  ASN  879    75.522  29.633  77.609  1.00  35.74    SOS
ATOM   2287  ND2  ASN  879    74.644  29.477  75.558  1.00  39.42    SOS
ATOM   2288  C    ASN  879    73.731  33.310  78.433  1.00  31.50    SOS
ATOM   2289  O    ASN  879    74.753  33.966  78.247  1.00  31.57    SOS
ATOM   2290  N    SER  880    72.609  33.864  78.874  1.00  29.56    SOS
ATOM   2291  CA   SER  880    72.582  35.286  79.158  1.00  31.67    SOS
ATOM   2292  CB   SER  880    71.153  35.768  79.356  1.00  31.36    SOS
ATOM   2293  OG   SER  880    70.595  35.260  80.549  1.00  38.87    SOS
ATOM   2294  C    SER  880    73.410  35.546  80.408  1.00  35.66    SOS
ATOM   2295  O    SER  880    73.639  34.636  81.203  1.00  41.76    SOS
ATOM   2296  N    SER  881    73.861  36.782  80.581  1.00  34.66    SOS
ATOM   2297  CA   SER  881    74.666  37.132  81.743  1.00  32.93    SOS
ATOM   2298  CB   SER  881    75.068  38.609  81.704  1.00  35.57    SOS
ATOM   2299  OG   SER  881    76.054  38.845  80.715  1.00  42.33    SOS
ATOM   2300  C    SER  881    74.026  36.820  83.088  1.00  28.46    SOS
ATOM   2301  O    SER  881    74.661  36.231  83.947  1.00  32.27    SOS
ATOM   2302  N    PRO  882    72.755  37.189  83.284  1.00  26.27    SOS
ATOM   2303  CD   PRO  882    71.861  38.016  82.462  1.00  22.52    SOS
ATOM   2304  CA   PRO  882    72.137  36.902  84.580  1.00  29.08    SOS
ATOM   2305  CB   PRO  882    70.774  37.596  84.475  1.00  24.26    SOS
ATOM   2306  CG   PRO  882    71.016  38.686  83.505  1.00  24.18    SOS
ATOM   2307  C    PRO  882    71.966  35.434  84.928  1.00  32.67    SOS
ATOM   2308  O    PRO  882    72.069  35.053  86.092  1.00  36.85    SOS
ATOM   2309  N    VAL  883    71.719  34.608  83.922  1.00  33.62    SOS
ATOM   2310  CA   VAL  883    71.475  33.199  84.173  1.00  32.43    SOS
ATOM   2311  CB   VAL  883    70.386  32.663  83.206  1.00  31.91    SOS
ATOM   2312  CG1  VAL  883    70.110  31.185  83.450  1.00  31.78    SOS
ATOM   2313  CG2  VAL  883    69.108  33.460  83.392  1.00  31.64    SOS
ATOM   2314  C    VAL  883    72.714  32.319  84.140  1.00  31.72    SOS
ATOM   2315  O    VAL  883    72.842  31.392  84.946  1.00  29.66    SOS
ATOM   2316  N    TYR  884    73.641  32.652  83.252  1.00  29.17    SOS
ATOM   2317  CA   TYR  884    74.861  31.881  83.070  1.00  31.62    SOS
ATOM   2318  CB   TYR  884    75.747  32.551  82.020  1.00  32.40    SOS
ATOM   2319  CG   TYR  884    77.031  31.815  81.712  1.00  39.50    SOS
ATOM   2320  CD1  TYR  884    77.022  30.667  80.924  1.00  43.42    SOS
ATOM   2321  CE1  TYR  884    78.209  30.022  80.571  1.00  44.73    SOS
ATOM   2322  CD2  TYR  884    78.262  32.300  82.152  1.00  38.98    SOS
ATOM   2323  CE2  TYR  884    79.454  31.662  81.807  1.00  42.88    SOS
ATOM   2324  CZ   TYR  884    79.420  30.525  81.012  1.00  45.53    SOS
ATOM   2325  OH   TYR  884    80.591  29.900  80.632  1.00  49.39    SOS
ATOM   2326  C    TYR  884    75.668  31.630  84.331  1.00  35.09    SOS
ATOM   2327  O    TYR  884    76.129  30.520  84.549  1.00  40.22    SOS
ATOM   2328  N    ARG  885    75.824  32.651  85.166  1.00  35.68    SOS
ATOM   2329  CA   ARG  885    76.621  32.531  86.383  1.00  38.34    SOS
ATOM   2330  CB   ARG  885    77.259  33.880  86.731  1.00  40.97    SOS
ATOM   2331  CG   ARG  885    76.301  35.060  86.668  1.00  41.60    SOS
ATOM   2332  CD   ARG  885    76.743  36.191  87.564  1.00  33.91    SOS
ATOM   2333  NE   ARG  885    75.764  36.339  88.618  1.00  36.07    SOS
ATOM   2334  CZ   ARG  885    76.025  36.249  89.916  1.00  39.61    SOS
ATOM   2335  NH1  ARG  885    77.265  36.026  90.351  1.00  29.34    SOS
ATOM   2336  NH2  ARG  885    75.016  36.317  90.776  1.00  35.12    SOS
ATOM   2337  C    ARG  885    75.970  31.959  87.632  1.00  38.17    SOS
ATOM   2338  O    ARG  885    76.585  31.970  88.695  1.00  41.34    SOS
ATOM   2339  N    LEU  886    74.742  31.470  87.527  1.00  36.83    SOS
ATOM   2340  CA   LEU  886    74.066  30.916  88.695  1.00  39.59    SOS
ATOM   2341  CB   LEU  886    72.551  30.956  88.510  1.00  35.37    SOS
ATOM   2342  CG   LEU  886    71.906  32.326  88.341  1.00  35.15    SOS
ATOM   2343  CD1  LEU  886    70.403  32.179  88.146  1.00  31.82    SOS
ATOM   2344  CD2  LEU  886    72.192  33.160  89.562  1.00  38.11    SOS
ATOM   2345  C    LEU  886    74.531  29.493  89.034  1.00  42.80    SOS
```

Figure 8-40

```
ATOM   2346  O    LEU  886      73.718  28.565  89.115  1.00 42.90      SOS
ATOM   2347  N    ASP  887      75.830  29.358  89.307  1.00 43.91      SOS
ATOM   2348  CA   ASP  887      76.469  28.081  89.639  1.00 44.24      SOS
ATOM   2349  CB   ASP  887      77.902  28.314  90.118  1.00 41.57      SOS
ATOM   2350  CG   ASP  887      78.768  29.012  89.076  1.00 47.33      SOS
ATOM   2351  OD1  ASP  887      78.521  28.834  87.861  1.00 50.16      SOS
ATOM   2352  OD2  ASP  887      79.699  29.749  89.474  1.00 48.29      SOS
ATOM   2353  C    ASP  887      75.722  27.219  90.656  1.00 46.42      SOS
ATOM   2354  O    ASP  887      75.681  25.996  90.514  1.00 48.95      SOS
ATOM   2355  N    HIS  888      75.133  27.846  91.673  1.00 45.04      SOS
ATOM   2356  CA   HIS  888      74.385  27.109  92.692  1.00 46.17      SOS
ATOM   2357  CB   HIS  888      73.953  28.020  93.845  1.00 45.57      SOS
ATOM   2358  CG   HIS  888      75.069  28.432  94.748  1.00 49.49      SOS
ATOM   2359  CD2  HIS  888      75.489  29.656  95.143  1.00 50.29      SOS
ATOM   2360  ND1  HIS  888      75.891  27.523  95.376  1.00 50.17      SOS
ATOM   2361  CE1  HIS  888      76.769  28.170  96.120  1.00 50.67      SOS
ATOM   2362  NE2  HIS  888      76.547  29.465  95.997  1.00 51.38      SOS
ATOM   2363  C    HIS  888      73.138  26.454  92.120  1.00 45.58      SOS
ATOM   2364  O    HIS  888      72.674  25.443  92.637  1.00 46.41      SOS
ATOM   2365  N    THR  889      72.576  27.057  91.080  1.00 43.87      SOS
ATOM   2366  CA   THR  889      71.370  26.526  90.474  1.00 42.45      SOS
ATOM   2367  CB   THR  889      70.622  27.606  89.670  1.00 40.53      SOS
ATOM   2368  OG1  THR  889      70.437  28.763  90.491  1.00 42.54      SOS
ATOM   2369  CG2  THR  889      69.253  27.105  89.243  1.00 40.21      SOS
ATOM   2370  C    THR  889      71.683  25.327  89.592  1.00 44.38      SOS
ATOM   2371  O    THR  889      71.130  24.247  89.799  1.00 43.40      SOS
ATOM   2372  N    PHE  890      72.605  25.500  88.647  1.00 45.76      SOS
ATOM   2373  CA   PHE  890      72.971  24.417  87.740  1.00 49.27      SOS
ATOM   2374  CB   PHE  890      73.853  24.933  86.599  1.00 44.03      SOS
ATOM   2375  CG   PHE  890      73.100  25.768  85.608  1.00 47.33      SOS
ATOM   2376  CD1  PHE  890      72.980  27.141  85.783  1.00 47.33      SOS
ATOM   2377  CD2  PHE  890      72.433  25.173  84.545  1.00 49.00      SOS
ATOM   2378  CE1  PHE  890      72.203  27.906  84.920  1.00 45.68      SOS
ATOM   2379  CE2  PHE  890      71.652  25.931  83.675  1.00 49.69      SOS
ATOM   2380  CZ   PHE  890      71.538  27.301  83.867  1.00 47.29      SOS
ATOM   2381  C    PHE  890      73.589  23.218  88.444  1.00 54.19      SOS
ATOM   2382  O    PHE  890      73.508  22.095  87.951  1.00 57.53      SOS
ATOM   2383  N    GLU  891      74.142  23.451  89.630  1.00 57.49      SOS
ATOM   2384  CA   GLU  891      74.750  22.389  90.425  1.00 60.15      SOS
ATOM   2385  CB   GLU  891      75.227  22.955  91.770  1.00 64.50      SOS
ATOM   2386  CG   GLU  891      75.979  21.969  92.649  1.00 67.35      SOS
ATOM   2387  CD   GLU  891      77.464  21.928  92.333  1.00 74.85      SOS
ATOM   2388  OE1  GLU  891      78.255  22.364  93.197  1.00 78.88      SOS
ATOM   2389  OE2  GLU  891      77.843  21.475  91.227  1.00 75.87      SOS
ATOM   2390  C    GLU  891      73.727  21.280  90.695  1.00 59.02      SOS
ATOM   2391  O    GLU  891      74.012  20.098  90.500  1.00 59.41      SOS
ATOM   2392  N    GLN  892      72.529  21.685  91.113  1.00 55.25      SOS
ATOM   2393  CA   GLN  892      71.463  20.752  91.446  1.00 54.27      SOS
ATOM   2394  CB   GLN  892      70.627  21.313  92.589  1.00 55.32      SOS
ATOM   2395  CG   GLN  892      71.400  21.434  93.882  1.00 63.03      SOS
ATOM   2396  CD   GLN  892      70.570  22.024  94.997  1.00 69.20      SOS
ATOM   2397  OE1  GLN  892      69.346  21.878  95.021  1.00 70.32      SOS
ATOM   2398  NE2  GLN  892      71.233  22.700  95.932  1.00 72.72      SOS
ATOM   2399  C    GLN  892      70.565  20.314  90.299  1.00 52.14      SOS
ATOM   2400  O    GLN  892      69.483  19.774  90.524  1.00 52.66      SOS
ATOM   2401  N    ILE  893      71.001  20.559  89.071  1.00 49.30      SOS
ATOM   2402  CA   ILE  893      70.229  20.149  87.906  1.00 48.65      SOS
ATOM   2403  CB   ILE  893      70.368  21.168  86.741  1.00 48.07      SOS
ATOM   2404  CG2  ILE  893      69.984  20.546  85.407  1.00 45.19      SOS
ATOM   2405  CG1  ILE  893      69.462  22.360  87.002  1.00 43.22      SOS
ATOM   2406  CD1  ILE  893      69.728  23.476  86.080  1.00 50.88      SOS
```

Figure 8-41

| ATOM | 2407 | C | ILE | 893 | 70.729 | 18.774 | 87.488 | 1.00 | 47.38 | sos |
|---|---|---|---|---|---|---|---|---|---|---|
| ATOM | 2408 | O | ILE | 893 | 71.934 | 18.560 | 87.338 | 1.00 | 45.95 | sos |
| ATOM | 2409 | N | PRO | 894 | 69.810 | 17.811 | 87.342 | 1.00 | 45.62 | sos |
| ATOM | 2410 | CD | PRO | 894 | 68.372 | 17.927 | 87.617 | 1.00 | 44.81 | sos |
| ATOM | 2411 | CA | PRO | 894 | 70.156 | 16.445 | 86.945 | 1.00 | 47.18 | sos |
| ATOM | 2412 | CB | PRO | 894 | 68.794 | 15.792 | 86.687 | 1.00 | 45.23 | sos |
| ATOM | 2413 | CG | PRO | 894 | 67.811 | 16.936 | 86.663 | 1.00 | 48.49 | sos |
| ATOM | 2414 | C | PRO | 894 | 71.085 | 16.361 | 85.746 | 1.00 | 50.07 | sos |
| ATOM | 2415 | O | PRO | 894 | 71.126 | 17.255 | 84.907 | 1.00 | 53.56 | sos |
| ATOM | 2416 | N | SER | 895 | 71.871 | 15.294 | 85.712 | 1.00 | 54.25 | sos |
| ATOM | 2417 | CA | SER | 895 | 72.837 | 15.061 | 84.649 | 1.00 | 56.16 | sos |
| ATOM | 2418 | CB | SER | 895 | 73.618 | 13.775 | 84.923 | 1.00 | 59.82 | sos |
| ATOM | 2419 | OG | SER | 895 | 74.170 | 13.781 | 86.228 | 1.00 | 64.94 | sos |
| ATOM | 2420 | C | SER | 895 | 72.218 | 14.986 | 83.261 | 1.00 | 56.38 | sos |
| ATOM | 2421 | O | SER | 895 | 72.675 | 15.677 | 82.353 | 1.00 | 55.87 | sos |
| ATOM | 2422 | N | ARG | 896 | 71.180 | 14.163 | 83.094 | 1.00 | 56.53 | sos |
| ATOM | 2423 | CA | ARG | 896 | 70.551 | 14.014 | 81.781 | 1.00 | 58.93 | sos |
| ATOM | 2424 | CB | ARG | 896 | 69.373 | 13.024 | 81.815 | 1.00 | 62.74 | sos |
| ATOM | 2425 | CG | ARG | 896 | 68.100 | 13.582 | 82.414 | 1.00 | 70.55 | sos |
| ATOM | 2426 | CD | ARG | 896 | 66.877 | 12.725 | 82.117 | 1.00 | 71.37 | sos |
| ATOM | 2427 | NE | ARG | 896 | 65.662 | 13.375 | 82.608 | 1.00 | 78.32 | sos |
| ATOM | 2428 | CZ | ARG | 896 | 65.441 | 13.714 | 83.880 | 1.00 | 81.02 | sos |
| ATOM | 2429 | NH1 | ARG | 896 | 66.348 | 13.461 | 84.818 | 1.00 | 78.58 | sos |
| ATOM | 2430 | NH2 | ARG | 896 | 64.324 | 14.348 | 84.214 | 1.00 | 83.13 | sos |
| ATOM | 2431 | C | ARG | 896 | 70.111 | 15.356 | 81.195 | 1.00 | 57.23 | sos |
| ATOM | 2432 | O | ARG | 896 | 70.322 | 15.620 | 80.006 | 1.00 | 55.04 | sos |
| ATOM | 2433 | N | GLN | 897 | 69.543 | 16.214 | 82.041 | 1.00 | 53.23 | sos |
| ATOM | 2434 | CA | GLN | 897 | 69.093 | 17.522 | 81.597 | 1.00 | 50.14 | sos |
| ATOM | 2435 | CB | GLN | 897 | 68.188 | 18.158 | 82.638 | 1.00 | 48.35 | sos |
| ATOM | 2436 | CG | GLN | 897 | 66.854 | 17.442 | 82.749 | 1.00 | 49.73 | sos |
| ATOM | 2437 | CD | GLN | 897 | 65.909 | 18.085 | 83.746 | 1.00 | 52.56 | sos |
| ATOM | 2438 | OE1 | GLN | 897 | 66.289 | 18.979 | 84.506 | 1.00 | 47.90 | sos |
| ATOM | 2439 | NE2 | GLN | 897 | 64.665 | 17.622 | 83.754 | 1.00 | 57.68 | sos |
| ATOM | 2440 | C | GLN | 897 | 70.250 | 18.439 | 81.211 | 1.00 | 50.15 | sos |
| ATOM | 2441 | O | GLN | 897 | 70.137 | 19.201 | 80.249 | 1.00 | 50.25 | sos |
| ATOM | 2442 | N | LYS | 898 | 71.371 | 18.339 | 81.925 | 1.00 | 48.22 | sos |
| ATOM | 2443 | CA | LYS | 898 | 72.546 | 19.147 | 81.606 | 1.00 | 49.84 | sos |
| ATOM | 2444 | CB | LYS | 898 | 73.680 | 18.924 | 82.611 | 1.00 | 54.56 | sos |
| ATOM | 2445 | CG | LYS | 898 | 73.562 | 19.670 | 83.937 | 1.00 | 60.77 | sos |
| ATOM | 2446 | CD | LYS | 898 | 74.790 | 19.383 | 84.801 | 1.00 | 59.71 | sos |
| ATOM | 2447 | CE | LYS | 898 | 74.668 | 19.968 | 86.189 | 1.00 | 58.47 | sos |
| ATOM | 2448 | NZ | LYS | 898 | 75.753 | 19.471 | 87.080 | 1.00 | 60.11 | sos |
| ATOM | 2449 | C | LYS | 898 | 73.064 | 18.774 | 80.228 | 1.00 | 49.31 | sos |
| ATOM | 2450 | O | LYS | 898 | 73.574 | 19.625 | 79.507 | 1.00 | 52.40 | sos |
| ATOM | 2451 | N | LYS | 899 | 72.947 | 17.496 | 79.876 | 1.00 | 48.92 | sos |
| ATOM | 2452 | CA | LYS | 899 | 73.416 | 17.001 | 78.583 | 1.00 | 49.75 | sos |
| ATOM | 2453 | CB | LYS | 899 | 73.561 | 15.477 | 78.615 | 1.00 | 53.80 | sos |
| ATOM | 2454 | CG | LYS | 899 | 74.555 | 14.966 | 79.644 | 0.00 | 52.63 | sos |
| ATOM | 2455 | CD | LYS | 899 | 74.605 | 13.448 | 79.654 | 0.00 | 53.17 | sos |
| ATOM | 2456 | CE | LYS | 899 | 75.577 | 12.935 | 80.703 | 0.00 | 53.10 | sos |
| ATOM | 2457 | NZ | LYS | 899 | 75.630 | 11.447 | 80.729 | 0.00 | 53.21 | sos |
| ATOM | 2458 | C | LYS | 899 | 72.502 | 17.432 | 77.434 | 1.00 | 47.22 | sos |
| ATOM | 2459 | O | LYS | 899 | 72.965 | 17.658 | 76.313 | 1.00 | 47.74 | sos |
| ATOM | 2460 | N | ILE | 900 | 71.207 | 17.525 | 77.722 | 1.00 | 44.71 | sos |
| ATOM | 2461 | CA | ILE | 900 | 70.204 | 17.954 | 76.749 | 1.00 | 41.05 | sos |
| ATOM | 2462 | CB | ILE | 900 | 68.799 | 17.895 | 77.371 | 1.00 | 42.02 | sos |
| ATOM | 2463 | CG2 | ILE | 900 | 67.813 | 18.727 | 76.569 | 1.00 | 41.13 | sos |
| ATOM | 2464 | CG1 | ILE | 900 | 68.349 | 16.444 | 77.535 | 1.00 | 38.96 | sos |
| ATOM | 2465 | CD1 | ILE | 900 | 67.044 | 16.311 | 78.293 | 1.00 | 39.67 | sos |
| ATOM | 2466 | C | ILE | 900 | 70.508 | 19.404 | 76.392 | 1.00 | 41.97 | sos |
| ATOM | 2467 | O | ILE | 900 | 70.456 | 19.801 | 75.225 | 1.00 | 41.45 | sos |

Figure 8-42

| ATOM | 2468 | N | LEU | 901 | 70.831 | 20.182 | 77.423 | 1.00 | 42.78 | SOS |
|---|---|---|---|---|---|---|---|---|---|---|
| ATOM | 2469 | CA | LEU | 901 | 71.162 | 21.594 | 77.277 | 1.00 | 44.78 | SOS |
| ATOM | 2470 | CB | LEU | 901 | 71.197 | 22.267 | 78.651 | 1.00 | 41.97 | SOS |
| ATOM | 2471 | CG | LEU | 901 | 71.565 | 23.748 | 78.651 | 1.00 | 41.65 | SOS |
| ATOM | 2472 | CD1 | LEU | 901 | 70.616 | 24.517 | 77.741 | 1.00 | 36.63 | SOS |
| ATOM | 2473 | CD2 | LEU | 901 | 71.520 | 24.278 | 80.076 | 1.00 | 41.13 | SOS |
| ATOM | 2474 | C | LEU | 901 | 72.503 | 21.774 | 76.568 | 1.00 | 45.37 | SOS |
| ATOM | 2475 | O | LEU | 901 | 72.633 | 22.606 | 75.677 | 1.00 | 45.17 | SOS |
| ATOM | 2476 | N | GLU | 902 | 73.495 | 20.988 | 76.964 | 1.00 | 49.18 | SOS |
| ATOM | 2477 | CA | GLU | 902 | 74.808 | 21.068 | 76.348 | 1.00 | 53.84 | SOS |
| ATOM | 2478 | CB | GLU | 902 | 75.797 | 20.144 | 77.061 | 1.00 | 58.20 | SOS |
| ATOM | 2479 | CG | GLU | 902 | 77.231 | 20.276 | 76.547 | 1.00 | 69.65 | SOS |
| ATOM | 2480 | CD | GLU | 902 | 78.118 | 19.100 | 76.939 | 1.00 | 74.06 | SOS |
| ATOM | 2481 | OE1 | GLU | 902 | 78.111 | 18.073 | 76.217 | 1.00 | 69.06 | SOS |
| ATOM | 2482 | OE2 | GLU | 902 | 78.826 | 19.211 | 77.965 | 1.00 | 77.63 | SOS |
| ATOM | 2483 | C | GLU | 902 | 74.686 | 20.683 | 74.876 | 1.00 | 55.31 | SOS |
| ATOM | 2484 | O | GLU | 902 | 75.262 | 21.343 | 74.008 | 1.00 | 55.16 | SOS |
| ATOM | 2485 | N | GLU | 903 | 73.917 | 19.629 | 74.600 | 1.00 | 56.38 | SOS |
| ATOM | 2486 | CA | GLU | 903 | 73.701 | 19.159 | 73.231 | 1.00 | 60.76 | SOS |
| ATOM | 2487 | CB | GLU | 903 | 72.789 | 17.924 | 73.236 | 1.00 | 66.25 | SOS |
| ATOM | 2488 | CG | GLU | 903 | 72.499 | 17.291 | 71.858 | 1.00 | 72.01 | SOS |
| ATOM | 2489 | CD | GLU | 903 | 71.383 | 16.227 | 71.902 | 1.00 | 76.13 | SOS |
| ATOM | 2490 | OE1 | GLU | 903 | 71.204 | 15.568 | 72.954 | 1.00 | 74.00 | SOS |
| ATOM | 2491 | OE2 | GLU | 903 | 70.675 | 16.057 | 70.881 | 1.00 | 74.40 | SOS |
| ATOM | 2492 | C | GLU | 903 | 73.063 | 20.292 | 72.419 | 1.00 | 59.95 | SOS |
| ATOM | 2493 | O | GLU | 903 | 73.378 | 20.484 | 71.241 | 1.00 | 59.33 | SOS |
| ATOM | 2494 | N | ALA | 904 | 72.193 | 21.056 | 73.080 | 1.00 | 56.64 | SOS |
| ATOM | 2495 | CA | ALA | 904 | 71.506 | 22.182 | 72.457 | 1.00 | 52.32 | SOS |
| ATOM | 2496 | CB | ALA | 904 | 70.358 | 22.651 | 73.339 | 1.00 | 49.36 | SOS |
| ATOM | 2497 | C | ALA | 904 | 72.468 | 23.332 | 72.191 | 1.00 | 50.59 | SOS |
| ATOM | 2498 | O | ALA | 904 | 72.468 | 23.909 | 71.104 | 1.00 | 51.28 | SOS |
| ATOM | 2499 | N | HIS | 905 | 73.293 | 23.658 | 73.182 | 1.00 | 49.43 | SOS |
| ATOM | 2500 | CA | HIS | 905 | 74.254 | 24.744 | 73.048 | 1.00 | 49.46 | SOS |
| ATOM | 2501 | CB | HIS | 905 | 75.008 | 24.965 | 74.363 | 1.00 | 52.81 | SOS |
| ATOM | 2502 | CG | HIS | 905 | 76.107 | 25.982 | 74.266 | 1.00 | 60.08 | SOS |
| ATOM | 2503 | CD2 | HIS | 905 | 77.382 | 25.879 | 73.817 | 1.00 | 60.16 | SOS |
| ATOM | 2504 | ND1 | HIS | 905 | 75.936 | 27.302 | 74.626 | 1.00 | 59.72 | SOS |
| ATOM | 2505 | CE1 | HIS | 905 | 77.054 | 27.968 | 74.399 | 1.00 | 60.01 | SOS |
| ATOM | 2506 | NE2 | HIS | 905 | 77.947 | 27.128 | 73.907 | 1.00 | 59.61 | SOS |
| ATOM | 2507 | C | HIS | 905 | 75.241 | 24.488 | 71.916 | 1.00 | 48.69 | SOS |
| ATOM | 2508 | O | HIS | 905 | 75.675 | 25.418 | 71.237 | 1.00 | 46.11 | SOS |
| ATOM | 2509 | N | GLU | 906 | 75.577 | 23.221 | 71.704 | 1.00 | 50.80 | SOS |
| ATOM | 2510 | CA | GLU | 906 | 76.522 | 22.848 | 70.658 | 1.00 | 51.31 | SOS |
| ATOM | 2511 | CB | GLU | 906 | 76.956 | 21.398 | 70.829 | 1.00 | 56.20 | SOS |
| ATOM | 2512 | CG | GLU | 906 | 77.829 | 21.168 | 72.058 | 1.00 | 63.74 | SOS |
| ATOM | 2513 | CD | GLU | 906 | 78.036 | 19.695 | 72.383 | 1.00 | 69.40 | SOS |
| ATOM | 2514 | OE1 | GLU | 906 | 77.836 | 18.834 | 71.489 | 1.00 | 69.83 | SOS |
| ATOM | 2515 | OE2 | GLU | 906 | 78.397 | 19.405 | 73.546 | 1.00 | 68.08 | SOS |
| ATOM | 2516 | C | GLU | 906 | 76.018 | 23.090 | 69.244 | 1.00 | 49.18 | SOS |
| ATOM | 2517 | O | GLU | 906 | 76.793 | 23.042 | 68.294 | 1.00 | 51.45 | SOS |
| ATOM | 2518 | N | LEU | 907 | 74.726 | 23.354 | 69.103 | 1.00 | 46.28 | SOS |
| ATOM | 2519 | CA | LEU | 907 | 74.156 | 23.616 | 67.792 | 1.00 | 44.89 | SOS |
| ATOM | 2520 | CB | LEU | 907 | 72.624 | 23.645 | 67.870 | 1.00 | 45.65 | SOS |
| ATOM | 2521 | CG | LEU | 907 | 71.908 | 22.288 | 67.971 | 1.00 | 44.17 | SOS |
| ATOM | 2522 | CD1 | LEU | 907 | 70.474 | 22.466 | 68.407 | 1.00 | 38.30 | SOS |
| ATOM | 2523 | CD2 | LEU | 907 | 71.972 | 21.573 | 66.629 | 1.00 | 43.88 | SOS |
| ATOM | 2524 | C | LEU | 907 | 74.699 | 24.934 | 67.252 | 1.00 | 46.39 | SOS |
| ATOM | 2525 | O | LEU | 907 | 74.959 | 25.066 | 66.062 | 1.00 | 48.25 | SOS |
| ATOM | 2526 | N | SER | 908 | 74.947 | 25.875 | 68.157 | 1.00 | 48.20 | SOS |
| ATOM | 2527 | CA | SER | 908 | 75.456 | 27.200 | 67.809 | 1.00 | 47.07 | SOS |
| ATOM | 2528 | CB | SER | 908 | 75.235 | 28.146 | 68.983 | 1.00 | 47.16 | SOS |

Figure 8-43

| | | | | | | | | | |
|---|---|---|---|---|---|---|---|---|---|
| ATOM | 2529 | OG | SER | 908 | 74.020 | 27.845 | 69.645 | 1.00 54.65 | SOS |
| ATOM | 2530 | C | SER | 908 | 76.938 | 27.224 | 67.448 | 1.00 48.96 | SOS |
| ATOM | 2531 | O | SER | 908 | 77.355 | 27.991 | 66.584 | 1.00 48.06 | SOS |
| ATOM | 2532 | N | GLU | 909 | 77.723 | 26.379 | 68.115 | 1.00 51.71 | SOS |
| ATOM | 2533 | CA | GLU | 909 | 79.170 | 26.313 | 67.919 | 1.00 52.81 | SOS |
| ATOM | 2534 | CB | GLU | 909 | 79.767 | 25.161 | 68.725 | 1.00 57.06 | SOS |
| ATOM | 2535 | CG | GLU | 909 | 79.603 | 25.302 | 70.233 | 1.00 64.34 | SOS |
| ATOM | 2536 | CD | GLU | 909 | 80.251 | 24.161 | 71.020 | 1.00 70.28 | SOS |
| ATOM | 2537 | OE1 | GLU | 909 | 80.379 | 23.033 | 70.480 | 1.00 70.28 | SOS |
| ATOM | 2538 | OE2 | GLU | 909 | 80.624 | 24.397 | 72.191 | 1.00 72.37 | SOS |
| ATOM | 2539 | C | GLU | 909 | 79.657 | 26.226 | 66.485 | 1.00 51.53 | SOS |
| ATOM | 2540 | O | GLU | 909 | 78.952 | 25.753 | 65.601 | 1.00 52.93 | SOS |
| ATOM | 2541 | N | ASP | 910 | 80.879 | 26.701 | 66.273 | 1.00 50.75 | SOS |
| ATOM | 2542 | CA | ASP | 910 | 81.509 | 26.688 | 64.964 | 1.00 52.24 | SOS |
| ATOM | 2543 | CB | ASP | 910 | 81.869 | 25.256 | 64.565 | 1.00 57.73 | SOS |
| ATOM | 2544 | CG | ASP | 910 | 83.240 | 24.842 | 65.059 | 1.00 61.23 | SOS |
| ATOM | 2545 | OD1 | ASP | 910 | 84.237 | 25.208 | 64.391 | 1.00 64.95 | SOS |
| ATOM | 2546 | OD2 | ASP | 910 | 83.320 | 24.151 | 66.101 | 1.00 60.29 | SOS |
| ATOM | 2547 | C | ASP | 910 | 80.658 | 27.338 | 63.888 | 1.00 50.80 | SOS |
| ATOM | 2548 | O | ASP | 910 | 80.667 | 26.909 | 62.733 | 1.00 50.10 | SOS |
| ATOM | 2549 | N | HIS | 911 | 79.938 | 28.386 | 64.278 | 1.00 49.45 | SOS |
| ATOM | 2550 | CA | HIS | 911 | 79.070 | 29.129 | 63.372 | 1.00 48.32 | SOS |
| ATOM | 2551 | CB | HIS | 911 | 79.868 | 29.666 | 62.174 | 1.00 48.45 | SOS |
| ATOM | 2552 | CG | HIS | 911 | 80.918 | 30.666 | 62.547 | 1.00 48.50 | SOS |
| ATOM | 2553 | CD2 | HIS | 911 | 81.967 | 30.582 | 63.399 | 1.00 48.77 | SOS |
| ATOM | 2554 | ND1 | HIS | 911 | 80.947 | 31.944 | 62.031 | 1.00 47.75 | SOS |
| ATOM | 2555 | CE1 | HIS | 911 | 81.965 | 32.604 | 62.551 | 1.00 44.82 | SOS |
| ATOM | 2556 | NE2 | HIS | 911 | 82.600 | 31.801 | 63.384 | 1.00 46.54 | SOS |
| ATOM | 2557 | C | HIS | 911 | 77.854 | 28.317 | 62.908 | 1.00 48.27 | SOS |
| ATOM | 2558 | O | HIS | 911 | 77.536 | 28.259 | 61.713 | 1.00 47.43 | SOS |
| ATOM | 2559 | N | TYR | 912 | 77.185 | 27.696 | 63.877 | 1.00 46.37 | SOS |
| ATOM | 2560 | CA | TYR | 912 | 75.986 | 26.900 | 63.638 | 1.00 49.11 | SOS |
| ATOM | 2561 | CB | TYR | 912 | 74.877 | 27.780 | 63.054 | 1.00 48.64 | SOS |
| ATOM | 2562 | CG | TYR | 912 | 74.320 | 28.819 | 63.999 | 1.00 46.06 | SOS |
| ATOM | 2563 | CD1 | TYR | 912 | 74.595 | 30.174 | 63.817 | 1.00 46.11 | SOS |
| ATOM | 2564 | CE1 | TYR | 912 | 74.041 | 31.138 | 64.649 | 1.00 47.73 | SOS |
| ATOM | 2565 | CD2 | TYR | 912 | 73.480 | 28.452 | 65.043 | 1.00 46.64 | SOS |
| ATOM | 2566 | CE2 | TYR | 912 | 72.919 | 29.408 | 65.883 | 1.00 51.30 | SOS |
| ATOM | 2567 | CZ | TYR | 912 | 73.202 | 30.747 | 65.678 | 1.00 48.94 | SOS |
| ATOM | 2568 | OH | TYR | 912 | 72.627 | 31.688 | 66.491 | 1.00 53.83 | SOS |
| ATOM | 2569 | C | TYR | 912 | 76.177 | 25.682 | 62.739 | 1.00 51.71 | SOS |
| ATOM | 2570 | O | TYR | 912 | 75.199 | 25.167 | 62.194 | 1.00 50.47 | SOS |
| ATOM | 2571 | N | LYS | 913 | 77.417 | 25.202 | 62.619 | 1.00 53.99 | SOS |
| ATOM | 2572 | CA | LYS | 913 | 77.726 | 24.054 | 61.769 | 1.00 53.13 | SOS |
| ATOM | 2573 | CB | LYS | 913 | 79.182 | 23.624 | 61.935 | 1.00 57.46 | SOS |
| ATOM | 2574 | CG | LYS | 913 | 79.638 | 22.625 | 60.877 | 1.00 61.18 | SOS |
| ATOM | 2575 | CD | LYS | 913 | 81.147 | 22.446 | 60.871 | 1.00 65.36 | SOS |
| ATOM | 2576 | CE | LYS | 913 | 81.597 | 21.652 | 59.643 | 1.00 70.45 | SOS |
| ATOM | 2577 | NZ | LYS | 913 | 83.082 | 21.654 | 59.456 | 1.00 72.56 | SOS |
| ATOM | 2578 | C | LYS | 913 | 76.802 | 22.866 | 62.005 | 1.00 52.79 | SOS |
| ATOM | 2579 | O | LYS | 913 | 76.314 | 22.259 | 61.046 | 1.00 51.68 | SOS |
| ATOM | 2580 | N | LYS | 914 | 76.549 | 22.550 | 63.274 | 1.00 49.69 | SOS |
| ATOM | 2581 | CA | LYS | 914 | 75.665 | 21.439 | 63.613 | 1.00 48.44 | SOS |
| ATOM | 2582 | CB | LYS | 914 | 75.878 | 20.977 | 65.050 | 1.00 44.11 | SOS |
| ATOM | 2583 | CG | LYS | 914 | 77.141 | 20.168 | 65.245 | 1.00 45.53 | SOS |
| ATOM | 2584 | CD | LYS | 914 | 77.188 | 19.601 | 66.641 | 1.00 49.53 | SOS |
| ATOM | 2585 | CE | LYS | 914 | 78.550 | 19.026 | 66.984 | 1.00 50.01 | SOS |
| ATOM | 2586 | NZ | LYS | 914 | 78.572 | 18.663 | 68.431 | 1.00 54.74 | SOS |
| ATOM | 2587 | C | LYS | 914 | 74.192 | 21.742 | 63.372 | 1.00 49.84 | SOS |
| ATOM | 2588 | O | LYS | 914 | 73.439 | 20.854 | 62.972 | 1.00 53.26 | SOS |
| ATOM | 2589 | N | TYR | 915 | 73.778 | 22.985 | 63.623 | 1.00 47.97 | SOS |

Figure 8-44

```
ATOM   2590  CA   TYR   915      72.392  23.383  63.403  1.00 42.57           SOS
ATOM   2591  CB   TYR   915      72.134  24.810  63.891  1.00 38.41           SOS
ATOM   2592  CG   TYR   915      70.887  25.432  63.292  1.00 33.23           SOS
ATOM   2593  CD1  TYR   915      69.618  25.081  63.746  1.00 33.30           SOS
ATOM   2594  CE1  TYR   915      68.481  25.594  63.156  1.00 32.15           SOS
ATOM   2595  CD2  TYR   915      70.977  26.321  62.230  1.00 30.81           SOS
ATOM   2596  CE2  TYR   915      69.847  26.840  61.629  1.00 30.91           SOS
ATOM   2597  CZ   TYR   915      68.602  26.475  62.095  1.00 33.16           SOS
ATOM   2598  OH   TYR   915      67.478  27.002  61.505  1.00 30.46           SOS
ATOM   2599  C    TYR   915      72.069  23.298  61.922  1.00 42.82           SOS
ATOM   2600  O    TYR   915      71.020  22.794  61.539  1.00 44.03           SOS
ATOM   2601  N    LEU   916      72.961  23.823  61.093  1.00 45.21           SOS
ATOM   2602  CA   LEU   916      72.749  23.798  59.654  1.00 47.30           SOS
ATOM   2603  CB   LEU   916      73.870  24.538  58.922  1.00 42.79           SOS
ATOM   2604  CG   LEU   916      73.928  26.057  59.129  1.00 47.64           SOS
ATOM   2605  CD1  LEU   916      74.999  26.665  58.227  1.00 48.44           SOS
ATOM   2606  CD2  LEU   916      72.578  26.695  58.829  1.00 43.45           SOS
ATOM   2607  C    LEU   916      72.647  22.359  59.170  1.00 50.76           SOS
ATOM   2608  O    LEU   916      71.830  22.045  58.299  1.00 53.92           SOS
ATOM   2609  N    ALA   917      73.431  21.481  59.790  1.00 49.90           SOS
ATOM   2610  CA   ALA   917      73.437  20.069  59.437  1.00 49.12           SOS
ATOM   2611  CB   ALA   917      74.621  19.380  60.077  1.00 48.74           SOS
ATOM   2612  C    ALA   917      72.144  19.376  59.847  1.00 49.95           SOS
ATOM   2613  O    ALA   917      71.562  18.627  59.064  1.00 53.14           SOS
ATOM   2614  N    LYS   918      71.685  19.648  61.064  1.00 48.98           SOS
ATOM   2615  CA   LYS   918      70.470  19.033  61.576  1.00 47.78           SOS
ATOM   2616  CB   LYS   918      70.313  19.313  63.071  1.00 46.11           SOS
ATOM   2617  CG   LYS   918      69.194  18.532  63.744  1.00 45.72           SOS
ATOM   2618  CD   LYS   918      69.346  18.611  65.252  1.00 51.11           SOS
ATOM   2619  CE   LYS   918      68.279  17.827  65.991  1.00 52.13           SOS
ATOM   2620  NZ   LYS   918      68.454  17.974  67.465  1.00 51.54           SOS
ATOM   2621  C    LYS   918      69.226  19.470  60.821  1.00 48.71           SOS
ATOM   2622  O    LYS   918      68.319  18.667  60.619  1.00 51.41           SOS
ATOM   2623  N    LEU   919      69.193  20.731  60.394  1.00 49.27           SOS
ATOM   2624  CA   LEU   919      68.053  21.269  59.652  1.00 49.27           SOS
ATOM   2625  CB   LEU   919      68.307  22.722  59.252  1.00 49.07           SOS
ATOM   2626  CG   LEU   919      67.180  23.749  59.407  1.00 49.61           SOS
ATOM   2627  CD1  LEU   919      67.473  24.938  58.499  1.00 50.70           SOS
ATOM   2628  CD2  LEU   919      65.835  23.159  59.058  1.00 50.91           SOS
ATOM   2629  C    LEU   919      67.874  20.437  58.392  1.00 50.95           SOS
ATOM   2630  O    LEU   919      66.773  19.983  58.093  1.00 49.53           SOS
ATOM   2631  N    ARG   920      68.977  20.224  57.678  1.00 52.42           SOS
ATOM   2632  CA   ARG   920      68.978  19.437  56.451  1.00 56.17           SOS
ATOM   2633  CB   ARG   920      70.383  19.403  55.836  1.00 57.65           SOS
ATOM   2634  CG   ARG   920      70.838  20.702  55.190  1.00 63.21           SOS
ATOM   2635  CD   ARG   920      72.158  20.529  54.437  1.00 62.33           SOS
ATOM   2636  NE   ARG   920      72.656  21.795  53.903  0.00 63.60           SOS
ATOM   2637  CZ   ARG   920      72.141  22.428  52.852  0.00 63.87           SOS
ATOM   2638  NH1  ARG   920      71.101  21.919  52.203  0.00 64.16           SOS
ATOM   2639  NH2  ARG   920      72.665  23.578  52.450  0.00 64.16           SOS
ATOM   2640  C    ARG   920      68.508  17.999  56.676  1.00 58.37           SOS
ATOM   2641  O    ARG   920      67.694  17.478  55.911  1.00 61.06           SOS
ATOM   2642  N    SER   921      69.002  17.382  57.747  1.00 56.83           SOS
ATOM   2643  CA   SER   921      68.686  15.998  58.082  1.00 57.26           SOS
ATOM   2644  CB   SER   921      69.661  15.479  59.144  1.00 58.43           SOS
ATOM   2645  OG   SER   921      69.105  15.587  60.448  1.00 55.03           SOS
ATOM   2646  C    SER   921      67.265  15.687  58.549  1.00 58.41           SOS
ATOM   2647  O    SER   921      66.898  14.512  58.642  1.00 61.66           SOS
ATOM   2648  N    ILE   922      66.481  16.706  58.892  1.00 55.18           SOS
ATOM   2649  CA   ILE   922      65.128  16.441  59.371  1.00 50.67           SOS
ATOM   2650  CB   ILE   922      64.764  17.271  60.639  1.00 48.00           SOS
```

Figure 8-45

| ATOM | 2651 | CG2 | ILE | 922 | 65.517 | 16.748 | 61.847 | 1.00 | 48.45 | SOS |
| --- | --- | --- | --- | --- | --- | --- | --- | --- | --- | --- |
| ATOM | 2652 | CG1 | ILE | 922 | 65.006 | 18.765 | 60.417 | 1.00 | 42.40 | SOS |
| ATOM | 2653 | CD1 | ILE | 922 | 63.826 | 19.508 | 59.851 | 1.00 | 40.11 | SOS |
| ATOM | 2654 | C | ILE | 922 | 64.034 | 16.596 | 58.340 | 1.00 | 49.75 | SOS |
| ATOM | 2655 | O | ILE | 922 | 64.242 | 17.169 | 57.272 | 1.00 | 48.57 | SOS |
| ATOM | 2656 | N | ASN | 923 | 62.871 | 16.049 | 58.674 | 1.00 | 50.49 | SOS |
| ATOM | 2657 | CA | ASN | 923 | 61.702 | 16.123 | 57.816 | 1.00 | 53.82 | SOS |
| ATOM | 2658 | CB | ASN | 923 | 61.089 | 14.727 | 57.593 | 1.00 | 61.32 | SOS |
| ATOM | 2659 | CG | ASN | 923 | 61.919 | 13.860 | 56.636 | 1.00 | 67.66 | SOS |
| ATOM | 2660 | OD1 | ASN | 923 | 62.445 | 12.815 | 57.029 | 1.00 | 69.64 | SOS |
| ATOM | 2661 | ND2 | ASN | 923 | 62.033 | 14.295 | 55.376 | 1.00 | 64.13 | SOS |
| ATOM | 2662 | C | ASN | 923 | 60.689 | 17.038 | 58.480 | 1.00 | 49.62 | SOS |
| ATOM | 2663 | O | ASN | 923 | 60.312 | 16.824 | 59.634 | 1.00 | 50.69 | SOS |
| ATOM | 2664 | N | PRO | 924 | 60.279 | 18.103 | 57.778 | 1.00 | 45.33 | SOS |
| ATOM | 2665 | CD | PRO | 924 | 60.871 | 18.569 | 56.517 | 1.00 | 46.12 | SOS |
| ATOM | 2666 | CA | PRO | 924 | 59.304 | 19.075 | 58.279 | 1.00 | 47.49 | SOS |
| ATOM | 2667 | CB | PRO | 924 | 59.075 | 20.001 | 57.071 | 1.00 | 48.41 | SOS |
| ATOM | 2668 | CG | PRO | 924 | 59.735 | 19.295 | 55.900 | 1.00 | 47.54 | SOS |
| ATOM | 2669 | C | PRO | 924 | 58.006 | 18.452 | 58.816 | 1.00 | 46.79 | SOS |
| ATOM | 2670 | O | PRO | 924 | 57.779 | 17.255 | 58.669 | 1.00 | 48.62 | SOS |
| ATOM | 2671 | N | PRO | 925 | 57.157 | 19.250 | 59.488 | 1.00 | 46.84 | SOS |
| ATOM | 2672 | CD | PRO | 925 | 55.988 | 18.666 | 60.172 | 1.00 | 44.41 | SOS |
| ATOM | 2673 | CA | PRO | 925 | 57.277 | 20.682 | 59.802 | 1.00 | 46.23 | SOS |
| ATOM | 2674 | CB | PRO | 925 | 55.934 | 20.989 | 60.451 | 1.00 | 47.40 | SOS |
| ATOM | 2675 | CG | PRO | 925 | 55.644 | 19.723 | 61.200 | 1.00 | 46.14 | SOS |
| ATOM | 2676 | C | PRO | 925 | 58.425 | 21.018 | 60.752 | 1.00 | 45.27 | SOS |
| ATOM | 2677 | O | PRO | 925 | 58.967 | 20.143 | 61.432 | 1.00 | 44.74 | SOS |
| ATOM | 2678 | N | CYS | 926 | 58.790 | 22.294 | 60.780 | 1.00 | 44.68 | SOS |
| ATOM | 2679 | CA | CYS | 926 | 59.862 | 22.785 | 61.638 | 1.00 | 40.95 | SOS |
| ATOM | 2680 | CB | CYS | 926 | 61.214 | 22.278 | 61.142 | 1.00 | 36.96 | SOS |
| ATOM | 2681 | SG | CYS | 926 | 61.805 | 23.134 | 59.673 | 1.00 | 35.53 | SOS |
| ATOM | 2682 | C | CYS | 926 | 59.885 | 24.307 | 61.620 | 1.00 | 39.14 | SOS |
| ATOM | 2683 | O | CYS | 926 | 59.323 | 24.939 | 60.722 | 1.00 | 39.53 | SOS |
| ATOM | 2684 | N | VAL | 927 | 60.508 | 24.894 | 62.634 | 1.00 | 35.38 | SOS |
| ATOM | 2685 | CA | VAL | 927 | 60.645 | 26.341 | 62.695 | 1.00 | 31.48 | SOS |
| ATOM | 2686 | CB | VAL | 927 | 60.010 | 26.939 | 63.982 | 1.00 | 28.21 | SOS |
| ATOM | 2687 | CG1 | VAL | 927 | 60.001 | 28.448 | 63.893 | 1.00 | 28.35 | SOS |
| ATOM | 2688 | CG2 | VAL | 927 | 58.588 | 26.419 | 64.204 | 1.00 | 22.59 | SOS |
| ATOM | 2689 | C | VAL | 927 | 62.151 | 26.652 | 62.676 | 1.00 | 34.16 | SOS |
| ATOM | 2690 | O | VAL | 927 | 62.844 | 26.491 | 63.684 | 1.00 | 39.68 | SOS |
| ATOM | 2691 | N | PRO | 928 | 62.701 | 27.005 | 61.508 | 1.00 | 32.22 | SOS |
| ATOM | 2692 | CD | PRO | 928 | 62.151 | 27.024 | 60.143 | 1.00 | 32.76 | SOS |
| ATOM | 2693 | CA | PRO | 928 | 64.135 | 27.308 | 61.497 | 1.00 | 32.49 | SOS |
| ATOM | 2694 | CB | PRO | 928 | 64.455 | 27.409 | 60.002 | 1.00 | 29.58 | SOS |
| ATOM | 2695 | CG | PRO | 928 | 63.186 | 27.844 | 59.406 | 1.00 | 29.45 | SOS |
| ATOM | 2696 | C | PRO | 928 | 64.469 | 28.614 | 62.212 | 1.00 | 33.46 | SOS |
| ATOM | 2697 | O | PRO | 928 | 63.581 | 29.425 | 62.489 | 1.00 | 32.90 | SOS |
| ATOM | 2698 | N | PHE | 929 | 65.739 | 28.775 | 62.579 | 1.00 | 36.55 | SOS |
| ATOM | 2699 | CA | PHE | 929 | 66.199 | 30.004 | 63.225 | 1.00 | 32.09 | SOS |
| ATOM | 2700 | CB | PHE | 929 | 67.529 | 29.790 | 63.939 | 1.00 | 26.80 | SOS |
| ATOM | 2701 | CG | PHE | 929 | 68.135 | 31.057 | 64.447 | 1.00 | 26.59 | SOS |
| ATOM | 2702 | CD1 | PHE | 929 | 67.474 | 31.815 | 65.412 | 1.00 | 25.03 | SOS |
| ATOM | 2703 | CD2 | PHE | 929 | 69.332 | 31.529 | 63.916 | 1.00 | 25.27 | SOS |
| ATOM | 2704 | CE1 | PHE | 929 | 67.991 | 33.017 | 65.831 | 1.00 | 21.25 | SOS |
| ATOM | 2705 | CE2 | PHE | 929 | 69.863 | 32.729 | 64.325 | 1.00 | 17.89 | SOS |
| ATOM | 2706 | CZ | PHE | 929 | 69.193 | 33.482 | 65.286 | 1.00 | 27.76 | SOS |
| ATOM | 2707 | C | PHE | 929 | 66.389 | 30.978 | 62.073 | 1.00 | 29.76 | SOS |
| ATOM | 2708 | O | PHE | 929 | 67.164 | 30.705 | 61.154 | 1.00 | 30.77 | SOS |
| ATOM | 2709 | N | PHE | 930 | 65.704 | 32.114 | 62.133 | 1.00 | 26.53 | SOS |
| ATOM | 2710 | CA | PHE | 930 | 65.756 | 33.089 | 61.049 | 1.00 | 27.13 | SOS |
| ATOM | 2711 | CB | PHE | 930 | 64.544 | 34.018 | 61.129 | 1.00 | 29.26 | SOS |

Figure 8-46

| ATOM | 2712 | CG | PHE | 930 | 63.929 | 34.330 | 59.798 | 1.00 | 28.00 | SOS |
| ATOM | 2713 | CD1 | PHE | 930 | 62.596 | 34.032 | 59.554 | 1.00 | 26.87 | SOS |
| ATOM | 2714 | CD2 | PHE | 930 | 64.685 | 34.905 | 58.782 | 1.00 | 27.99 | SOS |
| ATOM | 2715 | CE1 | PHE | 930 | 62.024 | 34.298 | 58.321 | 1.00 | 25.27 | SOS |
| ATOM | 2716 | CE2 | PHE | 930 | 64.123 | 35.172 | 57.547 | 1.00 | 27.66 | SOS |
| ATOM | 2717 | CZ | PHE | 930 | 62.789 | 34.867 | 57.316 | 1.00 | 26.15 | SOS |
| ATOM | 2718 | C | PHE | 930 | 67.027 | 33.911 | 60.905 | 1.00 | 27.03 | SOS |
| ATOM | 2719 | O | PHE | 930 | 67.442 | 34.230 | 59.784 | 1.00 | 25.87 | SOS |
| ATOM | 2720 | N | GLY | 931 | 67.625 | 34.265 | 62.036 | 1.00 | 28.95 | SOS |
| ATOM | 2721 | CA | GLY | 931 | 68.836 | 35.073 | 62.037 | 1.00 | 32.59 | SOS |
| ATOM | 2722 | C | GLY | 931 | 69.902 | 34.751 | 61.004 | 1.00 | 33.38 | SOS |
| ATOM | 2723 | O | GLY | 931 | 70.421 | 35.660 | 60.359 | 1.00 | 34.76 | SOS |
| ATOM | 2724 | N | ILE | 932 | 70.236 | 33.470 | 60.852 | 1.00 | 30.91 | SOS |
| ATOM | 2725 | CA | ILE | 932 | 71.243 | 33.051 | 59.891 | 1.00 | 28.45 | SOS |
| ATOM | 2726 | CB | ILE | 932 | 71.430 | 31.542 | 59.928 | 1.00 | 27.32 | SOS |
| ATOM | 2727 | CG2 | ILE | 932 | 72.561 | 31.126 | 59.011 | 1.00 | 27.12 | SOS |
| ATOM | 2728 | CG1 | ILE | 932 | 71.794 | 31.116 | 61.342 | 1.00 | 30.75 | SOS |
| ATOM | 2729 | CD1 | ILE | 932 | 71.880 | 29.636 | 61.524 | 1.00 | 33.98 | SOS |
| ATOM | 2730 | C | ILE | 932 | 70.887 | 33.501 | 58.474 | 1.00 | 32.12 | SOS |
| ATOM | 2731 | O | ILE | 932 | 71.751 | 33.960 | 57.723 | 1.00 | 34.42 | SOS |
| ATOM | 2732 | N | TYR | 933 | 69.613 | 33.385 | 58.113 | 1.00 | 32.30 | SOS |
| ATOM | 2733 | CA | TYR | 933 | 69.162 | 33.809 | 56.789 | 1.00 | 33.98 | SOS |
| ATOM | 2734 | CB | TYR | 933 | 67.681 | 33.470 | 56.588 | 1.00 | 33.42 | SOS |
| ATOM | 2735 | CG | TYR | 933 | 67.381 | 31.991 | 56.491 | 1.00 | 33.58 | SOS |
| ATOM | 2736 | CD1 | TYR | 933 | 66.417 | 31.402 | 57.314 | 1.00 | 30.32 | SOS |
| ATOM | 2737 | CE1 | TYR | 933 | 66.128 | 30.052 | 57.228 | 1.00 | 27.97 | SOS |
| ATOM | 2738 | CD2 | TYR | 933 | 68.052 | 31.181 | 55.572 | 1.00 | 30.42 | SOS |
| ATOM | 2739 | CE2 | TYR | 933 | 67.769 | 29.824 | 55.476 | 1.00 | 31.98 | SOS |
| ATOM | 2740 | CZ | TYR | 933 | 66.805 | 29.269 | 56.308 | 1.00 | 35.80 | SOS |
| ATOM | 2741 | OH | TYR | 933 | 66.507 | 27.931 | 56.212 | 1.00 | 45.16 | SOS |
| ATOM | 2742 | C | TYR | 933 | 69.369 | 35.317 | 56.622 | 1.00 | 34.51 | SOS |
| ATOM | 2743 | O | TYR | 933 | 69.807 | 35.788 | 55.566 | 1.00 | 31.15 | SOS |
| ATOM | 2744 | N | LEU | 934 | 69.053 | 36.064 | 57.679 | 1.00 | 36.03 | SOS |
| ATOM | 2745 | CA | LEU | 934 | 69.205 | 37.514 | 57.671 | 1.00 | 35.33 | SOS |
| ATOM | 2746 | CB | LEU | 934 | 68.733 | 38.107 | 58.994 | 1.00 | 32.91 | SOS |
| ATOM | 2747 | CG | LEU | 934 | 67.274 | 37.817 | 59.330 | 1.00 | 32.65 | SOS |
| ATOM | 2748 | CD1 | LEU | 934 | 66.899 | 38.478 | 60.637 | 1.00 | 28.03 | SOS |
| ATOM | 2749 | CD2 | LEU | 934 | 66.386 | 38.320 | 58.209 | 1.00 | 34.70 | SOS |
| ATOM | 2750 | C | LEU | 934 | 70.650 | 37.905 | 57.405 | 1.00 | 34.85 | SOS |
| ATOM | 2751 | O | LEU | 934 | 70.929 | 38.672 | 56.478 | 1.00 | 36.11 | SOS |
| ATOM | 2752 | N | THR | 935 | 71.569 | 37.323 | 58.173 | 1.00 | 33.09 | SOS |
| ATOM | 2753 | CA | THR | 935 | 72.991 | 37.618 | 58.013 | 1.00 | 34.65 | SOS |
| ATOM | 2754 | CB | THR | 935 | 73.867 | 36.915 | 59.071 | 1.00 | 34.56 | SOS |
| ATOM | 2755 | OG1 | THR | 935 | 73.516 | 37.391 | 60.381 | 1.00 | 32.55 | SOS |
| ATOM | 2756 | CG2 | THR | 935 | 75.342 | 37.204 | 58.811 | 1.00 | 27.55 | SOS |
| ATOM | 2757 | C | THR | 935 | 73.491 | 37.253 | 56.631 | 1.00 | 34.69 | SOS |
| ATOM | 2758 | O | THR | 935 | 74.295 | 37.981 | 56.050 | 1.00 | 38.00 | SOS |
| ATOM | 2759 | N | ASN | 936 | 72.998 | 36.143 | 56.093 | 1.00 | 36.78 | SOS |
| ATOM | 2760 | CA | ASN | 936 | 73.412 | 35.714 | 54.760 | 1.00 | 38.11 | SOS |
| ATOM | 2761 | CB | ASN | 936 | 73.072 | 34.243 | 54.531 | 1.00 | 40.14 | SOS |
| ATOM | 2762 | CG | ASN | 936 | 73.959 | 33.317 | 55.345 | 1.00 | 44.39 | SOS |
| ATOM | 2763 | OD1 | ASN | 936 | 75.143 | 33.591 | 55.529 | 1.00 | 43.22 | SOS |
| ATOM | 2764 | ND2 | ASN | 936 | 73.385 | 32.228 | 55.853 | 1.00 | 43.60 | SOS |
| ATOM | 2765 | C | ASN | 936 | 72.884 | 36.610 | 53.637 | 1.00 | 35.72 | SOS |
| ATOM | 2766 | O | ASN | 936 | 73.598 | 36.885 | 52.677 | 1.00 | 34.25 | SOS |
| ATOM | 2767 | N | ILE | 937 | 71.658 | 37.103 | 53.766 | 1.00 | 33.89 | SOS |
| ATOM | 2768 | CA | ILE | 937 | 71.126 | 37.993 | 52.743 | 1.00 | 33.35 | SOS |
| ATOM | 2769 | CB | ILE | 937 | 69.603 | 38.220 | 52.913 | 1.00 | 34.48 | SOS |
| ATOM | 2770 | CG2 | ILE | 937 | 69.108 | 39.266 | 51.928 | 1.00 | 31.14 | SOS |
| ATOM | 2771 | CG1 | ILE | 937 | 68.853 | 36.905 | 52.685 | 1.00 | 32.02 | SOS |
| ATOM | 2772 | CD1 | ILE | 937 | 67.409 | 36.958 | 53.088 | 1.00 | 30.48 | SOS |

Figure 8-47

| ATOM | 2773 | C | ILE | 937 | 71.877 | 39.332 | 52.802 | 1.00 | 34.21 | SOS |
| ATOM | 2774 | O | ILE | 937 | 72.401 | 39.797 | 51.791 | 1.00 | 34.04 | SOS |
| ATOM | 2775 | N | LEU | 938 | 71.988 | 39.916 | 53.994 | 1.00 | 34.23 | SOS |
| ATOM | 2776 | CA | LEU | 938 | 72.679 | 41.195 | 54.142 | 1.00 | 32.99 | SOS |
| ATOM | 2777 | CB | LEU | 938 | 72.684 | 41.655 | 55.609 | 1.00 | 30.55 | SOS |
| ATOM | 2778 | CG | LEU | 938 | 73.485 | 42.936 | 55.910 | 1.00 | 31.42 | SOS |
| ATOM | 2779 | CD1 | LEU | 938 | 72.779 | 44.149 | 55.351 | 1.00 | 32.59 | SOS |
| ATOM | 2780 | CD2 | LEU | 938 | 73.697 | 43.111 | 57.402 | 1.00 | 32.76 | SOS |
| ATOM | 2781 | C | LEU | 938 | 74.111 | 41.139 | 53.597 | 1.00 | 33.32 | SOS |
| ATOM | 2782 | O | LEU | 938 | 74.510 | 41.992 | 52.806 | 1.00 | 31.57 | SOS |
| ATOM | 2783 | N | LYS | 939 | 74.866 | 40.117 | 53.987 | 1.00 | 31.80 | SOS |
| ATOM | 2784 | CA | LYS | 939 | 76.245 | 39.982 | 53.530 | 1.00 | 33.04 | SOS |
| ATOM | 2785 | CB | LYS | 939 | 76.978 | 38.928 | 54.356 | 1.00 | 34.24 | SOS |
| ATOM | 2786 | CG | LYS | 939 | 77.313 | 39.373 | 55.774 | 1.00 | 31.56 | SOS |
| ATOM | 2787 | CD | LYS | 939 | 77.876 | 38.225 | 56.579 | 1.00 | 32.71 | SOS |
| ATOM | 2788 | CE | LYS | 939 | 78.502 | 38.680 | 57.887 | 1.00 | 35.48 | SOS |
| ATOM | 2789 | NZ | LYS | 939 | 79.199 | 37.545 | 58.575 | 1.00 | 31.28 | SOS |
| ATOM | 2790 | C | LYS | 939 | 76.371 | 39.692 | 52.036 | 1.00 | 36.31 | SOS |
| ATOM | 2791 | O | LYS | 939 | 77.311 | 40.167 | 51.390 | 1.00 | 35.36 | SOS |
| ATOM | 2792 | N | THR | 940 | 75.430 | 38.918 | 51.489 | 1.00 | 36.42 | SOS |
| ATOM | 2793 | CA | THR | 940 | 75.436 | 38.602 | 50.063 | 1.00 | 37.08 | SOS |
| ATOM | 2794 | CB | THR | 940 | 74.305 | 37.592 | 49.684 | 1.00 | 40.26 | SOS |
| ATOM | 2795 | OG1 | THR | 940 | 74.596 | 36.304 | 50.238 | 1.00 | 44.40 | SOS |
| ATOM | 2796 | CG2 | THR | 940 | 74.186 | 37.434 | 48.182 | 1.00 | 40.07 | SOS |
| ATOM | 2797 | C | THR | 940 | 75.247 | 39.912 | 49.298 | 1.00 | 38.78 | SOS |
| ATOM | 2798 | O | THR | 940 | 75.957 | 40.189 | 48.328 | 1.00 | 41.20 | SOS |
| ATOM | 2799 | N | GLU | 941 | 74.326 | 40.746 | 49.771 | 1.00 | 38.80 | SOS |
| ATOM | 2800 | CA | GLU | 941 | 74.069 | 42.026 | 49.122 | 1.00 | 40.13 | SOS |
| ATOM | 2801 | CB | GLU | 941 | 72.701 | 42.575 | 49.525 | 1.00 | 34.87 | SOS |
| ATOM | 2802 | CG | GLU | 941 | 71.539 | 41.680 | 49.091 | 1.00 | 42.43 | SOS |
| ATOM | 2803 | CD | GLU | 941 | 70.175 | 42.360 | 49.149 | 1.00 | 46.33 | SOS |
| ATOM | 2804 | OE1 | GLU | 941 | 70.022 | 43.354 | 49.896 | 1.00 | 45.38 | SOS |
| ATOM | 2805 | OE2 | GLU | 941 | 69.256 | 41.894 | 48.434 | 1.00 | 47.84 | SOS |
| ATOM | 2806 | C | GLU | 941 | 75.154 | 43.076 | 49.346 | 1.00 | 42.54 | SOS |
| ATOM | 2807 | O | GLU | 941 | 75.501 | 43.810 | 48.428 | 1.00 | 45.91 | SOS |
| ATOM | 2808 | N | GLU | 942 | 75.706 | 43.146 | 50.553 | 1.00 | 46.01 | SOS |
| ATOM | 2809 | CA | GLU | 942 | 76.739 | 44.135 | 50.832 | 1.00 | 48.66 | SOS |
| ATOM | 2810 | CB | GLU | 942 | 76.656 | 44.617 | 52.287 | 1.00 | 51.09 | SOS |
| ATOM | 2811 | CG | GLU | 942 | 75.443 | 45.530 | 52.562 | 1.00 | 59.51 | SOS |
| ATOM | 2812 | CD | GLU | 942 | 75.341 | 46.032 | 54.014 | 1.00 | 65.63 | SOS |
| ATOM | 2813 | OE1 | GLU | 942 | 74.593 | 47.004 | 54.262 | 1.00 | 67.90 | SOS |
| ATOM | 2814 | OE2 | GLU | 942 | 75.987 | 45.455 | 54.916 | 1.00 | 69.12 | SOS |
| ATOM | 2815 | C | GLU | 942 | 78.154 | 43.679 | 50.468 | 1.00 | 49.80 | SOS |
| ATOM | 2816 | O | GLU | 942 | 79.027 | 44.510 | 50.208 | 1.00 | 50.54 | SOS |
| ATOM | 2817 | N | GLY | 943 | 78.359 | 42.365 | 50.381 | 1.00 | 48.00 | SOS |
| ATOM | 2818 | CA | GLY | 943 | 79.672 | 41.836 | 50.045 | 1.00 | 45.15 | SOS |
| ATOM | 2819 | C | GLY | 943 | 79.962 | 41.559 | 48.575 | 1.00 | 44.56 | SOS |
| ATOM | 2820 | O | GLY | 943 | 81.023 | 41.033 | 48.257 | 1.00 | 46.05 | SOS |
| ATOM | 2821 | N | ASN | 944 | 79.009 | 41.855 | 47.694 | 1.00 | 42.47 | SOS |
| ATOM | 2822 | CA | ASN | 944 | 79.164 | 41.651 | 46.254 | 1.00 | 39.18 | SOS |
| ATOM | 2823 | CB | ASN | 944 | 78.305 | 40.483 | 45.778 | 1.00 | 36.64 | SOS |
| ATOM | 2824 | CG | ASN | 944 | 78.711 | 39.168 | 46.405 | 1.00 | 38.03 | SOS |
| ATOM | 2825 | OD1 | ASN | 944 | 79.667 | 38.529 | 45.974 | 1.00 | 43.35 | SOS |
| ATOM | 2826 | ND2 | ASN | 944 | 77.978 | 38.750 | 47.421 | 1.00 | 37.27 | SOS |
| ATOM | 2827 | C | ASN | 944 | 78.727 | 42.939 | 45.563 | 1.00 | 41.08 | SOS |
| ATOM | 2828 | O | ASN | 944 | 77.767 | 43.583 | 45.989 | 1.00 | 40.69 | SOS |
| ATOM | 2829 | N | PRO | 945 | 79.403 | 43.316 | 44.467 | 1.00 | 41.37 | SOS |
| ATOM | 2830 | CD | PRO | 945 | 80.424 | 42.530 | 43.749 | 1.00 | 44.44 | SOS |
| ATOM | 2831 | CA | PRO | 945 | 79.076 | 44.542 | 43.731 | 1.00 | 43.13 | SOS |
| ATOM | 2832 | CB | PRO | 945 | 80.170 | 44.595 | 42.664 | 1.00 | 42.32 | SOS |
| ATOM | 2833 | CG | PRO | 945 | 80.416 | 43.153 | 42.367 | 1.00 | 41.57 | SOS |

Figure 8-48

| | | | | | | | | | |
|---|---|---|---|---|---|---|---|---|---|
| ATOM | 2834 | C | PRO | 945 | 77.681 | 44.563 | 43.116 | 1.00 45.45 | SOS |
| ATOM | 2835 | O | PRO | 945 | 77.085 | 43.516 | 42.864 | 1.00 46.67 | SOS |
| ATOM | 2836 | N | GLU | 946 | 77.146 | 45.765 | 42.937 | 1.00 48.77 | SOS |
| ATOM | 2837 | CA | GLU | 946 | 75.828 | 45.947 | 42.337 | 1.00 56.46 | SOS |
| ATOM | 2838 | CB | GLU | 946 | 75.186 | 47.248 | 42.823 | 1.00 61.15 | SOS |
| ATOM | 2839 | CG | GLU | 946 | 74.569 | 47.178 | 44.205 | 1.00 71.93 | SOS |
| ATOM | 2840 | CD | GLU | 946 | 73.767 | 48.424 | 44.540 | 1.00 79.35 | SOS |
| ATOM | 2841 | OE1 | GLU | 946 | 74.381 | 49.499 | 44.742 | 1.00 81.51 | SOS |
| ATOM | 2842 | OE2 | GLU | 946 | 72.519 | 48.328 | 44.598 | 1.00 80.41 | SOS |
| ATOM | 2843 | C | GLU | 946 | 75.956 | 46.009 | 40.820 | 1.00 57.42 | SOS |
| ATOM | 2844 | O | GLU | 946 | 74.971 | 45.858 | 40.092 | 1.00 57.27 | SOS |
| ATOM | 2845 | N | VAL | 947 | 77.185 | 46.211 | 40.358 | 1.00 57.94 | SOS |
| ATOM | 2846 | CA | VAL | 947 | 77.476 | 46.340 | 38.943 | 1.00 56.01 | SOS |
| ATOM | 2847 | CB | VAL | 947 | 77.382 | 47.825 | 38.533 | 1.00 54.88 | SOS |
| ATOM | 2848 | CG1 | VAL | 947 | 78.251 | 48.108 | 37.343 | 1.00 59.70 | SOS |
| ATOM | 2849 | CG2 | VAL | 947 | 75.950 | 48.192 | 38.222 | 1.00 56.83 | SOS |
| ATOM | 2850 | C | VAL | 947 | 78.866 | 45.820 | 38.581 | 1.00 56.31 | SOS |
| ATOM | 2851 | O | VAL | 947 | 79.826 | 46.030 | 39.321 | 1.00 58.33 | SOS |
| ATOM | 2852 | N | LEU | 948 | 78.948 | 45.114 | 37.456 | 1.00 54.54 | SOS |
| ATOM | 2853 | CA | LEU | 948 | 80.211 | 44.600 | 36.943 | 1.00 53.27 | SOS |
| ATOM | 2854 | CB | LEU | 948 | 80.060 | 43.167 | 36.442 | 1.00 49.68 | SOS |
| ATOM | 2855 | CG | LEU | 948 | 79.860 | 42.039 | 37.451 | 1.00 48.63 | SOS |
| ATOM | 2856 | CD1 | LEU | 948 | 79.736 | 40.731 | 36.699 | 1.00 46.04 | SOS |
| ATOM | 2857 | CD2 | LEU | 948 | 81.035 | 41.978 | 38.414 | 1.00 50.15 | SOS |
| ATOM | 2858 | C | LEU | 948 | 80.550 | 45.504 | 35.766 | 1.00 57.14 | SOS |
| ATOM | 2859 | O | LEU | 948 | 79.656 | 45.890 | 35.010 | 1.00 60.06 | SOS |
| ATOM | 2860 | N | LYS | 949 | 81.819 | 45.878 | 35.627 | 1.00 58.62 | SOS |
| ATOM | 2861 | CA | LYS | 949 | 82.229 | 46.744 | 34.523 | 1.00 59.42 | SOS |
| ATOM | 2862 | CB | LYS | 949 | 83.114 | 47.893 | 35.018 | 1.00 62.41 | SOS |
| ATOM | 2863 | CG | LYS | 949 | 82.452 | 48.850 | 36.017 | 1.00 62.59 | SOS |
| ATOM | 2864 | CD | LYS | 949 | 81.383 | 49.717 | 35.377 | 1.00 61.61 | SOS |
| ATOM | 2865 | CE | LYS | 949 | 81.967 | 50.651 | 34.328 | 0.00 62.10 | SOS |
| ATOM | 2866 | NZ | LYS | 949 | 80.920 | 51.502 | 33.700 | 0.00 62.02 | SOS |
| ATOM | 2867 | C | LYS | 949 | 82.959 | 45.955 | 33.446 | 1.00 60.30 | SOS |
| ATOM | 2868 | O | LYS | 949 | 83.829 | 45.131 | 33.737 | 1.00 57.71 | SOS |
| ATOM | 2869 | N | ARG | 950 | 82.571 | 46.196 | 32.199 | 1.00 63.84 | SOS |
| ATOM | 2870 | CA | ARG | 950 | 83.170 | 45.529 | 31.047 | 1.00 65.83 | SOS |
| ATOM | 2871 | CB | ARG | 950 | 82.307 | 44.344 | 30.603 | 1.00 63.71 | SOS |
| ATOM | 2872 | CG | ARG | 950 | 82.183 | 43.209 | 31.613 | 1.00 60.21 | SOS |
| ATOM | 2873 | CD | ARG | 950 | 83.498 | 42.494 | 31.807 | 1.00 58.50 | SOS |
| ATOM | 2874 | NE | ARG | 950 | 83.369 | 41.283 | 32.616 | 1.00 58.72 | SOS |
| ATOM | 2875 | CZ | ARG | 950 | 83.474 | 41.243 | 33.943 | 1.00 62.20 | SOS |
| ATOM | 2876 | NH1 | ARG | 950 | 83.702 | 42.355 | 34.637 | 1.00 65.36 | SOS |
| ATOM | 2877 | NH2 | ARG | 950 | 83.390 | 40.081 | 34.578 | 1.00 59.20 | SOS |
| ATOM | 2878 | C | ARG | 950 | 83.274 | 46.536 | 29.908 | 1.00 68.64 | SOS |
| ATOM | 2879 | O | ARG | 950 | 82.293 | 47.215 | 29.582 | 1.00 65.86 | SOS |
| ATOM | 2880 | N | HIS | 951 | 84.472 | 46.650 | 29.334 | 1.00 72.30 | SOS |
| ATOM | 2881 | CA | HIS | 951 | 84.741 | 47.570 | 28.223 | 1.00 76.18 | SOS |
| ATOM | 2882 | CB | HIS | 951 | 84.213 | 46.997 | 26.896 | 1.00 80.25 | SOS |
| ATOM | 2883 | CG | HIS | 951 | 84.906 | 45.746 | 26.446 | 1.00 84.73 | SOS |
| ATOM | 2884 | CD2 | HIS | 951 | 84.419 | 44.524 | 26.123 | 1.00 85.81 | SOS |
| ATOM | 2885 | ND1 | HIS | 951 | 86.273 | 45.671 | 26.270 | 1.00 87.16 | SOS |
| ATOM | 2886 | CE1 | HIS | 951 | 86.596 | 44.457 | 25.859 | 1.00 87.75 | SOS |
| ATOM | 2887 | NE2 | HIS | 951 | 85.489 | 43.742 | 25.762 | 1.00 86.90 | SOS |
| ATOM | 2888 | C | HIS | 951 | 84.171 | 48.976 | 28.439 | 1.00 76.14 | SOS |
| ATOM | 2889 | O | HIS | 951 | 83.806 | 49.659 | 27.480 | 1.00 77.57 | SOS |
| ATOM | 2890 | N | GLY | 952 | 84.084 | 49.393 | 29.701 | 1.00 76.14 | SOS |
| ATOM | 2891 | CA | GLY | 952 | 83.564 | 50.714 | 30.022 | 1.00 74.65 | SOS |
| ATOM | 2892 | C | GLY | 952 | 82.053 | 50.806 | 30.122 | 1.00 73.85 | SOS |
| ATOM | 2893 | O | GLY | 952 | 81.506 | 51.894 | 30.299 | 1.00 71.91 | SOS |
| ATOM | 2894 | N | LYS | 953 | 81.374 | 49.670 | 29.989 | 1.00 73.26 | SOS |

Figure 8-49

```
ATOM   2895  CA   LYS  953      79.919  49.634  30.076  1.00  71.54      sos
ATOM   2896  CB   LYS  953      79.345  48.795  28.939  1.00  73.33      sos
ATOM   2897  CG   LYS  953      79.850  49.213  27.568  1.00  77.88      sos
ATOM   2898  CD   LYS  953      79.471  50.651  27.225  1.00  79.26      sos
ATOM   2899  CE   LYS  953      79.954  51.027  25.826  1.00  80.11      sos
ATOM   2900  NZ   LYS  953      79.511  52.388  25.403  1.00  80.55      sos
ATOM   2901  C    LYS  953      79.485  49.086  31.433  1.00  68.59      sos
ATOM   2902  O    LYS  953      80.182  48.267  32.037  1.00  66.25      sos
ATOM   2903  N    GLU  954      78.314  49.521  31.886  1.00  66.41      sos
ATOM   2904  CA   GLU  954      77.779  49.132  33.190  1.00  63.74      sos
ATOM   2905  CB   GLU  954      77.223  50.385  33.863  1.00  63.26      sos
ATOM   2906  CG   GLU  954      77.320  50.401  35.355  1.00  66.67      sos
ATOM   2907  CD   GLU  954      77.230  51.803  35.922  1.00  73.91      sos
ATOM   2908  OE1  GLU  954      78.291  52.458  36.060  1.00  71.39      sos
ATOM   2909  OE2  GLU  954      76.099  52.249  36.228  1.00  77.06      sos
ATOM   2910  C    GLU  954      76.722  48.009  33.170  1.00  60.57      sos
ATOM   2911  O    GLU  954      75.553  48.237  32.856  1.00  56.89      sos
ATOM   2912  N    LEU  955      77.135  46.800  33.540  1.00  58.29      sos
ATOM   2913  CA   LEU  955      76.221  45.660  33.557  1.00  58.06      sos
ATOM   2914  CB   LEU  955      76.874  44.421  32.932  1.00  58.48      sos
ATOM   2915  CG   LEU  955      77.830  44.572  31.748  1.00  57.76      sos
ATOM   2916  CD1  LEU  955      78.063  43.206  31.151  1.00  54.79      sos
ATOM   2917  CD2  LEU  955      77.263  45.507  30.704  1.00  58.49      sos
ATOM   2918  C    LEU  955      75.777  45.316  34.975  1.00  56.28      sos
ATOM   2919  O    LEU  955      76.600  45.252  35.890  1.00  58.79      sos
ATOM   2920  N    ILE  956      74.482  45.064  35.137  1.00  50.43      sos
ATOM   2921  CA   ILE  956      73.901  44.715  36.429  1.00  46.71      sos
ATOM   2922  CB   ILE  956      72.376  44.868  36.382  1.00  42.71      sos
ATOM   2923  CG2  ILE  956      71.739  44.327  37.645  1.00  38.41      sos
ATOM   2924  CG1  ILE  956      72.016  46.335  36.144  1.00  41.60      sos
ATOM   2925  CD1  ILE  956      70.579  46.561  35.727  1.00  39.13      sos
ATOM   2926  C    ILE  956      74.266  43.286  36.843  1.00  50.82      sos
ATOM   2927  O    ILE  956      74.059  42.341  36.085  1.00  53.08      sos
ATOM   2928  N    ASN  957      74.819  43.144  38.047  1.00  51.69      sos
ATOM   2929  CA   ASN  957      75.221  41.845  38.581  1.00  50.53      sos
ATOM   2930  CB   ASN  957      76.124  42.041  39.806  1.00  52.77      sos
ATOM   2931  CG   ASN  957      76.632  40.726  40.390  1.00  55.27      sos
ATOM   2932  OD1  ASN  957      76.104  39.652  40.104  1.00  55.07      sos
ATOM   2933  ND2  ASN  957      77.666  40.812  41.220  1.00  58.56      sos
ATOM   2934  C    ASN  957      73.979  41.080  38.985  1.00  50.28      sos
ATOM   2935  O    ASN  957      73.481  41.253  40.094  1.00  52.58      sos
ATOM   2936  N    PHE  958      73.492  40.217  38.101  1.00  48.79      sos
ATOM   2937  CA   PHE  958      72.289  39.447  38.404  1.00  47.01      sos
ATOM   2938  CB   PHE  958      71.596  38.984  37.126  1.00  47.54      sos
ATOM   2939  CG   PHE  958      70.217  38.463  37.356  1.00  43.00      sos
ATOM   2940  CD1  PHE  958      69.184  39.332  37.662  1.00  42.75      sos
ATOM   2941  CD2  PHE  958      69.961  37.099  37.322  1.00  44.01      sos
ATOM   2942  CE1  PHE  958      67.912  38.853  37.940  1.00  47.07      sos
ATOM   2943  CE2  PHE  958      68.696  36.609  37.599  1.00  45.47      sos
ATOM   2944  CZ   PHE  958      67.667  37.491  37.911  1.00  45.82      sos
ATOM   2945  C    PHE  958      72.566  38.259  39.309  1.00  45.59      sos
ATOM   2946  O    PHE  958      71.724  37.884  40.124  1.00  47.48      sos
ATOM   2947  N    SER  959      73.745  37.668  39.154  1.00  45.25      sos
ATOM   2948  CA   SER  959      74.165  36.526  39.961  1.00  48.51      sos
ATOM   2949  CB   SER  959      75.650  36.241  39.713  1.00  49.47      sos
ATOM   2950  OG   SER  959      76.185  35.367  40.694  1.00  53.06      sos
ATOM   2951  C    SER  959      73.927  36.769  41.454  1.00  48.32      sos
ATOM   2952  O    SER  959      73.480  35.882  42.185  1.00  50.28      sos
ATOM   2953  N    LYS  960      74.240  37.984  41.887  1.00  46.77      sos
ATOM   2954  CA   LYS  960      74.082  38.416  43.267  1.00  42.86      sos
ATOM   2955  CB   LYS  960      74.584  39.855  43.365  1.00  44.25      sos
```

Figure 8-50

```
ATOM   2956  CG   LYS  960    74.189  40.642  44.582  1.00  46.06      SOS
ATOM   2957  CD   LYS  960    74.728  42.044  44.418  1.00  46.54      SOS
ATOM   2958  CE   LYS  960    74.345  42.943  45.564  1.00  47.36      SOS
ATOM   2959  NZ   LYS  960    75.046  44.250  45.438  1.00  47.00      SOS
ATOM   2960  C    LYS  960    72.618  38.315  43.671  1.00  41.85      SOS
ATOM   2961  O    LYS  960    72.294  37.819  44.754  1.00  40.54      SOS
ATOM   2962  N    ARG  961    71.738  38.758  42.775  1.00  40.96      SOS
ATOM   2963  CA   ARG  961    70.301  38.714  43.015  1.00  41.94      SOS
ATOM   2964  CB   ARG  961    69.541  39.547  41.973  1.00  46.41      SOS
ATOM   2965  CG   ARG  961    69.473  41.066  42.266  1.00  47.57      SOS
ATOM   2966  CD   ARG  961    70.803  41.768  42.001  1.00  54.33      SOS
ATOM   2967  NE   ARG  961    70.763  43.204  42.290  1.00  57.32      SOS
ATOM   2968  CZ   ARG  961    71.590  44.106  41.759  1.00  55.15      SOS
ATOM   2969  NH1  ARG  961    72.537  43.739  40.905  1.00  52.19      SOS
ATOM   2970  NH2  ARG  961    71.451  45.387  42.061  1.00  55.46      SOS
ATOM   2971  C    ARG  961    69.796  37.275  43.029  1.00  42.62      SOS
ATOM   2972  O    ARG  961    68.857  36.948  43.753  1.00  42.74      SOS
ATOM   2973  N    ARG  962    70.445  36.410  42.251  1.00  43.04      SOS
ATOM   2974  CA   ARG  962    70.065  35.003  42.203  1.00  41.95      SOS
ATOM   2975  CB   ARG  962    70.798  34.275  41.080  1.00  44.78      SOS
ATOM   2976  CG   ARG  962    70.271  32.854  40.812  1.00  47.53      SOS
ATOM   2977  CD   ARG  962    71.170  32.085  39.850  1.00  51.09      SOS
ATOM   2978  NE   ARG  962    71.624  32.924  38.741  1.00  58.29      SOS
ATOM   2979  CZ   ARG  962    70.883  33.258  37.687  1.00  61.51      SOS
ATOM   2980  NH1  ARG  962    69.630  32.821  37.564  1.00  63.81      SOS
ATOM   2981  NH2  ARG  962    71.386  34.079  36.777  1.00  61.24      SOS
ATOM   2982  C    ARG  962    70.420  34.353  43.526  1.00  41.78      SOS
ATOM   2983  O    ARG  962    69.661  33.541  44.053  1.00  44.33      SOS
ATOM   2984  N    LYS  963    71.586  34.707  44.056  1.00  42.96      SOS
ATOM   2985  CA   LYS  963    72.040  34.157  45.326  1.00  43.27      SOS
ATOM   2986  CB   LYS  963    73.477  34.588  45.630  1.00  39.82      SOS
ATOM   2987  CG   LYS  963    74.530  33.657  45.040  1.00  37.49      SOS
ATOM   2988  CD   LYS  963    75.937  34.080  45.440  0.00  38.70      SOS
ATOM   2989  CE   LYS  963    76.282  35.464  44.909  0.00  38.58      SOS
ATOM   2990  NZ   LYS  963    77.650  35.889  45.314  0.00  38.88      SOS
ATOM   2991  C    LYS  963    71.096  34.537  46.462  1.00  44.33      SOS
ATOM   2992  O    LYS  963    70.875  33.740  47.382  1.00  43.72      SOS
ATOM   2993  N    VAL  964    70.510  35.731  46.375  1.00  42.38      SOS
ATOM   2994  CA   VAL  964    69.567  36.181  47.397  1.00  41.67      SOS
ATOM   2995  CB   VAL  964    69.198  37.679  47.234  1.00  41.32      SOS
ATOM   2996  CG1  VAL  964    68.243  38.108  48.324  1.00  34.58      SOS
ATOM   2997  CG2  VAL  964    70.448  38.536  47.286  1.00  44.39      SOS
ATOM   2998  C    VAL  964    68.299  35.338  47.295  1.00  41.15      SOS
ATOM   2999  O    VAL  964    67.806  34.815  48.303  1.00  39.53      SOS
ATOM   3000  N    ALA  965    67.821  35.171  46.059  1.00  41.26      SOS
ATOM   3001  CA   ALA  965    66.610  34.402  45.760  1.00  39.89      SOS
ATOM   3002  CB   ALA  965    66.311  34.456  44.281  1.00  35.28      SOS
ATOM   3003  C    ALA  965    66.655  32.952  46.243  1.00  40.61      SOS
ATOM   3004  O    ALA  965    65.621  32.395  46.620  1.00  36.39      SOS
ATOM   3005  N    GLU  966    67.844  32.347  46.235  1.00  41.19      SOS
ATOM   3006  CA   GLU  966    68.002  30.969  46.705  1.00  43.20      SOS
ATOM   3007  CB   GLU  966    69.396  30.434  46.375  1.00  46.49      SOS
ATOM   3008  CG   GLU  966    69.660  30.240  44.883  1.00  55.23      SOS
ATOM   3009  CD   GLU  966    71.132  29.995  44.549  1.00  57.37      SOS
ATOM   3010  OE1  GLU  966    71.952  29.772  45.475  1.00  52.53      SOS
ATOM   3011  OE2  GLU  966    71.466  30.038  43.345  1.00  59.09      SOS
ATOM   3012  C    GLU  966    67.757  30.882  48.212  1.00  42.86      SOS
ATOM   3013  O    GLU  966    67.128  29.934  48.692  1.00  44.23      SOS
ATOM   3014  N    ILE  967    68.250  31.876  48.953  1.00  41.38      SOS
ATOM   3015  CA   ILE  967    68.070  31.908  50.403  1.00  38.81      SOS
ATOM   3016  CB   ILE  967    68.927  33.002  51.064  1.00  34.99      SOS
```

Figure 8-51

| | | | | | | | | | |
|---|---|---|---|---|---|---|---|---|---|
| ATOM | 3017 | CG2 | ILE | 967 | 68.854 | 32.873 | 52.572 | 1.00 33.20 | SOS |
| ATOM | 3018 | CG1 | ILE | 967 | 70.383 | 32.851 | 50.627 | 1.00 31.94 | SOS |
| ATOM | 3019 | CD1 | ILE | 967 | 71.280 | 33.962 | 51.080 | 1.00 24.81 | SOS |
| ATOM | 3020 | C | ILE | 967 | 66.595 | 32.153 | 50.680 | 1.00 39.08 | SOS |
| ATOM | 3021 | O | ILE | 967 | 65.981 | 31.491 | 51.520 | 1.00 38.84 | SOS |
| ATOM | 3022 | N | THR | 968 | 66.022 | 33.085 | 49.934 | 1.00 39.52 | SOS |
| ATOM | 3023 | CA | THR | 968 | 64.610 | 33.388 | 50.065 | 1.00 39.92 | SOS |
| ATOM | 3024 | CB | THR | 968 | 64.216 | 34.503 | 49.089 | 1.00 40.00 | SOS |
| ATOM | 3025 | OG1 | THR | 968 | 64.371 | 35.763 | 49.744 | 1.00 47.85 | SOS |
| ATOM | 3026 | CG2 | THR | 968 | 62.791 | 34.349 | 48.599 | 1.00 45.60 | SOS |
| ATOM | 3027 | C | THR | 968 | 63.817 | 32.110 | 49.788 | 1.00 38.89 | SOS |
| ATOM | 3028 | O | THR | 968 | 62.970 | 31.717 | 50.590 | 1.00 35.16 | SOS |
| ATOM | 3029 | N | GLY | 969 | 64.156 | 31.442 | 48.683 | 1.00 39.31 | SOS |
| ATOM | 3030 | CA | GLY | 969 | 63.489 | 30.213 | 48.290 | 1.00 36.56 | SOS |
| ATOM | 3031 | C | GLY | 969 | 63.532 | 29.156 | 49.371 | 1.00 39.29 | SOS |
| ATOM | 3032 | O | GLY | 969 | 62.507 | 28.539 | 49.681 | 1.00 38.99 | SOS |
| ATOM | 3033 | N | GLU | 970 | 64.708 | 28.967 | 49.968 | 1.00 39.85 | SOS |
| ATOM | 3034 | CA | GLU | 970 | 64.866 | 27.992 | 51.041 | 1.00 40.37 | SOS |
| ATOM | 3035 | CB | GLU | 970 | 66.307 | 27.971 | 51.552 | 1.00 46.63 | SOS |
| ATOM | 3036 | CG | GLU | 970 | 66.561 | 26.936 | 52.654 | 1.00 54.11 | SOS |
| ATOM | 3037 | CD | GLU | 970 | 68.026 | 26.844 | 53.089 | 1.00 57.16 | SOS |
| ATOM | 3038 | OE1 | GLU | 970 | 68.265 | 26.435 | 54.251 | 1.00 50.60 | SOS |
| ATOM | 3039 | OE2 | GLU | 970 | 68.929 | 27.167 | 52.273 | 1.00 54.40 | SOS |
| ATOM | 3040 | C | GLU | 970 | 63.912 | 28.326 | 52.181 | 1.00 40.45 | SOS |
| ATOM | 3041 | O | GLU | 970 | 63.261 | 27.440 | 52.722 | 1.00 40.70 | SOS |
| ATOM | 3042 | N | ILE | 971 | 63.808 | 29.612 | 52.516 | 1.00 39.96 | SOS |
| ATOM | 3043 | CA | ILE | 971 | 62.919 | 30.066 | 53.587 | 1.00 38.47 | SOS |
| ATOM | 3044 | CB | ILE | 971 | 62.969 | 31.617 | 53.741 | 1.00 39.32 | SOS |
| ATOM | 3045 | CG2 | ILE | 971 | 61.824 | 32.131 | 54.595 | 1.00 33.01 | SOS |
| ATOM | 3046 | CG1 | ILE | 971 | 64.298 | 32.044 | 54.352 | 1.00 37.02 | SOS |
| ATOM | 3047 | CD1 | ILE | 971 | 64.531 | 33.516 | 54.262 | 1.00 34.62 | SOS |
| ATOM | 3048 | C | ILE | 971 | 61.489 | 29.635 | 53.297 | 1.00 37.74 | SOS |
| ATOM | 3049 | O | ILE | 971 | 60.846 | 29.014 | 54.136 | 1.00 39.30 | SOS |
| ATOM | 3050 | N | GLN | 972 | 61.020 | 29.938 | 52.089 | 1.00 39.14 | SOS |
| ATOM | 3051 | CA | GLN | 972 | 59.661 | 29.612 | 51.665 | 1.00 39.55 | SOS |
| ATOM | 3052 | CB | GLN | 972 | 59.363 | 30.220 | 50.292 | 1.00 40.62 | SOS |
| ATOM | 3053 | CG | GLN | 972 | 59.140 | 31.722 | 50.330 | 1.00 48.28 | SOS |
| ATOM | 3054 | CD | GLN | 972 | 58.877 | 32.328 | 48.958 | 1.00 51.83 | SOS |
| ATOM | 3055 | OE1 | GLN | 972 | 59.772 | 32.394 | 48.104 | 1.00 50.13 | SOS |
| ATOM | 3056 | NE2 | GLN | 972 | 57.650 | 32.806 | 48.752 | 1.00 50.20 | SOS |
| ATOM | 3057 | C | GLN | 972 | 59.347 | 28.125 | 51.664 | 1.00 38.20 | SOS |
| ATOM | 3058 | O | GLN | 972 | 58.217 | 27.724 | 51.941 | 1.00 35.92 | SOS |
| ATOM | 3059 | N | GLN | 973 | 60.349 | 27.305 | 51.375 | 1.00 37.71 | SOS |
| ATOM | 3060 | CA | GLN | 973 | 60.139 | 25.870 | 51.362 | 1.00 41.37 | SOS |
| ATOM | 3061 | CB | GLN | 973 | 61.409 | 25.146 | 50.918 | 1.00 45.84 | SOS |
| ATOM | 3062 | CG | GLN | 973 | 61.192 | 23.694 | 50.490 | 1.00 61.48 | SOS |
| ATOM | 3063 | CD | GLN | 973 | 60.289 | 23.529 | 49.255 | 1.00 63.88 | SOS |
| ATOM | 3064 | OE1 | GLN | 973 | 59.986 | 24.490 | 48.544 | 1.00 66.85 | SOS |
| ATOM | 3065 | NE2 | GLN | 973 | 59.876 | 22.293 | 48.995 | 1.00 66.02 | SOS |
| ATOM | 3066 | C | GLN | 973 | 59.695 | 25.404 | 52.747 | 1.00 42.10 | SOS |
| ATOM | 3067 | O | GLN | 973 | 58.720 | 24.666 | 52.873 | 1.00 45.36 | SOS |
| ATOM | 3068 | N | TYR | 974 | 60.351 | 25.911 | 53.788 | 1.00 41.97 | SOS |
| ATOM | 3069 | CA | TYR | 974 | 60.015 | 25.540 | 55.161 | 1.00 40.25 | SOS |
| ATOM | 3070 | CB | TYR | 974 | 61.167 | 25.890 | 56.104 | 1.00 38.89 | SOS |
| ATOM | 3071 | CG | TYR | 974 | 62.407 | 25.046 | 55.906 | 1.00 35.61 | SOS |
| ATOM | 3072 | CD1 | TYR | 974 | 63.615 | 25.624 | 55.512 | 1.00 33.58 | SOS |
| ATOM | 3073 | CE1 | TYR | 974 | 64.749 | 24.856 | 55.333 | 1.00 30.13 | SOS |
| ATOM | 3074 | CD2 | TYR | 974 | 62.375 | 23.671 | 56.114 | 1.00 30.89 | SOS |
| ATOM | 3075 | CE2 | TYR | 974 | 63.504 | 22.896 | 55.934 | 1.00 29.51 | SOS |
| ATOM | 3076 | CZ | TYR | 974 | 64.687 | 23.493 | 55.545 | 1.00 29.98 | SOS |
| ATOM | 3077 | OH | TYR | 974 | 65.810 | 22.721 | 55.374 | 1.00 34.05 | SOS |

Figure 8-52

| ATOM | 3078 | C | TYR | 974 | 58.701 | 26.128 | 55.688 | 1.00 | 39.49 | SOS |
|---|---|---|---|---|---|---|---|---|---|---|
| ATOM | 3079 | O | TYR | 974 | 58.292 | 25.833 | 56.807 | 1.00 | 37.13 | SOS |
| ATOM | 3080 | N | GLN | 975 | 58.026 | 26.934 | 54.875 | 1.00 | 41.18 | SOS |
| ATOM | 3081 | CA | GLN | 975 | 56.754 | 27.536 | 55.282 | 1.00 | 45.02 | SOS |
| ATOM | 3082 | CB | GLN | 975 | 56.623 | 28.950 | 54.705 | 1.00 | 46.36 | SOS |
| ATOM | 3083 | CG | GLN | 975 | 57.795 | 29.874 | 54.996 | 1.00 | 47.33 | SOS |
| ATOM | 3084 | CD | GLN | 975 | 57.569 | 31.270 | 54.461 | 1.00 | 49.02 | SOS |
| ATOM | 3085 | OE1 | GLN | 975 | 57.488 | 31.473 | 53.249 | 1.00 | 48.89 | SOS |
| ATOM | 3086 | NE2 | GLN | 975 | 57.461 | 32.247 | 55.366 | 1.00 | 45.28 | SOS |
| ATOM | 3087 | C | GLN | 975 | 55.537 | 26.710 | 54.841 | 1.00 | 47.02 | SOS |
| ATOM | 3088 | O | GLN | 975 | 54.398 | 27.065 | 55.157 | 1.00 | 46.13 | SOS |
| ATOM | 3089 | N | ASN | 976 | 55.783 | 25.621 | 54.107 | 1.00 | 47.93 | SOS |
| ATOM | 3090 | CA | ASN | 976 | 54.716 | 24.756 | 53.595 | 1.00 | 47.08 | SOS |
| ATOM | 3091 | CB | ASN | 976 | 55.253 | 23.829 | 52.491 | 1.00 | 47.37 | SOS |
| ATOM | 3092 | CG | ASN | 976 | 55.751 | 24.586 | 51.261 | 1.00 | 51.31 | SOS |
| ATOM | 3093 | OD1 | ASN | 976 | 55.205 | 25.629 | 50.885 | 1.00 | 53.34 | SOS |
| ATOM | 3094 | ND2 | ASN | 976 | 56.789 | 24.051 | 50.620 | 1.00 | 46.84 | SOS |
| ATOM | 3095 | C | ASN | 976 | 54.035 | 23.909 | 54.669 | 1.00 | 48.61 | SOS |
| ATOM | 3096 | O | ASN | 976 | 52.905 | 24.193 | 55.073 | 1.00 | 46.58 | SOS |
| ATOM | 3097 | N | GLN | 977 | 54.742 | 22.874 | 55.118 | 1.00 | 48.44 | SOS |
| ATOM | 3098 | CA | GLN | 977 | 54.257 | 21.930 | 56.118 | 1.00 | 49.81 | SOS |
| ATOM | 3099 | CB | GLN | 977 | 55.325 | 20.871 | 56.374 | 1.00 | 58.19 | SOS |
| ATOM | 3100 | CG | GLN | 977 | 55.482 | 19.872 | 55.251 | 1.00 | 68.58 | SOS |
| ATOM | 3101 | CD | GLN | 977 | 54.218 | 19.070 | 55.035 | 1.00 | 75.31 | SOS |
| ATOM | 3102 | OE1 | GLN | 977 | 53.886 | 18.184 | 55.831 | 1.00 | 76.15 | SOS |
| ATOM | 3103 | NE2 | GLN | 977 | 53.485 | 19.395 | 53.968 | 1.00 | 78.10 | SOS |
| ATOM | 3104 | C | GLN | 977 | 53.800 | 22.500 | 57.453 | 1.00 | 49.85 | SOS |
| ATOM | 3105 | O | GLN | 977 | 54.585 | 23.095 | 58.187 | 1.00 | 54.13 | SOS |
| ATOM | 3106 | N | PRO | 978 | 52.519 | 22.307 | 57.792 | 1.00 | 47.20 | SOS |
| ATOM | 3107 | CD | PRO | 978 | 51.488 | 21.788 | 56.877 | 1.00 | 49.75 | SOS |
| ATOM | 3108 | CA | PRO | 978 | 51.910 | 22.777 | 59.038 | 1.00 | 46.73 | SOS |
| ATOM | 3109 | CB | PRO | 978 | 50.444 | 22.901 | 58.652 | 1.00 | 49.20 | SOS |
| ATOM | 3110 | CG | PRO | 978 | 50.260 | 21.722 | 57.761 | 1.00 | 49.03 | SOS |
| ATOM | 3111 | C | PRO | 978 | 52.100 | 21.754 | 60.159 | 1.00 | 46.41 | SOS |
| ATOM | 3112 | O | PRO | 978 | 52.395 | 20.587 | 59.894 | 1.00 | 46.64 | SOS |
| ATOM | 3113 | N | TYR | 979 | 51.912 | 22.190 | 61.404 | 1.00 | 46.60 | SOS |
| ATOM | 3114 | CA | TYR | 979 | 52.072 | 21.315 | 62.573 | 1.00 | 43.72 | SOS |
| ATOM | 3115 | CB | TYR | 979 | 52.526 | 22.117 | 63.812 | 1.00 | 39.08 | SOS |
| ATOM | 3116 | CG | TYR | 979 | 54.024 | 22.262 | 63.929 | 1.00 | 32.43 | SOS |
| ATOM | 3117 | CD1 | TYR | 979 | 54.677 | 23.381 | 63.417 | 1.00 | 33.41 | SOS |
| ATOM | 3118 | CE1 | TYR | 979 | 56.065 | 23.485 | 63.455 | 1.00 | 35.28 | SOS |
| ATOM | 3119 | CD2 | TYR | 979 | 54.796 | 21.250 | 64.494 | 1.00 | 29.89 | SOS |
| ATOM | 3120 | CE2 | TYR | 979 | 56.180 | 21.343 | 64.542 | 1.00 | 33.56 | SOS |
| ATOM | 3121 | CZ | TYR | 979 | 56.812 | 22.463 | 64.016 | 1.00 | 37.27 | SOS |
| ATOM | 3122 | OH | TYR | 979 | 58.187 | 22.551 | 64.029 | 1.00 | 38.77 | SOS |
| ATOM | 3123 | C | TYR | 979 | 50.827 | 20.521 | 62.931 | 1.00 | 43.14 | SOS |
| ATOM | 3124 | O | TYR | 979 | 49.720 | 21.063 | 62.990 | 1.00 | 40.65 | SOS |
| ATOM | 3125 | N | CYS | 980 | 51.014 | 19.230 | 63.176 | 1.00 | 44.31 | SOS |
| ATOM | 3126 | CA | CYS | 980 | 49.895 | 18.387 | 63.562 | 1.00 | 48.01 | SOS |
| ATOM | 3127 | CB | CYS | 980 | 50.149 | 16.922 | 63.193 | 1.00 | 51.99 | SOS |
| ATOM | 3128 | SG | CYS | 980 | 48.742 | 15.819 | 63.546 | 1.00 | 62.82 | SOS |
| ATOM | 3129 | C | CYS | 980 | 49.760 | 18.541 | 65.069 | 1.00 | 45.64 | SOS |
| ATOM | 3130 | O | CYS | 980 | 50.172 | 17.664 | 65.841 | 1.00 | 44.69 | SOS |
| ATOM | 3131 | N | LEU | 981 | 49.228 | 19.689 | 65.478 | 1.00 | 38.97 | SOS |
| ATOM | 3132 | CA | LEU | 981 | 49.051 | 19.991 | 66.888 | 1.00 | 38.05 | SOS |
| ATOM | 3133 | CB | LEU | 981 | 50.233 | 20.799 | 67.432 | 1.00 | 38.97 | SOS |
| ATOM | 3134 | CG | LEU | 981 | 51.629 | 20.186 | 67.559 | 1.00 | 36.41 | SOS |
| ATOM | 3135 | CD1 | LEU | 981 | 52.608 | 21.267 | 67.947 | 1.00 | 39.22 | SOS |
| ATOM | 3136 | CD2 | LEU | 981 | 51.628 | 19.081 | 68.598 | 1.00 | 38.45 | SOS |
| ATOM | 3137 | C | LEU | 981 | 47.791 | 20.790 | 67.098 | 1.00 | 41.09 | SOS |
| ATOM | 3138 | O | LEU | 981 | 47.483 | 21.713 | 66.346 | 1.00 | 41.56 | SOS |

Figure 8-53

| | | | | | | | | | |
|---|---|---|---|---|---|---|---|---|---|
| ATOM | 3139 | N | ARG | 982 | 47.096 | 20.458 | 68.173 | 1.00 45.70 | SOS |
| ATOM | 3140 | CA | ARG | 982 | 45.860 | 21.120 | 68.532 | 1.00 48.55 | SOS |
| ATOM | 3141 | CB | ARG | 982 | 45.098 | 20.216 | 69.506 | 1.00 52.66 | SOS |
| ATOM | 3142 | CG | ARG | 982 | 43.587 | 20.313 | 69.436 | 1.00 64.07 | SOS |
| ATOM | 3143 | CD | ARG | 982 | 42.940 | 19.199 | 70.270 | 1.00 72.76 | SOS |
| ATOM | 3144 | NE | ARG | 982 | 43.325 | 17.866 | 69.801 | 1.00 74.14 | SOS |
| ATOM | 3145 | CZ | ARG | 982 | 42.485 | 16.981 | 69.265 | 1.00 73.64 | SOS |
| ATOM | 3146 | NH1 | ARG | 982 | 41.198 | 17.270 | 69.127 | 1.00 71.98 | SOS |
| ATOM | 3147 | NH2 | ARG | 982 | 42.938 | 15.814 | 68.830 | 1.00 73.04 | SOS |
| ATOM | 3148 | C | ARG | 982 | 46.182 | 22.479 | 69.171 | 1.00 49.82 | SOS |
| ATOM | 3149 | O | ARG | 982 | 47.064 | 22.580 | 70.030 | 1.00 53.00 | SOS |
| ATOM | 3150 | N | VAL | 983 | 45.508 | 23.523 | 68.697 | 1.00 47.50 | SOS |
| ATOM | 3151 | CA | VAL | 983 | 45.679 | 24.881 | 69.214 | 1.00 47.09 | SOS |
| ATOM | 3152 | CB | VAL | 983 | 45.166 | 25.949 | 68.179 | 1.00 45.18 | SOS |
| ATOM | 3153 | CG1 | VAL | 983 | 44.784 | 27.254 | 68.871 | 1.00 40.07 | SOS |
| ATOM | 3154 | CG2 | VAL | 983 | 46.227 | 26.232 | 67.133 | 1.00 43.69 | SOS |
| ATOM | 3155 | C | VAL | 983 | 44.864 | 25.043 | 70.493 | 1.00 48.14 | SOS |
| ATOM | 3156 | O | VAL | 983 | 43.739 | 24.562 | 70.575 | 1.00 51.66 | SOS |
| ATOM | 3157 | N | GLU | 984 | 45.448 | 25.671 | 71.507 | 1.00 49.35 | SOS |
| ATOM | 3158 | CA | GLU | 984 | 44.718 | 25.931 | 72.743 | 1.00 47.44 | SOS |
| ATOM | 3159 | CB | GLU | 984 | 45.410 | 25.335 | 73.966 | 1.00 46.26 | SOS |
| ATOM | 3160 | CG | GLU | 984 | 44.441 | 24.975 | 75.104 | 1.00 46.87 | SOS |
| ATOM | 3161 | CD | GLU | 984 | 43.540 | 26.129 | 75.529 | 1.00 47.11 | SOS |
| ATOM | 3162 | OE1 | GLU | 984 | 42.327 | 25.913 | 75.711 | 1.00 50.46 | SOS |
| ATOM | 3163 | OE2 | GLU | 984 | 44.034 | 27.257 | 75.683 | 1.00 49.81 | SOS |
| ATOM | 3164 | C | GLU | 984 | 44.722 | 27.439 | 72.817 | 1.00 47.78 | SOS |
| ATOM | 3165 | O | GLU | 984 | 45.720 | 28.044 | 73.183 | 1.00 46.26 | SOS |
| ATOM | 3166 | N | SER | 985 | 43.593 | 28.026 | 72.438 | 1.00 52.10 | SOS |
| ATOM | 3167 | CA | SER | 985 | 43.388 | 29.473 | 72.381 | 1.00 52.76 | SOS |
| ATOM | 3168 | CB | SER | 985 | 41.935 | 29.773 | 71.996 | 1.00 54.18 | SOS |
| ATOM | 3169 | OG | SER | 985 | 41.592 | 29.130 | 70.779 | 1.00 55.84 | SOS |
| ATOM | 3170 | C | SER | 985 | 43.775 | 30.298 | 73.605 | 1.00 52.46 | SOS |
| ATOM | 3171 | O | SER | 985 | 44.320 | 31.389 | 73.457 | 1.00 49.88 | SOS |
| ATOM | 3172 | N | ASP | 986 | 43.472 | 29.803 | 74.802 | 1.00 52.58 | SOS |
| ATOM | 3173 | CA | ASP | 986 | 43.802 | 30.536 | 76.022 | 1.00 54.44 | SOS |
| ATOM | 3174 | CB | ASP | 986 | 43.009 | 29.995 | 77.213 | 1.00 58.68 | SOS |
| ATOM | 3175 | CG | ASP | 986 | 41.509 | 30.195 | 77.054 | 1.00 64.04 | SOS |
| ATOM | 3176 | OD1 | ASP | 986 | 41.090 | 31.291 | 76.613 | 1.00 66.26 | SOS |
| ATOM | 3177 | OD2 | ASP | 986 | 40.750 | 29.251 | 77.367 | 1.00 67.74 | SOS |
| ATOM | 3178 | C | ASP | 986 | 45.300 | 30.552 | 76.325 | 1.00 52.70 | SOS |
| ATOM | 3179 | O | ASP | 986 | 45.852 | 31.598 | 76.656 | 1.00 53.82 | SOS |
| ATOM | 3180 | N | ILE | 987 | 45.953 | 29.402 | 76.193 | 1.00 48.36 | SOS |
| ATOM | 3181 | CA | ILE | 987 | 47.389 | 29.299 | 76.436 | 1.00 46.63 | SOS |
| ATOM | 3182 | CB | ILE | 987 | 47.860 | 27.831 | 76.348 | 1.00 43.56 | SOS |
| ATOM | 3183 | CG2 | ILE | 987 | 49.362 | 27.745 | 76.511 | 1.00 40.09 | SOS |
| ATOM | 3184 | CG1 | ILE | 987 | 47.173 | 26.998 | 77.430 | 1.00 45.63 | SOS |
| ATOM | 3185 | CD1 | ILE | 987 | 47.568 | 25.539 | 77.430 | 1.00 42.99 | SOS |
| ATOM | 3186 | C | ILE | 987 | 48.145 | 30.136 | 75.403 | 1.00 46.74 | SOS |
| ATOM | 3187 | O | ILE | 987 | 49.179 | 30.738 | 75.697 | 1.00 49.52 | SOS |
| ATOM | 3188 | N | LYS | 988 | 47.597 | 30.175 | 74.196 | 1.00 45.85 | SOS |
| ATOM | 3189 | CA | LYS | 988 | 48.169 | 30.911 | 73.083 | 1.00 44.60 | SOS |
| ATOM | 3190 | CB | LYS | 988 | 47.382 | 30.590 | 71.813 | 1.00 45.12 | SOS |
| ATOM | 3191 | CG | LYS | 988 | 47.732 | 31.425 | 70.605 | 1.00 50.79 | SOS |
| ATOM | 3192 | CD | LYS | 988 | 46.543 | 31.537 | 69.662 | 1.00 52.63 | SOS |
| ATOM | 3193 | CE | LYS | 988 | 46.882 | 32.357 | 68.429 | 1.00 53.56 | SOS |
| ATOM | 3194 | NZ | LYS | 988 | 47.955 | 31.692 | 67.621 | 1.00 58.23 | SOS |
| ATOM | 3195 | C | LYS | 988 | 48.099 | 32.400 | 73.374 | 1.00 46.07 | SOS |
| ATOM | 3196 | O | LYS | 988 | 49.027 | 33.138 | 73.071 | 1.00 49.55 | SOS |
| ATOM | 3197 | N | ARG | 989 | 47.004 | 32.834 | 73.988 | 1.00 48.10 | SOS |
| ATOM | 3198 | CA | ARG | 989 | 46.814 | 34.243 | 74.310 | 1.00 51.24 | SOS |
| ATOM | 3199 | CB | ARG | 989 | 45.353 | 34.503 | 74.677 | 1.00 54.21 | SOS |

Figure 8-54

```
ATOM   3200  CG   ARG  989   44.858  35.887  74.295  1.00  66.12   SOS
ATOM   3201  CD   ARG  989   43.327  35.948  74.278  1.00  75.02   SOS
ATOM   3202  NE   ARG  989   42.741  35.092  73.241  1.00  78.43   SOS
ATOM   3203  CZ   ARG  989   41.957  34.041  73.481  1.00  79.66   SOS
ATOM   3204  NH1  ARG  989   41.652  33.703  74.732  1.00  80.46   SOS
ATOM   3205  NH2  ARG  989   41.487  33.320  72.468  1.00  76.98   SOS
ATOM   3206  C    ARG  989   47.754  34.673  75.438  1.00  50.85   SOS
ATOM   3207  O    ARG  989   48.240  35.808  75.461  1.00  49.06   SOS
ATOM   3208  N    PHE  990   48.037  33.738  76.341  1.00  48.35   SOS
ATOM   3209  CA   PHE  990   48.929  33.977  77.463  1.00  48.32   SOS
ATOM   3210  CB   PHE  990   48.998  32.729  78.350  1.00  48.04   SOS
ATOM   3211  CG   PHE  990   49.986  32.836  79.480  1.00  47.78   SOS
ATOM   3212  CD1  PHE  990   49.638  33.475  80.669  1.00  43.04   SOS
ATOM   3213  CD2  PHE  990   51.275  32.313  79.347  1.00  44.81   SOS
ATOM   3214  CE1  PHE  990   50.558  33.597  81.709  1.00  40.31   SOS
ATOM   3215  CE2  PHE  990   52.200  32.430  80.380  1.00  45.07   SOS
ATOM   3216  CZ   PHE  990   51.842  33.074  81.564  1.00  41.57   SOS
ATOM   3217  C    PHE  990   50.333  34.346  76.970  1.00  50.12   SOS
ATOM   3218  O    PHE  990   50.897  35.357  77.399  1.00  48.99   SOS
ATOM   3219  N    PHE  991   50.887  33.525  76.077  1.00  47.76   SOS
ATOM   3220  CA   PHE  991   52.225  33.763  75.538  1.00  47.68   SOS
ATOM   3221  CB   PHE  991   52.809  32.478  74.923  1.00  44.16   SOS
ATOM   3222  CG   PHE  991   53.087  31.395  75.933  1.00  43.00   SOS
ATOM   3223  CD1  PHE  991   52.292  30.259  75.996  1.00  43.47   SOS
ATOM   3224  CD2  PHE  991   54.117  31.530  76.853  1.00  47.07   SOS
ATOM   3225  CE1  PHE  991   52.515  29.281  76.961  1.00  39.73   SOS
ATOM   3226  CE2  PHE  991   54.347  30.551  77.827  1.00  43.11   SOS
ATOM   3227  CZ   PHE  991   53.543  29.429  77.877  1.00  42.13   SOS
ATOM   3228  C    PHE  991   52.249  34.904  74.530  1.00  47.41   SOS
ATOM   3229  O    PHE  991   53.294  35.491  74.255  1.00  48.36   SOS
ATOM   3230  N    GLU  992   51.085  35.240  73.996  1.00  49.69   SOS
ATOM   3231  CA   GLU  992   50.994  36.317  73.024  1.00  48.81   SOS
ATOM   3232  CB   GLU  992   49.723  36.149  72.204  1.00  49.98   SOS
ATOM   3233  CG   GLU  992   49.839  36.573  70.762  1.00  53.94   SOS
ATOM   3234  CD   GLU  992   48.729  35.992  69.900  1.00  57.65   SOS
ATOM   3235  OE1  GLU  992   47.569  35.913  70.374  1.00  52.43   SOS
ATOM   3236  OE2  GLU  992   49.026  35.610  68.746  1.00  58.11   SOS
ATOM   3237  C    GLU  992   50.990  37.652  73.762  1.00  47.04   SOS
ATOM   3238  O    GLU  992   51.459  38.660  73.243  1.00  44.61   SOS
ATOM   3239  N    ASN  993   50.511  37.627  75.001  1.00  47.60   SOS
ATOM   3240  CA   ASN  993   50.435  38.822  75.834  1.00  47.52   SOS
ATOM   3241  CB   ASN  993   49.069  38.892  76.529  1.00  52.05   SOS
ATOM   3242  CG   ASN  993   47.923  39.069  75.548  1.00  58.72   SOS
ATOM   3243  OD1  ASN  993   48.081  39.689  74.492  1.00  61.15   SOS
ATOM   3244  ND2  ASN  993   46.761  38.523  75.892  1.00  61.29   SOS
ATOM   3245  C    ASN  993   51.555  38.985  76.869  1.00  44.69   SOS
ATOM   3246  O    ASN  993   51.486  39.882  77.715  1.00  47.57   SOS
ATOM   3247  N    LEU  994   52.568  38.121  76.825  1.00  37.93   SOS
ATOM   3248  CA   LEU  994   53.680  38.230  77.763  1.00  34.34   SOS
ATOM   3249  CB   LEU  994   54.686  37.092  77.590  1.00  29.91   SOS
ATOM   3250  CG   LEU  994   54.336  35.703  78.106  1.00  35.00   SOS
ATOM   3251  CD1  LEU  994   55.437  34.722  77.736  1.00  30.48   SOS
ATOM   3252  CD2  LEU  994   54.109  35.744  79.616  1.00  31.54   SOS
ATOM   3253  C    LEU  994   54.406  39.536  77.498  1.00  38.22   SOS
ATOM   3254  O    LEU  994   54.631  39.919  76.345  1.00  36.54   SOS
ATOM   3255  N    ASN  995   54.795  40.206  78.571  1.00  37.83   SOS
ATOM   3256  CA   ASN  995   55.517  41.456  78.453  1.00  39.15   SOS
ATOM   3257  CB   ASN  995   54.516  42.618  78.390  1.00  36.26   SOS
ATOM   3258  CG   ASN  995   55.176  43.951  78.115  1.00  33.99   SOS
ATOM   3259  OD1  ASN  995   54.761  44.969  78.650  1.00  26.42   SOS
ATOM   3260  ND2  ASN  995   56.208  43.951  77.277  1.00  35.99   SOS
```

Figure 8-55

| ATOM | 3261 | C | ASN | 995 | 56.457 | 41.566 | 79.660 | 1.00 | 39.02 | SOS |
|---|---|---|---|---|---|---|---|---|---|---|
| ATOM | 3262 | O | ASN | 995 | 56.230 | 42.355 | 80.575 | 1.00 | 41.44 | SOS |
| ATOM | 3263 | N | PRO | 996 | 57.539 | 40.768 | 79.663 | 1.00 | 37.44 | SOS |
| ATOM | 3264 | CD | PRO | 996 | 57.964 | 39.935 | 78.527 | 1.00 | 34.57 | SOS |
| ATOM | 3265 | CA | PRO | 996 | 58.543 | 40.733 | 80.735 | 1.00 | 34.46 | SOS |
| ATOM | 3266 | CB | PRO | 996 | 59.658 | 39.884 | 80.128 | 1.00 | 33.50 | SOS |
| ATOM | 3267 | CG | PRO | 996 | 58.959 | 39.023 | 79.168 | 1.00 | 37.66 | SOS |
| ATOM | 3268 | C | PRO | 996 | 59.084 | 42.116 | 81.093 | 1.00 | 33.65 | SOS |
| ATOM | 3269 | O | PRO | 996 | 59.207 | 42.462 | 82.265 | 1.00 | 34.12 | SOS |
| ATOM | 3270 | N | MET | 997 | 59.399 | 42.895 | 80.064 | 1.00 | 31.74 | SOS |
| ATOM | 3271 | CA | MET | 997 | 59.956 | 44.226 | 80.229 | 1.00 | 32.32 | SOS |
| ATOM | 3272 | CB | MET | 997 | 60.517 | 44.729 | 78.900 | 1.00 | 32.89 | SOS |
| ATOM | 3273 | CG | MET | 997 | 61.843 | 44.122 | 78.505 | 1.00 | 32.53 | SOS |
| ATOM | 3274 | SD | MET | 997 | 62.439 | 44.734 | 76.919 | 1.00 | 43.51 | SOS |
| ATOM | 3275 | CE | MET | 997 | 62.296 | 46.483 | 77.159 | 1.00 | 38.54 | SOS |
| ATOM | 3276 | C | MET | 997 | 59.038 | 45.282 | 80.827 | 1.00 | 32.88 | SOS |
| ATOM | 3277 | O | MET | 997 | 59.524 | 46.278 | 81.368 | 1.00 | 36.52 | SOS |
| ATOM | 3278 | N | GLY | 998 | 57.727 | 45.072 | 80.746 | 1.00 | 31.92 | SOS |
| ATOM | 3279 | CA | GLY | 998 | 56.792 | 46.051 | 81.282 | 1.00 | 31.78 | SOS |
| ATOM | 3280 | C | GLY | 998 | 56.956 | 47.388 | 80.577 | 1.00 | 34.52 | SOS |
| ATOM | 3281 | O | GLY | 998 | 56.942 | 47.441 | 79.349 | 1.00 | 35.74 | SOS |
| ATOM | 3282 | N | ASN | 999 | 57.162 | 48.457 | 81.343 | 1.00 | 35.75 | SOS |
| ATOM | 3283 | CA | ASN | 999 | 57.340 | 49.796 | 80.769 | 1.00 | 37.25 | SOS |
| ATOM | 3284 | CB | ASN | 999 | 56.545 | 50.833 | 81.568 | 1.00 | 41.53 | SOS |
| ATOM | 3285 | CG | ASN | 999 | 55.071 | 50.486 | 81.676 | 1.00 | 50.95 | SOS |
| ATOM | 3286 | OD1 | ASN | 999 | 54.516 | 49.792 | 80.821 | 1.00 | 56.83 | SOS |
| ATOM | 3287 | ND2 | ASN | 999 | 54.429 | 50.963 | 82.737 | 1.00 | 55.72 | SOS |
| ATOM | 3288 | C | ASN | 999 | 58.806 | 50.218 | 80.732 | 1.00 | 36.50 | SOS |
| ATOM | 3289 | O | ASN | 999 | 59.130 | 51.320 | 80.291 | 1.00 | 38.95 | SOS |
| ATOM | 3290 | N | SER | 1000 | 59.686 | 49.337 | 81.197 | 1.00 | 34.33 | SOS |
| ATOM | 3291 | CA | SER | 1000 | 61.116 | 49.611 | 81.249 | 1.00 | 34.64 | SOS |
| ATOM | 3292 | CB | SER | 1000 | 61.804 | 48.615 | 82.183 | 1.00 | 33.53 | SOS |
| ATOM | 3293 | OG | SER | 1000 | 61.080 | 48.449 | 83.392 | 1.00 | 39.73 | SOS |
| ATOM | 3294 | C | SER | 1000 | 61.783 | 49.545 | 79.883 | 1.00 | 35.38 | SOS |
| ATOM | 3295 | O | SER | 1000 | 61.326 | 48.834 | 78.993 | 1.00 | 37.97 | SOS |
| ATOM | 3296 | N | MET | 1001 | 62.862 | 50.301 | 79.720 | 1.00 | 35.25 | SOS |
| ATOM | 3297 | CA | MET | 1001 | 63.616 | 50.292 | 78.470 | 1.00 | 35.26 | SOS |
| ATOM | 3298 | CB | MET | 1001 | 64.420 | 51.588 | 78.326 | 1.00 | 35.94 | SOS |
| ATOM | 3299 | CG | MET | 1001 | 63.588 | 52.858 | 78.368 | 1.00 | 33.04 | SOS |
| ATOM | 3300 | SD | MET | 1001 | 62.425 | 52.961 | 77.002 | 1.00 | 44.08 | SOS |
| ATOM | 3301 | CE | MET | 1001 | 60.895 | 52.453 | 77.800 | 1.00 | 36.00 | SOS |
| ATOM | 3302 | C | MET | 1001 | 64.564 | 49.093 | 78.535 | 1.00 | 35.27 | SOS |
| ATOM | 3303 | O | MET | 1001 | 64.789 | 48.533 | 79.608 | 1.00 | 33.64 | SOS |
| ATOM | 3304 | N | GLU | 1002 | 65.134 | 48.715 | 77.400 | 1.00 | 37.32 | SOS |
| ATOM | 3305 | CA | GLU | 1002 | 66.040 | 47.575 | 77.343 | 1.00 | 42.68 | SOS |
| ATOM | 3306 | CB | GLU | 1002 | 66.775 | 47.551 | 76.002 | 1.00 | 46.50 | SOS |
| ATOM | 3307 | CG | GLU | 1002 | 67.347 | 46.196 | 75.642 | 1.00 | 54.76 | SOS |
| ATOM | 3308 | CD | GLU | 1002 | 68.302 | 46.246 | 74.461 | 1.00 | 59.17 | SOS |
| ATOM | 3309 | OE1 | GLU | 1002 | 69.471 | 45.839 | 74.639 | 1.00 | 60.77 | SOS |
| ATOM | 3310 | OE2 | GLU | 1002 | 67.890 | 46.676 | 73.359 | 1.00 | 59.82 | SOS |
| ATOM | 3311 | C | GLU | 1002 | 67.054 | 47.558 | 78.498 | 1.00 | 45.25 | SOS |
| ATOM | 3312 | O | GLU | 1002 | 66.961 | 46.719 | 79.389 | 1.00 | 47.62 | SOS |
| ATOM | 3313 | N | LYS | 1003 | 67.964 | 48.530 | 78.515 | 1.00 | 45.39 | SOS |
| ATOM | 3314 | CA | LYS | 1003 | 69.007 | 48.626 | 79.542 | 1.00 | 42.67 | SOS |
| ATOM | 3315 | CB | LYS | 1003 | 69.882 | 49.858 | 79.295 | 1.00 | 43.73 | SOS |
| ATOM | 3316 | CG | LYS | 1003 | 70.894 | 50.117 | 80.384 | 1.00 | 46.14 | SOS |
| ATOM | 3317 | CD | LYS | 1003 | 71.761 | 51.308 | 80.074 | 1.00 | 53.73 | SOS |
| ATOM | 3318 | CE | LYS | 1003 | 72.645 | 51.635 | 81.267 | 1.00 | 62.39 | SOS |
| ATOM | 3319 | NZ | LYS | 1003 | 73.434 | 50.451 | 81.735 | 1.00 | 67.57 | SOS |
| ATOM | 3320 | C | LYS | 1003 | 68.529 | 48.628 | 80.992 | 1.00 | 39.95 | SOS |
| ATOM | 3321 | O | LYS | 1003 | 69.129 | 47.996 | 81.853 | 1.00 | 36.15 | SOS |

Figure 8-56

```
ATOM   3322  N    GLU  1004    67.480  49.376  81.275  1.00  38.13      SOS
ATOM   3323  CA   GLU  1004    66.966  49.428  82.627  1.00  42.28      SOS
ATOM   3324  CB   GLU  1004    65.766  50.376  82.668  1.00  49.59      SOS
ATOM   3325  CG   GLU  1004    65.242  50.729  84.055  1.00  55.28      SOS
ATOM   3326  CD   GLU  1004    63.916  51.488  84.003  1.00  62.38      SOS
ATOM   3327  OE1  GLU  1004    63.158  51.420  84.998  1.00  59.62      SOS
ATOM   3328  OE2  GLU  1004    63.627  52.138  82.965  1.00  63.05      SOS
ATOM   3329  C    GLU  1004    66.570  48.008  83.071  1.00  42.74      SOS
ATOM   3330  O    GLU  1004    66.919  47.571  84.170  1.00  43.63      SOS
ATOM   3331  N    PHE  1005    65.897  47.280  82.180  1.00  41.13      SOS
ATOM   3332  CA   PHE  1005    65.436  45.922  82.451  1.00  36.34      SOS
ATOM   3333  CB   PHE  1005    64.427  45.475  81.385  1.00  34.27      SOS
ATOM   3334  CG   PHE  1005    63.772  44.148  81.681  1.00  27.01      SOS
ATOM   3335  CD1  PHE  1005    62.817  44.039  82.682  1.00  21.79      SOS
ATOM   3336  CD2  PHE  1005    64.130  43.009  80.974  1.00  20.76      SOS
ATOM   3337  CE1  PHE  1005    62.229  42.812  82.976  1.00  25.20      SOS
ATOM   3338  CE2  PHE  1005    63.552  41.784  81.262  1.00  23.76      SOS
ATOM   3339  CZ   PHE  1005    62.596  41.683  82.270  1.00  20.49      SOS
ATOM   3340  C    PHE  1005    66.588  44.934  82.521  1.00  36.00      SOS
ATOM   3341  O    PHE  1005    66.647  44.112  83.428  1.00  37.43      SOS
ATOM   3342  N    THR  1006    67.489  44.998  81.549  1.00  35.34      SOS
ATOM   3343  CA   THR  1006    68.644  44.111  81.518  1.00  36.27      SOS
ATOM   3344  CB   THR  1006    69.584  44.449  80.353  1.00  37.06      SOS
ATOM   3345  OG1  THR  1006    68.911  44.234  79.112  1.00  44.33      SOS
ATOM   3346  CG2  THR  1006    70.809  43.572  80.396  1.00  48.53      SOS
ATOM   3347  C    THR  1006    69.429  44.253  82.817  1.00  37.50      SOS
ATOM   3348  O    THR  1006    69.830  43.254  83.410  1.00  44.79      SOS
ATOM   3349  N    ASP  1007    69.644  45.495  83.251  1.00  35.64      SOS
ATOM   3350  CA   ASP  1007    70.383  45.775  84.481  1.00  33.01      SOS
ATOM   3351  CB   ASP  1007    70.645  47.291  84.651  1.00  31.17      SOS
ATOM   3352  CG   ASP  1007    71.692  47.851  83.650  1.00  36.72      SOS
ATOM   3353  OD1  ASP  1007    72.264  47.085  82.843  1.00  40.67      SOS
ATOM   3354  OD2  ASP  1007    71.944  49.076  83.661  1.00  33.23      SOS
ATOM   3355  C    ASP  1007    69.641  45.208  85.694  1.00  33.20      SOS
ATOM   3356  O    ASP  1007    70.261  44.708  86.632  1.00  36.05      SOS
ATOM   3357  N    TYR  1008    68.314  45.250  85.662  1.00  31.64      SOS
ATOM   3358  CA   TYR  1008    67.514  44.720  86.763  1.00  32.10      SOS
ATOM   3359  CB   TYR  1008    66.032  45.030  86.549  1.00  27.18      SOS
ATOM   3360  CG   TYR  1008    65.093  44.196  87.394  1.00  28.35      SOS
ATOM   3361  CD1  TYR  1008    64.834  44.528  88.717  1.00  28.53      SOS
ATOM   3362  CE1  TYR  1008    63.953  43.779  89.489  1.00  28.46      SOS
ATOM   3363  CD2  TYR  1008    64.447  43.083  86.860  1.00  31.02      SOS
ATOM   3364  CE2  TYR  1008    63.568  42.327  87.624  1.00  31.72      SOS
ATOM   3365  CZ   TYR  1008    63.327  42.680  88.938  1.00  31.37      SOS
ATOM   3366  OH   TYR  1008    62.474  41.923  89.708  1.00  32.06      SOS
ATOM   3367  C    TYR  1008    67.704  43.213  86.910  1.00  33.90      SOS
ATOM   3368  O    TYR  1008    67.791  42.695  88.024  1.00  32.37      SOS
ATOM   3369  N    LEU  1009    67.720  42.512  85.779  1.00  34.09      SOS
ATOM   3370  CA   LEU  1009    67.897  41.070  85.783  1.00  33.93      SOS
ATOM   3371  CB   LEU  1009    67.797  40.494  84.369  1.00  32.28      SOS
ATOM   3372  CG   LEU  1009    66.422  40.567  83.704  1.00  30.54      SOS
ATOM   3373  CD1  LEU  1009    66.497  39.956  82.322  1.00  25.84      SOS
ATOM   3374  CD2  LEU  1009    65.381  39.866  84.562  1.00  23.50      SOS
ATOM   3375  C    LEU  1009    69.244  40.738  86.382  1.00  35.33      SOS
ATOM   3376  O    LEU  1009    69.326  39.926  87.306  1.00  37.13      SOS
ATOM   3377  N    PHE  1010    70.288  41.416  85.904  1.00  32.23      SOS
ATOM   3378  CA   PHE  1010    71.634  41.173  86.409  1.00  32.78      SOS
ATOM   3379  CB   PHE  1010    72.684  41.887  85.569  1.00  26.02      SOS
ATOM   3380  CG   PHE  1010    74.065  41.348  85.771  1.00  27.29      SOS
ATOM   3381  CD1  PHE  1010    74.471  40.193  85.116  1.00  27.37      SOS
ATOM   3382  CD2  PHE  1010    74.956  41.979  86.633  1.00  25.11      SOS
```

Figure 8-57

| | | | | | | | | | |
|---|---|---|---|---|---|---|---|---|---|
| ATOM | 3383 | CE1 | PHE | 1010 | 75.745 | 39.671 | 85.311 | 1.00 28.73 | sos |
| ATOM | 3384 | CE2 | PHE | 1010 | 76.225 | 41.471 | 86.838 | 1.00 26.60 | sos |
| ATOM | 3385 | CZ | PHE | 1010 | 76.626 | 40.312 | 86.175 | 1.00 29.00 | sos |
| ATOM | 3386 | C | PHE | 1010 | 71.817 | 41.521 | 87.892 | 1.00 34.21 | sos |
| ATOM | 3387 | O | PHE | 1010 | 72.541 | 40.830 | 88.610 | 1.00 32.67 | sos |
| ATOM | 3388 | N | ASN | 1011 | 71.183 | 42.592 | 88.352 | 1.00 34.52 | sos |
| ATOM | 3389 | CA | ASN | 1011 | 71.300 | 42.944 | 89.759 | 1.00 39.38 | sos |
| ATOM | 3390 | CB | ASN | 1011 | 70.858 | 44.387 | 90.014 | 1.00 37.64 | sos |
| ATOM | 3391 | CG | ASN | 1011 | 71.786 | 45.401 | 89.358 | 1.00 45.29 | sos |
| ATOM | 3392 | OD1 | ASN | 1011 | 73.008 | 45.228 | 89.339 | 1.00 47.44 | sos |
| ATOM | 3393 | ND2 | ASN | 1011 | 71.206 | 46.458 | 88.798 | 1.00 48.36 | sos |
| ATOM | 3394 | C | ASN | 1011 | 70.502 | 41.946 | 90.601 | 1.00 40.68 | sos |
| ATOM | 3395 | O | ASN | 1011 | 70.796 | 41.739 | 91.777 | 1.00 46.37 | sos |
| ATOM | 3396 | N | LYS | 1012 | 69.525 | 41.293 | 89.978 | 1.00 39.02 | sos |
| ATOM | 3397 | CA | LYS | 1012 | 68.717 | 40.295 | 90.666 | 1.00 36.48 | sos |
| ATOM | 3398 | CB | LYS | 1012 | 67.435 | 40.021 | 89.892 | 1.00 31.20 | sos |
| ATOM | 3399 | CG | LYS | 1012 | 66.188 | 40.565 | 90.537 | 1.00 35.86 | sos |
| ATOM | 3400 | CD | LYS | 1012 | 65.962 | 39.916 | 91.877 | 1.00 37.23 | sos |
| ATOM | 3401 | CE | LYS | 1012 | 64.803 | 40.556 | 92.607 | 1.00 35.45 | sos |
| ATOM | 3402 | NZ | LYS | 1012 | 64.698 | 39.982 | 93.974 | 1.00 38.71 | sos |
| ATOM | 3403 | C | LYS | 1012 | 69.532 | 39.012 | 90.790 | 1.00 37.79 | sos |
| ATOM | 3404 | O | LYS | 1012 | 69.437 | 38.293 | 91.788 | 1.00 39.45 | sos |
| ATOM | 3405 | N | SER | 1013 | 70.326 | 38.727 | 89.764 | 1.00 31.71 | sos |
| ATOM | 3406 | CA | SER | 1013 | 71.169 | 37.550 | 89.767 | 1.00 33.20 | sos |
| ATOM | 3407 | CB | SER | 1013 | 71.858 | 37.400 | 88.410 | 1.00 30.48 | sos |
| ATOM | 3408 | OG | SER | 1013 | 72.816 | 36.355 | 88.422 | 1.00 29.43 | sos |
| ATOM | 3409 | C | SER | 1013 | 72.204 | 37.683 | 90.898 | 1.00 37.15 | sos |
| ATOM | 3410 | O | SER | 1013 | 72.424 | 36.740 | 91.656 | 1.00 38.69 | sos |
| ATOM | 3411 | N | LEU | 1014 | 72.796 | 38.871 | 91.030 | 1.00 37.90 | sos |
| ATOM | 3412 | CA | LEU | 1014 | 73.786 | 39.140 | 92.071 | 1.00 34.98 | sos |
| ATOM | 3413 | CB | LEU | 1014 | 74.405 | 40.521 | 91.890 | 1.00 29.45 | sos |
| ATOM | 3414 | CG | LEU | 1014 | 75.317 | 40.674 | 90.673 | 1.00 30.45 | sos |
| ATOM | 3415 | CD1 | LEU | 1014 | 75.709 | 42.113 | 90.533 | 1.00 21.32 | sos |
| ATOM | 3416 | CD2 | LEU | 1014 | 76.549 | 39.783 | 90.786 | 1.00 23.29 | sos |
| ATOM | 3417 | C | LEU | 1014 | 73.171 | 39.040 | 93.454 | 1.00 37.18 | sos |
| ATOM | 3418 | O | LEU | 1014 | 73.840 | 38.629 | 94.394 | 1.00 42.96 | sos |
| ATOM | 3419 | N | GLU | 1015 | 71.898 | 39.412 | 93.572 | 1.00 33.87 | sos |
| ATOM | 3420 | CA | GLU | 1015 | 71.182 | 39.348 | 94.843 | 1.00 32.26 | sos |
| ATOM | 3421 | CB | GLU | 1015 | 69.888 | 40.162 | 94.755 | 1.00 27.02 | sos |
| ATOM | 3422 | CG | GLU | 1015 | 68.917 | 39.964 | 95.927 | 1.00 34.19 | sos |
| ATOM | 3423 | CD | GLU | 1015 | 67.595 | 40.713 | 95.759 | 1.00 43.83 | sos |
| ATOM | 3424 | OE1 | GLU | 1015 | 67.378 | 41.332 | 94.693 | 1.00 47.98 | sos |
| ATOM | 3425 | OE2 | GLU | 1015 | 66.766 | 40.683 | 96.696 | 1.00 47.33 | sos |
| ATOM | 3426 | C | GLU | 1015 | 70.852 | 37.914 | 95.285 | 1.00 36.90 | sos |
| ATOM | 3427 | O | GLU | 1015 | 70.851 | 37.611 | 96.485 | 1.00 38.20 | sos |
| ATOM | 3428 | N | ILE | 1016 | 70.549 | 37.040 | 94.326 | 1.00 36.35 | sos |
| ATOM | 3429 | CA | ILE | 1016 | 70.186 | 35.666 | 94.660 | 1.00 35.84 | sos |
| ATOM | 3430 | CB | ILE | 1016 | 69.108 | 35.099 | 93.692 | 1.00 36.50 | sos |
| ATOM | 3431 | CG2 | ILE | 1016 | 67.886 | 35.994 | 93.691 | 1.00 31.67 | sos |
| ATOM | 3432 | CG1 | ILE | 1016 | 69.661 | 34.972 | 92.276 | 1.00 36.56 | sos |
| ATOM | 3433 | CD1 | ILE | 1016 | 68.598 | 34.712 | 91.254 | 1.00 40.13 | sos |
| ATOM | 3434 | C | ILE | 1016 | 71.393 | 34.737 | 94.752 | 1.00 34.57 | sos |
| ATOM | 3435 | O | ILE | 1016 | 71.320 | 33.663 | 95.358 | 1.00 32.46 | sos |
| ATOM | 3436 | N | GLU | 1017 | 72.498 | 35.155 | 94.145 | 1.00 28.69 | sos |
| ATOM | 3437 | CA | GLU | 1017 | 73.738 | 34.392 | 94.188 | 1.00 28.48 | sos |
| ATOM | 3438 | CB | GLU | 1017 | 73.809 | 33.374 | 93.055 | 1.00 23.95 | sos |
| ATOM | 3439 | CG | GLU | 1017 | 72.866 | 32.190 | 93.232 | 1.00 32.06 | sos |
| ATOM | 3440 | CD | GLU | 1017 | 73.173 | 31.021 | 92.302 | 1.00 35.24 | sos |
| ATOM | 3441 | OE1 | GLU | 1017 | 74.325 | 30.915 | 91.815 | 1.00 41.30 | sos |
| ATOM | 3442 | OE2 | GLU | 1017 | 72.266 | 30.194 | 92.078 | 1.00 30.51 | sos |
| ATOM | 3443 | C | GLU | 1017 | 74.918 | 35.353 | 94.122 | 1.00 34.11 | sos |

Figure 8-58

| ATOM | 3444 | O | GLU | 1017 | 75.554 | 35.503 | 93.079 | 1.00 | 36.22 | SOS |
| ATOM | 3445 | N | PRO | 1018 | 75.210 | 36.044 | 95.242 | 1.00 | 38.86 | SOS |
| ATOM | 3446 | CD | PRO | 1018 | 74.476 | 35.990 | 96.519 | 1.00 | 37.43 | SOS |
| ATOM | 3447 | CA | PRO | 1018 | 76.317 | 37.005 | 95.325 | 1.00 | 38.60 | SOS |
| ATOM | 3448 | CB | PRO | 1018 | 76.207 | 37.526 | 96.761 | 1.00 | 35.93 | SOS |
| ATOM | 3449 | CG | PRO | 1018 | 75.522 | 36.422 | 97.486 | 1.00 | 38.41 | SOS |
| ATOM | 3450 | C | PRO | 1018 | 77.668 | 36.378 | 95.029 | 1.00 | 40.60 | SOS |
| ATOM | 3451 | O | PRO | 1018 | 77.822 | 35.165 | 95.172 | 1.00 | 39.54 | SOS |
| ATOM | 3452 | N | ARG | 1019 | 78.624 | 37.204 | 94.595 | 1.00 | 43.68 | SOS |
| ATOM | 3453 | CA | ARG | 1019 | 79.972 | 36.747 | 94.248 | 1.00 | 53.25 | SOS |
| ATOM | 3454 | CB | ARG | 1019 | 80.818 | 37.900 | 93.710 | 1.00 | 53.95 | SOS |
| ATOM | 3455 | CG | ARG | 1019 | 80.386 | 38.445 | 92.367 | 1.00 | 53.55 | SOS |
| ATOM | 3456 | CD | ARG | 1019 | 81.494 | 39.307 | 91.765 | 1.00 | 56.28 | SOS |
| ATOM | 3457 | NE | ARG | 1019 | 81.066 | 40.019 | 90.564 | 1.00 | 59.34 | SOS |
| ATOM | 3458 | CZ | ARG | 1019 | 80.238 | 41.063 | 90.563 | 1.00 | 63.63 | SOS |
| ATOM | 3459 | NH1 | ARG | 1019 | 79.737 | 41.530 | 91.708 | 1.00 | 58.21 | SOS |
| ATOM | 3460 | NH2 | ARG | 1019 | 79.904 | 41.643 | 89.412 | 1.00 | 62.23 | SOS |
| ATOM | 3461 | C | ARG | 1019 | 80.748 | 36.025 | 95.360 | 1.00 | 59.66 | SOS |
| ATOM | 3462 | O | ARG | 1019 | 80.767 | 36.458 | 96.514 | 1.00 | 59.79 | SOS |
| ATOM | 3463 | N | ASN | 1020 | 81.448 | 34.971 | 94.947 | 1.00 | 65.67 | SOS |
| ATOM | 3464 | CA | ASN | 1020 | 82.254 | 34.074 | 95.787 | 1.00 | 72.37 | SOS |
| ATOM | 3465 | CB | ASN | 1020 | 83.604 | 33.788 | 95.119 | 1.00 | 74.06 | SOS |
| ATOM | 3466 | CG | ASN | 1020 | 83.597 | 32.494 | 94.323 | 1.00 | 76.63 | SOS |
| ATOM | 3467 | OD1 | ASN | 1020 | 82.820 | 31.576 | 94.609 | 1.00 | 71.80 | SOS |
| ATOM | 3468 | ND2 | ASN | 1020 | 84.472 | 32.411 | 93.320 | 1.00 | 78.08 | SOS |
| ATOM | 3469 | C | ASN | 1020 | 82.447 | 34.228 | 97.302 | 1.00 | 75.92 | SOS |
| ATOM | 3470 | O | ASN | 1020 | 81.865 | 33.453 | 98.079 | 1.00 | 76.41 | SOS |
| ATOM | 3471 | N | PRO | 1021 | 83.265 | 35.206 | 97.750 | 1.00 | 75.87 | SOS |
| ATOM | 3472 | CD | PRO | 1021 | 83.870 | 36.337 | 97.019 | 1.00 | 75.75 | SOS |
| ATOM | 3473 | CA | PRO | 1021 | 83.468 | 35.355 | 99.198 | 1.00 | 73.46 | SOS |
| ATOM | 3474 | CB | PRO | 1021 | 84.456 | 36.518 | 99.286 | 1.00 | 72.38 | SOS |
| ATOM | 3475 | CG | PRO | 1021 | 84.066 | 37.367 | 98.117 | 1.00 | 76.57 | SOS |
| ATOM | 3476 | C | PRO | 1021 | 82.189 | 35.623 | 99.995 | 1.00 | 72.37 | SOS |
| ATOM | 3477 | O | PRO | 1021 | 82.137 | 35.370 | 101.199 | 1.00 | 76.49 | SOS |
| ATOM | 3478 | N | LYS | 1022 | 81.156 | 36.109 | 99.315 | 1.00 | 66.09 | SOS |
| ATOM | 3479 | CA | LYS | 1022 | 79.887 | 36.409 | 99.962 | 1.00 | 64.03 | SOS |
| ATOM | 3480 | CB | LYS | 1022 | 79.168 | 37.532 | 99.200 | 1.00 | 67.17 | SOS |
| ATOM | 3481 | CG | LYS | 1022 | 80.117 | 38.643 | 98.724 | 1.00 | 72.16 | SOS |
| ATOM | 3482 | CD | LYS | 1022 | 79.423 | 39.780 | 97.981 | 1.00 | 70.86 | SOS |
| ATOM | 3483 | CE | LYS | 1022 | 78.694 | 40.710 | 98.933 | 1.00 | 71.52 | SOS |
| ATOM | 3484 | NZ | LYS | 1022 | 78.135 | 41.905 | 98.238 | 1.00 | 70.32 | SOS |
| ATOM | 3485 | C | LYS | 1022 | 79.022 | 35.145 | 100.031 | 1.00 | 61.33 | SOS |
| ATOM | 3486 | O | LYS | 1022 | 78.709 | 34.535 | 99.009 | 1.00 | 62.61 | SOS |
| ATOM | 3487 | N | PRO | 1023 | 78.637 | 34.728 | 101.248 | 1.00 | 57.36 | SOS |
| ATOM | 3488 | CD | PRO | 1023 | 78.892 | 35.438 | 102.514 | 1.00 | 55.59 | SOS |
| ATOM | 3489 | CA | PRO | 1023 | 77.809 | 33.535 | 101.477 | 1.00 | 53.25 | SOS |
| ATOM | 3490 | CB | PRO | 1023 | 77.680 | 33.503 | 102.999 | 1.00 | 54.32 | SOS |
| ATOM | 3491 | CG | PRO | 1023 | 77.757 | 34.957 | 103.377 | 1.00 | 55.29 | SOS |
| ATOM | 3492 | C | PRO | 1023 | 76.434 | 33.608 | 100.804 | 1.00 | 49.96 | SOS |
| ATOM | 3493 | O | PRO | 1023 | 75.844 | 34.684 | 100.701 | 1.00 | 50.39 | SOS |
| ATOM | 3494 | N | LEU | 1024 | 75.938 | 32.457 | 100.351 | 1.00 | 45.19 | SOS |
| ATOM | 3495 | CA | LEU | 1024 | 74.642 | 32.367 | 99.686 | 1.00 | 38.20 | SOS |
| ATOM | 3496 | CB | LEU | 1024 | 74.517 | 31.032 | 98.944 | 1.00 | 37.80 | SOS |
| ATOM | 3497 | CG | LEU | 1024 | 73.177 | 30.775 | 98.240 | 1.00 | 40.96 | SOS |
| ATOM | 3498 | CD1 | LEU | 1024 | 73.129 | 31.543 | 96.942 | 1.00 | 40.84 | SOS |
| ATOM | 3499 | CD2 | LEU | 1024 | 72.986 | 29.301 | 97.962 | 1.00 | 42.47 | SOS |
| ATOM | 3500 | C | LEU | 1024 | 73.483 | 32.500 | 100.673 | 1.00 | 37.42 | SOS |
| ATOM | 3501 | O | LEU | 1024 | 73.261 | 31.621 | 101.510 | 1.00 | 37.28 | SOS |
| ATOM | 3502 | N | PRO | 1025 | 72.736 | 33.611 | 100.604 | 1.00 | 33.68 | SOS |
| ATOM | 3503 | CD | PRO | 1025 | 72.972 | 34.874 | 99.877 | 1.00 | 31.71 | SOS |
| ATOM | 3504 | CA | PRO | 1025 | 71.624 | 33.730 | 101.549 | 1.00 | 33.72 | SOS |

Figure 8-59

| ATOM | 3505 | CB | PRO | 1025 | 71.281 | 35.224 | 101.494 | 1.00 | 34.22 | SOS |
|---|---|---|---|---|---|---|---|---|---|---|
| ATOM | 3506 | CG | PRO | 1025 | 71.707 | 35.647 | 100.125 | 1.00 | 29.65 | SOS |
| ATOM | 3507 | C | PRO | 1025 | 70.441 | 32.848 | 101.159 | 1.00 | 32.73 | SOS |
| ATOM | 3508 | O | PRO | 1025 | 70.441 | 32.230 | 100.098 | 1.00 | 35.40 | SOS |
| ATOM | 3509 | N | ARG | 1026 | 69.469 | 32.749 | 102.054 | 1.00 | 32.19 | SOS |
| ATOM | 3510 | CA | ARG | 1026 | 68.268 | 31.963 | 101.815 | 1.00 | 34.72 | SOS |
| ATOM | 3511 | CB | ARG | 1026 | 67.920 | 31.106 | 103.034 | 1.00 | 35.94 | SOS |
| ATOM | 3512 | CG | ARG | 1026 | 68.866 | 29.958 | 103.293 | 1.00 | 41.49 | SOS |
| ATOM | 3513 | CD | ARG | 1026 | 68.364 | 29.105 | 104.440 | 1.00 | 38.52 | SOS |
| ATOM | 3514 | NE | ARG | 1026 | 69.222 | 27.946 | 104.664 | 1.00 | 44.88 | SOS |
| ATOM | 3515 | CZ | ARG | 1026 | 70.147 | 27.865 | 105.616 | 1.00 | 49.90 | SOS |
| ATOM | 3516 | NH1 | ARG | 1026 | 70.352 | 28.880 | 106.448 | 1.00 | 52.41 | SOS |
| ATOM | 3517 | NH2 | ARG | 1026 | 70.857 | 26.753 | 105.747 | 1.00 | 52.31 | SOS |
| ATOM | 3518 | C | ARG | 1026 | 67.107 | 32.907 | 101.559 | 1.00 | 36.75 | SOS |
| ATOM | 3519 | O | ARG | 1026 | 67.025 | 33.982 | 102.152 | 1.00 | 37.78 | SOS |
| ATOM | 3520 | N | PHE | 1027 | 66.195 | 32.499 | 100.688 | 1.00 | 37.59 | SOS |
| ATOM | 3521 | CA | PHE | 1027 | 65.036 | 33.326 | 100.401 | 1.00 | 35.04 | SOS |
| ATOM | 3522 | CB | PHE | 1027 | 65.116 | 33.865 | 98.978 | 1.00 | 36.06 | SOS |
| ATOM | 3523 | CG | PHE | 1027 | 66.331 | 34.722 | 98.720 | 1.00 | 31.03 | SOS |
| ATOM | 3524 | CD1 | PHE | 1027 | 67.550 | 34.143 | 98.400 | 1.00 | 29.45 | SOS |
| ATOM | 3525 | CD2 | PHE | 1027 | 66.248 | 36.107 | 98.793 | 1.00 | 24.42 | SOS |
| ATOM | 3526 | CE1 | PHE | 1027 | 68.675 | 34.932 | 98.151 | 1.00 | 32.70 | SOS |
| ATOM | 3527 | CE2 | PHE | 1027 | 67.354 | 36.896 | 98.552 | 1.00 | 25.93 | SOS |
| ATOM | 3528 | CZ | PHE | 1027 | 68.578 | 36.306 | 98.227 | 1.00 | 31.08 | SOS |
| ATOM | 3529 | C | PHE | 1027 | 63.779 | 32.501 | 100.607 | 1.00 | 35.26 | SOS |
| ATOM | 3530 | O | PHE | 1027 | 63.808 | 31.278 | 100.496 | 1.00 | 35.20 | SOS |
| ATOM | 3531 | N | PRO | 1028 | 62.671 | 33.153 | 100.979 | 1.00 | 36.76 | SOS |
| ATOM | 3532 | CD | PRO | 1028 | 62.571 | 34.590 | 101.286 | 1.00 | 36.59 | SOS |
| ATOM | 3533 | CA | PRO | 1028 | 61.388 | 32.477 | 101.213 | 1.00 | 39.55 | SOS |
| ATOM | 3534 | CB | PRO | 1028 | 60.521 | 33.590 | 101.801 | 1.00 | 36.25 | SOS |
| ATOM | 3535 | CG | PRO | 1028 | 61.091 | 34.826 | 101.202 | 1.00 | 36.68 | SOS |
| ATOM | 3536 | C | PRO | 1028 | 60.751 | 31.871 | 99.960 | 1.00 | 42.98 | SOS |
| ATOM | 3537 | O | PRO | 1028 | 61.045 | 32.283 | 98.841 | 1.00 | 42.12 | SOS |
| ATOM | 3538 | N | LYS | 1029 | 59.900 | 30.868 | 100.151 | 1.00 | 49.52 | SOS |
| ATOM | 3539 | CA | LYS | 1029 | 59.224 | 30.235 | 99.024 | 1.00 | 53.66 | SOS |
| ATOM | 3540 | CB | LYS | 1029 | 58.517 | 28.945 | 99.456 | 1.00 | 56.78 | SOS |
| ATOM | 3541 | CG | LYS | 1029 | 59.442 | 27.727 | 99.548 | 1.00 | 60.05 | SOS |
| ATOM | 3542 | CD | LYS | 1029 | 58.670 | 26.449 | 99.883 | 1.00 | 60.94 | SOS |
| ATOM | 3543 | CE | LYS | 1029 | 57.656 | 26.070 | 98.790 | 1.00 | 65.68 | SOS |
| ATOM | 3544 | NZ | LYS | 1029 | 58.273 | 25.599 | 97.508 | 1.00 | 61.29 | SOS |
| ATOM | 3545 | C | LYS | 1029 | 58.238 | 31.210 | 98.370 | 1.00 | 55.92 | SOS |
| ATOM | 3546 | O | LYS | 1029 | 57.607 | 32.033 | 99.050 | 1.00 | 56.70 | SOS |
| ATOM | 3547 | N | LYS | 1030 | 58.143 | 31.124 | 97.044 | 1.00 | 54.61 | SOS |
| ATOM | 3548 | CA | LYS | 1030 | 57.287 | 31.985 | 96.231 | 1.00 | 51.01 | SOS |
| ATOM | 3549 | CB | LYS | 1030 | 58.088 | 32.453 | 95.014 | 1.00 | 51.72 | SOS |
| ATOM | 3550 | CG | LYS | 1030 | 57.459 | 33.525 | 94.149 | 1.00 | 46.27 | SOS |
| ATOM | 3551 | CD | LYS | 1030 | 58.239 | 33.625 | 92.838 | 1.00 | 49.80 | SOS |
| ATOM | 3552 | CE | LYS | 1030 | 58.440 | 35.061 | 92.383 | 1.00 | 51.39 | SOS |
| ATOM | 3553 | NZ | LYS | 1030 | 57.161 | 35.776 | 92.112 | 1.00 | 58.17 | SOS |
| ATOM | 3554 | C | LYS | 1030 | 56.045 | 31.234 | 95.766 | 1.00 | 50.24 | SOS |
| ATOM | 3555 | O | LYS | 1030 | 54.939 | 31.763 | 95.814 | 1.00 | 50.83 | SOS |
| ATOM | 3556 | N | TYR | 1031 | 56.237 | 29.994 | 95.326 | 1.00 | 48.18 | SOS |
| ATOM | 3557 | CA | TYR | 1031 | 55.138 | 29.169 | 94.829 | 1.00 | 49.55 | SOS |
| ATOM | 3558 | CB | TYR | 1031 | 55.639 | 28.274 | 93.693 | 1.00 | 42.70 | SOS |
| ATOM | 3559 | CG | TYR | 1031 | 56.454 | 29.007 | 92.651 | 1.00 | 39.34 | SOS |
| ATOM | 3560 | CD1 | TYR | 1031 | 57.737 | 28.589 | 92.335 | 1.00 | 34.93 | SOS |
| ATOM | 3561 | CE1 | TYR | 1031 | 58.502 | 29.263 | 91.388 | 1.00 | 32.25 | SOS |
| ATOM | 3562 | CD2 | TYR | 1031 | 55.946 | 30.130 | 91.989 | 1.00 | 35.70 | SOS |
| ATOM | 3563 | CE2 | TYR | 1031 | 56.707 | 30.816 | 91.036 | 1.00 | 25.87 | SOS |
| ATOM | 3564 | CZ | TYR | 1031 | 57.984 | 30.372 | 90.743 | 1.00 | 31.60 | SOS |
| ATOM | 3565 | OH | TYR | 1031 | 58.756 | 31.018 | 89.800 | 1.00 | 31.36 | SOS |

Figure 8-60

```
ATOM   3566  C    TYR  1031    54.467  28.313  95.912  1.00  52.44      sos
ATOM   3567  O    TYR  1031    55.143  27.616  96.676  1.00  54.23      sos
ATOM   3568  N    SER  1032    53.134  28.361  95.957  1.00  53.97      sos
ATOM   3569  CA   SER  1032    52.353  27.598  96.932  1.00  55.36      sos
ATOM   3570  CB   SER  1032    51.290  28.489  97.602  1.00  56.79      sos
ATOM   3571  OG   SER  1032    50.293  28.916  96.685  1.00  60.79      sos
ATOM   3572  C    SER  1032    51.695  26.348  96.342  1.00  53.81      sos
ATOM   3573  O    SER  1032    50.642  25.915  96.806  1.00  56.17      sos
ATOM   3574  N    TYR  1033    52.316  25.784  95.310  1.00  52.37      sos
ATOM   3575  CA   TYR  1033    51.824  24.567  94.655  1.00  52.43      sos
ATOM   3576  CB   TYR  1033    51.085  24.904  93.346  1.00  46.79      sos
ATOM   3577  CG   TYR  1033    51.798  25.881  92.435  1.00  43.89      sos
ATOM   3578  CD1  TYR  1033    52.980  25.526  91.779  1.00  42.24      sos
ATOM   3579  CE1  TYR  1033    53.632  26.424  90.930  1.00  44.77      sos
ATOM   3580  CD2  TYR  1033    51.284  27.159  92.220  1.00  38.71      sos
ATOM   3581  CE2  TYR  1033    51.924  28.063  91.376  1.00  37.85      sos
ATOM   3582  CZ   TYR  1033    53.095  27.691  90.732  1.00  43.47      sos
ATOM   3583  OH   TYR  1033    53.721  28.574  89.878  1.00  46.51      sos
ATOM   3584  C    TYR  1033    53.022  23.634  94.418  1.00  53.02      sos
ATOM   3585  O    TYR  1033    54.165  24.080  94.469  1.00  57.16      sos
ATOM   3586  N    PRO  1034    52.787  22.323  94.213  1.00  53.33      sos
ATOM   3587  CD   PRO  1034    51.512  21.584  94.215  1.00  55.22      sos
ATOM   3588  CA   PRO  1034    53.915  21.406  93.991  1.00  52.03      sos
ATOM   3589  CB   PRO  1034    53.231  20.042  93.847  1.00  51.71      sos
ATOM   3590  CG   PRO  1034    51.851  20.378  93.375  1.00  52.42      sos
ATOM   3591  C    PRO  1034    54.806  21.745  92.799  1.00  50.79      sos
ATOM   3592  O    PRO  1034    54.321  22.095  91.728  1.00  55.89      sos
ATOM   3593  N    LEU  1035    56.115  21.647  93.007  1.00  49.64      sos
ATOM   3594  CA   LEU  1035    57.100  21.949  91.973  1.00  48.69      sos
ATOM   3595  CB   LEU  1035    58.324  22.618  92.592  1.00  52.99      sos
ATOM   3596  CG   LEU  1035    58.040  23.882  93.388  1.00  53.80      sos
ATOM   3597  CD1  LEU  1035    57.790  23.510  94.838  1.00  59.44      sos
ATOM   3598  CD2  LEU  1035    59.218  24.812  93.276  1.00  54.82      sos
ATOM   3599  C    LEU  1035    57.546  20.724  91.189  1.00  48.49      sos
ATOM   3600  O    LEU  1035    58.526  20.772  90.437  1.00  46.00      sos
ATOM   3601  N    LYS  1036    56.851  19.612  91.391  1.00  50.15      sos
ATOM   3602  CA   LYS  1036    57.194  18.384  90.688  1.00  51.26      sos
ATOM   3603  CB   LYS  1036    56.589  17.166  91.404  1.00  52.45      sos
ATOM   3604  CG   LYS  1036    57.052  15.819  90.871  1.00  50.08      sos
ATOM   3605  CD   LYS  1036    56.386  14.674  91.617  0.00  51.03      sos
ATOM   3606  CE   LYS  1036    56.838  13.323  91.084  0.00  50.88      sos
ATOM   3607  NZ   LYS  1036    58.301  13.108  91.258  0.00  51.10      sos
ATOM   3608  C    LYS  1036    56.662  18.490  89.264  1.00  48.71      sos
ATOM   3609  O    LYS  1036    55.513  18.870  89.051  1.00  47.52      sos
ATOM   3610  N    SER  1037    57.527  18.223  88.295  1.00  46.28      sos
ATOM   3611  CA   SER  1037    57.137  18.265  86.897  1.00  48.14      sos
ATOM   3612  CB   SER  1037    58.375  18.335  85.999  1.00  48.77      sos
ATOM   3613  OG   SER  1037    58.026  18.146  84.635  1.00  44.69      sos
ATOM   3614  C    SER  1037    56.345  17.013  86.540  1.00  50.68      sos
ATOM   3615  O    SER  1037    56.682  15.910  86.977  1.00  50.07      sos
ATOM   3616  N    PRO  1038    55.267  17.169  85.756  1.00  50.43      sos
ATOM   3617  CD   PRO  1038    54.632  18.419  85.305  1.00  53.61      sos
ATOM   3618  CA   PRO  1038    54.466  16.012  85.361  1.00  49.70      sos
ATOM   3619  CB   PRO  1038    53.205  16.652  84.775  1.00  51.38      sos
ATOM   3620  CG   PRO  1038    53.699  17.929  84.215  1.00  53.77      sos
ATOM   3621  C    PRO  1038    55.220  15.184  84.328  1.00  49.14      sos
ATOM   3622  O    PRO  1038    54.771  14.107  83.941  1.00  52.32      sos
ATOM   3623  N    GLY  1039    56.381  15.678  83.906  1.00  46.48      sos
ATOM   3624  CA   GLY  1039    57.174  14.960  82.928  1.00  51.54      sos
ATOM   3625  C    GLY  1039    56.982  15.441  81.500  1.00  55.26      sos
ATOM   3626  O    GLY  1039    56.078  16.230  81.209  1.00  55.05      sos
```

Figure 8-61

```
ATOM   3627  N    VAL  1040      57.808  14.916  80.598  1.00  56.00      sos
ATOM   3628  CA   VAL  1040      57.774  15.297  79.193  1.00  56.85      sos
ATOM   3629  CB   VAL  1040      59.212  15.641  78.718  1.00  55.66      sos
ATOM   3630  CG1  VAL  1040      59.737  14.632  77.687  1.00  57.12      sos
ATOM   3631  CG2  VAL  1040      59.250  17.049  78.197  1.00  51.43      sos
ATOM   3632  C    VAL  1040      57.107  14.267  78.268  1.00  60.22      sos
ATOM   3633  O    VAL  1040      56.887  14.533  77.082  1.00  59.88      sos
ATOM   3634  N    ARG  1041      56.787  13.096  78.814  1.00  63.28      sos
ATOM   3635  CA   ARG  1041      56.137  12.035  78.048  1.00  63.28      sos
ATOM   3636  CB   ARG  1041      56.533  10.671  78.610  1.00  66.56      sos
ATOM   3637  CG   ARG  1041      58.032  10.398  78.554  1.00  72.12      sos
ATOM   3638  CD   ARG  1041      58.409   9.167  79.369  1.00  74.84      sos
ATOM   3639  NE   ARG  1041      58.100   9.331  80.788  0.00  74.15      sos
ATOM   3640  CZ   ARG  1041      58.310   8.401  81.715  0.00  74.40      sos
ATOM   3641  NH1  ARG  1041      58.833   7.228  81.382  0.00  74.35      sos
ATOM   3642  NH2  ARG  1041      57.996   8.645  82.980  0.00  74.35      sos
ATOM   3643  C    ARG  1041      54.618  12.206  78.103  1.00  63.76      sos
ATOM   3644  O    ARG  1041      54.042  12.361  79.180  1.00  63.08      sos
ATOM   3645  N    PRO  1042      53.953  12.196  76.935  1.00  65.39      sos
ATOM   3646  CD   PRO  1042      54.554  12.027  75.600  1.00  63.39      sos
ATOM   3647  CA   PRO  1042      52.495  12.351  76.834  1.00  67.30      sos
ATOM   3648  CB   PRO  1042      52.265  12.393  75.323  1.00  64.74      sos
ATOM   3649  CG   PRO  1042      53.383  11.563  74.784  1.00  63.48      sos
ATOM   3650  C    PRO  1042      51.683  11.243  77.518  1.00  71.91      sos
ATOM   3651  O    PRO  1042      52.174  10.126  77.711  1.00  70.71      sos
ATOM   3652  N    SER  1043      50.438  11.569  77.868  1.00  78.21      sos
ATOM   3653  CA   SER  1043      49.521  10.647  78.552  1.00  84.35      sos
ATOM   3654  CB   SER  1043      48.125  11.270  78.673  1.00  82.31      sos
ATOM   3655  OG   SER  1043      47.546  11.487  77.396  1.00  82.51      sos
ATOM   3656  C    SER  1043      49.413   9.253  77.927  1.00  88.20      sos
ATOM   3657  O    SER  1043      49.727   8.251  78.582  1.00  89.03      sos
ATOM   3658  N    ASN  1044      48.949   9.195  76.677  1.00  90.11      sos
ATOM   3659  CA   ASN  1044      48.795   7.934  75.946  1.00  93.28      sos
ATOM   3660  CB   ASN  1044      47.445   7.267  76.272  1.00  93.92      sos
ATOM   3661  CG   ASN  1044      47.504   6.379  77.517  1.00  94.38      sos
ATOM   3662  OD1  ASN  1044      48.099   5.294  77.499  1.00  91.81      sos
ATOM   3663  ND2  ASN  1044      46.866   6.829  78.595  1.00  93.17      sos
ATOM   3664  C    ASN  1044      48.915   8.150  74.436  1.00  93.94      sos
ATOM   3665  O    ASN  1044      49.192   7.155  73.728  1.00  92.95      sos
ATOM   3666  OT   ASN  1044    9999.0009999.0009999.000  1.00   0.00      sos
ATOM   3667  CB   MET     1      98.896  28.177  63.709  1.00  64.21      ras
ATOM   3668  CG   MET     1      97.614  28.013  62.921  1.00  60.52      ras
ATOM   3669  SD   MET     1      97.711  28.897  61.353  1.00  67.68      ras
ATOM   3670  CE   MET     1      96.745  27.822  60.275  1.00  66.31      ras
ATOM   3671  C    MET     1      97.855  27.918  65.978  1.00  69.17      ras
ATOM   3672  O    MET     1      96.864  27.226  66.252  1.00  65.74      ras
ATOM   3673  N    MET     1      98.797  25.938  64.784  1.00  70.44      ras
ATOM   3674  CA   MET     1      98.937  27.403  65.030  1.00  68.67      ras
ATOM   3675  N    THR     2      98.056  29.134  66.479  1.00  67.94      ras
ATOM   3676  CA   THR     2      97.106  29.743  67.401  1.00  66.23      ras
ATOM   3677  CB   THR     2      97.756  30.897  68.196  1.00  68.13      ras
ATOM   3678  OG1  THR     2      98.957  30.428  68.820  1.00  72.20      ras
ATOM   3679  CG2  THR     2      96.810  31.400  69.279  1.00  69.27      ras
ATOM   3680  C    THR     2      95.858  30.251  66.676  1.00  63.62      ras
ATOM   3681  O    THR     2      95.935  30.805  65.569  1.00  58.44      ras
ATOM   3682  N    GLU     3      94.709  30.034  67.309  1.00  60.32      ras
ATOM   3683  CA   GLU     3      93.431  30.458  66.764  1.00  59.63      ras
ATOM   3684  CB   GLU     3      92.479  29.263  66.702  1.00  65.92      ras
ATOM   3685  CG   GLU     3      91.101  29.577  66.139  1.00  73.93      ras
ATOM   3686  CD   GLU     3      90.202  28.353  66.090  1.00  78.86      ras
ATOM   3687  OE1  GLU     3      89.227  28.296  66.876  1.00  78.18      ras
```

Figure 8-62

| ATOM | 3688 | OE2 | GLU | 3 | 90.478 | 27.446 | 65.268 | 1.00 | 81.55 | ras |
| ATOM | 3689 | C | GLU | 3 | 92.827 | 31.560 | 67.632 | 1.00 | 55.33 | ras |
| ATOM | 3690 | O | GLU | 3 | 92.618 | 31.369 | 68.834 | 1.00 | 55.49 | ras |
| ATOM | 3691 | N | TYR | 4 | 92.573 | 32.717 | 67.028 | 1.00 | 48.88 | ras |
| ATOM | 3692 | CA | TYR | 4 | 91.979 | 33.840 | 67.752 | 1.00 | 43.76 | ras |
| ATOM | 3693 | CB | TYR | 4 | 92.715 | 35.144 | 67.448 | 1.00 | 41.90 | ras |
| ATOM | 3694 | CG | TYR | 4 | 94.164 | 35.151 | 67.853 | 1.00 | 42.99 | ras |
| ATOM | 3695 | CD1 | TYR | 4 | 95.168 | 35.247 | 66.895 | 1.00 | 39.72 | ras |
| ATOM | 3696 | CE1 | TYR | 4 | 96.497 | 35.267 | 67.255 | 1.00 | 42.34 | ras |
| ATOM | 3697 | CD2 | TYR | 4 | 94.533 | 35.074 | 69.195 | 1.00 | 42.32 | ras |
| ATOM | 3698 | CE2 | TYR | 4 | 95.866 | 35.093 | 69.569 | 1.00 | 43.19 | ras |
| ATOM | 3699 | CZ | TYR | 4 | 96.845 | 35.188 | 68.593 | 1.00 | 45.54 | ras |
| ATOM | 3700 | OH | TYR | 4 | 98.176 | 35.184 | 68.949 | 1.00 | 49.20 | ras |
| ATOM | 3701 | C | TYR | 4 | 90.513 | 34.017 | 67.389 | 1.00 | 40.08 | ras |
| ATOM | 3702 | O | TYR | 4 | 90.173 | 34.198 | 66.217 | 1.00 | 39.51 | ras |
| ATOM | 3703 | N | LYS | 5 | 89.644 | 33.953 | 68.389 | 1.00 | 36.05 | ras |
| ATOM | 3704 | CA | LYS | 5 | 88.224 | 34.145 | 68.140 | 1.00 | 39.51 | ras |
| ATOM | 3705 | CB | LYS | 5 | 87.384 | 33.217 | 69.020 | 1.00 | 41.71 | ras |
| ATOM | 3706 | CG | LYS | 5 | 87.517 | 31.769 | 68.592 | 1.00 | 47.56 | ras |
| ATOM | 3707 | CD | LYS | 5 | 86.450 | 30.881 | 69.206 | 1.00 | 56.96 | ras |
| ATOM | 3708 | CE | LYS | 5 | 86.435 | 29.514 | 68.525 | 1.00 | 60.92 | ras |
| ATOM | 3709 | NZ | LYS | 5 | 86.206 | 29.628 | 67.047 | 1.00 | 61.12 | ras |
| ATOM | 3710 | C | LYS | 5 | 87.831 | 35.617 | 68.297 | 1.00 | 37.04 | ras |
| ATOM | 3711 | O | LYS | 5 | 87.789 | 36.172 | 69.399 | 1.00 | 36.97 | ras |
| ATOM | 3712 | N | LEU | 6 | 87.586 | 36.256 | 67.164 | 1.00 | 34.50 | ras |
| ATOM | 3713 | CA | LEU | 6 | 87.229 | 37.661 | 67.144 | 1.00 | 35.89 | ras |
| ATOM | 3714 | CB | LEU | 6 | 88.022 | 38.374 | 66.043 | 1.00 | 31.73 | ras |
| ATOM | 3715 | CG | LEU | 6 | 89.536 | 38.108 | 66.065 | 1.00 | 28.35 | ras |
| ATOM | 3716 | CD1 | LEU | 6 | 90.235 | 38.966 | 64.998 | 1.00 | 22.14 | ras |
| ATOM | 3717 | CD2 | LEU | 6 | 90.104 | 38.375 | 67.470 | 1.00 | 12.88 | ras |
| ATOM | 3718 | C | LEU | 6 | 85.736 | 37.869 | 66.936 | 1.00 | 36.19 | ras |
| ATOM | 3719 | O | LEU | 6 | 85.098 | 37.129 | 66.190 | 1.00 | 39.15 | ras |
| ATOM | 3720 | N | VAL | 7 | 85.183 | 38.867 | 67.621 | 1.00 | 34.20 | ras |
| ATOM | 3721 | CA | VAL | 7 | 83.765 | 39.192 | 67.507 | 1.00 | 28.91 | ras |
| ATOM | 3722 | CB | VAL | 7 | 83.002 | 38.898 | 68.799 | 1.00 | 24.45 | ras |
| ATOM | 3723 | CG1 | VAL | 7 | 81.555 | 39.337 | 68.659 | 1.00 | 18.95 | ras |
| ATOM | 3724 | CG2 | VAL | 7 | 83.080 | 37.419 | 69.127 | 1.00 | 27.16 | ras |
| ATOM | 3725 | C | VAL | 7 | 83.595 | 40.663 | 67.198 | 1.00 | 29.95 | ras |
| ATOM | 3726 | O | VAL | 7 | 84.230 | 41.509 | 67.819 | 1.00 | 35.73 | ras |
| ATOM | 3727 | N | VAL | 8 | 82.739 | 40.962 | 66.229 | 1.00 | 29.89 | ras |
| ATOM | 3728 | CA | VAL | 8 | 82.466 | 42.337 | 65.837 | 1.00 | 25.87 | ras |
| ATOM | 3729 | CB | VAL | 8 | 82.421 | 42.458 | 64.333 | 1.00 | 19.37 | ras |
| ATOM | 3730 | CG1 | VAL | 8 | 82.120 | 43.870 | 63.933 | 1.00 | 25.11 | ras |
| ATOM | 3731 | CG2 | VAL | 8 | 83.719 | 42.000 | 63.749 | 1.00 | 23.08 | ras |
| ATOM | 3732 | C | VAL | 8 | 81.119 | 42.761 | 66.400 | 1.00 | 27.93 | ras |
| ATOM | 3733 | O | VAL | 8 | 80.138 | 42.028 | 66.287 | 1.00 | 35.49 | ras |
| ATOM | 3734 | N | VAL | 9 | 81.081 | 43.931 | 67.025 | 1.00 | 26.90 | ras |
| ATOM | 3735 | CA | VAL | 9 | 79.851 | 44.465 | 67.602 | 1.00 | 28.06 | ras |
| ATOM | 3736 | CB | VAL | 9 | 79.858 | 44.380 | 69.155 | 1.00 | 26.74 | ras |
| ATOM | 3737 | CG1 | VAL | 9 | 80.086 | 42.952 | 69.613 | 1.00 | 28.81 | ras |
| ATOM | 3738 | CG2 | VAL | 9 | 80.939 | 45.248 | 69.721 | 1.00 | 34.61 | ras |
| ATOM | 3739 | C | VAL | 9 | 79.687 | 45.925 | 67.172 | 1.00 | 30.28 | ras |
| ATOM | 3740 | O | VAL | 9 | 80.673 | 46.641 | 66.965 | 1.00 | 31.12 | ras |
| ATOM | 3741 | N | GLY | 10 | 78.442 | 46.357 | 67.021 | 1.00 | 31.28 | ras |
| ATOM | 3742 | CA | GLY | 10 | 78.182 | 47.723 | 66.607 | 1.00 | 30.62 | ras |
| ATOM | 3743 | C | GLY | 10 | 76.791 | 47.876 | 66.033 | 1.00 | 32.79 | ras |
| ATOM | 3744 | O | GLY | 10 | 76.166 | 46.888 | 65.651 | 1.00 | 32.25 | ras |
| ATOM | 3745 | N | ALA | 11 | 76.310 | 49.113 | 65.950 | 1.00 | 31.58 | ras |
| ATOM | 3746 | CA | ALA | 11 | 74.976 | 49.384 | 65.422 | 1.00 | 28.79 | ras |
| ATOM | 3747 | CB | ALA | 11 | 74.672 | 50.874 | 65.486 | 1.00 | 28.24 | ras |
| ATOM | 3748 | C | ALA | 11 | 74.802 | 48.887 | 63.996 | 1.00 | 29.83 | ras |

Figure 8-63

```
ATOM   3749  O    ALA  11    75.758  48.858  63.217  1.00  24.58      ras
ATOM   3750  N    GLY  12    73.580  48.461  63.680  1.00  32.69      ras
ATOM   3751  CA   GLY  12    73.279  47.991  62.344  1.00  33.41      ras
ATOM   3752  C    GLY  12    72.804  49.153  61.488  1.00  37.17      ras
ATOM   3753  O    GLY  12    72.639  50.273  61.977  1.00  39.12      ras
ATOM   3754  N    GLY  13    72.604  48.901  60.200  1.00  38.09      ras
ATOM   3755  CA   GLY  13    72.127  49.944  59.315  1.00  36.40      ras
ATOM   3756  C    GLY  13    73.152  50.965  58.877  1.00  34.79      ras
ATOM   3757  O    GLY  13    72.788  51.969  58.275  1.00  37.97      ras
ATOM   3758  N    VAL  14    74.424  50.732  59.181  1.00  32.97      ras
ATOM   3759  CA   VAL  14    75.474  51.663  58.778  1.00  31.46      ras
ATOM   3760  CB   VAL  14    75.984  52.508  59.957  1.00  29.51      ras
ATOM   3761  CG1  VAL  14    74.837  53.333  60.540  1.00  25.85      ras
ATOM   3762  CG2  VAL  14    76.603  51.619  61.024  1.00  29.24      ras
ATOM   3763  C    VAL  14    76.630  50.933  58.112  1.00  33.37      ras
ATOM   3764  O    VAL  14    77.726  51.470  57.979  1.00  37.97      ras
ATOM   3765  N    GLY  15    76.371  49.691  57.718  1.00  34.90      ras
ATOM   3766  CA   GLY  15    77.356  48.880  57.020  1.00  35.10      ras
ATOM   3767  C    GLY  15    78.592  48.375  57.735  1.00  34.45      ras
ATOM   3768  O    GLY  15    79.671  48.375  57.141  1.00  34.67      ras
ATOM   3769  N    LYS  16    78.445  47.884  58.964  1.00  32.21      ras
ATOM   3770  CA   LYS  16    79.594  47.375  59.703  1.00  33.47      ras
ATOM   3771  CB   LYS  16    79.229  47.081  61.160  1.00  29.51      ras
ATOM   3772  CG   LYS  16    78.312  45.903  61.341  1.00  26.74      ras
ATOM   3773  CD   LYS  16    78.025  45.607  62.784  1.00  21.31      ras
ATOM   3774  CE   LYS  16    76.729  44.824  62.885  1.00  23.59      ras
ATOM   3775  NZ   LYS  16    76.295  44.522  64.284  1.00  24.66      ras
ATOM   3776  C    LYS  16    80.169  46.111  59.064  1.00  36.18      ras
ATOM   3777  O    LYS  16    81.323  45.774  59.292  1.00  40.41      ras
ATOM   3778  N    SER  17    79.367  45.420  58.257  1.00  37.90      ras
ATOM   3779  CA   SER  17    79.814  44.189  57.618  1.00  33.18      ras
ATOM   3780  CB   SER  17    78.667  43.520  56.868  1.00  31.75      ras
ATOM   3781  OG   SER  17    78.174  44.362  55.843  1.00  35.33      ras
ATOM   3782  C    SER  17    80.983  44.416  56.679  1.00  32.80      ras
ATOM   3783  O    SER  17    81.764  43.496  56.427  1.00  33.91      ras
ATOM   3784  N    ALA  18    81.124  45.642  56.181  1.00  29.29      ras
ATOM   3785  CA   ALA  18    82.225  45.946  55.264  1.00  32.79      ras
ATOM   3786  CB   ALA  18    82.151  47.388  54.782  1.00  31.17      ras
ATOM   3787  C    ALA  18    83.590  45.668  55.881  1.00  32.59      ras
ATOM   3788  O    ALA  18    84.535  45.342  55.173  1.00  34.96      ras
ATOM   3789  N    LEU  19    83.679  45.778  57.204  1.00  31.66      ras
ATOM   3790  CA   LEU  19    84.928  45.547  57.915  1.00  30.79      ras
ATOM   3791  CB   LEU  19    84.724  45.768  59.406  1.00  29.97      ras
ATOM   3792  CG   LEU  19    85.721  46.656  60.124  1.00  31.50      ras
ATOM   3793  CD1  LEU  19    85.783  46.213  61.567  1.00  30.98      ras
ATOM   3794  CD2  LEU  19    87.083  46.559  59.477  1.00  31.11      ras
ATOM   3795  C    LEU  19    85.457  44.131  57.695  1.00  32.45      ras
ATOM   3796  O    LEU  19    86.482  43.934  57.054  1.00  30.89      ras
ATOM   3797  N    THR  20    84.742  43.148  58.226  1.00  33.56      ras
ATOM   3798  CA   THR  20    85.145  41.758  58.101  1.00  36.39      ras
ATOM   3799  CB   THR  20    84.226  40.867  58.938  1.00  34.40      ras
ATOM   3800  OG1  THR  20    84.304  41.282  60.306  1.00  34.94      ras
ATOM   3801  CG2  THR  20    84.632  39.407  58.832  1.00  31.53      ras
ATOM   3802  C    THR  20    85.202  41.256  56.650  1.00  40.45      ras
ATOM   3803  O    THR  20    86.031  40.403  56.315  1.00  41.25      ras
ATOM   3804  N    ILE  21    84.350  41.807  55.787  1.00  40.32      ras
ATOM   3805  CA   ILE  21    84.319  41.389  54.391  1.00  40.25      ras
ATOM   3806  CB   ILE  21    83.016  41.845  53.685  1.00  39.42      ras
ATOM   3807  CG2  ILE  21    83.137  41.694  52.171  1.00  32.60      ras
ATOM   3808  CG1  ILE  21    81.842  41.004  54.205  1.00  36.21      ras
ATOM   3809  CD1  ILE  21    80.497  41.447  53.712  1.00  34.78      ras
```

Figure 8-64

```
ATOM   3810  C    ILE   21      85.555  41.849  53.639  1.00 42.12      ras
ATOM   3811  O    ILE   21      86.184  41.057  52.934  1.00 43.78      ras
ATOM   3812  N    GLN   22      85.931  43.110  53.829  1.00 42.34      ras
ATOM   3813  CA   GLN   22      87.110  43.660  53.172  1.00 41.07      ras
ATOM   3814  CB   GLN   22      87.226  45.163  53.427  1.00 41.89      ras
ATOM   3815  CG   GLN   22      86.187  46.014  52.696  1.00 42.18      ras
ATOM   3816  CD   GLN   22      86.419  47.507  52.887  1.00 47.35      ras
ATOM   3817  OE1  GLN   22      86.148  48.071  53.958  1.00 48.68      ras
ATOM   3818  NE2  GLN   22      86.937  48.154  51.852  1.00 49.92      ras
ATOM   3819  C    GLN   22      88.388  42.943  53.614  1.00 39.88      ras
ATOM   3820  O    GLN   22      89.320  42.796  52.832  1.00 43.76      ras
ATOM   3821  N    LEU   23      88.430  42.485  54.859  1.00 38.90      ras
ATOM   3822  CA   LEU   23      89.601  41.773  55.348  1.00 40.70      ras
ATOM   3823  CB   LEU   23      89.445  41.424  56.827  1.00 37.24      ras
ATOM   3824  CG   LEU   23      90.536  40.522  57.407  1.00 36.44      ras
ATOM   3825  CD1  LEU   23      91.848  41.281  57.469  1.00 34.77      ras
ATOM   3826  CD2  LEU   23      90.144  40.043  58.794  1.00 37.25      ras
ATOM   3827  C    LEU   23      89.742  40.488  54.553  1.00 44.83      ras
ATOM   3828  O    LEU   23      90.774  40.238  53.929  1.00 44.30      ras
ATOM   3829  N    ILE   24      88.654  39.723  54.525  1.00 51.04      ras
ATOM   3830  CA   ILE   24      88.594  38.439  53.841  1.00 57.57      ras
ATOM   3831  CB   ILE   24      87.541  37.527  54.524  1.00 54.03      ras
ATOM   3832  CG2  ILE   24      87.556  36.135  53.922  1.00 59.68      ras
ATOM   3833  CG1  ILE   24      87.876  37.400  56.007  1.00 50.73      ras
ATOM   3834  CD1  ILE   24      87.096  36.354  56.727  1.00 44.71      ras
ATOM   3835  C    ILE   24      88.349  38.530  52.330  1.00 62.59      ras
ATOM   3836  O    ILE   24      87.466  37.879  51.791  1.00 66.56      ras
ATOM   3837  N    GLN   25      89.137  39.350  51.650  1.00 69.35      ras
ATOM   3838  CA   GLN   25      89.026  39.513  50.205  1.00 75.82      ras
ATOM   3839  CB   GLN   25      87.968  40.555  49.833  1.00 74.81      ras
ATOM   3840  CG   GLN   25      86.538  40.046  49.871  1.00 74.11      ras
ATOM   3841  CD   GLN   25      85.550  41.024  49.269  1.00 76.38      ras
ATOM   3842  OE1  GLN   25      85.746  42.240  49.317  1.00 75.82      ras
ATOM   3843  NE2  GLN   25      84.477  40.493  48.693  1.00 77.92      ras
ATOM   3844  C    GLN   25      90.372  39.948  49.668  1.00 82.87      ras
ATOM   3845  O    GLN   25      91.159  40.575  50.379  1.00 86.41      ras
ATOM   3846  N    ASN   26      90.636  39.606  48.414  1.00 89.55      ras
ATOM   3847  CA   ASN   26      91.898  39.954  47.775  1.00 96.55      ras
ATOM   3848  CB   ASN   26      92.508  38.712  47.114  1.00 99.02      ras
ATOM   3849  CG   ASN   26      92.262  37.439  47.912  1.00101.37      ras
ATOM   3850  OD1  ASN   26      91.828  36.425  47.363  1.00103.47      ras
ATOM   3851  ND2  ASN   26      92.536  37.487  49.210  1.00101.47      ras
ATOM   3852  C    ASN   26      91.668  41.033  46.720  1.00 99.43      ras
ATOM   3853  O    ASN   26      90.527  41.402  46.437  1.00 98.60      ras
ATOM   3854  N    HIS   27      92.758  41.537  46.142  1.00103.37      ras
ATOM   3855  CA   HIS   27      92.668  42.560  45.102  1.00105.64      ras
ATOM   3856  CB   HIS   27      94.072  42.973  44.625  1.00102.92      ras
ATOM   3857  CG   HIS   27      94.983  43.412  45.732  0.00103.19      ras
ATOM   3858  CD2  HIS   27      96.059  42.811  46.290  0.00102.84      ras
ATOM   3859  ND1  HIS   27      94.829  44.613  46.395  0.00102.84      ras
ATOM   3860  CE1  HIS   27      95.774  44.728  47.312  0.00102.81      ras
ATOM   3861  NE2  HIS   27      96.533  43.650  47.269  0.00102.81      ras
ATOM   3862  C    HIS   27      91.839  41.955  43.963  1.00107.45      ras
ATOM   3863  O    HIS   27      91.957  40.761  43.671  1.00109.51      ras
ATOM   3864  N    PHE   28      90.939  42.762  43.403  1.00108.72      ras
ATOM   3865  CA   PHE   28      90.018  42.365  42.327  1.00109.86      ras
ATOM   3866  CB   PHE   28      90.733  42.107  40.977  1.00108.97      ras
ATOM   3867  CG   PHE   28      91.413  40.763  40.860  0.00107.25      ras
ATOM   3868  CD1  PHE   28      90.678  39.607  40.608  0.00106.62      ras
ATOM   3869  CD2  PHE   28      92.795  40.662  40.957  0.00106.62      ras
ATOM   3870  CE1  PHE   28      91.311  38.371  40.454  0.00106.07      ras
```

Figure 8-65

```
ATOM   3871  CE2 PHE    28      93.438  39.435  40.806  0.00106.07      ras
ATOM   3872  CZ  PHE    28      92.695  38.287  40.553  0.00105.94      ras
ATOM   3873  C   PHE    28      89.023  41.252  42.687  1.00109.95      ras
ATOM   3874  O   PHE    28      88.266  40.778  41.833  1.00111.13      ras
ATOM   3875  N   VAL    29      89.033  40.850  43.957  1.00107.43      ras
ATOM   3876  CA  VAL    29      88.128  39.823  44.467  1.00104.88      ras
ATOM   3877  CB  VAL    29      88.860  38.831  45.415  1.00106.44      ras
ATOM   3878  CG1 VAL    29      87.885  37.852  46.042  1.00105.85      ras
ATOM   3879  CG2 VAL    29      89.918  38.079  44.638  1.00108.37      ras
ATOM   3880  C   VAL    29      86.997  40.549  45.205  1.00102.41      ras
ATOM   3881  O   VAL    29      87.157  40.983  46.349  1.00101.78      ras
ATOM   3882  N   ASP    30      85.891  40.769  44.503  1.00100.00      ras
ATOM   3883  CA  ASP    30      84.736  41.437  45.089  1.00 96.73      ras
ATOM   3884  CB  ASP    30      84.296  42.610  44.211  1.00 96.24      ras
ATOM   3885  CG  ASP    30      85.360  43.692  44.119  0.00 96.14      ras
ATOM   3886  OD1 ASP    30      85.421  44.554  45.025  0.00 95.97      ras
ATOM   3887  OD2 ASP    30      86.151  43.665  43.153  0.00 95.97      ras
ATOM   3888  C   ASP    30      83.595  40.445  45.298  1.00 94.60      ras
ATOM   3889  O   ASP    30      82.475  40.833  45.628  1.00 96.50      ras
ATOM   3890  N   GLU    31      83.906  39.159  45.128  1.00 91.89      ras
ATOM   3891  CA  GLU    31      82.953  38.058  45.305  1.00 87.27      ras
ATOM   3892  CB  GLU    31      83.412  36.829  44.519  1.00 88.86      ras
ATOM   3893  CG  GLU    31      83.742  37.097  43.064  1.00 94.52      ras
ATOM   3894  CD  GLU    31      84.866  36.208  42.550  1.00 98.83      ras
ATOM   3895  OE1 GLU    31      84.719  34.963  42.593  1.00 99.32      ras
ATOM   3896  OE2 GLU    31      85.904  36.762  42.121  1.00 98.61      ras
ATOM   3897  C   GLU    31      82.901  37.679  46.785  1.00 81.60      ras
ATOM   3898  O   GLU    31      83.917  37.754  47.488  1.00 83.19      ras
ATOM   3899  N   TYR    32      81.735  37.246  47.252  1.00 71.10      ras
ATOM   3900  CA  TYR    32      81.591  36.866  48.649  1.00 62.58      ras
ATOM   3901  CB  TYR    32      81.392  38.110  49.531  1.00 59.55      ras
ATOM   3902  CG  TYR    32      81.576  37.849  51.016  1.00 57.68      ras
ATOM   3903  CD1 TYR    32      82.824  37.506  51.529  1.00 55.91      ras
ATOM   3904  CE1 TYR    32      83.002  37.242  52.888  1.00 58.04      ras
ATOM   3905  CD2 TYR    32      80.500  37.928  51.903  1.00 56.98      ras
ATOM   3906  CE2 TYR    32      80.667  37.667  53.266  1.00 57.80      ras
ATOM   3907  CZ  TYR    32      81.923  37.322  53.750  1.00 59.28      ras
ATOM   3908  OH  TYR    32      82.106  37.034  55.086  1.00 57.17      ras
ATOM   3909  C   TYR    32      80.447  35.885  48.858  1.00 58.35      ras
ATOM   3910  O   TYR    32      79.314  36.139  48.456  1.00 55.09      ras
ATOM   3911  N   ASP    33      80.771  34.744  49.457  1.00 56.72      ras
ATOM   3912  CA  ASP    33      79.794  33.705  49.748  1.00 55.66      ras
ATOM   3913  CB  ASP    33      80.108  32.424  48.961  1.00 57.45      ras
ATOM   3914  CG  ASP    33      79.023  31.352  49.105  1.00 62.57      ras
ATOM   3915  OD1 ASP    33      77.946  31.636  49.679  1.00 64.59      ras
ATOM   3916  OD2 ASP    33      79.250  30.216  48.638  1.00 61.10      ras
ATOM   3917  C   ASP    33      79.865  33.457  51.248  1.00 53.22      ras
ATOM   3918  O   ASP    33      80.720  32.723  51.737  1.00 52.02      ras
ATOM   3919  N   PRO    34      78.957  34.085  52.000  1.00 52.62      ras
ATOM   3920  CD  PRO    34      77.890  34.956  51.475  1.00 50.65      ras
ATOM   3921  CA  PRO    34      78.869  33.978  53.457  1.00 53.48      ras
ATOM   3922  CB  PRO    34      77.798  35.012  53.790  1.00 52.62      ras
ATOM   3923  CG  PRO    34      76.901  34.949  52.591  1.00 51.04      ras
ATOM   3924  C   PRO    34      78.500  32.596  53.991  1.00 54.52      ras
ATOM   3925  O   PRO    34      77.967  32.474  55.088  1.00 55.79      ras
ATOM   3926  N   THR    35      78.813  31.551  53.244  1.00 58.47      ras
ATOM   3927  CA  THR    35      78.467  30.210  53.692  1.00 64.56      ras
ATOM   3928  CB  THR    35      77.402  29.593  52.768  1.00 64.69      ras
ATOM   3929  OG1 THR    35      76.237  30.431  52.780  1.00 62.13      ras
ATOM   3930  CG2 THR    35      77.010  28.201  53.248  1.00 68.96      ras
ATOM   3931  C   THR    35      79.680  29.295  53.818  1.00 67.20      ras
```

Figure 8-66

| ATOM | 3932 | O | THR | 35 | 79.670 | 28.331 | 54.586 | 1.00 | 67.05 | ras |
|---|---|---|---|---|---|---|---|---|---|---|
| ATOM | 3933 | N | ILE | 36 | 80.736 | 29.630 | 53.088 | 1.00 | 69.42 | ras |
| ATOM | 3934 | CA | ILE | 36 | 81.969 | 28.860 | 53.106 | 1.00 | 72.57 | ras |
| ATOM | 3935 | CB | ILE | 36 | 82.822 | 29.222 | 51.871 | 1.00 | 75.23 | ras |
| ATOM | 3936 | CG2 | ILE | 36 | 84.078 | 28.351 | 51.806 | 1.00 | 79.10 | ras |
| ATOM | 3937 | CG1 | ILE | 36 | 81.977 | 29.065 | 50.604 | 1.00 | 78.33 | ras |
| ATOM | 3938 | CD1 | ILE | 36 | 82.677 | 29.490 | 49.321 | 1.00 | 85.02 | ras |
| ATOM | 3939 | C | ILE | 36 | 82.759 | 29.186 | 54.379 | 1.00 | 72.69 | ras |
| ATOM | 3940 | O | ILE | 36 | 82.619 | 30.277 | 54.931 | 1.00 | 71.94 | ras |
| ATOM | 3941 | N | GLU | 37 | 83.566 | 28.240 | 54.859 | 1.00 | 72.05 | ras |
| ATOM | 3942 | CA | GLU | 37 | 84.385 | 28.484 | 56.046 | 1.00 | 71.30 | ras |
| ATOM | 3943 | CB | GLU | 37 | 85.124 | 27.219 | 56.474 | 1.00 | 74.02 | ras |
| ATOM | 3944 | CG | GLU | 37 | 84.336 | 26.301 | 57.388 | 1.00 | 81.59 | ras |
| ATOM | 3945 | CD | GLU | 37 | 85.153 | 25.109 | 57.868 | 1.00 | 86.24 | ras |
| ATOM | 3946 | OE1 | GLU | 37 | 86.402 | 25.158 | 57.777 | 1.00 | 86.76 | ras |
| ATOM | 3947 | OE2 | GLU | 37 | 84.543 | 24.121 | 58.338 | 1.00 | 88.52 | ras |
| ATOM | 3948 | C | GLU | 37 | 85.407 | 29.587 | 55.775 | 1.00 | 69.81 | ras |
| ATOM | 3949 | O | GLU | 37 | 85.855 | 30.260 | 56.697 | 1.00 | 65.94 | ras |
| ATOM | 3950 | N | ASP | 38 | 85.778 | 29.749 | 54.506 | 1.00 | 70.84 | ras |
| ATOM | 3951 | CA | ASP | 38 | 86.745 | 30.764 | 54.078 | 1.00 | 71.58 | ras |
| ATOM | 3952 | CB | ASP | 38 | 87.142 | 30.546 | 52.610 | 1.00 | 71.34 | ras |
| ATOM | 3953 | CG | ASP | 38 | 88.411 | 29.727 | 52.451 | 1.00 | 72.38 | ras |
| ATOM | 3954 | OD1 | ASP | 38 | 89.103 | 29.916 | 51.427 | 1.00 | 67.63 | ras |
| ATOM | 3955 | OD2 | ASP | 38 | 88.716 | 28.898 | 53.337 | 1.00 | 72.83 | ras |
| ATOM | 3956 | C | ASP | 38 | 86.214 | 32.183 | 54.219 | 1.00 | 71.85 | ras |
| ATOM | 3957 | O | ASP | 38 | 86.983 | 33.140 | 54.128 | 1.00 | 72.81 | ras |
| ATOM | 3958 | N | SER | 39 | 84.902 | 32.309 | 54.424 | 1.00 | 69.98 | ras |
| ATOM | 3959 | CA | SER | 39 | 84.249 | 33.609 | 54.548 | 1.00 | 66.26 | ras |
| ATOM | 3960 | CB | SER | 39 | 82.760 | 33.493 | 54.210 | 1.00 | 67.89 | ras |
| ATOM | 3961 | OG | SER | 39 | 82.053 | 32.764 | 55.198 | 1.00 | 67.90 | ras |
| ATOM | 3962 | C | SER | 39 | 84.420 | 34.284 | 55.904 | 1.00 | 63.85 | ras |
| ATOM | 3963 | O | SER | 39 | 84.245 | 35.498 | 56.014 | 1.00 | 64.22 | ras |
| ATOM | 3964 | N | TYR | 40 | 84.748 | 33.502 | 56.929 | 1.00 | 59.66 | ras |
| ATOM | 3965 | CA | TYR | 40 | 84.943 | 34.042 | 58.271 | 1.00 | 60.29 | ras |
| ATOM | 3966 | CB | TYR | 40 | 83.736 | 33.729 | 59.158 | 1.00 | 59.53 | ras |
| ATOM | 3967 | CG | TYR | 40 | 83.369 | 32.266 | 59.252 | 1.00 | 61.70 | ras |
| ATOM | 3968 | CD1 | TYR | 40 | 83.877 | 31.459 | 60.273 | 1.00 | 63.06 | ras |
| ATOM | 3969 | CE1 | TYR | 40 | 83.475 | 30.124 | 60.411 | 1.00 | 63.86 | ras |
| ATOM | 3970 | CD2 | TYR | 40 | 82.455 | 31.702 | 58.363 | 1.00 | 63.75 | ras |
| ATOM | 3971 | CE2 | TYR | 40 | 82.044 | 30.374 | 58.491 | 1.00 | 64.02 | ras |
| ATOM | 3972 | CZ | TYR | 40 | 82.554 | 29.591 | 59.517 | 1.00 | 66.19 | ras |
| ATOM | 3973 | OH | TYR | 40 | 82.127 | 28.287 | 59.649 | 1.00 | 66.63 | ras |
| ATOM | 3974 | C | TYR | 40 | 86.244 | 33.612 | 58.961 | 1.00 | 60.01 | ras |
| ATOM | 3975 | O | TYR | 40 | 86.560 | 34.089 | 60.051 | 1.00 | 61.34 | ras |
| ATOM | 3976 | N | ARG | 41 | 86.991 | 32.715 | 58.321 | 1.00 | 59.17 | ras |
| ATOM | 3977 | CA | ARG | 41 | 88.261 | 32.217 | 58.846 | 1.00 | 56.28 | ras |
| ATOM | 3978 | CB | ARG | 41 | 88.185 | 30.713 | 59.110 | 1.00 | 55.38 | ras |
| ATOM | 3979 | CG | ARG | 41 | 87.273 | 30.337 | 60.267 | 1.00 | 60.83 | ras |
| ATOM | 3980 | CD | ARG | 41 | 86.991 | 28.841 | 60.304 | 1.00 | 62.22 | ras |
| ATOM | 3981 | NE | ARG | 41 | 87.171 | 28.277 | 61.639 | 1.00 | 60.37 | ras |
| ATOM | 3982 | CZ | ARG | 41 | 88.316 | 27.766 | 62.084 | 1.00 | 60.85 | ras |
| ATOM | 3983 | NH1 | ARG | 41 | 89.387 | 27.747 | 61.302 | 1.00 | 60.27 | ras |
| ATOM | 3984 | NH2 | ARG | 41 | 88.390 | 27.266 | 63.307 | 1.00 | 61.31 | ras |
| ATOM | 3985 | C | ARG | 41 | 89.382 | 32.506 | 57.859 | 1.00 | 56.73 | ras |
| ATOM | 3986 | O | ARG | 41 | 89.334 | 32.100 | 56.698 | 1.00 | 59.88 | ras |
| ATOM | 3987 | N | LYS | 42 | 90.383 | 33.239 | 58.318 | 1.00 | 56.01 | ras |
| ATOM | 3988 | CA | LYS | 42 | 91.513 | 33.580 | 57.474 | 1.00 | 54.08 | ras |
| ATOM | 3989 | CB | LYS | 42 | 91.401 | 35.034 | 57.012 | 1.00 | 51.53 | ras |
| ATOM | 3990 | CG | LYS | 42 | 92.531 | 35.472 | 56.108 | 1.00 | 51.49 | ras |
| ATOM | 3991 | CD | LYS | 42 | 92.364 | 36.892 | 55.627 | 1.00 | 50.03 | ras |
| ATOM | 3992 | CE | LYS | 42 | 93.461 | 37.238 | 54.637 | 1.00 | 52.95 | ras |

Figure 8-67

| | | | | | | | | | | |
|---|---|---|---|---|---|---|---|---|---|---|
| ATOM | 3993 | NZ | LYS | 42 | 93.397 | 38.649 | 54.157 | 1.00 | 61.11 | ras |
| ATOM | 3994 | C | LYS | 42 | 92.796 | 33.385 | 58.265 | 1.00 | 54.61 | ras |
| ATOM | 3995 | O | LYS | 42 | 92.822 | 33.629 | 59.472 | 1.00 | 54.93 | ras |
| ATOM | 3996 | N | GLN | 43 | 93.832 | 32.860 | 57.615 | 1.00 | 56.41 | ras |
| ATOM | 3997 | CA | GLN | 43 | 95.108 | 32.684 | 58.297 | 1.00 | 58.18 | ras |
| ATOM | 3998 | CB | GLN | 43 | 95.732 | 31.307 | 58.026 | 1.00 | 60.23 | ras |
| ATOM | 3999 | CG | GLN | 43 | 96.551 | 31.181 | 56.750 | 1.00 | 67.52 | ras |
| ATOM | 4000 | CD | GLN | 43 | 97.766 | 30.280 | 56.935 | 1.00 | 70.11 | ras |
| ATOM | 4001 | OE1 | GLN | 43 | 97.653 | 29.159 | 57.437 | 1.00 | 69.99 | ras |
| ATOM | 4002 | NE2 | GLN | 43 | 98.939 | 30.780 | 56.548 | 1.00 | 67.23 | ras |
| ATOM | 4003 | C | GLN | 43 | 96.015 | 33.823 | 57.847 | 1.00 | 56.44 | ras |
| ATOM | 4004 | O | GLN | 43 | 96.112 | 34.122 | 56.654 | 1.00 | 55.04 | ras |
| ATOM | 4005 | N | VAL | 44 | 96.602 | 34.514 | 58.816 | 1.00 | 54.97 | ras |
| ATOM | 4006 | CA | VAL | 44 | 97.476 | 35.641 | 58.523 | 1.00 | 56.46 | ras |
| ATOM | 4007 | CB | VAL | 44 | 96.797 | 36.978 | 58.883 | 1.00 | 57.60 | ras |
| ATOM | 4008 | CG1 | VAL | 44 | 95.643 | 37.272 | 57.927 | 1.00 | 57.82 | ras |
| ATOM | 4009 | CG2 | VAL | 44 | 96.313 | 36.943 | 60.325 | 1.00 | 55.47 | ras |
| ATOM | 4010 | C | VAL | 44 | 98.806 | 35.562 | 59.262 | 1.00 | 56.75 | ras |
| ATOM | 4011 | O | VAL | 44 | 98.981 | 34.752 | 60.174 | 1.00 | 57.63 | ras |
| ATOM | 4012 | N | VAL | 45 | 99.745 | 36.403 | 58.845 | 1.00 | 57.17 | ras |
| ATOM | 4013 | CA | VAL | 45 | 101.063 | 36.457 | 59.468 | 1.00 | 61.29 | ras |
| ATOM | 4014 | CB | VAL | 45 | 102.198 | 36.347 | 58.413 | 1.00 | 62.94 | ras |
| ATOM | 4015 | CG1 | VAL | 45 | 103.521 | 36.025 | 59.097 | 1.00 | 61.07 | ras |
| ATOM | 4016 | CG2 | VAL | 45 | 101.859 | 35.300 | 57.360 | 1.00 | 62.53 | ras |
| ATOM | 4017 | C | VAL | 45 | 101.171 | 37.806 | 60.178 | 1.00 | 60.61 | ras |
| ATOM | 4018 | O | VAL | 45 | 101.246 | 38.849 | 59.528 | 1.00 | 62.86 | ras |
| ATOM | 4019 | N | ILE | 46 | 101.161 | 37.788 | 61.506 | 1.00 | 58.33 | ras |
| ATOM | 4020 | CA | ILE | 46 | 101.233 | 39.021 | 62.282 | 1.00 | 58.98 | ras |
| ATOM | 4021 | CB | ILE | 46 | 99.975 | 39.188 | 63.177 | 1.00 | 57.99 | ras |
| ATOM | 4022 | CG2 | ILE | 46 | 100.079 | 40.439 | 64.022 | 1.00 | 56.10 | ras |
| ATOM | 4023 | CG1 | ILE | 46 | 98.719 | 39.271 | 62.313 | 1.00 | 55.51 | ras |
| ATOM | 4024 | CD1 | ILE | 46 | 97.448 | 39.364 | 63.112 | 1.00 | 58.43 | ras |
| ATOM | 4025 | C | ILE | 46 | 102.486 | 39.056 | 63.148 | 1.00 | 59.99 | ras |
| ATOM | 4026 | O | ILE | 46 | 102.640 | 38.235 | 64.060 | 1.00 | 57.79 | ras |
| ATOM | 4027 | N | ASP | 47 | 103.359 | 40.031 | 62.873 | 1.00 | 61.13 | ras |
| ATOM | 4028 | CA | ASP | 47 | 104.623 | 40.200 | 63.603 | 1.00 | 60.63 | ras |
| ATOM | 4029 | CB | ASP | 47 | 104.357 | 40.551 | 65.076 | 1.00 | 59.46 | ras |
| ATOM | 4030 | CG | ASP | 47 | 103.670 | 41.894 | 65.252 | 1.00 | 59.19 | ras |
| ATOM | 4031 | OD1 | ASP | 47 | 103.669 | 42.705 | 64.299 | 1.00 | 56.94 | ras |
| ATOM | 4032 | OD2 | ASP | 47 | 103.137 | 42.135 | 66.358 | 1.00 | 56.66 | ras |
| ATOM | 4033 | C | ASP | 47 | 105.477 | 38.929 | 63.521 | 1.00 | 60.66 | ras |
| ATOM | 4034 | O | ASP | 47 | 106.049 | 38.482 | 64.520 | 1.00 | 58.61 | ras |
| ATOM | 4035 | N | GLY | 48 | 105.535 | 38.343 | 62.330 | 1.00 | 60.80 | ras |
| ATOM | 4036 | CA | GLY | 48 | 106.295 | 37.123 | 62.140 | 1.00 | 64.28 | ras |
| ATOM | 4037 | C | GLY | 48 | 105.576 | 35.865 | 62.611 | 1.00 | 66.53 | ras |
| ATOM | 4038 | O | GLY | 48 | 105.799 | 34.783 | 62.064 | 1.00 | 68.48 | ras |
| ATOM | 4039 | N | GLU | 49 | 104.724 | 35.991 | 63.625 | 1.00 | 67.16 | ras |
| ATOM | 4040 | CA | GLU | 49 | 103.999 | 34.836 | 64.146 | 1.00 | 69.14 | ras |
| ATOM | 4041 | CB | GLU | 49 | 103.741 | 34.995 | 65.644 | 1.00 | 70.93 | ras |
| ATOM | 4042 | CG | GLU | 49 | 103.246 | 33.725 | 66.313 | 1.00 | 77.78 | ras |
| ATOM | 4043 | CD | GLU | 49 | 103.031 | 33.897 | 67.804 | 1.00 | 82.68 | ras |
| ATOM | 4044 | OE1 | GLU | 49 | 101.885 | 33.708 | 68.267 | 1.00 | 87.24 | ras |
| ATOM | 4045 | OE2 | GLU | 49 | 104.009 | 34.217 | 68.514 | 1.00 | 84.60 | ras |
| ATOM | 4046 | C | GLU | 49 | 102.689 | 34.591 | 63.394 | 1.00 | 69.18 | ras |
| ATOM | 4047 | O | GLU | 49 | 101.742 | 35.373 | 63.492 | 1.00 | 72.39 | ras |
| ATOM | 4048 | N | THR | 50 | 102.656 | 33.498 | 62.638 | 1.00 | 67.02 | ras |
| ATOM | 4049 | CA | THR | 50 | 101.495 | 33.115 | 61.844 | 1.00 | 63.79 | ras |
| ATOM | 4050 | CB | THR | 50 | 101.910 | 32.105 | 60.739 | 1.00 | 64.24 | ras |
| ATOM | 4051 | OG1 | THR | 50 | 100.750 | 31.511 | 60.149 | 1.00 | 60.94 | ras |
| ATOM | 4052 | CG2 | THR | 50 | 102.819 | 31.020 | 61.308 | 1.00 | 68.55 | ras |
| ATOM | 4053 | C | THR | 50 | 100.360 | 32.557 | 62.710 | 1.00 | 62.19 | ras |

Figure 8-68

| ATOM | 4054 | O | THR | 50 | 100.610 | 31.839 | 63.683 | 1.00 | 61.68 | ras |
|---|---|---|---|---|---|---|---|---|---|---|
| ATOM | 4055 | N | CYS | 51 | 99.118 | 32.909 | 62.362 | 1.00 | 57.84 | ras |
| ATOM | 4056 | CA | CYS | 51 | 97.950 | 32.458 | 63.119 | 1.00 | 54.63 | ras |
| ATOM | 4057 | CB | CYS | 51 | 97.744 | 33.337 | 64.347 | 1.00 | 51.75 | ras |
| ATOM | 4058 | SG | CYS | 51 | 97.367 | 35.038 | 63.927 | 1.00 | 50.39 | ras |
| ATOM | 4059 | C | CYS | 51 | 96.655 | 32.432 | 62.317 | 1.00 | 53.94 | ras |
| ATOM | 4060 | O | CYS | 51 | 96.616 | 32.835 | 61.153 | 1.00 | 51.28 | ras |
| ATOM | 4061 | N | LEU | 52 | 95.589 | 31.996 | 62.983 | 1.00 | 53.92 | ras |
| ATOM | 4062 | CA | LEU | 52 | 94.265 | 31.879 | 62.380 | 1.00 | 53.64 | ras |
| ATOM | 4063 | CB | LEU | 52 | 93.795 | 30.427 | 62.461 | 1.00 | 59.51 | ras |
| ATOM | 4064 | CG | LEU | 52 | 92.411 | 30.096 | 61.902 | 1.00 | 63.64 | ras |
| ATOM | 4065 | CD1 | LEU | 52 | 92.448 | 30.136 | 60.382 | 1.00 | 64.77 | ras |
| ATOM | 4066 | CD2 | LEU | 52 | 91.990 | 28.719 | 62.395 | 1.00 | 66.37 | ras |
| ATOM | 4067 | C | LEU | 52 | 93.213 | 32.781 | 63.027 | 1.00 | 50.40 | ras |
| ATOM | 4068 | O | LEU | 52 | 92.938 | 32.688 | 64.229 | 1.00 | 47.98 | ras |
| ATOM | 4069 | N | LEU | 53 | 92.586 | 33.604 | 62.195 | 1.00 | 46.63 | ras |
| ATOM | 4070 | CA | LEU | 53 | 91.555 | 34.540 | 62.627 | 1.00 | 42.13 | ras |
| ATOM | 4071 | CB | LEU | 53 | 91.707 | 35.854 | 61.849 | 1.00 | 39.29 | ras |
| ATOM | 4072 | CG | LEU | 53 | 92.455 | 37.059 | 62.439 | 1.00 | 40.74 | ras |
| ATOM | 4073 | CD1 | LEU | 53 | 93.736 | 36.663 | 63.144 | 1.00 | 33.28 | ras |
| ATOM | 4074 | CD2 | LEU | 53 | 92.720 | 38.066 | 61.338 | 1.00 | 36.74 | ras |
| ATOM | 4075 | C | LEU | 53 | 90.158 | 33.982 | 62.390 | 1.00 | 41.88 | ras |
| ATOM | 4076 | O | LEU | 53 | 89.816 | 33.638 | 61.261 | 1.00 | 40.71 | ras |
| ATOM | 4077 | N | ASP | 54 | 89.373 | 33.849 | 63.458 | 1.00 | 42.31 | ras |
| ATOM | 4078 | CA | ASP | 54 | 87.991 | 33.370 | 63.349 | 1.00 | 41.58 | ras |
| ATOM | 4079 | CB | ASP | 54 | 87.735 | 32.192 | 64.288 | 1.00 | 41.34 | ras |
| ATOM | 4080 | CG | ASP | 54 | 86.407 | 31.504 | 64.012 | 1.00 | 45.99 | ras |
| ATOM | 4081 | OD1 | ASP | 54 | 85.353 | 32.128 | 64.224 | 1.00 | 48.67 | ras |
| ATOM | 4082 | OD2 | ASP | 54 | 86.407 | 30.334 | 63.580 | 1.00 | 51.70 | ras |
| ATOM | 4083 | C | ASP | 54 | 87.109 | 34.573 | 63.712 | 1.00 | 42.80 | ras |
| ATOM | 4084 | O | ASP | 54 | 86.997 | 34.957 | 64.878 | 1.00 | 44.58 | ras |
| ATOM | 4085 | N | ILE | 55 | 86.455 | 35.138 | 62.705 | 1.00 | 41.61 | ras |
| ATOM | 4086 | CA | ILE | 55 | 85.650 | 36.343 | 62.883 | 1.00 | 40.62 | ras |
| ATOM | 4087 | CB | ILE | 55 | 86.085 | 37.374 | 61.823 | 1.00 | 39.83 | ras |
| ATOM | 4088 | CG2 | ILE | 55 | 85.603 | 38.762 | 62.197 | 1.00 | 38.10 | ras |
| ATOM | 4089 | CG1 | ILE | 55 | 87.616 | 37.359 | 61.710 | 1.00 | 33.50 | ras |
| ATOM | 4090 | CD1 | ILE | 55 | 88.138 | 37.951 | 60.456 | 1.00 | 30.99 | ras |
| ATOM | 4091 | C | ILE | 55 | 84.125 | 36.200 | 62.857 | 1.00 | 39.70 | ras |
| ATOM | 4092 | O | ILE | 55 | 83.550 | 35.840 | 61.829 | 1.00 | 44.14 | ras |
| ATOM | 4093 | N | LEU | 56 | 83.480 | 36.523 | 63.982 | 1.00 | 38.25 | ras |
| ATOM | 4094 | CA | LEU | 56 | 82.018 | 36.461 | 64.112 | 1.00 | 33.86 | ras |
| ATOM | 4095 | CB | LEU | 56 | 81.591 | 35.958 | 65.492 | 1.00 | 31.30 | ras |
| ATOM | 4096 | CG | LEU | 56 | 80.072 | 35.851 | 65.711 | 1.00 | 33.00 | ras |
| ATOM | 4097 | CD1 | LEU | 56 | 79.512 | 34.704 | 64.887 | 1.00 | 29.85 | ras |
| ATOM | 4098 | CD2 | LEU | 56 | 79.740 | 35.619 | 67.179 | 1.00 | 29.18 | ras |
| ATOM | 4099 | C | LEU | 56 | 81.414 | 37.839 | 63.913 | 1.00 | 34.76 | ras |
| ATOM | 4100 | O | LEU | 56 | 81.628 | 38.746 | 64.718 | 1.00 | 36.90 | ras |
| ATOM | 4101 | N | ASP | 57 | 80.639 | 37.984 | 62.848 | 1.00 | 33.26 | ras |
| ATOM | 4102 | CA | ASP | 57 | 79.990 | 39.248 | 62.546 | 1.00 | 28.29 | ras |
| ATOM | 4103 | CB | ASP | 57 | 80.662 | 39.900 | 61.336 | 1.00 | 26.76 | ras |
| ATOM | 4104 | CG | ASP | 57 | 80.012 | 41.200 | 60.930 | 1.00 | 28.13 | ras |
| ATOM | 4105 | OD1 | ASP | 57 | 79.118 | 41.700 | 61.642 | 1.00 | 32.83 | ras |
| ATOM | 4106 | OD2 | ASP | 57 | 80.400 | 41.738 | 59.883 | 1.00 | 35.05 | ras |
| ATOM | 4107 | C | ASP | 57 | 78.529 | 38.954 | 62.265 | 1.00 | 27.17 | ras |
| ATOM | 4108 | O | ASP | 57 | 78.143 | 38.750 | 61.122 | 1.00 | 29.15 | ras |
| ATOM | 4109 | N | THR | 58 | 77.720 | 38.956 | 63.317 | 1.00 | 27.08 | ras |
| ATOM | 4110 | CA | THR | 58 | 76.294 | 38.670 | 63.213 | 1.00 | 26.11 | ras |
| ATOM | 4111 | CB | THR | 58 | 75.733 | 38.266 | 64.591 | 1.00 | 28.17 | ras |
| ATOM | 4112 | OG1 | THR | 58 | 75.918 | 39.332 | 65.526 | 1.00 | 28.22 | ras |
| ATOM | 4113 | CG2 | THR | 58 | 76.465 | 37.055 | 65.113 | 1.00 | 33.15 | ras |
| ATOM | 4114 | C | THR | 58 | 75.417 | 39.771 | 62.588 | 1.00 | 26.73 | ras |

Figure 8-69

```
ATOM   4115  O    THR  58    74.225  39.858  62.871  1.00  32.11     ras
ATOM   4116  N    ALA  59    75.997  40.582  61.713  1.00  23.87     ras
ATOM   4117  CA   ALA  59    75.270  41.655  61.037  1.00  28.47     ras
ATOM   4118  CB   ALA  59    76.130  42.244  59.919  1.00  27.17     ras
ATOM   4119  C    ALA  59    73.918  41.205  60.471  1.00  30.41     ras
ATOM   4120  O    ALA  59    73.814  40.159  59.821  1.00  29.81     ras
ATOM   4121  N    GLY  60    72.900  42.031  60.686  1.00  30.33     ras
ATOM   4122  CA   GLY  60    71.568  41.713  60.213  1.00  26.72     ras
ATOM   4123  C    GLY  60    70.714  41.156  61.335  1.00  30.07     ras
ATOM   4124  O    GLY  60    69.480  41.202  61.264  1.00  30.03     ras
ATOM   4125  N    GLN  61    71.362  40.652  62.385  1.00  29.87     ras
ATOM   4126  CA   GLN  61    70.643  40.074  63.525  1.00  31.51     ras
ATOM   4127  CB   GLN  61    71.283  38.754  63.947  1.00  30.16     ras
ATOM   4128  CG   GLN  61    71.280  37.672  62.892  1.00  30.24     ras
ATOM   4129  CD   GLN  61    71.990  36.422  63.373  1.00  31.78     ras
ATOM   4130  OE1  GLN  61    71.628  35.845  64.396  1.00  27.94     ras
ATOM   4131  NE2  GLN  61    73.021  36.010  62.646  1.00  32.53     ras
ATOM   4132  C    GLN  61    70.498  40.981  64.761  1.00  30.65     ras
ATOM   4133  O    GLN  61    70.185  40.494  65.853  1.00  30.29     ras
ATOM   4134  N    GLU  62    70.671  42.289  64.577  1.00  26.11     ras
ATOM   4135  CA   GLU  62    70.557  43.251  65.675  1.00  26.63     ras
ATOM   4136  CB   GLU  62    70.781  44.673  65.168  1.00  24.29     ras
ATOM   4137  CG   GLU  62    72.190  44.972  64.676  1.00  28.07     ras
ATOM   4138  CD   GLU  62    72.530  44.266  63.384  1.00  31.19     ras
ATOM   4139  OE1  GLU  62    71.660  44.187  62.489  1.00  32.48     ras
ATOM   4140  OE2  GLU  62    73.677  43.803  63.263  1.00  32.78     ras
ATOM   4141  C    GLU  62    69.260  43.235  66.490  1.00  27.11     ras
ATOM   4142  O    GLU  62    69.267  43.618  67.656  1.00  32.25     ras
ATOM   4143  N    GLU  63    68.143  42.841  65.890  1.00  25.19     ras
ATOM   4144  CA   GLU  63    66.881  42.823  66.628  1.00  24.49     ras
ATOM   4145  CB   GLU  63    65.673  42.708  65.693  1.00  26.72     ras
ATOM   4146  CG   GLU  63    65.157  44.034  65.176  1.00  26.61     ras
ATOM   4147  CD   GLU  63    64.461  44.853  66.241  1.00  41.08     ras
ATOM   4148  OE1  GLU  63    64.746  46.068  66.299  1.00  49.94     ras
ATOM   4149  OE2  GLU  63    63.620  44.302  67.002  1.00  37.46     ras
ATOM   4150  C    GLU  63    66.862  41.709  67.644  1.00  23.86     ras
ATOM   4151  O    GLU  63    66.058  41.722  68.578  1.00  25.54     ras
ATOM   4152  N    TYR  64    67.715  40.717  67.438  1.00  20.48     ras
ATOM   4153  CA   TYR  64    67.801  39.613  68.375  1.00  24.94     ras
ATOM   4154  CB   TYR  64    68.430  38.391  67.701  1.00  24.96     ras
ATOM   4155  CG   TYR  64    67.534  37.673  66.720  1.00  22.61     ras
ATOM   4156  CD1  TYR  64    67.665  37.880  65.349  1.00  21.72     ras
ATOM   4157  CE1  TYR  64    66.876  37.195  64.441  1.00  18.89     ras
ATOM   4158  CD2  TYR  64    66.577  36.759  67.158  1.00  22.88     ras
ATOM   4159  CE2  TYR  64    65.779  36.073  66.254  1.00  23.04     ras
ATOM   4160  CZ   TYR  64    65.941  36.297  64.898  1.00  22.35     ras
ATOM   4161  OH   TYR  64    65.187  35.602  63.990  1.00  29.93     ras
ATOM   4162  C    TYR  64    68.690  40.124  69.512  1.00  27.20     ras
ATOM   4163  O    TYR  64    69.792  39.620  69.742  1.00  26.43     ras
ATOM   4164  N    SER  65    68.211  41.158  70.195  1.00  27.29     ras
ATOM   4165  CA   SER  65    68.954  41.775  71.281  1.00  30.18     ras
ATOM   4166  CB   SER  65    68.186  42.976  71.815  1.00  32.61     ras
ATOM   4167  OG   SER  65    66.893  42.596  72.244  1.00  37.98     ras
ATOM   4168  C    SER  65    69.319  40.822  72.421  1.00  29.46     ras
ATOM   4169  O    SER  65    70.450  40.841  72.910  1.00  34.32     ras
ATOM   4170  N    ALA  66    68.377  39.972  72.820  1.00  26.50     ras
ATOM   4171  CA   ALA  66    68.601  39.023  73.902  1.00  21.32     ras
ATOM   4172  CB   ALA  66    67.291  38.416  74.340  1.00  18.09     ras
ATOM   4173  C    ALA  66    69.578  37.927  73.533  1.00  22.32     ras
ATOM   4174  O    ALA  66    69.885  37.078  74.358  1.00  27.39     ras
ATOM   4175  N    MET  67    70.093  37.969  72.309  1.00  24.71     ras
```

Figure 8-70

| ATOM | 4176 | CA | MET | 67 | 71.020 | 36.948 | 71.823 | 1.00 | 27.27 | ras |
| ATOM | 4177 | CB | MET | 67 | 70.590 | 36.525 | 70.414 | 1.00 | 25.56 | ras |
| ATOM | 4178 | CG | MET | 67 | 70.761 | 35.061 | 70.112 | 1.00 | 32.40 | ras |
| ATOM | 4179 | SD | MET | 67 | 69.945 | 34.548 | 68.593 | 1.00 | 34.90 | ras |
| ATOM | 4180 | CE | MET | 67 | 68.339 | 33.964 | 69.301 | 1.00 | 37.21 | ras |
| ATOM | 4181 | C | MET | 67 | 72.474 | 37.441 | 71.822 | 1.00 | 30.61 | ras |
| ATOM | 4182 | O | MET | 67 | 73.403 | 36.675 | 71.565 | 1.00 | 31.76 | ras |
| ATOM | 4183 | N | ARG | 68 | 72.660 | 38.713 | 72.161 | 1.00 | 32.17 | ras |
| ATOM | 4184 | CA | ARG | 68 | 73.974 | 39.343 | 72.191 | 1.00 | 30.68 | ras |
| ATOM | 4185 | CB | ARG | 68 | 73.818 | 40.837 | 72.460 | 1.00 | 29.43 | ras |
| ATOM | 4186 | CG | ARG | 68 | 74.391 | 41.719 | 71.373 | 1.00 | 37.63 | ras |
| ATOM | 4187 | CD | ARG | 68 | 73.557 | 42.979 | 71.183 | 1.00 | 41.31 | ras |
| ATOM | 4188 | NE | ARG | 68 | 73.299 | 43.660 | 72.446 | 1.00 | 44.50 | ras |
| ATOM | 4189 | CZ | ARG | 68 | 72.263 | 44.462 | 72.665 | 1.00 | 46.02 | ras |
| ATOM | 4190 | NH1 | ARG | 68 | 71.387 | 44.703 | 71.697 | 1.00 | 48.67 | ras |
| ATOM | 4191 | NH2 | ARG | 68 | 72.054 | 44.955 | 73.876 | 1.00 | 45.00 | ras |
| ATOM | 4192 | C | ARG | 68 | 74.948 | 38.721 | 73.185 | 1.00 | 30.50 | ras |
| ATOM | 4193 | O | ARG | 68 | 76.098 | 38.468 | 72.839 | 1.00 | 31.20 | ras |
| ATOM | 4194 | N | ASP | 69 | 74.500 | 38.482 | 74.416 | 1.00 | 32.47 | ras |
| ATOM | 4195 | CA | ASP | 69 | 75.369 | 37.879 | 75.430 | 1.00 | 31.42 | ras |
| ATOM | 4196 | CB | ASP | 69 | 74.628 | 37.659 | 76.757 | 1.00 | 28.24 | ras |
| ATOM | 4197 | CG | ASP | 69 | 74.353 | 38.947 | 77.505 | 1.00 | 32.96 | ras |
| ATOM | 4198 | OD1 | ASP | 69 | 75.000 | 39.976 | 77.207 | 1.00 | 33.92 | ras |
| ATOM | 4199 | OD2 | ASP | 69 | 73.479 | 38.930 | 78.403 | 1.00 | 34.59 | ras |
| ATOM | 4200 | C | ASP | 69 | 75.896 | 36.547 | 74.917 | 1.00 | 32.41 | ras |
| ATOM | 4201 | O | ASP | 69 | 77.092 | 36.294 | 74.969 | 1.00 | 33.04 | ras |
| ATOM | 4202 | N | GLN | 70 | 75.006 | 35.723 | 74.370 | 1.00 | 35.04 | ras |
| ATOM | 4203 | CA | GLN | 70 | 75.408 | 34.426 | 73.849 | 1.00 | 38.14 | ras |
| ATOM | 4204 | CB | GLN | 70 | 74.235 | 33.696 | 73.198 | 1.00 | 40.88 | ras |
| ATOM | 4205 | CG | GLN | 70 | 74.566 | 32.241 | 72.898 | 1.00 | 48.54 | ras |
| ATOM | 4206 | CD | GLN | 70 | 73.596 | 31.601 | 71.949 | 1.00 | 52.73 | ras |
| ATOM | 4207 | OE1 | GLN | 70 | 72.459 | 31.315 | 72.312 | 1.00 | 60.15 | ras |
| ATOM | 4208 | NE2 | GLN | 70 | 74.039 | 31.366 | 70.716 | 1.00 | 54.95 | ras |
| ATOM | 4209 | C | GLN | 70 | 76.526 | 34.570 | 72.827 | 1.00 | 38.95 | ras |
| ATOM | 4210 | O | GLN | 70 | 77.591 | 33.968 | 72.978 | 1.00 | 41.60 | ras |
| ATOM | 4211 | N | TYR | 71 | 76.274 | 35.371 | 71.795 | 1.00 | 36.90 | ras |
| ATOM | 4212 | CA | TYR | 71 | 77.241 | 35.606 | 70.733 | 1.00 | 33.20 | ras |
| ATOM | 4213 | CB | TYR | 71 | 76.651 | 36.550 | 69.678 | 1.00 | 35.41 | ras |
| ATOM | 4214 | CG | TYR | 71 | 75.682 | 35.922 | 68.690 | 1.00 | 35.80 | ras |
| ATOM | 4215 | CD1 | TYR | 71 | 74.447 | 36.513 | 68.431 | 1.00 | 35.00 | ras |
| ATOM | 4216 | CE1 | TYR | 71 | 73.573 | 35.982 | 67.483 | 1.00 | 33.07 | ras |
| ATOM | 4217 | CD2 | TYR | 71 | 76.021 | 34.771 | 67.971 | 1.00 | 35.71 | ras |
| ATOM | 4218 | CE2 | TYR | 71 | 75.151 | 34.229 | 67.012 | 1.00 | 29.11 | ras |
| ATOM | 4219 | CZ | TYR | 71 | 73.930 | 34.845 | 66.774 | 1.00 | 33.89 | ras |
| ATOM | 4220 | OH | TYR | 71 | 73.076 | 34.354 | 65.813 | 1.00 | 25.97 | ras |
| ATOM | 4221 | C | TYR | 71 | 78.558 | 36.188 | 71.252 | 1.00 | 32.72 | ras |
| ATOM | 4222 | O | TYR | 71 | 79.643 | 35.743 | 70.856 | 1.00 | 27.77 | ras |
| ATOM | 4223 | N | MET | 72 | 78.459 | 37.173 | 72.145 | 1.00 | 33.23 | ras |
| ATOM | 4224 | CA | MET | 72 | 79.640 | 37.843 | 72.698 | 1.00 | 34.10 | ras |
| ATOM | 4225 | CB | MET | 72 | 79.234 | 39.013 | 73.582 | 1.00 | 31.99 | ras |
| ATOM | 4226 | CG | MET | 72 | 78.826 | 40.248 | 72.830 | 1.00 | 32.07 | ras |
| ATOM | 4227 | SD | MET | 72 | 78.172 | 41.441 | 73.980 | 1.00 | 34.73 | ras |
| ATOM | 4228 | CE | MET | 72 | 77.943 | 42.801 | 72.897 | 1.00 | 31.43 | ras |
| ATOM | 4229 | C | MET | 72 | 80.524 | 36.922 | 73.497 | 1.00 | 34.87 | ras |
| ATOM | 4230 | O | MET | 72 | 81.745 | 37.071 | 73.501 | 1.00 | 33.09 | ras |
| ATOM | 4231 | N | ARG | 73 | 79.893 | 35.961 | 74.160 | 1.00 | 36.49 | ras |
| ATOM | 4232 | CA | ARG | 73 | 80.599 | 35.007 | 74.995 | 1.00 | 39.03 | ras |
| ATOM | 4233 | CB | ARG | 73 | 79.600 | 34.083 | 75.706 | 1.00 | 37.79 | ras |
| ATOM | 4234 | CG | ARG | 73 | 80.260 | 32.948 | 76.475 | 1.00 | 47.27 | ras |
| ATOM | 4235 | CD | ARG | 73 | 79.451 | 32.521 | 77.688 | 1.00 | 51.20 | ras |
| ATOM | 4236 | NE | ARG | 73 | 79.364 | 33.578 | 78.690 | 1.00 | 46.38 | ras |

Figure 8-71

```
ATOM   4237  CZ   ARG  73      78.217  34.051  79.154  1.00 46.68      ras
ATOM   4238  NH1  ARG  73      78.204  35.018  80.056  1.00 49.23      ras
ATOM   4239  NH2  ARG  73      77.082  33.539  78.719  1.00 43.64      ras
ATOM   4240  C    ARG  73      81.621  34.194  74.218  1.00 38.81      ras
ATOM   4241  O    ARG  73      82.700  33.891  74.728  1.00 40.67      ras
ATOM   4242  N    THR  74      81.309  33.922  72.958  1.00 36.94      ras
ATOM   4243  CA   THR  74      82.168  33.117  72.113  1.00 36.75      ras
ATOM   4244  CB   THR  74      81.487  32.787  70.749  1.00 38.71      ras
ATOM   4245  OG1  THR  74      81.452  33.952  69.910  1.00 41.36      ras
ATOM   4246  CG2  THR  74      80.074  32.286  70.971  1.00 35.01      ras
ATOM   4247  C    THR  74      83.557  33.666  71.834  1.00 36.59      ras
ATOM   4248  O    THR  74      84.472  32.881  71.585  1.00 41.44      ras
ATOM   4249  N    GLY  75      83.727  34.986  71.910  1.00 33.83      ras
ATOM   4250  CA   GLY  75      85.018  35.581  71.588  1.00 37.35      ras
ATOM   4251  C    GLY  75      86.015  35.931  72.679  1.00 41.01      ras
ATOM   4252  O    GLY  75      85.665  36.038  73.855  1.00 43.05      ras
ATOM   4253  N    GLU  76      87.271  36.121  72.280  1.00 40.18      ras
ATOM   4254  CA   GLU  76      88.314  36.489  73.231  1.00 44.61      ras
ATOM   4255  CB   GLU  76      89.449  35.451  73.253  1.00 49.52      ras
ATOM   4256  CG   GLU  76      90.400  35.481  72.055  1.00 60.05      ras
ATOM   4257  CD   GLU  76      91.589  34.525  72.210  1.00 67.62      ras
ATOM   4258  OE1  GLU  76      91.878  33.775  71.248  1.00 70.96      ras
ATOM   4259  OE2  GLU  76      92.242  34.529  73.284  1.00 68.27      ras
ATOM   4260  C    GLU  76      88.860  37.885  72.929  1.00 42.71      ras
ATOM   4261  O    GLU  76      89.724  38.391  73.647  1.00 42.81      ras
ATOM   4262  N    GLY  77      88.326  38.504  71.878  1.00 36.86      ras
ATOM   4263  CA   GLY  77      88.750  39.835  71.482  1.00 36.64      ras
ATOM   4264  C    GLY  77      87.613  40.503  70.739  1.00 36.18      ras
ATOM   4265  O    GLY  77      86.928  39.836  69.971  1.00 40.35      ras
ATOM   4266  N    PHE  78      87.428  41.810  70.913  1.00 30.38      ras
ATOM   4267  CA   PHE  78      86.318  42.491  70.254  1.00 27.89      ras
ATOM   4268  CB   PHE  78      85.245  42.831  71.285  1.00 24.66      ras
ATOM   4269  CG   PHE  78      84.737  41.648  72.039  1.00 23.18      ras
ATOM   4270  CD1  PHE  78      83.526  41.063  71.700  1.00 23.43      ras
ATOM   4271  CD2  PHE  78      85.482  41.093  73.068  1.00 21.73      ras
ATOM   4272  CE1  PHE  78      83.066  39.935  72.375  1.00 26.18      ras
ATOM   4273  CE2  PHE  78      85.032  39.968  73.749  1.00 20.04      ras
ATOM   4274  CZ   PHE  78      83.827  39.388  73.403  1.00 22.43      ras
ATOM   4275  C    PHE  78      86.613  43.747  69.438  1.00 29.88      ras
ATOM   4276  O    PHE  78      87.522  44.507  69.748  1.00 31.55      ras
ATOM   4277  N    LEU  79      85.837  43.944  68.374  1.00 29.54      ras
ATOM   4278  CA   LEU  79      85.955  45.133  67.540  1.00 29.05      ras
ATOM   4279  CB   LEU  79      86.139  44.776  66.073  1.00 28.26      ras
ATOM   4280  CG   LEU  79      87.471  44.225  65.592  1.00 29.77      ras
ATOM   4281  CD1  LEU  79      87.354  42.719  65.469  1.00 31.86      ras
ATOM   4282  CD2  LEU  79      87.807  44.843  64.241  1.00 23.15      ras
ATOM   4283  C    LEU  79      84.658  45.915  67.677  1.00 31.52      ras
ATOM   4284  O    LEU  79      83.625  45.496  67.150  1.00 37.59      ras
ATOM   4285  N    CYS  80      84.689  47.011  68.430  1.00 29.88      ras
ATOM   4286  CA   CYS  80      83.502  47.847  68.609  1.00 27.61      ras
ATOM   4287  CB   CYS  80      83.549  48.549  69.959  1.00 23.89      ras
ATOM   4288  SG   CYS  80      83.424  47.355  71.291  1.00 25.66      ras
ATOM   4289  C    CYS  80      83.476  48.828  67.449  1.00 26.74      ras
ATOM   4290  O    CYS  80      84.267  49.766  67.384  1.00 26.73      ras
ATOM   4291  N    VAL  81      82.570  48.579  66.516  1.00 25.28      ras
ATOM   4292  CA   VAL  81      82.484  49.380  65.313  1.00 25.48      ras
ATOM   4293  CB   VAL  81      82.357  48.467  64.084  1.00 26.03      ras
ATOM   4294  CG1  VAL  81      82.543  49.264  62.816  1.00 33.94      ras
ATOM   4295  CG2  VAL  81      83.357  47.336  64.157  1.00 23.51      ras
ATOM   4296  C    VAL  81      81.350  50.387  65.271  1.00 26.02      ras
ATOM   4297  O    VAL  81      80.216  50.080  65.646  1.00 32.11      ras
```

Figure 8-72

```
ATOM   4298  N    PHE  82   81.668  51.588  64.799  1.00  22.07      ras
ATOM   4299  CA   PHE  82   80.682  52.649  64.647  1.00  24.46      ras
ATOM   4300  CB   PHE  82   80.750  53.667  65.799  1.00  25.12      ras
ATOM   4301  CG   PHE  82   81.915  54.615  65.724  1.00  25.02      ras
ATOM   4302  CD1  PHE  82   81.840  55.770  64.960  1.00  19.81      ras
ATOM   4303  CD2  PHE  82   83.083  54.360  66.434  1.00  23.79      ras
ATOM   4304  CE1  PHE  82   82.910  56.652  64.904  1.00  23.72      ras
ATOM   4305  CE2  PHE  82   84.156  55.239  66.381  1.00  23.77      ras
ATOM   4306  CZ   PHE  82   84.066  56.388  65.613  1.00  22.22      ras
ATOM   4307  C    PHE  82   80.935  53.324  63.309  1.00  26.91      ras
ATOM   4308  O    PHE  82   82.019  53.189  62.733  1.00  31.81      ras
ATOM   4309  N    ALA  83   79.933  54.024  62.797  1.00  24.99      ras
ATOM   4310  CA   ALA  83   80.090  54.705  61.525  1.00  26.80      ras
ATOM   4311  CB   ALA  83   78.829  54.583  60.691  1.00  26.17      ras
ATOM   4312  C    ALA  83   80.420  56.167  61.769  1.00  31.19      ras
ATOM   4313  O    ALA  83   79.693  56.873  62.474  1.00  29.48      ras
ATOM   4314  N    ILE  84   81.509  56.611  61.152  1.00  33.20      ras
ATOM   4315  CA   ILE  84   81.992  57.979  61.252  1.00  34.13      ras
ATOM   4316  CB   ILE  84   83.335  58.087  60.509  1.00  36.54      ras
ATOM   4317  CG2  ILE  84   83.556  59.464  59.901  1.00  40.45      ras
ATOM   4318  CG1  ILE  84   84.454  57.718  61.472  1.00  37.91      ras
ATOM   4319  CD1  ILE  84   85.761  57.530  60.800  1.00  43.98      ras
ATOM   4320  C    ILE  84   80.978  59.028  60.787  1.00  36.89      ras
ATOM   4321  O    ILE  84   81.094  60.206  61.130  1.00  40.46      ras
ATOM   4322  N    ASN  85   79.952  58.592  60.062  1.00  38.22      ras
ATOM   4323  CA   ASN  85   78.918  59.503  59.580  1.00  38.29      ras
ATOM   4324  CB   ASN  85   78.722  59.355  58.069  1.00  45.21      ras
ATOM   4325  CG   ASN  85   78.568  57.913  57.640  1.00  55.17      ras
ATOM   4326  OD1  ASN  85   79.475  57.095  57.835  1.00  65.48      ras
ATOM   4327  ND2  ASN  85   77.426  57.589  57.047  1.00  53.70      ras
ATOM   4328  C    ASN  85   77.585  59.339  60.298  1.00  35.88      ras
ATOM   4329  O    ASN  85   76.614  59.990  59.934  1.00  34.66      ras
ATOM   4330  N    ASN  86   77.543  58.484  61.322  1.00  34.66      ras
ATOM   4331  CA   ASN  86   76.324  58.249  62.101  1.00  30.45      ras
ATOM   4332  CB   ASN  86   75.774  56.846  61.819  1.00  23.84      ras
ATOM   4333  CG   ASN  86   74.356  56.648  62.349  1.00  29.04      ras
ATOM   4334  OD1  ASN  86   74.145  56.140  63.458  1.00  32.05      ras
ATOM   4335  ND2  ASN  86   73.375  57.027  61.548  1.00  28.73      ras
ATOM   4336  C    ASN  86   76.665  58.394  63.589  1.00  34.94      ras
ATOM   4337  O    ASN  86   77.196  57.469  64.208  1.00  38.78      ras
ATOM   4338  N    THR  87   76.340  59.550  64.165  1.00  35.03      ras
ATOM   4339  CA   THR  87   76.629  59.834  65.572  1.00  31.23      ras
ATOM   4340  CB   THR  87   76.187  61.269  65.950  1.00  31.51      ras
ATOM   4341  OG1  THR  87   76.898  62.216  65.149  1.00  37.29      ras
ATOM   4342  CG2  THR  87   76.478  61.560  67.391  1.00  26.65      ras
ATOM   4343  C    THR  87   75.991  58.845  66.537  1.00  31.90      ras
ATOM   4344  O    THR  87   76.601  58.474  67.542  1.00  33.13      ras
ATOM   4345  N    LYS  88   74.770  58.406  66.239  1.00  31.12      ras
ATOM   4346  CA   LYS  88   74.087  57.467  67.128  1.00  28.19      ras
ATOM   4347  CB   LYS  88   72.639  57.248  66.693  1.00  26.48      ras
ATOM   4348  CG   LYS  88   71.644  57.101  67.842  1.00  27.73      ras
ATOM   4349  CD   LYS  88   71.475  55.673  68.319  1.00  34.43      ras
ATOM   4350  CE   LYS  88   70.424  55.601  69.431  1.00  41.39      ras
ATOM   4351  NZ   LYS  88   70.234  54.215  69.984  1.00  42.22      ras
ATOM   4352  C    LYS  88   74.833  56.137  67.215  1.00  29.90      ras
ATOM   4353  O    LYS  88   74.840  55.508  68.276  1.00  26.26      ras
ATOM   4354  N    SER  89   75.480  55.725  66.118  1.00  24.30      ras
ATOM   4355  CA   SER  89   76.232  54.479  66.143  1.00  24.94      ras
ATOM   4356  CB   SER  89   76.613  53.999  64.732  1.00  26.40      ras
ATOM   4357  OG   SER  89   77.645  54.768  64.140  1.00  28.35      ras
ATOM   4358  C    SER  89   77.465  54.680  67.015  1.00  26.50      ras
```

Figure 8-73

| | | | | | | | | | |
|---|---|---|---|---|---|---|---|---|---|
| ATOM | 4359 | O   | SER | 89 | 78.008 | 53.727 | 67.560 | 1.00 31.98 | ras |
| ATOM | 4360 | N   | PHE | 90 | 77.881 | 55.932 | 67.173 | 1.00 26.48 | ras |
| ATOM | 4361 | CA  | PHE | 90 | 79.027 | 56.252 | 68.010 | 1.00 29.25 | ras |
| ATOM | 4362 | CB  | PHE | 90 | 79.606 | 57.616 | 67.648 | 1.00 29.36 | ras |
| ATOM | 4363 | CG  | PHE | 90 | 80.826 | 57.989 | 68.432 | 1.00 27.23 | ras |
| ATOM | 4364 | CD1 | PHE | 90 | 80.812 | 59.102 | 69.277 | 1.00 28.08 | ras |
| ATOM | 4365 | CD2 | PHE | 90 | 81.996 | 57.250 | 68.314 | 1.00 30.70 | ras |
| ATOM | 4366 | CE1 | PHE | 90 | 81.951 | 59.483 | 69.996 | 1.00 22.23 | ras |
| ATOM | 4367 | CE2 | PHE | 90 | 83.149 | 57.617 | 69.027 | 1.00 35.26 | ras |
| ATOM | 4368 | CZ  | PHE | 90 | 83.119 | 58.742 | 69.872 | 1.00 31.38 | ras |
| ATOM | 4369 | C   | PHE | 90 | 78.608 | 56.248 | 69.466 | 1.00 30.19 | ras |
| ATOM | 4370 | O   | PHE | 90 | 79.251 | 55.603 | 70.293 | 1.00 31.67 | ras |
| ATOM | 4371 | N   | GLU | 91 | 77.510 | 56.933 | 69.774 | 1.00 30.50 | ras |
| ATOM | 4372 | CA  | GLU | 91 | 77.028 | 56.997 | 71.159 | 1.00 32.87 | ras |
| ATOM | 4373 | CB  | GLU | 91 | 75.874 | 57.993 | 71.294 | 1.00 33.18 | ras |
| ATOM | 4374 | CG  | GLU | 91 | 76.214 | 59.398 | 70.815 | 1.00 39.61 | ras |
| ATOM | 4375 | CD  | GLU | 91 | 74.991 | 60.287 | 70.610 | 1.00 45.97 | ras |
| ATOM | 4376 | OE1 | GLU | 91 | 75.188 | 61.512 | 70.431 | 1.00 45.72 | ras |
| ATOM | 4377 | OE2 | GLU | 91 | 73.845 | 59.768 | 70.618 | 1.00 47.57 | ras |
| ATOM | 4378 | C   | GLU | 91 | 76.605 | 55.636 | 71.702 | 1.00 30.20 | ras |
| ATOM | 4379 | O   | GLU | 91 | 76.537 | 55.454 | 72.908 | 1.00 32.09 | ras |
| ATOM | 4380 | N   | ASP | 92 | 76.344 | 54.685 | 70.805 | 1.00 28.72 | ras |
| ATOM | 4381 | CA  | ASP | 92 | 75.940 | 53.329 | 71.179 | 1.00 27.86 | ras |
| ATOM | 4382 | CB  | ASP | 92 | 75.345 | 52.598 | 69.971 | 1.00 30.79 | ras |
| ATOM | 4383 | CG  | ASP | 92 | 73.861 | 52.871 | 69.768 | 1.00 30.60 | ras |
| ATOM | 4384 | OD1 | ASP | 92 | 73.254 | 53.654 | 70.528 | 1.00 27.98 | ras |
| ATOM | 4385 | OD2 | ASP | 92 | 73.299 | 52.279 | 68.825 | 1.00 33.59 | ras |
| ATOM | 4386 | C   | ASP | 92 | 77.102 | 52.494 | 71.699 | 1.00 28.76 | ras |
| ATOM | 4387 | O   | ASP | 92 | 76.896 | 51.460 | 72.341 | 1.00 31.38 | ras |
| ATOM | 4388 | N   | ILE | 93 | 78.320 | 52.925 | 71.387 | 1.00 29.13 | ras |
| ATOM | 4389 | CA  | ILE | 93 | 79.524 | 52.213 | 71.793 | 1.00 24.79 | ras |
| ATOM | 4390 | CB  | ILE | 93 | 80.789 | 52.944 | 71.331 | 1.00 20.41 | ras |
| ATOM | 4391 | CG2 | ILE | 93 | 82.021 | 52.310 | 71.950 | 1.00 16.70 | ras |
| ATOM | 4392 | CG1 | ILE | 93 | 80.873 | 52.917 | 69.804 | 1.00 19.72 | ras |
| ATOM | 4393 | CD1 | ILE | 93 | 80.860 | 51.509 | 69.207 | 1.00 14.18 | ras |
| ATOM | 4394 | C   | ILE | 93 | 79.621 | 51.963 | 73.281 | 1.00 27.14 | ras |
| ATOM | 4395 | O   | ILE | 93 | 79.861 | 50.830 | 73.710 | 1.00 28.78 | ras |
| ATOM | 4396 | N   | HIS | 94 | 79.408 | 53.006 | 74.074 | 1.00 27.42 | ras |
| ATOM | 4397 | CA  | HIS | 94 | 79.508 | 52.851 | 75.515 | 1.00 28.70 | ras |
| ATOM | 4398 | CB  | HIS | 94 | 79.119 | 54.135 | 76.250 | 1.00 30.71 | ras |
| ATOM | 4399 | CG  | HIS | 94 | 79.336 | 54.055 | 77.727 | 1.00 36.51 | ras |
| ATOM | 4400 | CD2 | HIS | 94 | 78.480 | 53.781 | 78.741 | 1.00 38.54 | ras |
| ATOM | 4401 | ND1 | HIS | 94 | 80.587 | 54.149 | 78.297 | 1.00 38.15 | ras |
| ATOM | 4402 | CE1 | HIS | 94 | 80.495 | 53.925 | 79.595 | 1.00 39.37 | ras |
| ATOM | 4403 | NE2 | HIS | 94 | 79.227 | 53.698 | 79.890 | 1.00 42.28 | ras |
| ATOM | 4404 | C   | HIS | 94 | 78.728 | 51.664 | 76.070 | 1.00 27.17 | ras |
| ATOM | 4405 | O   | HIS | 94 | 79.265 | 50.878 | 76.840 | 1.00 29.71 | ras |
| ATOM | 4406 | N   | GLN | 95 | 77.488 | 51.492 | 75.636 | 1.00 30.36 | ras |
| ATOM | 4407 | CA  | GLN | 95 | 76.679 | 50.389 | 76.136 | 1.00 32.04 | ras |
| ATOM | 4408 | CB  | GLN | 95 | 75.201 | 50.614 | 75.806 | 1.00 31.39 | ras |
| ATOM | 4409 | CG  | GLN | 95 | 74.257 | 49.550 | 76.347 | 1.00 44.63 | ras |
| ATOM | 4410 | CD  | GLN | 95 | 74.437 | 49.249 | 77.842 | 1.00 50.89 | ras |
| ATOM | 4411 | OE1 | GLN | 95 | 74.808 | 50.128 | 78.644 | 1.00 49.09 | ras |
| ATOM | 4412 | NE2 | GLN | 95 | 74.159 | 47.995 | 78.221 | 1.00 46.16 | ras |
| ATOM | 4413 | C   | GLN | 95 | 77.174 | 49.014 | 75.667 | 1.00 32.52 | ras |
| ATOM | 4414 | O   | GLN | 95 | 77.135 | 48.035 | 76.431 | 1.00 26.20 | ras |
| ATOM | 4415 | N   | TYR | 96 | 77.665 | 48.939 | 74.431 | 1.00 32.01 | ras |
| ATOM | 4416 | CA  | TYR | 96 | 78.180 | 47.670 | 73.923 | 1.00 31.34 | ras |
| ATOM | 4417 | CB  | TYR | 96 | 78.611 | 47.785 | 72.461 | 1.00 34.45 | ras |
| ATOM | 4418 | CG  | TYR | 96 | 77.460 | 47.839 | 71.488 | 1.00 37.62 | ras |
| ATOM | 4419 | CD1 | TYR | 96 | 76.487 | 46.844 | 71.478 | 1.00 37.68 | ras |

Figure 8-74

```
ATOM   4420  CE1 TYR  96      75.415  46.897  70.596  1.00 41.39      ras
ATOM   4421  CD2 TYR  96      77.335  48.891  70.584  1.00 39.08      ras
ATOM   4422  CE2 TYR  96      76.264  48.952  69.698  1.00 39.51      ras
ATOM   4423  CZ  TYR  96      75.306  47.954  69.712  1.00 40.78      ras
ATOM   4424  OH  TYR  96      74.219  48.028  68.866  1.00 43.01      ras
ATOM   4425  C   TYR  96      79.356  47.234  74.785  1.00 31.83      ras
ATOM   4426  O   TYR  96      79.403  46.086  75.238  1.00 28.42      ras
ATOM   4427  N   ARG  97      80.270  48.169  75.062  1.00 30.31      ras
ATOM   4428  CA  ARG  97      81.433  47.859  75.890  1.00 30.06      ras
ATOM   4429  CB  ARG  97      82.374  49.057  75.989  1.00 28.86      ras
ATOM   4430  CG  ARG  97      83.635  48.791  76.799  1.00 27.81      ras
ATOM   4431  CD  ARG  97      84.519  50.014  76.840  1.00 31.48      ras
ATOM   4432  NE  ARG  97      85.164  50.159  78.141  1.00 40.53      ras
ATOM   4433  CZ  ARG  97      86.275  49.523  78.504  1.00 48.88      ras
ATOM   4434  NH1 ARG  97      86.780  49.715  79.716  1.00 50.67      ras
ATOM   4435  NH2 ARG  97      86.894  48.708  77.653  1.00 49.76      ras
ATOM   4436  C   ARG  97      81.023  47.358  77.281  1.00 30.07      ras
ATOM   4437  O   ARG  97      81.546  46.354  77.757  1.00 32.73      ras
ATOM   4438  N   GLU  98      80.054  48.020  77.906  1.00 27.73      ras
ATOM   4439  CA  GLU  98      79.577  47.596  79.219  1.00 30.13      ras
ATOM   4440  CB  GLU  98      78.449  48.501  79.718  1.00 33.28      ras
ATOM   4441  CG  GLU  98      78.864  49.924  80.081  1.00 44.17      ras
ATOM   4442  CD  GLU  98      79.895  49.977  81.195  1.00 44.23      ras
ATOM   4443  OE1 GLU  98      80.986  50.543  80.961  1.00 45.22      ras
ATOM   4444  OE2 GLU  98      79.614  49.439  82.290  1.00 43.73      ras
ATOM   4445  C   GLU  98      79.043  46.185  79.141  1.00 32.04      ras
ATOM   4446  O   GLU  98      79.082  45.452  80.113  1.00 38.13      ras
ATOM   4447  N   GLN  99      78.512  45.816  77.981  1.00 36.53      ras
ATOM   4448  CA  GLN  99      77.953  44.485  77.793  1.00 35.89      ras
ATOM   4449  CB  GLN  99      77.015  44.473  76.595  1.00 38.24      ras
ATOM   4450  CG  GLN  99      75.973  43.392  76.662  1.00 41.78      ras
ATOM   4451  CD  GLN  99      74.896  43.566  75.630  1.00 44.64      ras
ATOM   4452  OE1 GLN  99      74.762  44.633  75.022  1.00 46.06      ras
ATOM   4453  NE2 GLN  99      74.104  42.518  75.429  1.00 45.44      ras
ATOM   4454  C   GLN  99      79.052  43.449  77.620  1.00 35.19      ras
ATOM   4455  O   GLN  99      78.973  42.356  78.177  1.00 36.49      ras
ATOM   4456  N   ILE 100      80.073  43.792  76.845  1.00 30.37      ras
ATOM   4457  CA  ILE 100      81.188  42.886  76.643  1.00 31.19      ras
ATOM   4458  CB  ILE 100      82.190  43.472  75.638  1.00 30.53      ras
ATOM   4459  CG2 ILE 100      83.362  42.529  75.448  1.00 27.62      ras
ATOM   4460  CG1 ILE 100      81.495  43.710  74.298  1.00 33.21      ras
ATOM   4461  CD1 ILE 100      82.282  44.567  73.336  1.00 33.34      ras
ATOM   4462  C   ILE 100      81.869  42.627  78.002  1.00 33.76      ras
ATOM   4463  O   ILE 100      82.098  41.470  78.375  1.00 36.80      ras
ATOM   4464  N   LYS 101      82.128  43.698  78.757  1.00 28.56      ras
ATOM   4465  CA  LYS 101      82.764  43.596  80.074  1.00 29.64      ras
ATOM   4466  CB  LYS 101      82.896  44.983  80.716  1.00 29.57      ras
ATOM   4467  CG  LYS 101      84.083  45.806  80.229  1.00 32.63      ras
ATOM   4468  CD  LYS 101      83.869  47.294  80.472  1.00 39.41      ras
ATOM   4469  CE  LYS 101      83.726  47.620  81.954  1.00 44.50      ras
ATOM   4470  NZ  LYS 101      83.340  49.041  82.177  1.00 46.05      ras
ATOM   4471  C   LYS 101      81.977  42.678  81.007  1.00 28.98      ras
ATOM   4472  O   LYS 101      82.541  41.847  81.709  1.00 27.85      ras
ATOM   4473  N   ARG 102      80.662  42.833  80.997  1.00 28.49      ras
ATOM   4474  CA  ARG 102      79.800  42.022  81.828  1.00 26.91      ras
ATOM   4475  CB  ARG 102      78.375  42.569  81.795  1.00 23.08      ras
ATOM   4476  CG  ARG 102      77.375  41.695  82.513  1.00 24.75      ras
ATOM   4477  CD  ARG 102      76.545  42.490  83.493  1.00 35.90      ras
ATOM   4478  NE  ARG 102      75.557  43.346  82.853  1.00 42.73      ras
ATOM   4479  CZ  ARG 102      75.035  44.433  83.415  1.00 49.72      ras
ATOM   4480  NH1 ARG 102      74.136  45.148  82.758  1.00 58.43      ras
```

Figure 8-75

| | | | | | | | | | |
|---|---|---|---|---|---|---|---|---|---|
| ATOM | 4481 | NH2 | ARG | 102 | 75.420 | 44.822 | 84.622 | 1.00 48.40 | ras |
| ATOM | 4482 | C | ARG | 102 | 79.799 | 40.537 | 81.461 | 1.00 29.95 | ras |
| ATOM | 4483 | O | ARG | 102 | 79.853 | 39.700 | 82.351 | 1.00 34.44 | ras |
| ATOM | 4484 | N | VAL | 103 | 79.768 | 40.200 | 80.171 | 1.00 30.73 | ras |
| ATOM | 4485 | CA | VAL | 103 | 79.722 | 38.788 | 79.789 | 1.00 37.32 | ras |
| ATOM | 4486 | CB | VAL | 103 | 79.224 | 38.564 | 78.339 | 1.00 37.36 | ras |
| ATOM | 4487 | CG1 | VAL | 103 | 77.974 | 39.367 | 78.097 | 1.00 45.16 | ras |
| ATOM | 4488 | CG2 | VAL | 103 | 80.290 | 38.916 | 77.334 | 1.00 46.10 | ras |
| ATOM | 4489 | C | VAL | 103 | 81.016 | 38.034 | 80.011 | 1.00 36.20 | ras |
| ATOM | 4490 | O | VAL | 103 | 81.003 | 36.857 | 80.367 | 1.00 35.19 | ras |
| ATOM | 4491 | N | LYS | 104 | 82.132 | 38.717 | 79.817 | 1.00 38.07 | ras |
| ATOM | 4492 | CA | LYS | 104 | 83.427 | 38.096 | 80.007 | 1.00 40.22 | ras |
| ATOM | 4493 | CB | LYS | 104 | 84.423 | 38.657 | 78.993 | 1.00 39.84 | ras |
| ATOM | 4494 | CG | LYS | 104 | 83.934 | 38.579 | 77.544 | 1.00 43.17 | ras |
| ATOM | 4495 | CD | LYS | 104 | 84.771 | 37.627 | 76.690 | 1.00 44.51 | ras |
| ATOM | 4496 | CE | LYS | 104 | 84.602 | 36.174 | 77.104 | 1.00 46.30 | ras |
| ATOM | 4497 | NZ | LYS | 104 | 85.511 | 35.270 | 76.341 | 1.00 45.22 | ras |
| ATOM | 4498 | C | LYS | 104 | 83.916 | 38.310 | 81.443 | 1.00 41.88 | ras |
| ATOM | 4499 | O | LYS | 104 | 85.043 | 37.943 | 81.774 | 1.00 44.68 | ras |
| ATOM | 4500 | N | ASP | 105 | 83.052 | 38.890 | 82.283 | 1.00 40.36 | ras |
| ATOM | 4501 | CA | ASP | 105 | 83.338 | 39.172 | 83.697 | 1.00 42.95 | ras |
| ATOM | 4502 | CB | ASP | 105 | 83.101 | 37.914 | 84.535 | 1.00 43.72 | ras |
| ATOM | 4503 | CG | ASP | 105 | 83.095 | 38.195 | 86.031 | 1.00 48.68 | ras |
| ATOM | 4504 | OD1 | ASP | 105 | 82.581 | 39.254 | 86.454 | 1.00 51.36 | ras |
| ATOM | 4505 | OD2 | ASP | 105 | 83.590 | 37.341 | 86.792 | 1.00 52.22 | ras |
| ATOM | 4506 | C | ASP | 105 | 84.759 | 39.703 | 83.925 | 1.00 43.92 | ras |
| ATOM | 4507 | O | ASP | 105 | 85.551 | 39.093 | 84.646 | 1.00 43.78 | ras |
| ATOM | 4508 | N | SER | 106 | 85.058 | 40.851 | 83.324 | 1.00 42.62 | ras |
| ATOM | 4509 | CA | SER | 106 | 86.383 | 41.454 | 83.406 | 1.00 44.60 | ras |
| ATOM | 4510 | CB | SER | 106 | 87.352 | 40.660 | 82.519 | 1.00 41.74 | ras |
| ATOM | 4511 | OG | SER | 106 | 88.526 | 41.409 | 82.238 | 1.00 50.25 | ras |
| ATOM | 4512 | C | SER | 106 | 86.382 | 42.915 | 82.963 | 1.00 45.68 | ras |
| ATOM | 4513 | O | SER | 106 | 85.709 | 43.270 | 81.995 | 1.00 45.22 | ras |
| ATOM | 4514 | N | ASP | 107 | 87.159 | 43.751 | 83.651 | 1.00 47.39 | ras |
| ATOM | 4515 | CA | ASP | 107 | 87.239 | 45.165 | 83.300 | 1.00 50.41 | ras |
| ATOM | 4516 | CB | ASP | 107 | 87.566 | 46.036 | 84.514 | 1.00 56.56 | ras |
| ATOM | 4517 | CG | ASP | 107 | 86.378 | 46.201 | 85.452 | 1.00 65.47 | ras |
| ATOM | 4518 | OD1 | ASP | 107 | 86.594 | 46.243 | 86.680 | 1.00 70.32 | ras |
| ATOM | 4519 | OD2 | ASP | 107 | 85.225 | 46.285 | 84.969 | 1.00 68.20 | ras |
| ATOM | 4520 | C | ASP | 107 | 88.212 | 45.434 | 82.169 | 1.00 50.18 | ras |
| ATOM | 4521 | O | ASP | 107 | 88.189 | 46.511 | 81.580 | 1.00 51.60 | ras |
| ATOM | 4522 | N | ASP | 108 | 89.094 | 44.481 | 81.883 | 1.00 49.01 | ras |
| ATOM | 4523 | CA | ASP | 108 | 90.017 | 44.666 | 80.771 | 1.00 52.07 | ras |
| ATOM | 4524 | CB | ASP | 108 | 91.441 | 45.093 | 81.211 | 1.00 57.29 | ras |
| ATOM | 4525 | CG | ASP | 108 | 92.236 | 43.980 | 81.880 | 1.00 64.88 | ras |
| ATOM | 4526 | OD1 | ASP | 108 | 91.729 | 43.353 | 82.835 | 1.00 73.22 | ras |
| ATOM | 4527 | OD2 | ASP | 108 | 93.393 | 43.751 | 81.463 | 1.00 64.57 | ras |
| ATOM | 4528 | C | ASP | 108 | 89.989 | 43.458 | 79.843 | 1.00 50.11 | ras |
| ATOM | 4529 | O | ASP | 108 | 90.569 | 42.404 | 80.121 | 1.00 51.00 | ras |
| ATOM | 4530 | N | VAL | 109 | 89.182 | 43.608 | 78.795 | 1.00 46.58 | ras |
| ATOM | 4531 | CA | VAL | 109 | 88.974 | 42.596 | 77.769 | 1.00 38.54 | ras |
| ATOM | 4532 | CB | VAL | 109 | 87.462 | 42.420 | 77.483 | 1.00 36.56 | ras |
| ATOM | 4533 | CG1 | VAL | 109 | 87.226 | 41.340 | 76.456 | 1.00 39.60 | ras |
| ATOM | 4534 | CG2 | VAL | 109 | 86.733 | 42.072 | 78.750 | 1.00 40.29 | ras |
| ATOM | 4535 | C | VAL | 109 | 89.645 | 43.129 | 76.524 | 1.00 33.51 | ras |
| ATOM | 4536 | O | VAL | 109 | 89.540 | 44.311 | 76.229 | 1.00 36.22 | ras |
| ATOM | 4537 | N | PRO | 110 | 90.381 | 42.280 | 75.798 | 1.00 31.92 | ras |
| ATOM | 4538 | CD | PRO | 110 | 90.717 | 40.869 | 76.052 | 1.00 31.46 | ras |
| ATOM | 4539 | CA | PRO | 110 | 91.043 | 42.758 | 74.587 | 1.00 32.74 | ras |
| ATOM | 4540 | CB | PRO | 110 | 91.750 | 41.506 | 74.065 | 1.00 28.50 | ras |
| ATOM | 4541 | CG | PRO | 110 | 91.997 | 40.710 | 75.283 | 1.00 29.23 | ras |

Figure 8-76

```
ATOM   4542  C    PRO  110    90.016  43.265  73.576  1.00  36.53    ras
ATOM   4543  O    PRO  110    89.223  42.496  73.040  1.00  40.80    ras
ATOM   4544  N    MET  111    89.980  44.574  73.377  1.00  38.62    ras
ATOM   4545  CA   MET  111    89.065  45.147  72.415  1.00  34.61    ras
ATOM   4546  CB   MET  111    87.697  45.461  73.032  1.00  36.33    ras
ATOM   4547  CG   MET  111    87.577  46.718  73.877  1.00  41.05    ras
ATOM   4548  SD   MET  111    85.827  46.981  74.348  1.00  42.89    ras
ATOM   4549  CE   MET  111    85.554  45.562  75.348  1.00  33.81    ras
ATOM   4550  C    MET  111    89.684  46.372  71.791  1.00  34.96    ras
ATOM   4551  O    MET  111    90.652  46.929  72.317  1.00  37.97    ras
ATOM   4552  N    VAL  112    89.134  46.758  70.647  1.00  31.93    ras
ATOM   4553  CA   VAL  112    89.605  47.905  69.904  1.00  28.79    ras
ATOM   4554  CB   VAL  112    90.528  47.428  68.758  1.00  29.36    ras
ATOM   4555  CG1  VAL  112    89.726  46.958  67.561  1.00  26.90    ras
ATOM   4556  CG2  VAL  112    91.495  48.498  68.385  1.00  36.07    ras
ATOM   4557  C    VAL  112    88.385  48.660  69.369  1.00  28.06    ras
ATOM   4558  O    VAL  112    87.345  48.061  69.125  1.00  34.41    ras
ATOM   4559  N    LEU  113    88.476  49.983  69.294  1.00  28.07    ras
ATOM   4560  CA   LEU  113    87.386  50.819  68.781  1.00  25.02    ras
ATOM   4561  CB   LEU  113    87.283  52.107  69.595  1.00  21.40    ras
ATOM   4562  CG   LEU  113    86.373  53.212  69.069  1.00  19.88    ras
ATOM   4563  CD1  LEU  113    84.932  52.850  69.288  1.00  23.94    ras
ATOM   4564  CD2  LEU  113    86.671  54.478  69.817  1.00  23.55    ras
ATOM   4565  C    LEU  113    87.701  51.156  67.327  1.00  27.33    ras
ATOM   4566  O    LEU  113    88.722  51.791  67.047  1.00  28.89    ras
ATOM   4567  N    VAL  114    86.839  50.708  66.412  1.00  26.31    ras
ATOM   4568  CA   VAL  114    87.014  50.935  64.974  1.00  24.24    ras
ATOM   4569  CB   VAL  114    86.936  49.613  64.189  1.00  24.54    ras
ATOM   4570  CG1  VAL  114    87.212  49.859  62.715  1.00  28.38    ras
ATOM   4571  CG2  VAL  114    87.896  48.598  64.759  1.00  22.17    ras
ATOM   4572  C    VAL  114    85.962  51.878  64.386  1.00  24.95    ras
ATOM   4573  O    VAL  114    84.764  51.636  64.512  1.00  28.31    ras
ATOM   4574  N    GLY  115    86.418  52.936  63.725  1.00  23.90    ras
ATOM   4575  CA   GLY  115    85.506  53.890  63.121  1.00  28.42    ras
ATOM   4576  C    GLY  115    85.557  53.719  61.620  1.00  34.16    ras
ATOM   4577  O    GLY  115    86.563  54.015  60.988  1.00  35.95    ras
ATOM   4578  N    ASN  116    84.462  53.240  61.047  1.00  40.31    ras
ATOM   4579  CA   ASN  116    84.379  52.973  59.617  1.00  42.55    ras
ATOM   4580  CB   ASN  116    83.526  51.716  59.421  1.00  44.24    ras
ATOM   4581  CG   ASN  116    83.240  51.414  57.970  1.00  50.67    ras
ATOM   4582  OD1  ASN  116    84.141  51.426  57.116  1.00  51.53    ras
ATOM   4583  ND2  ASN  116    81.973  51.128  57.679  1.00  50.47    ras
ATOM   4584  C    ASN  116    83.844  54.164  58.819  1.00  42.65    ras
ATOM   4585  O    ASN  116    82.916  54.843  59.252  1.00  45.11    ras
ATOM   4586  N    LYS  117    84.431  54.414  57.654  1.00  43.03    ras
ATOM   4587  CA   LYS  117    84.015  55.536  56.822  1.00  48.43    ras
ATOM   4588  CB   LYS  117    85.196  56.478  56.592  1.00  48.89    ras
ATOM   4589  CG   LYS  117    84.844  57.734  55.812  1.00  53.86    ras
ATOM   4590  CD   LYS  117    86.032  58.206  55.002  1.00  57.77    ras
ATOM   4591  CE   LYS  117    85.610  59.182  53.914  1.00  63.27    ras
ATOM   4592  NZ   LYS  117    86.665  59.297  52.858  1.00  63.79    ras
ATOM   4593  C    LYS  117    83.403  55.154  55.475  1.00  53.12    ras
ATOM   4594  O    LYS  117    83.916  54.295  54.758  1.00  53.06    ras
ATOM   4595  N    CYS  118    82.305  55.822  55.140  1.00  61.54    ras
ATOM   4596  CA   CYS  118    81.594  55.610  53.880  1.00  71.48    ras
ATOM   4597  CB   CYS  118    80.132  55.253  54.162  1.00  74.52    ras
ATOM   4598  SG   CYS  118    79.058  55.239  52.716  1.00  80.85    ras
ATOM   4599  C    CYS  118    81.686  56.917  53.087  1.00  76.03    ras
ATOM   4600  O    CYS  118    81.141  57.944  53.505  1.00  79.63    ras
ATOM   4601  N    ASP  119    82.362  56.869  51.941  1.00  79.14    ras
ATOM   4602  CA   ASP  119    82.576  58.050  51.100  1.00  82.11    ras
```

Figure 8-77

```
ATOM   4603  CB   ASP  119      83.403  57.677  49.864  1.00  86.58      ras
ATOM   4604  CG   ASP  119      84.342  58.796  49.430  1.00  90.60      ras
ATOM   4605  OD1  ASP  119      85.500  58.810  49.908  1.00  91.32      ras
ATOM   4606  OD2  ASP  119      83.924  59.659  48.622  1.00  89.50      ras
ATOM   4607  C    ASP  119      81.331  58.825  50.668  1.00  81.94      ras
ATOM   4608  O    ASP  119      81.433  59.969  50.228  1.00  81.54      ras
ATOM   4609  N    LEU  120      80.163  58.209  50.807  1.00  82.74      ras
ATOM   4610  CA   LEU  120      78.909  58.847  50.423  1.00  82.51      ras
ATOM   4611  CB   LEU  120      77.766  57.822  50.433  1.00  84.98      ras
ATOM   4612  CG   LEU  120      77.922  56.578  49.545  1.00  89.71      ras
ATOM   4613  CD1  LEU  120      76.701  55.676  49.693  1.00  87.10      ras
ATOM   4614  CD2  LEU  120      78.119  56.981  48.085  1.00  89.88      ras
ATOM   4615  C    LEU  120      78.529  60.056  51.287  1.00  80.53      ras
ATOM   4616  O    LEU  120      78.412  61.172  50.776  1.00  82.27      ras
ATOM   4617  N    ALA  121      78.370  59.837  52.593  1.00  75.55      ras
ATOM   4618  CA   ALA  121      77.968  60.896  53.522  1.00  68.08      ras
ATOM   4619  CB   ALA  121      77.020  60.329  54.572  1.00  69.04      ras
ATOM   4620  C    ALA  121      79.081  61.714  54.195  1.00  63.21      ras
ATOM   4621  O    ALA  121      80.273  61.488  53.966  1.00  62.81      ras
ATOM   4622  N    ALA  122      78.658  62.672  55.020  1.00  54.57      ras
ATOM   4623  CA   ALA  122      79.553  63.570  55.744  1.00  47.69      ras
ATOM   4624  CB   ALA  122      78.927  64.949  55.847  1.00  46.58      ras
ATOM   4625  C    ALA  122      79.908  63.077  57.133  1.00  43.56      ras
ATOM   4626  O    ALA  122      79.070  62.530  57.842  1.00  47.26      ras
ATOM   4627  N    ARG  123      81.145  63.335  57.534  1.00  38.05      ras
ATOM   4628  CA   ARG  123      81.646  62.939  58.840  1.00  36.68      ras
ATOM   4629  CB   ARG  123      83.157  63.184  58.901  1.00  33.60      ras
ATOM   4630  CG   ARG  123      83.783  62.983  60.264  1.00  33.76      ras
ATOM   4631  CD   ARG  123      85.244  63.380  60.261  1.00  25.51      ras
ATOM   4632  NE   ARG  123      86.078  62.421  59.540  1.00  29.08      ras
ATOM   4633  CZ   ARG  123      86.543  61.283  60.055  1.00  29.44      ras
ATOM   4634  NH1  ARG  123      86.268  60.939  61.309  1.00  24.21      ras
ATOM   4635  NH2  ARG  123      87.259  60.465  59.298  1.00  33.23      ras
ATOM   4636  C    ARG  123      80.941  63.738  59.931  1.00  38.95      ras
ATOM   4637  O    ARG  123      80.821  64.956  59.825  1.00  41.45      ras
ATOM   4638  N    THR  124      80.445  63.050  60.958  1.00  37.94      ras
ATOM   4639  CA   THR  124      79.765  63.716  62.064  1.00  36.74      ras
ATOM   4640  CB   THR  124      78.284  63.345  62.129  1.00  37.25      ras
ATOM   4641  OG1  THR  124      78.151  61.938  62.369  1.00  42.57      ras
ATOM   4642  CG2  THR  124      77.599  63.699  60.826  1.00  33.15      ras
ATOM   4643  C    THR  124      80.432  63.375  63.392  1.00  38.85      ras
ATOM   4644  O    THR  124      80.005  63.845  64.454  1.00  42.61      ras
ATOM   4645  N    VAL  125      81.452  62.520  63.327  1.00  35.36      ras
ATOM   4646  CA   VAL  125      82.221  62.124  64.503  1.00  34.45      ras
ATOM   4647  CB   VAL  125      82.115  60.622  64.811  1.00  32.97      ras
ATOM   4648  CG1  VAL  125      82.910  60.296  66.058  1.00  32.27      ras
ATOM   4649  CG2  VAL  125      80.672  60.205  64.977  1.00  32.25      ras
ATOM   4650  C    VAL  125      83.657  62.411  64.130  1.00  36.78      ras
ATOM   4651  O    VAL  125      84.219  61.733  63.267  1.00  37.16      ras
ATOM   4652  N    GLU  126      84.234  63.443  64.740  1.00  39.83      ras
ATOM   4653  CA   GLU  126      85.613  63.824  64.449  1.00  37.95      ras
ATOM   4654  CB   GLU  126      85.904  65.237  64.949  1.00  39.78      ras
ATOM   4655  CG   GLU  126      85.064  66.334  64.303  1.00  43.78      ras
ATOM   4656  CD   GLU  126      85.229  66.426  62.787  1.00  47.47      ras
ATOM   4657  OE1  GLU  126      86.386  66.438  62.294  1.00  46.50      ras
ATOM   4658  OE2  GLU  126      84.188  66.501  62.092  1.00  48.25      ras
ATOM   4659  C    GLU  126      86.582  62.846  65.081  1.00  36.49      ras
ATOM   4660  O    GLU  126      86.282  62.239  66.108  1.00  38.33      ras
ATOM   4661  N    SER  127      87.738  62.683  64.451  1.00  35.17      ras
ATOM   4662  CA   SER  127      88.758  61.775  64.952  1.00  35.51      ras
ATOM   4663  CB   SER  127      90.021  61.855  64.090  1.00  37.90      ras
```

Figure 8-78

| ATOM | 4664 | OG  | SER | 127 | 90.225 | 63.160 | 63.564 | 1.00 | 46.43 | ras |
| ATOM | 4665 | C   | SER | 127 | 89.085 | 62.005 | 66.426 | 1.00 | 35.79 | ras |
| ATOM | 4666 | O   | SER | 127 | 89.164 | 61.043 | 67.201 | 1.00 | 35.46 | ras |
| ATOM | 4667 | N   | ARG | 128 | 89.204 | 63.273 | 66.825 | 1.00 | 35.69 | ras |
| ATOM | 4668 | CA  | ARG | 128 | 89.511 | 63.620 | 68.214 | 1.00 | 37.26 | ras |
| ATOM | 4669 | CB  | ARG | 128 | 89.639 | 65.139 | 68.384 | 1.00 | 42.71 | ras |
| ATOM | 4670 | CG  | ARG | 128 | 90.005 | 65.607 | 69.801 | 1.00 | 50.29 | ras |
| ATOM | 4671 | CD  | ARG | 128 | 91.320 | 64.998 | 70.289 | 1.00 | 56.35 | ras |
| ATOM | 4672 | NE  | ARG | 128 | 91.672 | 65.452 | 71.634 | 1.00 | 60.48 | ras |
| ATOM | 4673 | CZ  | ARG | 128 | 92.727 | 66.215 | 71.928 | 1.00 | 61.33 | ras |
| ATOM | 4674 | NH1 | ARG | 128 | 92.957 | 66.574 | 73.188 | 1.00 | 55.18 | ras |
| ATOM | 4675 | NH2 | ARG | 128 | 93.556 | 66.619 | 70.968 | 1.00 | 57.47 | ras |
| ATOM | 4676 | C   | ARG | 128 | 88.508 | 63.052 | 69.227 | 1.00 | 37.08 | ras |
| ATOM | 4677 | O   | ARG | 128 | 88.914 | 62.441 | 70.215 | 1.00 | 32.60 | ras |
| ATOM | 4678 | N   | GLN | 129 | 87.208 | 63.215 | 68.982 | 1.00 | 38.36 | ras |
| ATOM | 4679 | CA  | GLN | 129 | 86.230 | 62.682 | 69.930 | 1.00 | 39.21 | ras |
| ATOM | 4680 | CB  | GLN | 129 | 84.810 | 63.217 | 69.698 | 1.00 | 37.59 | ras |
| ATOM | 4681 | CG  | GLN | 129 | 84.336 | 63.287 | 68.270 | 1.00 | 43.52 | ras |
| ATOM | 4682 | CD  | GLN | 129 | 82.969 | 63.952 | 68.151 | 1.00 | 43.31 | ras |
| ATOM | 4683 | OE1 | GLN | 129 | 82.677 | 64.634 | 67.164 | 1.00 | 45.38 | ras |
| ATOM | 4684 | NE2 | GLN | 129 | 82.127 | 63.751 | 69.157 | 1.00 | 35.28 | ras |
| ATOM | 4685 | C   | GLN | 129 | 86.254 | 61.172 | 70.044 | 1.00 | 37.78 | ras |
| ATOM | 4686 | O   | GLN | 129 | 86.002 | 60.632 | 71.127 | 1.00 | 39.32 | ras |
| ATOM | 4687 | N   | ALA | 130 | 86.622 | 60.495 | 68.957 | 1.00 | 35.54 | ras |
| ATOM | 4688 | CA  | ALA | 130 | 86.708 | 59.032 | 68.963 | 1.00 | 35.96 | ras |
| ATOM | 4689 | CB  | ALA | 130 | 86.615 | 58.484 | 67.559 | 1.00 | 34.63 | ras |
| ATOM | 4690 | C   | ALA | 130 | 88.036 | 58.647 | 69.595 | 1.00 | 36.61 | ras |
| ATOM | 4691 | O   | ALA | 130 | 88.172 | 57.596 | 70.225 | 1.00 | 31.58 | ras |
| ATOM | 4692 | N   | GLN | 131 | 89.014 | 59.531 | 69.429 | 1.00 | 40.59 | ras |
| ATOM | 4693 | CA  | GLN | 131 | 90.341 | 59.334 | 69.991 | 1.00 | 40.20 | ras |
| ATOM | 4694 | CB  | GLN | 131 | 91.293 | 60.393 | 69.440 | 1.00 | 43.47 | ras |
| ATOM | 4695 | CG  | GLN | 131 | 92.753 | 60.014 | 69.499 | 1.00 | 54.26 | ras |
| ATOM | 4696 | CD  | GLN | 131 | 93.175 | 59.119 | 68.354 | 1.00 | 58.42 | ras |
| ATOM | 4697 | OE1 | GLN | 131 | 93.139 | 59.530 | 67.190 | 1.00 | 59.02 | ras |
| ATOM | 4698 | NE2 | GLN | 131 | 93.604 | 57.895 | 68.677 | 1.00 | 55.27 | ras |
| ATOM | 4699 | C   | GLN | 131 | 90.217 | 59.451 | 71.512 | 1.00 | 37.26 | ras |
| ATOM | 4700 | O   | GLN | 131 | 90.677 | 58.568 | 72.236 | 1.00 | 37.81 | ras |
| ATOM | 4701 | N   | ASP | 132 | 89.533 | 60.501 | 71.981 | 1.00 | 36.13 | ras |
| ATOM | 4702 | CA  | ASP | 132 | 89.318 | 60.730 | 73.420 | 1.00 | 35.75 | ras |
| ATOM | 4703 | CB  | ASP | 132 | 88.556 | 62.036 | 73.681 | 1.00 | 34.78 | ras |
| ATOM | 4704 | CG  | ASP | 132 | 89.405 | 63.287 | 73.445 | 1.00 | 41.42 | ras |
| ATOM | 4705 | OD1 | ASP | 132 | 88.811 | 64.377 | 73.302 | 1.00 | 39.44 | ras |
| ATOM | 4706 | OD2 | ASP | 132 | 90.653 | 63.193 | 73.397 | 1.00 | 45.68 | ras |
| ATOM | 4707 | C   | ASP | 132 | 88.560 | 59.585 | 74.079 | 1.00 | 33.84 | ras |
| ATOM | 4708 | O   | ASP | 132 | 88.904 | 59.152 | 75.180 | 1.00 | 35.32 | ras |
| ATOM | 4709 | N   | LEU | 133 | 87.540 | 59.084 | 73.392 | 1.00 | 31.84 | ras |
| ATOM | 4710 | CA  | LEU | 133 | 86.739 | 57.986 | 73.909 | 1.00 | 28.69 | ras |
| ATOM | 4711 | CB  | LEU | 133 | 85.537 | 57.724 | 72.995 | 1.00 | 29.78 | ras |
| ATOM | 4712 | CG  | LEU | 133 | 84.615 | 56.586 | 73.451 | 1.00 | 32.23 | ras |
| ATOM | 4713 | CD1 | LEU | 133 | 83.897 | 56.985 | 74.725 | 1.00 | 26.55 | ras |
| ATOM | 4714 | CD2 | LEU | 133 | 83.620 | 56.236 | 72.363 | 1.00 | 32.38 | ras |
| ATOM | 4715 | C   | LEU | 133 | 87.568 | 56.716 | 74.043 | 1.00 | 27.76 | ras |
| ATOM | 4716 | O   | LEU | 133 | 87.387 | 55.939 | 74.988 | 1.00 | 27.92 | ras |
| ATOM | 4717 | N   | ALA | 134 | 88.467 | 56.498 | 73.090 | 1.00 | 23.60 | ras |
| ATOM | 4718 | CA  | ALA | 134 | 89.303 | 55.312 | 73.114 | 1.00 | 25.39 | ras |
| ATOM | 4719 | CB  | ALA | 134 | 90.066 | 55.177 | 71.809 | 1.00 | 22.66 | ras |
| ATOM | 4720 | C   | ALA | 134 | 90.262 | 55.367 | 74.296 | 1.00 | 29.43 | ras |
| ATOM | 4721 | O   | ALA | 134 | 90.508 | 54.360 | 74.965 | 1.00 | 31.72 | ras |
| ATOM | 4722 | N   | ARG | 135 | 90.784 | 56.556 | 74.564 | 1.00 | 30.99 | ras |
| ATOM | 4723 | CA  | ARG | 135 | 91.711 | 56.731 | 75.663 | 1.00 | 32.98 | ras |
| ATOM | 4724 | CB  | ARG | 135 | 92.427 | 58.074 | 75.539 | 1.00 | 36.31 | ras |

Figure 8-79

| ATOM | 4725 | CG | ARG | 135 | 93.291 | 58.429 | 76.722 | 1.00 | 34.04 | ras |
| ATOM | 4726 | CD | ARG | 135 | 94.375 | 59.391 | 76.317 | 1.00 | 36.97 | ras |
| ATOM | 4727 | NE | ARG | 135 | 95.647 | 58.694 | 76.150 | 1.00 | 39.27 | ras |
| ATOM | 4728 | CZ | ARG | 135 | 96.251 | 58.512 | 74.984 | 1.00 | 40.93 | ras |
| ATOM | 4729 | NH1 | ARG | 135 | 97.407 | 57.867 | 74.943 | 1.00 | 35.06 | ras |
| ATOM | 4730 | NH2 | ARG | 135 | 95.700 | 58.978 | 73.859 | 1.00 | 45.53 | ras |
| ATOM | 4731 | C | ARG | 135 | 91.028 | 56.587 | 77.017 | 1.00 | 33.49 | ras |
| ATOM | 4732 | O | ARG | 135 | 91.649 | 56.133 | 77.978 | 1.00 | 36.94 | ras |
| ATOM | 4733 | N | SER | 136 | 89.751 | 56.950 | 77.099 | 1.00 | 31.27 | ras |
| ATOM | 4734 | CA | SER | 136 | 89.040 | 56.821 | 78.367 | 1.00 | 30.97 | ras |
| ATOM | 4735 | CB | SER | 136 | 87.744 | 57.632 | 78.368 | 1.00 | 26.61 | ras |
| ATOM | 4736 | OG | SER | 136 | 86.707 | 56.966 | 77.681 | 1.00 | 39.64 | ras |
| ATOM | 4737 | C | SER | 136 | 88.776 | 55.347 | 78.688 | 1.00 | 30.12 | ras |
| ATOM | 4738 | O | SER | 136 | 88.577 | 54.991 | 79.842 | 1.00 | 27.40 | ras |
| ATOM | 4739 | N | TYR | 137 | 88.805 | 54.496 | 77.660 | 1.00 | 33.73 | ras |
| ATOM | 4740 | CA | TYR | 137 | 88.601 | 53.049 | 77.823 | 1.00 | 35.00 | ras |
| ATOM | 4741 | CB | TYR | 137 | 87.793 | 52.453 | 76.661 | 1.00 | 33.68 | ras |
| ATOM | 4742 | CG | TYR | 137 | 86.362 | 52.934 | 76.565 | 1.00 | 36.06 | ras |
| ATOM | 4743 | CD1 | TYR | 137 | 85.683 | 53.386 | 77.693 | 1.00 | 33.29 | ras |
| ATOM | 4744 | CE1 | TYR | 137 | 84.381 | 53.850 | 77.606 | 1.00 | 34.15 | ras |
| ATOM | 4745 | CD2 | TYR | 137 | 85.692 | 52.954 | 75.339 | 1.00 | 35.98 | ras |
| ATOM | 4746 | CE2 | TYR | 137 | 84.380 | 53.418 | 75.242 | 1.00 | 35.22 | ras |
| ATOM | 4747 | CZ | TYR | 137 | 83.735 | 53.866 | 76.381 | 1.00 | 35.02 | ras |
| ATOM | 4748 | OH | TYR | 137 | 82.458 | 54.354 | 76.311 | 1.00 | 34.03 | ras |
| ATOM | 4749 | C | TYR | 137 | 89.942 | 52.340 | 77.881 | 1.00 | 34.41 | ras |
| ATOM | 4750 | O | TYR | 137 | 90.011 | 51.161 | 78.225 | 1.00 | 38.75 | ras |
| ATOM | 4751 | N | GLY | 138 | 91.002 | 53.056 | 77.524 | 1.00 | 30.33 | ras |
| ATOM | 4752 | CA | GLY | 138 | 92.328 | 52.467 | 77.524 | 1.00 | 29.39 | ras |
| ATOM | 4753 | C | GLY | 138 | 92.511 | 51.438 | 76.423 | 1.00 | 27.77 | ras |
| ATOM | 4754 | O | GLY | 138 | 93.130 | 50.392 | 76.632 | 1.00 | 25.61 | ras |
| ATOM | 4755 | N | ILE | 139 | 91.948 | 51.731 | 75.255 | 1.00 | 25.41 | ras |
| ATOM | 4756 | CA | ILE | 139 | 92.033 | 50.841 | 74.109 | 1.00 | 24.60 | ras |
| ATOM | 4757 | CB | ILE | 139 | 90.706 | 50.084 | 73.852 | 1.00 | 26.61 | ras |
| ATOM | 4758 | CG2 | ILE | 139 | 90.316 | 49.281 | 75.068 | 1.00 | 23.18 | ras |
| ATOM | 4759 | CG1 | ILE | 139 | 89.589 | 51.053 | 73.454 | 1.00 | 27.23 | ras |
| ATOM | 4760 | CD1 | ILE | 139 | 88.328 | 50.350 | 72.995 | 1.00 | 26.53 | ras |
| ATOM | 4761 | C | ILE | 139 | 92.371 | 51.665 | 72.885 | 1.00 | 25.85 | ras |
| ATOM | 4762 | O | ILE | 139 | 92.152 | 52.878 | 72.871 | 1.00 | 30.51 | ras |
| ATOM | 4763 | N | PRO | 140 | 92.931 | 51.022 | 71.846 | 1.00 | 23.26 | ras |
| ATOM | 4764 | CD | PRO | 140 | 93.374 | 49.619 | 71.854 | 1.00 | 20.40 | ras |
| ATOM | 4765 | CA | PRO | 140 | 93.319 | 51.681 | 70.593 | 1.00 | 23.44 | ras |
| ATOM | 4766 | CB | PRO | 140 | 94.129 | 50.600 | 69.871 | 1.00 | 19.82 | ras |
| ATOM | 4767 | CG | PRO | 140 | 94.562 | 49.678 | 70.965 | 1.00 | 23.28 | ras |
| ATOM | 4768 | C | PRO | 140 | 92.127 | 52.104 | 69.732 | 1.00 | 27.00 | ras |
| ATOM | 4769 | O | PRO | 140 | 91.046 | 51.515 | 69.825 | 1.00 | 26.80 | ras |
| ATOM | 4770 | N | TYR | 141 | 92.329 | 53.135 | 68.912 | 1.00 | 25.97 | ras |
| ATOM | 4771 | CA | TYR | 141 | 91.298 | 53.611 | 68.003 | 1.00 | 27.64 | ras |
| ATOM | 4772 | CB | TYR | 141 | 90.997 | 55.089 | 68.222 | 1.00 | 28.94 | ras |
| ATOM | 4773 | CG | TYR | 141 | 90.091 | 55.682 | 67.157 | 1.00 | 26.44 | ras |
| ATOM | 4774 | CD1 | TYR | 141 | 88.832 | 55.140 | 66.905 | 1.00 | 26.23 | ras |
| ATOM | 4775 | CE1 | TYR | 141 | 87.996 | 55.676 | 65.946 | 1.00 | 22.47 | ras |
| ATOM | 4776 | CD2 | TYR | 141 | 90.490 | 56.784 | 66.412 | 1.00 | 25.52 | ras |
| ATOM | 4777 | CE2 | TYR | 141 | 89.660 | 57.332 | 65.447 | 1.00 | 26.83 | ras |
| ATOM | 4778 | CZ | TYR | 141 | 88.414 | 56.770 | 65.222 | 1.00 | 27.46 | ras |
| ATOM | 4779 | OH | TYR | 141 | 87.586 | 57.308 | 64.268 | 1.00 | 27.03 | ras |
| ATOM | 4780 | C | TYR | 141 | 91.859 | 53.441 | 66.613 | 1.00 | 31.51 | ras |
| ATOM | 4781 | O | TYR | 141 | 93.005 | 53.802 | 66.371 | 1.00 | 36.56 | ras |
| ATOM | 4782 | N | ILE | 142 | 91.054 | 52.913 | 65.692 | 1.00 | 35.13 | ras |
| ATOM | 4783 | CA | ILE | 142 | 91.504 | 52.699 | 64.317 | 1.00 | 31.73 | ras |
| ATOM | 4784 | CB | ILE | 142 | 91.846 | 51.228 | 64.081 | 1.00 | 27.10 | ras |
| ATOM | 4785 | CG2 | ILE | 142 | 92.480 | 51.050 | 62.706 | 1.00 | 15.67 | ras |

Figure 8-80

```
ATOM   4786  CG1 ILE 142    92.792 50.750 65.179  1.00 23.98      ras
ATOM   4787  CD1 ILE 142    92.821 49.289 65.356  1.00 31.23      ras
ATOM   4788  C   ILE 142    90.445 53.099 63.307  1.00 33.54      ras
ATOM   4789  O   ILE 142    89.350 52.549 63.317  1.00 40.35      ras
ATOM   4790  N   GLU 143    90.764 54.070 62.458  1.00 30.75      ras
ATOM   4791  CA  GLU 143    89.831 54.510 61.436  1.00 30.42      ras
ATOM   4792  CB  GLU 143    89.993 55.994 61.127  1.00 31.06      ras
ATOM   4793  CG  GLU 143    89.275 56.869 62.106  1.00 33.85      ras
ATOM   4794  CD  GLU 143    88.853 58.222 61.550  1.00 39.08      ras
ATOM   4795  OE1 GLU 143    89.075 58.501 60.353  1.00 34.80      ras
ATOM   4796  OE2 GLU 143    88.272 59.012 62.324  1.00 42.20      ras
ATOM   4797  C   GLU 143    90.076 53.689 60.191  1.00 32.43      ras
ATOM   4798  O   GLU 143    91.212 53.357 59.883  1.00 38.54      ras
ATOM   4799  N   THR 144    89.005 53.379 59.472  1.00 33.98      ras
ATOM   4800  CA  THR 144    89.084 52.565 58.270  1.00 34.43      ras
ATOM   4801  CB  THR 144    88.642 51.116 58.566  1.00 34.35      ras
ATOM   4802  OG1 THR 144    87.222 51.083 58.767  1.00 36.77      ras
ATOM   4803  CG2 THR 144    89.313 50.597 59.823  1.00 28.88      ras
ATOM   4804  C   THR 144    88.154 53.099 57.188  1.00 37.34      ras
ATOM   4805  O   THR 144    87.166 53.774 57.483  1.00 39.02      ras
ATOM   4806  N   SER 145    88.470 52.772 55.940  1.00 40.33      ras
ATOM   4807  CA  SER 145    87.654 53.175 54.798  1.00 44.04      ras
ATOM   4808  CB  SER 145    88.523 53.853 53.739  1.00 42.89      ras
ATOM   4809  OG  SER 145    87.746 54.281 52.632  1.00 39.80      ras
ATOM   4810  C   SER 145    86.980 51.936 54.198  1.00 47.52      ras
ATOM   4811  O   SER 145    87.613 50.897 54.026  1.00 49.05      ras
ATOM   4812  N   ALA 146    85.689 52.032 53.906  1.00 51.96      ras
ATOM   4813  CA  ALA 146    84.968 50.908 53.307  1.00 54.95      ras
ATOM   4814  CB  ALA 146    83.490 50.995 53.645  1.00 51.70      ras
ATOM   4815  C   ALA 146    85.159 50.879 51.787  1.00 56.42      ras
ATOM   4816  O   ALA 146    84.939 49.863 51.141  1.00 58.52      ras
ATOM   4817  N   LYS 147    85.598 52.000 51.232  1.00 60.15      ras
ATOM   4818  CA  LYS 147    85.799 52.149 49.797  1.00 62.34      ras
ATOM   4819  CB  LYS 147    85.394 53.575 49.392  1.00 64.73      ras
ATOM   4820  CG  LYS 147    85.666 53.942 47.939  1.00 70.11      ras
ATOM   4821  CD  LYS 147    85.674 55.447 47.737  1.00 72.20      ras
ATOM   4822  CE  LYS 147    85.966 55.793 46.285  1.00 77.40      ras
ATOM   4823  NZ  LYS 147    86.125 57.261 46.077  1.00 80.49      ras
ATOM   4824  C   LYS 147    87.224 51.862 49.299  1.00 62.91      ras
ATOM   4825  O   LYS 147    87.409 51.476 48.139  1.00 64.68      ras
ATOM   4826  N   THR 148    88.222 52.045 50.162  1.00 58.14      ras
ATOM   4827  CA  THR 148    89.616 51.857 49.766  1.00 52.41      ras
ATOM   4828  CB  THR 148    90.411 53.164 49.959  1.00 51.99      ras
ATOM   4829  OG1 THR 148    90.455 53.491 51.353  1.00 48.72      ras
ATOM   4830  CG2 THR 148    89.765 54.307 49.203  1.00 51.18      ras
ATOM   4831  C   THR 148    90.374 50.761 50.502  1.00 50.64      ras
ATOM   4832  O   THR 148    91.540 50.502 50.203  1.00 52.35      ras
ATOM   4833  N   ARG 149    89.722 50.134 51.472  1.00 48.50      ras
ATOM   4834  CA  ARG 149    90.332 49.083 52.290  1.00 45.39      ras
ATOM   4835  CB  ARG 149    90.841 47.905 51.438  1.00 46.80      ras
ATOM   4836  CG  ARG 149    90.911 46.595 52.232  1.00 53.56      ras
ATOM   4837  CD  ARG 149    91.602 45.426 51.513  1.00 55.50      ras
ATOM   4838  NE  ARG 149    91.660 44.241 52.382  1.00 52.88      ras
ATOM   4839  CZ  ARG 149    92.776 43.704 52.871  1.00 46.33      ras
ATOM   4840  NH1 ARG 149    92.717 42.641 53.660  1.00 46.20      ras
ATOM   4841  NH2 ARG 149    93.955 44.208 52.553  1.00 46.94      ras
ATOM   4842  C   ARG 149    91.446 49.624 53.206  1.00 43.06      ras
ATOM   4843  O   ARG 149    92.101 48.856 53.917  1.00 43.99      ras
ATOM   4844  N   GLN 150    91.637 50.945 53.216  1.00 39.08      ras
ATOM   4845  CA  GLN 150    92.648 51.565 54.077  1.00 34.98      ras
ATOM   4846  CB  GLN 150    92.753 53.071 53.816  1.00 33.52      ras
```

Figure 8-81

```
ATOM   4847  CG   GLN  150     93.352  53.487  52.491  1.00  34.22      ras
ATOM   4848  CD   GLN  150     93.448  55.000  52.349  1.00  37.95      ras
ATOM   4849  OE1  GLN  150     92.553  55.649  51.798  1.00  37.26      ras
ATOM   4850  NE2  GLN  150     94.539  55.568  52.845  1.00  38.50      ras
ATOM   4851  C    GLN  150     92.267  51.371  55.545  1.00  33.31      ras
ATOM   4852  O    GLN  150     91.135  51.652  55.939  1.00  32.99      ras
ATOM   4853  N    GLY  151     93.206  50.874  56.342  1.00  33.35      ras
ATOM   4854  CA   GLY  151     92.960  50.680  57.761  1.00  30.37      ras
ATOM   4855  C    GLY  151     92.410  49.341  58.206  1.00  33.41      ras
ATOM   4856  O    GLY  151     92.566  48.985  59.367  1.00  33.92      ras
ATOM   4857  N    VAL  152     91.779  48.594  57.301  1.00  36.30      ras
ATOM   4858  CA   VAL  152     91.192  47.296  57.643  1.00  33.95      ras
ATOM   4859  CB   VAL  152     90.542  46.630  56.424  1.00  33.22      ras
ATOM   4860  CG1  VAL  152     89.924  45.300  56.812  1.00  33.95      ras
ATOM   4861  CG2  VAL  152     89.474  47.528  55.868  1.00  31.32      ras
ATOM   4862  C    VAL  152     92.134  46.315  58.334  1.00  36.15      ras
ATOM   4863  O    VAL  152     91.797  45.789  59.396  1.00  35.10      ras
ATOM   4864  N    GLU  153     93.305  46.066  57.749  1.00  39.86      ras
ATOM   4865  CA   GLU  153     94.264  45.150  58.368  1.00  41.52      ras
ATOM   4866  CB   GLU  153     95.539  45.030  57.541  1.00  45.51      ras
ATOM   4867  CG   GLU  153     95.360  44.441  56.156  1.00  58.86      ras
ATOM   4868  CD   GLU  153     96.527  43.547  55.748  1.00  64.28      ras
ATOM   4869  OE1  GLU  153     97.671  43.784  56.221  1.00  63.29      ras
ATOM   4870  OE2  GLU  153     96.285  42.595  54.968  1.00  62.65      ras
ATOM   4871  C    GLU  153     94.636  45.663  59.751  1.00  41.05      ras
ATOM   4872  O    GLU  153     94.426  44.987  60.756  1.00  40.07      ras
ATOM   4873  N    ASP  154     95.166  46.881  59.783  1.00  41.55      ras
ATOM   4874  CA   ASP  154     95.585  47.535  61.017  1.00  41.98      ras
ATOM   4875  CB   ASP  154     95.772  49.033  60.742  1.00  45.25      ras
ATOM   4876  CG   ASP  154     96.554  49.752  61.828  1.00  51.92      ras
ATOM   4877  OD1  ASP  154     97.264  49.091  62.625  1.00  51.51      ras
ATOM   4878  OD2  ASP  154     96.471  51.004  61.862  1.00  57.26      ras
ATOM   4879  C    ASP  154     94.561  47.290  62.137  1.00  39.90      ras
ATOM   4880  O    ASP  154     94.919  46.888  63.242  1.00  39.23      ras
ATOM   4881  N    ALA  155     93.285  47.437  61.808  1.00  36.72      ras
ATOM   4882  CA   ALA  155     92.214  47.226  62.765  1.00  35.26      ras
ATOM   4883  CB   ALA  155     90.880  47.435  62.095  1.00  40.16      ras
ATOM   4884  C    ALA  155     92.283  45.835  63.378  1.00  34.56      ras
ATOM   4885  O    ALA  155     92.394  45.692  64.595  1.00  33.83      ras
ATOM   4886  N    PHE  156     92.236  44.812  62.529  1.00  35.79      ras
ATOM   4887  CA   PHE  156     92.297  43.427  62.992  1.00  33.23      ras
ATOM   4888  CB   PHE  156     91.925  42.473  61.873  1.00  27.57      ras
ATOM   4889  CG   PHE  156     90.471  42.482  61.547  1.00  27.45      ras
ATOM   4890  CD1  PHE  156     89.979  43.292  60.531  1.00  28.01      ras
ATOM   4891  CD2  PHE  156     89.591  41.662  62.239  1.00  27.64      ras
ATOM   4892  CE1  PHE  156     88.631  43.286  60.201  1.00  24.89      ras
ATOM   4893  CE2  PHE  156     88.239  41.643  61.922  1.00  28.91      ras
ATOM   4894  CZ   PHE  156     87.758  42.458  60.897  1.00  30.70      ras
ATOM   4895  C    PHE  156     93.629  43.027  63.612  1.00  32.93      ras
ATOM   4896  O    PHE  156     93.650  42.460  64.695  1.00  34.20      ras
ATOM   4897  N    TYR  157     94.739  43.338  62.953  1.00  34.46      ras
ATOM   4898  CA   TYR  157     96.046  42.994  63.514  1.00  38.67      ras
ATOM   4899  CB   TYR  157     97.186  43.390  62.566  1.00  39.66      ras
ATOM   4900  CG   TYR  157     97.276  42.563  61.295  1.00  43.32      ras
ATOM   4901  CD1  TYR  157     96.302  41.621  60.972  1.00  42.37      ras
ATOM   4902  CE1  TYR  157     96.398  40.857  59.812  1.00  46.60      ras
ATOM   4903  CD2  TYR  157     98.349  42.719  60.419  1.00  45.75      ras
ATOM   4904  CE2  TYR  157     98.457  41.960  59.256  1.00  44.00      ras
ATOM   4905  CZ   TYR  157     97.481  41.032  58.956  1.00  49.74      ras
ATOM   4906  OH   TYR  157     97.581  40.289  57.794  1.00  51.25      ras
ATOM   4907  C    TYR  157     96.231  43.652  64.891  1.00  38.80      ras
```

Figure 8-82

| ATOM | 4908 | O | TYR | 157 | 96.768 | 43.028 | 65.813 | 1.00 | 40.75 | ras |
| ATOM | 4909 | N | THR | 158 | 95.758 | 44.891 | 65.047 | 1.00 | 35.11 | ras |
| ATOM | 4910 | CA | THR | 158 | 95.880 | 45.570 | 66.335 | 1.00 | 31.71 | ras |
| ATOM | 4911 | CB | THR | 158 | 95.316 | 47.016 | 66.332 | 1.00 | 27.49 | ras |
| ATOM | 4912 | OG1 | THR | 158 | 96.108 | 47.851 | 65.484 | 1.00 | 30.09 | ras |
| ATOM | 4913 | CG2 | THR | 158 | 95.369 | 47.599 | 67.722 | 1.00 | 23.73 | ras |
| ATOM | 4914 | C | THR | 158 | 95.159 | 44.772 | 67.412 | 1.00 | 32.12 | ras |
| ATOM | 4915 | O | THR | 158 | 95.709 | 44.576 | 68.489 | 1.00 | 34.06 | ras |
| ATOM | 4916 | N | LEU | 159 | 93.948 | 44.290 | 67.123 | 1.00 | 31.36 | ras |
| ATOM | 4917 | CA | LEU | 159 | 93.205 | 43.521 | 68.119 | 1.00 | 30.98 | ras |
| ATOM | 4918 | CB | LEU | 159 | 91.801 | 43.158 | 67.627 | 1.00 | 27.46 | ras |
| ATOM | 4919 | CG | LEU | 159 | 90.983 | 42.311 | 68.615 | 1.00 | 31.35 | ras |
| ATOM | 4920 | CD1 | LEU | 159 | 90.868 | 43.012 | 69.950 | 1.00 | 33.01 | ras |
| ATOM | 4921 | CD2 | LEU | 159 | 89.612 | 41.993 | 68.072 | 1.00 | 31.71 | ras |
| ATOM | 4922 | C | LEU | 159 | 93.968 | 42.267 | 68.536 | 1.00 | 33.71 | ras |
| ATOM | 4923 | O | LEU | 159 | 94.016 | 41.923 | 69.723 | 1.00 | 32.03 | ras |
| ATOM | 4924 | N | VAL | 160 | 94.588 | 41.605 | 67.560 | 1.00 | 35.72 | ras |
| ATOM | 4925 | CA | VAL | 160 | 95.358 | 40.399 | 67.829 | 1.00 | 37.53 | ras |
| ATOM | 4926 | CB | VAL | 160 | 95.924 | 39.812 | 66.533 | 1.00 | 37.45 | ras |
| ATOM | 4927 | CG1 | VAL | 160 | 96.971 | 38.754 | 66.837 | 1.00 | 42.21 | ras |
| ATOM | 4928 | CG2 | VAL | 160 | 94.806 | 39.200 | 65.727 | 1.00 | 40.43 | ras |
| ATOM | 4929 | C | VAL | 160 | 96.481 | 40.717 | 68.816 | 1.00 | 39.35 | ras |
| ATOM | 4930 | O | VAL | 160 | 96.661 | 40.016 | 69.817 | 1.00 | 36.57 | ras |
| ATOM | 4931 | N | ARG | 161 | 97.198 | 41.806 | 68.547 | 1.00 | 39.14 | ras |
| ATOM | 4932 | CA | ARG | 161 | 98.286 | 42.249 | 69.409 | 1.00 | 40.11 | ras |
| ATOM | 4933 | CB | ARG | 161 | 98.957 | 43.501 | 68.821 | 1.00 | 35.29 | ras |
| ATOM | 4934 | CG | ARG | 161 | 99.609 | 43.256 | 67.473 | 1.00 | 30.12 | ras |
| ATOM | 4935 | CD | ARG | 161 | 100.321 | 44.486 | 66.931 | 1.00 | 31.35 | ras |
| ATOM | 4936 | NE | ARG | 161 | 101.023 | 44.166 | 65.687 | 1.00 | 36.97 | ras |
| ATOM | 4937 | CZ | ARG | 161 | 100.716 | 44.650 | 64.482 | 1.00 | 38.66 | ras |
| ATOM | 4938 | NH1 | ARG | 161 | 99.707 | 45.505 | 64.334 | 1.00 | 37.06 | ras |
| ATOM | 4939 | NH2 | ARG | 161 | 101.403 | 44.250 | 63.413 | 1.00 | 32.26 | ras |
| ATOM | 4940 | C | ARG | 161 | 97.770 | 42.513 | 70.831 | 1.00 | 42.84 | ras |
| ATOM | 4941 | O | ARG | 161 | 98.427 | 42.167 | 71.810 | 1.00 | 45.27 | ras |
| ATOM | 4942 | N | GLU | 162 | 96.572 | 43.082 | 70.938 | 1.00 | 43.77 | ras |
| ATOM | 4943 | CA | GLU | 162 | 95.972 | 43.358 | 72.239 | 1.00 | 45.50 | ras |
| ATOM | 4944 | CB | GLU | 162 | 94.657 | 44.117 | 72.073 | 1.00 | 45.29 | ras |
| ATOM | 4945 | CG | GLU | 162 | 94.828 | 45.572 | 71.666 | 1.00 | 49.28 | ras |
| ATOM | 4946 | CD | GLU | 162 | 95.393 | 46.433 | 72.783 | 1.00 | 49.96 | ras |
| ATOM | 4947 | OE1 | GLU | 162 | 94.893 | 46.306 | 73.919 | 1.00 | 50.13 | ras |
| ATOM | 4948 | OE2 | GLU | 162 | 96.322 | 47.235 | 72.526 | 1.00 | 45.47 | ras |
| ATOM | 4949 | C | GLU | 162 | 95.729 | 42.065 | 73.012 | 1.00 | 45.57 | ras |
| ATOM | 4950 | O | GLU | 162 | 95.812 | 42.049 | 74.238 | 1.00 | 49.62 | ras |
| ATOM | 4951 | N | ILE | 163 | 95.441 | 40.985 | 72.291 | 1.00 | 43.63 | ras |
| ATOM | 4952 | CA | ILE | 163 | 95.199 | 39.689 | 72.912 | 1.00 | 43.70 | ras |
| ATOM | 4953 | CB | ILE | 163 | 94.518 | 38.721 | 71.929 | 1.00 | 42.08 | ras |
| ATOM | 4954 | CG2 | ILE | 163 | 94.293 | 37.369 | 72.586 | 1.00 | 39.47 | ras |
| ATOM | 4955 | CG1 | ILE | 163 | 93.195 | 39.313 | 71.452 | 1.00 | 38.60 | ras |
| ATOM | 4956 | CD1 | ILE | 163 | 92.460 | 38.442 | 70.479 | 1.00 | 40.43 | ras |
| ATOM | 4957 | C | ILE | 163 | 96.515 | 39.073 | 73.389 | 1.00 | 46.62 | ras |
| ATOM | 4958 | O | ILE | 163 | 96.614 | 38.592 | 74.519 | 1.00 | 46.18 | ras |
| ATOM | 4959 | N | ARG | 164 | 97.521 | 39.089 | 72.519 | 1.00 | 49.07 | ras |
| ATOM | 4960 | CA | ARG | 164 | 98.835 | 38.543 | 72.846 | 1.00 | 48.45 | ras |
| ATOM | 4961 | CB | ARG | 164 | 99.784 | 38.670 | 71.653 | 1.00 | 46.05 | ras |
| ATOM | 4962 | CG | ARG | 164 | 99.500 | 37.700 | 70.529 | 1.00 | 45.27 | ras |
| ATOM | 4963 | CD | ARG | 164 | 100.329 | 38.016 | 69.297 | 1.00 | 45.53 | ras |
| ATOM | 4964 | NE | ARG | 164 | 100.096 | 37.039 | 68.239 | 1.00 | 44.23 | ras |
| ATOM | 4965 | CZ | ARG | 164 | 100.571 | 37.135 | 67.002 | 1.00 | 44.50 | ras |
| ATOM | 4966 | NH1 | ARG | 164 | 101.320 | 38.175 | 66.648 | 1.00 | 43.21 | ras |
| ATOM | 4967 | NH2 | ARG | 164 | 100.277 | 36.195 | 66.112 | 1.00 | 43.19 | ras |
| ATOM | 4968 | C | ARG | 164 | 99.441 | 39.239 | 74.056 | 1.00 | 48.10 | ras |

Figure 8-83

```
ATOM   4969  O    ARG  164      99.888  38.581  74.989  1.00 49.06      ras
ATOM   4970  N    GLN  165      99.415  40.568  74.049  1.00 49.21      ras
ATOM   4971  CA   GLN  165      99.972  41.360  75.141  1.00 55.72      ras
ATOM   4972  CB   GLN  165     100.255  42.780  74.661  1.00 58.53      ras
ATOM   4973  CG   GLN  165     101.227  42.844  73.500  1.00 66.52      ras
ATOM   4974  CD   GLN  165     101.412  44.249  72.960  1.00 70.16      ras
ATOM   4975  OE1  GLN  165     102.113  44.450  71.965  1.00 73.83      ras
ATOM   4976  NE2  GLN  165     100.784  45.231  73.610  1.00 69.19      ras
ATOM   4977  C    GLN  165      99.068  41.401  76.366  1.00 57.35      ras
ATOM   4978  O    GLN  165      99.171  42.300  77.201  1.00 58.59      ras
ATOM   4979  N    HIS  166      98.199  40.407  76.480  1.00 59.52      ras
ATOM   4980  CA   HIS  166      97.269  40.321  77.595  1.00 63.45      ras
ATOM   4981  CB   HIS  166      95.834  40.359  77.055  1.00 66.59      ras
ATOM   4982  CG   HIS  166      94.782  40.297  78.115  1.00 70.68      ras
ATOM   4983  CD2  HIS  166      93.954  41.249  78.604  1.00 72.45      ras
ATOM   4984  ND1  HIS  166      94.486  39.140  78.802  1.00 73.34      ras
ATOM   4985  CE1  HIS  166      93.521  39.382  79.671  1.00 75.61      ras
ATOM   4986  NE2  HIS  166      93.181  40.655  79.571  1.00 75.70      ras
ATOM   4987  C    HIS  166      97.522  39.031  78.378  1.00 63.34      ras
ATOM   4988  O    HIS  166      97.543  39.110  79.621  1.00 59.29      ras
ATOM   4989  OT   HIS  166    9999.0009999.0009999.000  1.00  0.00      ras
ATOM   4990  O    HOH    1      69.299  32.369  96.154  1.00 25.14      wat
ATOM   4991  O    HOH    2      55.542  23.355  83.075  1.00 41.80      wat
ATOM   4992  O    HOH    3      63.755  32.926  64.057  1.00 39.83      wat
ATOM   4993  O    HOH    4      73.092  45.998  59.527  1.00 24.81      wat
ATOM   4994  O    HOH    5      74.894  61.523  62.272  1.00 31.78      wat
ATOM   4995  O    HOH    6      82.477  43.373  59.812  1.00 33.10      wat
ATOM   4996  O    HOH    7      81.024  40.935  57.522  1.00 32.38      wat
ATOM   4997  O    HOH    8      77.096  40.473  68.317  1.00 31.48      wat
ATOM   4998  O    HOH    9      68.149  28.273  59.475  1.00 25.69      wat
ATOM   4999  O    HOH   10      66.815  33.640  28.729  1.00 53.77      wat
ATOM   5000  O    HOH   11      65.439  51.704  26.104  1.00 40.04      wat
ATOM   5001  O    HOH   12      61.946  44.526  49.630  1.00 29.31      wat
ATOM   5002  O    HOH   13      63.194  49.565  54.927  1.00 28.90      wat
ATOM   5003  O    HOH   14      43.364  25.822  87.328  1.00 60.71      wat
ATOM   5004  O    HOH   15      41.602  26.163  72.376  1.00 35.06      wat
ATOM   5005  O    HOH   16      49.525  28.716  70.468  1.00 43.22      wat
ATOM   5006  O    HOH   17      78.124  23.228  66.046  1.00 35.79      wat
ATOM   5007  O    HOH   18      79.663  55.785  72.976  1.00 35.57      wat
ATOM   5008  O    HOH   19      58.528  42.327  77.044  1.00 34.00      wat
ATOM   5009  O    HOH   20      77.367  40.161  94.623  1.00 29.24      wat
ATOM   5010  O    HOH   21      60.209  17.900  88.460  1.00 36.53      wat
ATOM   5011  O    HOH   22      77.995  41.999  64.087  1.00 47.66      wat
ATOM   5012  O    HOH   23      76.550  44.191  67.484  1.00 38.12      wat
ATOM   5013  O    HOH   24      75.990  48.437  60.460  1.00 32.28      wat
ATOM   5014  O    HOH   25      81.857  38.271  57.371  1.00 34.53      wat
ATOM   5015  O    HOH   26      89.482  37.565  76.274  1.00 38.75      wat
END
```

CRYSTAL OF A RAS-SOS COMPLEX AND METHODS OF USE THEREOF

GOVERNMENTAL SUPPORT

The research leading to the present invention was supported, at least in part, by grants from National Institutes of Health, Grant No. F32 DK09664-1, Grant No. 5P01 CA2814618, and Grant No. 5R01 CA5536008-1. Accordingly, the Government may have certain rights in the invention.

FIELD OF THE INVENTION

The present invention provides a crystal of a complex of Ras with the Son of sevenless (Sos) protein. The three-dimensional structural information is included in the invention. The interaction between these two proteins plays a key role in the regulation of cell proliferation. Therefore, the present invention provides procedures for identifying agents that can inhibit tumor proliferation through the use of rational drug design predicated on the crystallographic data.

BACKGROUND OF THE INVENTION

Ras proteins are highly conserved guanine nucleotide binding enzymes that couple cell surface receptors to intracellular signaling pathways controlling cell proliferation and differentiation [Bourne et al., *Nature*, 349:117–127 (1991); Boguski and McCormick, *Nature*, 366:643–654 (1993)]. Ras proteins act as molecular switches by cycling between an active GTP-bound state and an inactive GDP-bound state. The nucleotide bound state of Ras is not determined by intrinsic equilibrium with cytoplasmic pools of guanine nucleotides but by the relative activities of two classes of regulatory proteins: GTPase activating proteins (GAPs) and guanine nucleotide exchange factors (GEFs). Exchange factors promote the activation of Ras by catalyzing exchange of GDP for GTP, whereas activating proteins control the conversion of Ras to the inactive state by stimulating the hydrolysis of GTP to GDP [Boguski and McCormick, *Nature*, 366:643–654 (1993)].

Cell surface receptors that signal via tyrosine kinases activate Ras by stimulating the guanine nucleotide exchange reaction [Medema et al., *Molec. Cell. Biol.*, 13:155–162 (1993); Buday and Downward, *Cell*, 73:611–620 (1993); Gale et al., *Nature*, 363:88–92 (1993)]. Genetic and biochemical studies have indicated that this reaction is controlled by the Ras guanine nucleotide exchange factor Son of sevenless (Sos) [Bar-Sagi, *Trends Endocrin. Metab.*, 5:165–169 (1994)]. Following ligand binding, Sos is recruited from the cytoplasm to the activated receptor in a phosphotyrosine-dependent manner through adapter proteins such as Grb2. Grb2 contains SH3 domains that are bound constitutively to a C-terminal proline-rich region of Sos, and the Grb2-Sos complex is recruited to activated receptors by interactions between the SH2 domain of Grb2 and phosphotyrosine residues on the receptor [Schlessinger, *Trends Biochem. Sci.*, 18:273–275 (1994)]. Since Ras is localized to the membrane, receptor activation results in an increase in the effective concentration of Sos in the vicinity of Ras, thereby facilitating the exchange of bound guanine nucleotide for free cellular guanine nucleotides. The cellular concentrations of GTP are $^{18}10$ fold higher than that of GDP, and Sos-mediated guanine nucleotide exchange on Ras thus leads to transient accumulation of active GTP-bound Ras molecules.

Sos proteins are large (Mr ~150 kD) and contain several functional domains [Chardin et al., *Science*, 260:1338–1343 (1993)]. They are expressed in a wide range of tissues, consistent with their role as activators of the ubiquitously expressed Ras genes. The region of Sos that is functional for nucleotide exchange on Ras spans about 500 residues, and contains blocks of sequence that are conserved in other Ras-specific nucleotide exchange factors such as Cdc25, Sdc25 and Ras guanine nucleotide release factor (GRF) [Boguski and McCormick, *Nature*, 366:643–654 (1993); Poullet et al., *Eur. J. Biochem.*, 227:537–544 (1995)] (FIG. 1). Biochemical studies on these proteins have shown that the Ras-exchange factor complex is stable in the absence of nucleotides, and that the complex is dissociated by the re-binding of either GDP or GTP [Powers et al., *Molec. and Cell. Biol.*, 9:390–395 (1989); Mistou et al., *EMBO J.*, 11:2391–2397 (1992); Lai et al., *Mol. Cell. Biol.*, 13:1345–1352 (1993); Haney and Broach, *J. Biol. Chem.*, 269:16541–16548 (1994)]. The principal role for the exchange factor is to facilitate nucleotide release, and it does not appear to control the preferential rebinding of GTP over GDP to a significant extent [Haney and Broach, *J. Biol. Chem.*, 269:16541–16548 (1994); Klebe et al., *Biochemistry*, 34:12543–12552 (1995)].

The utilization of nucleotide exchange to control the timing of critical molecular events is a mechanism that is common to many different cellular regulators. In addition to small guanine nucleotide binding proteins (G-proteins) homologous to Ras, such as the Arf, Rab, Rho, Rac and Ran, nucleotide exchange is also crucial to the timing cycles of the heterotrimeric G-proteins and ribosomal elongation factor Tu, which have catalytic cores that are structurally and functionally similar to Ras [Bourne et al., *Nature*, 349:117–127 (1991)]. Nucleotide exchange is also critical to the cycles of the protein chaperones of the DnaK/Hsp70 family, which utilize ATP to bind and release peptides and are unrelated in sequence or structure to the GTPases [Harrison et al., *Science*, 276:431–435 (1997)].

In contrast to the high degree of structural conservation seen in the GTPases, there are distinct families of nucleotide exchange factors that are unrelated to each other. The structures of several small G-protein exchange factors have been determined in isolation, revealing a variety of protein architectures (Mss4 [Yu and Schreiber, *Nature*, 376:788–791 (1995)], ARNO/Sec7 [Mossessova et al., *Cell*, 92:415–423 (1998); Cherfils et al., *Nature*, 392:101–105 (1998)] and RCC1 [Renault et al., *Nature*, 392:97–101 (1998)]). At the present time the structure of only one nucleotide exchange factor bound to its cognate guanine nucleotide binding proteins has been determined, that of EF-Tu bound to its exchange factor EF-Ts [Wang et al., *Nat. Struct. Biol.*, 4:650–656 (1997); Kawashima et al., *Nature*, 379:511–518 (1996)]. In addition, the structure of the ATPase domain of DnaK bound to its exchange factor GrpE has also been determined [Harrison et al., *Science*, 276:431–435 (1997)]. No structural information is available on Ras-type small G-proteins complexed with their nucleotide exchange factors.

One means of modulating cellular proliferation and/or differentiation is to either inhibit or facilitate the Ras-Sos interaction. Therefore, there is a need to identify agonists or antagonists to the Ras-Sos complex. Unfortunately, such identification has heretofore relied on serendipity and/or systematic screening of large numbers of natural and synthetic compounds. A far superior method of drug-screening relies on structure based drug design. In this case, the three dimensional structure of Ras-Sos complex is determined and potential agonists and/or potential antagonists are designed with the aid of computer modeling [Bugg et al., *Scientific*

American, Dec.:92–98 (1993); West et al., *TIPS*, 16:67–74 (1995); Dunbrack et al., *Folding & Design*, 2:27–42 (1997)]. However, heretofore the three-dimensional structure of the Ras-Sos complex has remained unknown. Therefore, there is a need for obtaining a crystal of a Ras-Sos complex with sufficient quality to allow high quality crystallographic data to be obtained. Furthermore there is a need for the determination of the three-dimensional structure of such crystals. Finally, there is a need for procedures for related structural based drug design predicated on such crystallographic data.

The citation of any reference herein should not be construed as an admission that such reference is available as "Prior Art" to the instant application.

SUMMARY OF THE INVENTION

The present invention provides crystals of the Ras-Son of sevenless protein-protein binding complex (Ras-Sos complex). In addition, the present invention also provides detailed three-dimensional structural data for the Ras-Sos complex. Since the interaction between Ras and Sos plays a key role in the regulation of cell propagation and differentiation, the structural data obtained for the Ras-Sos complex can be used for the rational design of drugs that modulate cell proliferation. Therefore, the present invention further provides methods of identifying agonists or antagonists of the Ras-Sos complex which can be used in the regulation of cellular proliferation and/or differentiation. In a particular embodiment, such methodology can be used in the identification of drugs that inhibit tumor proliferation.

One aspect of the present invention provides crystals of the Ras-Sos complex that can effectively diffract X-rays for the determination of the atomic coordinates of the complex to a resolution of better than 5.0 Angstroms. In a preferred embodiment the crystal effectively diffracts X-rays for the determination of the atomic coordinates of the protein-ligand complex to a resolution of better than 3.0 Angstroms. In a particular embodiment the crystal effectively diffracts X-rays for the determination of the atomic coordinates of the protein-ligand complex to a resolution of 2.8 Angstroms.

In one embodiment, the crystal of the Ras-Sos complex comprises a full length Ras and a full length Sos. In a preferred embodiment of this type the full length Ras has the amino acid sequence of SEQ ID No:1 or the amino acid sequence of SEQ ID No:1 having one or more conservative amino acid substitutions and the full length Sos has the amino acid sequence of SEQ ID NO:2 or the amino acid sequence of SEQ ID NO:2 having one or more conservative amino acid substitutions. In another embodiment, the Ras-Sos complex comprises a full length Ras and a fragment of the Sos which minimally contains a Sos catalytic domain. In yet another embodiment, the Ras-Sos complex comprises a full length Sos and a fragment of the Ras which minimally contains the Sos contacting region.

In a related feature of the invention the crystal of the Ras-Sos complex comprises a Ras fragment, and a Sos fragment. In one such embodiment the Ras fragment comprises a Sos contacting region and the Sos fragment comprises a Sos catalytic domain. In a particular embodiment of this type the Sos catalytic domain comprises the amino acid sequence of amino acids 781 to 1017 of SEQ ID NO:2. In another embodiment the Sos catalytic domain comprises amino acid sequence of amino acid 781 to 1017 of SEQ ID NO:2 having one or more conservative amino acid substitutions. In a preferred embodiment of this type the Sos fragment contains amino acids 752 to 1044 of the amino acid sequence of SEQ ID NO:2. In a related embodiment the Sos fragment contains amino acids 752 to 1044 of SEQ ID NO:2 having one or more conservative amino acid substitutions. In a particular embodiment the Sos fragment comprises the Sos catalytic domain and an N-Domain. In a preferred embodiment of this type the Sos fragment comprises the amino acid sequence of amino acids 564 to 1049 of SEQ ID NO:2. In yet another embodiment the Sos fragment comprises the amino acid sequence of amino acid 564 to 1049 of SEQ ID NO:2 having one or more conservative amino acid substitutions.

In another particular embodiment the crystal of the Ras-Sos complex comprises a Ras fragment containing the Sos contacting region having the amino acid sequence of amino acids 5 to 105 of SEQ ID NO: 1. In another embodiment, the crystal comprises a Ras fragment that further comprises the amino acid sequence of amino acids 1 to 4 and 106 to 166 of SEQ ID NO: 1 (i.e., the Ras fragment comprises amino acids 1 to 166 of SEQ ID NO:1). In another embodiment, the Ras fragment contains a Sos contacting region having the amino acid sequence of amino acid 5 to 105 of SEQ ID NO: 1 having one or more conservative amino acid substitutions. In a related embodiment, the Ras fragment further comprises amino acids 1 to 4 and 106 to 166 of SEQ ID NO:1 having one or more conservative amino acid substitutions (i.e., the Ras fragment comprises amino acids 1 to 166 of SEQ ID NO:1 having one or more conservative amino acid substitutions). In still another embodiment of this type the crystal comprises a Ras fragment that contains amino acids 5 to 160 of the amino acid sequence of SEQ ID NO:1. In a related embodiment the crystal comprises a Ras fragment that contains amino acids 5 to 160 of SEQ ID NO:1 having one or more conservative amino acid substitutions.

In a preferred embodiment the crystal comprises a Ras fragment comprising amino acids 1 to 166 of SEQ ID NO:1 or a Ras fragment comprising amino acids 1 to 166 of SEQ ID NO:1 having one or more conservative amino acid substitutions and a Sos fragment comprising the amino acid sequence of amino acids 564 to 1049 of SEQ ID NO:2, or the amino acid sequence of amino acid 564 to 1049 of SEQ ID NO:2 having one or more conservative amino acid substitutions.

A crystal of the present invention may take a variety of forms all of which are included in the present invention. In one embodiment the crystal has a space group of I4 or I422 and a unit cell of dimensions of a=124.6 Å, b=124.6 Å and c=314.9 Å. In a preferred embodiment the crystal has a space group of I422 and a unit cell of dimensions of a=142.7 Å, b=142.7 Å and c=207.9 Å.

The present invention further provides portions of Ras and Sos that not only bind to form a Ras-Sos complex, but in addition, form complexes that are amenable to crystallization. Preferably, these portions (e.g., Ras and/or Sos fragments) are soluble in aqueous solutions. Therefore this aspect of the present invention provides a Ras fragment that comprises the Sos contacting region. In a particular embodiment of this type, the Ras fragment contains amino acids 5 to 105 of the amino acid sequence of SEQ ID NO:1. In a related embodiment the Ras fragment contains amino acids 5 to 105 of SEQ ID NO:1 having one or more conservative amino acid substitutions. In a preferred embodiment of this type the Ras fragment contains amino acids 5 to 160 of the amino acid sequence of SEQ ID NO:1. In a related embodiment the Ras fragment contains amino acids 5 to 160 of SEQ ID NO:1 having one or more conservative amino acid substitutions. In a more preferred embodiment of this type the Ras fragment contains amino acids 1 to 166 of the amino acid sequence of SEQ ID NO:1. In a related embodiment the Ras fragment contains amino acids 1 to 166 of SEQ ID NO:1 having one or more conservative amino acid substitutions.

In another embodiment a Sos fragment of the present invention comprises the Sos catalytic domain. In a particular embodiment of this type, the Sos fragment contains amino acids 781 to 1017 of the amino acid sequence of SEQ ID NO:2. In a related embodiment the Sos fragment contains amino acids 781 to 1017 of SEQ ID NO:2 having one or more conservative amino acid substitutions. In a preferred embodiment of this type the Sos fragment contains amino acids 752 to 1044 of the amino acid sequence of SEQ ID NO:2. In a related embodiment the Sos fragment contains amino acids 752 to 1044 of SEQ ID NO:2 having one or more conservative amino acid substitutions. In a more preferred embodiment of this type the Sos fragment contains amino acids 564 to 1049 of the amino acid sequence of SEQ ID NO:2. In a related embodiment the Sos fragment contains amino acids 564 to 1049 of SEQ ID NO:2 having one or more conservative amino acid substitutions.

The present invention also includes nucleic acids encoding the Ras fragments and Sos fragments of the present invention. In a particular embodiment of this type, the nucleic acid encodes a Ras fragment that contains amino acids 5 to 105 of the amino acid sequence of SEQ ID NO:1. In a related embodiment the nucleic acid encodes a Ras fragment that contains amino acids 5 to 105 of SEQ ID NO:1 having one or more conservative amino acid substitutions. In a preferred embodiment of this type the nucleic acid encodes a Ras fragment that contains amino acids 5 to 160 of the amino acid sequence of SEQ ID NO:1. In a related embodiment the nucleic acid encodes a Ras fragment that contains amino acids 5 to 160 of SEQ ID NO:1 having one or more conservative amino acid substitutions. In a more preferred embodiment of this type the nucleic acid encodes a Ras fragment that contains amino acids 1 to 166 of the amino acid sequence of SEQ ID NO:1. In a related embodiment the nucleic acid encodes a Ras fragment that contains amino acids 1 to 166 of SEQ ID NO:1 having one or more conservative amino acid substitutions.

In another embodiment the nucleic acid encodes a Sos fragment of the present invention that comprises the Sos catalytic domain. In a particular embodiment of this type, the nucleic acid encodes a Sos fragment that contains amino acids 781 to 1017 of the amino acid sequence of SEQ ID NO:2. In a related embodiment the nucleic acid encodes a Sos fragment that contains amino acids 781 to 1017 of SEQ ID NO:2 having one or more conservative amino acid substitutions. In a preferred embodiment of this type the nucleic acid encodes a Sos fragment that contains amino acids 752 to 1044 of the amino acid sequence of SEQ ID NO:2. In a related embodiment the nucleic acid encodes a Sos fragment that contains amino acids 752 to 1044 of SEQ ID NO:2 having one or more conservative amino acid substitutions. In a more preferred embodiment of this type the nucleic acid encodes a Sos fragment that contains amino acids 564 to 1049 of the amino acid sequence of SEQ ID NO:2. In a related embodiment the nucleic acid encodes a Sos fragment that contains amino acids 564 to 1049 of SEQ ID NO:2 having one or more conservative amino acid substitutions.

The present invention also provides expression vectors which comprise a nucleic acid of the present invention (as exemplified above) operatively associated with an expression control sequence. The present invention further includes a cell transfected or transformed with an expression vector of the present invention. In one such embodiment the cell is a prokaryotic cell. In a preferred embodiment of this type the prokaryotic cell is an *E. coli* cell. In another embodiment the cell is a eukaryotic cell. In one such embodiment of this type the eukaryotic cell is an insect cell. In another such embodiment the eukaryotic cell is a vertebrate cell. In a preferred embodiment the vertebrate cell is a mammalian cell.

The present invention also includes methods of expressing the nucleic acids of the present invention comprising culturing a cell that expresses the Ras fragment or Sos fragment of the present invention, for example, in an appropriate cell culture medium under conditions that provide for expression of the protein by the cell. Any of the cells mentioned above may be employed in this method. In a particular embodiment the cell is an *E.coli* cell which has been manipulated to express a Ras fragment or Sos fragment of the present invention. In a preferred embodiment, the method further includes the step of purifying the Ras fragment or Sos fragment.

The present invention further includes methods of using the Ras fragments and Sos fragments of the present invention to grow a crystal of the Ras-Sos complex. One such method comprises contacting the Ras fragment and Sos fragment under conditions in which a Ras-Sos complex is formed and growing the crystal of the Ras-Sos complex. Preferably the crystal effectively diffracts X-rays for the determination of the atomic coordinates of the protein-ligand complex to a resolution of better than 5.0 Angstroms. In one such embodiment the Ras fragment is between about 100 to 170 amino acids and contains amino acids 5 to 105 of SEQ ID NO:1, or amino acids 5 to 105 of SEQ ID NO:1 having one or more conservative amino acid substitutions. In another embodiment the Sos fragment is between about 230 to 500 amino acids and contains amino acids 781 to 1017 of SEQ ID NO:2, or the amino acids 781 to 1017 of SEQ ID NO:2 having one or more conservative amino acid substitutions.

In a particular embodiment the crystal is grown by vapor diffusion. In one such embodiment the crystal is grown by hanging-drop vapor diffusion. In another embodiment the crystal is grown by sitting-drop vapor diffusion. Standard micro and/or macro seeding may be used to obtain a crystal of X-ray quality, i.e. a crystal that will diffract to allow resolution better than 5.0 Angstoms. Although the full length Ras protein and any number of Ras fragments containing the Sos contacting region may be used, preferably the Ras fragment comprises amino acids 5 to 160 of SEQ ID NO:1. Similarly in a preferred embodiment a Sos fragment is used comprising amino acids 752 to 1044 of the amino acid sequence of SEQ ID NO:2.

Still another aspect of the present invention comprises a method of using a crystal of the present invention and/or a dataset comprising the three-dimensional coordinates obtained from the crystal in a drug screening assay. Example 2 below, exemplifies the use of such information to rationally design potentially important compounds that in turn can minimally be used as starting points in the drug screens.

In addition, the present invention provides three-dimensional coordinates for the Ras-Sos complex. In a particular embodiment the coordinates are for the human Ras-Sos complex as disclosed in FIGS. 8-1 through 8-75. Thus the data set of FIGS. 8-1 through 8-75, below, is part of the present invention. Furthermore, the data set of FIGS. 8-1 through 8-75, below, in a computer readable form is also part of the present invention. In addition, methods of using such coordinates (including in computer readable form) in the drug assays and drug screens as exemplified herein, are also part of the present invention. In a particular embodiment of this type, the coordinates contained in the data set of FIGS. 8-1 through 8-75, below, can be used to identify potential modulators of the Ras-Sos interaction. In one such embodiment the potential modulator is an inhibitor of the Sos nucleotide exchange reaction with Ras.

Accordingly, the present invention provides methods of identifying an agent or drug that stabilizes the Ras-Sos complex, or alternatively inhibit the formation of the Ras-Sos complex (see Example 2, below). The identification of such drugs can aid in the treatment of cancer, since activated Ras is involved in the proliferation of tumor cells, and the association and subsequent dissociation of Sos from Ras is a required step for the activation of Ras.

One such embodiment comprises selecting a potential agent that can stabilize the Ras-Sos complex by performing rational drug design with the three-dimensional coordinates determined for the crystal. Preferably the selection is performed in conjunction with computer modeling. The potential agent is then contacted with the Ras-Sos complex and the stability of the Ras-Sos complex is determined. A potential agent (or drug) is selected as an agent (or drug) that can stabilize the Ras-Sos complex when there is an increase in the stability of the Ras-Sos complex.

In a particular embodiment of this type, the method further comprises growing a supplemental crystal containing a Ras-Sos complex formed in the presence of the potential agent. Preferably the resulting crystal effectively diffracts X-rays for the determination of the atomic coordinates of the protein-ligand complex to a resolution of better than 5.0 Angstroms (more preferably better than 3.0 Angstroms). The three-dimensional coordinates of the supplemental crystal is determined with molecular replacement analysis and a second generation agent (or drug) is selected by performing rational drug design with the three-dimensional coordinates determined for the supplemental crystal. Preferably, the selection is performed in conjunction with computer modeling.

As should be readily apparent the three-dimensional structure of a supplemental crystal can be determined by molecular replacement analysis or multiwavelength anomalous dispersion or multiple isomorphous replacement. A candidate drug is then selected by performing rational drug design with the three-dimensional structure determined for the supplemental crystal, preferably in conjunction with computer modeling. The candidate drug can then be tested in a large number of drug screening assays using standard biochemical methodology exemplified herein.

The present invention further provides methods of selecting an agent that inhibits the binding of GTP to the Ras protein contained in a Ras-Sos complex using a crystal of the present invention or a dataset comprising the three-dimensional coordinates obtained from the crystal. One such embodiment comprises selecting a potential agent by performing rational drug design with the three-dimensional coordinates determined for the crystal. Preferably the selection is performed in conjunction with computer modeling. The potential agent is then contacted with (i) a Ras-Sos complex, and (ii) GTP or a GTP analog, under conditions in which the Ras-Sos complex can bind GTP and/or the GTP analog in the absence of the agent. The binding affinity of the Ras-Sos complex with GTP and/or the GTP analog is determined. A potential agent is selected as an agent that inhibits the binding of GTP to a Ras contained in a Ras-Sos complex when there is a decrease in the binding affinity of GTP or the GTP analog with the Ras in the presence of the agent. In a particular embodiment of this type, labeled GTP or a labeled GTP analog is used, and the binding affinity of GTP and/or the GTP analog for Ras is determined through the detection of the label.

In a particular embodiment of this type, the method further comprises growing a supplemental crystal containing a Ras-Sos complex formed in the presence of the potential agent. The crystal grown effectively diffracts X-rays for the determination of the atomic coordinates of the protein-ligand complex to a resolution of better than 5.0 Angstroms (preferably better than 3.0 Angstroms). The three-dimensional coordinates of the supplemental crystal is determined with molecular replacement analysis and a second generation agent (or drug) is selected by performing rational drug design with the three-dimensional coordinates determined for the supplemental crystal. Preferably, the selection is performed in conjunction with computer modeling. As discussed above, the three-dimensional structure of a supplemental crystal can be determined by molecular replacement analysis or multiwavelength anomalous dispersion or multiple isomorphous replacement and the candidate drug can then be selected by performing rational drug design with the three-dimensional structure determined for the supplemental crystal, preferably in conjunction with computer modeling. The candidate drug can then be tested in a large number of drug screening assays using standard biochemical methodology exemplified herein.

The present invention further provides methods of identifying agents (or drugs) that inhibit the formation of the Ras-Sos complex using a crystal of the present invention, and/or a dataset comprising the three-dimensional coordinates obtained from the crystal. One such embodiment comprises the selection of a potential agent that mimics a structural feature of Ras formed when Ras is bound to Sos. The selection is performed using rational drug design with the three-dimensional coordinates determined for the crystal. Preferably the selection is performed in conjunction with computer modeling. The potential agent is then contacted with either Sos alone or Sos in the presence of Ras under conditions in which the Ras-Sos complex can form in the absence of the potential agent. In the former case, after the contacting of the Sos with the agent, the Sos and potential agent are then contacted with Ras under conditions in which the Ras-Sos complex can form in the absence of the potential agent. The binding affinity of Ras for Sos is then determined (e.g., measured) and a potential agent is identified as an agent that inhibits the formation of the Ras-Sos complex when there is an decrease in the binding affinity of Ras for Sos.

In a particular embodiment of this type, the structural feature of Ras formed when Ras is bound to Sos is the β-turn of amino acids 64 to 67 of SEQ ID NO:1 as described in Example 2, below.

Computer analysis may be performed with one or more of the computer programs including: QUANTA, CHARMM, INSIGHT, SYBYL, MACROMODEL and ICM [Dunbrack et al., *Folding & Design*, 2:27–42 (1997)]. In a further embodiment of this aspect of the invention, an initial drug screening assay is performed using the three-dimensional structure so obtained, preferably along with a docking computer program. Such computer modeling can be performed with one or more Docking programs such as DOC, GRAM and AUTO DOCK [Dunbrack et al., *Folding & Design*, 2:27–42 (1997)].

It should be understood that in all of the drug screening assays provided herein, a number of iterative cycles of any or all of the steps may be performed to optimize the selection. For example, assays and drug screens that monitor the nucleotide exchange rate of Ras catalyzed by Sos in the presence and/or absence of a potential modulator (or potential drug) are also included in the present invention and can be employed as the sole assay or drug screen, or more preferably as a single step in a multi-step protocol for identifying modulators of Ras-dependent cellular proliferation and the like.

The present invention further provides the novel agents (modulators or drugs) that are identified by a method of the present invention, along with the method of using agents (modulators or drugs) identified by a method of the present invention, for inhibiting Ras-dependent cellular proliferation.

Accordingly, it is a principal object of the present invention to provide a crystal containing the Ras-Sos complex.

It is a further object of the present invention to provide the three-dimensional coordinates of the Ras-Sos complex.

It is a further object of the present invention to provide soluble fragments of Sos that bind Ras.

It is a further object of the present invention to provide soluble fragments of Ras that bind Sos.

It is a further object of the present invention to provide methods of identifying drugs that can modulate cellular proliferation.

It is a further object of the present invention to provide methods for the rational design of drugs that stabilize the Ras-Sos complex It is a further object of the present invention to provide methods for the rational design of drugs that bind to Sos and prevent it from interacting with Ras.

These and other aspects of the present invention will be better appreciated by reference to the following drawings and Detailed Description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 2A shows a ribbon diagram of the Ras-Sos complex. The N-Domain of Sos (residues 568 to 741) is blue; the catalytic domain (residues 752 to 1044) is green; Ras is shaded gray. Conserved regions among Ras family exchange factors are indicated and shaded red (SCR1, SCR2, and SCR3 [Boguski and McCormick, Nature, 366:643–654 (1993)]) and cyan (SCR0 [Lai et al., Mol. Cell. Biol., 13:1345–1352 (1993)]). Disordered residues of Sos (591–596, 654–675, 742–751) are shown as dotted lines. All ribbon diagrams were generated using RIBBONS [Carson, J Appl. Cryst., 24:958–961 (1991)]. FIG. 2B shows the Ras-Sos complex with the catalytic domain of Sos depicted as a molecular surface. The N-Domain is shown as a ribbon with the same color scheme as FIG. 2A,); disordered residues connecting the N-Domain and the catalytic domain are not represented. Conserved residues Ile 956 and Phe 958 in the catalytic domain that form a hydrophobic interface with the N-Domain are labeled. The polypeptide backbone is shown in white, except the P-loop and surrounding residues (1–25) which are red and the Switch 1 (residues 25–40) and Switch 2 (residues 57–75) segments which are orange. This and all figures with molecular surfaces were generated using GRASP [Nicholls et al, Proteins: Struct. Funct. and Genetics, 11:281–296 (1991)].

FIG. 4A shows the structure of Ras in the Ras-Sos complex. Residues that form direct interactions with Sos are shown as red spheres; additional residues at the interface are shown as orange spheres. The primary sequence of Ras is shown above with the Switch 1 and Switch 2 regions indicated. GTP and magnesium ion are shown for reference purposes only. FIG. 4B shows the interface surface of Ras; the orientation of Ras is the same as FIG. 4A. The surface is colored using a gradient: bright orange indicates atoms <4 Å from Sos, white indicates atoms >7 Å from Sos, lighter shades of orange indicate intermediate distances. Sos (N-Domain deleted) is shown as a green ribbon.

FIG. 5A depicts selected interactions between Ras and GTP (521P [the code for the coordinates for the 1.35 Å structure of Ras (1–166) bound to a GTP analogue in the Protein Data Bank, Pai et al., EMBO J., 9:2351–2359 (1990)]). Backbone atoms of Ras residues 10–15 (P-loop), 28–35 (Switch 1), and 57–62 (Switch 2) and selected side chains are shown and labeled; water molecules are depicted as red spheres. Selected interactions are shown as dotted lines. GTP is shaded pink and magnesium ion is shown as a magenta sphere. FIG. 5B depicts selected interactions between Ras and Sos in the same orientation as in FIG. 5A. Backbone atoms of Ras residues 10–15, 28–35 and 57–62 and selected side chains are shown and labeled; only helix αH of Sos and selected side chains are shown. GTP and magnesium ion are shown for reference purposes only. FIG. 5C depicts the GTP binding site on the surface of Ras in Ras-GTP (521P [Pai et al., EMBO J., 9:2351–2359 (1990)]). GTP is shaded pink and the magnesium ion is a magenta sphere. The side chain of Tyrosine32 was deleted from the surface calculations in the interests of clarity. FIG. 5D depicts the surface of Ras in the Ras-Sos complex with the backbone of Sos as a green ribbon. Ras is in a slightly different orientation than Ras-GTP in FIG. 5C). The GTP and magnesium ion are shown for reference purposes only.

FIGS. 6A–C show the differences in the Switch 2 regions of Ras-GTP (521P [Pai et al., EMBO J., 9:2351–2359 (1990)]) and Ras-Sos: FIG. 6A is a schematic of the Switch 2 region in Ras-GTP. FIG. 6B is a schematic of the Switch 2 region in Ras-Sos. The loop containing residues 57–67 of Ras is rearranged to form a new series of β-turns and new inter- and intramolecular interactions. Hydrogen bonds are shown as dashed lines, hydrophobic interactions re shown as solid arcs. Magnesium is shown for reference purposes only. FIG. 6C shows that the Switch 2 region of Ras in the Ras-Sos complex is superimposed on the surface of Sos. Selected residues of Sos that make important interactions with Ras are indicated with black labels; residues of Ras are indicated with orange labels. Magnesium and nucleotide are shown for reference purposes only.

FIGS. 8-1 through 8-75 shows the set of atomic coordinates determined by X-ray crystallography of the Ras-Sos complex.

DETAILED DESCRIPTION OF THE INVENTION

Figure 1B:
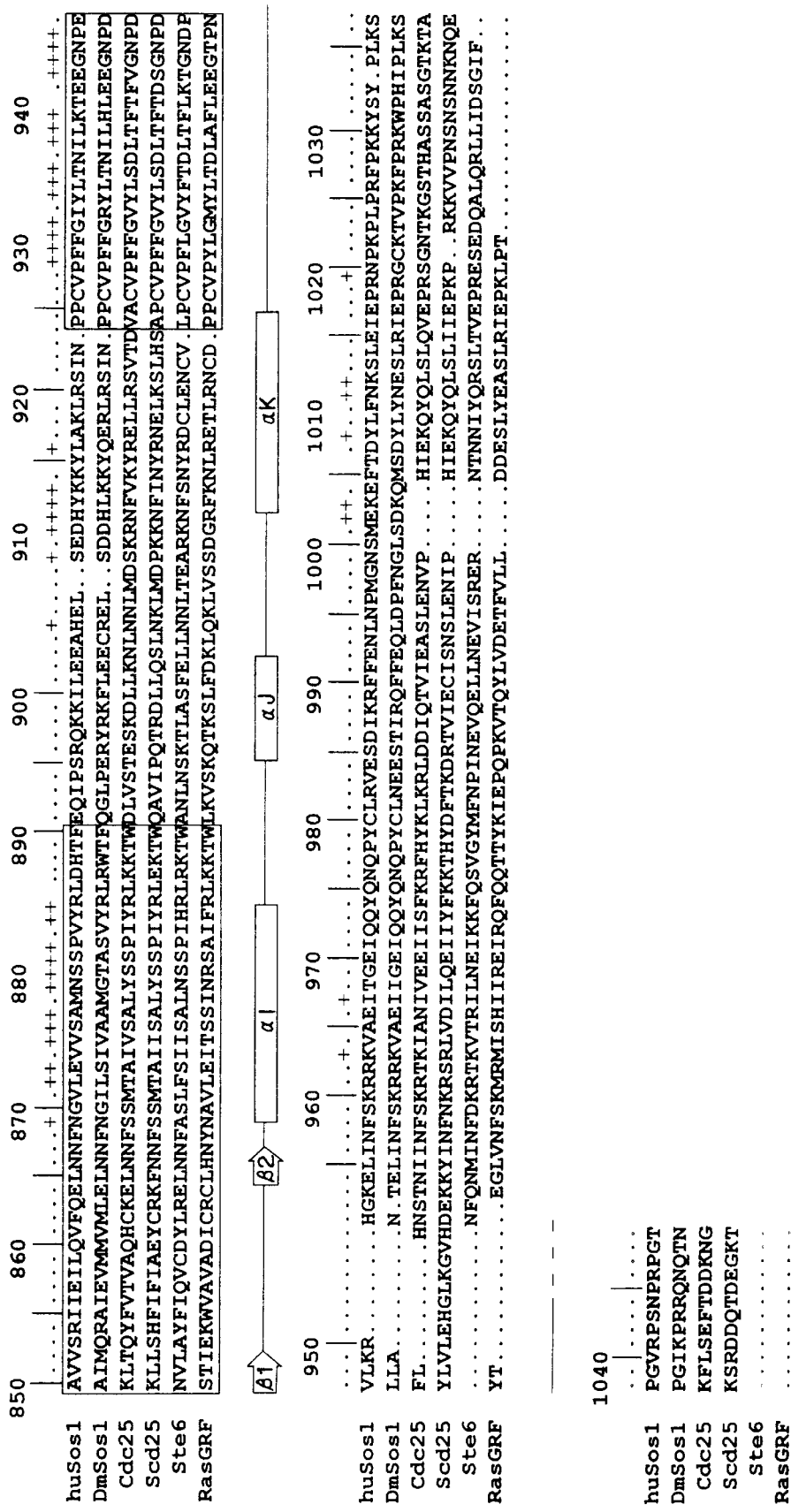
FIG. 1 shows the sequence alignment of Ras-binding exchange factors shown with the secondary structure and residue numbers of Sos indicated. The secondary structure elements (α-helices are shown as rectangles, β-sheets are shown as arrows, coil regions are shown as a solid line, disordered residues are shown as dashed lines) of the N-Domain are blue and of the catalytic domain are green. Conserved regions SCR 1–3 are shaded with red, SCR0 is shaded with blue. Residues of Sos at the Ras interface are indicated with +; residues in the N-Domain that form the hydrophobic core with the catalytic domain are indicated with #. Sequences have been omitted where the sequence similarity between exchange factors is low; residue numbers are indicated at the beginning of alignments.

The present invention provides crystals of a complex of human H-Ras with the Ras guanine nucleotide exchange factor region of the Son of sevenless protein, Sos. Moreover, the present invention provides the structural determination of such crystals by X-ray crystallography. In one such embodiment, the structure of the crystal has been determined at a resolution of 2.8 Å.

The impetus for the present invention was partially based on the fact that the proliferation of cells is critically dependent on the activation state of Ras, and that the nucleotide exchange factor region of Sos is required for the activation of Ras. The present invention therefore employs the three-dimensional structural determination of the Ras-Sos complex disclosed herein, for identifying drugs that can modulate the proliferation of cells. In a particular embodiment, the three-dimensional structural information is used in the design of an inhibitor of cell proliferation for the treatment of cancer.

As a nucleotide exchange factor, Sos functions under two apparently conflicting imperatives. On the one hand, the interaction between Sos and Ras must be sufficiently strong so as to dislodge the tightly bound nucleotide. However, too tight an interaction between Ras and Sos would lead to dead-end complexes, and so the Ras-Sos complex needs to be poised for subsequent displacement by incoming nucleotides. The structure of the Ras-Sos complex disclosed herein demonstrates that Ras and Sos meet these demands by forming a tight complex that is anchored at one end of the nucleotide binding site, where phosphate and magnesium are normally bound. The interface between Sos and Ras is mainly hydrophilic, suggesting a ready unzippering via water mediated displacements of the coordinating sidechains. The main interacting elements of Sos avoid direct occlusion of the nucleotide binding site, excepting the region where the terminal phosphate groups and the magnesium ion are bound. This architectural feature of the complex provides opportunities for incoming nucleotides to reverse the process by competing for the groups that ligate the phosphate and metal ion.

The structural determinations of the present invention show that nucleotide release is facilitated by a large Sos-mediated displacement of the Switch 1 region of Ras, which is responsible for stabilizing the nucleotide in Ras. The conformation of Ras in the complex is inconsistent with nucleotide binding being due to changes in the Switch 1 and Switch 2 regions. The Switch 2 segment is completely buried in the Ras-Sos interface, and changes in its structure result in the disruption of the binding sites for the phosphate groups of the nucleotide and the associated magnesium ion. Sos does not impede the binding sites for the base and the ribose of GTP or GDP, and thus the Ras-Sos complex maintains a structure that permits nucleotide release and rebinding.

The structural information provided by the present invention facilitates the design of inhibitors that can block the activation of Ras by Sos. For example, nucleotide analogs that are designed to recognize the altered nucleotide binding site in the Ras-Sos complex may help to stabilize the Ras-Sos complex, mimicking the action of dominant negative alleles of Ras. Alternatively, hydrophobic compounds that bind to the core hydrophobic region at the heart of the binding site for Ras on Sos may be effective inhibitors of Sos action.

Therefore, the present invention provides methods of identifying agents or drugs that can be used to control the proliferative status of cells, and in particular the proliferation of tumor cells. For example, small-molecule inhibitors of the nucleotide exchange region of Sos can be designed for use as drugs in the treatment of cancer. Similarly, nucleotide analogs can be designed that stabilize the Ras-Sos complex.

Therefore, if appearing herein, the following terms shall have the definitions set out below:

As used herein the term "Ras-Sos complex" denotes the tight protein-protein complex formed between Ras and Sos in the absence of nucleotides. Although the Ras-Sos complex is naturally formed by the full length Ras and Sos proteins, as used herein, the Ras-Sos complex also includes complexes that minimally contain a Sos catalytic domain and the Sos contacting domain of Ras. The three-dimensional structure of the human Ras-Sos complex is disclosed in Example 1, below.

As used herein a "Sos contacting region" of Ras is the region of the Ras protein that is directly involved in binding the nucleotide exchange factor region of Sos. In the human Ras, this region comprises amino acid residues 5–105 of SEQ ID NO:1.

As used herein a "Ras fragment" of the invention that contains a "Sos contacting region" is a fragment of the Ras protein that comprises the portion of the protein that is directly involved in binding the nucleotide exchange domain of Sos.

As used herein, the terms "catalytic domain" of Sos or the "nucleotide exchange factor region" of Sos or the "nucleotide exchange domain" of Sos are terms that are used interchangeably and denote the portion of Sos that binds to Ras and is directly involved in the nucleotide exchange of Ras, (i.e., the release of GDP from Ras). The catalytic domain of Sos can span about 500 amino acid residues, and is exemplified by amino acid residues 781–1017 of SEQ ID NO:2 of human Sos.

As used herein an "active fragment of a Sos" is used interchangeably with the phrase "Sos active fragment" and is a fragment of Sos that minimally contains the catalytic domain of a Sos.

As used herein the "N-Domain" of a Sos is a region of the Sos protein that plays a key role in the stabilization of the Sos catalytic domain. The Sos N-Domain comprises amino acid residues 568–741 of SEQ ID NO:2 of human Sos.

As used herein a "GTP analog" is a small organic molecule (less than 3 Kd) that contains several structural features of guanosine 5'triphosphate but differs from GTP by one or more functional substitutions. Similarly, a "GDP analog" is a small organic molecule (less than 3 Kd) that contains several structural features of guanosine 5'diphosphate but differs from GDP by one or more functional substitutions. Examples of such analogs include those described in Example 2, below.

As used herein a "soluble" Sos fragment or Ras fragment is a fragment of Ras or Sos that is soluble in a buffered aqueous solution at a concentration of about 0.5 mg/ml.

As used herein a "small molecule β-turn mimic" of Ras is used interchangeably with a "β-turn small molecule mimic" of Ras and is a small molecule (less than 3 Kd) that mimics the conformational change in Ras that takes place upon Ras binding of Sos including those described herein. Such small molecule β-turn mimics are exemplified in Example 2, below.

As used herein a "β-turn of amino acids" is a unit of protein secondary structure that is maintained by a hydrogen bond between a backbone carbonyl oxygen from a given amino acid residue at position X in the amino acid sequence and a backbone NH from a residue at the position of X+4 in the amino acid sequence. A β-turn of amino amino acids is exemplified in FIG. 7E.

As used herein the term "about" means within 10 to 15%, preferably within 5 to 10%. For example an amino acid sequence that contains about 60 amino acid residues can contain between 51 to 69 amino acid residues to, more preferably 57 to 63 amino acid residues.

Genes Encoding Ras or Sos Proteins

The present invention contemplates isolation of a gene encoding either a Ras or a Sos of the invention, including a full length, i.e., naturally occurring form of the Ras or Sos from any eukaryote. The present invention further provides for subsequent modification of that coding region of the gene to generate a fragment of the Ras or Sos that will form a Ras-Sos complex. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment.

A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA—RNA and RNA—RNA helices are possible.

The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5x SSC, 0.1% SDS, 0.25% milk, and no formamide; or 30% formamide, 5x SSC, 0.5% SDS). Moderate stringency hybridization conditions correspond to a higher $T_m$, e.g., 40% formamide, with 5x or 6x SCC. High stringency hybridization conditions correspond to the highest $T_m$, e.g., 50% formamide, 5x or 6x SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., *Cell,* 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding a Ras or Sos, whether genomic DNA or cDNA, can be isolated from any source, particularly from a human cDNA or genomic library. In view and in conjunction with the present teachings, methods well known in the art, as described above can be used for obtaining Ras or Sos genes from any source [see, e.g., Sambrook et al., 1989, supra].

Accordingly, any eucaryotic cell potentially can serve as the nucleic acid source for the molecular cloning of an Ras or Sos gene. The DNA may be obtained by standard procedures known in the art from cloned DNA (e.g., a DNA "library"), and preferably is obtained from a cDNA library prepared from tissues with high level expression of the protein by chemical synthesis, by cDNA cloning, or by the cloning of genomic DNA, or fragments thereof, purified from the desired cell [See, for example, Sambrook et al., 1989, supra; Glover, D. M. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The present invention also relates to cloning vectors containing genes encoding analogs and derivatives of Ras or Sos including and more preferably the Sos and Ras fragments of the present invention, that can form Ras-Sos complexes. Included are homologs of Ras and Sos and fragments thereof, from other species. Therefore the production and use of derivatives and analogs related to Ras and Sos are within the scope of the present invention.

Ras and Sos derivatives can be made by altering encoding nucleic acid sequences by substitutions, additions or deletions that provide for functionally equivalent molecules. Preferably, derivatives are made that are capable of forming crystals of the Ras-Sos complex that effectively diffract X-rays for the determination of the atomic coordinates of the protein-ligand complex to a resolution of better than 5.0 Angstroms, preferably to a resolution of better than 3 Angstroms.

Due to the degeneracy of nucleotide coding sequences, other DNA sequences which encode substantially the same amino acid sequence as a Ras or Sos gene may be used in the practice of the present invention. These include but are not limited to allelic genes, homologous genes from other species, and nucleotide sequences comprising all or portions of Ras and/or Sos genes which are altered by the substitution of different codons that encode the same amino acid residue within the sequence, thus producing a silent change. Likewise, the Ras or Sos derivatives of the invention include, but are not limited to, those containing, as a primary amino acid sequence, all or part of the amino acid sequence of a Ras or a Sos protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding Ras or Sos derivatives and analogs of the invention can be produced by various methods known in the art. The manipulations which result in their production can occur at the gene or protein level. For example, the cloned Ras or Sos gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of Ras or Sos, care should be taken to ensure that the modified gene remains within the same translational reading frame as the Ras or Sos gene, uninterrupted by translational stop signals, in the gene region where the desired activity is encoded.

Additionally, the Ras or Sos-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated Ras or Sos gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61–70].

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Ras and Sos

The nucleotide sequence coding for Ras or Sos, a fragment of Ras or Sos or a derivative or analog thereof, including a functionally active derivative, such as a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a Ras or Sos of the invention or a fragment thereof is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding Ras or Sos and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant Ras or Sos protein of the invention, or Ras or Sos fragment, derivative, chimeric construct, or analog thereof, may be expressed chromosomally, after integration of the coding sequence by recombination. In this regard, any of a number of amplification systems may be used to achieve high levels of stable gene expression [See Sambrook et al., 1989, supra].

The cell containing the recombinant vector comprising the nucleic acid encoding Ras or Sos is cultured in an appropriate cell culture medium under conditions that provide for expression of Ras or Sos by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of Ras or Sos protein may be controlled by any promoter/enhancer element known in the art, but these regulatory elements must be functional in the host selected for expression. Promoters which may be used to control Ras or Sos gene expression include, but are not limited to, the SV40 early promoter region [Benoist and Chambon, *Nature*, 290:304–310 (1981)], the promoter contained in the 3' long terminal repeat of Rous sarcoma virus [Yamamoto et al., *Cell*, 22:787–797 (1980)], the herpes thymidine kinase promoter [Wagner et al., *Proc. Natl. Acad. Sci. U.S.A.*, 78:1441–1445 (1981)], the regulatory sequences of the metallothionein gene [Brinster et al., *Nature* 296:39–42 (1982)]; prokaryotic expression vectors such as the β-lactamase promoter [Villa-Kamaroff, et al., *Proc. Natl. Acad. Sci. U.S.A.*, 75:3727–3731 (1978)], or the tac promoter [DeBoer, et al., *Proc. Natl. Acad. Sci. U.S.A.*, 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell*, 38:639–646 (1984); Ornitz et al., *Cold Spring Harbor Symp. Quant. Biol.*, 50:399–409 (1986); MacDonald, *Hepatology*, 7:425–515 (1987)]; insulin gene control region which is active in pancreatic beta cells [Hanahan, *Nature*, 315:115–122 (1985)], immunoglobulin gene control region which is active in lymphoid cells [Grosschedl et al., *Cell*, 38:647–658 (1984); Adames et al., *Nature*, 318:533–538 (1985); Alexander et al., *Mol. Cell. Biol.*, 7:1436–1444 (1987)], mouse mammary tumor virus control region which is active in testicular, breast, lymphoid and mast cells [Leder et al., *Cell*, 45:485–495 (1986)], albumin gene control region which is active in liver [Pinkert et al., *Genes and Devel.*, 1:268–276 (1987)], alpha-fetoprotein gene control region which is active in liver [Krumlauf et al., *Mol. Cell. Biol.*, 5:1639–1648 (1985); Hammer et al., *Science*, 235:53–58 (1987)], alpha 1-antitrypsin gene control region which is active in the liver [Kelsey et al., *Genes and Devel.*, 1:161–171 (1987)], beta-globin gene control region which is active in myeloid cells [Mogram et al., *Nature*, 315:338–340 (1985); Kollias et al., *Cell*, 46:89–94 (1986)], myelin basic protein gene control region which is active in oligodendrocyte cells in the brain [Readhead et al., *Cell*, 48:703–712 (1987)], myosin light chain-2 gene control region which is active in skeletal muscle [Sani, *Nature*, 314:283–286 (1985)], and gonadotropic releasing hormone gene control region which is active in the hypothalamus [Mason et al., *Science*, 234:1372–1378 (1986)].

Expression vectors containing a nucleic acid encoding an Ras or Sos of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding Ras or Sos is inserted within the "selection marker" gene sequence of the vector, recombinants containing the Ras or Sos insert can be identified by the absence of the selection marker gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX [Smith et al., *Gene*, 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2 μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (Bg/II, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthetase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamHI, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK— and β-gal selection), pMJ601 (SalI, SmaI, AflI, NarI, BspMII, BamHI, ApaI, NheI, SacII, KpnI, and HindIII cloning site; TK— and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the Ras or Sos protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with Pro-Bond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., J. Biol. Chem., 267:963–967 (1992); Wu and Wu, J. Biol. Chem., 263:14621–14624 (1988); Hartmut et al., Canadian Patent Application No. 2,012,311, filed Mar. 15, 1990).

Peptide Synthesis

Synthetic polypeptides, prepared using the well known techniques of solid phase, liquid phase, or peptide condensation techniques, or any combination thereof, can include natural and unnatural amino acids. Amino acids used for peptide synthesis may be standard Boc (N$^\alpha$-amino protected N$^\alpha$-t-butyloxycarbonyl) amino acid resin with the standard deprotecting, neutralization, coupling and wash protocols of the original solid phase procedure of Merrifield [J. Am. Chem. Soc., 85:2149–2154 (1963)], or the base-labile N$^\alpha$-amino protected 9-fluorenylmethoxycarbonyl (Fmoc) amino acids first described by Carpino and Han [J. Org. Chem., 37:3403–3409 (1972)]. Both Fmoc and Boc N$^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other N$^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine.

Additionally, by assigning specific amino acids at specific coupling steps, α-helices, β turns, β sheets, γ-turns, and cyclic peptides can be generated.

Isolation and Crystallization of the Ras-Sos complex

The present invention provides Ras fragments and Sos fragments that retain their ability to form a protein-protein complex (a Ras-Sos complex) and in addition can be crystallized into a crystal that effectively diffracts X-rays for the determination of the atomic coordinates of the Ras-Sos complex to a resolution of better than 5.0 Angstroms. The Ras and Sos fragments (plus an initiator methionine when appropriate) can be expressed either as described below in Example 1, or as described above. The Ras fragments of the present invention are constructed to contain the Sos contacting region whereas the Sos fragments are constructed to retain all of the Sos catalytic domain. Generally additional portions of the two proteins are also retained. Thus, in Example 1 below, the Ras fragment contains the N-terminal 166 amino acids of SEQ ID NO:1, whereas the Sos contacting region of human Ras is contained by amino acids 5 to 105 of SEQ ID NO:1. Similarly, whereas the Sos catalytic domain of human Sos comprises amino acids 781–1017 of SEQ ID NO:2, the Sos fragment used in Example 1 below, contains amino acids 564–1049 of SEQ ID NO:2. Of course, the specific Ras and Sos fragments provided herein serve only as examples, since the crystallization process can tolerate a broad range of fragment lengths. Therefore, any person with skill in the art of protein crystallization having the present teachings and without undue experimentation could crystallize a large number of alternative forms of the Ras-Sos complex from a variety of different Ras and Sos fragments, or alternatively using either or both the full length Ras and Sos. As mentioned above, Ras and Sos, and Ras and Sos fragments having conservative substitutions in their amino acid sequence are also included in the invention, including a selenomethionine substituted form.

In addition, crystals can be prepared using modified fragments of Ras and Sos and are fully contemplated by the present invention. For example, a number of mutations in Ras have highlighted the importance of the Switch 1 and Switch 2 regions in the interaction with nucleotide exchange factors [Mistou et al., *EMBO J.*, 11:2391–2397 (1992); Verrotti et al., *EMBO J.*, 11:2855–2862 (1992); Segal et al., *Proc. Natl. Acad. Sci.*, 90:5564–5568 (1993); Mosteller et al., *Molec. Cell. Biol.*, 14:1104–1112 (1994); Segal et al., *Eur. J. Biochem.*, 228:96–101 (1995); Leonardsen et al., Oncogene, 13:2177–2187 (1996); Crechet et al., *J. Biol. Chem.*, 271:17234–17240 (1996); Quilliam et al., *J. Biol. Chem.*, 271:11076–11082 (1996)]. The importance of helix α3 (residues 102–105) has also been noted [Segal et al., *Proc. Natl. Acad. Sci.*, 90:5564–5568 (1993); Segal et al., *Eur. J. Biochem.*, 228:96–101 (1995); Leonardsen et al., Oncogene, 13:2177–2187 (1996)]. Similarly, in the structure of the Ras-Sos complex disclosed in Example 1 below, Glu 62 and 63 of SEQ ID NO:1 appear to be crucial to the interaction with Sos and are therefore candidates for modification for generating crystals the Ras-Sos complex having a substantially different structural configuration. Similarly, dominant negative mutants of Ras have been identified that appear to act by binding to and sequestering nucleotide exchange factors [Feig and Cooper, *Molec. Cell. Biol.*, 8:3235–3243 (1988); Chen et al., *Oncogene*, 9:2691–2698 (1994)]. The most straightforward explanation of the action of these mutations is that they destabilize nucleotide binding [Haney and Broach, *J Biol. Chem.*, 269:16541–16548 (1994); Chen et al., *Oncogene*, 9:2691–2698 (1994); Powers et al., *Cell*, 65:1225–1231 (1991)], thereby increasing the apparent affinity of Ras for Sos or other exchange factors. Some of the dominant negative mutations may, in addition, result in stronger interactions between Ras and the exchange factor. For example, Ser 17 in SEQ ID NO:1 forms a hydrogen bond with Glu 942 in SEQ ID NO:2, in FIG. 5B, below. In addition the mutation of Ser 17 of SEQ ID NO:1 to Asn 17 results in a dominant negative Ras, and Asn at this position in Ras may be positioned so as to interact more strongly with Glu 942 of SEQ ID NO:2.

In addition, substitution of Arg 80, Asn 81 of *S. cerevisiae* Ras2p (Arg 73, Thr 74 in SEQ ID NO:1) with Asp—Asp in the mutant (Ser 17→Asn) results in a loss of sensitivity to the corresponding *S. cerevisiae* nucleotide exchange protein Sdc25 and reversion of the dominant negative phenotype [Crechet et al., *J. Biol. Chem.*, 271: 17234–17240 (1996)]. In the Ras-Sos complex, Arg 73 of SEQ ID NO:1 (Arg 80 in Ras2p) is involved in interactions with two residues of Sos (SEQ ID NO:2) (FIG. 6A), and a mutation to Asp would clearly be disruptive.

Crystals of the Ras-Sos complex can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used. Exemplified below is the hanging-drop vapor diffusion procedure. Hanging drops of Ras-Sos complex (2.5 μl, 10 mg/ml) in 20 mM Tris, pH=8.0, 100 mM NaCl were mixed with an equal amount of reservoir buffer containing 2.7–3.2 M sodium formate and 100 mM Tris buffer, pH=8.0, and kept at 4° C. Crystal showers appeared after 1–2 days with large single crystals growing to full size (0.3×0.3×0.15 mm$^3$) within 2–3 weeks. Crystals were harvested in 3.5 M sodium formate and 100 mM Tris buffer, pH=8.0 and cryoprotected in 3.5 M sodium formate, 100 mM Tris buffer, pH=8.0, 10% (w/v) sucrose, and 10% (v/v) ethylene glycol before flash freezing in liquid propane.

Once a crystal of the present invention is grown, X-ray diffraction data can be collected. In Example 1 below, this analysis were measured at Brookhaven National Laboratories on beamline X25 using the Brandies 2×2 (four module) CCD-based detector [Westbrook and Naday, *Meth. Enzymol.*, 276:244–268 (1997)]. A mercury derivative data set (PCMB) was measured at Cornell High Energy Synchrotron Source on beamline F2 using the Q1 CCD-based detector (ADSC). Data processing was performed using Denzo and data reduction was performed using Scalepack [Otwinowski and Minor, *Meth. Enzymol.*, 276:307–326 (1997)]. MIR phases were calculated using MLPHARE as implemented in the CCP4 suite of programs [Collaborative Computing Project, N. The CCP4 Suite: Programs for protein cyrstallography. *Acta Cryst.*, D50:760–763 (1994)]. Solvent flattening was performed using DM [Cowtan, *Joint CCP4 and ESF-EACBM Newsletter on Protein Crystallography*, 31:34–38 (1994)].

Alternative methods may also be used. For example, crystals can be characterized by using X-rays produced in a conventional source (such as a sealed tube or a rotating anode) or using a synchrotron source. Methods of characterization include, but are not limited to, precision photography, oscillation photography and diffractometer data collection. Selenium-Methionine may be used in place of PCMB derivitization as described in Example 1, and multiwavelength anomalous dispersion data [Hendrickson, *Science*, 254:51–58 (1991)] can be collected on CHESS F2, using reverse-beam geometry to record Friedel pairs at four X-ray wavelengths, corresponding to two remote points above and below the Se absorption edge ($\lambda_1$ and $\lambda_4$) and the absorption edge inflection point ($\lambda_2$) and peak ($\lambda_3$). Data can be processed using DENZO and SCALEPACK (Z. Otwinowski and W. Minor). Selenium sites can be located using SHELXS-90 in Patterson search mode (G. M. Sheldrick). Experimental phases ($\alpha_{MAD}$) can be estimated via a multiple isomorphous replacement/anomalous scattering strategy using MLPHARE (Z. Otwinowski, Southwestern University of Texas, Dallas) with three of the wavelengths treated as derivatives and one ($\lambda_2$) treated as the parent for example. Alternatively, X-PLOR [Brüger, X-PLOR v. 3.1 Manual, New Haven: Yale University, (1993B)] or Heavy [T. Terwilliger, Los Alamos National Laboratory] may be used.

After density modification and non-crystallographic averaging, the protein can be built into a electron density map using the program O [Jones et al., *Acta Cryst.*, A47:110–119 (1991)]. Coordinates for the GTP bound form of Ras (521P) [Pai et al., *EMBO J*, 9:2351–2359 (1990)] can be obtained from the Protein Data Bank [Bernstein et al., *Archives of Biochemistry & Biophysics*, 185:584–591 (1978)]. The molecule, with Switch 1 and Switch 2 regions deleted, was fit into density in Example 1. After an initial round of model building and positional refinement using CNS with bulk solvent corrections and anisotropic B-factor scaling protocols utilized, phase combination methods using Sigma [read, *Acta Cryst.*, A42:140–149 (1986)] can result in a much improved map. In Example 1, below the Switch 2 region of Ras, the catalytic domain of Sos, and the N-terminal helices of Sos were built by this methodology. Electron density maps based on multiple simulated annealing models [Brünger et al., *Structure*, 5:325–336 (1997)] allowed the remaining regions of Ras and Sos to be placed into density, Example 1, below. Residues 564–567 (N-terminal), 591–597, 654–675, 742–751, and 1045–1049 (C-terminal) are disordered and not modeled in Sos; no residues of Ras are disordered. For the crystal structure of Example 1, the Ramachandran plot showed 89% of all residues are in the most favored regions and no residues are in disallowed regions.

Protein-Structure Based Design of Modulators of Cellular Proliferation

Once the three-dimensional structure of a crystal comprising a Ras-Sos complex is determined, (e.g., see the coordinates in FIGS 8-1 through 8-75 below) a potential modulator of Ras activity, can be examined through the use of computer modeling using a docking program such as GRAM, DOCK, or AUTODOCK [Dunbrack et al., 1997, supra], to identify potential modulators of the Ras-Sos nucleotide exchange interaction. This procedure can include computer fitting of potential modulators to the Ras-Sos complex to ascertain how well the shape and the chemical structure of the potential modulator will bind to either the nucleotide exchange region of Sos or to the Ras-Sos complex, e.g., to act as a stabilizer. [Bugg et al., *Scientific American*, Dec.:92–98 (1993); West et al., *TIPS*, 16:67–74 (1995)]. Computer programs can also be employed to estimate the attraction, repulsion, and steric hindrance of the two binding partners (e.g., the Ras-Sos complex and a potential stabilizer). Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

Initially GTP analogs, for example, can be systematically modified by computer modeling programs until one or more promising potential analogs are identified. Examples of GTP analogs that have been designed in view of the structural information provided by the present invention are included in Example 2, below. In addition systematic modification of selected analogs can then be systematically modified by computer modeling programs until one or more potential analogs are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, *Perspectives in Drug Discovery and Design* 1:23–48 (1993); Erickson, *Perspectives in Drug Discovery and Design* 1:109–128 (1993)]. Alternatively a potential modulator could be obtained by initially screening a random peptide library produced by recombinant bacteriophage for example, [Scott and Smith, *Science*, 249:386–390 (1990); Cwirla et al., *Proc. Natl. Acad. Sci.*, 87:6378–6382 (1990); Devlin et al., *Science*, 249:404–406 (1990)]. A peptide selected in this manner would then be systematically modified by computer modeling programs as described above, and then treated analogously to a structural analog as described below.

Figure 7A:
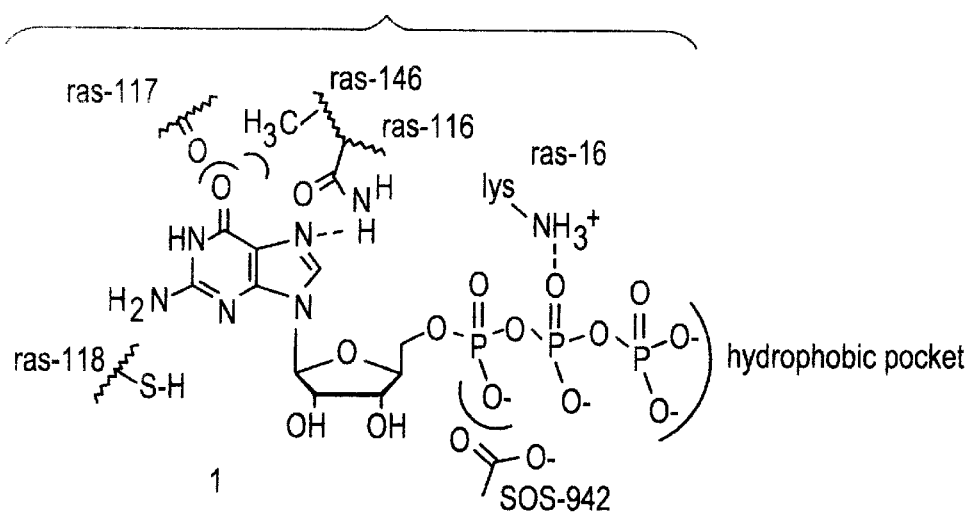
FIG. 7A shows a schematic of GTP bound in the Ras-Sos complex.
Figure 7B:
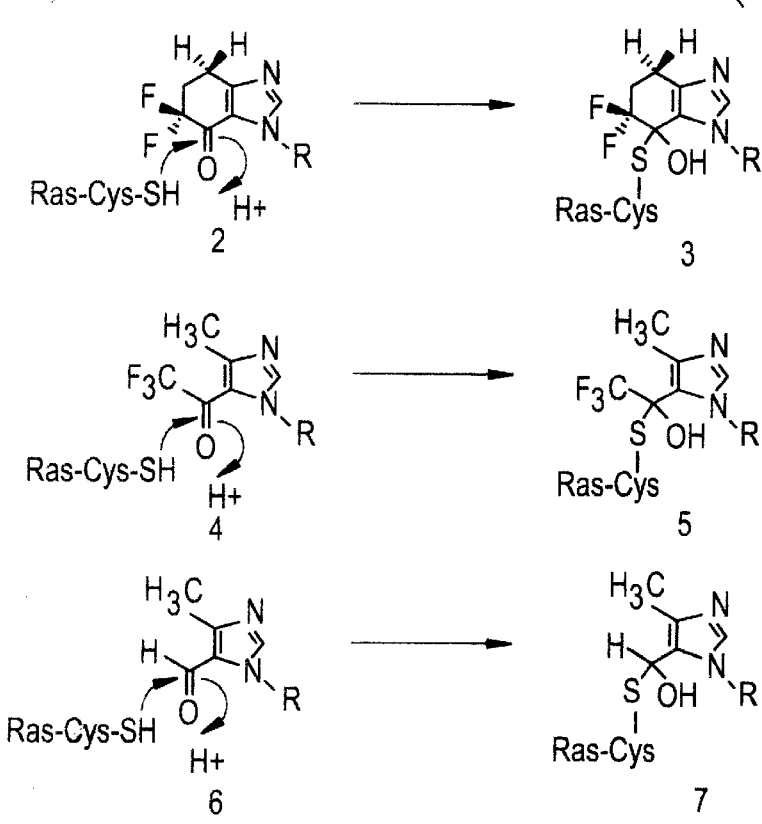
FIGS. 7B–7C shows putative inhibitors and modes of inhibition of the Ras-Sos interaction.
Figure 7C:
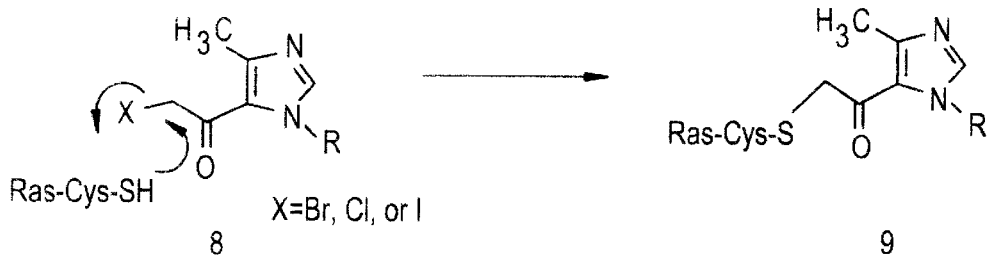
Figure 7C:
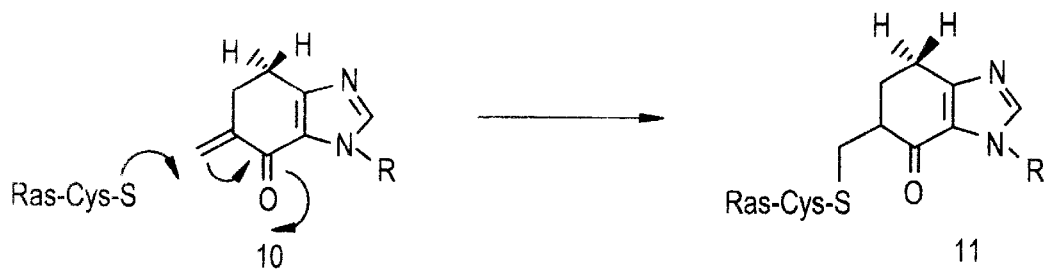
Figure 7C:
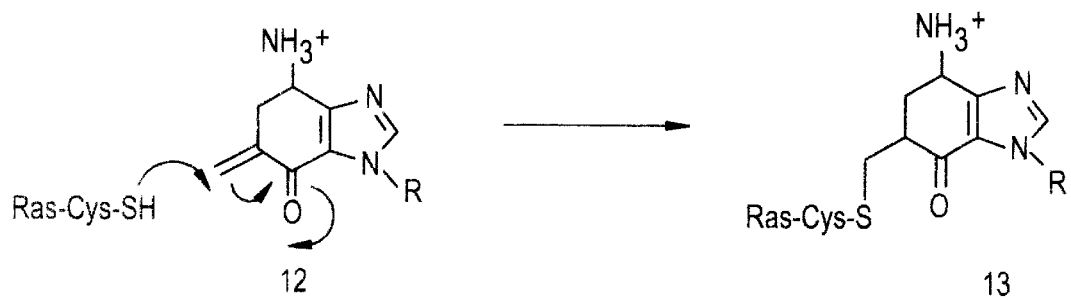
Figure 7C:
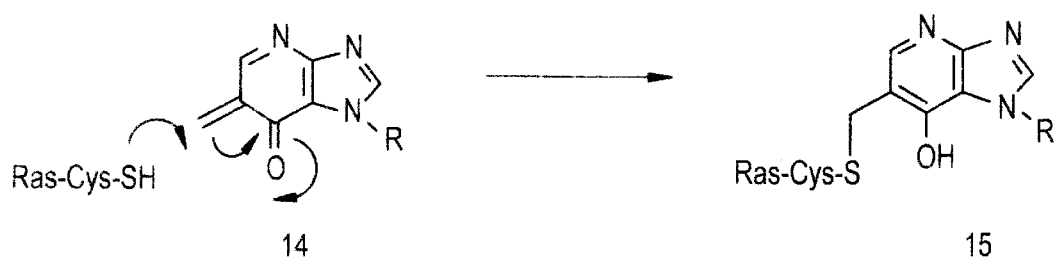
Figure 7C:
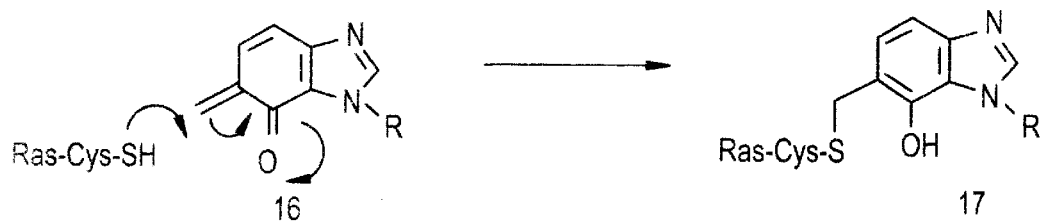
Figure 7D:
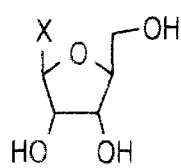
FIG. 7D shows potential inhibitors that assume that guanine binding would induce the Sos-free conformation of Ras, i.e., modifying the guanosine analogs at sites other than on the purine.
Figure 7D:
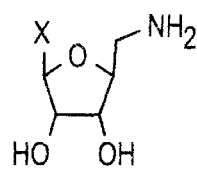
Figure 7D:
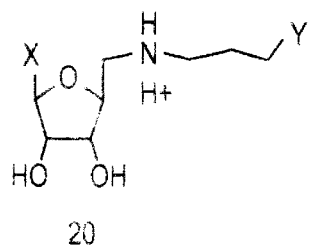
Figure 7D:
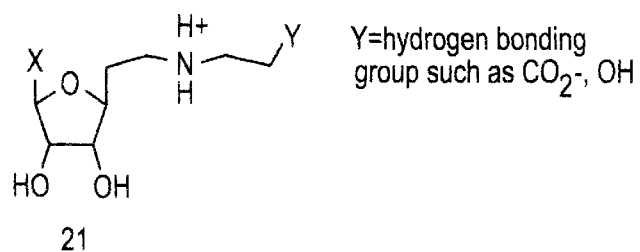
Figure 7D:
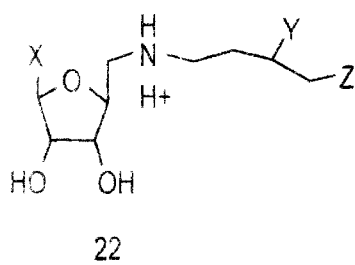
Figure 7D:
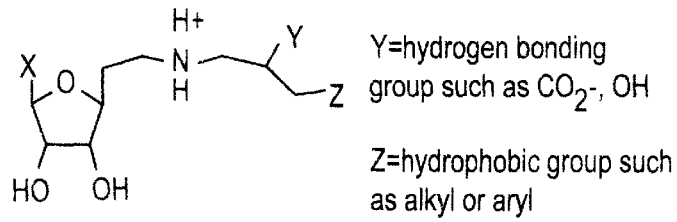
Figure 7E:
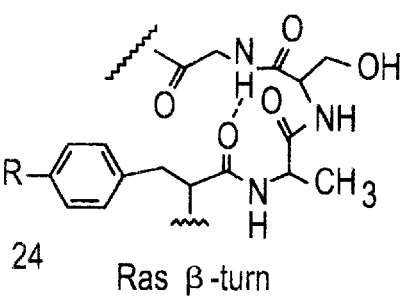
FIG. 7E depicts putative inhibitors of Sos that mimick the β-turn of Ras.
Figure 7E:
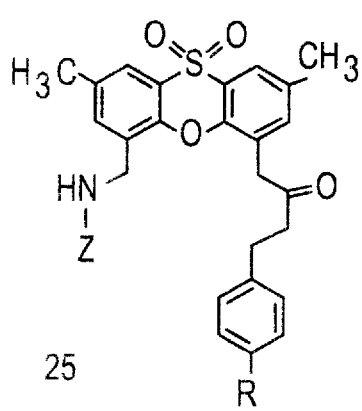
Figure 7E:
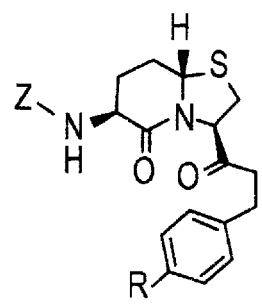
Figure 7E:
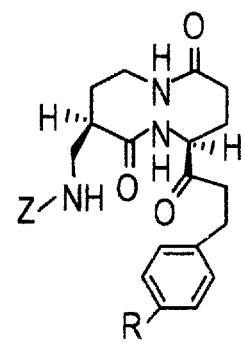
Figure 7E:
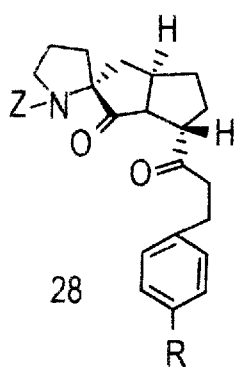
Figure 7E:
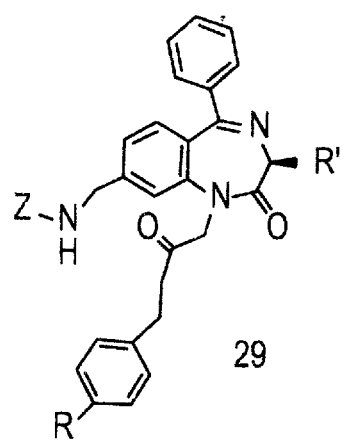

Another example of a potential modulator is compound that is a β-turn small molecule mimic, as exemplified in FIG. 7E. The β-turn small molecule mimic is designed to simulate the conformational change in Ras which appears to take place when Ras binds to Sos, as disclosed herein. Countless modifications of such a β-turn small molecule mimic can be made, any one of which could lead to a useful drug. Each modification requires additional chemical steps, which while being reasonable for the synthesis of a few of these compounds, quickly becomes overwhelming if all of these compounds need to be synthesized. However, through the use of the three-dimensional structure disclosed herein and computer modeling, a large number of these compounds can be rapidly screened on the computer monitor screen, and a few likely candidates can be determined without the laborious synthesis of untold numbers of compounds.

Once a potential modulator is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. As mentioned above, the de novo synthesis of one or even a relatively small group of specific compounds is reasonable in the art of drug design. The potential modulator can be placed into a standard binding assay with Sos and/or Ras, or fragments of Sos and Ras which contain the portions of these proteins involved in their protein-protein interaction. The Ras fragments and Sos fragments can be synthesized by either standard peptide synthesis described above, or generated through recombinant DNA technology or classical proteolysis. Alternatively the corresponding full-length proteins may be used in these assays.

For example, the Sos catalytic domain can be attached to a solid support. Methods for placing the Sos catalytic domain on the solid support are well known in the art and include such things as linking biotin to the Sos catalytic domain and linking avidin to the solid support. The solid support can be washed to remove unreacted species. A solution of a labeled potential modulator can be contacted with the solid support. The solid support is washed again to remove the potential modulator not bound to the support.

The amount of labeled potential modulator remaining with the solid support and thereby bound to the Sos catalytic domain can be determined. Alternatively, or in addition, the dissociation constant between the labeled potential modulator and the Sos catalytic domain can be determined. Suitable labels are exemplified below.

In another aspect of the present invention a potential modulator is assayed for its ability to stabilize the Ras-Sos complex. A modulator that stabilizes the Ras-Sos complex is selected as an inhibitor of Ras activation (i.e., an inhibitor of cellular proliferation).

In a particular embodiment, the effect of a potential modulator on the catalytic activity of Sos is determined. In one such embodiment, Ras or a fragment thereof (e.g., a fragment of the Ras which contains the Sos contacting region and the nucleotide binding domain) is contacted with Sos (or a fragment thereof containing the catalytic domain) in the presence of a labeled nucleotide.

In a particular embodiment, isothermal calorimetry can be used to determine the stability of the Ras-Sos complex in the absence and presence of the potential modulator.

In another embodiment, a Biacore machine can be used to determine the binding constant of the Ras-Sos complex in the presence and absence of the potential modulator. In a particular embodiment of this type, Ras or a fragment thereof (e.g., a fragment of the Ras which minimally contains the Sos contacting region) can be immobilized on a sensor chip. Sos or a fragment thereof (e.g., a fragment which contains the Sos catalytic domain) can then be contacted with (e.g., flowed over) the sensor chip to form a Ras-Sos complex.

For example, Ras can be immobilized on a sensor chip and Sos can then be flowed over the sensor chip to form the Ras-Sos complex. The dissociation constant for the Ras-Sos complex can be determined by monitoring changes in the refractive index with respect to time as buffer is passed over the chip. [O'Shannessy et al. Anal. Biochem. 212:457–468 (1993); Schuster et al., *Nature* 365:343–347 (1993)]. Scatchard Plots, for example, can be used in the analysis of the response functions using different concentrations of Sos. Flowing a potential modulator at various concentrations over the Ras-Sos complex and monitoring the response function (e.g., the change in the refractive index with respect to time) allows the Ras-Sos complex dissociation constant to be determined in the presence of the potential modulator and thereby indicates whether the potential modulator is either an inhibitor, or an agonist of the Ras-Sos complex. Alternatively, the potential modulator can be flowed over the immobilized Ras with the Sos in order to determine if it effects the Ras-Sos binding.

In a particular embodiment Ras can be used which is free of nucleotides. In a related embodiment, nucleotide-free Ras can be prepared after the Ras is immobilized on the sensor chip. In one such embodiment a solution of approximately 40 mM EDTA is passed over the immobilized Ras to remove the ions (e.g., $Mg^{+2}$) involved in nucleotide binding. Alternatively, the analogous procedure can be performed using the an immobilized Sos (or fragment thereof) on the sensor chip and contacting Ras (or fragment thereof) with the sensor chip to form a Ras-Sos complex.

In still another embodiment, the binding affinity can be determined for an immobilized Ras, or Ras fragment that contains the Sos contacting region of Ras and a labeled, free Sos (or Sos fragment that minimally contains the Sos catalytic domain) in the absence and presence of the potential modulator. In a related embodiment, the binding affinity can be determined for an immobilized Sos, or Sos fragment (that minimally contains the Sos catalytic domain) and a labeled, free Ras (or Ras fragment that contains the Sos contacting region of Ras) in the absence and presence of the potential modulator. In yet another embodiment, the binding affinity of a potential modulator (preferably labeled) for the Sos catalytic domain can be determined using an immobilized Sos, or Sos fragment (that minimally contains the Sos catalytic domain) in the absence and presence of the potential modulator.

In a particular embodiment, GTP binding to Ras can be determined using labeled GTP or an appropriate labeled GTP analog in the absence and presence of the potential modulator.

In a preferred embodiment, the effect of the potential modulator on the catalytic activity of Sos is determined (either independently, or subsequent to a binding assay as exemplified above). In one such embodiment, the rate of the Sos-mediated guanine nucleotide exchange of Ras is determined. For example, a recombinant Ras protein can be incubated with Sos in the presence of labeled nucleotide. The amount of nucleotide bound to Ras is then determined. This assay can be performed using a real-time assay e.g., with a fluorescent analog of GDP or GTP and e.g., relying on the difference in quenching of the fluorescence when the nucleotide is bound to Ras and when it is free in solution. Alternatively, the determination can include the withdrawal of aliquots from the incubation mixture at defined intervals and subsequent placing of the aliquots on nitrocellulose paper in a nitrocellulose filter binding assay [Chardin et al., *Science* 260:1338–1343 (1993)]. In a particular embodiment the potential modulator is selected when it is an inhibitor of the Sos exchange reaction, i.e., the rate of nucleotide release by Ras is decreased.

When suitable potential modulators are identified, a supplemental crystal can be grown which comprises the Ras-Sos complex and the potential modulator. Preferably the crystal effectively diffracts X-rays for the determination of the atomic coordinates of the protein-ligand complex to a resolution of better than 5.0 Angstroms, more preferably better than 3.0 Angstroms. The three-dimensional structure of the supplemental crystal is determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR (see above), CNS, (Crystallography and NMR System, a next level of XPLOR), and AMORE [J. Navaza, *Acta Crystallographics ASO,* 157–163 (1994)]. Once the position and orientation are known an electron density map can be calculated using the search model to provide X-ray phases. Thereafter, the electron density is inspected for structural differences and the search model is modified to conform to the new structure. Using this approach, it will be possible to use the claimed crystal of the Ras-Sos complexes to solve the three-dimensional structures of any Ras-Sos complex having a pre-ascertained amino acid sequence. Other computer programs that can be used to solve the structures of the Ras-Sos complexes from other organisms include: QUANTA, CHARMM; INSIGHT; SYBYL; MACROMODE; and ICM.

A candidate drug can be selected by performing rational drug design with the three-dimensional structure determined for the supplemental crystal, preferably in conjunction with computer modeling discussed above. The candidate drug (e.g., a potential modulator of Ras activation) can then be assayed as exemplified above, or in situ. A candidate drug can be identified as a drug, for example, if it inhibits cellular proliferation in a cell. The cell can be either isolated from an animal, including a transformed cultured cell; or alternatively, in a living animal. Preferably the cell is an isolated cell such as a HeLa cell or a NIH/3T3 cell.

A potential modulator (e.g., a candidate drug) would be expected to interfere with a growth factor-induced effect that is dependent on Ras. Therefore, an assay that can measure a Ras-dependent effect may be used to identify a candidate drug. Examples of assays involving growth factor-induced effects that are dependent on Ras include but are not limited to cell growth assays, and assays that involve transcriptional activation of a specific promoter. In the latter case, the activation of the promoter can be monitored through the use of a reporter gene that encodes a marker protein, e.g., luciferase, green fluorescent protein, β-Gal, CAT etc. Suitable cells for performing such assays include mouse or rat fibroblasts (NIH3T3, REF-52, Rat-1); cell lines that overexpress a receptor tyrosine kinase (e.g., an A431 human epidermoid carcinoma cell which overexpresses the EGF receptor); and cell lines that are derived from tumors arising in transgenic mice (e.g., MG 1361 is a breast carcinoma cell line obtained from the MMTV-neu transgenic mouse [Sacco et al., *Breast Cancer Res. Treat.*, 47:171–180 (1998)]). In one such embodiment the potential modulator (e.g., the candidate drug) is contacted with the cell and the rate of cell proliferation is determined (e.g., measuring doubling time). An inhibitor of the Sos nucleotide exchange reaction is identified if the rate of cellular proliferation is decreased.

In an alternative embodiment, the transcriptional activation of a reporter gene can be determined in the absence and presence of the potential modulator. The transcription of the reporter gene can be detected by either the enzymatic activity of the translated protein (e.g., luciferase) or the a detectable property of the translated protein (e.g., the fluorescence of green fluorescence protein). An inhibitor of the Sos nucleotide exchange reaction would cause a decrease of the activation of the promoter and therefore a decrease in the enzymatic activity or protein fluorescence respectively.

The present invention further provides methods of testing a potential modulator (e.g., the candidate drug) in mouse-tumor models of cancer. One such embodiment involves a nude-mouse xenograft assay. One such nude-mouse xenograft assay model monitors tumor formation following subcantaneous implantation of transformed cells [Blair et al., *Science* 218:1122–1125 (1982)]. Cells that can be used for this assay include those that are transformed by the overexpression of Ras or a growth factor receptor. The ability of the potential modulator to inhibit tumor formation or growth is then ascertained. In one embodiment the size of the tumor is monitored by determining the tumor size and/or weight. The potential modulators can be administered by a variety of ways including orally, subcutaneously, or intraperitoneally. Generally, at least two groups of animals are used in the assay, with at least one group being a control group which is administered the administration vehicle without the potential modulator.

The present invention also provides methods of testing a potential modulator (e.g., the candidate drug) in a transgenic mouse assay. Transgenic mice are produced that express a transforming agent (e.g., a growth factor receptor) under the control of a tissue specific promoter. Such mice develop carcinomas that have genetic and pathological features that closely resemble human cancers. For example, in a MMTV-neu transgenic mouse lineage, 100% of the female mice develop mammary adenocarcinomas [Sacco et al., *Gene Therapy* 2:493–497 (1995); Sacco et al., *Gene Therapy* 5:383–393 (1998)]. The ability of the potential modulator to inhibit tumor formation or growth is then ascertained. In one embodiment the size of the tumor is monitored by determining the tumor size and/or weight. The potential modulators can be administered by a variety of ways including orally, subcutaneously, or intraperitoneally. Generally, at least two groups of animals are used in the assay, with at least one group being a control group which is administered the administration vehicle without the potential modulator.

For all of the drug screening assays described herein further refinements to the structure of the drug will generally be necessary and can be made by the successive iterations of any and/or all of the steps provided by the particular drug screening assay.

Labels

Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores and including fluorescent GTP and GDP analogs such as mantGTP and mantGDP, chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Patent No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymoiogy*, 70:419–439 (1980) and in U.S. Pat. No. 4,857,453.

Suitable enzymes include, but are not limited to, alkaline phosphatase and horseradish peroxidase. Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^{3}H$]-amino acids (with the tritium substituted at non-labile positions).

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Structural Basis for the Activation of RAS by SOS

Summary

In order to clarify the molecular mechanism of the activation of Ras by Sos the crystal structure of the complex of a C-terminally truncated form of human H-Ras (residues 1–166 of SEQ ID NO:1, hereafter referred to as Ras), with the guanine nucleotide-exchange factor region of human Sos1 (residues 564–1049 of SEQ ID NO:2, hereafter referred to as Sos) was determined. The structure reveals that Sos interacts extensively with Ras and stabilizes it in a nucleotide-free state by displacing the residues that coordinate the magnesium ion and the phosphate groups of the nucleotide and by partially occluding the magnesium binding site. The structure also suggests a pathway for the rebinding of nucleotides to Ras, with consequent release of Sos, a process that is crucial for the functioning of Sos as a nucleotide exchanger rather than a binding inhibitor.

Methods

Expression and Purification: E. coli cells (BL21-DE3) were transformed with a pProEX HTb vector (Life Technologies) containing Ras (residues 1–166) linked to an N-terminal polyhistidine tag using the BamHI and XhoI restriction sites. Protein production was induced with 250 mM IPTG at a cell density of O.D.$_{600}$=0.5. Protein was expressed at 30° C. for 6 hours. Cells were harvested by centrifugation, resuspended in 20 mM Tris, pH=8.0, 300 mM NaCl at 4° C., flash frozen and stored at −80° C. until needed. Once thawed, cells were lysed using a french press (EmulsiFlex-C5, Avestin, Inc), cell debris was removed by centrifugation, and resulting cell lysate loaded onto a charged nickel binding column (HisBind; Novagen) pre-equilibrated with 20 mM Tris, pH=8.0, 500 mM NaCl, and 20 mM imidazole. Protein was eluted using an imidazole gradient. Fractions containing Ras were pooled, dialyzed into Buffer A (20 mM Tris, pH=8.0, 100 mM NaCl), and concentrated. The polyhistidine tag was cleaved by tobacco etch virus (TEV) in Buffer A at 4° C. for 48 hours. After cleavage, protein was passed over a charged nickel binding column preequilibrated with Buffer A to remove uncleaved protein. Fractions containing pure Ras were pooled and concentrated. Expression and purification of Sos (residues 564–1049) was performed as above, with an additional purification step utilizing a HiQ (Biorad) column preequilibrated with Buffer A. Fractions containing Sos were concentrated in Buffer A.

The Ras-Sos complex was formed by incubating concentrated Sos with 3–5 fold excess Ras in Buffer A for 1 hour at 4° C. Protein was loaded onto a Sephadex 75 gel filtration column (Pharmacia Biotech) preequilibrated with Buffer A. Fractions containing complex were pooled and concentrated to 10 mg/ml. Approximately 30 mgs of purified complex could be obtained from 16 liters of E. coli cell culture grown in LB expressing Sos, the limiting reagent.

Crystallization, data collection, and data processing: Hanging drops of Ras-Sos complex (2.5 µL, 10 mg/ml) in Buffer A were mixed with an equal amount of reservoir buffer containing 2.7–3.2 M sodium formate and 100 mM Tris buffer, pH=8.0, and kept at 4° C. Crystal showers appeared after 1–2 days with large single crystals growing to full size (0.3×0.3×0.15 mm$^3$) within 2–3 weeks. The crystals contain 1 heterodimeric complex per asymmetric unit and belong to space group I422 (a=b=142.7 Å, c=207.9 Å). Crystals were harvested in 3.5 M sodium formate and 100 mM Tris buffer, pH=8.0 and cryoprotected in 3.5 M sodium formate, 100 mM Tris buffer, pH=8.0, 10% (w/v) sucrose, and 10% (v/v) ethylene glycol before flash freezing in liquid propane. Heavy atom derivatives were prepared by soaking crystals in harvesting buffer containing heavy atom solutions. Crystals were also obtained from sodium/potassium phosphate (space group I422, a=b=142 Å, c=315 Å). However, due to the limited diffraction from these crystals (3.8 Å resolution), structure determination was not pursued.

All but one of the data sets used in this analysis were measured at Brookhaven National Laboratories on beamline X25 using the Brandies 2×2 (four module) CCD-based detector [Westbrook and Naday, *Meth. Enzymol.*, 276:244–268 (1997)]. A mercury derivative data set (PCMB) was measured at Cornell High Energy Synchrotron Source on beamline F2 using the Q1 CCD-based detector (ADSC). Data processing was performed using Denzo and data reduction was performed using Scalepack [Otwinowski and Minor, *Meth. Enzymol.*, 276:307–326 (1997)]. MIR phases were calculated using MLPHARE as implemented in the CCP4 suite of programs [Collaborative Computing Project, N. The CCP4 Suite: Programs for protein cyrstallography. *Acta Cryst.*, D50:760–763 (1994)]. Solvent flattening was performed using DM [Cowtan, *Joint CCP4 and ESF-EACBM Newsletter on Protein Crystallography*, 31:34–38 (1994)].

Model Building and Refinement: Model building was performed using O [Jones et al, *Acta Crystallogr.*, A47:110–119 (1991)]. Coordinates for the GTP bound form of Ras (521P) [Pai et al., *EMBO J.*, 9:2351–2359 (1990)] were obtained from the Protein Data Bank [Bernstein et al., *Archives of Biochemistry & Biophysics*, 185:584–591 (1978)] and the molecule, with Switch 1 and Switch 2 regions deleted, was fit into density. After an initial round of model building and positional refinement using CNS with bulk solvent corrections and anisotropic B-factor scaling protocols utilized, phase combination methods using Sigmaa [Read, *Acta Cryst., A*42: 140–149 (1986)] resulted in a much improved map into which the Switch 2 region of Ras, the catalytic domain of Sos, and the N-terminal helices of Sos were built. Electron density maps based on multiple simulated annealing models [Brunger et al., *Structure*, 5:325–336 (1997)] allowed the remaining regions of Ras and Sos to be placed into density. Residues 564–567 (N-terminal), 591–597, 654–675, 742–751, and 1045–1049 (C-terminal) are disordered and not modeled in Sos; no residues of Ras are disordered. The Ramachandran plot shows 89% of all residues are in the most favored regions and no residues are in disallowed regions.

Results

Structure Determination: Ras and Sos form a tight complex in the absence of nucleotides. Crystals of this complex were obtained (I-centered tetragonal, a=b=142.7 Å, c=207.9 Å) with one Ras-Sos complex ($M_r$=75 kD) in the asymmetric unit. The structure was determined by multiple isomorphous replacement using 9 heavy atom derivatives (Tables 1 and 2). The molecular model was refined against data to 2.8 Å, resulting in a crystallographic R-value of 22.2% (free R-value of 28.1%). The final model includes 439 residues of Sos, 166 residues of Ras, and 26 water molecules. There is no nucleotide or magnesium present in the crystals. The coordinates for the human Ras-Sos complex are compiled in the data set in FIGS. 8-1 through 8-75.

and Sos have shown that the relatively well conserved C-terminal catalytic domain suffices for catalytic activity [Chardin et al., *Science*, 260:1338–1343 (1993)]. However, recombinant fragments of Sos that span the catalytic domain, but which lack some or all of the N-Domain, are expressed poorly and have low solubility, whereas the fragment used for the structure determination includes both domains and results in relatively high yields of soluble protein. The formation of a Ras-Sos complex results in the protection from proteolysis of both the N- and catalytic domains, suggesting that they stabilize each other during complex formation.

Figure 2A:
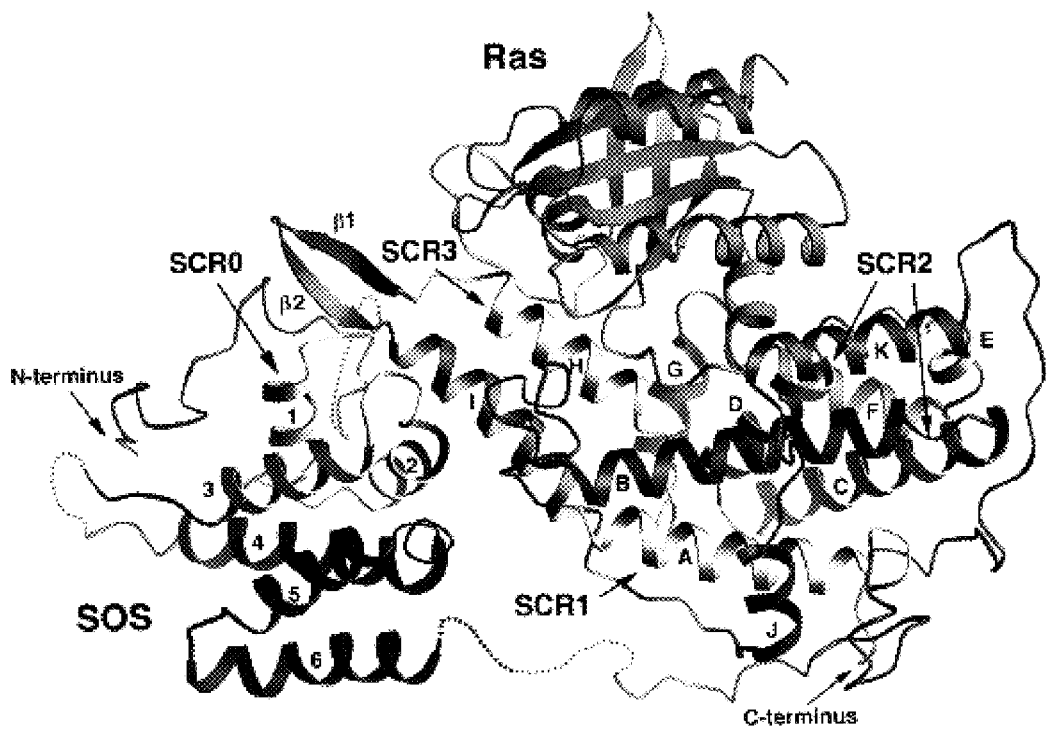
FIGS. 2A–2B show the complex of H-Ras with the exchange factor region of human Sos1.
Figure 2B:
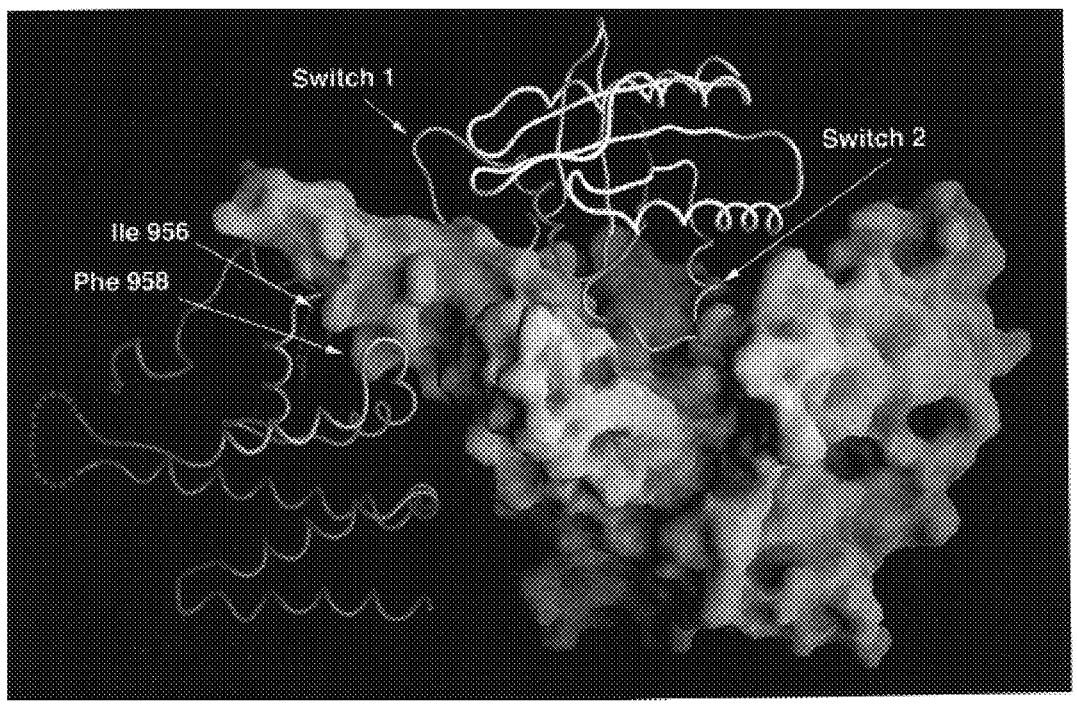

The interaction between the two domains of Sos is localized to one end of the catalytic domain. The N-Domain contains six helices ($\alpha$1 to $\alpha$6). Helices $\alpha$3 to $\alpha$6 form a 4-helix bundle that supports helices $\alpha$1 and $\alpha$2. $\alpha$1 and $\alpha$2 together form a small hydrophobic groove into which are inserted two conserved hydrophobic sidechains from the catalytic domain (Ile 956 and Phe 958; FIG. 2B). The packing of these sidechains into the $\alpha$1–$\alpha$2 groove, along with several adjacent inter-domain interactions, is likely to

TABLE 1

Data collection, structure determination and refinement statistics

| Data set | Resolution (Å) | Observations Total/Unique | $R_{sym}$* (%) | Completeness (%) | $R_{iso}^\dagger$ (%) | Sites (No.) | Phasing Power[‡] |
|---|---|---|---|---|---|---|---|
| Native | 2.8 | 283114/26562 | 5.3 (28.7) | 99.3 (99.9) | | | |
| PCMB[+] | 3.1 | 616299/19766 | 7.7 (28.9) | 93.4 (87.9) | 22.8 | 5 | 1.68 |
| Baker's Dimercurial[+] | 3.25 | 640979/16988 | 7.6 (19.3) | 96.9 (98.6) | 21.5 | 6 | 0.80 |
| EMTS[+] | 3.25 | 634455/17174 | 7.3 (35.1) | 95.4 (97.2) | 20.0 | 4 | 1.94 |
| Trimethyl Lead Acetate[+] | 2.9 | 523356/23842 | 5.9 (27.0) | 98.2 (99.3) | 22.5 | 6 | 0.77 |
| Selenomethionine | 3.0 | 543633/21735 | 6.5 (29.7) | 96.1 (93.2) | 15.4 | 10 | 1.44 |
| Gold Cyanide[+] | 3.05 | 368880/20927 | 5.4 (28.6) | 98.3 (96.5) | 33.5 | 3 | 1.46 |
| Platinum Terpyridine | 3.25 | 240941/16915 | 10.6 (36.7) | 98.9 (99.3) | 18.5 | 6 | 1.35 |
| Osmium Chloride | 3.1 | 202555/20025 | 6.8 (29.4) | 99.6 (99.9) | 23.5 | 4 | 1.55 |
| PCMB/Trimethyl Lead Acetate[+] | 3.3 | 571428/16485 | 7.8 (30.0) | 99.8 (99.5) | 26.6 | 9 | 1.91 |

Overall Figure of Merit[#] = 0.70

TABLE 2

Refinement Statistics

| | Resolution | | | | rmsd from ideal values | |
|---|---|---|---|---|---|---|
| Data Set | (Å) | Reflections | Total atoms | R-factor/R | bonds (Å) | angles (°) |
| Native | 30–2.8 | 26502 | 5010 | 0.222/0.281 | 0.007 | 1.26 |

*$R_{sym} = 100 \times \Sigma | I - <I> | / \Sigma I$, where I is the integrated intensity of a given reflection. For $R_{sym}$ and completeness, numbers in parentheses refer to data in the highest resolution shell.
†$R_{iso} = 100 \times \Sigma | F_{PH} - F_P | / \Sigma F_P$, where $F_{PH}$ and $F_P$ are the derivative and native structure factor amplitudes, respectively.
‡Phasing power = $\Sigma | F_{PH(calc)} |^2 / \Sigma \{ | F_{PH(obs)} - F_{P(calc)} |^2 \}^{1/2}$.
[+]Anomolous data was used in the phasing of these derivatives.
Figure of Merit = $<|\Sigma P(\alpha)e^{i\alpha} / \Sigma P(\alpha)|>$, where $\alpha$ is the phase and $P(\alpha)$ is the phase probability distribution.
¶R-factor = $\Sigma | F_P - F_{P(calc)} | / \Sigma F_P$; $R_{free}$ was calculated with 5% of the data.

Structure of Sos: The structure of the Ras exchange factor region of Sos (residues 568 to 1044 of SEQ ID NO:2) consists of two distinct $\alpha$-helical structural domains (FIG. 2). The amino-terminal domain (N-Domain, residues 568 to 741 of SEQ ID NO:2) does not interact with Ras, and appears to play a purely structural role. The carboxy-terminal domain (residues 752 to 1044 of SEQ ID NO:2) contains within it all the residues that interact with Ras, and this region will be referred to as the catalytic domain. Analyses of the exchange factor activity of Cdc25, Sdc25 be important for the stability and correct placement of a hairpin structure formed by helices $\alpha$H and $\alpha$1 in the catalytic domain (FIG. 2). This hairpin protrudes from the core of the catalytic domain, and helix $\alpha$H plays a key role in the nucleotide exchange mechanism.

The structure of the catalytic domain consists of a series of helical hairpins that pack against each other, with no significant similarity to proteins in the databank (based on a DALI search [Holm and Sander, *J Mol. Biol.*, 233:123–138 (1993)]). In particular, there is no structural similarity between this domain and the catalytic domain of Ras guanine activating protein [Scheffzek et al., *Nature*, 384:591–596 (1996)] which is also α-helical. Helices αA to αG, along with αJ and αK, form a compact core region, out of which is extruded the hairpin formed by helices αH and αI. It is this projection out of the core that appears to require interaction with the N-Domain for stabilization. Structural Relationship between Sos and other nucleotide exchange factors for Ras: Sos is related in sequence to the yeast proteins Cdc25, Sdc25, and the mammalian exchange factor (FIG. 1). The structure of the Ras nucleotide exchange factor region of Sos described here is likely to be a good model for the general architecture of these guanine nucleotide exchange factors. Three regions of sequence conservation within the catalytic domain had been identified previously, and are named structurally conserved regions (SCR) 1–3 [Boguski and McCormick, *Nature*, 366:643–654 (1993)]. These regions are either important for the structural integrity of the domain (SCRI, helix αA and SCR2, helix αC) or for the interaction with Ras (SCR2 helix αD and SCR3; FIG. 2A). The region of the N-Domain spanning helices α1, α2 and α3 is highly conserved among Ras-specific nucleotide exchange factors (SCR0 in FIG. 2A) [Lai et al., *Mol. Cell. Biol*, 13:1345–1352 (1993)]. This sequence conservation argues for a conservation between Sos, Cdc25, Sdc25, and RasGRF for the particular relative arrangement of the N-Domain and the catalytic domain that is seen in Sos. The hydrophobic nature of the groove between helices α1 and α2 is conserved, as are the residues on the catalytic domain that interact with the groove and the adjoining surface of the N-Domain.

Figure 3A:
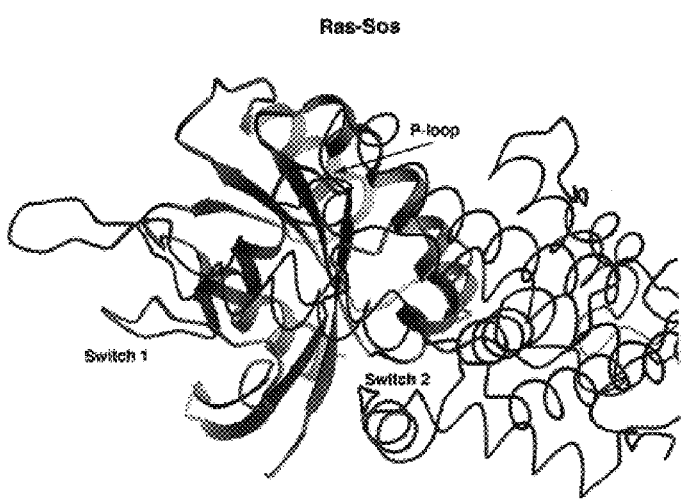
FIGS. 3A–3B show the comparison of Ras complexed with Sos (FIG. 3A) and b) GTP (FIG. 3B) [Pai.et al., EMBO J., 9:2351–2359 (1990)]. The coloring scheme for Ras is the same as FIG. 2B.; GTP is pink and the magnesium ion is shown as a magenta sphere. Sos is shown as a green ribbon; the PDB code for GTP-Ras used for these figures is also indicated. Secondary structure elements of Ras that are important in nucleotide binding and Sos binding are labeled.
Figure 3B:
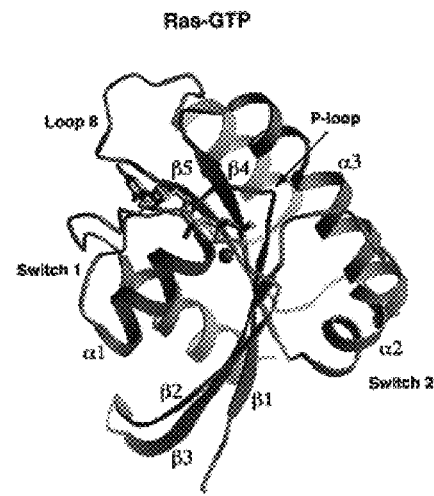

Structure of the Ras-SOS interface: The structure of Ras in the nucleotide bound form consists of a six-stranded β sheet, flanked by 5 α-helices (FIG. 3). Two segments of Ras, Switch 1 (residues 25–40) and Switch 2 (residues 57–75), adopt distinct conformations in the GDP and GTP bound states [Melbum et al, *Science*, 247:939–945 (1990)]. In the nucleotide bound forms, Switch 1 interacts with the base, the ribose group, the phosphates, and the magnesium ion. The Switch 2 region includes the loop following α3 and helix α2 and interacts with the magnesium ion and the phosphate of GTP.

Figure 4A:
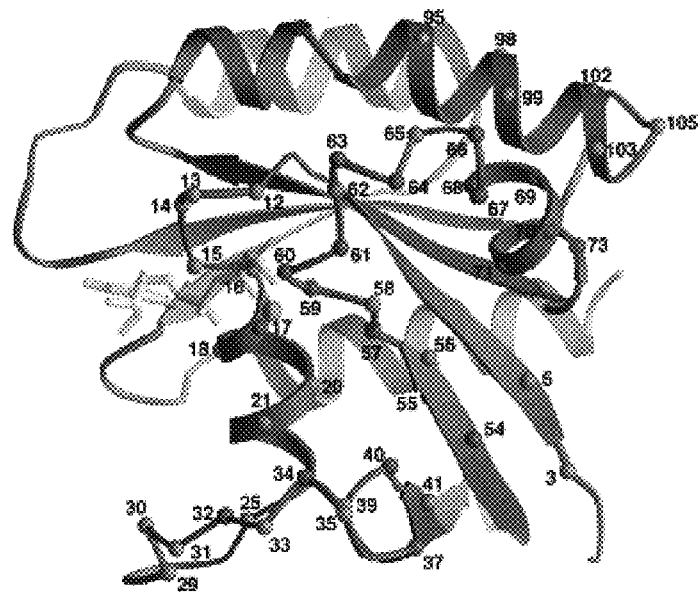
FIGS. 4A–4B show the interface surfaces of the Ras-Sos complex.
Figure 4B:
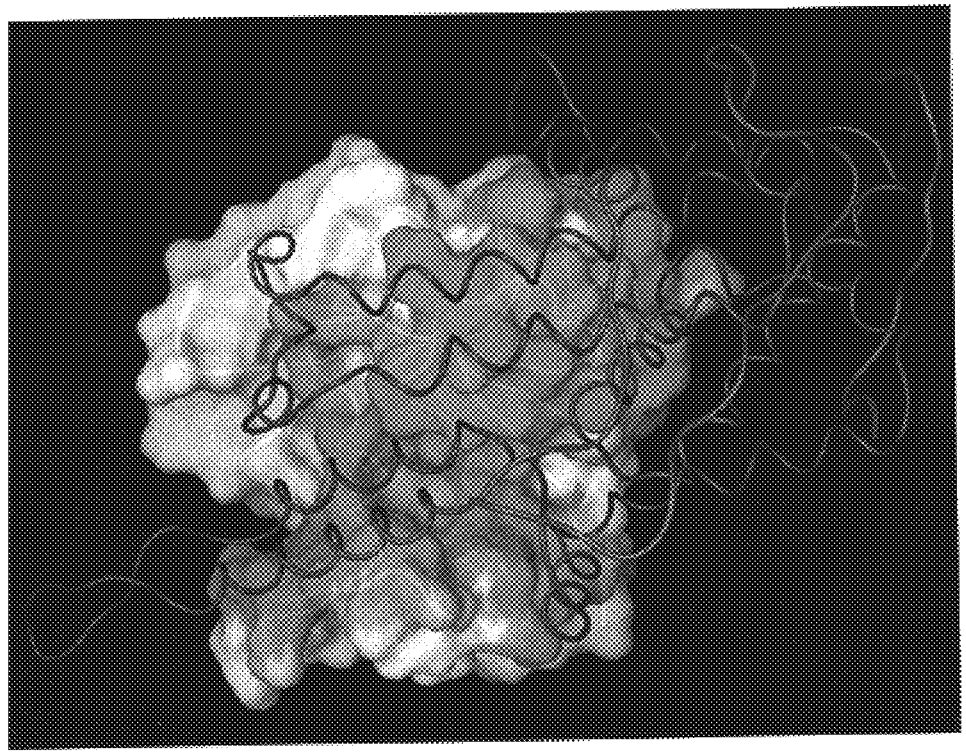
Figure 4C:
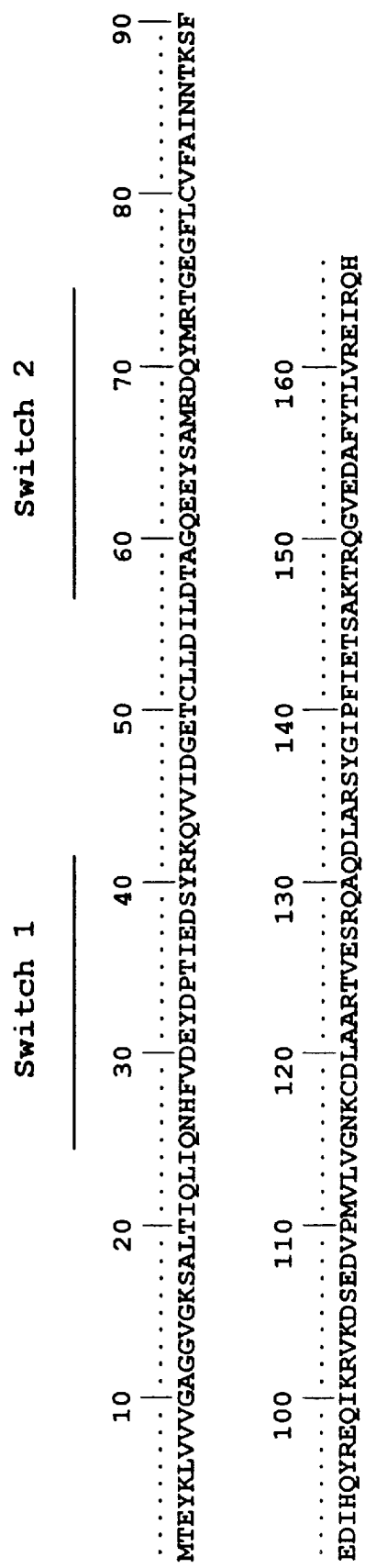

The overall shape of the catalytic domain of Sos is that of an oblong bowl (FIG. 2). The conserved regions SCR 1–3 are in the center of the bowl, which forms the binding site for Ras (FIG. 2B). The regions of Ras that interact most closely with Sos include the P-loop region (strand β1, the P-loop and helix α1), the Switch 1 region and the Switch 2 region. Additional interactions are seen with helix α3 (residues 95–105; FIG. 4A and 4B). The interface between Ras and Sos is very extensive, with 3,600 Å$^2$ of surface area buried in the complex. At the heart of the interface between Switch 2 and Sos is a cluster of three hydrophobic sidechains from Ras (Tyr 64, Met 67 and Tyr 71) that are buried into the hydrophobic core of Sos at the base of the binding site. Surrounding this hydrophobic anchor is an array of polar and charged interactions between Sos and Ras that results in almost every external sidechain of Switch 2 being coordinated by Sos. The interaction surface is primarily hydrophilic, with less than 25% of the buried surface area corresponding to hydrophobic and aromatic residues.

The most obvious effect of Sos binding to Ras is the opening of the nucleotide binding site due to the displacement of Switch 1 by the insertion of the helical hairpin formed by αH and αI (FIG. 5). Although the changes in the Switch 1 segment are large, there are few specific interactions between Ras and Sos in this region. Only three residues of Sos (Lys 913, Asn 936 and Asn 944) are involved in direct hydrogen bonds and only two residues (His 911 and Lys 939) are involved in hydrophobic van der Waals contacts or stacking interactions with Switch 1 residues. Of these five residues, four (His 911, Lys 913, Asn 936 and Lys 939) are not conserved among Ras exchange factors, suggestive that the helical hairpin plays a steric rather than a sequence specific role in keeping the Switch 1 region distant from the nucleotide binding site. Consistent with this idea, the temperature factors in the Switch 1 region are relatively high (average backbone B-value of 81 Å$^2$ for Switch 1, compared to 46 Å$^2$ for the entire Ras backbone).

Figure 6A:
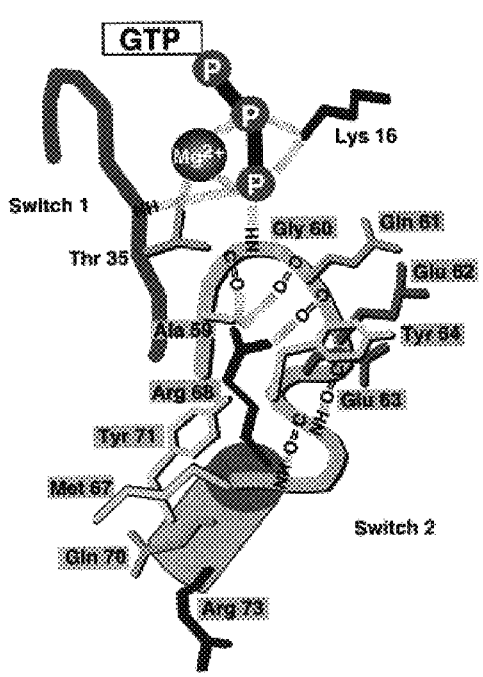
Figure 6B:
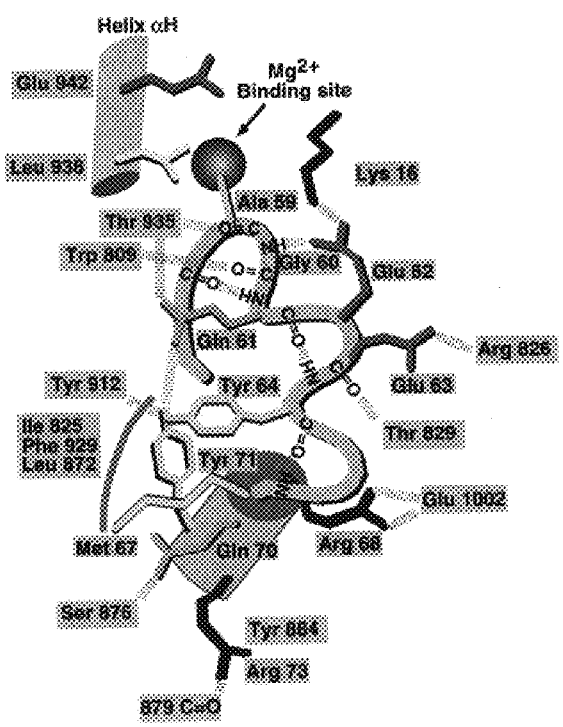

In contrast to the loose interaction between Sos and the Switch 1 region, the Switch 2 region is held in a very tight embrace by Sos. The temperature factors for all atoms of Switch 2 are low (34 Å$^2$, compared with the average value of 49 Å$^2$ for all of Ras). The C-terminal end of Switch 2 is farthest from the nucleotide binding site, and sidechains in this region interact with Sos but do not change their position significantly. However, closer to the nucleotide binding site the interactions between Sos and the sidechains of Switch 2 results in a restructuring of the polypeptide backbone connecting β3 and α2 (FIG. 6A and 6B). The restructuring of the backbone is a crucial determinant of nucleotide exclusion.

Switch 1 and Switch 2 are the only regions of Ras in which structural changes are directly induced by Sos. Comparison of the structure of Ras in the Ras-Sos complex with that of the nucleotide bound forms shows that there are also structural changes in the loops that bind the nucleotide base (Loop 8, between β5 and α5, residues 118–123) and the phosphate (the P-loop, residues 10 to 15). The changes in these loops appear to be a simple consequence of the absence of nucleotide.

Structural Changes at the Nucleotide Binding Site: The modes of binding of GTP and GDP to Ras are very similar [Milburn el al., *Science*, 247: 939–945 (1990)]. β-strand 1 leads into the phosphate binding loop (P-loop), which contains a sequence motif (GX$_4$GKT) that is seen in many nucleotide binding proteins. The structural element encompassing β1, the P-loop and α1 is common to many nucleotide binding proteins, and is colored red in FIGS. 2B and 3. The phosphate groups of the nucleotide are cradled between the P-loop and helix α1 such that the helix dipole of α1 interacts favorably with the negatively charged phosphates. An important component of the phosphate binding site is a magnesium ion, which coordinates the P phosphate (and the γ phosphate in GTP). In the GTP complex, octahedral coordination of the Mg$^{2+}$ ion is completed by the sidechains of Ser 17 and Thr 35 of Ras and two water molecules [Pai et al., *EMBO J*, 9:2351–2359 (1990)]. The guanine base is recognized by sidechains presented by the two loops immediately following strands β4 and β6. The ribose ring interacts mainly with the Switch 1 region.

Figure 5A:
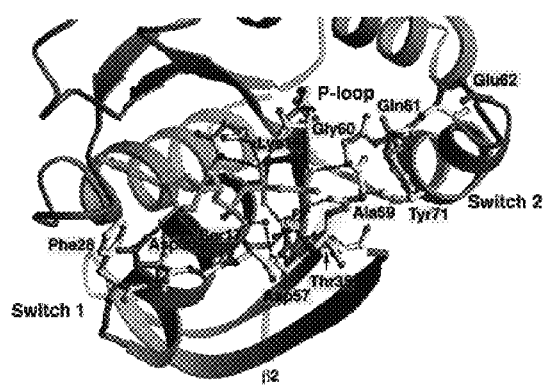
FIG. 5A–5D shows the interactions at the nucleotide binding site.

The conformation of helix α2 in the Switch 2 region differs greatly in the GDP- and GTP-bound forms of Ras. The sensitivity of Switch 2 to the presence of GTP versus GDP is a consequence of the coordination of the terminal phosphate of GTP by the backbone amide nitrogen of Gly 60 (FIGS. 5A and 6A). In the Ras-GDP complex, the backbone is not engaged in such interactions, presumably allowing α2 to rotate away. The conformation of the Switch 2 region in the Ras-Sos complex can be compared to that seen in the GTP-bound form of Ras, since the Switch 2 region is less well ordered in the GDP bound form [Milburn et al., *Science*, 247:939–945 (1990)]. The GTP-bound form is also a natural structure for comparison to the nucleotide-free structure of Ras in the Sos complex, since it represents the structure of Ras when the binding site is fully ligated.

The changes in the structure of Switch 1 and Switch 2 that are induced by Sos result in the exclusion of nucleotide by disruption of the magnesium and phosphate binding sites, and removal of the interactions between Switch 1 and the nucleotide (FIG. 5). Three specific features of the Switch 2 conformation are correlated with disruption of nucleotide binding. The backbone conformation in the central region of Switch 2 is compressed in the Ras-Sos complex due to the formation of three consecutive β turns (between residues 58 to 61, 61 to 64 and 64 to 67; an S-shaped curve with β turns between residues 62 and 65 and also 64 and 67 is present in the GTP bound form of Ras, FIG. 6A and 6B). As a consequence of the first β turn, the methyl sidechain of Ala 59 is turned in towards the phosphate binding site and occludes the position that would be occupied by the $Mg^{2+}$ ion in nucleotide complexes. In the GTP-bound form, the amide nitrogen of Gly 60 coordinates an oxygen atom of the terminal phosphate in the GTP complex. Due to the formation of the second β turn, the sidechain of Glu 62 moves from a position distant from the phosphate binding site to one where it now coordinates both the amide nitrogen of Gly 60 and the sidechain of Lys 16 (part of the conserved Walker motif, Lys 16 normally coordinates the oxygen atoms of the phosphates, FIG. 5A and 6A).

In the GTP bound form the polypeptide backbone of the β3–α2 loop adopts a conformation wherein three carbonyl groups (that of 59, 60, 61 are pointed inwards. The resultant anion hole coordinates the sidechain of Arg 68, and positions the methyl group of Ala 59 away from the magnesium binding site. In the Sos complex, Arg 68 is removed from this internal location by interactions with Glu 1002 of Sos, and the anion hole is disrupted by the formation of the first two β turns in the structure (FIG. 6A and 6B).

Figure 5B:
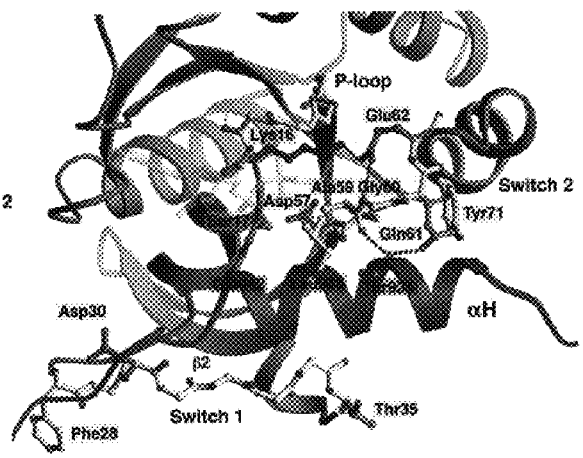
Figure 5C:
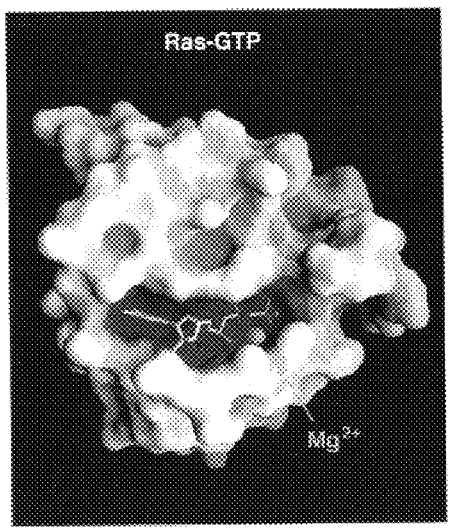

The change in the Switch 1 region of Ras when bound to Sos is drastic. The C-terminal of helix α1 is shortened by about 1 helical turn. Switch 1 normally rises up from the end of α1 towards the P-loop region, so as to sandwich the nucleotide between it and the rest of Ras (FIG. 5A and 5C). In the nucleotide complexes, Switch 1 approaches the Switch 2 region closely and strand β2 in Switch 1 forms an antiparallel interaction with strand β3, which leads into Switch 2. In the Sos complex, this anti-parallel β-sheet interaction is completely disrupted and strand β2 is melted, and Switch 1 is completely removed from the nucleotide binding site (FIG. 5B and 5D).

Figure 5D:
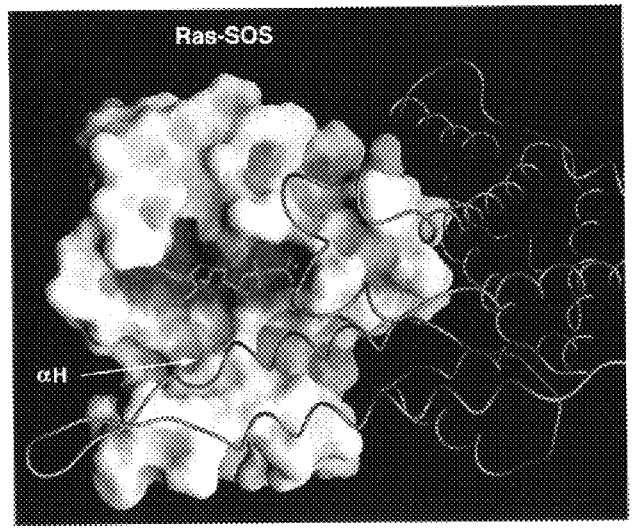

One important aspect of the insertion of the hairpin into the Switch 1 region is that it does not result in a significant occlusion of the nucleotide binding site (FIG. 5D). Rather, the main effect of this structural distortion is to break the network of direct and water-mediated hydrogen bonds that form between Switch 1 and the nucleotide, which is an effective method for destabilizing the nucleotide. In the GDP and GTP complexes, Phe 28 of Ras interacts with the guanine base through a perpendicular aromatic-aromatic interaction (FIG. 5A). Mutations at this position (Phe 28→Leu) result in a 18-fold increase in the intrinsic rate of dissociation of nucleotide from Ras [Mistou et al., *EMBO J*, 11:2391–2397 (1992)]. In the Sos complex, the Cα atom of Phe 28 moves 9.6 Å and the sidechain no longer interacts with the nucleotide binding site (FIG. 5B). Moreover, two sidechains presented by helix αH of Sos, Leu 938 and Glu 942, directly impede the binding of magnesium and phosphate, respectively. The carboxylate group of Glu 942 is positioned near the location of the a phosphate of GTP or GDP in the nucleotide bound forms of Ras, and in the SOS complex Glu 942 forms a hydrogen bond with Ser 17 of Ras, a ligand of the magnesium ion in the nucleotide complexes of Ras. Leu 938 further increases the hydrophobicity of the magnesium binding site in the Sos complex, which is also occupied by Ala 59 from Switch 2.

Implications for the Reaction Mechanism: The mechanism of nucleotide release by the catalytic domain of murine Cdc25 has been investigated recently using fluorescently labeled nucleotides [Lenzen et al., *Biochemistry* 37:7420–7430 (1998)]. The affinity of Cdc25 for nucleotide-free Ras (Kd=4.6 nM) is found to be several orders of magnitude higher than that for nucleotide bound Ras, and the maximal acceleration by Cdc25 of the rate of dissociation of nucleotide is greater than 10,000-fold. Cdc25 acts primarily by facilitating the dissociation of nucleotide, with no preference for GTP or GDP.

Kinetic analysis of the association of nucleotides shows that the reaction proceeds via the formation ternary complex of a loosely bound nucleotide and Ras-Cdc25 followed by a conversion to a form in which the nucleotide is tightly bound to Ras [Lenzen et al, *Biochemistry* 37:7420–7430 (1998)]. In light of the structure of the Ras-Sos complex, the first step can be interpreted as the interaction of the base and the ribose of the nucleotide with the part of the Ras binding site that is not occluded by Sos. The second step would involve a conformational change in the Switch 2 segment and release of Switch 1, resulting in the restructuring of a competent binding site for phosphate and magnesium. It is expected that Sos would dissociate from Ras in parallel or after the second step. These studies also show that the mechanism by which Cdc25 displaces the nucleotide does not depend solely on expulsion of the magnesium [Lenzen et al., *Biochemistry* 37:7420–7430 (1998)]. This is consistent with the Ras-Sos structure, since the mechanism involves both the removal of the Switch 1-nucleotide interactions as well as interference with the phosphate groups.

Analysis of RAS Mutations: The interaction of Ras with Cdc25 and Sdc25 has been studied extensively by mutagenesis and biochemical methods. However, no studies detailing the thermodynamics and kinetics of Sos and Ras and effects of Sos mutations have been reported as yet. Although SOS, Cdc25 and Sdc25 are likely to share the same general features of the mechanism of nucleotide release, the relatively low sequence identity between them (FIG. 1) means that comparisons must be made cautiously.

The structure of the Ras-Sos complex is consistent with a number of mutations in Ras that have highlighted the importance of the Switch 1 and Switch 2 regions in the interaction with nucleotide exchange factors [Mistou et al., *EMBO J*, 11:2391–2397 (1992); Verrotti et al., *EMBO J.*, 11:2855–2862 (1992); Segal et al., *Proc. Natl. Acad. Sci.*, 90:5564–5568 (1993); Mosteller et al., *Molec. Cell. Biol.*, 14:1104–1112 (1994); Segal et al., *Eur. J Biochem.*, 228:96–101 (1995); Leonardsen et al., *Oncogene*, 13:2177–2187 (1996); Crechet et al., *J. Biol. Chem.*, 271:17234–17240 (1996); Quilliam et al., *J. Biol. Chem.*, 271:11076–11082 (1996)]. The importance of helix α3 (residues 102–105) has also been noted [Segal et al., *Proc. Natl. Acad. Sci.*, 90:5564–5568 (1993); Segal et al., *Eur. J Biochem.*, 228:96–101 (1995); Leonardsen et al., *Oncogene*, 13:2177–2187 (1996)]. The importance of Switch 2 for the recognition of the exchange factor is demonstrated by the analysis of mutations in residues that are not directly involved in nucleotide binding, but which are affected in GDP-GTP exchange. Mutation of Glu 62 and Glu 63 to histidine had no significant effect on the stability of the Ras-GDP complex [Nitsou et al., *EMBO J.*, 11:2391–2397

(1992)]. However, both Ras mutants were severely compromised in their ability to be activated by Sdc25 [Mitsou et al., *EMBO J*, 11:2391–2397 (1992)]. In the structure of the Ras-Sos complex, Glu 62 and 63 of Ras are both seen to be crucial to the interaction with Sos (FIGS. 5B and 6B).

Of particular interest are dominant negative mutants of Ras that appear to act by binding to and sequestering nucleotide exchange factors [Feig and Cooper, *Molec. Cell. Biol.*, 8:3235–3243 (1988); Chen et al., *Oncogene*, 9:2691–2698 (1994)]. The most straightforward explanation of the action of these mutations is that they destabilize nucleotide binding [Haney and Broach, *J. Biol. Chem.*, 269:16541–16548 (1994); Chen et al., *Oncogene*, 9:2691–2698 (1994); Powers et al., *Cell*, 65:1225–1231 (1991)], thereby increasing the apparent affinity of Ras for Sos or other exchange factors. Some of the dominant negative mutations may, in addition, result in stronger interactions between Ras and the exchange factor. For example, Ser 17 in Ras forms a hydrogen bond with Glu 942 in Sos (FIG. 5B). Mutation of Ser 17 to Asn 17 results in a dominant negative Ras, and Asn at this position in Ras may be positioned so as to interact more strongly with Glu 942 of Sos.

That the dominant negative mutant Ras proteins act by binding to the exchange factor is also suggested by the fact that mutations at residues that are important for the formation of the Ras-Sos interface result in a reversion of the dominant negative behavior [Mosteller et al., *Molec. Cell. Biol.*, 14:1104–1112 (1994); Crechet et al., *J. Biol. Chem.*, 271:17234–17240 (1996)]. For example, in *S. cerevisiae* Ras2p, Ser 24→Asn (corresponding to Ser 17→Asn in H-Ras) is a dominant negative mutation [Chen et al., *Oncogene* 9:2691–2698 (1994)]. Substitution of Arg 80, Asn 81 (Arg 73, Thr 74 in H-Ras) with Asp—Asp in the mutant (Ser 24 Asn) Ras2p results in a loss of sensitivity to Sdc25 and reversion of the dominant negative phenotype [Crechet et al., *J. Biol. Chem.*, 271:17234–17240 (1996)]. In the Ras-Sos complex, Arg 73 (Arg 80 in Ras2p) is involved in interactions with two residues of Sos (FIG. 6A), and mutation to Asp would clearly be disruptive.

Comparison with EF—Tu/EF—Ts and GrpE/DnaK. At present, only two other structures of nucleotide binding proteins complexed to their exchange factors are known: EF—Tu—EF—Ts and GrpE-DnaK. EF—Tu is a GTPase that contains a nucleotide binding domain that is topologically similar to Ras as well as two additional domains [Jurnak, *Science*, 230:32–36 (1985)]. The EF—Tu—EF—Ts complex, like the Ras-Sos complex, stimulates nucleotide release by disrupting the interactions of the phosphate groups of the nucleotide, leaving the binding site for the base and ribose unimpeded [Wang et al., *Nat. Struct. Biol.*, 4:650–656 (1997); Kawashima et al., *Nature*, 379:511–518 (1996)]. Reorientation of a peptide bond in the phosphate binding P-loop, induced by EF-Ts binding, results in the placement of a carbonyl oxygen in a position where it would collide with the β phosphate of the nucleotide. In addition, conformational changes in the Switch 2 region remove sidechains that interact with the magnesium ion via water molecules.

Strikingly, *E. coli* EF-Ts introduces a C-terminal α-helix into the region of the nucleotide binding site near the Switch 1 region [Kawashima et al, *Nature*, 379:511–518 (1996)]. However, this helix is further removed from the nucleotide binding site than helix αI in Sos, and no corresponding helix is seen in EF-Ts from Thermus thermophilus [Wang et al., *Nat. Struct. Biol.*, 4:650–656 (1997)]. In contrast to Ras, the Switch 1 region of nucleotide-bound EF-Tu does not interact extensively with the nucleotide binding site. Consequently, disruption of the Switch 1 structure does not appear to be a major component of the mechanism of EF-Ts action.

The mechanism of nucleotide release from DnaK by GrpE is fundamentally different from that seen in Ras and EF-Tu. The ATPase domain of DnaK is much larger than Ras (166 residues for Ras compared to 383 residues for DnaK) and contains two subdomains that form a deep cleft in which nucleotide binds. GrpE acts by binding to the mouth of the cleft and wedging apart the two sides of the binding site [Harrison et al., *Science*, 276:431–435 (1997)].

EXAMPLE 2

Identifying Medicinal Chemicals for Rational Drug Design Using the Three-dimensional Structure of the RAS-SOS Complex Introduction Through the use of the three-dimensional structure of the Ras-Sos complex, described in Example 1, potential drugs can be rationally designed to inhibit the conversion of the inactive form of Ras (Ras-GDP) to the active form (Ras-GTP).

This aspect of the present invention takes advantage of the requisite role of the nucleotide exchange factor of Sos to catalyze this conversion. Since the active form of Ras is required for cellular proliferation, such drugs can be used to inhibit the proliferation of cancer cells, for example. Therefore compounds that e.g., (i) stabilize the Ras-Sos complex, and thereby prevent GTP from binding Ras, or (ii) inhibit the nucleotide exchange factor of Sos, can used in the development of drugs that inhibit the activation of Ras. Once such compounds are synthesized, they can be experimentally tested and then further refined by the methodology exemplified above.

Analogs of the Nucleoside Component of GTP as stabilizers of Ras-Sos: From Example 1, above, it is known that the purine binding loop of Ras undergoes a major conformational change upon binding to Sos. In so doing, electronic repulsion of the guanine carbonyl (O—6) by a Ras-backbone carbonyl (lys-117) and potentially a Ras-sidechain alanine methyl (ala-146) could take place [1, FIG. 7A.] At the same time, the 7-N of the guanine appears to be able to make a hydrogen bond with a Ras-side-chain amide (asn-116). Importantly, a cysteine (cys-118) swings out in this new structure which is positioned not far from the 3-N of guanine. While the cysteine thiol may have the opportunity to form an H-bond with the 3-N, it affords other more interesting opportunities as described below.

Compound 2 [FIG. 7B] incorporates a guanine analog which has three important differences in the 6-membered ring. (i) the 3-N is replaced with a carbonyl; (ii) the O—6 is replaced by an sp3 center with 2 hydrogen atoms; and (iii) the 1 and 2 positions of the ring now are replaced by an all carbon ring and include a difluoro substitution at the 2-position. These changes should allow better accommodation of the Ras protein vis-a-vis the 6-position because of the lack of steric or electronic repulsion. The incorporation of the α-difluoroketone functionality seems poised to undergo nucleophilic attack by the Ras-cysteine thiol to afford the ketalic structure in 3 [FIG. 7B]. Such structures are stable because of the well-known tendency of fluoroketones to exist as hydrated structures. This would be a covalent but somewhat reversible interaction.

Compound 4 [FIG. 7B] is a close relative of Compound 3. It lacks the guanine N-1 atom and may be considered a flexible guanosine analog. Since the absolute requirements are not known, this increase in flexibility may allow a tighter fit into Ras. In addition, the additional fluorine in the trifluoroketone functionality should drive the equilibrium between ketone (4) and thioketal (5) [FIG. 7B] more toward the thioketal (5) as compared to the case with Compound 2.

Compound 6 [FIG. 7B] is a further modification of Compound 4. In 6, the trifluoromethyl-group is replaced by a hydrogen. This aldehyde 6 should still be able to undergo thio-ketal formation giving 7 [FIG. 7B] because of the known reactivity of such functional groups. However, the lack of a trifluoromethyl group may also be beneficial in the case of unforeseen steric or electronic repulsion of this grouping.

Compound 8 [FIG. 7C] is related to Compounds 4 and 6. Replacement of the hydrogen atom (or trifluoromethyl) with a mono-halomethyl may afford the possibility of irreversible alkylation of the Ras cysteine thiol to produce Compound 9 [FIG. 7C]. Unlike thioketal formation, $S_N2$ displacement of the halide (chloride, bromide, iodide; fluoride is a relatively poor leaving group for such reactions) should be kinetically as well as thermodynamically stable. Such irreversible inactivation of Ras may be desirable because new protein would have to be synthesized to recover biological function.

Compound 10 [FIG. 7C] has similarities to Compound 2 but by incorporation of the exomethylene instead of the difluoro-substitution, reactivity would be expected to be quite different. It is reasonable to predict that Compound 10 could be a potent Michael acceptor which would result in the formation of 11 [FIG. 7C]. Again, 11 would be expected to be very stable like 9 and would thus lead to permanent Ras inactivation.

In place of hydrogen atoms at the 6-position of Compounds 2 and 10, Compound 12 [FIG. 7C] contains an amino group. Such an amine may be able to form a stabilizing hydrogen bond with the Ras backbone carbonyl and therefore result in greater binding energy. Although 12 is shown with the exomethylene function as 10 and could potentially form 13 [FIG. 7C], there is no reason that the amino group could not be used along with the other congeners described above.

Likewise, Compounds 14 and 16 [FIG. 7C] place different steric requirements at the guanine 6-position that might serendipitously be well-tolerated. Perhaps more importantly, they would be expected to be even more chemically reactive as Michael acceptors than 10 and 12 because of the formation of an aromatic ring in the reaction as exemplified by the production of 15 and 17 [FIG. 7C]. Such aromatization might help accelerate the reactions of 14 and 16 leading to Ras-inactivation.

Instead of the assumption that the binding pocket of Ras would be altered when a purine were to bind, it is conceivable that the guanine binding would induce the Sos-free conformation of Ras. Thus, guanine may end up being the preferred substructure for nucleoside inhibitor design.

Modifications of the Ribose Triphosphate Structure: The structure of 1 [FIG. 7A] illustrates that the triphosphate of GTP might be very poorly accommodated in a Ras-Sos complex. Thus, the focus of attention could be on replacements of this portion of the molecule. Note that all of the purine derivatives described above could be interfaced with the ribose triphosphate substitutions described below.

To start with, just the standard ribose ring could be employed. The deletion of the triphosphate completely resulting in 18 [FIG. 7D] could allow favorable binding. Moreover, the amine function in 19 [FIG. 7D] could potentially allow a hydrogen bond with the Ras-carboxylate near the α-phosphate position. Repositioning of the amino-function, extension of the tether and the placement of suitable hydrogen bond acceptors (Y) in Compounds 20–23 [FIG. 7D] are logical derivatives to target. The use of hydrophobic substitutions in the terminus of the molecules (Z of 22 and 23) may be important to interact with the hydrophobic side chains that are found in Ras in the Ras-Sos complex. It should also be mentioned that for inhibitor design purposes the ribose ring could be truncated since there are no obvious contacts with this group.

β-Turn Mimics that Bind to Sos: With the aid of the three-dimensional structure of the Ras-Sos complex, Example 1, above, binding partners for Sos which will inhibit the binding of Sos and Ras can be rationally designed. For example, upon binding to Sos, a conformational change in Ras appears to take place which results in the formation of a β-turn from amino acids 64 to 67 (24) [FIG. 7E]. Amino acid 64 contains a tyrosine which appears to make a key hydrophobic interaction with Sos. Also of potential importance is a hydrophobic methionine which emerges from the C-terminal side of the β-turn. There are a large number of β-turn small molecule mimics which have been designed and synthesized and shown to be effective. These compounds hold the amine and carboxy-terminus in relatively fixed positions that mimic those of the real turn. At this time, it is not possible to predict with confidence whether the one or more of Compounds 25–29 [FIG. 7E] would complement the Sos binding surface so all types would need to be screened. The key additions to these known compounds would be to place an aromatic at the N-terminal side of the turn and probably a hydrophobic substituent (aryl or alkyl) at the C-terminal side.

It is important to emphasize that the compounds presented throughout the present Disclosure, are simply used to illustrate potential starting points for identifying drugs that can be used for treating diseases involving Ras. Any person having skill in the art of medicinal chemistry would readily realize that although the compounds exemplified above, are an excellent starting point for the drug screens, it is highly unlikely that any of the listed compounds will themselves be successful drug candidates.

Relevant References Include

Silverman, R. B. The Organic Chemistry of Drug Design and Drug Action. Academic Press, New York, 1992.

Nicholson et al. *Nature* 376:37 (1995).

Rotunda et al. *Nature Structural Biology* 3:619–625 (1996).

Gante, Angew. *Chem. Int. Ed. Engl.* 33:1699–1720 (1994).

Peigel, *J. Am. Chem. Soc.* 108:181 (1986).

Wagner, and Feigel, *Tetrahedron* 49:10831 (1993).

Brandmeier et al. *Helv. Chim. Acta.* 77: 70 (1994).

Sato, and Nagai *J. Chem. Soc. Perkin Trans.* 1:1231 (1986).

Nagai et al., *Tetrahedron* 49:3577 (1993).

Kemp, and Stites, *Tetrahedron Lett.* 29:5057 (1988).

Genin, and Johnson, *J. Am. Chem. Soc.* 114:8778 (1992).

Ripka et al., *Tetrahedron* 49:3593 (1993).

The present invention is not to be limited in scope by the specific embodiments describe herein. Indeed, various modifications of the invention in addition to those described herein will become apparent to those skilled in the art from the foregoing description and the accompanying figures.

Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

---

What is claimed is:

1. A method of identifying a compound that stabilizes a RAS-Son of sevenless complex (Ras-Sos) complex using the three-dimensional structure of the Ras-Sos complex comprising:
    (a) selecting a potential compound by performing rational drug design with the set of atomic coordinates in FIGS. 8-1 through 8-75, wherein said selecting is performed in conjunction with computer modeling;
    (b) contacting the potential compound with a Ras-Sos complex comprising a Ras or a RAS fragment, and a Sos or a Sos fragment; and
    (c) measuring the stability of the Ras-Sos complex; wherein a potential compound is identified as a compound that stabilizes the Ras-Sos complex when there is an increase in the stability of the Ras-Sos complex.

2. The method of claim 1, wherein the Ras fragment comprises a Sos contacting region.

3. The method of claim 2, wherein the Sos fragment comprises the amino acid sequence of amino acids 781 to 1017 of SEQ ID NO:2, or the amino acid sequence of amino acid 781 to 1017 of SEQ ID NO:2 comprising one or more conservative amino acid substitutions.

4. The method of claim 2, wherein the Sos fragment further comprises an N-Domain comprising amino acid residues 568–741 of SEQ ID NO:2 or amino acid residues 568–741 of SEQ ID NO:2 comprising one or more conservative amino acid substitutions.

5. The method of claim 2, wherein the Sos fragment comprises the amino acid sequence of amino acids 564 to 1049 of SEQ ID NO:2, or the amino acid sequence of amino acid 564 to 1049 of SEQ ID NO:2 comprising one or more conservative amino acid substitutions.

6. The method of claim 2, wherein the Sos contacting region of the Ras fragment comprises the amino acid sequence of amino acids 5 to 105 of SEQ ID NO:1, or the amino acid sequence of amino acid 5 to 105 of SEQ ID NO:1 comprising one or more conservative amino acid substitutions.

7. The method of claim 6, wherein the Ras fragment further comprises the amino acid sequence of amino acids 1 to 4 and 106 to 166 of SEQ ID NO:1, or further comprises the amino acid sequence of 1 to 4 and 106 to 166 of SEQ ID NO:1 comprising one or more conservative amino acid substitutions.

8. The method of claim 7, wherein the Sos fragment comprises the amino acid sequence of amino acids 564 to 1049 of SEQ ID NO:2, or the amino acid sequence of amino acid 564 to 1049 of SEQ ID NO:2 comprising one or more conservative amino acid substitutions.

9. A method of identifying a compound that inhibits the binding of GTP to Ras using the three-dimensional structure of a Ras-Sos complex comprising:
    (a) selecting a potential compound by performing rational drug design with the set of atomic coordinates in FIGS. 8-1 through 8-75, wherein said selecting is performed in conjunction with computer modeling;
    (b) contacting the potential compound with;
        (i) a Ras-Sos complex comprising a Ras or a Ras fragment, and a Sos or a Sos fragment, and
        (ii) GTP or a GTP analog; under conditions in which Ras or the Ras fragment of the Ras-Sos complex can bind GTP in the absence of the compound; and
    (c) measuring the binding affinity of Ras or the Ras fragment with GTP or the GTP analog; wherein a potential compound is identified as a compound and that inhibits GTP from binding to Ras when there is a decrease in the binding affinity of GTP or the GTP analog with the Ras or the Ras fragment in the presence of the compound.

10. The method of claim 9, wherein the Sos fragment comprises the amino acid sequence or amino acids 781 to 1017 of SEQ ID NO:2, or the amino acid sequence of amino acid 791 to 1017 of SEQ ID NO:2 comprising one or more conservative amino acid substitutions.

11. The method of claim 9, wherein the Sos fragment comprises an N-Domain comprising amino acid residues 568–741 of SEQ ID NO:2 or amino acid residues 568–741 of SEQ ID NO:2 comprising one or more conservative amino acid substitutions.

12. The method of claim 9, wherein the Sos fragment comprises the amino acid sequence of amino acids 564 to 1049 of SEQ ID NO:2, or the amino acid sequence of amino acid 564 to 1049 of SEQ ID NO:2 comprising one or more conservative amino acid substitutions.

13. The method of claim 9, wherein the Ras fragment comprises a Sos contacting region.

14. The method of claim 13, wherein the Sos contacting region of the Ras fragment comprises the amino acid sequence of amino acids 5 to 105 of SEQ ID NO:1 or the amino acid sequence of amino acid 5 to 105 of SEQ ID NO:1 comprising one or more conservative amino acid substituting.

15. The method of claim 14, wherein the Ras fragment further comprises the amino acid sequence of amino acids 1 to 4 and 106 to 166 of SEQ ID NO:1, or further comprises the amino acid sequence of 1 to 4 and 106 to 166 of SEQ ID NO:1 comprising one or more conservative amino acid substitution.

16. The method of claim 15, wherein the Sos fragment comprises the amino acid sequence of amino acids 564 to 1049 of SEQ ID NO:2, or the amino acid sequence of amino acid 564 to 1049 of SEQ ID No:2 comprising one or more conservative amino acid substitutions.

17. A method of identifying a compound that inhibits the formation of a Ras-Sos complex using the three-dimensional structure of the Ras-Sos complex comprising:

(a) selecting a potential compound that binds to Sos on a portion of Sos that is involved in the binding of Sos to Ras in the Ras-Sos binding complex, wherein said selecting is performed using rational drug design with the set of atomic coordinates in FIGS. 8-1 through 8-75, and is performed in conjunction with computer modeling;

(b) contacting the potential compound with Sos or a Sos fragment and Ras or a Ras fragment under conditions in which the Ras-Sos complex can form in the absence of the potential compound; and (c) measuring the binding affinity of Ras or the Ras fragment for Sos or the Sos fragment; wherein a potential compound is identified as a compound that inhibits the formation of the Ras-Sos complex when there is a decrease in the binding affinity of Ras or a Ras fragment for Sos or the Sos fragment.

18. The method of claim 17 wherein the potential compound binds to Sos at the site where the β-turn of amino acids 64 to 67 of SEQ ID NO:1 of Ras binds Sos in the Ras-Sos complex.

19. The method of claim 17, wherein the Sos fragment comprises the amino acid sequence of amino acids 781 to 1017 of SEQ ID NO:2, or the amino acid sequence of amino acid 781 to 1017 of SEQ ID NO:2 comprising one or more conservative amino acid substitutions.

20. The method of claim 17, wherein the Sos fragment comprises an N-Domain comprising amino acid residues 568–741 of SEQ ID NO:2 or amino acid residues 568–741 of SEQ ID NO:2 comprising one or more conservative amino acid substitutions.

21. The method of claim 20, wherein the Sos fragment comprises the amino acid sequence of amino acids 564 to 1049 of SEQ ID NO:2, or the amino acid sequence of amino acid 564 to 1049 of SEQ ID NO:2 comprising one or more conservative amino acid substitutions.

22. The method of claim 17, wherein the Ras fragment comprises a Sos contacting region.

23. The method of claim 22, wherein the Sos contacting region of the Ras fragment comprises the amino acid sequence of amino acids 5 to 105 of SEQ ID NO:1 or the amino acid sequence of amino acid 5 to 105 of SEQ ID NO:1 comprising one or more conservative amino acid substitutions.

24. The method of claim 23, wherein the Ras fragment further comprises the amino acid sequence of amino acids 1 to 4 and 106 to 166 of SEQ ID NO:1 or further comprises the amino acid sequence of 1 to 4 and 106 to 166 of SEQ ID NO:1 comprising one or more conservative amino acid substitutions.

25. The method of claim 24, wherein the Sos fragment comprises the amino acid sequence of amino acids 564 to 1049 of SEQ ID NO:2, or the amino acid sequence of amino acid 564 to 1049 of SEQ ID NO:2 comprising one or more conservative amino acid substitutions.

26. A method of identifying a compound that stabilizes a Ras-Sos complex comprising:

(a) obtaining a set of atomic coordinates defining the three-dimensional structure of a Ras-Sos complex consisting of a fragment of Ras consisting of amino acids 1 to 166 of SEQ ID NO:1 and a fragment of Sos consisting of amino acids 564 to 1049 of SEQ ID NO:2 using a crystal having a space group selected from the group consisting of T422 with unit cell dimensions of a=142.7, b=142.7 and c=207.9 and I4 with unit cell dimensions of a=124.6 Å, b=124.6 Å and c=314.9 Å;

(b) selecting a potential compound by performing rational drug design with the atomic coordinates obtained in step (a), wherein said selecting is performed in conjunction with computer modeling:

(c) contacting the potential compound with a Ras-Sos complex; wherein said Ras-Sos complex comprises a Ras or a Ras fragment, and a Sos or a Sos fragment; and (d) measuring the stability of the Ras-Sos complex of step (c); wherein a potential compound is identified as a compound that stabilizes the Ras-Sos complex when there is an increase in the stability of the Ras-Sos complex of step (c).

27. A method or identifying a compound that inhibits the binding of GTP to Ras comprising:

(a) obtaining a set of atomic coordinates defining the three-dimensional structure of a Ras-Sos complex consisting of a fragment of Ras consisting of amino acids 1 to 166 of SEQ ID NO:1 and a fragment of Sos consisting of amino acids 564 to 1049 of SEQ ID NO:2 using a crystal having a spare group selected from the group consisting of I422 with unit cell dimensions of a=142.7, b=142.7 and c=207.9 and I4 with unit cell dimensions of a=124.6 Å, b=124.6 Å and c=314.9 Å; 42.7 and c=207.9 and I4 with a unit cell of dimensions a=124.6 Å, b=124.6 Å and c=314.9 Å;

(b) selecting a potential compound by performing rational drug design with the atomic coordinates obtained in step (a), wherein said selecting is performed in conjunction with computer modeling;

(c) contacting the potential compound with:

(i) a Ras-Sos complex comprising a Ras or a Ras fragment, and a Sos or a Sos fragment, and (ii) GTP or a GTP analog; under conditions in which Ras or the Ras fragment of the Ras-Sos complex can bind GTP in the absence of the compound; and (d) measuring the binding affinity of Ras or the Ras fragment with GTP or the GTP analog; wherein a potential compound is identified as a compound that inhibits GTP from binding to Ras when there is a decrease in the binding affinity of GTP or the GTP analog with the Ras or the Ras fragment in the presence of the compound.

28. A method of identifying a compound that inhibits the formation of the Ras-Sos complex comprising:
(a) obtaining a set of atomic coordinates defining the three-dimensional structure of a Ras-Sos complex consisting of a fragment of Ras consisting of amino acids 1 to 166 of SEQ ID NO:1 and a fragment of Sos consisting of amino acids 564 to 1049 of SEQ ID NO:2 using a crystal having a space group selected from the group consisting of I422 with unit cell dimensions of a=142.7, b=142.7 and c=207.9 and I4 with unit cell dimensions of a=124.6 Å, b=124.6 Å and c=314.9 Å;
(b) selecting a potential compound that binds to Sos on a portion of Sos that is involved in the binding of Sos to Ras in the Ras-Sos binding complex using the atomic coordinates obtained in step (a)
(c) contacting the potential compound with Sos or a Sos fragment and Ras or a Ras fragment under conditions in which the Ras-Sos complex can form in the absence of the potential compound; and
(d) measuring the binding affinity of Ras or the Ras fragment for Sos or the Sos fragment; wherein a potential compound is identified as a compound that inhibits the formation of the Ras-Sos complex when there is a decrease in the binding affinity of Ras or a Ras fragment for Sos or the Sos fragment.

29. The method of claim 28 herein the potential compound binds to Sos at the site where else β-turn of amino acids 64 to 67 of SEQ ID NO:1 of Ras binds Sos in the Ras-Sos complex.

30. A method of selecting at least one compound that potentially inhibits the conversion of Ras from its inactive form to its active form comprising:
(a) defining the structure of the Ras-Sos complex by the atomic coordinates in FIGS. 8-1 through 8-75 or a portion thereof; and
(b) selecting at least one compound which potentially inhibits the conversion of Ras from its inactive form to its active form; wherein said selecting is performed with the aid of the structure defined in step (a).

31. The method of claim 30 wherein a selected compound potentially inhibits the conversion of Ras from its inactive form to its active form when it stabilizes the Ras-Sos complex, inhibits GTP from binding Ras of the Ras-Sos complex, or inhibits the binding of Sos to Ras.

32. A method of selecting at least one compound that potentially binds to Sos or the Ras-Sos complex comprising:
(a) defining the structure of the Ras-Sos complex by the atomic coordinates in FIGS. 8-1 through 8-75 or a portion thereof; and
(b) selecting at least one compound which potentially binds Sos or to the Ras-Sos complex; wherein said selecting is performed with the aid of the structure defined in step (a).

* * * * *

UNITED STATES PATENT AND TRADEMARK OFFICE
CERTIFICATE OF CORRECTION

PATENT NO.   : 6,156,526
DATED        : December 5, 2000
INVENTOR(S)  : Ann Boriack-Sjodin et al.

It is certified that error appears in the above-identified patent and that said Letters Patent is hereby corrected as shown below:

<u>Title page,</u>
Item [73], please change the Assignee from "The Rockerfeller University" to read -- The Rockefeller University --.

Signed and Sealed this

Twenty-fifth Day of September, 2001

Attest:

*Attesting Officer*

NICHOLAS P. GODICI
*Acting Director of the United States Patent and Trademark Office*

SEQUENCE LISTING

<160> NUMBER OF SEQ ID NOS: 14

<210> SEQ ID NO 1
<211> LENGTH: 189
<212> TYPE: PRT
<213> ORGANISM: Homo sapiens

<400> SEQUENCE: 1

```
Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 2
<211> LENGTH: 1333
<212> TYPE: PRT
<213> ORGANISM: Homo sapiens

<400> SEQUENCE: 2

```
Met Gln Ala Gln Gln Leu Pro Tyr Glu Phe Phe Ser Glu Glu Asn Ala
 1               5                  10                  15

Pro Lys Trp Arg Gly Leu Leu Val Pro Ala Leu Lys Lys Val Gln Gly
            20                  25                  30

Gln Val His Pro Thr Leu Glu Ser Asn Asp Asp Ala Leu Gln Tyr Val
        35                  40                  45

Glu Glu Leu Ile Leu Gln Leu Leu Asn Met Leu Cys Gln Ala Gln Pro
    50                  55                  60

Arg Ser Ala Ser Asp Val Glu Glu Arg Val Gln Lys Ser Phe Pro His
65                  70                  75                  80

Pro Ile Asp Lys Trp Ala Ile Ala Asp Ala Gln Ser Ala Ile Glu Lys
                85                  90                  95
```

-continued

```
Arg Lys Arg Arg Asn Pro Leu Ser Leu Pro Val Glu Lys Ile His Pro
            100                 105                 110
Leu Leu Lys Glu Val Leu Gly Tyr Lys Ile Asp His Gln Val Ser Val
        115                 120                 125
Tyr Ile Val Ala Val Leu Glu Tyr Ile Ser Ala Asp Ile Leu Lys Leu
    130                 135                 140
Val Gly Asn Tyr Val Arg Asn Ile Arg His Tyr Glu Ile Thr Lys Gln
145                 150                 155                 160
Asp Ile Lys Val Ala Met Cys Ala Asp Lys Val Leu Met Asp Met Phe
                165                 170                 175
His Gln Asp Val Glu Asp Ile Asn Ile Leu Ser Leu Thr Asp Glu Glu
            180                 185                 190
Pro Ser Thr Ser Gly Glu Gln Thr Tyr Tyr Asp Leu Val Lys Ala Phe
        195                 200                 205
Met Ala Glu Ile Arg Gln Tyr Ile Arg Glu Leu Asn Leu Ile Ile Lys
    210                 215                 220
Val Phe Arg Glu Pro Phe Val Ser Asn Ser Lys Leu Phe Ser Ala Asn
225                 230                 235                 240
Asp Val Glu Asn Ile Phe Ser Arg Ile Val Asp Ile His Glu Leu Ser
                245                 250                 255
Val Lys Leu Leu Gly His Ile Glu Asp Thr Val Glu Met Thr Asp Glu
            260                 265                 270
Gly Ser Pro His Pro Leu Val Gly Ser Cys Phe Glu Asp Leu Ala Glu
        275                 280                 285
Glu Leu Ala Phe Asp Pro Tyr Glu Ser Tyr Ala Arg Asp Ile Leu Arg
    290                 295                 300
Pro Gly Phe His Asp Arg Phe Leu Ser Gln Leu Ser Lys Pro Gly Ala
305                 310                 315                 320
Ala Leu Tyr Leu Gln Ser Ile Gly Glu Gly Phe Lys Glu Ala Val Gln
                325                 330                 335
Tyr Val Leu Pro Arg Leu Leu Leu Ala Pro Val Tyr His Cys Leu His
            340                 345                 350
Tyr Phe Glu Leu Leu Lys Gln Leu Glu Glu Lys Ser Glu Asp Gln Glu
        355                 360                 365
Asp Lys Glu Cys Leu Lys Gln Ala Ile Thr Ala Leu Leu Asn Val Gln
    370                 375                 380
Ser Gly Met Glu Lys Ile Cys Ser Lys Ser Leu Ala Lys Arg Arg Leu
385                 390                 395                 400
Ser Glu Ser Ala Cys Arg Phe Tyr Ser Gln Gln Met Lys Gly Lys Gln
                405                 410                 415
Leu Ala Ile Lys Lys Met Asn Glu Ile Gln Lys Asn Ile Asp Gly Trp
            420                 425                 430
Glu Gly Lys Asp Ile Gly Gln Cys Cys Asn Glu Phe Ile Met Glu Gly
        435                 440                 445
Thr Leu Thr Arg Val Gly Ala Lys His Glu Arg His Ile Phe Leu Phe
    450                 455                 460
Asp Gly Leu Met Ile Cys Cys Lys Ser Asn His Gly Gln Pro Arg Leu
465                 470                 475                 480
Pro Gly Ala Ser Asn Ala Glu Tyr Arg Leu Lys Glu Lys Phe Phe Met
                485                 490                 495
Arg Lys Val Gln Ile Asn Asp Lys Asp Asp Thr Asn Glu Tyr Lys His
            500                 505                 510
```

```
Ala Phe Glu Ile Ile Leu Lys Asp Glu Asn Ser Val Ile Phe Ser Ala
    515                 520                 525

Lys Ser Ala Glu Glu Lys Asn Asn Trp Met Ala Ala Leu Ile Ser Leu
530                 535                 540

Gln Tyr Arg Ser Thr Leu Glu Arg Met Leu Asp Val Thr Met Leu Gln
545                 550                 555                 560

Glu Glu Lys Glu Glu Gln Met Arg Leu Pro Ser Ala Asp Val Tyr Arg
                565                 570                 575

Phe Ala Glu Pro Asp Ser Glu Glu Asn Ile Ile Phe Glu Glu Asn Met
                580                 585                 590

Gln Pro Lys Ala Gly Ile Pro Ile Lys Ala Gly Thr Val Ile Lys
                595                 600                 605

Leu Ile Glu Arg Leu Thr Tyr His Met Tyr Ala Asp Pro Asn Phe Val
610                 615                 620

Arg Thr Phe Leu Thr Thr Tyr Arg Ser Phe Cys Lys Pro Gln Glu Leu
625                 630                 635                 640

Leu Ser Leu Ile Ile Glu Arg Phe Glu Ile Pro Glu Pro Glu Pro Thr
                645                 650                 655

Glu Ala Asp Arg Ile Ala Ile Glu Asn Gly Asp Gln Pro Leu Ser Ala
                660                 665                 670

Glu Leu Lys Arg Phe Arg Lys Glu Tyr Ile Gln Pro Val Gln Leu Arg
                675                 680                 685

Val Leu Asn Val Cys Arg His Trp Val Glu His Phe Tyr Asp Phe
690                 695                 700

Glu Arg Asp Ala Tyr Leu Leu Gln Arg Met Glu Glu Phe Ile Gly Thr
705                 710                 715                 720

Val Arg Gly Lys Ala Met Lys Lys Trp Val Glu Ser Ile Thr Lys Ile
                725                 730                 735

Ile Gln Arg Lys Lys Ile Ala Arg Asp Asn Gly Pro Gly His Asn Ile
                740                 745                 750

Thr Phe Gln Ser Ser Pro Pro Thr Val Glu Trp His Ile Ser Arg Pro
    755                 760                 765

Gly His Ile Glu Thr Phe Asp Leu Leu Thr Leu His Pro Ile Glu Ile
    770                 775                 780

Ala Arg Gln Leu Thr Leu Leu Glu Ser Asp Leu Tyr Arg Ala Val Gln
785                 790                 795                 800

Pro Ser Glu Leu Val Gly Ser Val Trp Thr Lys Glu Asp Lys Glu Ile
                805                 810                 815

Asn Ser Pro Asn Leu Leu Lys Met Ile Arg His Thr Thr Asn Leu Thr
                820                 825                 830

Leu Trp Phe Glu Lys Cys Ile Val Glu Thr Glu Asn Leu Glu Glu Arg
                835                 840                 845

Val Ala Val Val Ser Arg Ile Ile Glu Ile Leu Gln Val Phe Gln Glu
850                 855                 860

Leu Asn Asn Phe Asn Gly Val Leu Glu Val Val Ser Ala Met Asn Ser
865                 870                 875                 880

Ser Pro Val Tyr Arg Leu Asp His Thr Phe Glu Gln Ile Pro Ser Arg
                885                 890                 895

Gln Lys Lys Ile Leu Glu Glu Ala His Glu Leu Ser Glu Asp His Tyr
                900                 905                 910

Lys Lys Tyr Leu Ala Lys Leu Arg Ser Ile Asn Pro Pro Cys Val Pro
                915                 920                 925

Phe Phe Gly Ile Tyr Leu Thr Asn Ile Leu Lys Thr Glu Glu Gly Asn
```

```
            930                 935                 940
Pro Glu Val Leu Lys Arg His Gly Lys Glu Leu Ile Asn Phe Ser Lys
945                 950                 955                 960

Arg Arg Lys Val Ala Glu Ile Thr Gly Glu Ile Gln Gln Tyr Gln Asn
                965                 970                 975

Gln Pro Tyr Cys Leu Arg Val Glu Ser Asp Ile Lys Arg Phe Phe Glu
                980                 985                 990

Asn Leu Asn Pro Met Gly Asn Ser Met Glu Lys Glu Phe Thr Asp Tyr
            995                 1000                1005

Leu Phe Asn Lys Ser Leu Glu Ile Glu Pro Arg Asn Pro Lys Pro Leu
    1010                1015                1020

Pro Arg Phe Pro Lys Lys Tyr Ser Tyr Pro Leu Lys Ser Pro Gly Val
1025                1030                1035                1040

Arg Pro Ser Asn Pro Arg Pro Gly Thr Met Arg His Pro Thr Pro Leu
                1045                1050                1055

Gln Gln Glu Pro Arg Lys Ile Ser Tyr Ser Arg Ile Pro Glu Ser Glu
            1060                1065                1070

Thr Glu Ser Thr Ala Ser Ala Pro Asn Ser Pro Arg Thr Pro Leu Thr
        1075                1080                1085

Pro Pro Pro Ala Ser Gly Ala Ser Ser Thr Thr Asp Val Cys Ser Val
    1090                1095                1100

Phe Asp Ser Asp His Ser Ser Pro Phe His Ser Ser Asn Asp Thr Val
1105                1110                1115                1120

Phe Ile Gln Val Thr Leu Pro His Gly Pro Arg Ser Ala Ser Val Ser
                1125                1130                1135

Ser Ile Ser Leu Thr Lys Gly Thr Asp Glu Val Pro Val Pro Pro Pro
            1140                1145                1150

Val Pro Pro Arg Arg Arg Pro Glu Ser Ala Pro Ala Glu Ser Ser Pro
        1155                1160                1165

Ser Lys Ile Met Ser Lys His Leu Asp Ser Pro Pro Ala Ile Pro Pro
    1170                1175                1180

Arg Gln Pro Thr Ser Lys Ala Tyr Ser Pro Arg Tyr Ser Ile Ser Asp
1185                1190                1195                1200

Arg Thr Ser Ile Ser Asp Pro Glu Ser Pro Pro Leu Leu Pro Pro
            1205                1210                1215

Arg Glu Pro Val Arg Thr Pro Asp Val Phe Ser Ser Ser Pro Leu His
        1220                1225                1230

Leu Gln Pro Pro Pro Leu Gly Lys Lys Ser Asp His Gly Asn Ala Phe
    1235                1240                1245

Phe Pro Asn Ser Pro Ser Pro Phe Thr Pro Pro Pro Gln Thr Pro
1250                1255                1260

Ser Pro His Gly Thr Arg Arg His Leu Pro Ser Pro Pro Leu Thr Gln
1265                1270                1275                1280

Glu Val Asp Leu His Ser Ile Ala Gly Pro Pro Val Pro Pro Arg Gln
            1285                1290                1295

Ser Thr Ser Gln His Ile Pro Lys Leu Pro Pro Lys Thr Tyr Lys Arg
        1300                1305                1310

Glu His Thr His Pro Ser Met His Arg Asp Gly Pro Pro Leu Leu Glu
    1315                1320                1325

Asn Ala His Ser Ser
    1330

<210> SEQ ID NO 3
```

```
<211> LENGTH: 1596
<212> TYPE: PRT
<213> ORGANISM: Drosophila melanogaster

<400> SEQUENCE: 3

Met Phe Ser Gly Pro Ser Gly His Ala His Thr Ile Ser Tyr Gly Gly
1               5                   10                  15

Gly Ile Gly Leu Gly Thr Gly Gly Gly Gly Ser Gly Gly Ser Gly
            20                  25                  30

Ser Gly Ser Gln Gly Gly Gly Gly Ile Gly Ile Gly Gly Gly Gly
        35                  40                  45

Val Ala Gly Leu Gln Asp Cys Asp Gly Tyr Asp Phe Thr Lys Cys Glu
    50                  55                  60

Asn Ala Ala Arg Trp Arg Gly Leu Phe Thr Pro Ser Leu Lys Lys Val
65                  70                  75                  80

Leu Glu Gln Val His Pro Arg Val Thr Ala Lys Glu Asp Ala Leu Leu
                85                  90                  95

Tyr Val Glu Lys Leu Cys Leu Arg Leu Leu Ala Met Leu Cys Ala Lys
                100                 105                 110

Pro Leu Pro His Ser Val Gln Asp Val Glu Glu Lys Val Asn Lys Ser
            115                 120                 125

Phe Pro Ala Pro Ile Asp Gln Trp Ala Leu Asn Glu Ala Lys Glu Val
    130                 135                 140

Ile Asn Ser Lys Lys Arg Lys Ser Val Leu Pro Thr Glu Lys Val His
145                 150                 155                 160

Thr Leu Leu Gln Lys Asp Val Leu Gln Tyr Lys Ile Asp Ser Ser Val
                165                 170                 175

Ser Ala Phe Leu Val Ala Val Leu Glu Tyr Ile Ser Ala Asp Ile Leu
            180                 185                 190

Lys Met Ala Gly Asp Tyr Val Ile Lys Ile Ala His Cys Glu Ile Thr
        195                 200                 205

Lys Glu Asp Ile Glu Val Val Met Asn Ala Asp Arg Val Leu Met Asp
    210                 215                 220

Met Leu Asn Gln Ser Glu Ala His Ile Leu Pro Ser Pro Leu Ser Leu
225                 230                 235                 240

Pro Ala Gln Arg Ala Ser Ala Thr Tyr Glu Glu Thr Val Lys Glu Leu
                245                 250                 255

Ile His Asp Glu Lys Gln Tyr Gln Arg Asp Leu His Met Ile Ile Arg
            260                 265                 270

Val Phe Arg Glu Glu Leu Val Lys Ile Val Ser Asp Pro Arg Glu Leu
        275                 280                 285

Glu Pro Ile Phe Ser Asn Ile Met Asp Ile Tyr Glu Val Thr Val Thr
    290                 295                 300

Leu Leu Gly Ser Leu Glu Asp Val Ile Glu Met Ser Gln Glu Gln Ser
305                 310                 315                 320

Ala Pro Cys Val Gly Ser Cys Phe Glu Glu Leu Ala Glu Ala Glu Glu
                325                 330                 335

Phe Asp Val Tyr Lys Lys Tyr Ala Tyr Asp Val Thr Ser Gln Ala Ser
            340                 345                 350

Arg Asp Ala Leu Asn Asn Leu Ser Lys Pro Gly Ala Ser Ser Leu
        355                 360                 365

Thr Thr Ala Gly His Gly Phe Arg Asp Ala Val Lys Tyr Tyr Leu Pro
    370                 375                 380

Lys Leu Leu Leu Val Pro Ile Cys His Ala Phe Val Tyr Phe Asp Tyr
```

```
                385             390             395             400
Ile Lys His Leu Lys Asp Leu Ser Ser Gln Asp Ile Glu Ser
                405                 410             415

Phe Glu Gln Val Gln Gly Leu Leu His Pro Leu His Cys Asp Leu Glu
                420             425             430

Lys Val Met Ala Ser Leu Ser Lys Glu Arg Gln Val Pro Val Ser Gly
                435             440             445

Arg Val Arg Arg Gln Leu Ala Ile Glu Arg Thr Arg Glu Leu Gln Met
            450             455             460

Lys Val Glu His Trp Glu Asp Lys Asp Val Gly Gln Asn Cys Asn Glu
465             470             475             480

Phe Ile Arg Glu Asp Ser Leu Ser Lys Leu Gly Ser Gly Lys Arg Ile
                485             490             495

Trp Ser Glu Arg Lys Val Phe Leu Phe Asp Gly Leu Met Val Leu Cys
            500             505             510

Lys Ala Asn Thr Lys Lys Gln Thr Pro Ser Ala Gly Ala Thr Ala Tyr
            515             520             525

Asp Tyr Arg Leu Lys Glu Lys Tyr Phe Met Arg Arg Val Asp Ile Asn
            530             535             540

Asp Arg Pro Asp Ser Asp Asp Leu Lys Asn Ser Phe Glu Leu Ala Pro
545             550             555             560

Arg Met Gln Pro Pro Ile Val Leu Thr Ala Lys Asn Ala Gln His Lys
                565             570             575

His Asp Trp Met Ala Asp Leu Leu Met Val Ile Thr Lys Ser Met Leu
            580             585             590

Asp Arg His Leu Asp Ser Ile Leu Gln Asp Ile Glu Arg Lys His Pro
            595             600             605

Leu Arg Met Pro Ser Pro Glu Ile Tyr Lys Phe Ala Val Pro Asp Ser
        610             615             620

Gly Asp Asn Ile Val Leu Glu Glu Arg Glu Ser Ala Gly Val Pro Met
625             630             635             640

Ile Lys Gly Ala Thr Leu Cys Lys Leu Ile Glu Arg Leu Thr Tyr His
                645             650             655

Ile Tyr Ala Asp Pro Thr Phe Val Arg Thr Phe Leu Thr Thr Tyr Arg
            660             665             670

Tyr Phe Cys Ser Pro Gln Gln Leu Leu Gln Leu Leu Val Glu Arg Phe
            675             680             685

Asn Ile Pro Asp Pro Ser Leu Val Tyr Gln Asp Thr Gly Thr Ala Gly
        690             695             700

Ala Gly Gly Met Gly Gly Val Gly Gly Asp Lys Glu His Lys Asn Ser
705             710             715             720

His Arg Glu Asp Trp Lys Arg Tyr Arg Lys Glu Tyr Val Gln Pro Val
                725             730             735

Gln Phe Arg Val Leu Asn Val Leu Arg His Trp Val Asp His His Phe
            740             745             750

Tyr Asp Phe Glu Lys Asp Pro Met Leu Leu Glu Lys Leu Leu Asn Phe
            755             760             765

Leu Glu His Val Asn Gly Lys Ser Met Arg Lys Trp Val Asp Ser Val
        770             775             780

Leu Lys Ile Val Gln Arg Lys Asn Glu Gln Glu Lys Ser Asn Lys Lys
785             790             795             800

Ile Val Tyr Ala Tyr Gly His Asp Pro Pro Ile Glu His Leu
                805             810             815
```

-continued

```
Ser Val Pro Asn Asp Glu Ile Thr Leu Leu Thr Leu His Pro Leu Glu
            820                 825                 830

Leu Ala Arg Gln Leu Thr Leu Leu Glu Phe Glu Met Tyr Lys Asn Val
        835                 840                 845

Lys Pro Ser Glu Leu Val Gly Ser Pro Trp Thr Lys Asp Lys Glu
    850                 855                 860

Val Lys Ser Pro Asn Leu Leu Lys Ile Met Lys His Thr Thr Asn Val
865                 870                 875                 880

Thr Arg Trp Ile Glu Lys Ser Ile Thr Glu Ala Glu Asn Tyr Glu Glu
                885                 890                 895

Arg Leu Ala Ile Met Gln Arg Ala Ile Glu Val Met Met Val Met Leu
                900                 905                 910

Glu Leu Asn Asn Phe Asn Gly Ile Leu Ser Ile Val Ala Ala Met Gly
            915                 920                 925

Thr Ala Ser Val Tyr Arg Leu Arg Trp Thr Phe Gln Gly Leu Pro Glu
        930                 935                 940

Arg Tyr Arg Lys Phe Leu Glu Glu Cys Arg Glu Leu Ser Asp Asp His
945                 950                 955                 960

Leu Lys Lys Tyr Gln Glu Arg Leu Arg Ser Ile Asn Pro Pro Cys Val
                965                 970                 975

Pro Phe Phe Gly Arg Tyr Leu Thr Asn Ile Leu His Leu Glu Glu Gly
            980                 985                 990

Asn Pro Asp Leu Leu Ala Asn Thr Glu Leu Ile Asn Phe Ser Lys Arg
            995                 1000                1005

Arg Lys Val Ala Glu Ile Ile Gly Glu Ile Gln Gln Tyr Gln Asn Gln
    1010                1015                1020

Pro Tyr Cys Leu Asn Glu Glu Ser Thr Ile Arg Gln Phe Phe Glu Gln
1025                1030                1035                1040

Leu Asp Pro Phe Asn Gly Leu Ser Asp Lys Gln Met Ser Asp Tyr Leu
            1045                1050                1055

Tyr Asn Glu Ser Leu Arg Ile Glu Pro Arg Gly Cys Lys Thr Val Pro
                1060                1065                1070

Lys Phe Pro Arg Lys Trp Pro His Ile Pro Leu Lys Ser Pro Gly Ile
    1075                1080                1085

Lys Pro Arg Arg Gln Asn Gln Thr Asn Ser Ser Ser Lys Leu Ser Asn
    1090                1095                1100

Ser Thr Ser Ser Val Ala Ala Ala Ala Ala Ser Ser Thr Ala Thr
1105                1110                1115                1120

Ser Ile Ala Thr Ala Ser Ala Pro Ser Leu His Ala Ser Ser Ile Met
        1125                1130                1135

Asp Ala Pro Thr Ala Ala Ala Ala Asn Ala Gly Ser Gly Thr Leu Ala
            1140                1145                1150

Gly Glu Gln Ser Pro Gln His Asn Pro His Ala Phe Ser Val Phe Ala
        1155                1160                1165

Pro Val Ile Ile Pro Glu Arg Asn Thr Ser Ser Trp Ser Gly Thr Pro
    1170                1175                1180

Gln His Thr Arg Thr Asp Gln Asn Asn Gly Glu Val Ser Val Pro Ala
1185                1190                1195                1200

Pro His Leu Pro Lys Lys Pro Gly Ala His Val Trp Ala Asn Asn Asn
                1205                1210                1215

Ser Thr Leu Ala Ser Ala Ser Ala Met Asp Val Val Phe Ser Pro Ala
        1220                1225                1230
```

Leu Pro Glu His Leu Pro Pro Gln Ser Leu Pro Asp Ser Asn Pro Phe
    1235                1240                1245

Ala Ser Asp Thr Glu Ala Pro Pro Ser Pro Leu Pro Lys Leu Val Val
    1250                1255                1260

Ser Pro Arg His Glu Thr Gly Asn Arg Ser Pro Phe His Gly Arg Met
1265                1270                1275                1280

Gln Asn Ser Pro Thr His Ser Thr Ala Ser Thr Val Thr Leu Thr Gly
            1285                1290                1295

Met Ser Thr Ser Gly Gly Glu Glu Phe Cys Ala Gly Gly Phe Tyr Phe
            1300                1305                1310

Asn Ser Ala His Gln Gly Gln Pro Gly Ala Val Pro Ile Ser Pro His
            1315                1320                1325

Val Asn Val Pro Met Ala Thr Asn Met Glu Tyr Arg Ala Val Pro Pro
    1330                1335                1340

Pro Leu Pro Pro Arg Arg Lys Glu Arg Thr Glu Ser Cys Ala Asp Met
1345                1350                1355                1360

Ala Gln Lys Arg Gln Ala Pro Asp Ala Pro Thr Leu Pro Pro Arg Asp
            1365                1370                1375

Gly Glu Leu Ser Pro Pro Pro Ile Pro Pro Arg Leu Asn His Ser Thr
            1380                1385                1390

Gly Ile Ser Tyr Leu Arg Gln Ser His Gly Lys Ser Lys Glu Phe Val
    1395                1400                1405

Gly Asn Ser Ser Leu Leu Leu Pro Asn Thr Ser Ser Ile Met Ile Arg
    1410                1415                1420

Arg Asn Ser Ala Ile Glu Lys Arg Ala Ala Ala Thr Ser Gln Pro Asn
1425                1430                1435                1440

Gln Ala Ala Ala Gly Pro Ile Ser Thr Thr Leu Val Thr Val Ser Gln
            1445                1450                1455

Ala Val Ala Thr Asp Glu Pro Leu Pro Leu Pro Ile Ser Pro Ala Ala
            1460                1465                1470

Ser Ser Ser Thr Thr Thr Ser Pro Leu Thr Pro Ala Met Ser Pro Met
    1475                1480                1485

Ser Pro Asn Ile Pro Ser His Pro Val Glu Ser Thr Ser Ser Ser Tyr
    1490                1495                1500

Ala His Gln Leu Arg Met Arg Gln Gln Gln Gln Gln Thr His Pro
1505                1510                1515                1520

Ala Ile Tyr Ser Gln His His Gln His His Ala Thr His Leu Pro His
            1525                1530                1535

His Pro His Gln His His Ser Asn Pro Thr Gln Ser Arg Ser Ser Pro
            1540                1545                1550

Lys Glu Phe Phe Pro Ile Ala Thr Ser Leu Glu Gly Thr Pro Lys Leu
    1555                1560                1565

Pro Pro Lys Pro Ser Leu Ser Ala Asn Phe Tyr Asn Asn Pro Asp Lys
    1570                1575                1580

Gly Thr Met Phe Leu Tyr Pro Ser Thr Asn Glu Glu
1585                1590                1595

<210> SEQ ID NO 4
<211> LENGTH: 1589
<212> TYPE: PRT
<213> ORGANISM: Saccharomyces cerevisiae

<400> SEQUENCE: 4

Met Ser Asp Thr Asn Thr Ser Ile Pro Asn Thr Ser Ser Ala Arg Glu
1               5                   10                  15

-continued

Ala Gly Asn Ala Ser Gln Thr Pro Ser Ile Ser Ser Ser Asn Thr
            20                  25                  30

Ser Thr Thr Thr Asn Thr Glu Ser Ser Ala Ser Leu Ser Ser Ser
        35                  40                  45

Pro Ser Thr Ser Glu Leu Thr Ser Ile Arg Pro Ile Gly Ile Val Val
    50                  55                  60

Ala Ala Tyr Asp Phe Asn Tyr Pro Ile Lys Lys Asp Ser Ser Ser Gln
65                  70                  75                  80

Leu Leu Ser Val Gln Gln Gly Glu Thr Ile Tyr Ile Leu Asn Lys Asn
                85                  90                  95

Ser Ser Gly Trp Trp Asp Gly Leu Val Ile Asp Asp Ser Asn Gly Lys
            100                 105                 110

Val Asn Arg Gly Trp Phe Pro Gln Asn Phe Gly Arg Pro Leu Arg Asp
    115                 120                 125

Ser His Leu Arg Lys His Ser His Pro Met Lys Lys Tyr Ser Ser Ser
    130                 135                 140

Lys Ser Ser Arg Arg Ser Ser Leu Asn Ser Leu Gly Asn Ser Ala Tyr
145                 150                 155                 160

Leu His Val Pro Arg Asn Pro Ser Lys Ser Arg Arg Gly Ser Ser Thr
                165                 170                 175

Leu Ser Ala Ser Leu Ser Asn Ala His Asn Ala Glu Thr Ser Ser Gly
            180                 185                 190

His Asn Asn Thr Val Ser Met Asn Asn Ser Pro Phe Ser Ala Pro Asn
    195                 200                 205

Asp Ala Ser His Ile Thr Pro Gln Ser Ser Asn Phe Asn Ser Asn Ala
    210                 215                 220

Ser Leu Ser Gln Asp Met Thr Lys Ser Ala Asp Gly Ser Ser Glu Met
225                 230                 235                 240

Asn Thr Asn Ala Ile Met Asn Asn Asn Glu Thr Asn Leu Gln Thr Ser
                245                 250                 255

Gly Glu Lys Ala Gly Pro Pro Leu Val Ala Glu Glu Thr Ile Lys Ile
            260                 265                 270

Leu Pro Leu Glu Glu Ile Glu Met Ile Ile Asn Gly Ile Arg Ser Asn
    275                 280                 285

Ile Ala Ser Thr Trp Ser Pro Ile Pro Leu Ile Thr Lys Thr Ser Asp
    290                 295                 300

Tyr Lys Leu Val Tyr Tyr Asn Lys Asp Leu Asp Ile Tyr Cys Ser Glu
305                 310                 315                 320

Leu Pro Leu Ile Ser Asn Ser Ile Met Glu Ser Asp Ile Cys Asp
                325                 330                 335

Ser Glu Pro Lys Phe Pro Pro Asn Asp His Leu Val Asn Leu Tyr Thr
            340                 345                 350

Arg Asp Leu Arg Lys Asn Ala Asn Ile Glu Asp Ser Ser Thr Arg Ser
    355                 360                 365

Lys Gln Ser Glu Ser Glu Gln Asn Arg Ser Ser Leu Leu Met Glu Lys
    370                 375                 380

Gln Asp Ser Lys Glu Thr Asp Gly Asn Asn Asn Ser Ile Asn Asp Asp
385                 390                 395                 400

Asp Asn Asn Asn Glu Asn Asn Lys Asn Glu Phe Asn Glu Ala Gly Pro
                405                 410                 415

Ser Ser Leu Asn Ser Leu Ser Ala Pro Asp Leu Thr Gln Asn Ile Gln
            420                 425                 430

-continued

```
Ser Arg Val Val Ala Pro Ser Arg Ser Ile Leu Ala Lys Ser Asp
        435                 440                 445

Ile Phe Tyr His Tyr Ser Arg Asp Ile Lys Leu Trp Thr Glu Leu Gln
450                 455                 460

Asp Leu Thr Val Tyr Tyr Thr Lys Thr Ala His Lys Met Phe Leu Lys
465                 470                 475                 480

Glu Asn Arg Leu Asn Phe Thr Lys Tyr Phe Asp Leu Ile Ser Asp Ser
                485                 490                 495

Ile Val Phe Thr Gln Leu Gly Cys Arg Leu Met Gln His Glu Ile Lys
                500                 505                 510

Ala Lys Ser Cys Ser Lys Glu Ile Lys Lys Ile Phe Lys Gly Leu Ile
            515                 520                 525

Ser Ser Leu Ser Arg Ile Ser Ile Asn Ser His Leu Tyr Phe Asp Ser
530                 535                 540

Ala Phe His Arg Lys Lys Met Asp Thr Met Asn Asp Lys Asp Asn Asp
545                 550                 555                 560

Asn Gln Glu Asn Asn Cys Ser Arg Thr Glu Gly Asp Gly Lys Ile
                565                 570                 575

Glu Val Asp Ser Val His Asp Leu Val Ser Val Pro Leu Ser Gly Lys
                580                 585                 590

Arg Asn Val Ser Thr Ser Thr Thr Asp Thr Leu Thr Pro Met Arg Ser
            595                 600                 605

Ser Phe Ser Thr Val Asn Glu Asn Asp Met Glu Asn Phe Ser Val Leu
610                 615                 620

Gly Pro Arg Asn Ser Val Asn Ser Val Val Thr Pro Arg Thr Ser Ile
625                 630                 635                 640

Gln Asn Ser Thr Leu Glu Asp Phe Ser Pro Ser Asn Lys Asn Phe Lys
                645                 650                 655

Ser Ala Lys Ser Ile Tyr Glu Met Val Asp Val Glu Phe Ser Lys Phe
                660                 665                 670

Leu Arg His Val Gln Leu Leu Tyr Phe Val Leu Gln Ser Ser Val Phe
            675                 680                 685

Ser Asp Asp Asn Thr Leu Pro Gln Leu Leu Pro Arg Phe Phe Lys Gly
690                 695                 700

Ser Phe Ser Gly Gly Ser Trp Thr Asn Pro Phe Ser Thr Phe Ile Thr
705                 710                 715                 720

Asp Glu Phe Gly Asn Ala Thr Lys Asn Lys Ala Val Thr Ser Asn Glu
                725                 730                 735

Val Thr Ala Ser Ser Ser Lys Asn Ser Ser Ile Ser Arg Ile Pro Pro
            740                 745                 750

Lys Met Ala Asp Ala Ile Ala Ser Ala Ser Gly Tyr Ser Ala Asn Ser
            755                 760                 765

Glu Thr Asn Ser Gln Ile Asp Leu Lys Ala Ser Ser Ala Ala Ser Gly
770                 775                 780

Ser Val Phe Thr Pro Phe Asn Arg Pro Ser His Asn Arg Thr Phe Ser
785                 790                 795                 800

Arg Ala Arg Val Ser Lys Arg Lys Lys Tyr Pro Leu Thr Val Asp
                805                 810                 815

Thr Leu Asn Thr Met Lys Lys Ser Ser Gln Ile Phe Glu Lys Leu
                820                 825                 830

Asn Asn Ala Thr Gly Glu His Leu Lys Ile Ile Ser Lys Pro Lys Ser
            835                 840                 845

Arg Ile Arg Asn Leu Glu Ile Asn Ser Ser Thr Tyr Glu Gln Ile Asn
```

```
               850                 855                 860
Gln Asn Val Leu Leu Glu Ile Leu Glu Asn Leu Asp Leu Ser Ile
865                 870                 875                 880

Phe Ile Asn Leu Lys Asn Leu Ile Lys Thr Pro Ser Ile Leu Leu Asp
                885                 890                 895

Leu Glu Ser Glu Glu Phe Leu Val His Ala Met Ser Ser Val Ser Ser
            900                 905                 910

Val Leu Thr Glu Phe Phe Asp Ile Lys Gln Ala Phe His Asp Ile Val
            915                 920                 925

Ile Arg Leu Ile Met Thr Thr Gln Gln Thr Leu Asp Asp Pro Tyr
930                 935                 940

Leu Phe Ser Ser Met Arg Ser Asn Phe Pro Val Gly His His Glu Pro
945                 950                 955                 960

Phe Lys Asn Ile Ser Asn Thr Pro Leu Val Lys Gly Pro Phe His Lys
                965                 970                 975

Lys Asn Glu Gln Leu Ala Leu Ser Leu Phe His Val Leu Val Ser Gln
            980                 985                 990

Asp Val Glu Phe Asn Asn Leu Glu Phe Leu Asn Asn Ser Asp Asp Phe
            995                1000                1005

Lys Asp Ala Cys Glu Lys Tyr Val Glu Ile Ser Asn Leu Ala Cys Ile
         1010                1015                1020

Ile Val Asp Gln Leu Ile Glu Glu Arg Glu Asn Leu Leu Asn Tyr Ala
1025                1030                1035                1040

Ala Arg Met Met Lys Asn Asn Leu Thr Ala Glu Leu Leu Lys Gly Glu
                1045                1050                1055

Gln Glu Lys Trp Phe Asp Ile Tyr Ser Glu Asp Tyr Ser Asp Asp
            1060                1065                1070

Ser Glu Asn Asp Glu Ala Ile Ile Asp Asp Glu Leu Gly Ser Glu Asp
         1075                1080                1085

Tyr Ile Glu Arg Lys Ala Ala Asn Ile Glu Lys Asn Leu Pro Trp Phe
         1090                1095                1100

Leu Thr Ser Asp Tyr Glu Thr Ser Leu Val Tyr Asp Ser Arg Gly Lys
1105                1110                1115                1120

Ile Arg Gly Gly Thr Lys Glu Ala Leu Ile Glu His Leu Thr Ser His
                1125                1130                1135

Glu Leu Val Asp Ala Ala Phe Asn Val Thr Met Leu Ile Thr Phe Arg
            1140                1145                1150

Ser Ile Leu Thr Thr Arg Glu Phe Phe Tyr Ala Leu Ile Tyr Arg Tyr
         1155                1160                1165

Asn Leu Tyr Pro Pro Glu Gly Leu Ser Tyr Asp Tyr Asn Ile Trp
         1170                1175                1180

Ile Glu Lys Lys Ser Asn Pro Ile Lys Cys Arg Val Val Asn Ile Met
1185                1190                1195                1200

Arg Thr Phe Leu Thr Gln Tyr Trp Thr Arg Asn Tyr Tyr Glu Pro Gly
                1205                1210                1215

Ile Pro Leu Ile Leu Asn Phe Ala Lys Met Val Val Ser Glu Lys Ile
            1220                1225                1230

Pro Gly Ala Glu Asp Leu Leu Gln Lys Ile Asn Glu Lys Leu Ile Asn
         1235                1240                1245

Glu Asn Glu Lys Glu Pro Val Asp Pro Lys Gln Gln Asp Ser Val Ser
         1250                1255                1260

Ala Val Val Gln Thr Thr Lys Arg Asp Asn Lys Ser Pro Ile His Met
1265                1270                1275                1280
```

```
Ser Ser Ser Ser Leu Pro Ser Ser Ala Ser Ser Ala Phe Phe Arg Leu
            1285                1290                1295

Lys Lys Leu Lys Leu Leu Asp Ile Asp Pro Tyr Thr Tyr Ala Thr Gln
        1300                1305                1310

Leu Thr Val Leu Glu His Asp Leu Tyr Leu Arg Ile Thr Met Phe Glu
        1315                1320                1325

Cys Leu Asp Arg Ala Trp Gly Thr Lys Tyr Cys Asn Met Gly Gly Ser
        1330                1335                1340

Pro Asn Ile Thr Lys Phe Ile Ala Asn Ala Asn Thr Leu Thr Asn Phe
1345                1350                1355                1360

Val Ser His Thr Ile Val Lys Gln Ala Asp Val Lys Thr Arg Ser Lys
            1365                1370                1375

Leu Thr Gln Tyr Phe Val Thr Val Ala Gln His Cys Lys Glu Leu Asn
            1380                1385                1390

Asn Phe Ser Ser Met Thr Ala Ile Val Ser Ala Leu Tyr Ser Ser Pro
        1395                1400                1405

Ile Tyr Arg Leu Lys Lys Thr Trp Asp Leu Val Ser Thr Glu Ser Lys
        1410                1415                1420

Asp Leu Leu Lys Asn Leu Asn Asn Leu Met Asp Ser Lys Arg Asn Phe
1425                1430                1435                1440

Val Lys Tyr Arg Glu Leu Leu Arg Ser Val Thr Asp Val Ala Cys Val
            1445                1450                1455

Pro Phe Phe Gly Val Tyr Leu Ser Asp Leu Thr Phe Thr Phe Val Gly
            1460                1465                1470

Asn Pro Asp Phe Leu His Asn Ser Thr Asn Ile Ile Asn Phe Ser Lys
        1475                1480                1485

Arg Thr Lys Ile Ala Asn Ile Val Glu Glu Ile Ile Ser Phe Lys Arg
        1490                1495                1500

Phe His Tyr Lys Leu Lys Arg Leu Asp Asp Ile Gln Thr Val Ile Glu
1505                1510                1515                1520

Ala Ser Leu Glu Asn Val Pro His Ile Glu Lys Gln Tyr Gln Leu Ser
            1525                1530                1535

Leu Gln Val Glu Pro Arg Ser Gly Asn Thr Lys Gly Ser Thr His Ala
            1540                1545                1550

Ser Ser Ala Ser Gly Thr Lys Thr Ala Lys Phe Leu Ser Glu Phe Thr
            1555                1560                1565

Asp Asp Lys Asn Gly Asn Phe Leu Lys Leu Gly Lys Lys Lys Pro Pro
        1570                1575                1580

Ser Arg Leu Phe Arg
1585

<210> SEQ ID NO 5
<211> LENGTH: 1048
<212> TYPE: PRT
<213> ORGANISM: Saccharomyces cerevisiae

<400> SEQUENCE: 5

Met Pro Ile Thr Ser Ser Pro Asp Leu Phe Tyr Leu Asn Asp Cys Asp
 1                5                  10                  15

Val Val Tyr Trp Tyr Asp Leu Thr Arg Leu Val Cys His Tyr Val Asn
                20                  25                  30

Leu Thr Glu Arg Asp Leu Leu Ala Asn Glu Arg Glu Lys Phe Leu Thr
        35                  40                  45
```

```
Ser Leu Asp Leu Leu Thr Ala Gln Ile Thr Tyr Val Tyr Met Leu Phe
     50                  55                  60

Arg Asn Leu Arg Leu Val Glu Asp Ser Phe Lys Lys Thr Leu Lys Lys
 65                  70                  75                  80

Leu Ile Tyr Thr Leu Ser Arg Phe Ser Ile Asn Ala Asn Ile Trp Phe
                 85                  90                  95

His Ser Thr Leu Phe Glu Glu Arg Glu Ala Ile Ala Ser Gln Lys Asp
                100                 105                 110

Pro Glu Arg Arg Ser Pro Leu Leu Gln Ser Ile Leu Gly Thr Phe Gln
                115                 120                 125

Lys Phe His Phe Leu Leu Arg Leu Leu His Phe Leu Ser Asn Pro Asn
130                 135                 140

Glu Leu Thr Ile Leu Pro Gln Leu Thr Pro Arg Phe Phe Lys Asp Ser
145                 150                 155                 160

Phe Asn Thr Ile Ser Trp Asn Asn Pro Phe Leu Arg Lys Arg Leu Asn
                165                 170                 175

Gln His Met Ser His Asp Leu Pro Arg Gln Met Ile Lys Ala Val Ala
                180                 185                 190

Gly Ala Ser Gly Ile Val Ala Glu Asn Ile Asp Glu Ile Pro Ala Ser
                195                 200                 205

Lys Gln Gly Thr Ser Cys Ser Ser Glu Thr Ser His His Ser Pro Ser
210                 215                 220

Ala Pro Phe Gln Arg Arg Arg Arg Gly Thr Ile Phe Ser Asn Val Ser
225                 230                 235                 240

Gly Ser Ser Asp Glu Ser Asp Thr Ile Trp Ser Lys Arg Lys Lys Pro
                245                 250                 255

Tyr Pro Leu Asn Glu Glu Thr Leu Ser Leu Val Arg Ala Arg Lys Lys
                260                 265                 270

Gln Leu Asp Gly Lys Leu Lys Gln Met Ile Lys Ser Ala Asn Glu Tyr
                275                 280                 285

Leu Ser Asn Thr Ala Asn Phe Ser Lys Met Leu Asn Phe Glu Met Asn
290                 295                 300

Phe Lys Thr Tyr Glu Glu Val Ser Gly Thr Ile Pro Ile Ile Asp Ile
305                 310                 315                 320

Leu Glu Asn Leu Asp Leu Thr Ile Phe Leu Asn Leu Arg Glu Leu Gly
                325                 330                 335

Asp Glu Asn Arg Val Phe Asp Glu Asp Val Ala Ile Asp Asp Glu Asp
                340                 345                 350

Glu Glu Phe Leu Lys His Ser Leu Ser Ser Leu Ser Tyr Ile Leu Ser
                355                 360                 365

Asp Tyr Phe Asn Met Lys Gln Tyr Phe His Asp Val Val Lys Phe
                370                 375                 380

Ile Ile Val Ala Gln His Leu Thr Leu Glu Asp Pro Phe Val Phe Ser
385                 390                 395                 400

Pro Met Gln Asn Asp Leu Pro Thr Gly Tyr Tyr Glu Pro Met Lys Pro
                405                 410                 415

Ser Ser Leu Asn Leu Asp Asn Ala Lys Asp Lys Lys Asn Gly Ser Gln
                420                 425                 430

Asn Thr Asp Ile Gln Glu Glu Glu Asp Glu Tyr Glu Pro Asp Pro Asp
                435                 440                 445

Ser Leu Ile Leu Phe His Asn Leu Ile Asn Gln Asp Ser Asp Phe Asn
450                 455                 460

Asp Leu Lys Phe Phe Asn Leu Ala His Val Phe Lys Lys Ser Cys Asp
```

-continued

```
465                 470                 475                 480
Asp Tyr Phe Asp Val Leu Lys Leu Ala Ile Glu Phe Val Asn Gln Leu
                485                 490                 495
Ile Leu Glu Arg Glu Asn Leu Leu Asn Tyr Ala Ala Arg Met Met Lys
                500                 505                 510
Asn Asn Ile Thr Glu Leu Leu Leu Arg Gly Glu Glu Gly Tyr Gly Ser
                515                 520                 525
Tyr Asp Gly Gly Glu Thr Ala Glu Lys Ser Asp Thr Asn Ala Val Tyr
                530                 535                 540
Ala Asp Ser Asp Thr Lys Asp Asn Asp Glu Trp Arg Asp Ser Gln Val
545                 550                 555                 560
Lys Leu Pro Arg Tyr Leu Gln Arg Glu Tyr Asp Ser Glu Leu Ile Trp
                565                 570                 575
Gly Ser Asn Asn Arg Ile Lys Gly Gly Ser Lys His Ala Leu Ile Ser
                580                 585                 590
Tyr Leu Thr Asp Asn Glu Lys Lys Asp Leu Phe Phe Asp Ile Thr Phe
                595                 600                 605
Leu Ile Thr Phe Arg Ser Ile Phe Thr Thr Thr Glu Phe Leu Ser Tyr
                610                 615                 620
Leu Ile Ser Gln Tyr Asn Leu Asp Pro Pro Glu Asp Leu Cys Phe Glu
625                 630                 635                 640
Glu Tyr Asn Glu Trp Val Thr Lys Lys Leu Ile Pro Val Lys Cys Arg
                645                 650                 655
Val Val Glu Ile Met Thr Thr Phe Phe Lys Gln Tyr Trp Phe Leu Gly
                660                 665                 670
Tyr Asp Glu Pro Asp Leu Ala Thr Leu Asn Leu Asp Tyr Phe Ala Gln
                675                 680                 685
Val Ala Ile Lys Glu Asn Ile Thr Gly Ser Val Glu Leu Leu Lys Glu
                690                 695                 700
Val Asn Gln Lys Phe Lys His Gly Asn Ile Gln Glu Ala Thr Ala Pro
705                 710                 715                 720
Met Lys Thr Leu Asp Gln Gln Ile Cys Gln Asp His Tyr Ser Gly Thr
                725                 730                 735
Leu Tyr Ser Thr Thr Glu Ser Ile Leu Ala Val Asp Pro Val Leu Phe
                740                 745                 750
Ala Thr Gln Leu Thr Ile Leu Glu His Glu Ile Tyr Cys Glu Ile Thr
                755                 760                 765
Ile Phe Asp Cys Leu Gln Lys Ile Trp Lys Asn Lys Tyr Thr Lys Ser
                770                 775                 780
Tyr Gly Ala Ser Pro Gly Leu Asn Glu Phe Ile Ser Phe Ala Asn Lys
785                 790                 795                 800
Leu Thr Asn Phe Ile Ser Tyr Ser Val Val Lys Glu Ala Asp Lys Ser
                805                 810                 815
Lys Arg Ala Lys Leu Leu Ser His Phe Ile Phe Ile Ala Glu Tyr Cys
                820                 825                 830
Arg Lys Phe Asn Asn Phe Ser Met Thr Ala Ile Ser Ala Leu
                835                 840                 845
Tyr Ser Ser Pro Ile Tyr Arg Leu Glu Lys Thr Trp Gln Ala Val Ile
                850                 855                 860
Pro Gln Thr Arg Asp Leu Leu Gln Ser Leu Asn Lys Leu Met Asp Pro
865                 870                 875                 880
Lys Lys Asn Phe Ile Asn Tyr Arg Asn Glu Leu Lys Ser Leu His Ser
                885                 890                 895
```

```
Ala Pro Cys Val Pro Phe Phe Gly Val Tyr Leu Ser Asp Leu Thr Phe
            900                 905                 910

Thr Asp Ser Gly Asn Pro Asp Tyr Leu Val Leu Glu His Gly Leu Lys
        915                 920                 925

Gly Val His Asp Glu Lys Lys Tyr Ile Asn Phe Asn Lys Arg Ser Arg
    930                 935                 940

Leu Val Asp Ile Leu Gln Glu Ile Tyr Phe Lys Lys Thr His Tyr
945                 950                 955                 960

Asp Phe Thr Lys Asp Arg Thr Val Ile Glu Cys Ile Ser Asn Ser Leu
            965                 970                 975

Glu Asn Ile Pro His Ile Glu Lys Gln Tyr Gln Leu Ser Leu Ile Ile
        980                 985                 990

Glu Pro Lys Pro Arg Lys Lys Val Pro Asn Ser Asn Ser Asn Asn
    995                 1000                1005

Lys Ser Gln Glu Lys Ser Arg Asp Asp Gln Thr Asp Glu Gly Lys Thr
    1010                1015                1020

Ser Thr Lys Lys Asp Arg Phe Pro Lys Phe Gln Leu His Lys Thr Lys
1025                1030                1035                1040

Lys Lys Ala Pro Lys Val Ser Lys
            1045

<210> SEQ ID NO 6
<211> LENGTH: 911
<212> TYPE: PRT
<213> ORGANISM: Schizosaccharomyces pombe

<400> SEQUENCE: 6

Met Arg Phe Gln Thr Thr Ala Ile Ser Asp Tyr Glu Asn Ser Ser Asn
1               5                   10                  15

Pro Ser Phe Leu Lys Phe Ser Ala Gly Asp Thr Ile Val Ile Glu
            20                  25                  30

Val Leu Glu Asp Gly Trp Cys Asp Gly Ile Cys Ser Glu Lys Arg Gly
        35                  40                  45

Trp Phe Pro Thr Ser Cys Ile Asp Ser Ser Lys Ile Gln Asn Phe Phe
    50                  55                  60

Ser Ser Phe His Ser Ser Asn Glu Lys Asp Pro Asn Ala Gln Cys Cys
65                  70                  75                  80

Ala Pro Phe His Val Glu Ala His Leu Gln Asp Ser Ala Trp Phe Glu
            85                  90                  95

Lys His Gly Val Gln Ala Ile Asn Ser Ile Pro Ser Ser Glu Glu Phe
            100                 105                 110

Leu Arg Lys Asn Leu Gln Asn Asp Ile His His Leu Val Lys Gly Ile
        115                 120                 125

Leu Thr Thr Ala Ala Val Ser Gln Ser Ile Lys Lys Glu Gly Thr
    130                 135                 140

Gln Val Ile Val Phe Gly Ile Glu Thr Val Arg Ser Met Val Leu Ser
145                 150                 155                 160

Phe Pro Leu Ile Ile Leu Ser Thr Leu Asp Glu Asn Phe Leu Ser Glu
            165                 170                 175

Val Ala Gln Val Phe Ser Ser Leu Asn Leu Pro Glu Leu Ser Arg
            180                 185                 190

Met Gly Cys Thr Tyr Gly Glu Leu Cys Ile Arg Phe Thr Lys Leu Leu
        195                 200                 205

Lys Gln Leu Ala Asn Lys Phe Leu Phe Phe Arg Pro Asp Val Ser
```

```
            210                 215                 220
Phe Pro Ser Tyr Phe Leu Gly Ser Leu Ile Ala His Glu Ile His Phe
225                 230                 235                 240
Leu Pro Trp Asp Phe Asn Met Leu Cys Ser Asn Ser Val Gln Ser Ala
                245                 250                 255
His Thr Asn Leu Gln Pro Asp Ile Thr Ser Phe Val Ala Ile Leu Ser
                260                 265                 270
Leu Ser His Glu Ala Tyr His Cys Thr Glu Asn Glu Phe Trp Asn Leu
            275                 280                 285
Glu Ala Gln Lys Leu Thr Glu Asn Thr Thr Gln Lys Val Leu Gln Leu
290                 295                 300
Val Ala Glu Asp Ala Leu Glu Ala Trp Lys Leu Asp Ile Leu Glu Asp
305                 310                 315                 320
Ile Asp Arg Cys Ile Gln Cys Cys Arg Arg Phe Leu Ser Ala Asn Gln
                325                 330                 335
Arg Ile Asn Tyr Ser Ser Ser Glu Asn Asn Pro Phe Ser Phe Thr Ser
                340                 345                 350
Gln Asp Val Glu Ala Leu Lys Asp Glu Leu Ser Ser Asn Leu Cys Asp
            355                 360                 365
Leu Tyr Leu Trp Ser Ile Asp Leu Glu Gln Ile Ser Pro Ser Asp Cys
370                 375                 380
Leu Leu Asp Asn Tyr Ser Leu Phe Val Asp Leu Leu Val Thr Leu Lys
385                 390                 395                 400
Val Ser Leu Leu Arg Ile Lys Ser Ile Ile Val Gln Phe Ser Glu Arg
                405                 410                 415
Ile Val Phe Leu Ser Leu Glu Tyr Lys Phe Leu Thr Asn Ile Gln Pro
            420                 425                 430
Glu Leu Asn Asp Ala Glu Lys Ser Gln Leu Asp Gly Phe Asp Leu Asn
            435                 440                 445
Lys Thr Asn Trp Phe Asp Ser Lys Gly Leu Val Cys Tyr Leu Met Lys
            450                 455                 460
Gln Thr Ser Pro Glu Pro Leu Leu Ile Arg Asn Leu Leu Phe Ser Phe
465                 470                 475                 480
Trp Ser Cys Asn Gly Lys Ile Glu Gln Asp Gly Lys Ile Lys Thr Ala
                485                 490                 495
Thr Leu Val Phe Ile Ile Asn Tyr Leu Leu Arg Thr Asp Ile Asp Ser
                500                 505                 510
Thr Phe Phe Thr Thr Ile Phe Leu Asn Thr Tyr Ala Ser Met Ile Ser
            515                 520                 525
Ser Ser Asp Leu Phe Ser Ile Leu Gly Ala His Phe Arg Phe Ile Cys
            530                 535                 540
Ser Leu Asn Phe Gly Lys Ile Ser Phe Ile Ser His Glu Phe Tyr Arg
545                 550                 555                 560
Val Ser Lys Arg Phe Leu Asp Ile Leu Leu Ile Trp Phe Glu Ser Tyr
                565                 570                 575
Leu Val Glu Glu Leu Asp Asn Ser Ser Lys Ser Ile Phe Phe Leu Phe Lys
            580                 585                 590
Ile Tyr Lys Val Phe Glu Val Phe Val Pro His Phe Ala Ser Ala
                595                 600                 605
Glu Glu Leu Leu His Ser Leu Ser His Leu His His Pro Ser Thr
            610                 615                 620
Lys Arg Ser His Lys Met Leu Glu Gly Lys Glu Leu Ser Gln Glu Leu
625                 630                 635                 640
```

```
Glu Asp Leu Ser Leu His Asn Ser Pro Asp Pro Ile Ile Tyr Lys Asp
                645                 650                 655

Glu Leu Val Leu Leu Pro Pro Arg Glu Ile Ala Lys Gln Leu Cys
        660                 665                 670

Ile Leu Glu Phe Gln Ser Phe Ser His Ile Ser Arg Ile Gln Phe Leu
            675                 680                 685

Thr Lys Ile Trp Asp Asn Leu Asn Arg Phe Ser Pro Lys Glu Lys Thr
        690                 695                 700

Ser Thr Phe Tyr Leu Ser Asn His Leu Val Asn Phe Val Thr Glu Thr
705                 710                 715                 720

Ile Val Gln Glu Glu Pro Arg Arg Thr Asn Val Leu Ala Tyr
            725                 730                 735

Phe Ile Gln Val Cys Asp Tyr Leu Arg Glu Leu Asn Asn Phe Ala Ser
            740                 745                 750

Leu Phe Ser Ile Ile Ser Ala Leu Asn Ser Ser Pro Ile His Arg Leu
        755                 760                 765

Arg Lys Thr Trp Ala Asn Leu Asn Ser Lys Thr Leu Ala Ser Phe Glu
    770                 775                 780

Leu Leu Asn Asn Leu Thr Glu Ala Arg Lys Asn Phe Ser Asn Tyr Arg
785                 790                 795                 800

Asp Cys Leu Glu Asn Cys Val Leu Pro Cys Val Pro Phe Leu Gly Val
            805                 810                 815

Tyr Phe Thr Asp Leu Thr Phe Leu Lys Thr Gly Asn Lys Asp Asn Phe
            820                 825                 830

Gln Asn Met Ile Asn Phe Asp Lys Arg Thr Lys Val Thr Arg Ile Leu
        835                 840                 845

Asn Glu Ile Lys Lys Phe Gln Ser Val Gly Tyr Met Phe Asn Pro Ile
850                 855                 860

Asn Glu Val Gln Glu Leu Leu Asn Glu Val Ile Ser Arg Glu Arg Asn
865                 870                 875                 880

Thr Asn Asn Ile Tyr Gln Arg Ser Leu Thr Val Glu Pro Arg Glu Ser
            885                 890                 895

Glu Asp Gln Ala Leu Gln Arg Leu Leu Ile Asp Ser Gly Ile Phe
        900                 905                 910

<210> SEQ ID NO 7
<211> LENGTH: 1244
<212> TYPE: PRT
<213> ORGANISM: Rattus rattus

<400> SEQUENCE: 7

Met Gln Lys Ala Ile Arg Leu Asn Asp Gly His Val Val Ser Leu Gly
1               5                   10                  15

Leu Leu Ala Gln Arg Asp Gly Thr Arg Lys Gly Tyr Leu Ser Lys Arg
            20                  25                  30

Ser Ser Asp Asn Pro Lys Trp Gln Thr Lys Trp Phe Ala Leu Leu Gln
        35                  40                  45

Asn Leu Leu Phe Tyr Phe Glu Ser Asp Ser Ser Arg Pro Ser Gly
    50                  55                  60

Leu Tyr Leu Leu Glu Gly Ser Ile Cys Lys Arg Met Pro Ser Pro Lys
65              70                  75                  80

Arg Gly Thr Ser Ser Lys Glu Ser Asp Lys Gln His His Tyr Phe Thr
            85                  90                  95

Val Asn Phe Ser Asn Asp Ser Gln Lys Ser Leu Glu Leu Arg Thr Asp
```

-continued

```
                  100                 105                 110
Asp Ser Lys Asp Cys Asp Glu Trp Val Ala Ala Ile Ala Arg Ala Ser
            115                 120                 125
Tyr Lys Ile Leu Ala Thr Glu His Glu Ala Leu Met Gln Lys Tyr Leu
        130                 135                 140
His Leu Leu Gln Val Val Glu Thr Glu Lys Thr Val Ala Lys Gln Leu
145                 150                 155                 160
Arg Gln Gln Leu Glu Asp Gly Glu Val Glu Ile Glu Arg Leu Lys Ala
                165                 170                 175
Glu Ile Ala Asn Leu Ile Lys Asp Asn Glu Arg Ile Gln Ser Asn Gln
            180                 185                 190
Leu Val Ala Pro Glu Asp Glu Asp Ser Asp Ile Lys Lys Ile Lys Lys
        195                 200                 205
Val Gln Ser Phe Leu Arg Gly Trp Leu Cys Arg Arg Lys Trp Lys Asn
210                 215                 220
Ile Ile Gln Asp Tyr Ile Arg Ser Pro His Ala Asp Ser Met Arg Lys
225                 230                 235                 240
Arg Asn Gln Val Val Phe Ser Met Leu Glu Ala Glu Ala Glu Tyr Val
                245                 250                 255
Gln Gln Leu His Ile Leu Val Asn Asn Phe Leu Arg Pro Leu Arg Met
            260                 265                 270
Ala Ala Ser Ser Lys Lys Pro Pro Ile Thr His Asp Asp Val Ser Ser
        275                 280                 285
Ile Phe Leu Asn Ser Glu Thr Ile Met Phe Leu His Gln Ile Phe Tyr
290                 295                 300
Gln Gly Leu Lys Ala Arg Ile Ala Ser Trp Pro Thr Leu Val Leu Ala
305                 310                 315                 320
Asp Leu Phe Asp Ile Leu Leu Pro Met Leu Asn Ile Tyr Gln Glu Phe
                325                 330                 335
Val Arg Asn His Gln Tyr Ser Leu Gln Ile Leu Ala His Cys Lys Gln
            340                 345                 350
Asn Arg Asp Phe Asp Lys Leu Leu Lys Gln Tyr Glu Ala Lys Pro Asp
        355                 360                 365
Cys Glu Glu Arg Thr Leu Glu Thr Phe Leu Thr Tyr Pro Met Phe Gln
370                 375                 380
Ile Pro Arg Tyr Ile Leu Thr Leu His Glu Leu Leu Ala His Thr Pro
385                 390                 395                 400
His Glu His Val Glu Arg Asn Ser Leu Asp Tyr Ala Lys Ser Lys Leu
                405                 410                 415
Glu Glu Leu Ser Arg Val Met His Asp Glu Val Ser Glu Thr Glu Asn
            420                 425                 430
Ile Arg Lys Asn Leu Ala Ile Glu Arg Met Ile Thr Glu Gly Cys Glu
        435                 440                 445
Ile Leu Leu Asp Thr Ser Gln Thr Phe Val Arg Gln Gly Ser Leu Ile
450                 455                 460
Gln Val Pro Met Ser Glu Lys Gly Lys Ile Asn Lys Gly Arg Leu Gly
465                 470                 475                 480
Ser Leu Ser Leu Lys Lys Glu Gly Glu Arg Gln Cys Phe Leu Phe Ser
                485                 490                 495
Lys His Leu Ile Ile Cys Thr Arg Gly Ser Gly Ser Lys Leu His Leu
            500                 505                 510
Thr Lys Asn Gly Val Ile Ser Leu Ile Asp Cys Thr Leu Leu Asp Asp
        515                 520                 525
```

-continued

```
Pro Glu Asn Met Asp Asp Gly Lys Gly Gln Glu Val Asp His Leu
    530                 535                 540
Asp Phe Lys Ile Trp Val Glu Pro Lys Asp Ser Pro Pro Phe Thr Val
545                 550                 555                 560
Ile Leu Val Ala Ser Ser Arg Gln Glu Lys Ala Ala Trp Thr Ser Asp
                565                 570                 575
Ile Ile Gln Cys Val Asp Asn Ile Arg Cys Asn Gly Leu Met Met Asn
            580                 585                 590
Ala Phe Glu Glu Asn Ser Lys Val Thr Val Pro Gln Met Ile Lys Ser
        595                 600                 605
Asp Ala Ser Leu Tyr Cys Asp Asp Val Asp Ile Arg Phe Ser Lys Thr
    610                 615                 620
Met Asn Ser Cys Lys Val Leu Gln Ile Arg Tyr Ala Ser Val Glu Arg
625                 630                 635                 640
Leu Leu Glu Arg Leu Thr Asp Leu Arg Phe Leu Ser Ile Asp Phe Leu
                645                 650                 655
Asn Thr Phe Leu His Ser Tyr Arg Val Phe Thr Asp Ala Val Val Val
            660                 665                 670
Leu Asp Lys Leu Ile Ser Ile Tyr Lys Lys Pro Ile Thr Ala Ile Pro
        675                 680                 685
Ala Arg Ser Leu Glu Leu Leu Phe Ser Ser Ser His Asn Thr Lys Leu
    690                 695                 700
Leu Tyr Gly Asp Ala Pro Lys Ser Pro Arg Ala Ser Arg Lys Phe Ser
705                 710                 715                 720
Ser Pro Pro Leu Ala Ile Gly Thr Ser Ser Pro Val Arg Arg Arg
                725                 730                 735
Lys Leu Ser Leu Asn Ile Pro Ile Ile Thr Gly Gly Lys Ala Leu Glu
                740                 745                 750
Leu Ala Ser Leu Gly Cys Pro Ser Asp Gly Tyr Thr Asn Ile His Ser
    755                 760                 765
Pro Ile Ser Pro Phe Gly Lys Thr Thr Leu Asp Thr Ser Lys Leu Cys
    770                 775                 780
Val Ala Ser Ser Leu Thr Arg Thr Pro Glu Glu Ile Asp Met Thr Thr
785                 790                 795                 800
Leu Glu Glu Ser Ser Gly Phe Arg Lys Pro Thr Ser Asp Ile Leu Lys
                805                 810                 815
Glu Glu Ser Asp Asp Asp Gln Ser Asp Val Asp Thr Glu Val Ser
            820                 825                 830
Pro Pro Thr Pro Lys Ser Phe Arg Asn Arg Ile Thr Gln Glu Phe Pro
        835                 840                 845
Leu Phe Asn Tyr Asn Ser Gly Ile Met Met Thr Cys Arg Asp Leu Met
    850                 855                 860
Asp Ser Asn Arg Ser Pro Leu Ser Ala Thr Ser Ala Phe Ala Ile Ala
865                 870                 875                 880
Thr Ala Gly Ala Asn Glu Ser Pro Ala Asn Lys Glu Ile Tyr Arg Arg
                885                 890                 895
Met Ser Leu Ala Asn Thr Gly Tyr Ser Ser Asp Gln Arg Asn Ile Asp
            900                 905                 910
Lys Glu Phe Val Ile Arg Arg Ala Ala Thr Asn Arg Val Leu Asn Val
        915                 920                 925
Leu Arg His Trp Val Thr Lys His Ser Gln Asp Phe Glu Thr Asp Asp
    930                 935                 940
```

```
Leu Leu Lys Tyr Lys Val Ile Cys Phe Leu Glu Glu Val Met His Asp
945                 950                 955                 960

Pro Asp Leu Leu Pro Gln Glu Arg Lys Ala Ala Ala Asn Ile Met Arg
            965                 970                 975

Thr Leu Thr Gln Glu Glu Ile Thr Glu Asn His Ser Met Leu Asp Glu
            980                 985                 990

Leu Leu Leu Met Thr Glu Gly Val Lys Thr Glu Pro Phe Glu Asn His
            995                 1000                1005

Ser Ala Met Glu Ile Ala Glu Gln Leu Thr Leu Leu Asp His Leu Val
        1010                1015                1020

Phe Lys Ser Ile Pro Tyr Glu Glu Phe Phe Gly Gln Gly Trp Met Lys
1025                1030                1035                1040

Ala Asp Lys Asn Glu Arg Thr Pro Tyr Ile Met Lys Thr Thr Arg His
                1045                1050                1055

Phe Asn His Ile Ser Asn Leu Ile Ala Ser Glu Ile Leu Arg Asn Glu
            1060                1065                1070

Glu Val Ser Ala Arg Ala Ser Thr Ile Glu Lys Trp Val Ala Val Ala
        1075                1080                1085

Asp Ile Cys Arg Cys Leu His Asn Tyr Asn Ala Val Leu Glu Ile Thr
    1090                1095                1100

Ser Ser Ile Asn Arg Ser Ala Ile Phe Arg Leu Lys Lys Thr Trp Leu
1105                1110                1115                1120

Lys Val Ser Lys Gln Thr Lys Ser Leu Phe Asp Lys Leu Gln Lys Leu
                1125                1130                1135

Val Ser Ser Asp Gly Arg Phe Lys Asn Leu Arg Glu Thr Leu Arg Asn
            1140                1145                1150

Cys Asp Pro Pro Cys Val Pro Tyr Leu Gly Met Tyr Leu Thr Asp Leu
        1155                1160                1165

Ala Phe Leu Glu Glu Gly Thr Pro Asn Tyr Thr Glu Asp Gly Leu Val
    1170                1175                1180

Asn Phe Ser Lys Met Arg Met Ile Ser His Ile Ile Arg Glu Ile Arg
1185                1190                1195                1200

Gln Phe Gln Gln Thr Thr Tyr Lys Ile Glu Pro Gln Pro Lys Val Thr
                1205                1210                1215

Gln Tyr Leu Val Asp Glu Thr Phe Val Leu Asp Asp Glu Ser Leu Tyr
            1220                1225                1230

Glu Ala Ser Leu Arg Ile Glu Pro Lys Leu Pro Thr
        1235                1240

<210> SEQ ID NO 8
<211> LENGTH: 6453
<212> TYPE: DNA
<213> ORGANISM: Homo sapiens

<400> SEQUENCE: 8
ggatcccagc ctttccccag cccgtagccc cgggacctcc gcggtgggcg gcgccgcgct    60
gccggcgcag ggagggcctc tggtgcaccg gcaccgctga gtcgggttct ctcgccggcc   120
tgttcccggg agagcccggg gccctgctcg agatgccgc cccgggcccc cagacaccgg    180
ctccctggcc ttcctcgagc aaccccgagc tcggctccgg tctccagcca agcccaaccc   240
cgagaggccg cggccctact ggctccgcct ccgcgttgc tcccggaagc ccgcccgac    300 cgcggctcct gacagacggg ccgctcagcc aaccggggtg gggcgggcc cgatggcgcg   360 cagccaatgg taggccgcgc ctggcagacg gacgggcgcg gggcggggcg tgcgcaggcc   420
```

-continued

```
cgcccgagtc tccgccgccc gtgccctgcg cccgcaaccc gagccgcacc cgccgcggac    480
ggagcccatg cgcggggcga accgcgcgcc cccgccccg ccccgcccg gcctcggccc      540 cggccctggc cccgggggca gtcgcgcctg tgaacggtga gtgcgggcag ggatcggccg    600
ggccgcgcgc cctcctcgcc cccaggcggc agcaatacgc gcggcgcggg ccgggggcgc    660
ggggccggcg ggcgtaagcg gcggcggcgg cggcgggtgg gtggggccgg gcggggcccg    720
cgggcacagg tgagcgggcg tcgggggctg cggcgggcgg gggccccttc ctccctgggg    780
cctgcgggaa tccggccccc acccgtggcc tcgcgctggg cacggtcccc acgccggcgt    840
acccgggagc ctcgggcccg gcgccctcac acccgggggc gtctgggagg aggcggccgc    900
ggccacggca cgcccgggca ccccgattc agcatcacag gtcgcggacc aggcggggg     960 cctcagcccc agtgcctttt ccctctccgg gtctcccgcg ccgcttctcg gccccttcct    1020
gtcgctcagt ccctgcttcc caggagctcc tctgtcttct ccagctttct gtggctgaaa    1080 gatgccccg gttcccgcc ggggtgcgg ggcgctgccc gggtctgccc tcccctcggc       1140
ggcgcctagt acgcagtagg cgctcagcaa atacttgtcg gaggcaccag cgccgcgggg    1200
cctgcaggct ggcactagcc tgcccgggca cgccgtggcc cgctccgccg tggccagacc    1260
tgttctggag gacggtaacc tcagccctcg ggcgcctccc tttagccttt ctgccgaccc    1320
agcagcttct aatttgggtg cgtggttgag agcgctcagc tgtcagccct gcctttgagg    1380
gctgggtccc ttttcccatc actgggtcat taagagcaag tgggggcgag gcgacagccc    1440
tcccgcacgc tgggttgcag ctgcacaggt aggcacgctg cagtccttgc tgcctggcgt    1500
tggggcccag ggaccgctgt gggtttgccc ttcagatggc cctgccagca gctgccctgt    1560
ggggcctggg gctgggcctg gcctggctg agcagggcc tccttggcag gtggggcagg     1620
agaccctgta ggaggacccc gggccgcagg cccctgagga gcgatgacgg aatataagct    1680
ggtggtggtg ggcgccggcg gtgtgggcaa gagtgcgctg accatccagc tgatccagaa    1740
ccattttgtg gacgaatacg accccactat agaggtgagc ctagcgccgc cgtccaggtg    1800
ccagcagctg ctgcgggcga gcccaggaca cagccaggat agggctggct gcagcccctg    1860
gtcccctgca tggtgctgtg gccctgtctc ctgcttcctc tagaggaggg gagtccctcg    1920
tctcagcacc ccaggagagg aggggcatg aggggcatga gaggtaccag ggagaggctg     1980
gctgtgtgaa ctccccccac ggaaggtcct gagggggtcc ctgagccctg tcctcctgca    2040
ggattcctac cggaagcagg tggtcattga tggggagacg tgcctgttgg acatcctgga    2100
taccgccggc caggaggagt acagcgccat gcgggaccag tacatgcgca ccggggaggg    2160
cttcctgtgt gtgtttgcca tcaacaacac caagtctttt gaggacatcc accagtacag    2220
gtgaaccccg tgaggctggc ccgggagccc acgccgcaca ggtggggcca ggccggctgc    2280
gtccaggcag gggcctcctg tcctctctgc gcatgtcctg gatgccgctg cgcctgcagc    2340
ccccgtagcc agctctcgct ttccacctct cagggagcag atcaaacggg tgaaggactc    2400
ggatgacgtg cccatggtgc tggtggggaa caagtgtgac ctggctgcac gcactgtgga    2460
atctcggcag gctcaggacc tcgcccgaag ctacggcatc ccctacatcg agacctcggc    2520
caagacccgg caggtgaggc agctctccac cccacagcta gccagggacc cgccccgccc    2580
cgccccagcc agggagcagc actcactgac cctctccctt gacacagggc agccgctctg    2640
gctctagctc cagctccggg accctctggg accccccggg accatgtgac cccagcggcc    2700
cctcgcactg taggtctccc gggacggcag ggcagtgagg gaggcgaggg ccgggtctg     2760 ggctcacgcc ctgcagtcct gggccgacac agctccgggg aaggcggagg tccttgggga    2820
```

```
gagctgccct gagccaggcc ggagcggtga ccctggggcc cggcccctct tgtccccaga    2880
gtgtcccacg ggcacctgtt ggttctgagt cttagtgggg ctactgggga cacgggccgt    2940
agctgagtcg agagctgggt gcagggtggt caaaccctgg ccagacctgg agttcaggag    3000
ggccccgggc caccctgacc tttgaggggc tgctgtagca tgatgcgggt ggccctgggc    3060
acttcgagat ggccagagtc cagcttcccg tgtgtgtggt gggcctgggg aagtggctgg    3120
tggagtcggg agcttcgggc caggcaaggc ttgatcccac agcagggagc ccctcaccca    3180
ggcaggcggc cacaggccgg tccctcctga tcccatccct cctttcccag ggagtggagg    3240
atgccttcta cacgttggtg cgtgagatcc ggcagcacaa gctgcggaag ctgaaccctc    3300
ctgatgagag tggccccggc tgcatgagct gcaagtgtgt gctctcctga cgcaggtgag    3360
ggggactccc agggcggccg ccacgcccac cggatgaccc cggctccccg ccctgccgg     3420 tctcctggcc tgcggtcagc agcctccctt gtgccccgcc cagcacaagc tcaggacatg    3480
gaggtgccgg atgcaggaag gaggtgcaga cggaaggagg aggaaggaag gacggaagca    3540
aggaaggaag gaagggctgc tggagcccag tcaccccggg accgtgggcc gaggtgactg    3600
cagaccctcc cagggaggct gtgcacagac tgtcttgaac atcccaaatg ccaccggaac    3660 cccagcccctt agctcccctc ccaggcctct gtgggccctt gtcgggcaca gatgggatca    3720
cagtaaatta ttggatggtc ttgatcttgg ttttcggctg agggtgggac acggtgcgcg    3780
tgtggcctgg catgaggtat gtcggaacct caggcctgtc cagccctggg ctctccatag    3840
cctttgggag gggggaggttg ggagaggccg gtcagggggtc tgggctgtgg tgctctctcc   3900
tcccgcctgc cccagtgtcc acggcttctg gcagagagct ctggacaagc aggcagatca    3960
taaggacaga gagcttactg tgcttctacc aactaggagg gcgtcctggt cctccagagg    4020
gaggtggttt caggggttgg ggatctgtgc cggtggctct ggtctctgct gggagccttc    4080
ttggcggtga gaggcatcac ctttcctgac ttgctcccag cgtgaaatgc acctgccaag    4140
aatggcagac atagggaccc cgcctcctgg gccttcacat gcccagtttt cttcggctct    4200
gtggcctgaa gcggtctgtg gaccttggaa gtagggctcc agcaccgact ggcctcaggc    4260
ctctgcctca ttggtggtcg ggtagcggcc agtagggcgt gggagcctgg ccatccctgc    4320
ctcctggagt ggacgaggtt ggcagctggt ccgtctgctc ctgccccact ctcccccgcc    4380
cctgccctca ccctaccctt gccccacgcc tgcctcatgg ctggttgctc ttggagcctg    4440
gtagtgtcac tggctcagcc ttgctgggta tacacaggct ctgccaccca ctctgctcca    4500
aggggcttgc cctgccttgg gccaagttct aggtctggcc acagccacag acagctcagt    4560
cccctgtgtg gtcatcctgg cttctgctgg gggcccacag cgccctggt gccctcccc      4620 tcccagggcc cgggttgagg ctgggccagg ccctctggga cggggacttg tgccctgtca    4680
gggttcccta tccctgaggt tgggggagag ctagcagggc atgccgctgg ctggccaggg    4740
ctgcagggac actccccctt ttgtccaggg aataccacac tcgcccttct ctccagcgaa    4800
caccacactc gcccttctct ccaggggacg ccacactccc ccttctgtcc aggggacgcc    4860
acactccccc ttctctccag gggacgccac actcgccctt ctctccaggg gacgccacac    4920
tcgcccttct ctcagggga cgccacactc gcccttctgt ccaggggacg ccacactcgc     4980
ccttctctcc aggggacgcc acactcgccc ttctctccag gggacgccac actcccccctt   5040 ctgtccaggg gacgccacac tccccttct ctccagggga cgccacactc cccttctct     5100 ccaggggacg ccacactcgc ccttctctcc aggggacgcc acactccccc ttctgtccag    5160
```

```
gggacgccac actcgccctt ctctccaggg gacgccacac tcgcccttct ctccagggga      5220
cgccacactc ccccttctct caggggacg ccacactccc ccttctctcc agggacgcc         5280 acactccccc ttctgtccag gggacgccac actcgcccctt ctctccaggg gacgccacac     5340 tccccttct ctcaggggac gccacactc ccccttctct caggggacg ccacactccc          5400 ccttctgtcc aggggacgcc acactcgccc ttctctccag gggacgccac actcgcccctt     5460 ctctccaggg gacgccacac tcgcccttct ctccagggga cgccacactt gcccttctgt      5520
ccagggaatg ccacactccc ccttctcccc agcagcctcc gagtgaccag cttcccatc        5580 gatagacttc ccgaggccag gagccctcta gggctgccgg gtgccaccct ggctccttcc      5640
acaccgtgct ggtcactgcc tgctgggggc gtcagatgca ggtgaccctg tgcaggaggt     5700
atctctggac ctgcctcttg gtcattacgg ggctgggcag ggcctggtat cagggccccg     5760
ctggggttgc agggctgggc ctgtgctgtg gtcctgggt gtccaggaca gacgtggagg       5820
ggtcagggcc cagcaccct gctccatgct gaactgtggg aagcatccag gtccctgggt       5880
ggcttcaaca ggagttccag cacgggaacc actggacaac ctgggtgtg tcctgatctg      5940 gggacaggcc agccacaccc cgagtcctag ggactccaga gagcagccca ctgccctggg     6000
ctccacggaa gccccctcat gccgctaggc cttggcctcg gggacagccc agctaggcca     6060
gtgtgtggca ggaccaggcc cccatgtggg agctgacccc ttgggattct ggagctgtgc     6120
tgatgggcag gggagagcca gctcctcccc ttgaggagg gtcttgatgc ctggggttac     6180
ccgcagaggc ctgggtgccg ggacgctccc cggtttggct gaaaggaaag cagatgtggt    6240
cagcttctcc actgagccca tctggtcttc ccggggctgg gccccataga tctgggtccc     6300
tgtgtggccc cctggtctg atgccgagga taccctgca aactgccaat cccagaggac      6360
aagactggga agtccctgca gggagagccc atccccgcac cctgacccac aagagggact    6420
cctgctgccc accaggcatc cctccaggga tcc                                       6453

<210> SEQ ID NO 9
<211> LENGTH: 4002
<212> TYPE: DNA
<213> ORGANISM: Homo sapiens

<400> SEQUENCE: 9
atgcaggcgc agcagctgcc ctacgagttt ttcagcgaag agaacgcgcc caagtggcgg      60
ggactactgg tgcctgcgct gaaaaaggtc caggggcaag ttcatcctac tctcgagtct    120
aatgatgatg ctcttcagta tgttgaagaa ttaattttgc aattattaaa tatgctatgc    180
caagctcagc cccgaagtgc ttcagatgta gaggaacgtg ttcaaaaaag tttccctcat    240
ccaattgata aatgggcaat agctgatgcc caatcagcta ttgaaaagag gaagcgaaga    300 aacccttat ctctcccagt agaaaaaatt catcctttat taaggaggt cctaggttat       360 aaaattgacc accaggtttc tgtttacata gtagcagtct tagaatacat ttctgcagac    420
attttaaagc tggttgggaa ttatgtaaga aatatacggc attatgaaat tacaaaacaa    480
gatattaaag tggcaatgtg tgctgacaag gtattgatgg atatgtttca tcaagatgta   540
gaagatatta atatattatc tttaactgac gaagagcctt ccacctcagg agaacaaact    600
tactatgatt tggtaaaagc atttatggca gaaattcgac aatatataag ggaactaaat   660
ctaattataa agttttttag agagcccttt gtctccaatt caaaattgtt ttcagctaat    720
gatgtagaaa atatatttag tcgcatagta gatatacatg aacttagtgt aaagttactg   780
ggccatatag aagatacagt agaaatgaca gatgaaggca gtccccatcc actagtagga    840
```

```
agctgctttg aagacttagc agaggaactg gcatttgatc catatgaatc gtatgctcga      900
gatattttgc gacctggttt tcatgatcgt ttccttagtc agttatcaaa gcctggggca      960
gcactttatt tgcagtcaat aggcgaaggt ttcaaagaag ctgttcaata tgttttaccc     1020
aggctgcttc tggcccctgt ttaccactgt ctccattact ttgaactttt gaagcagtta     1080
gaagaaaaaa gtgaagatca agaagacaag gaatgtttaa acaagcaat  aacagctttg     1140
cttaatgttc agagtggtat ggaaaaaata tgttctaaaa gtcttgcaaa acgaagactg     1200
agtgaatctg catgtcggtt ttatagtcag caaatgaagg ggaaacaact agcaatcaag     1260
aagatgaacg agattcagaa gaatattgat ggttgggagg gaaaagacat tggacagtgt     1320
tgtaatgaat ttataatgga aggaactctt acacgtgtag gagccaaaca tgagagacac     1380
atatttctct tgatggctt  aatgatttgc tgtaaatcaa atcatgggca gccaagactt     1440
cctggtgcta gcaatgcaga atatcgtctt aaagaaaagt tttttatgcg aaaggtacaa     1500
attaatgata aagatgacac caatgaatac aagcatgctt ttgaaataat tttaaaagat     1560
gaaaatagtg ttatatttt  tgccaagtca gctgaagaga aaaacaattg gatggcagca     1620
ttgatatctt tacagtaccg gagtacactg gaaaggatgc ttgatgtaac aatgctacag     1680
gaagagaaag aggagcagat gaggctgcct agtgctgatg tttatagatt tgcagagcct     1740
gactctgaag agaatattat atttgaagag aacatgcagc ccaaggctgg aattccaatt     1800
atcaaagcag gaactgttat taaacttata gagaggctta cgtaccatat gtacgcagat     1860
cccaattttg ttcggacatt tcttacaaca tacagatcct tttgcaaacc tcaagaacta     1920
ctgagtctta taatagaaag gtttgaaatt ccagagcctg agccaacaga agctgatcgc     1980
atagctatag agaatggaga tcaacccttg agtgcagaac tgaaaagatt tagaaaagaa     2040
tatatacagc ctgtgcaact gcgagtatta atgtatgtc  ggcactgggt agagcaccac     2100
ttctatgatt ttgaaagaga tgcatatctt ttgcaacgaa tggaagaatt tattggaaca     2160
gtaagaggta aagcaatgaa aaaatgggtt gaatccatca ctaaaataat ccaaaggaaa     2220
aaaattgcaa gagacaatgg accaggtcat aatattacat ttcagagttc acctcccaca     2280
gttgagtggc atataagcag acctgggcac atagagactt ttgacctgct caccttacac     2340
ccaatagaaa ttgctcgaca actcacttta cttgaatcag atctataccg agctgtacag     2400
ccatcagaat tagttggaag tgtgtggaca aaagaagaca agaaattaa  ctctcctaat     2460
cttctgaaaa tgattcgaca taccaccaac ctcactctgt ggtttgagaa atgtattgta     2520
gaaactgaaa atttagaaga aagagtagct gtggtgagtc gaattattga gattctacaa     2580
gtctttcaag agttgaacaa ctttaatggt gtccttgagg ttgtcagtgc tatgaattca     2640
tcacctgttt acagactaga ccacacattt gagcaaatac caagtcgcca gaagaaaatt     2700
ttagaagaag ctcatgaatt gagtgaagat cactataaga aatatttggc aaaactcagg     2760
tctattaatc caccatgtgt gccttttctt ggaatttatc tcactaatat cttgaaaaca     2820
gaagaaggca accctgaggt cctaaaaaga catggaaaag agcttataaa ctttagcaaa     2880
aggaggaaag tagcagaaat aacaggagag atccagcagt accaaaatca gccttactgt     2940
ttacgagtag aatcagatat caaaaggttc tttgaaaact tgaatccgat gggaaatagc     3000
atggagaagg aatttacaga ttatcttttc aacaaatccc tagaaataga accacgaaac     3060
cctaagcctc tcccaagatt tccaaaaaaa tatagctatc ccctaaaatc tcctggtgtt     3120
cgtccatcaa acccaagacc aggtaccatg aggcatccca cacctctgca gcaggagcca     3180
```

-continued

| | |
|---|---|
| aggaaaatta gttatagtag gatccctgaa agtgaaacag aaagtacagc atctgcacca | 3240 |
| aattctccaa gaacaccgtt aacacctccg cctgcttctg gtgcttccag taccacagat | 3300 |
| gtttgcagtg tatttgattc cgatcattcg agccctttc actcaagcaa tgataccgtc | 3360 |
| tttatccaag ttactctgcc ccatggccca agatctgctt ctgtatcatc tataagttta | 3420 |
| accaaaggca ctgatgaagt gcctgtccct cctcctgttc ctccacgaag acgaccagaa | 3480 |
| tctgccccag cagaatcttc accatctaag attatgtcta agcatttgga cagtccccca | 3540 |
| gccattcctc ctaggcaacc cacatcaaaa gcctattcac cacgatattc aatatcagac | 3600 |
| cggacctcta tctcagaccc tcctgaaagc cctcccttat taccaccacg agaacctgtg | 3660 |
| aggacacctg atgttttctc aagctcacca ctacatctcc aacctccccc tttgggcaaa | 3720 |
| aaaagtgacc atggcaatgc cttcttccca aacagcccct cccccttac accacctcct | 3780 |
| cctcaaacac cttctcctca cggcacaaga aggcatctgc catcaccacc attgacacaa | 3840 |
| gaagtggacc ttcattccat tgctgggccg cctgttcctc cacgacaaag cacttctcaa | 3900 |
| catatcccta actccctcc aaaaacttac aaaagggagc acacacaccc atccatgcac | 3960 |
| agagatggac caccactgtt ggagaatgcc cattcttcct ga | 4002 |

<210> SEQ ID NO 10
<211> LENGTH: 6601
<212> TYPE: DNA
<213> ORGANISM: Drosophila melanogaster

<400> SEQUENCE: 10

| | |
|---|---|
| aagcttcgac ttctggaagc tagctcccta actgtttttg gttttttgtat tctgttgcat | 60 |
| tgcattgctt tcatatgttt aattgtttca actgaacaca ttgtacttgt tttcgattta | 120 |
| gaagcgttga aagcggatgt atcttacatt atccaagtaa aataagggat gagtcgatat | 180 |
| gtatgttgca tatctcctta cgattttaga taaggaaaga catttttataa atataaatat | 240 |
| aaatttcttg aaatataaac attgaagaga taattaaatt catttttttt gggtaaatta | 300 |
| taatatattt taaacctgct cgttgcaatt taaattcaaa atgcttcttc ttctgctaaa | 360 |
| aaagccattc aacacgaatg ctctctacat tggattttt agtacattct taagcatcga | 420 |
| atcagggctg tcgcgagca tttactggat ttaggcagtg ccgcactctg gtcacaccgc | 480 |
| gaaaaatatt atattgagtt gaagattata ttatacatat atatatcgaa gatacatatt | 540 |
| ctgaaaacaa gtgctgaagc ccaagcgatt tgcaaacgaa acggacgcgc gagccccgtt | 600 |
| caagattcga aacgagttca gtgcgtgcgc ttgagtgtgt gtgactgcca tgcgacgttc | 660 |
| gcccgggtga tccggctgtg ccaggtgccc cacggttcca ggtttccagt ttccaggttc | 720 |
| cgctccactc cactcgtcgc tggattcagt gcacaacaca gcgggcgggg aggcggaggg | 780 |
| caggcggcca acgaaggtgc tccacggcag gctctcgtcg gctactccac ggcgcacaga | 840 |
| atgttctcgg ggcccagcgg ccatgcccac accattagct acggggcgg gatcggtctg | 900 |
| ggcactggag gcggcggcgg cagcggtggt agtggtagtg gctcacaggg cggaggcggt | 960 |
| ggtattggca ttggcggcgg tggcgtggct gggctgcagg attgcgatgg ctatgacttc | 1020 |
| accaagtgcg agaatgctgc gagatggagg ggcttgttta cgccatcgct aaagaaggtg | 1080 |
| ctggagcaag tgcatccacg ggttaccgcc aaggaggacg cactgctgta tgtggagaaa | 1140 |
| ctctgtctgc ggcttctggc catgctgtgc gccaagccgc tgccccattc cgtgcaggat | 1200 |
| gtggaggaga aggtgaacaa gtcctttcca gcgcccatcg atcagtgggc cctgaacgag | 1260 |
| gccaaggagg tgatcaactc gaagaaacgc aagtctgtcc tgcccacgga aaaggtgcac | 1320 |

```
acgctgctcc agaaggatgt gttgcagtac aagatcgata gctccgtgtc cgccttcctg   1380
gtggccgtgc tcgagtacat ctcagcggac atactcaaaa tggccggcga ctatgtgatc   1440
aagatcgccc actgcgagat caccaaggag gacatcgagg tggtgatgaa cgccgatcgt   1500
gtgctaatgg acatgctcaa ccagagcgaa gcccacatcc tgcccagtcc cctgtcactt   1560
cccgcgcagc gtgcaagtgc cacctacgag gagacggtca aggagctgat ccacgacgag   1620
aagcagtacc aacgcgacct gcacatgatc atacgcgtct ttcgtgagga gctggtgaag   1680
atcgtgtccg atccgcgcga gctggaaccg atattctcca acataatgga catttacgag   1740
gtgacggtca ctctgctcgg ctccctggag gacgtcatcg agatgtccca ggagcagagt   1800
gccccctgcg tcggtagctg ctttgaggaa ctggccgagg ccgaggagtt cgatgtgtac   1860
aagaagtacg cctacgacgt tacctcgcag gcctcacggg atgctctcaa caatctcctg   1920
tctaagccag gggtaagtat tgatacCttc tgtgcgaaga atttctactaa atccCtgct   1980 tttaggcctc atctctgacc acagccggcc atggcttccg cgatgcggtc aaatactatt   2040
tgcccaagct gcttctggtg cccatttgcc atgccttcgt gtatttcgac tacatcaagc   2100
atctcaagga tctcagctct tcgcaggacg acatcgagag cttcgaacag gtacagggac   2160
tgttgcatcc actccactgc gatctcgaaa aggtaatggc cagcctgtcc aaggagcgac   2220
aagttccggt tagcggtcga gtgcgccgcc agctggcaat cgagcggaca cgggagctcc   2280
aaatgaaggt ggagcactgg gaggacaagg acgtgggcca gaattgcaat gaatttattc   2340
gcggtaagtg ctggcaacga aagttacttg catcctccaa ctaaaatggt atttcaaatt   2400
tacagaggat tcgctgagca aacttggatc gggaaaacga atctgagcg agcgcaaggt   2460 attcctcttc gacgggctaa tggtgctatg caaggcaaac accaagaaac aaacaccatc   2520
ggcaggagca acggcctacg actaccgact gaaggagaag tatttcatgc gacgcgtgga   2580
tatcaacgat cgaccggaca gcgatgatct gaagaacagt tttgagttgg cacccCggat   2640
gcagccgccc attgtgctga ccgccaagaa tgcacagcac aagcacgact ggatggcaga   2700
cctgctgatg gttatcacca agtcgatgct ggaccggcac ttggacagca tattgcaaga   2760
catcgagcga aagcatccgc tgcggatgcc cagtccggag atttacaagt cgcggtgcc    2820 ggacagcggt gacaatatcg tgttggagga gcgcgaaagc gcaggagtgc cgatgatcaa   2880
gggagcgacg ctttgcaagc taatcgagcg cctcacctat cacatctacg ccgatccgac   2940
ttttgtgcgc accttcctca ccacatatcg ctacttctgc tcgccgcagc aattgctgca   3000
actgctggtg gaacgcttta acataccgga tcccagcctg gtctatcaag acacgggcac   3060
agcaggtgcg ggtggaatgg gcggcgttgg cggtgacaag gagcacaaga actcgcatcg   3120
cgaggactgg aaacgatatc gcaaggagta cgtgcagcca gtgcagtttc gagtgctcaa   3180
cgtactcgcg cattgggtcg accatcattt ttacgatttc gagaaggatc ccatgttgct   3240
ggagaagctg ctgaactttc tggagcacgt gaatggcaaa tcgatgcgca gtgggtgga   3300 ttccgtgctt aagattgttc agagaaaggt gagtagttgg tcaacagcat aatgtggaag   3360
tatcgttatc attttttcaaa tattatttac agaacgagca ggagaaaagc aataaaaaga   3420
ttgtatacgc ctatggccac gatccgccgc ccattgcgca tcaccttagt gtacccaacg   3480
acgagataac gctcctcacc ctgcacccac tggaactggc ccgtcagctc actctactgg   3540
aattcgagat gtacaagaat gtaaagccgt ctgagttggt cggatcaccc tggacgaaaa   3600
aggacaagga ggtgaagagc cctaatctac tgaagataat gaagcacacc acgaacgtca   3660
```

```
cccgctggat tgaaaaatcc atcaccgaag cggagaacta cgaggaacgc ctggctatta    3720
tgcaacgcgc aatcgaagtg atgatggtga tgctggaatt gaacaatttt aatggaatcc    3780
tctcgattgt cgcggctatg ggcacggcat ctgtttatcg actgcggtgg acattccagg    3840
gattgcccga acgctacaga aaattcttgg aggaatgccg cgagctcagc gacgatcatc    3900
tcaaaaagta tcaggagcga ttgcgatcca tcaatccgcc ttgtgtgcca ttttcggtc     3960 gctacttgac caacatactc cacttggagg agggtaaccc cgacctgcta gccaacacag    4020
agctaattaa cttttccaaa cgacggaaag tggccgagat tattggcgag attcaacagt    4080
accagaacca gccatactgc ctcaacgagg agtccacaat acgacagttc ttcgagcaac    4140
tggatccgtt taacggactg tccgacaaac agatgtccga ctatctctat aacgaaagcc    4200
tgcgcattga gccaaggggc tgcaagacag tgccgaaatt cgtaagtata atgcttcaaa    4260
gtttacaagt catataggaa atttaaccat tttccttcg tagcctcgaa aatggccgca     4320
cattccgctc aaatcgccgg gcatcaagcc gcgtcgccag aatcagacca acagcagtag    4380
caagctgtcg aacagcacgt cgtccgtggc ggcggcagcg gcagcatcgt caacggccac    4440
ctcaatagct acggcatcgg cgccatcttt gcacgcctcc agcataatgg atgcgccaac    4500
agcagcagca gctaatgctg gatctggaac tctcgctggc gagcaaagtc cgcagcacaa    4560
tccgcacgct ttctccgttt tcgcccctgt tattataccc gaacgaaaca ccagcagctg    4620
gagtggaacg ccacagcaca ctcgaacgga ccagaacaac ggggaggttt cggtgccggc    4680
gccacatctc cccaagaaac cgggcgcgca tgtctgggct aacaacaact cgacactggc    4740
cagtgcgtcg gcaatggatg ttgtgttcag tccagcgctg ccggagcatc tgccaccgca    4800
gtccctgccg gacagcaatc cattcgcatc ggacacggaa gctccaccgt cgccgctgcc    4860
caagctagtg gtcagtccgc gtcacgaaac cggcaatcga tcaccattcc atgggcgcat    4920
gcagaacagc ccaacgcata gcactgccag taccgtgacc cttacaggca tgtctacatc    4980
gggcggggag gaattctgcg cgggtggatt ctactttaac agtgcccatc agggacagcc    5040
gggggcagtg cccatctcgc cgcatgtcaa cgttccgatg ccaccaata tggagtaccg     5100 agcagtgccg cctccactgc cacccagacg caaggagcgc actgagagct gtgcggacat    5160
ggcgcaaaag cgtcaggcgc cagacgcacc cacagtaagt agcctcactt acttctaatt    5220
tgtagtagca gatgacagca atcattttac gtatccttgc agttacccc gcgtgatggc     5280 gaactcagtc cgccgccgat accgccacgg ctcaaccatt ccacgggcat cagctacttg    5340
cgacaaagcc acggcaagag caaggagttt gtgggcaaca gcagtctgct cctgcccaac    5400
accagcagta ttatgatacg ccgcaactcg gcgatcgaga agcgggcagc ggcaactagc    5460
cagccaaacc aggcggcggc gggacccatc agcacgacac tagtgaccgt gtcgcaggca    5520
gtggcgacgg acgaaccgct gccgctaccg atctcgccag cggcaagctc ctcgacgacc    5580
acatcaccgc tgacacccgc catgtcgccc atgtctccca acattcccag ccatccggtg    5640
gagagcacgt cgagcagcta tgcccaccaa ctgcgaatgc ggcagcagca gcagcagcag    5700
acgcatccag cgatctactc gcagcaccat caacatcatg ccacccatct gccgcaccat    5760
ccgcaccagc accattcgaa tccgacgcag tcgcgctcgt cccccaagga gttctttccg    5820
attgccacga gcctcgaggg cacacccaaa cttccaccaa aacctagtct aagcgctaac    5880
ttctataaca atccaggtga gtgctaccaa ctcggcccgt gataacgtgt ttcctaaccc    5940
aaccatccta tccgtttgca gataaaggta cgatgttct ttacccaagt acaaacgaag     6000
aataatttaa attgcctggc gatgtgataa ggacgaaaac tacgagtatg atccgtaaga    6060
```

```
ttcaaagttg cgagcactgc ttgagtgcag atatatatat gagagaacgg aacgtgagat     6120
atatatatat atatatacat atacgctag gcgcagttta tgtattctag tatgaaacga     6180
gttggaaccg ctgatttaga ttattcgcca ctcatttaac aaggtagaac agacagacag     6240
acaaaatacg ctctcattta cacacaacag gcacgcgcat atggatagga atgcaggaca     6300
cacaaaccaa gcaagcaacc aagcaaccaa caagaaatgc aaacaagaaa ttatgttatt     6360
atataattac tattataaat atttgtaaat atcgagaaca ttgtattgat cgtagaacgt     6420
aaaacaataa agtataaccc tattgttaga cacttggcga catctttcga tgaccagaaa     6480
tatagagtat tgtagccaaa gtcaaggcaa tctgagcaaa tagcatagat tatcaaggct     6540
tttccaacgt ttaaagatcg tgggtattct ttatgtgccc agtggccttg atgaagtcga     6600
c                                                                   6601
```

<210> SEQ ID NO 11
<211> LENGTH: 5398
<212> TYPE: DNA
<213> ORGANISM: Saccharomyces cerevisiae

<400> SEQUENCE: 11

```
gtcgacgtca gtcacctcca ggttattatg taattcgcta aaacgacttt taaacatcgc       60
gggagacgga tctttgacag agacctggag gaaaaaataa aatagaaaaa taagctcaaa      120
agttacagag aaaactgcat caccaacacg gcggagacag ttatagtgac ttgatcaccg      180
tgaagcaatt cctttagtta gatagactgt ttctttttcg gaaagaaatt gaataaaaag      240
agccacattt ttcttcgaat aaatactaaa aaataaaacg aaaaagcaag gtggatattg      300
gatagttgta tcatgtccga tactaacacg tctattccca atacaagttc tgcaagggag      360
gcaggcaatg cttcacaaac tccatcgatc agctcttcat ctaacacttc cactaccact      420
aacacagaat catcctcagc ttctcttttct tcttcccct cgacaagtga gttgaccagc      480
attcgtccaa ttggaatagt agtcgctgct tatgacttta attatcccat taaaaaagac      540
agttcttcgc aacttttgtc tgtacaacaa ggggaaacca tttatatact taacaaaaac      600
tcatctgggt ggtgggatgg attagttatt gacgacagta atgggaaagt taacagaggc      660
tggtttcctc aaaacttcgg tagacccttta agagacagtc atctcagaaa gcacagtcat      720
ccgatgaaaa aatatagttc cagtaagagc tcaaggcgca gcagcttaaa tagcttgggc      780
aatagtgcat atttacatgt gcctagaaat ccgagcaaga gcaggagggg gagttctact      840
ttatcagcgt ctttatcaaa tgcccacaat gcagaaacaa gttccggcca caataacacc      900
gtatcgatga ataattctcc cttttcagcg ccaaacgatg cttcccacat aacccctcaa      960
tcttcgaact ttaattccaa tgctagtcta tcccaggata tgacaaagag tgcagatggc     1020
tcatctgaga tgaatacaaa cgcaattatg aataacaatg aaacaaattt acaaacttct     1080
ggtgagaaag caggtccccc actagtagca gaagaaacaa ttaagatatt accgttggaa     1140
gagatagaaa tgattattaa tggtatacgt tcgaacattg cttcgacttg gtcccccata     1200
ccactgataa cgaaaacatc cgattacaag ttggtatact ataacaaaga ccttgatata     1260
tactgttcag aattacccctt gatttctaac tcaattatgg aatccgatga catttgtgac     1320
agcgaaccaa aattcccgcc caatgatcat cttgttaacc tatatactag agatctgagg     1380
aaaaatgcga atattgagga cagttctacg agatcgaagc aatcggaaag tgaacaaaat     1440
agatcaagcc ttctaatgga aaaacaggat tcaaaagaaa ctgatggaaa taataacagt     1500
```

```
attaatgatg atgataataa taacgaaaat aacaaaaacg aattcaatga ggctggtcct    1560
tcatcattaa attctttatc tgctccagat ttaacgcaga atattcaatc aagggtagtt    1620
gccccaagtc gctcttctat actggccaag agtgacatct tttatcacta ttcaagagat    1680
ataaaattgt ggacagaatt acaagaccta acagtttatt atactaaaac ggctcacaag    1740
atgttcctta aagagaatcg tctcaatttc acgaaatact ttgatttgat atcagattca    1800
atagtcttca cacagttagg ctgcaggcta atgcaacatg aaattaaagc caaaagttgc    1860
agcaaggaga ttaagaagat tttcaaaggt ctaatctctt cattgtcaag ataagtatc     1920 aattctcatt tatatttcga ttcagctttt cacagaaaaa aatggatac tatgaatgac     1980 aaggataacg ataatcagga aaataattgt tctaggacgg aaggggatga tggtaaaatt    2040
gaagtagata gtgtacatga tctagtttca gttccattgt ccggtaaacg taatgtaagt    2100
accagtacaa cggatacatt gactccaatg agatcatcat tcagtacagt caatgagaac    2160
gatatggaaa atttctcagt cttaggtcca agaaatagtg ttaattctgt cgtaacacca    2220
aggacttcaa tacaaaattc tactttggaa gattttcac cgtccaacaa aaattttaag     2280
tcagctaaat cgatttacga aatggttgat gtggaattct cgaaattttt aaggcatgtt    2340
cagttacttt attttgtgtt acagagctca gtcttctcag atgataatac tttaccacag    2400
ttgctcccaa gatttttaa aggttcattt agcggtggtt cttggacaaa tccattttcg      2460
acttttatta cggatgaatt tggtaatgcg acaaagaaca aagctgtcac atctaatgaa    2520
gtgaccgctt cgtcgtccaa aaattcctca atatcaagga ttccaccaaa gatggcagat    2580
gctattgcct ctgcgtcagg atatagcgct aattcagaaa caattccca aattgattta      2640 aaagcaagca gtgccgcgtc tggttcagtt tttacacctt tcaaccgtcc ttctcataac    2700 agaaccttt caagagcaag agtttcaaaa aggaagaaaa aatatccatt aactgtagac     2760
actttgaata caatgaagaa gaaatcctcg caaattttg aaaaattaaa taatgctaca      2820
ggtgaacact taaaaattat aagtaaaccc aaaagcagaa ttaggaattt ggaaataaat    2880
tcaagcacat acgaacaaat aaatcagaat gttttactat tggagatact ggagaattta    2940
gatctgtcaa ttttcatcaa tttgaaaaac ctgattaaga cacccagtat tttgttggat    3000
ttggaaagcg aggaattttt agttcacgcc atgtcttcgg tctcctcagt actaacagag    3060
ttttttgata taaagcaggc ttttcatgac atcgtcatca gattaataat gacaacgcaa    3120
caaacgacct tagacgaccc gtatttgttt tcctcaatga ggtccaattt ccctgtcgga    3180
catcatgaac cttcaagaa tatctctaat acacctttgg tcaagggccc cttccataaa      3240
aaaaatgaac aattggcact ctccttattt cacgtattgg tgagtcaaga tgtggagttc    3300 ataaccttg aattttaaa caactccgac gattttaaag atgcttgtga aaagtatgtc        3360
gagatttcta atcttgcgtg tattattgtt gatcaattga ttgaagaaag agaaatttg     3420 ctgaactacg cagcaagaat gatgaagaat aatttgactg cagaactatt gaaaggtgag    3480
caagaaaaat ggtttgatat ttattccgag gactatagtg atgacgattc agaaaatgat    3540
gaagctatca tcgatgacga attaggatct gaggactata ttgaacgcaa agctgcgaac    3600
atagagaaaa accttccatg gttttttaact tcagattatg aaactagtct tgtctatgac    3660
tcaagaggaa aaattcgtgg cgggacaaaa gaggcactga ttgaacattt aaccagtcat    3720
gaacttgttg atgcggcttt caatgttaca atgttaataa ctttcagaag tatattaacc    3780
acaagagagt ttttttatgc cctgatttac aggtacaact tgtatcctcc tgaagggctg    3840
agttacgatg attacaatat ttggatagaa aaaaagtcaa acccgattaa atgccgtgtg    3900
```

```
gtcaacatta tgagaacatt tttgacgcag tattggacaa gaaattatta tgaacctggc    3960
ataccactga ttctaaattt tgccaagatg gttgtatcgg agaaaatacc gggggcagag    4020
gatcttttgc aaaagataaa tgaaaaactg ataaatgaga atgagaaaga accagtggat    4080
cctaagcaac aagattcggt atcggcagtc gtacagacaa ctaaacgtga caataaatca    4140
ccgatacaca tgtcttcgtc ttctttacca tcttctgctt cttcagcgtt ttttagattg    4200
aagaaattga agctcttgga tattgaccca tacacatatg ccacacaatt gactgtactt    4260
gaacatgact tatacctcag gatcactatg tttgaatgct tggatagggc atggggtacc    4320
aagtattgta atatgggtgg ttctccgaac attacgaaat ttatagctaa tgctaatacg    4380
ctaactaatt ttgtttctca taccattgta aaacaggcag atgtcaagac acgttcaaaa    4440
ttaacgcaat attttgttac cgttgcccag cattgtaaag agttgaataa ttttcttca     4500 atgactgcca tagtgtccgc tttgtattcc tccccaatct accgactgaa aaagacatgg    4560
gatttagttt ccactgagtc gaaggacctt ctgaagaacc taaacaacct tatggattcc    4620
aagagaaatt ttgtgaagta tagagagctg ttgcgatccg tgacggacgt tgcatgtgtt    4680
cccttttttg gtgtatacct atctgattta acatttacgt ttgtcggaaa cccagatttt    4740
cttcacaatt caaccaacat aataaacttc agcaagagga ctaaaatcgc aaatatagtg    4800
gaggaaatta taagctttaa aagattccat tacaagctga acgattgga tgatattcag     4860 accgttatag aagcgtcttt ggaaaatgtc ccccacattg aaaagcagta tcaattatca    4920
ctgcaagtgg aaccgagatc aggaaacacc aaaggcagta cgcatgcttc ttctgctagc    4980
ggtacaaaaa ctgcaaaatt cctaagtgaa tttacagatg ataaaaatgg caatttttttg   5040 aagctaggta agaaaaaacc tccttctagg ttatttcgat aaaagtttat acaatttgct    5100
aatcaagaag aaccttagct ttatgtttga ttgctacact ctattattta agatggctgc    5160
ttttacttaa tattcttcgt gataatactg tactggtgga gtgtttttcg ttttcgagga    5220
tttgagagta cgcttcattt gcagttcttc ttgataaagt tcgttttata tatatatatc    5280
tattttatat ctttatatat tttattacac ccagttaagt tatcgatcca agattttaaa    5340
tgcccgatta gaggaaactt attacctgaa aaaatatcaa ttagtgattc tatgaaaaa    5398

<210> SEQ ID NO 12
<211> LENGTH: 43676
<212> TYPE: DNA
<213> ORGANISM: Saccharomyces cerevisiae

<400> SEQUENCE: 12
gatcaatggc aacttaccgt agttgtcctt tgcggtgtct tcggcagcgg ctttcttttc      60
acgggcttct ctttcagctt ccaactggag agctctttcc tccttctttc tctgtttctc     120
ttgctctttc tgcaatttct tcaaggcctt cttggacaat ggcttaccat cttccccaag     180
aataacttga gcaggttctg cggattcttc aacagctttg acaatatttt cgtcttgaga     240
catcacgtaa aatgtttctt ttttttcttt acaattaacc ttaagaggcc gttccagcca     300
atgatcgaaa acttaaacaa atcggttgtc ttgcttcatc cttatatgac attaaataat     360
ttttcatttc ttctttttc acgaaaatgc gtcataaggt actcgtcact gatgatttca      420
tagacaataa agcaacagca caacgtaaaa gagttcttat ggatgagtcc caatcctatt     480
gttttctgta gcctaatggt acaaaatgtg acggtaatag aatatatact ttcataatat     540
cataggaaca tcttcagctt ggcctgtctc tttgagaaac aaaaactgca tgtgcacaat     600
```

-continued

```
tactgcagat gaacttcaag gaaacatatg tcctgcttgg aggaccagaa gcaaaccatt      660
ctagctgtat ttgcaacgct tttgtaccaa atgtacgtta ttatgttatg tcgtcagtgt      720
agatatatta gatttacatg cggctgtacc gcatcattgg aaaataatgt ctgcaggctc      780
gcaaaattta agggttccct tctacaatag tagtcaaaat tgcttttttg catataacaa      840
agtgaaaaaa aaaaaaaata tgagagacat atctaaaaga catatataat ctgccaccag      900
aatgagttgc actgcgtcat atgccggcat gacaactccg gtgaaggata aggaaggcca      960
cgggattcca tgcttacaac ctatcgatgt agtggaatgt acctatcaat attttacaaa     1020
atcacggaat aaactgtctt taagggtagg cgatttgatt tacgtactca ctaaaggttc     1080
taatggctgg tgggatggtg ttcttatcag acacagcgct aataataata ataattcgtt     1140
gatactagac agaggttggt tccccccttc tttttacacg gtccattcta aacgaactac     1200
acggggtgcc tgacatcggt aatgaattgg aaatatttca agcgggtctt aatcttaaac     1260
tggaattatc aagcaaccca gtgatcttat cattggaaga cttttagac tgctgtcgcg      1320 atattgaatt caaggaacaa ctggcttggt cacctactcc cgtccacgaa aggaaaggct     1380
gctgtgagct gctgtactat aaccaggatt tagatgttta ttgtcgcacg ttaccatatt     1440
taccacaaaa tcaagttgaa accgtgaacg actattcgtc ttttcctgca atatcgaaga     1500
tagctggtaa aaagatgcct ataacgtcaa gccccgatct gttctatctc aatgattgtg     1560
atgtcgtcta ttggtatgac ctcactcgct tagtgtgtca ttatgttaat ttaacagagc     1620
gcgacctatt ggcaaatgaa cgggaaaagt ttctaacttc cttggattta ttaacagctc     1680
aaataaccta tgtttatatg cttttcagga atctccgttt agttgaagat agtttcaaaa     1740
aaaccctcaa aaactaatt tacaccttgt ctaggttttc aataaatgca atatttggt       1800 ttcattccac attgtttgaa gaaagagaag ccatagcctc ccagaaggat ccagaaagaa     1860 gatccctct tctacagtca atcctaggaa ccttccaaaa atttcatttt ctactgcgtt      1920
tactacattt cctctcaaat cctaacgaac ttacaatact gcctcaattg actcctcgat     1980 tttcaagga ttcttcaat acaatttcat ggaataaccc gttttgcgt aagcgtctca       2040 accagcatat gtcccatgac ctaccgagac agatgattaa agccgttgct ggtgcttcag     2100
gaattgttgc ggaaaatatt gatgaaattc cagcttccaa acagggcact tcatgctcgt     2160
cagaaacgtc tcaccattca ccatcagccc cgtttcaaag aaggagaaga ggtaccattt     2220
tctctaatgt gtcaggaagt tccgatgagt ctgacaccat atggtccaaa aggaaaaaac     2280
catacccgct aaatgaagaa actctaagcc ttgtaagggc caggaagaag cagcttgatg     2340
gtaaactaaa acaaatgatc aaaagtgcta atgaatatct cagtaacacg gctaatttt      2400 caaaaatgtt gaattttgaa atgaattca aaacctacga agaagtaagc ggaacaattc      2460
ctataattga tattctggaa aacctagatt taactatttt tctaaacttg agagagttgg     2520
gagatgagaa tagagttttt gacgaagatg tcgctattga tgatgaagat gaagagtttt    2580
tgaaacattc tttatcatcc ctatcgtata tcttatccga ctattttaat atgaagcaat     2640 atttttcatga tgtagtagtg aaatttataa ttgtcgccca gcatttgaca ttagaggatc    2700
ctttcgtttt ctcgccaatg caaaacgact tgcctaccgg ttattatgaa ccaatgaaac     2760
cttcatcctt gaatttagat aatgccaagg ataagaagaa tgggagccaa atactgata     2820 tccaagagga ggaagatgaa tatgagccaa acccggatag tcttattctc ttccacaacc     2880
tcatcaatca agattctgat ttcaatgatt taagttttt taatctcgcc cacgttttta     2940
aaaaatcctg tgatgactat tttgatgtgc ttaaactagc cattgagttc gtgaatcaat     3000
```

```
taattctaga aagagagaat tgttaaatt atgctgctag aatgatgaaa acaatatca    3060 cggaattgct attgcgcggg gaagaaggct atgggtccta tgacggcggt gaaactgccg   3120
aaaaaagtga cacgaatgct gtttatgcag attcagatac taaagacaat gacgaatggc   3180
gtgacagcca agtcaaatta ccgaggtatt tgcagcgcga gtatgacagt gaactgattt   3240
ggggctctaa caataggatt aaaggtggtt ctaaacacgc actgatctct tacttgacag   3300
ataatgaaaa gaaggatcta tttttcgata ttacttttt aatcactttc agaagcatct    3360
ttactacaac ggagttttta agctacttga tttcgcaata taatttggat ccaccagagg   3420
atttgtgctt tgaagaatac aatgaatggg tgacgaaaaa gcttataccg gttaaatgta   3480
gggtggttga gattatgaca acctttttca agcaatattg gttcctgggc tatgatgagc   3540
ccgatcttgc gaccctaaat ctggattatt ttgcgcaagt agcaatcaag gaaaatataa   3600
caggatctgt ggaattacta aaggaggtca atcagaagtt taaacatggt aatatacaag   3660
aagcgactgc accaatgaaa acgttagatc aacagatctg ccaggaccat tactcgggca   3720
ctttatactc taccacggaa tccatttggg ccgtcgatcc agttttattt gccactcaat   3780
taacgatact agagcatgaa atttattgtg agataaccat ttttgattgt ttacaaaaaa   3840
tttggaagaa caagtataca aaatcgtatg gggcttcacc gggtttgaac gagtttatca   3900
gttttgccaa taaactgaca aatttcatat cctactctgt tgtaaaggag gctgataaaa   3960
gtaagcgcgc caagctactc tctcatttta tttttatcgc agaatattgt aggaaattca   4020 ataactttc ttccatgact gcaatcattt cagcattata ttcttcacca atttatcgtt    4080
tagagaaaac ctggcaggca gttattcctc aaacgagaga tctattgcag tcactgaaca   4140
agttgatgga tcccaagaaa aatttcataa attacagaaa cgagctgaaa tctttacata   4200
gcgctccctg cgtaccgttt ttcggcgttt atttatctga tctaaccttt actgattccg   4260
gaaatccgga ttatcttgtc ttggaacatg gtttaaaggg tgtccatgat gagaagaaat   4320
atataaactt caacaaaagg agcagacttg ttgatatctt acaagagatc atatatttca   4380
agaaaacaca ttatgatttc actaaagatc ggacggtaat tgaatgtata tcaaattcat   4440
tggaaaacat cccccatatt gagaaacaat accaattatc attaattatt gaaccaaaac   4500
caagaaagaa agtcgttccg aattccaatt cgaataataa atcacaagaa aaatccaggg   4560
atgaccaaac cgatgaagga aaaacatcca ctaagaaaga cagatttcca aaatttcaat   4620
tacataagac aaagaaaaaa gctcccaagg tttctaagta acggcgccgt atgttcgatt   4680
tccttctctc ggtggattaa ttattttgtt tgttttctcc tgttatatta tttattgatc   4740
actatagtaa actatgtccg tcatcaagcc cgacggctgc tatcccacaa tgttgatcgt   4800
attgtttgcc tagtttatta tatatttgct tatttatagc ataccataat atttaaatgc   4860
cctcaaattt ttggccgtag cgacatcgcg ataattccaa ttcccttttaa aaaattgcgc   4920 ctgagtataa gttaattcag ccagttctcc aaattaaaat cgcatactcc tgaacctatc   4980
aacagattgt cctcgcatac ttttctatac caaggtctct tctgaacata tattagcagt   5040
ggttaatttt aaagagatca taaagaaaat tttgtctaaa aagattaat ataaagacaa     5100 tgtcttcact agaagtggta gatgggtgcc cctatggata ccgaccatat ccagatagtg   5160
gcacaaatgc attaaatcca tgttttatat cagtaatatc cgcctggcaa gccgtctttt   5220
tcctattgat tggtagctat caattgtgga aactttataa gaacaataaa gtaccaccca   5280
gatttaagaa ctttcctaca ttaccaagta aaatcaacag tcgacatcta acgcatttga   5340
```

```
ccaatgtttg ctttcagtcc acgcttataa tttgtgaact ggccttggta tcccaatcta   5400
gcgatagggt ttatccattt atactaaaga aggctctgta cttgaatctc cttttcaatt   5460
tgggtatttc tctccctact caatacttag cttattttaa aagtacattt tcaatgggca   5520
accagctttt ctattacatg tttcaaattc ttctacagct cttcttgata ttgcagaggt   5580
actatcatgg ttctagtaac gaaaggctta ctgttattag cggacaaact gctatgattt   5640
tagaagtgct ccttcttttc aattctgtgg caattttat ttatgatcta tgcattttg    5700 agccaattaa cgaattatct gaatactaca agaaaaatgg gtggtatccc cccgttcatg   5760
tactatccta tattacattt atctggatga acaaactgat tgtggaaact taccgtaaca   5820
agaaaatcaa agatcctaac cagttaccat tgccgccagt agatctgaat attaagtcga   5880
taagtaagga atttaaggct aactgggaat tggaaaaatg gttgaataga aattctcttt   5940
ggagggccat ttggaagtca tttggtagga ctatttctgt ggctatgctg tatgaaacga   6000
catctgattt actttctgta gtacagcccc agtttctacg atattcata  gatggtttga   6060 acccggaaac atcttctaaa tatcctcctt taaatggtgt atttattgct ctaaccecttt   6120 tcgtaatcag cgtggtttct gtgttcctca ccaatcaatt ttatattgga attttgagg   6180 ctggtttggg gataagaggc tctttagctt ctttagtgta tcagaagtcc ttaagattga   6240
cgctagcaga gcgtaacgaa aaatctactg gtgacatctt aaatttgatg tctgtggatg   6300
tgttaaggat ccagcggttt ttcgaaaatg cccaaaccat tattggcgct cctattcaga   6360
ttattgttgt attaacttcc ctgtactggt tgctaggaaa ggctgttatt ggagggttgg   6420
ttactatggc tattatgatg cctatcaatg ccttcttatc tagaaaggta aaaaagctat   6480
caaaaactca aatgaagtat aaggacatga gaatcaagac tattacagag cttttgaatg   6540
ctataaaatc tattaaatta tacgcctggg aggaacctat gatggcaaga ttgaatcatg   6600
ttcgtaatga tatggagttg aaaaattttc ggaaaattgg tatagtgagc aatctgatat   6660
attttgcgtg gaattgtgta cctttaatgg tgacatgttc cacatttggc ttattttctt   6720
tatttagtga ttctccgtta tctcctgcca ttgtcttccc ttcattatct ttatttaata   6780
ttttgaacag tgccatctat tccgttccat ccatgataaa taccattata gagacaagcg   6840
tttctatgga aagattaaag tcattcctac ttagtgacga aattgatgat tcgttcatcg   6900
aacgtattga tccttcagcg gatgaaagag cgttacctgc tatagagatg aataatatta   6960 cattttatg  gaaatcaaaa gaagtattaa catctagcca atctggagat aatttgagga   7020
cagatgaaga gtctattatc ggatcttctc aaattgcgtt gaagaatatc gatcattttg   7080
aagcaaaaag gggtgattta gtttgtgttg ttggtcgggt aggagctggt aaatcaacat   7140
ttttgaaggc aattcttggt caacttcctt gcatgagtgg ttctagggac tcgataccac   7200
ctaaactgat cattagatca tcgtctgtag cctactgttc acaagaatcc tggataatga   7260
acgcatctgt aagagaaaac attctatttg gtcacaagtt cgaccaagat tattatgacc   7320
tcactattaa agcatgtcaa ttgctacccg atttgaaaat actaccagat ggtgatgaaa   7380
ctttggtagg tgaaagggc atttccctat caggcggtca gaaggcccgt ctttcattag   7440
ccagagcggt gtactcgaga gcagatattt atttgttgga tgacattta  tctgctgttg   7500 atgcagaagt tagtaaaaat attattgaat atgttttgat cggaaagacg gctttattaa   7560
aaaataaaac aattattta  actaccaata ctgtatcaat tttaaacat  tcgcagatga   7620 tatatgcgct agaaaacggt gaaattgttg aacaaggaa  ttatgaggat gtaatgaacc   7680
gtaagaacaa tacttcaaaa ctgaaaaaat tactagagga atttgattct ccgattgata   7740
```

```
atggaaatga aagcgatgtc caaactgaac accgatccga aagtgaagtg gatgaacctc   7800
tgcagcttaa agtaactgaa tcagaaactg aggatgaggt tgttactgag agtgaattag   7860
aactaatcaa agccaattct agaagagctt ctctagctac gctaagacct agaccctttg   7920
tgggagcaca attggattcc gtgaagaaaa cggcgcaaaa ggccgagaag acagaggtgg   7980
gaagagtcaa aacaaagatt tatcttgcgt atattaaggc ttgtggagtt ttaggtgttg   8040 ttttatttt cttgtttatg atattaacaa gggttttcga cttagcagag aattttggt   8100 taaagtactg gtcagaatct aatgaaaaaa atggttcaaa tgaaagggtt tggatgtttg   8160
ttggtgtgta ttccttaatc ggagtagcat cggccgcatt caataattta cggagtatta   8220
tgatgctact gtattgttct attaggggtt ctaagaaact gcatgaaagc atggccaaat   8280
ctgtaattag aagtcctatg actttctttg agactacacc agttggaagg atcataaaca   8340
ggttctcatc tgatatggat gcagtggaca gtaatctaca gtacattttc tccttttttt   8400
tcaaatcaat actaacctat ttggttactg ttatattagt cgggtacaat atgccatggt   8460
ttttagtgtt caatatgttt ttggtggtta tctatattta ctatcaaaca ttttacattg   8520
tgctatctag ggagctaaaa agattgatca gtatatctta ctctccgatt atgtccttaa   8580
tgagtgagag cttgaacggt tattctatta ttgatgcata cgatcatttt gagagattca   8640
tctatctaaa ttatgaaaaa atccaataca acgttgattt tgtcttcaac tttagatcaa   8700
cgaatagatg gttatccgtg agattgcaaa ctattggtgc tacaattgtt ttggctactg   8760
caatcttagc actagcaaca atgaatacta aaaggcaact aagttcgggt atggttggtc   8820
tactaatgag ctattcatta gaggttacag gttcattgac ttggattgta aggacaactg   8880
tgacgattga aaccaacatt gtatcagtgg agagaattgt tgagtactgc gaattaccac   8940
ctgaagcaca gtccattaac cctgaaaaga ggccagatga aaattggcca tcaaagggtg   9000
gtattgaatt caaaaactat tccacaaaat acagagaaaa tttggatcca gtgctgaata   9060
atattaacgt gaagattgag ccatgtgaaa aggttgggat tgttggcaga acaggtgcag   9120
ggaagtctac actgagcctg gcattattta gaatactaga acctaccgaa ggtaaaatta   9180
ttattgacgg cattgatata tccgacatag gtctgttcga tttaagaagc catttggcaa   9240
ttattcctca ggatgcacaa gcttttgaag gtacagtaaa gaccaatttg gacccttca   9300 atcgttattc agaagatgaa cttaaaaggg ctgttgagca ggcacattta aagcctcatc   9360
tggaaaaaat gctgcacagt aaaccaagag gtgatgattc taatgaagag gatggcaatg   9420
ttaatgatat tctggatgtc aagattaatg agaacggtag taacttgtca gtggggcaaa   9480
gacaactact atgtttggca agagcgctgc taaaccgttc caaatattg gtccttgatg   9540 aagcaacggc ttctgtggat atggaaaccg ataaaattat ccaagacact ataagaagag   9600
aatttaagga ccgtaccatc ttaacaattg cacatcgtat cgacactgta ttggacagtg   9660
ataagataat tgttcttgac cagggtagtg tgagggaatt cgattcaccc tcgaaattgt   9720
tatccgataa aacgtctatt ttttacagtc tttgtgagaa aggtgggtat ttgaaataat   9780
gacattgatt attatatatg aagatataga acatttaatg cgctgcaata tgtacggtca   9840
cgccaattct ttttctttct atatgctttc tagtaacccg ggtaatcaca aatgaagcta   9900
gtagagatat aactaaatac aacttaattt taaccttatg ttggattgct caagcagtgt   9960
tcgagaaaga cagcggcaga cagatagaaa tgagctcaaa tgaagaggta tttactcaga  10020
taaacgcaac tgcgaatgtg gttgataata agaagcgttt acttttcgtg caagatagct  10080
```

-continued

```
cagcacttgt tctagggctt gttgcaggat ttttgcaaat cgagtcagtc catgggttta    10140
tttggttcct gattctgtac aacttgatta atgtcattta cattgtttgg atctgtcaac    10200
ttcaaccagg aaagttctac caaagcccac ttcatgacat tttttttcgaa tcgtttttta    10260 gagagataac tggttttgtc atggcatgga catttggata cgccctaatc ggatgaacat    10320
ataagaacta cttctataaa cggttagaaa caggcttgat ttattatgta cagtaaatat    10380
aatgttattt gtgttttttt tttttaaatt tttttagttc cttctatgta aaaagacatg    10440
acaacagtat tctcagtcaa atgatttcaa atacacaatg ttaaattctc tatctgttgc    10500
agaaataaga agagcgtaag agcgcaaaga tttttgcaga aaaatagaga tgaggtacaa    10560
aaagtaggta atggaaaaaa gcaaataatg aatataggg aacataaatg ttatggacaa    10620
gagtagatat caaataaaa caaataaaa tagagtaagt gaaagacaaa tggaggaaaa    10680
aaaaaaaaaa aaaaaaaaaa aaaaaatagt aaaagtgaa aggagaacga tgataacact    10740
aatcacacct ccgcattttc aaccaatgct gcaagtttct caacactggc taaatgtcta    10800
tttcctaggg agttagattt gtttagttta tccaaatatg ctctaatggc aatgacgatc    10860
aatttcttac cctcaccctc agagacatta actaattttt gaatcacata gttggcaaat    10920
tgatccttga tcattaaaat cattggagaa tcgtcttcca gattcaaagc atgattttg    10980 tctcttggta aaatcttaga aattattaaa tccttctgat ttttagagcc ataaagaata    11040 gattttttcga ccacgttgga ggcaaattta tgtttagagt attcgacaac attattggcc    11100
acagtttcta tgatttcctg tttgatatcg accatttcct tattggtgaa ctgatcttgt    11160
tgcaaaacat attgaatgac atagttacca tattggtctt gaattagata tggtatgaaa    11220
tctttcaatt cgtttaaaat gctttcctga tcttcgctcg aaccaaattc taacaatctt    11280
tgaatgaccc tacagccgta ggagtgggta gatagatggt aaatgtggcc agttaaagaa    11340
cttaagataa aaggtaattt ttcgatagga attgtttcga tggcctttg aattacgtga    11400 ttaccgttct gatctttgat catttgcaaa acggagtcag ataattccag gactaactca    11460
attctttgat tggaatcaat atattctaac gccttttgaa ttacacgaca tgcgtacatt    11520
tgtagagata actgtttcat gttacccttta aattgatcaa ccaaagtatt tttttgaatt    11580
ttgctaccaa attcaaaaaa cttctgaatg acgtaattac caaatacatc gttcgaaagc    11640
tcaatggcgt catcgcgaat ttcattgaat atgacctcct tttctgaggc tggtgaggtg    11700
gccaactcgc gctgaatgaa ccgtgaacca tgttgatctt tgcaaaactc taaggaatgg    11760
ccaaagatgt cttttagtga catgttcgag tttgaatttt tgtcagaact actgtttctt    11820
agttgctcta acaacggcga tcgatgatac gtttgctgct gttgctgtag actttgagaa    11880
tgaggatgag aatgagagtg agatttatgg ttgttggccg ttgactcatt agatttggaa    11940
gaagcattct tttagaggt attctttgtg ggtatagaat tttctagata aggatttgcc    12000
tgtttgttgg cgttgttgga gttatttgca ggatgattct tgttatttct tttcttgaag    12060 gtttttttcgt ccttgggcat tttgacaggt ataggatttg gagtagggta gtaaatataa    12120
ggattctcct gttgctgttg ctgttgttgg tcttcttgtt gttgttgttg ttgctgttgc    12180
tgttgttgct ggggagcaga gagtggtgga ggtggcataa acatcattgg gttgggggtag    12240 gcaaacggga acggagaatt gtttggaggg gacgaaggtg aagaaacaga agaaggtctg    12300
tttgccttct tcttttcttt accatttgag tcttcggtgt cttcatttgc tggaatctgt    12360
actgaaatca tctgggagat gaaatttgaa ggagatccga tcaagtagtt ggggaagttt    12420
tggtaatgag ggccctgatg aaactgattg ggtgggaagc cgttcatgta ggggggaaa    12480
```

```
ttgttatttg caggcccatc ttgttggtta ggaagcgcga catttgtggc cccaacagcg   12540
gctggattgt tactaggtct aaatactggt gtgttggcta cgttccagat atttctcttg   12600
gggtaatgag cattttcgga ctctaaagac gcagatgagc ctgaatttga actggagtgg   12660
taaagcgaac cactgttagt agtgttccta ttcaatttgt tgaagttttt gtcagactcg   12720
acattttgct cgaaagtatt ctgtgtgtct aagctggcgt tagagacgct ttttgatatg   12780
aattgggact gagtattgac agcgtcgggt ctatcttgag attccagttc ccttgtaccg   12840
tcaatcaaag attttccgaa cttctcaaaa aacccttccc caccagagtt gttgttgtca   12900
ttgccattgt agtaaacggg accagcaatg gaagctgaat actggcccag aagatggttg   12960
accttgttgt ttttcccgag attagccgca gtatgatgag tatgatagtt attgtacgat   13020
gcggatgaca gggaggcagt gtcggttgat ctgtactggt aataattgcc gccgttacca   13080 aaaaacttttt tcgagttcgt ggagaatggc ggagcagtac caactgatag ggcggttttc   13140
ttgaagatcg gtgaagattc actggaaccg tgaagcagca agatctctga atctacttca   13200
tttgccgtgg tgaaactcga ccttctgaag ccgccaattt gctgtgatcc agcagcaccg   13260
ccgttcacaa tgccggccgc ggcggcctga ccgccgttgt tgttactatg ggacagggcg   13320
cttaaagaag aaactatgga tgcgagttcc atatccatat ccatatccat gttcatttcc   13380
atttataccc gcaatattgc gttattcaga agaaatttaa atgcgtagtt cttgtttgtt   13440
ttcttgtttg cttgcgtact tctatgctta tagatatatc agtagcaagg aagtttcctt   13500
ttcaccgcct ttcaatgttc ctatcttttt cttatgtttc tctttagaga ccagatgacc   13560
agaaaaaaat tagctaagca gtgttatact atttacagta gatattcaaa tatgtgcagg   13620
caccacttat ttttcttttt ccttcttttc tttgttttttt tttttctcct attcatcaag   13680
cttcatacat ccaatataca ttctcaagtg tgctaatggt acatttggga aattatcttc   13740
ctctctccac aattttttaga aggaaaaaag aaatgcagtt cagggtaaca gagtgcgcaa   13800
ttaccgtaga tagcgatcgg atgtttatct ttagccctct ttttctagct caaaccccgg   13860
cacgaatttt ttaggtcttg ctgctctgcc ctcgggcact tttcttcgag aagttctggg   13920
gcggtctgat cgggaaaaaa cgttcccttt tcggacgtat cgcaggcaat gtgcaaaagc   13980
ttattatata cgagaaaaga aacgcgaagg aacgaaagaa gatgaaaaaa atgcagcgat   14040
aaaatgatat tgtggttaat ctaaatttat atatatatat atatatacat atatatatag   14100
aaatctattg ttatacacaa aaatacttat ttttttaatat agatggctgc agataaagta   14160
atagttttat atataggtat atttactgca caattcacac gatgggtgtt tctgcggtgt   14220
tgaaaagagc taggaattta ctagcaacgt tcatagtctg ctgttttatg gcagtagtgc   14280
ttgttctggc gctggcacac cattttataa atgagcacag agacactagg agttcatcga   14340
cccaaatcga agttgatgac gaaagtaaaa gaaacgtaca ccatgaccat gttctcacta   14400
gaaccaatgc atacgcgacg ccatacctcg atctggaaca tgacaagaaa aacggtatcg   14460
tctacgatca tacaagaacg gttgtccgta aaaagaacca cgaagtgggg tcctcgtcac   14520
tgcataaaaa ccttttttcac aaatttttga caaagcttat ttttaggttt atcgagaagg   14580
aaaaagttac cgaaggcgta acgcaaggaa agttcaataa tagtagcaat gaattgcca    14640 atcatgaacc ggttttttgaa aaaattcctg tacagtgcga caatccatta cagaatctaa   14700
tcttatcgga agacttgaca ttagttgcgg atcttaatta ttattttaac cagtacaata   14760
ttcaaataga ggaattttaga ttggagaccg aagatgggtt tgttatagat ttgtggcact   14820
```

```
tgataccaaa atatagaacg acagattctg acaagaagaa gaggccaccc attttgatgc    14880
tacatggcct tttgcaaagc agtggttcgt tcgcatccaa tggtagaaaa tctctggcat    14940
attttctgta tcaatccggt tacgacatat ggttagggaa taacagatgc gggtttaggc    15000
cggaatggaa cgaagcgaaa gtaccgacac tagcttccag gtgggactgg gaccttcgcg    15060
agatggttaa gtacgatctg acccttttga ttgataccgt gttagctaag acgcagtttg    15120
aaaagcttac tttgatctcg cattctcagg gcactacaca ggggtttatg ggcttggtca    15180
acgaagataa gttttttccct cccggttcgg gatctaaaga atcttttttc acttctaaga    15240
tcgcaaacta tattgccttg gcccccgcag tgtatcctgg tcccttactt aacgagaaat    15300
tgtttgttaa gcttatgaca aaggaaatcg aaaatccctg gttctttggt gaaacgagct    15360
tttttgagat aatgatgatt gtaagaaact tgtgcgttgg tgagagcttg ttctcctttg    15420
tttgttacac catcttcaat tacctgtttg attggaacga tacccttttgg gataccgcat    15480 taagagatcg ccatttcctg ttttcgccag tccatgtttc agtgaagttg atgcaatggt    15540
ggctgtcacc cgaccccaac aaggtaagtt ttaaatttgg ttcccataag atgttccccg    15600
acaatgttaa gtggttttca gacgcatcaa aggccccaaa tatctacttg tttgttccaa    15660
agcaagatag attggtggac ggagaaagac taatcaatca tttcgtcaat gtggagtcga    15720
atgtcaacta caagatctgg tacattgatg agtatgccca tattgatgtc ctatgggcac    15780
atgatgtcat agagagaatt ggtaaaccaa ttttacagaa tttgaacaac tattactcca    15840
agaagccatc cagcgccttt gaaagtgatt gttcggacac agaggtggaa acggagctgg    15900
aaatggttgc tgagaaggct tgaagaggaa gcatgatata taggttaata taaattatac    15960
ttgggaatac atagatagag ggctagtaaa ttttttagttt ttaattgttc tttttttttg    16020
aagtattgtg tcacaaattg tcgggagttg ggacatcacc gtgcataacg atacattttt    16080
ttgaaaaatt tgatattgaa aaaaaatcga tgagtttgaa ttacattaca gttgtataaa    16140
gcaaccgcat ttcattaacg tagtttgact cgcgaagata aggcgttaaa atgaagatta    16200
agaccattaa aagaagtgct gatgactatg tccctgttaa aagtacgcag gaatctcaaa    16260
tgcccaggaa tttgaaccct gaattgcatc cttttgaaag ggcacgtgaa tatactaaag    16320
ctttgaatgc caccaaattg gaaagaatgt ttgctaaacc ctttgtgggt cagttaggat    16380
acggtcatag agatggtgtt tatgctattg ccaaaaatta tggtagtctg aataaattgg    16440
ctactggttc tgcagatggt gtgattaaat actggaacat gtctactaga gaagaatttg    16500
tttcctttaa ggcgcattat ggactcgtta ctggtctttg tgtgacacag cctcgttttc    16560
atgacaagaa gccagatttg aagagccaaa atttttatgtt atcttgcagt gatgacaaaa    16620
ctgtcaagct atggtcaata aatgttgatg attactccaa taaaaactcc agtgataacg    16680
actccgttac taacgaggaa ggtttgattc gtacttttga cggtgaatct gcatttcaag    16740
gtatcgattc gcacagagaa aactccacgt ttgccacagg tggggccaag atccatcttt    16800
gggacgttaa cagattgaag ccagtttccg atctatcatg gggagcagac aacattacta    16860
gtttaaaatt caatcaaaat gaaacagata tcttggccag tactggtagt gataattcta    16920 ttgttctttta cgacttgaga accaactccc ccacacaaaa gattgttcaa acaatgagga    16980
cgaatgctat ttgctggaat ccaatggagg ccttcaactt tgtaactgcc aatgaagatc    17040
ataacgccta ctattatgat atgaggaatt tatcacgttc attgaatgta ttcaaagatc    17100
acgtcagcgc agtaatggat gttgactttt ctcctacggg ggatgagatt gttactggtt    17160
cgtacgataa gagtatcaga atatataaga cgaatcacgg acattcgaga gaaatttatc    17220
```

```
atacgaagag aatgcagcat gttttccagg ttaaatattc catggattct aaatatatta    17280
tcagtggatc tgatgatggg aatgttaggc tatggagaag taaagcttgg gagaggtcta    17340
atgtcaaaac tactcgtgaa aagaataaat tagaatatga cgaaaaatta aaagaaagat    17400
ttagacatat gccggagatc aaaagaatca gtagacatag acacgtgcca caagtcatca    17460
aaaaggctca ggaaattaag aacattgagt tgagttctat taagagaaga gaagctaatg    17520
aaaggcgtac tagaaaggat atgccataca tttccgaaag gaagaaacaa atcgttggta    17580
ccgtgcacaa atatgaagat tcaggaagag ataggaaaag aagaaaggaa gatgacaaac    17640
gtgatactca agaaaagtag ttattctgtt ttatgttgtc tgtatataca catatgtaca    17700
atatttgcat ttttttaatt tttaattcac atgtatttga taaatgttca cgccagtccc    17760
gttaaattaa aattaccatt ttattagatt atgaatttat atatgaatac attgtgtcgt    17820
aatggtagaa gaagttgaaa aaaaaaatgt caagggacag catgggtaca gtgtgttgag    17880
ccaaaaaaaa aagaaaaaa aagaaaaaa cttttgttc tctggttctt ttcttcatct    17940
tcttcatctt cattctttgg tagcgggggc cacaagaaat tcgggcgaaa gtgctcatta    18000
tattgttaca tccaaaattt tgcccacatc cagtgaggtt ttcacagaaa ggtcttctaa    18060
aagaggaata atatctaata attcgttatc atgagtatct gagaaccagg acgaaatcgg    18120
tattgcatgt tggggatgaa aaatataaga tgccggagag ttatcgagaa tgatgatatc    18180
tgataacggc cttccaatct gggataagtt tttttatatag tttccttcat agttatagca    18240
agcctctctg aataatctgt gatgaatgac tttatctgtg tctaatatat caagcaaagg    18300
atcaccgtat cgagagacac tagccgtgaa gactacaacc tcgaataatt ttccgactct    18360
ttccaaaaat tcttccacac caggtctttt aatgacatag acattgtgta cttggtcatc    18420
tatttccaca gacaaaacaa aatccgcaga tcgtaagtat ttgaaagaag agtgtaccaa    18480
ggtttcatcc aggtccagta ttaggcattt cttgcccttt gtactttcat cttgtggggg    18540
gagcagagtg ttgtaacctg gtgcatgata ctggccctgc tgcaaaagcg ttagatcaat    18600
atattcttca tcttcatcgt cttcgtcgtc ggcatcgttg gaagtttcac tggcttgaga    18660
gctgctactt accctactca aattcatatc ttggataaga tggtcagacg atacttgtac    18720
agtaggccct cgctgctgcg actgcgactg cgactgtgac tgtgactgtg actggggttg    18780
tggttgtggt tgtgactgtt gttgttgttg ctgctgttgt tttttctgcc tggaagtatc    18840
tttcacagca tctcctttt cctgtacaat gccacgactg cgacggttat cttcatcgtc    18900
gatctcttca tcttcgtcaa cctcgtattt ttcctcgtaa agatcatctt tactaattcg    18960
cttctctact tttgtcatat tattagtagt agtggcggtg acggctgcag tcggcgacga    19020
tggcttcttt ttttcattat cgttcgtgct tatcccagat ttaccggtgg atcgttcagt    19080
ggaactgaaa gtagcggctg aatttgtctt agaaggagga gagtttgtct gatgtacgcc    19140
acgggttcgg cttttcgtgt tggaatgttt aacgcttctg tttttattga gagaactgct    19200
ctgttgttgg cgataagcag aattggaatt ggattgtgtc gtctcggaag agcagcacag    19260
tattgacgat atgaaaccca tactgttttg ctacttattg ttgttaaagc ttacgaacac    19320
gaatgtaggc aaataaaaag cttggataaa cgcacaatga aagggaagt gcgattgatt    19380 atgctataag gaatgacacg aagagagcag actataggct aggcaggcga taaaggaagg    19440
agttgtactt gacgacaacg taataaagag ttcaatgaaa gagtattgtg agcagtatgg    19500
ttcaacgagc acttcttctc gacacctatt tctatacttt ttcacttaat atacactaac    19560
```

```
taatcccaga cttttttttt tttccgttct ttccagaaaa aaaagaaaca aagcaagcgt    19620
gccctgactt agggtttcct aaaaaagtta ttaggtttgt gtcacgtgat acgtccttt     19680 ctggtcacgt ggtcttagaa cactcttaag gggccaagca caagaggaca gtgctagcag    19740
tagaagtggt gtagtagtga tgaggtaatg ttaattgtgc atcgcacata tttacaggta    19800
gtatatacta tagtttgtga atacctattc ttatatatac aagaaatggt tgtcggcaga    19860
ctgtcagtaa gactaatttg cacttggaac ttcgaagcca taaccttca tgcactcttt     19920 gtacttttca atgaattcct tgcatttttc agagtcttgt ccattgaata agatgcatgt    19980
atcccgctcc tccttttctg cttacaaac gcaacatggc ttaggtttgt cctcgcactc     20040
cgcgtggttt tcttgttctt gtttcttgtc agtttcagtc attgggtata attgattgtg    20100
tagttatctg attgtgtaca ctaaaatttt gtttagttgt actagagaca agtagttagg    20160
tggttactag attctgattc gccgctatat atcgtcattt tatcttttt tgaaggagat     20220 aggtagggtt ataacattat ccgggtaatg atttgaaaaa aaattttcaa aaaatgcgat    20280
gagatgaggt tgaaaattgt aagttagaat atgcttagat agtatgagta tttacgttgg    20340
taacttgggt ttcgaattgg agctgtgtgc ctacaacagc gtcttatata tatactatgg    20400
tggtaggaac taaaaaatac tctaatttgg actttgtccc tacaatcagt gacagtgaag    20460
acgatgttcc aattctagat tcttctgatg acgaaaaagt cgaggctaag aagactacga    20520
agaagcggaa gggtaagaat aacaagaaaa aggttagtga gggggataac ctcgatgagg    20580
atgttcatga ggacttggac gcggggttta agtttgattt ggacgccgat gataccactt    20640
cgaacttcca aggctggaac tttctagcag agggcgagtc caataaggac gatgccgaag    20700 ctttttgtgaa gaaggacgtt gacttggata agattattag aagaaaaggt gggctggtga    20760
aaatggccca tattgatagt aaacaagaag aagaaaccga gaaagaaaaa gtagaaaaag    20820
aaaacgatag cgacgatgag gaattagcaa tggacgggtt cggtatggga gctcccatga    20880
acaatggaga cgaaaatcag tcagaagaag aagaagaaga ggaggaaaag gaagaggaag    20940
aggaggaaga ggaggaacaa gaagagatga cgttagaaaa aggcggcaaa gatgacgaaa    21000
tagatgaaga agacgattct gaagaggcaa aagccgattt ctatgcgcct gaaactgagg    21060
gagatgaagc taaaaagcaa atgtacgaaa atttcaacag tttgtcttta tctcgtccgg    21120
ttcttaaggg ccttgcaagt ttgggttacg tcaagccttc ccctattcaa agcgccacaa    21180
tccccattgc cttattgggt aaagacatca ttgccggtgc tgtgactggt tccggtaaga    21240
ctgctgcgtt tatgattccc ataatcgagc gtttgttgta taaccagcc aaaatcgctt     21300 ccaccagagt tattgttcta ttgcccactc gtgagttagc tatccaagtc gctgacgttg    21360
gtaaacaaat tgcacgtttc gtctccggta taaccttgg tctggccgtt ggtggtttga    21420
acttgagaca acaagaacaa atgttgaaat ctcgtccgga catcgtcatt gctaccccag    21480
gtagattcat tgatcatatc aggaactcag caagttttaa tgtggactca gtagagattc    21540
tggttatgga tgaagccgat agaatgttag aagaaggttt tcaagatgaa ctgaacgaaa    21600
ttatgggcct attaccaagc aatagacaga acctattgtt ttctgctaca atgaactcca    21660
aaattaaaag tttagttagt ctttctctaa aaaaccagt aaggattatg attgatcctc     21720
caaagaaagc tgctactaag ttgacacaag aattcgttcg tattcgtaaa agagaccatt    21780
tgaagcctgc cttgttattt aatttgatta ggaaattgga tccaacgggt caaagagga    21840 ttgtcgtttt tgtggctaga aaagaaactg ctcataggtt aaggattatc atgggtcttt    21900
taggtatgag tgtgggtgaa ttacacggtt cttaacccca agaacagcgt ttagattccg    21960
```

-continued

```
ttaataaatt caaaaatttg gaagttcctg tacttatctg tacggatttg gcctccagag     22020
gtcttgatat ccccaagatt gaggttgtta tcaactacga tatgcccaag agttatgaga     22080
tctacctgca tagagttggt cgtaccgcca gagctggtag ggaaggtcgt tccgtcacct     22140
tcgtcggtga atcatctcaa gatagaagta ttgtacgtgc tgctataaag agtgtagaag     22200
aaaataagtc cctaactcaa ggtaaagcac ttggtagaaa cgtagactgg gttcaaatcg     22260
aagaaacaaa caaacttgtt gaatccatga acgatacgat tgaagatatt ctggtggaag     22320
aaaaggagga gaaggaaata ttaagggctg aaatgcaatt aagaaagggt gaaaatatgt     22380
tgaagcataa aaaggaaatc caggcaagac caagaaggac atggttccaa agcgaatcag     22440
ataagaaaaa ttccaaagta ttaggtgctt tatcaaggaa caagaaagtc actaacagca     22500 aaagagaaa gcgtgaagaa gctaaggcag atggcaatgg tgcacgttct tatagaaaaa     22560
ccaaaaccga ccgtattgca gatcaagaaa gaacttttaa aaagcagaag agtacaaatt     22620
caaataagaa gaagggcttc aaaagccgta ggtaataatt ttcatcgtca ttatcataaa     22680
atatcaacat acttatcact gtcattatat tattaatact ttgtatttaa atatcattaa     22740
ttcatctaat aaacagggga ttagtcaaaa attccttttt ttttgttgaa tctgtagaag     22800
tgagtattaa taaactgcaa gctatatgct atattaaaag gattttcaa gtacaaacga     22860 actgaatgga gactcaagct acttgcggga aagaattaca aaattacatt ccattctagt     22920
aaaaaaaagt tataaataaa aaaaaatcgt ctgacgacaa atttgtatct taatcaaaat     22980
aaaaattttg ggttactttc tttaacgttt ccaagttata aaattcttca tcttcgtcct     23040
cgtcgcttgg ttcaggtgga ggcactatga tgtcctgacg aacgttcaaa tttatcatct     23100
gaacattttt cctcaaatca aataaagtgt ctatttgttc tttcgtgtct tctgatatat     23160
cttcatgctg gaatggagat atcaatttca atccgtctag ccatatatat cttccctctt     23220
ctgtgtctaa ataaaatttc aaaactgtcc tgtcgttacg atcttttaat tcaactccag     23280
tgtacacatt ggcttcatct aatttgatgt aaacattact gctcgtccga cgactcggtg     23340
tagtaagttc tatgcttttg aaagaggtta tatgtttcaa acaacaact tttgttctgc      23400 cattagctaa tgcctcagaa cctggacttg ttaaaatttt attgtcgaat agataaggta     23460
aatcgtttgt ttgtgtttcg aattctctgg ctaataaatt tgcgtggtta tctgaaacta     23520
tgaggaagta gactttaggc gtgccagctt caggattcag tgggttctct gcgtaaaccc     23580
acgttccctt ttgcaattga agaagtcttt gatgacgaac gtaatcacga acctggcctg     23640
atagcatggt atcgaagcta gcgatactag atgaccaggt tcgatactgt tctttttga      23700 ttgagtctaa ttgtaatgtt cttgcaaatt tatatctcat agagtcaagt gcaacaactt     23760
gggtcttgag aagggatttc gtctgtattg ctgcttccaa atcactggat gacaaacaaa     23820
catattttaa agtgataata gctaaattta acagtgaaac caaatcactt tgcgattttg     23880
ctaatgattc tatccaaaat ctcaaaaaca actcgagtgt tttgtaaaaa catgtttgtc     23940
gattgagaac agcggtagca atttgtaatt ttaaatcacg ctctgagtct gagtattggt     24000
tctctttttt cccacttaga ttgaaaagtc ttctaaattg gtctgaaagt ttaaatattg     24060
cttcataaag agggaaatcg ttctcgccaa acaacaattg ttcagtgtaa agtctcttga     24120
aagacccatt aggactgttt aagaatgtga atgtatcata cgcatttaat aaatttatac     24180
tgggaagatc gcccatttcc atttctaacc cttttggaa tacggagtta tctttgatgg      24240
ctgtaagaag atcagcttta agcgaacagg aataatcatc aatactaacc gaagatagaa     24300
```

```
aatttattag cctctgcttt aacggtacaa attcttcaag gattagtggt tgcaagtctt   24360
ctatgtaaag taattcagac atggaagctg gaaagttata ctgaaatagc aaaatgagga   24420
ttctgggtac aaattctacg gcgtgtgata gtgatgtctc acataatgta agtgagcatt   24480
ttaaaaatag ggttatgcat agtatagtgt ccgtaaacaa cggtatatga ataggtcttt   24540
gggacaaaag ttgtaaaagt attccaatga gctgagagtt ctctctggag atgtggcaga   24600
tgctcacaat aacttcattc ttattagaat cttggcattt aagggctaca ttaaaaatcc   24660
taatgagatt tgctaccaac gtttctgacc ttagcttttg gcaattatca cacaatatag   24720
cccaaaatcg ggaatctgga attacggttt tacataggta ttttttcatca caaaggagga   24780 tatagtttgc caataacttt tcgtattcat cacttgtctt gttcaaattt ttattactga   24840
tcagcgtatg atagcaagct tttgattgtg cactcgtaag tgacttgact ggctttccta   24900
atttaggatt cagtagcact tttatgtttt ccaagcttcc atctggcatc tgcctgttat   24960
gcttcattgc ttatgccgtt atttgaggtt actttaatct attttcctac tgatgacaca   25020
attgagtcaa tccaacgtgg aacgggttgc ccttgtatac atttcagttt acttcttttc   25080
atgtatttcc ttaatagttt attttttcac tttctgccta tccgtttcaa ttccgaagaa   25140
ccgtcaacat ccaataaaga tcatctacaa caataagtgc ccctcataat tttctcaatg   25200
agatgaaaga actttgagag agtcaatata ataccctgtag ccttttttctg aaaatgactg   25260 atagtgagaa tgaatccacc gaaacggatt cgttaatgac gtttgacgat tatataagca   25320
aagagctacc tgaacattta cagagactaa tcatggagaa tttgaagggt tctactacta   25380
atgacttaaa gcaaacttca aacaactcag agtttaatgt cagtaaaaac gggagcttca   25440
aaggtctcga tgatgcaatt caagctttgc aaatgcaaag cgtgttgcat ccttcttcgt   25500
taggatcgtt agcaacgtcc tccaaatttt ctggatggtc gtttgctcaa gggttttttg   25560
taggacagct aagcatagtg ttgttgttca tcttttttcct aaagttcttt atattcagtg   25620
atgagccatc taaaagtaag aatccgaaac ctgcagcctc ccgtcacaga tcaaaattta   25680
aagaatatcc ctttatatct cgcgaattcc tgacttctct tgttaggaag ggtgctaaac   25740
aacactacga gctcaatgaa gaggcagaaa atgaacatct tcaagaacta gctcttatttt  25800 tagagaaaac ctattataat gtcgacgtgc accctgcaga gtcattggac tggttcaacg   25860
ttttagttgc ccaaataata cagcaattcc gcagtgaggc ttggcacagg acaatatcc   25920 ttcattcctt gaatgatttt attggaagaa atcacccga tctgcctgaa tatttggata   25980
ccataaaaat aactgaactg gatacaggtg atgatttccc catttctcg aattgcagaa   26040 tacaatattc gccaaattca ggaaataaaa agctagaggc taaaattgat atagatttaa   26100
atgaccactt aactttagga gtagaaacaa aactattact taactatcca aagcctggta   26160
ttgccgcact ccccataaat ctagtagtgt caattgtgag gtttcaggcg tgtttgaccg   26220
tatctttaac taatgcagag gagtttgctt ctacttcgaa cggtagcagt agtgaaaacg   26280
gtatggaggg caattcagga tactttttga tgtttttcttt ttctcctgaa tatagaatgg   26340
aatttgaaat caagtcgcta attggctcac ggtctaaact tgaaaatatt cccaagatcg   26400
gcagtgtcat tgaataccaa ataaaaaaat ggttcgttga acgatgcgtt gaaccaagat   26460
tccaatttgt caggttacca agtatgtggc cacgtagtaa aaatacgaga gaagaaaagc   26520
ctacagagtt ataaatattt atgtacaaat ttttgttct atcttttttcc tatcttctct   26580 gcctcatttt tggtgttcca gttttggtta gtgcaagtgg ctattctcca agtgacaatc   26640
accaaataaa ttcattgaat acatattaag atcgaattttc aggtgatacg acttctccaa   26700
```

```
aaatgattgt tcttcttcag aaattcctag tttgtccctt ggtagccaaa tttcatccga    26760
atttctacaa atggagaaaa tatcatggaa agtataactt tcttgacaga attggtcctt    26820
cctttcctct gttagattcg acaagtattc caaagttggt atgcgttgag gcttcgattt    26880
tatttgtttg gagattttgg agtgcgtgat tactgttaga gcaaagacaa caagcattat    26940
agttgacaat gtgtattgat caaaaagagt gaacagcccg agtaaacaaa attccatgaa    27000
ataaatgccc gcgtacaatt gcataagggc ctgtatgtac aatttaccga acgtttcaga    27060
atagttctct ttgttatatt ggtatttgaa caagtaactg aaagaaaaga aaaccatcga    27120
aaatgagatg caacataata ataatataat aggagcaaca acactgtata tgataccaat    27180
acagcccaac actgagaata taggataaat agatcctagt tggaaaaata aagatgtctt    27240
taacctctta aattgagcat gtggagtact cctttccat ttatagtaga acaattcaaa    27300
aagtagctct tttattctta acaaattacc gcctgcataa gccattcccc taatcaaaac    27360
aaaagaacag aaaagtttg cgcatttagg caagtcgttg gccaggagag cagggatact    27420
gacaggattg ttaagaagcc tctcaataat tatagaaaat ccagaagata ttgtaacaac    27480
tacgaaaaga tgaatgaaga caaagacgaa ataccaattc tggacatcag cttctatttg    27540
cgctccagtt ttcaaccctc gaaggtaact cagccaacgg aaaaagtagg gtacgatttc    27600
tattattatt attaaggtta ctattggaat caaattcttt gccacttctc ttataaatgg    27660
agattggaaa tgaattattt ttgtaaacgt tattagtgag gaaatatttg gtatttgtga    27720
tattaaccca aggaacgcga caggcaaaat ccagcctata atcacaaaaa ttcgcaatat    27780
atttgccgag aaatatttgg cacttttcca aagggggtgat gaatcgagga tatttctcca    27840
aataatgtca ttaacattgg ggcctattat tactttaaaa ttttgggtgg gtagtctata    27900
cgaaagcaac tcacctataa cgtttgacaa taatgtggac ttgaaggtaa tgaacatctt    27960
atccatataa atgtctgtgc ccgacgataa atcgtcgggc agtgcctgct tggtttctga    28020
agttgctttc aaggaattta cttggaattt aatgagtttt ccttgcgta ttattttatc    28080 aaggattctg tatttccttt ctaatattgt ttctgtattt acatacagtt tagggtaata    28140
taacggaaag atgcttgact ttttccagcg cagacgaatt tttgtgcaat agtatgaaat    28200
tctaaattga gttaaaaata ccaattttt gtactgaaat aatagatggt ttttcaactt    28260 tgaaagaaa aatcttttgt gatttgctat caaatgcctg tgtattgaaa ctcttctaaa    28320
atatttctct aaaataatct caaagataat ttgttctttt gattttgta atttatttaa    28380 ctttatttct aatttgtgga cttctcttcaa atttttggaa atgaaatgcg tcacgccaaa    28440
gcaatcactg tgtagcggct gaaaaaagt ttctaaagaa atactttggg taaccaattt    28500
acttgagaat ccttccaaat atagaatgtt ttggtattta cttttcgtca aaacggaata    28560
tcctagtcga ttaacgaacc tcagttccga agaaagaatg aagtgaaacc agagtacaac    28620
aaagatactc aaaacaagt gacagattaa agtattcgat gaattaggtg atagatttga    28680
catggtccac ttgtcaagtt tacttgtcgt cctgaaactt tgctcataac gttcaccttc    28740
attttctttc aaaatatccc tggaaaaata atggattgga attagtattg gaatgttgat    28800
aattgataac actgcaaaaa agaatatcaa agtttgaga aaccgtaaaa atagataatt    28860
gtctaggcca taccttctcgt ttcgttcgaa ttttccata ggatctaaca ttcttccggg    28920
aagttgcttg agaaatgcaa ataatgacca ataatttttt attttttct tagcaaaaca    28980 aactttagaa cctggatgga ttttcagaac gacattggcc tgatatatag tcttgaatct    29040
```

```
tgatcttaaa ataataaaga gtgacagctg aaataaaaag tacaaaaaag aaaacaatat   29100
accagatatg aacccttta gtgagattcc agcatgtctt tgcgcagatc caaatctttc    29160
tttgtcttga aatttattca gtaaattaaa agtcagttct ttagtagcat tcatcttctt   29220
ggtaagtctt tttcttgttt ttgaaaaaga gttcctgaag tttgtctact gtgaatatac   29280
tttgcacatt tgtttaattt ttaaacacgc tataatttgt gtcataaaga attttttgta   29340
gaatagcttt ttttttaata ggaaaaaaaa ataaaaaaag gtggaaaaga caatcttttc   29400
cagaaacttg aaactatact ggagatgaag ggttgtcgtt ggttgcgtta cgagacaggc   29460
ttgacaattt cacaagagta atgtttcatt acctgctgtt ttattatctt tatatttagt   29520
aagaccagca gaaacgctac acgtgatgat aatggaacta agcattctgt tagatggtaa   29580
gaattttttt taccttccat taccactaac gccttttta gtgtcttttt gatatttact   29640
gacgtatttt tccgcaccgt aatttgaaga aaagaaaag tgacaaaaga tggcattgtt   29700
tacatacaga gtcgtagtat cacaagagta gtccaacagg atgagcgacc ttaaccaatc   29760 caaaagatg aacgtcagcg agtttgctga cgcccaaagg agccactata cagtataccc    29820
cagtttgcct caaagtaaca aaaatgataa acacattccc tttgtcaaac ttctatcagg   29880
caaagaatcg gaagtgaacg tggaaaaaag atgggaattg tatcatcagt tacattccca   29940
ctttcatgat caagtagatc atattatcga taatattgaa gcagacttga aagcagagat   30000 ttcagaccctt ttatatagtg aaactactca gaaaaggcga tgctttaaca ctattttcct   30060
attaggttca gatagtacga caaaaattga acttaaagac gaatcttctc gctacaacgt   30120
tttgattgaa ttgactccga aagaatctcc gaatgtaaga atgatgcttc gtaggtctat   30180
gtacaaactt tacagcgcag ctgatgcaga agaacatcca actatcaagt atgaagacat   30240
taacgatgaa gatggcgatt ttaccgagca aaacaatgat gtatcatacg atctgtcact   30300
tgtggaaaac ttcaaaaggc ttttggaaa agacttagca atggtattta attttaaaga   30360
tgtagattct attaacttca acacattgga taacttcata attctattga aaagtgcctt   30420
caagtatgac catgttaaaa taagtttaat ctttaatatt aatacaaact tgtcaaatat   30480
tgagaaaaat ttgagacaat caaccatacg acttctgaag agaaattatc ataaactaga   30540
cgtgtcgagt aataaaggat ttaagtacgg aaaccaaatc tttcaaagct ttttggatac   30600
ggttgatggc aaactaaatc tttcagatcg ttttgtggaa ttcattctca gcaagatggc   30660
aaataatact aatcacaact tacaattatt gacgaagatg ctggattatt cgttgatgtc   30720 gtacttttc cagaatgcct tttcagtatt cattgaccct gtaaatgttg attttttgaa    30780
cgacgactac ttaaaaatac tgagcagatg tcctacattc atgttctttg tcgaaggtct   30840
tataaagcag catgctcctg ctgacgaaat tctttcatta ttgacaaaca aaacagagg    30900 cctagaagag tttttttgttg agttttggt aagagagaac ccgattaacg ggcatgctaa    30960
gtttgttgct cgattcctcg aagaagaatt gaatataacc aatttaatc tgatagaatt    31020 atatcataat ttgcttattg gcaaactaga ctcctatcta gatcgttggt cagcatgtaa   31080
agagtataag gatcggcttc attttgaacc cattgataca atttttcaag agctatttac   31140
tttggacaac agaagtggat tacttaccca gtcgattttc ccttcttaca agtcaaatat   31200
cgaagataac ttactaagtt gggagcaggt gctgccttcg cttgataaag aaaattatga   31260
tactctttct ggagatttgg ataaaataat ggctccggta ctgggtcagc tattcaagct   31320
ttatcgtgag gcgaatatga ctatcaacat ttacgatttc tacattgcgt tcagagaaac   31380
attaccaaaa gaggaaatat taaatttcat aagaaaagat ccctccaaca ccaaactctt   31440
```

-continued

```
agaactagca gaaacaccgg acgcatttga caaagtagca ctaattttat tcatgcaagc    31500
aatcttcgcc tttgaaaaca tgggtctcat taagtttcaa agcaccaaga gttacgatct    31560
ggtagaaaaa tgtgtctgga gaggaattta gataaagaat gcacggataa ataagtaaat    31620
aaataaccat acatatatag aaccatagaa ccacgttttt gtaatgaaca gtctacctgt    31680
atctcatcat ttttctgtgt taactattat tattattatt atcgaatgga gggtaatatt    31740
atgtataggt aaaataaata gatagtgcca tgatgcgcga agattggcaa tgggaaactc    31800
aagaaggcag caacaaaaaa ataaaggtgg cctattaatc acaatctatt gcctatatgt    31860
gctaggttat gggcaaattc ggcacgacaa ataaatcaac ggagaatctt ctgcgtgata    31920
aattcgtacc cgagacatct ccaactaata ttcccactga tgtactcatc aagcaagggc    31980
aaataacgga ttccaccgaa tcactaattc atggaggcgc agaaaggtat attgttaacg    32040
ctttaaagcc tatagaatta aataaaactg aaggcttttt cgaagacccg ccgttccatc    32100
ttccttctcc accggttgat tcgacaaatc tggagtatga agacgttacc gatcttccta    32160
agaatggttt acgatatgat ttgaatgata tatccgttga ggtaatcgaa gatttatacc    32220
gccagattga agcttttttg gttcatttca aactatccag aagttttta caaatttca    32280 aaaactatgt caatattctt attcaagaag gcatcaatcc tttacgcgat gagtacttca    32340
caatattgga agatgaactg aaaggttttt tcactttcaa ttctgttata aagagattt    32400 tagaaatatt tttaatccac cctcgcaaca aattcattgc attgtccctt gcagaatata    32460
cctacgctaa gaacaaaatc agaagacatt ttaatcactg gaagactgta tgtgaattga    32520
atgaagaggc aaacaggttt gcaaatcaag caaagctgag ggtacaggaa gccgtcttct    32580
atatttggag tgataaaaca ttaaaatact cacagatggc caacgatgaa gctgaaagtt    32640
ttaggaatac ttggctacta tttcgctcgt tccaacaatg gataactta acacaaactc    32700 ttaaggagca gtcaaggtta gcagatcagg ccttttgaa taagatgttt aggaaaattt    32760
taaaggcaca agagcattgg aaacacttag aaactgttaa cactgacaac attaagaaga    32820
tatttttacg aacaacattt catatatgga agctaagaca taaagaaata aactaccacg    32880
ggttggaaag aaggattttc gaaagaataa aacagaaagt tataaactat gaatacaata    32940
agagcattgc agaaaaagtg aggtcgtttt ctctacaaag aaaatatctg aataaatggg    33000
aaaagaaaaa cattgaaaac gaagataaac ttgggggcact ttatgaactg gagaataaat    33060
tcatcaaaca aaagtttttt cgcaaattaa accggtcatt tcaacatagt caacaagagg    33120
caattgcaaa gagtaaacta atcagacac ttttgaggtg cgttttgag aagatgtggc    33180 tgaaaagatt cgaagaccat ctgcatttgt attcaattgt aagtctaaaa gaggctaacc    33240
tcgtgaagcg tattttcat tcatggaaaa aacttctata tattgacctc aaagcaagcg    33300
attattcgag gactaatttg ctcaagtcat cattgcgaag ttggaaactt gaagtaaagt    33360 taaaatatt tgagcagaaa tgtaaaaaga gtattcaagc aagcgcgtat cgtacatgga    33420
ggaaaagaat acagtatggg aaaatatcga gcgaacatgt taaaacggca ttttgtgcaa    33480
aatatcttgg tgtgtggaaa aggaggatgc tacaaatgaa ttctatgaat gacgaagcat    33540
ccaaatttta cgaagagggt ctcgtaaatg agtgtctagc tatatggaaa gaacgcctga    33600
ttaaaactaa ggaattggag gatagataca atttcttatg taagacacat gcaattttga    33660
ctgtaaaacg gacgctaatg catattgata atgttcattt gctatatacg aaactggcgc    33720
cctctatgga tagagtaaag ctttctaagg cctttttaaa gtggcggaaa gccacaaggt    33780
```

-continued

```
tcaaagtcag gcataagtta aacgatattt tacacgtttg tgaaaagagt aaagagcgcg   33840
aacttcaaag ccaactgttc aacgcttggc gaaatagatt ttgcttctac acagaagaat   33900
gtaacattca ggctatttca aagagaaact accagcttga aaaatggtg ctgaagaaat    33960 ttagagaaag acttttagag atagtaaaat cagaagaatt agcagacgaa gttcgcgaag   34020
aatttgtgtt agtcaagacg ttttatattt ggaaaactca tctagacgaa atattttata   34080
tgagtacatt attggaacaa tcggaagcta ataacaatt cataattaca tccaaattct    34140
tgaaaatgtg gagtcttcga ttcctaaaaa ttaagcgtaa tgatgagaca gtcgaggtgt   34200
ttcgtcatcg gtgggacagg gccactgtaa ggggattgtt attattatgg aaaaatcgtt   34260
cagacagttc tccaaagaga aggaaggact tcaatcttaa acatgaacta aaaactccca   34320
taagatcaga ctctcaaaac gcctcaacca taccaggctc agaaagaata aagcagcaca   34380
gaatggaagc gatgaagtcg cattatagca gggcaagaag agccatacca agtccggtga   34440
aatcttccag tgttcttgat tctacagcta aaaaacagat caaccttgaa agtacgacag   34500
gcttaaacgg atctccgacg cgaggaaaac ctctaaggta ttctcctagg cgtaccacta   34560
gaaacatgcc atccaaagtt gaccatattg attttggcag aatacccgct gtaccttta    34620 gcctaagcgc caattctcct aaaatcgatc aagatatgga ttatataaga gagcatgata   34680
aatccccgtt aagtcgtaaa cgtcaataga tatatatatt atgtacgtat gtatgtgtgc   34740
atatgtagtc gtaaccttc ttgcttctga gatgcataca attactaata atattctcca    34800
ggtctatgaa aacatcacaa catactatac ttttcgtgtt cgcgttgtaa gctataatgg   34860
aaaatggacg ccataacgca ttacttaaca aactacagtt tgtcaataga gttgtccagt   34920
agagttaaaa ggtcaattca accggtcttc aataagacat gtcactgaat gacttcctaa   34980
gttccgtgct acctgtcagt gaacaatttg aatacttatc gttgcaatct attccgttag   35040
aaacccatgc tgtcgtaacc ccaaataagg acgacaaaag ggtcccaaaa agcacgatca   35100
agactcaaca cttctttagt ctatttcacc aaggaaaagt ttttttttca ttagaagtgt   35160
atgtgtatgt cacgctttgg gatgaagcag atgccgaacg gttaatattt gtatcaaagg   35220
cagacactaa tggttattgt aatacgaggg taagcgttag agatattaca aaaataatat   35280
tagaatttat attatcaatc gacccgaatt actatcttca aaaagtaaaa ccggcaataa   35340
gatcatataa gaagatatcc cccgagctga ttagcgcagc cagtacgcca gcaagaactt   35400
taaggatttt ggctagaagg cttaaacagt caggcagcac cgttttgaaa gaaatagaat   35460
ctccacgttt tcaacaagat ctttatctct cattcacctg tcctcgtgag attttgacca   35520
aaatttgttt atttactaga cctgcatccc agtacctctt cccagattct tcaaaaaaca   35580
gcaaaaagca tatactaaat ggcgaggaac taatgaaatg gtgggctttt attttggata   35640
gattactaat tgaatgcttt caaaatgata cacaagcaaa attaaggata ccgggcgaag   35700
atcctgctcg agtaagatca tacctaagag ggatgaaata tccactatgg caagtgggtg   35760
atatatttac ctctaaagaa aattctcttg cggtatataa tattccatta ttcccagacg   35820
atcctaaggc tagatttata caccaattgg cagaggaaga tcgcctcctc aaagtaagct   35880
tatcatcctt ctggattgaa ctacaagagc gtcaagagtt caaattaagt gtcacatcat   35940
ctgtaatggg tatttcggga tactctcttg ccactccatc tttatttcca tctagtgccg   36000
atgttattgt accgaagtca aggaagcagt ttagggcaat caagaagtac attactggag   36060
aggaatacga tacagaggaa ggcgcaatag aagctttcac caatattcgt gattttctat   36120
tgctcagaat ggcaacaaat cttcaatctt taacagggaa gagggagcat cgggagagaa   36180
```

```
atcagccggt tcctgcaagc aacatcaaca cgttggcgat aacaatgcta aaaccgcgta    36240
aaaaagctaa agccttgcct aaaacttgat acatattgat atttattatt tagtacacgt    36300
atgtagcatc gatcttagaa aatgcatgtt tgtatttatt gttagtacct tgatcgccac    36360 cttctaggt aatgataggt cctcaacttt tactacgcgg tgcacgcctg taaggtcggg     36420
caaaacaaag tgtgggaaca ataaataaga gggtaggat aaatattacc tttactctac    36480
tgctcaggtt ggccacaatt tgctaaagag tttatcatta agtagctacc agcgaatcta    36540
aatacgacgg ataaagaatg gctagtttag aagatcttat tcctactgtc aacaagctgc    36600
aggatgttat gtacgactcc gggatcgata cactcgattt gcccatttta gctgttgttg    36660
ggtcacaatc ctccgggaaa tcctcgatat tggaaacgtt agttggaaga gattttttac    36720
ctaggggtac tggtattgtc acaagaagac cgttagttct tcaacttaat aacatatctc    36780
caaattctcc tctaatagag gaagatgata actcagttaa tccacatgat gaagttacaa    36840
aaatatcagg attcgaagct ggtacgaagc ccttggagta taggggcaag gaaagaaatc    36900
atgcagatga gtgggggaa ttcctgcata taccaggaaa acggttttat gatttcgacg     36960
atatcaaaag agaaatcgaa aacgaaacag cgaggatagc cggtaaggat aagggcatca    37020
gtaagattcc gattaatttg aaagtgtttt cccctcatgt tttgaatcta acgctagtag    37080
atttgcctgg gattacaaag gttcctattg gggaacaacc acctgatatt gaaaagcaaa    37140
tcaagaattt gatcctagac tatatagcca ctccaaattg tttaatcttg gccgtctctc    37200
cagctaacgt tgatcttgtt aattctgaat ccttaaagtt ggccagagag gtagaccctc    37260
agggcaaaag gactattggt gtcattacca aattagattt gatggattct gggactaatg    37320
ctctagatat cttgtctgga aaaatgtatc ctctgaaatt ggggtttgtt ggtgtagtga    37380
atcgctcgca acaggatatt caattgaaca aaaccgttga agaatcattg acaaagaag    37440 aggactattt caggaaacat ccagtctaca gaactatttc aacaaagtgt ggtacgcgtt    37500
atttagctaa attgctaaac cagacattat taagccacat tagagacaag cttccggata    37560
ttaaaaccaa gttaaatacc ctgatctctc aaaccgaaca agagctcgct agatacggtg    37620
gcgtaggagc tactactaat gaaagcagag ctagccttgt tcttcaacta atgaataagt    37680
tttctacaaa cttcatttca tctatagatg gtacatcctc cgacattaat acgaaggaac    37740
tctgtggtgg tgcccgtatt tattacattt acaataatgt ttttgggaat tctttgaagt    37800
cgattgatcc aacttctaat ttatccgttc ttgatgttag aacagcgatt agaaattcta    37860
ctggtccccg tcctacatta tttgtacctg agttggcttt tgacctattg gttaaacctc    37920
aaattaaact tttactagaa ccatctcaac gttgcgtcga gttagtttac gaggagctga    37980
tgaaaatatg ccataaatgt ggctccgctg agctagctag atatcctaaa ttgaagagta    38040
tgttaataga agttataagc gaactactta gagaaaggtt acaacctact cgctcttacg    38100
ttgaaagctt gattgacata catcgagcct acatcaatac taatcatcct aattttttaa    38160
gtgcaacaga agcaatggat gacatcatga aaacgcgtag aaaacggaat caagagttat    38220 tgaaagtaa gttgtctcaa caggagaatg gacaaaccaa cggtattaat ggtacttcat    38280
ctatctcttc gaatatagat caagattctg ctaaaaacag tgactacgat gatgatggta    38340
tcgacgcaga atcgaagcaa acgaaggaca aattttttaaa ttatttcttt ggcaaggata    38400
aaaagggtca acctgtgttc gatgcatcag acaagaaaag atccattgcc ggtgatgaa    38460 atattgaaga tttagaaat ttacaaatat cagatttttc actgggcgat atagatgacc     38520
```

```
ttgaaaacgc tgaacctcca ctgaccgaga gagaagaatt ggagtgcgaa ttaattaaac   38580
gtctgattgt ttcatacttt gatattataa gagaaatgat tgaagatcaa gtaccaaagg   38640
cagttatgtg tttactcgtc aattattgta aggattctgt tcaaaacaga ttggtaacca   38700
aactctacaa agaaacactg tttgaagaac ttttagttga ggatcaaact ttagctcaag   38760
atagagaact atgtgtgaaa tcactcggag tttataaaaa ggctgcaacc cttattagta   38820
atattctgta attgcataat tcatctcatt tttgatctta cttcaacatt gcgggcgtga   38880
ttataggtca gtgtttattc ctttactcag ttgatgattt caaatgtgct ctcctctcca   38940 ttcttttttct tgttaataaa aatccataac taaataaata acaaatatta gcaatcgcaa   39000
aagtattaac taagctagag aaccttcact agagaagctc tacctaaagg tatagaacag   39060
gaaaaagtgt ttttattttg gcggacttcg tggaagattg ccttccatca ataataagcg   39120
tagtccatag gtacgatcat ttcctttta accgttaagc aagcgacaag atgtattttg    39180
tttaccagcg aatgctctta tttatcttct gcgccttttcc aataatctaa ttatcaatgc   39240
tacgaatgat tatagttta actagatgaa cgaaatttct aggttattaa agagtacgtt    39300
atgcatcaaa agaatatcag tcataataag cagatagacc ttctacatgg tttgtagaca   39360
accaaactgg tgtatgctaa tatcaacgag taaacgctta ctttctaaa gttgaatatt    39420 tgaagtacac acccgcgtaa agagttttta ccccgaaaac aaatttttat gcttgaaaaa   39480
tagctaataa aatgttttta ttgttcggat aacaaataca atagtgttat taaaaaataa   39540
aacttattta aaaatagtaa tttaaattat tattttattt taataaactt tttaataata   39600
tttattacac gtgatttaat atatcctgtt ttttttcat cattctcttt ctttcttatg     39660
ttaacctcgt actacaagtt ttctccttat aaaaagctga ctaaaattag agattgataa   39720
tcataaataa atttagtagc catttccatt tttacatttt gatttaatcg acactcaaag   39780
ttcttatttg aaagctagtt tagaacttat ttgtttgctc cttgatgaat ataatgagaa   39840
gaaattccac tcagattaaa tatgaagatt gttaacggca agacgctaaa agaaaaggaa   39900
aggaagtaga tgatggcaaa taaggtcact ttccttgttag ttacatatac tttcacgaaa   39960
acttgaaaat aaccacaaaa cttaaaacga acgttatttt gttcaattgc ttaatttgtg   40020
aagatattat ctactactta aatgatatat taacacttat gaggtactga cactgcgacc   40080
gcccttttga tctgatccca cccttcgtat atctctgggg gtttgtatag cgttcacaga   40140
atatgaacct tcaaaagtgg gttgagaaag tggtgataaa tgcgctgttg ccgagtaaga   40200 aggggttgtgg attatcggag agtgttgaat cagtggtgtt gttgctcgat catttctccc   40260
tctttgattt ttgtctttta cttttccacc cctggtaatt attatgcaaa acaataaaga   40320
aatggctatg gtaacaccta ttataacccc aaatccaacc gctatccctg gcaagcgcag   40380
atggtatttc tcgctgtttta gccaagataa ggatatgggt ttgtcgatca gaaatatgca   40440
tgaacttttc aaattagtag tgcatcctgt tttaagaact ctaacttcct tggtccagtc    40500
gccctgtatg ctaacaaaaa cgttgtccag atgatctttt ctgcagttta gttttgtacc   40560
tagtttagtg ctaatggagc cattgcagtc tagtaggttt tgcgttacat tagcaggaat   40620
caaatggagt tcgaggaatt ttcttaagtt tgtcgagttc gccgtgatgc cacttaatgg   40680
aatagaagaa gccgttggaa ctaaaagcga gtactcttcg ttattccaaa tgattgaaga   40740
aaggtcataa aacaagttaa aaaagtcaaa tatttctttt gttccagtag tttctatcag   40800 ctctttttagg gatatctcca aatcgactgg aaaatccaat tggtctatag gatggataac   40860
tccctggttg aaaaatatat cggaactctc ctcaataata atactttcct ttatagtact   40920
```

```
cactgagatt ttcgtaaggt tttggcttcc cacaattttt tgtacgccaa tagatacaga    40980
atttccgtat aaattcttga cagtagtcga aatactataa ttgttggaat aaataaggtc    41040
ttcgaagatt aggttcctca taagtaaatt tagggcggtt ttgtttgacc tcaaatagtc    41100
tatagtcaaa tcattattgt cccatgaatt catacatgga agaagtatcg tgtacccctt    41160
atgatttgat ggtagatcca aaaggttaag ttccttcaag agcattaggg aaatagaaca    41220
gtggttttct ggtgctaatg acaacactaa gtcgcccggt aattgaagat catcgtcaat    41280
agaataaatg gacgtattac caatctcata aggttttgtg tttaaaatct tgaagcgacc    41340
attgatgtaa taacctttat tagaccttgt gattttgaac ttttggcagt gtccacctag    41400
tcttttagct aagagcaaa aggcggagtc ataaatttgg gtaggtgcgt attgaatcgg    41460
gcgcaatgag gaaagtcct gttcaaggtc aattttacct tctacaaaat ggtacagaag    41520
tgatggtttt gtgtacccac gatcctcatt aaaagaggct tgtggtacaa atatggtgat    41580
tttccttccg ttttgaatga attttcaag gtctctgaag tataactcct ttacgaattc    41640
tgagcagttc aaaccgtgca agtacttttc agcatcaaac tgtatatgcg ttcgtaaaaa    41700
gtctaagtca gaaaatccat gcacgacgcc tatttcaaaa attctgtttg atatgggtga    41760
gtaatctgaa ttatttacac ttactgatgt accttctgaa ttactcttca taaaaagttt    41820
tcgattgttt ttattttcta aaattagttc cttgggtaaa ataccaccat acacgtcatc    41880
aataatgagt tcttgaagaa gggaagttct atctgcggcc catttggcct gagaaattgt    41940
attagattta cccaatttat tatatttgtc aagtagatag tttatttcga ttgtattgaa    42000
gaattttcga aaattaacat ctaagggcac taaaactgtg gatgagtttg tatatgcatt    42060
atagtttgaa aaactgctga taaaatcact aaatatcttt aaatcttggg tttcttcatc    42120
tagttgtacc agcaactcat ttatttgagg ttgaattagt aaaagattgt taataccttg    42180
taatgaagca ttctggaaac taggcagcaa atcgggttcg acaacagcaa tttcattgac    42240
aaagcaatgg cgctcatgct ttctcagcaa taaaggtgct tttgcagctc ttttctccag    42300
gtaggtaccg ttttcaaggt ctctcacttg caatacccta tcatgaataa ggaaatcttc    42360
aatatggaaa tgctcctcaa attggtctgt ggtttggtcc cccttaataa atgctgaatt    42420
aatcggagca aaaagtgtaa agttctgtag ctcatttaag tactgtacgt gaccagtttt    42480
ctgaataatc cttaaaaaag ttgagaattc aacattttct gagaggatat ctattactgt    42540
gctaaatgga aaatcgtccc ctgggttttg tagaagtgct tgtgtaagcc ctaatatcgg    42600
cagtagccaa aaaatgtatt taattgtttg gattgccatg ttcatcaaag ggctccgttt    42660
gattcagtta atacatgctg tcactcacag cagcttagat aagaagccgt tttgtcttat    42720
tttctaggcc cttaatatac gcctaatggg gaagtccgac cgaacaaaat tctcctaccg    42780
ggttttcacg gtaatgttct tccataaaaa aagacaatat agtaagctgt taatattgat    42840
ttggtgaact tgaatctgat atttgtttct attgcttacg tataatactt ttgcggtaat    42900
tcattcaaat ttcatacaat gctaatattt atacaattct actcgacacg gcaaaaatga    42960
ttggctaacg ataatcgtgg ctctttatat acttaatata taggatctag ctatttagaa    43020
cactctttag atctagatga tagagagcgt agccccttg taactacagg acaataatgc    43080
ttttcaagaa gagcattatc ccataaggtt gctgcctctg ggttactcct tgaaggatta    43140
tcggcttcca ttatgaaatg accgttgcct attctatcct cggaagagta aaggcctgaa    43200
atttctggat atctattcat taatttatca ataaatttaa gaatggcaat acttgttttt    43260
```

-continued

```
tctgggtat ggctgatgca catgtacaat cttttggtaa acgccgtagc ccttcttta    43320 gtccctgatt tagagcggaa aaatacatgg tccagagcct ttagcagaag ttctgctttg    43380
gtagaaacgt taactgatgg ttttattatt tcgttattga gtgggtcagc caaccttagc    43440
gatctataag ataattcgat gtctgcatca agacagatat aaggtaatag cgcgtaaagc    43500
ccatcgacga atttggacaa atccacatta actttcatat attgtgtatt tgaaataagt    43560
gagaatgcac taacgataca aagcaaagcc ttacggacct cagcagagga aaggttatcg    43620
aattcagtgt cactaataag ttctttcatt acttcgagga agtcccctaa tagatc    43676
```

<210> SEQ ID NO 13
<211> LENGTH: 3268
<212> TYPE: DNA
<213> ORGANISM: Schizosaccharomyces pombe

<400> SEQUENCE: 13

```
gaattcaact ttttttttta gaaaaacgct accagaagga caatctgttt tatttttcag      60
gaagaacatt tttctttctg tatttattga atagcgaagg atagggttga atagtgaaaa     120
caacgaagta ttactgtatt gcggaatagt cgcataccca caggttttag gtgagtccat     180
tgtgaaagtg attgacaaca tagtctagtg aaatactgta tgtaatatta cagttgcgta     240
gtgacaaaac gcgacgcgcc aaattcacag gtaatttcta ttgtagtagc ccattgttag     300
taaacaaaga aattcccaaa atggctaata atgggaaaac aagctttttt tttaaataaa     360
cgggtgtttt ctttatttta aaagcaggaa atactgaaa taacttaaga aggtatattt     420
cctcttttct ttcaaaaata aatgaatcgt ggaattgata gcattcatgg acccttacga     480
aaatgaggtt tcaaacgacc gcaataagtg attatgagaa cagctctaat ccttcatttt     540
taaaattttc tgcaggagac actatcatag ttatagaagt gctcgaggac ggttggtgcg     600
acggaatttg ctcagaaaaa cgaggttggt tccccacgtc gtgcattgat tcttcaaaaa     660
ttcaaaattt tttttcaagt tttcattcat cgaatgagaa agacccaaat gctcaatgtt     720
gtgcgccgtt tcacgtagag gctcatcttc aagattctgc atggtttgag aaacacggag     780
tgcaagcgat aaatagtatc ccttcttcag aagagttctt aagaaaaaat cttcaaaatg     840
acattcacca ccttgtaaaa gggattctca ccaccgctgc cgctgtgtca caatctataa     900
aaaaggaagg cactcaagtg atcgttttttg gaattgaaac tgttcgtagt atggttcttt     960
catttccctt gataatcctt tctacattag atgaaaattt tctctcagaa gtcgcgcaag    1020
tgttctcctc attaaattta ttgccagagt tgagccgaat gggttgcact tatggtgaac    1080
tttgcatcag atttactaag cttttgaagc aattggctaa taagtttttg tttttcttca    1140
ggcccgatgt ttccttccct tcttactttt tgggctcttt gatagcgcat gaaatacatt    1200
tcttgccatg ggatttttaat atgctctgtt ccaattctgt acaatcagca catacaaatc    1260
tccaacctga tattacttcc tttgttgcaa ttttgtcact ttcacacgaa gcttaccatt    1320
gcactgagaa tgaattttgg aatttagaag cacagaagct aactgaaaat acaacccaaa    1380
aagtactaca gctagttgcg gaagatgcac tagaagcttg gaaactagat attctagagg    1440
acatcgatag atgcattcaa tgttgtaggc gattcttgtc tgcaaatcaa agaataaatt    1500
attcttcctc tgaaaataac cctttttctt tcacttctca agatgttgaa gccttgaagg    1560
atgaactgtc ttctaactta tgtgatttat atttgtggag tatcgacttg gagcaaatct    1620
cacctagcga ttgtttactg gacaattatt ccctttttgt tgatttacta gtaaccttga    1680
aagtatccct tcttcggatc aagtcaataa ttgttcaatt ttcagaaaga attgtgtttc    1740
```

-continued

```
tttctctaga atacaaattc ctcacaaata tccaaccaga attgaatgat gcggagaagt    1800
cccaacttga tggttttgac ctcaataaaa ccaactggtt cgactctaaa ggattagttt    1860
gttatttaat gaaacagact tcaccagagc cattattgat ccgaaacctt ttgttttcat    1920
tttggtcatg taatggtaaa attgaacaag atggaaaaat aaaaacagcc actttagtgt    1980
tcattataaa ttaccttcta aggacagata tagatagtac attttttact actatctttt    2040
taaacacata cgctagtatg atcagttctt cagatttatt ttccatactt ggagcacatt    2100
ttcggttcat ctgctcatta aattttggaa aaatttcttt tatttctcac gaattttacc    2160
gagttagtaa gaggttttg gatatacttc ttatttggtt cgaatcgtat cttgttgaag    2220
agttggacaa ttccaagtca atattctttt tgtttaaaat ttataaagtt tttgaagtct    2280
ttgtagttcc acattttgca tctgctgaag aattattgca ttctttatca cacctacttc    2340
atcatccctc tacaaaaaga tcacataaaa tgctagaggg aaaagagcta tcccaagaat    2400
tagaggatct ttctctccat aattcccctg atccaattat atataaggat gaattggttt    2460
tacttctacc tcctcgtgaa attgcaaagc agttatgtat cttagagttt caatcatttt    2520
cacacatatc aaggattcag ttcctaacta aaatctggga caatcttaac agattctcac    2580
ccaaagaaaa aacttcgacc tttttatttgt cgaatcatct ggttaacttt gtgaccgaaa    2640
ccatcgtgca agaagaagaa cctcgcagac gtaccaatgt gctagcatat tttattcagg    2700
tctgtgatta tttgagagag cttaacaatt ttgctagttt attttccatc atttctgcgt    2760
taaattcctc acccattcat cggctgcgta agacatgggc aaatttgaat agtaaaacat    2820
tggctagttt tgagcttcta aacaatttga cagaggcaag gaaaaatttc agtaattata    2880
gagattgtct ggagaactgt gtcttgccat gtgtcccttt cttaggtgtt tacttcactg    2940
atctgacttt ccttaaaact ggaaataaag ataactttca aaacatgatc aatttcgata    3000
agcgcaccaa agtcactaga attttgaatg agataaaaaa gtttcaatct gttgggtaca    3060
tgtttaatcc catcaacgaa gttcaagagc ttcttaatga agttatatcg agagagcgaa    3120
acacgaataa catctatcaa agaagtttaa ctgtagaacc acgtgaatct gaagatcaag    3180
ccttacaacg cttgctaatt gattctggca ttttttgaag cgtgaacgtt aacagtgatt    3240
taagttttta tgagcttgct tcgaattc                                     3268
```

<210> SEQ ID NO 14
<211> LENGTH: 3804
<212> TYPE: DNA
<213> ORGANISM: Rattus rattus

<400> SEQUENCE: 14

```
ccgacgaggg gcagtcgggt gcctctcgga gatgtttagt gcgtgaggtc tctctggcct      60
ccaagcacca tgcagaaagc catccgactg aacgatggcc acgtcgtgtc cctgggactg     120
ctggcccaga gagacggtac gcgcaaaggc tacctgagca agaggagttc ggacaaccca     180
aaatggcaaa ccagtggtt tgcgctgctg cagaacctgc tcttctactt cgaaagtgac     240
tcgagctctc ggccctcggg gctctacctg ctggagggca gtatctgcaa acgcatgccc     300 tccccccaagc gagggacctc ctccaaggag tccgacaaac agcatcatta cttcacagtg     360
aacttctcca atgacagcca gaagtcccta gagctgagga ccgatgactc caaggactgt     420
gacgagtggg tggcagcgat tgctcgcgcc agctacaaga tactggccac agagcatgag     480
gcgctcatgc agaagtacct gcacctgctg caggtggtgg agacagagaa gaccgtggct     540
```

```
aagcagctgc gacagcagct cgaggatggc gaggtcgaga tcgagcgcct gaaggcagag    600
attgcaaacc tgatcaagga caatgaacgt atccagtcca accagctggt tgcccctgag    660
gatgaggaca gtgacatcaa gaaaattaag aaggtacaga gtttccttcg cggatggctg    720
tgccggcgaa agtggaagaa catcatccag gactacatcc ggtctcctca tgccgacagc    780
atgcgcaaga ggaaccaggt ggtgttcagc atgctggaag ctgaggccga gtacgtgcag    840
caactacaca tccttgtcaa caattttctg cgcccactgc gcatggccgc cagctctaag    900 aaaccccta taacacatga cgacgtcagc agtatctttc tgaacagtga gaccatcatg    960
ttcctgcacc agatcttcta ccaaggcctg aaggcccgta tcgccagctg gcccacccctg   1020 gttctggcgg acctgttcga catcctgctg ccaatgctta acatctacca ggagttcgtc   1080
cgcaaccacc agtacagtct ccagatccta gcacactgca agcaaaaccg ggactttgac   1140
aagctcctca agcagtatga ggccaagcca gactgcgagg agcgcacact ggagaccttc   1200
ctcacctatc caatgttcca gatccccagg tacatcctga cactccatga gctgctggcc   1260
cacacacctc atgagcatgt ggagcgcaac agcctggact atgccaaatc caaactagag   1320
gagctgtcca gggtcatgca cgacgaagtc agtgagaccg agaacatccg caaaaacctg   1380
gccattgagc gtatgatcac cgagggctgt gagatcctcc ttgacaccag ccagacccttt   1440 gtgcgccaag gttccctcat ccaggtgccc atgtcagaaa agggcaagat caacaagggc   1500
cgcctggggt ctctgtccct taagaaagaa ggtgagcgcc agtgttcct gttctccaag   1560 catctcatca tctgcaccag aggctctggt agcaaactgc acctaaccaa gaatggcgtg   1620
atttccctca ttgactgcac tctactggat gatccagaaa acatggatga tgacggcaaa   1680
ggacaagagg tagatcacct ggactttaag atttgggtgg agccaaagga ttccccaccc   1740
ttcacagtca tcctggtggc ctcatccagg caggagaagg cggcatggac cagtgacatc   1800
atccagtgcg tggataatat ccgctgcaac gggctcatga tgaatgcctt tgaagaaaat   1860
tccaaggtca ccgtgccgca gatgatcaag tctgatgctt ccttatactg tgatgatgtt   1920
gacattcgct tcagcaaaac catgaattct tgcaaagtgc tgcagatccg ctatgccagc   1980
gtggagcgcc tgctggagcg cctgactgat cttcgcttcc tgagtattga ctttctcaac   2040
accttcctgc actcctatcg agtcttcacc gatgctgtgg tggtcctaga caagctgatc   2100
agcatctaca aaaagcccat cactgcgatt cctgccaggt cactggaact cctgttctcc   2160
agtagccaca acaccaaact tctgtacgga gatgcccca gtcgcctcg tgccagccgc   2220 aagttctcct cgccgccgcc cttggccatc ggcacttcgt ccccagtccg ccgccggaag   2280
ttgtctctca acattcccat catcacaggc ggcaaggcgc tggaactggc ttcgctcggg   2340
tgcccctccg acggctacac caacatacac tcgcccatat ctcccttcgg caaaaccacg   2400
ctggacacca gcaagctctg tgtggccagc agcttgacca gaacgccgga ggagattgat   2460
atgaccactc tagaggagtc atcaggcttc aggaagccga cctcagacat cttgaaagaa   2520
gagtctgatg atgaccagag tgatgtagac gacacagaag tgtctccacc aacaccgaaa   2580
tcattcagaa acagaatcac tcaagagttc ccactctttta actacaacag tggaatcatg   2640
atgacatgtc gcgatctgat ggacagtaac cgcagccctc tgtcagctac ctctgccttt   2700
gccatagcga ctgcaggagc caatgaaagc cccgcaaaca aggagatata tcgaaggatg   2760
tctttggcca acacagggta ttcctctgac cagagaaata tcgacaaaga gttcgtgatc   2820
cgcagagcgg ccaccaaccg tgtactgaat gtgttgcgcc actgggtcac caagcactcc   2880
caggactttg aaactgacga cctcctcaaa tacaaggtga tctgctttct ggaagaggtc   2940
```

-continued

```
atgcatgacc cagaccttct accacaagag cgaaaggcag cagccaacat catgaggact    3000
ctgacccagg aagaaataac tgaaaaccat agcatgctgg atgagctctt actaatgacg    3060
gagggtgtga agactgagcc cttcgaaaac cactcagcca tggagatagc agagcagctg    3120
accctgctgg atcaccttgt cttcaagagt attccttatg aggaattctt tggccagggc    3180
tggatgaagg cagataagaa tgaaaggaca ccttacatta tgaaaaccac cagacatttc    3240
aaccatatca gtaacttgat cgcttcagaa attctccgaa acgaggaggt cagtgcaagg    3300
gcaagcacca tcgagaagtg ggtggctgtt gccgacattt gccgctgcct gcacaactac    3360
aatgctgtgc tggagatcac ttcctccatc aaccgcagcg caatcttccg actcaagaag    3420
acatggctca aagtttctaa gcagacgaaa tctctgtttg acaagctcca aaagcttgtg    3480
tcatcagatg gccgatttaa gaacctcaga gaaactttgc gaaattgtga tccaccctgt    3540
gtcccttacc tggggatgta cctgaccgac ttggcattcc tcgaggaagg aacacccaat    3600
tacacagagg acggcctggt caacttctcc aagatgagga tgatctccca tattatccgc    3660
gagattcgcc agtttcagca gactacttac aaaatcgagc cccagccaaa ggtaactcag    3720
tacttagtgg atgaaacctt tgtgttggac gacgaaagtc tgtatgaggc ctccctccga    3780
attgaaccaa aactccccac atga                                          3804
```